US012083099B2

(12) United States Patent
Brown et al.

(10) Patent No.: US 12,083,099 B2
(45) Date of Patent: Sep. 10, 2024

(54) METHODS OF TREATING SYMPTOMS OF CORONAVIRUS INFECTION WITH VIRAL PROTEASE INHIBITORS

(71) Applicant: Accencio LLC, Philadelphia, PA (US)

(72) Inventors: Kevin Brown, Philadelphia, PA (US); Kevin Brogle, Philadelphia, NJ (US)

(73) Assignee: Accencio LLC, Philadelphia, PA (US)

( * ) Notice: Subject to any disclaimer, the term of this patent is extended or adjusted under 35 U.S.C. 154(b) by 0 days.

(21) Appl. No.: 17/513,284

(22) Filed: Oct. 28, 2021

(65) Prior Publication Data

US 2023/0113114 A1    Apr. 13, 2023

Related U.S. Application Data

(60) Provisional application No. 63/106,529, filed on Oct. 28, 2020.

(51) Int. Cl.
A61K 31/4709 (2006.01)
A61K 9/00 (2006.01)
A61K 31/407 (2006.01)

(52) U.S. Cl.
CPC .......... A61K 31/407 (2013.01); A61K 9/0014 (2013.01); A61K 31/4709 (2013.01)

(58) Field of Classification Search
CPC . A61K 31/407; A61K 9/0014; A61K 31/4709
See application file for complete search history.

(56) References Cited

U.S. PATENT DOCUMENTS

| | | | |
|---|---|---|---|
| 6,391,919 B1 | 5/2002 | Kaltenbach et al. | |
| 8,188,137 B2 | 5/2012 | Niu et al. | |
| 8,618,152 B2 | 12/2013 | Farmer et al. | |
| 9,346,820 B2 | 5/2016 | Ghosh et al. | |
| 2008/0267917 A1 | 10/2008 | Niu et al. | |

FOREIGN PATENT DOCUMENTS

| | | |
|---|---|---|
| AR | 071258 A1 | 9/2010 |
| CN | 101448781 A | 6/2009 |
| JP | 2000159746 A | 6/2000 |
| PE | 20091208 A1 | 8/2009 |
| WO | 1993023379 A1 | 11/1993 |
| WO | 1994004492 A1 | 3/1994 |
| WO | 1994005639 A1 | 3/1994 |
| WO | 1994011361 A1 | 5/1994 |
| WO | 1998019997 A2 | 5/1998 |
| WO | 2000015634 A2 | 5/1998 |
| WO | 1998029435 A1 | 7/1998 |
| WO | 1999033815 A1 | 7/1999 |
| WO | 1999036404 A1 | 7/1999 |
| WO | 1999050229 A1 | 10/1999 |
| WO | 1999064442 A1 | 12/1999 |
| WO | 1999067254 A2 | 12/1999 |
| WO | 2000047551 A2 | 8/2000 |
| WO | 2000076961 A1 | 12/2000 |
| WO | 2001000635 A2 | 1/2001 |
| WO | 2001038332 A1 | 5/2001 |
| WO | 2001047948 A1 | 7/2001 |
| WO | 2002006292 A1 | 1/2002 |
| WO | 2002008244 A2 | 1/2002 |
| WO | 2002008256 A2 | 1/2002 |
| WO | 2002018369 A2 | 3/2002 |
| WO | 2002042277 A1 | 5/2002 |
| WO | 02100844 A2 | 12/2002 |
| WO | 2003051910 A2 | 6/2003 |
| WO | 2003064416 A1 | 8/2003 |
| WO | 2003064455 A2 | 8/2003 |
| WO | 2003064456 A1 | 8/2003 |
| WO | 2003078438 A1 | 9/2003 |
| WO | 2003099274 A1 | 12/2003 |
| WO | 2004101605 A1 | 3/2004 |
| WO | 2004037855 A1 | 5/2004 |
| WO | 2004043355 A2 | 5/2004 |
| WO | 2004043911 A2 | 5/2004 |
| WO | 2004056764 A1 | 7/2004 |
| WO | 2004092161 A1 | 10/2004 |
| WO | 2004103996 A1 | 12/2004 |
| WO | 2005028501 A1 | 3/2005 |
| WO | 2005030796 A1 | 4/2005 |
| WO | 2005037214 A2 | 4/2005 |
| WO | 2005037791 A1 | 4/2005 |
| WO | 2005051410 A1 | 6/2005 |
| WO | 2005058841 A2 | 6/2005 |
| WO | 2005061450 A2 | 7/2005 |
| WO | 2005073195 A2 | 8/2005 |
| WO | 2005085275 A1 | 9/2005 |
| WO | 2005087731 A1 | 9/2005 |
| WO | 2005097767 A1 | 10/2005 |
| WO | WO2005097767 A1 * 10/2005 ........... C07D 277/60 |
| WO | 2005107745 A1 | 11/2005 |
| WO | 2006007708 A1 | 1/2006 |
| WO | 2006073456 A2 | 7/2006 |
| WO | 2007016441 A1 | 7/2006 |
| WO | 2006084688 A1 | 8/2006 |
| WO | 2006104646 A1 | 10/2006 |
| WO | 2007001406 A2 | 1/2007 |
| WO | 2007002172 A2 | 1/2007 |
| WO | 2007015787 A1 | 2/2007 |
| WO | 2007015824 A2 | 2/2007 |
| WO | 2007033175 A1 | 3/2007 |
| WO | 2007044893 A2 | 4/2007 |

(Continued)

Primary Examiner — Joseph K McKane
Assistant Examiner — David M Shim
(74) Attorney, Agent, or Firm — LEASON ELLIS LLP

(57) ABSTRACT

The present disclosure relates to a method of reducing or arresting viral load in a subject infected with a coronavirus, the method comprising the step of administering to the subject a therapeutically effective amount of a viral protease inhibitor. In some embodiments, the subject is a human. In one embodiment, the coronavirus is SARS-COV-19 and the viral protease inhibitor is E)-N-(4-(3-(tert-butyl)-5-(2,4-di-oxo-3,4-dihydropyrimidin-1(2H)-yl)-2-methoxystyryl)phenyl)methanesulfonamide; (R)-3-((2S,3S)-2-hydroxy-3-(3-hydroxy-2-methylbenzamido)-4-phenylbutanoyl)-5,5-dimethyl-N-(2-methylbenzyl)thiazolidine-4-carboxamide; R)—N-allyl-3-((2S,3S)-2-hydroxy-3-(3-hydroxy-2-methylbenzamido)-4-phenylbutanoyl)-5,5-dimethylthiazolidine-4-carboxamide; (4-((N-(5-cyclopropyl-2-(4-fluorophenyl)-3-(methylcarbamoyl)benzofuran-6-yl)methylsulfonamido)methyl)-2-fluorophenyl)boronic acid or salts thereof.

3 Claims, No Drawings

(56) References Cited

FOREIGN PATENT DOCUMENTS

| | | |
|---|---|---|
| WO | 2007070201 A1 | 6/2007 |
| WO | 2007117560 A2 | 10/2007 |
| WO | 2007121124 A2 | 10/2007 |
| WO | 2007133865 A2 | 11/2007 |
| WO | 2007136982 A1 | 11/2007 |
| WO | 2007140109 A1 | 12/2007 |
| WO | 2007147884 A1 | 12/2007 |
| WO | 2008008502 A1 | 1/2008 |
| WO | 2008011117 A2 | 1/2008 |
| WO | 2008013834 A1 | 1/2008 |
| WO | 2008057208 A2 | 5/2008 |
| WO | 2008057209 A1 | 5/2008 |
| WO | 2008078200 A2 | 7/2008 |
| WO | 2008115894 A | 9/2008 |
| WO | 2008118849 A2 | 10/2008 |
| WO | 2008124148 A2 | 10/2008 |
| WO | 2008134395 A1 | 11/2008 |
| WO | 2008137779 A2 | 11/2008 |
| WO | 2009005674 A2 | 1/2009 |
| WO | 2009005676 A2 | 1/2009 |
| WO | 2009008913 A2 | 1/2009 |
| WO | 2009014730 A1 | 1/2009 |
| WO | 2009042093 A1 | 4/2009 |
| WO | 2009053828 A2 | 4/2009 |
| WO | 2009070689 A1 | 6/2009 |
| WO | 2009070692 A1 | 6/2009 |
| WO | 2009076173 A2 | 6/2009 |
| WO | 2009082697 A1 | 7/2009 |
| WO | 2009139792 A1 | 11/2009 |
| WO | 2010011566 A1 | 1/2010 |
| WO | 2010030359 A2 | 3/2010 |
| WO | 2010135424 A1 | 11/2010 |
| WO | 2011002807 A1 | 1/2011 |
| WO | 2011002808 A1 | 1/2011 |
| WO | 2011014487 A1 | 2/2011 |
| WO | 2011034518 A1 | 3/2011 |
| WO | 2011038283 A1 | 3/2011 |
| WO | 2011091757 A1 | 8/2011 |
| WO | 2011103063 A1 | 8/2011 |
| WO | 2011150190 A2 | 12/2011 |
| WO | 2012031237 A1 | 3/2012 |
| WO | 2012040167 A1 | 3/2012 |
| WO | 2012040242 A1 | 3/2012 |
| WO | 2012055031 A1 | 5/2012 |
| WO | 2012092168 A1 | 7/2012 |
| WO | 2012092409 A2 | 7/2012 |
| WO | 2012151195 A1 | 11/2012 |
| WO | 201418727 A1 | 1/2014 |
| WO | 2012040040 A1 | 1/2014 |
| WO | 2014008285 A1 | 1/2014 |
| WO | 2014070974 A1 | 5/2014 |
| WO | 2014145095 A1 | 9/2014 |
| WO | 2014164667 A1 | 10/2014 |
| WO | 2014187271 A1 | 11/2014 |
| WO | 2015197028 A1 | 12/2015 |
| WO | 2016069955 A1 | 5/2016 |
| WO | 2016127859 A1 | 8/2016 |
| WO | 2016141890 A1 | 9/2016 |
| WO | 2017031220 A1 | 2/2017 |

* cited by examiner

METHODS OF TREATING SYMPTOMS OF CORONAVIRUS INFECTION WITH VIRAL PROTEASE INHIBITORS

CROSS REFERENCE TO RELATED APPLICATION

The present application claims the benefit of U.S. patent application Ser. No. 63/106,529, filed Oct. 28, 2020, which is hereby incorporated by reference in its entirety.

FIELD

The present disclosure relates to methods of treating symptoms of a coronavirus infection, e.g., SARS-COV-19, by administering a viral protease inhibitor.

BACKGROUND

The novel virus 2019-nCOV (SARS-COV-19, COVID-19), is the third well-known coronavirus to cross species to infect human populations in the past two decades. The previous two are the severe acute respiratory syndrome coronavirus (SARS-COV) outbreak in 2002 and the Middle East respiratory syndrome coronavirus (MERS-COV) outbreak in 2012. Like SARS-COV and MERs-COV, SARS-COV-19 causes severe respiratory illness, and is highly transmissible from human-to-human. On Mar. 11, 2020, the World Health Organization (WHO) declared SARS-CoV-19 a global pandemic. Since then, over 20 million people have been infected, and over 750,000 people have died worldwide from the virus. In the United States alone there have been over 5 million infections to date, with over 160,000 deaths.

Most of the critically ill patients do not develop severe clinical manifestations in early stages of the diseases; however, these patients rapidly deteriorate in the later stages of the disease, presenting with Acute Respiratory Distress Syndrome (ARDS) and multiple-organ failure, resulting in death within a short time. Evidence suggests that proinflammatory responses play a role in the pathogenesis of SARS-COV-19 and other coronaviruses. Dysregulations of cytokine-chemokine responses cause the immune system to become hyperactive and induce a condition called a cytokine storm, which is considered to be one of the major causes of ARDS and multiple-organ failure in these patients. Targeting cytokines during the management of SARS-COV-19 patients could improve survival rates and reduce mortality.

To date, no treatment or vaccine has been approved to combat SARS-COV-19. There is therefore an urgent and unmet need for effective means to combat the symptoms of SARS-COV-19 and other coronaviruses such as SARS-COV and MERS-COV.

SUMMARY

The present disclosure relates to methods of treating one or more symptoms of a coronavirus infection, particularly SARS-COV-19. The present disclosure further relates to methods of treating or preventing an acute inflammatory response, e.g., a cytokine storm in a coronavirus patient, by administering a viral protease inhibitor, in particular a viral polymerase inhibitor.

Broadly, protease inhibitors prevent viral replication by selectively binding to viral proteases (e.g. HIV-1 protease) and blocking proteolytic cleavage of protein precursors that are necessary for the production of infectious viral particles. The present disclosure is based on the discovery that viral protease inhibitors may have therapeutic utility in the treatment of coronavirus symptoms, in particular in reducing inflammation and preventing cytokine storms in patients with coronavirus infections, in particular SARS-COV-19.

Thus, in some embodiments, the present disclosure relates to a method of treating or alleviating at least one symptom of a coronavirus infection in a subject, by administering to the subject a therapeutically effective amount of a viral protease inhibitor. In some embodiments, the symptom is selected from the group consisting of fever, cough, tiredness, sore throat, diarrhea, conjunctivitis, headache, loss of taste, loss of smell, rash, difficulty breathing, shortness of breath, chest pain, chest pressure, Acute Respiratory Distress Syndrome (ARDS) and organ failure. In some embodiments, the subject is a human.

In some embodiments, the present disclosure relates to a method of treating an acute inflammatory condition in a subject infected with a coronavirus, the method comprising the step of administering to the subject a therapeutically effective amount of a viral protease inhibitor. In some embodiments, the inflammatory condition comprises a cytokine storm. In some embodiments, the subject is a human.

In some embodiments, the present disclosure relates to a method of preventing a cytokine storm in a subject infected with a coronavirus, the method comprising the step of administering to the subject a therapeutically effective amount of a viral protease inhibitor. In some embodiments, the subject is a human.

In some embodiments, the present disclosure relates to a method of reducing or arresting viral load in a subject infected with a coronavirus, the method comprising the step of administering to the subject a therapeutically effective amount of a viral protease inhibitor. In some embodiments, the subject is a human.

In some embodiments, the coronavirus is a severe acute respiratory syndrome coronavirus (SARS-COV). In some embodiments, the coronavirus is a novel virus 2019-nCOV (SARS-COV-19). In some embodiments, the coronavirus is a Middle East respiratory syndrome coronavirus (MERS-COV). In one preferred embodiment, the coronavirus is SARS-COV-19.

In some embodiments, the viral protease inhibitor is E)-N-(4-(3-(tert-butyl)-5-(2,4-dioxo-3,4-dihydropyrimidin-1(2H)-yl)-2-methoxystyryl)phenyl)methanesulfonamide; (R)-3-((2S,3S)-2-hydroxy-3-(3-hydroxy-2-methylbenzamido)-4-phenylbutanoyl)-5,5-dimethyl-N-(2-methylbenzyl)thiazolidine-4-carboxamide; R)—N-allyl-3-((2S,3S)-2-hydroxy-3-(3-hydroxy-2-methylbenzamido)-4-phenylbutanoyl)-5,5-dimethylthiazolidine-4-carboxamide; (4-((N-(5-cyclopropyl-2-(4-fluorophenyl)-3-(methylcarbamoyl)benzofuran-6-yl)methylsulfonamido)methyl)-2-fluorophenyl)boronic acid or salts thereof. Combinations of viral protease inhibitors may also be used in the methods of the present disclosure.

In some embodiments, the viral protease inhibitors are selected from the group consisting of a compound of any one of Table 1.

In some embodiments, viral protease inhibitor is administered according to a dose regimen selected from the group consisting of once daily (q.d.), twice daily (b.i.d.) thrice daily (t.i.d.), once a week, twice a week, three times a week, once every 2 weeks, once every three weeks, or once a month.

In some embodiments, the viral protease inhibitor is administered in a pharmaceutical composition, wherein the composition further comprises at least one pharmaceutically acceptable excipient.

In some embodiments, the viral protease inhibitor is administered in a form selected from the group consisting of a solution, a suspension, a syrup, an emulsion, a dispersion, a tablet, a pill, a capsule, a pellet, granules, a powder, an ointment, an elixir, a wafer, coated or uncoated beads, a lozenge, a sachet, a cachet, a depot system, a patch, an aerosol, an oil, an ointment, a suppository, a gel, and a cream.

In some embodiments, the pharmaceutical composition is formulated for oral, topical, mucosal, intranasal, parenteral, gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic, transdermal, rectal, buccal, epidural, sublingual oral, intranasal, intravenous, intraarterial, intrathecal, vaginal, rectal or subcutaneous administration.

In some embodiments, the present disclosure relates to a topical pharmaceutical composition in a form selected from the group consisting of ointment, a gel, a drop, a patch and a cream, the composition comprising a viral protease inhibitor and at least one topically acceptable excipient, wherein the viral protease inhibitor is selected from the group consisting of the compounds provided in Table 1.

Further embodiments and the full scope of applicability of the present disclosure will become apparent from the detailed description given hereinafter. However, it should be understood that the detailed description and specific examples, while indicating preferred embodiments of the disclosure, are given by way of illustration only, since various changes and modifications within the spirit and scope of the present disclosure will become apparent to those skilled in the art from this detailed description

DETAILED DESCRIPTION

As used herein and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

As used herein and as well understood in the art, the term an "effective amount," "sufficient amount" or "therapeutically effective amount" of an agent as used herein interchangeably, is that amount sufficient to effectuate beneficial or desired results, including preclinical and/or clinical results and, as such, an "effective amount" or its variants depends upon the context in which it is being applied. The response is in some embodiments preventative, in others therapeutic, and in others a combination thereof. The term "effective amount" also includes the amount of a compound of the disclosure, which is "therapeutically effective" and which avoids or substantially attenuates undesirable side effects.

As used herein and as well known in the art, and unless otherwise defined, the term "subject" means an animal, including but not limited a human, monkey, cow, horse, sheep, pig, chicken, turkey, quail, cat, dog, mouse, rat, rabbit, or guinea pig. In one embodiment, the subject is a mammal and in another embodiment the subject is a human coronavirus patient.

Molecular studies have indicated that viral proteases play a critical role in the life cycle of many viruses. Broadly, protease inhibitors prevent viral replication by selectively binding to viral proteases (e.g. HIV-1 protease) and blocking proteolytic cleavage of protein precursors that are necessary for the production of infectious viral particles. According to current research, proteases provide utility by effecting the cleavage of high-molecular-weight viral polyprotein precursors to yield functional products. Likewise, proteases have utility in catalyzing the processing of the structural proteins necessary for assembly and morphogenesis of virus particles. Viral protease inhibitors targets these functions from being carried out and preset mechanisms for treating an acute viral infection.

Viral proteases have been developed to treat Human Immunodeficiency Virus (HIV) and hepatitis C. deficiency. Because other viruses also encode for the same proteases that are essential to viral replication, the present disclosure extends the utility of protease inhibitors for other viruses, such as SARS-COV-19, where the processing site sequence and the catalytic mechanism are known and understood.

For example, a compound for use in the method of the present disclosure is a viral protease inhibitor.

In one implementation, the compound is 4-PBA, or sodium 4-phenylbutanoate. In one particular implementation, the compound is described in WO2000015634 the contents of which are hereby incorporated by reference for all purposes and the specific purposes identified herein. In some embodiments, such compounds are represented by any one or more of the structures shown in Table 1. Any one of the compounds depicted in Table 1 is suitable for use in the methods of the present disclosure.

TABLE 1

Compound

TABLE 1-continued

Compound

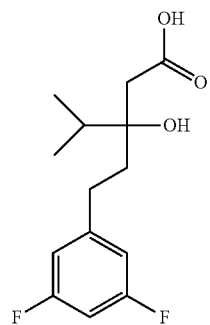 [SMILES: CC(C)C(O)(CCc1cc(F)cc(F)c1)CC(=O)O]

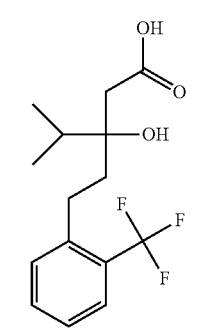 [SMILES: CC(C)C(O)(CCc1ccccc1C(F)(F)F)CC(=O)O]

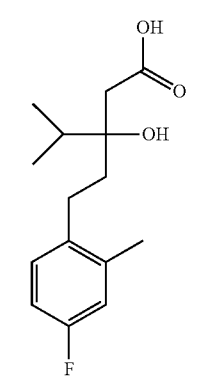 [SMILES: Cc1cc(F)ccc1CCC(O)(CC(=O)O)C(C)C]

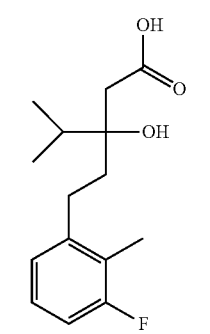 [SMILES: Cc1c(F)cccc1CCC(O)(CC(=O)O)C(C)C]

TABLE 1-continued

Compound

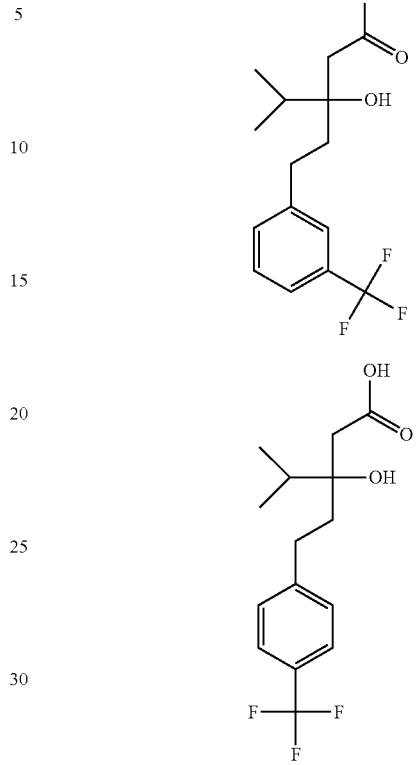

In one implementation, the compound is A-837093, a drug investigated in Phase 1 clinical trials as a NS5A Protein Inhibitor and having the formula:

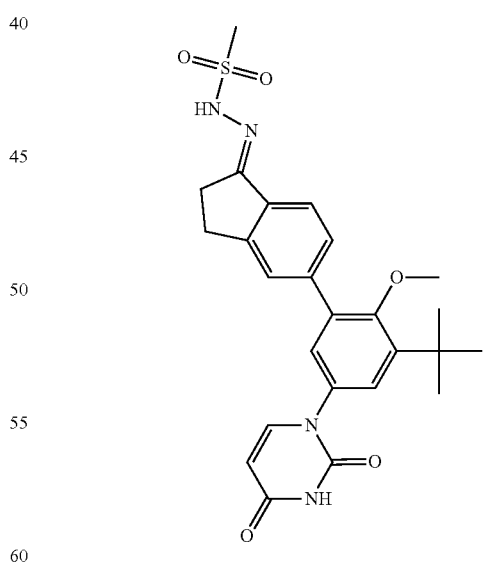

In one particular implementation, the compound, or variations and permutations thereof, is described in WO2015197028 the contents of which are hereby incorporated by reference for all purposes and the specific purposes identified herein. In some embodiments, such compounds are represented by any one or more of the structures shown in Table 2. Any one of the compounds depicted in Table 2 is suitable for use in the methods of the present disclosure.

TABLE 2

Compound

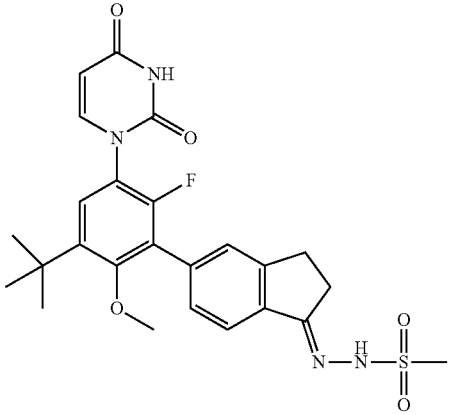 [SMILES: COc1c(C(C)(C)C)cc(-n2ccc(=O)[nH]c2=O)c(F)c1-c1ccc2c(c1)CC/C2=N\NS(C)(=O)=O]

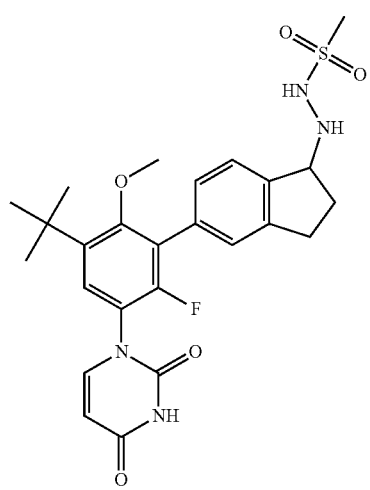 [SMILES: COc1c(C(C)(C)C)cc(-n2ccc(=O)[nH]c2=O)c(F)c1-c1ccc2c(c1)CCC2NNS(C)(=O)=O]

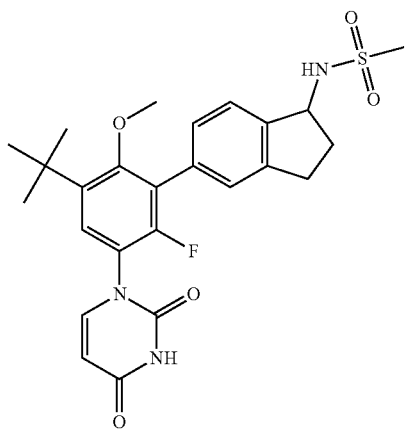 [SMILES: COc1c(C(C)(C)C)cc(-n2ccc(=O)[nH]c2=O)c(F)c1-c1ccc2c(c1)CCC2NS(C)(=O)=O]

TABLE 2-continued

Compound

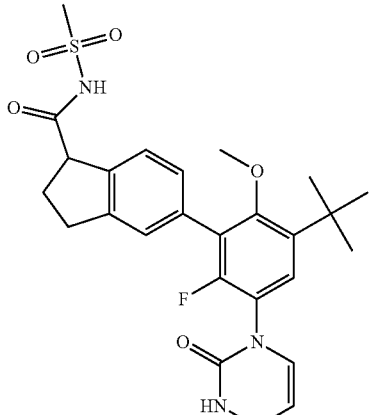

In one implementation, the compound is ABT-072, E)-N-(4-(3-(tert-butyl)-5-(2,4-dioxo-3,4-dihydropyrimidin-1(2H)-yl)-2-methoxystyryl)phenyl)methanesulfonamide. In one particular implementation, the compound, or variations and permutations thereof, is described in WO2015197028 the contents of which are hereby incorporated by reference for all purposes and the specific purposes identified herein.

In one implementation, the compound is, ACT-519276, a glucosylceramide synthase inhibitor or Non lysosomal glucosylceramidase inhibitor, that has been clinically evaluated. In one implementation, the compound is represented by the following:

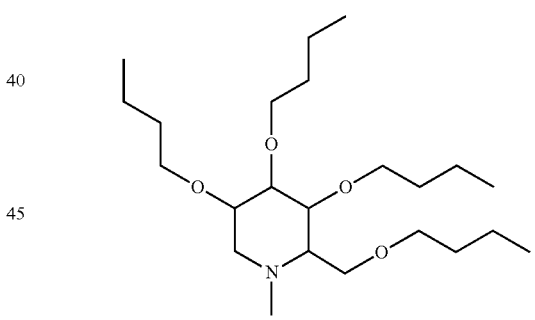

In one particular implementation, the compound, or variations and permutations thereof, is described in WO2006073456 the contents of which are hereby incorporated by reference for all purposes and the specific purposes identified herein.

In one implementation, the compound is AG-1776, a HIV protease inhibitor under clinical investigation and having the formula (R)-3-((2S,3S)-2-hydroxy-3-(3-hydroxy-2-methylbenzamido)-4-phenylbutanoyl)-5,5-dimethyl-N-(2-methylbenzyl)thiazolidine-4-carboxamide. In one particular implementation, the compound, or variations and permutations thereof, is described in WO02100844; and WO2001047948 the contents of which are hereby incorporated by reference for all purposes and the specific purposes identified herein In one implementation, the compound is AG-1859, R)—N-allyl-3-((2S,3S)-2-hydroxy-3-(3-hydroxy-2-methylbenzamido)-4-phenylbutanoyl)-5,5-dimethylthiazolidine-4- carboxamide, acting as a HIV protease inhibitor. In one particular implementation, the compound, or variations and permutations thereof, is described in WO02100844 the contents of which are hereby incorporated by reference for all purposes and the specific purposes identified herein. In some embodiments, such compounds are represented by any one or more of the structures shown in Table 5. Any one of the compounds depicted in Table 1 is suitable for use in the methods of the present disclosure.

TABLE 3

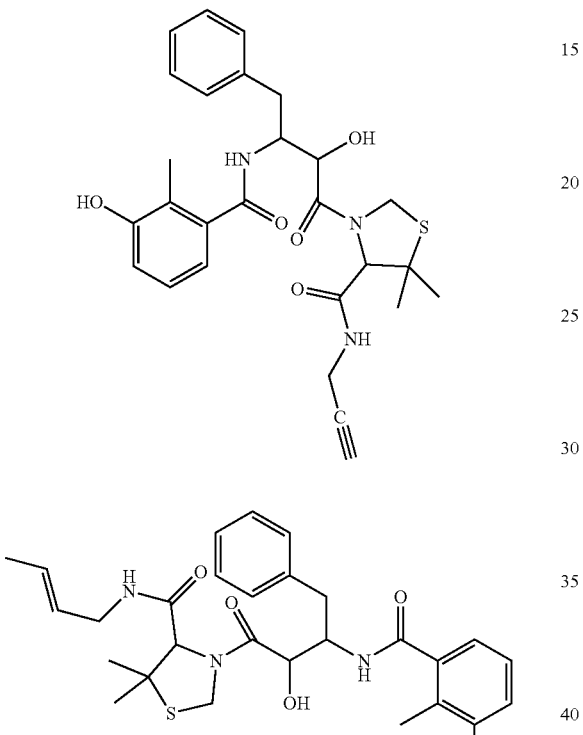

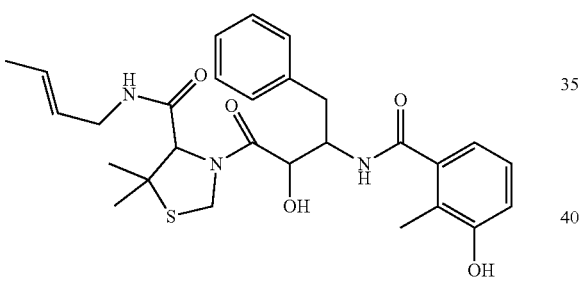

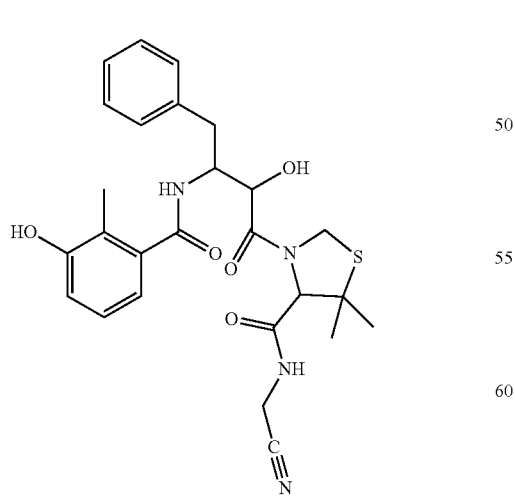

TABLE 3-continued

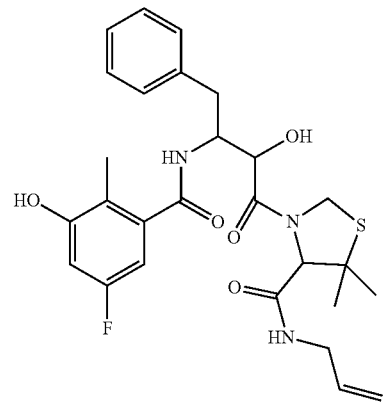 [SMILES: C=CCNC(=O)C1N(C(=O)C(O)C(Cc2ccccc2)NC(=O)c2cc(F)cc(O)c2C)CSC1(C)C]

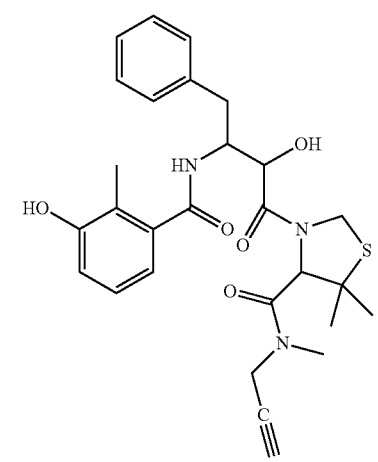 [SMILES: C#CCN(C)C(=O)C1N(C(=O)C(O)C(Cc2ccccc2)NC(=O)c2cccc(O)c2C)CSC1(C)C]

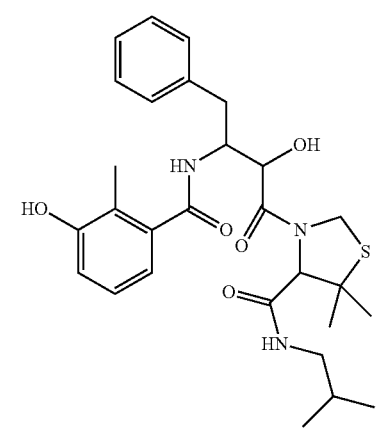 [SMILES: Cc1c(O)cccc1C(=O)NC(Cc1ccccc1)C(O)C(=O)N1CSC(C)(C)C1C(=O)NCC(C)C]

TABLE 3-continued

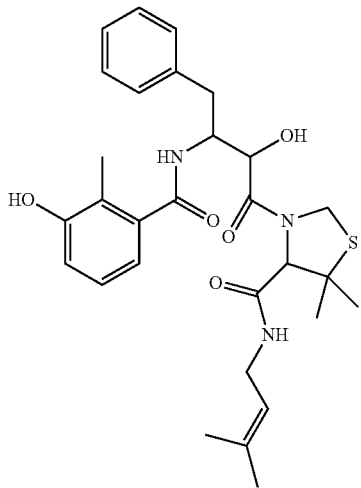 [SMILES: CC(C)=CCNC(=O)C1N(C(=O)C(O)C(Cc2ccccc2)NC(=O)c2cccc(O)c2C)CSC1(C)C]

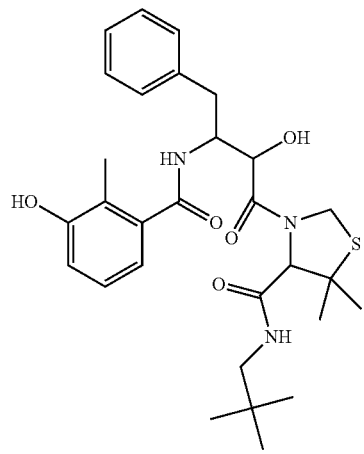 [SMILES: Cc1c(O)cccc1C(=O)NC(Cc1ccccc1)C(O)C(=O)N1CSC(C)(C)C1C(=O)NCC(C)(C)C]

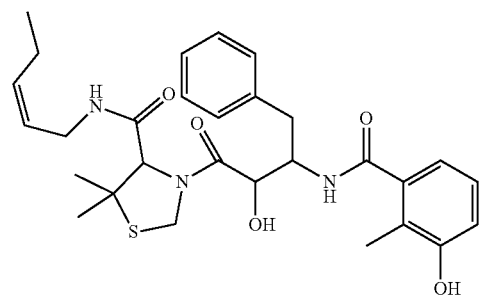 [SMILES: CC/C=C\CNC(=O)C1N(C(=O)C(O)C(Cc2ccccc2)NC(=O)c2cccc(O)c2C)CSC1(C)C]

In one implementation, the compound is Allotrap((4S)-5-[[(2S)-1-[[(2S)-1-[[(2S)-1-[[(2S)-4-amino-1-[[(2S)-1-[-[[(2S)-1-[[2-[[(1S)-1-carboxy-2-(4-hydroxyphenyl)ethyl]amino]-2-oxoethyl]amino]-5-(diaminomethylideneamino)-1-oxopentan-2-yl]amino]-4-methyl-1-oxopentan-2-yl]amino]-1,4-dioxobutan-2-yl]amino]-5-(diaminomethylideneamino)-1-oxopentan-2-yl]amino]-4-methyl-1-oxopentan-2-yl]amino]-3-hydroxy-1-oxopropan-2-yl]amino]-4-[[(2S)-2-amino-5-(diaminomethylideneamino)pentanoyl]amino]-5-oxopentanoic acid)-2702, a clinically investigated compound for NS3-serine protease inhibitors and having the formula:

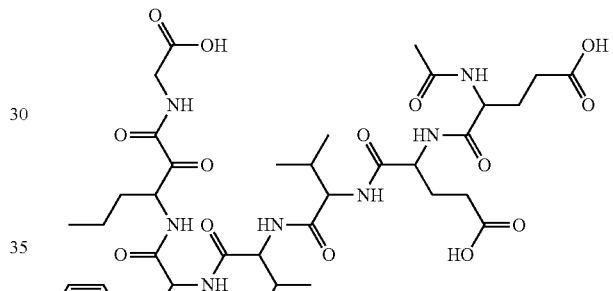

In one particular implementation, the compound, or variations and permutations thereof, is described in WO2002008256 the contents of which are hereby incorporated by reference for all purposes and the specific purposes identified herein. In one implementation, the compound is BMS-605339, a clinically investigated NS3 protease inhibitor. In one particular implementation, the compound, or variations and permutations thereof, is described in WO2003099274; WO2005051410; WO2006007708; WO2009082697; WO2011002807; WO2012040242; and WO2012151195 the contents of which are hereby incorporated by reference for all purposes and the specific purposes identified herein. In some embodiments, such compounds are represented by any one or more of the structures shown in Table 6. Any one of the compounds depicted in Table 6 is suitable for use in the methods of the present disclosure.

TABLE 4
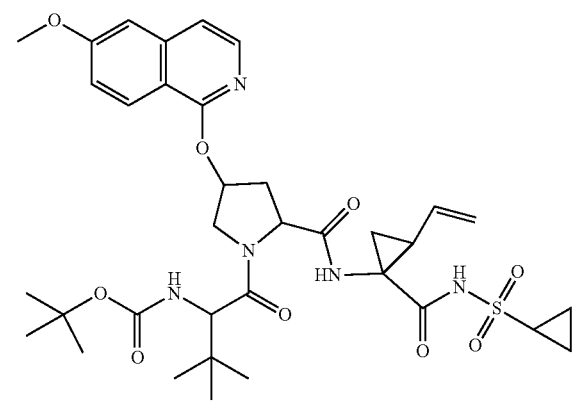 [SMILES: C=CC1CC1(NC(=O)C1CC(Oc2nccc3cc(OC)ccc23)CN1C(=O)C(NC(=O)OC(C)(C)C)C(C)(C)C)C(=O)NS(=O)(=O)C1CC1]
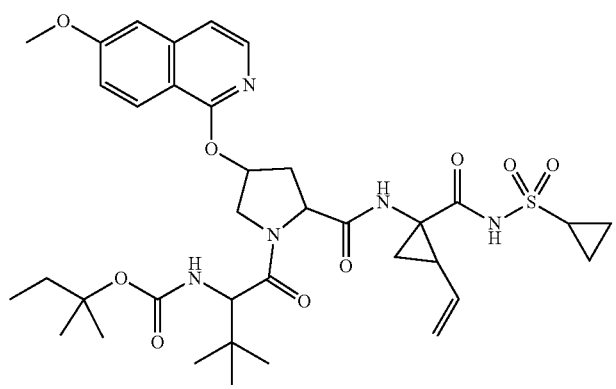 [SMILES: C=CC1CC1(NC(=O)C1CC(Oc2nccc3cc(OC)ccc23)CN1C(=O)C(NC(=O)OC(C)(C)CC)C(C)(C)C)C(=O)NS(=O)(=O)C1CC1]
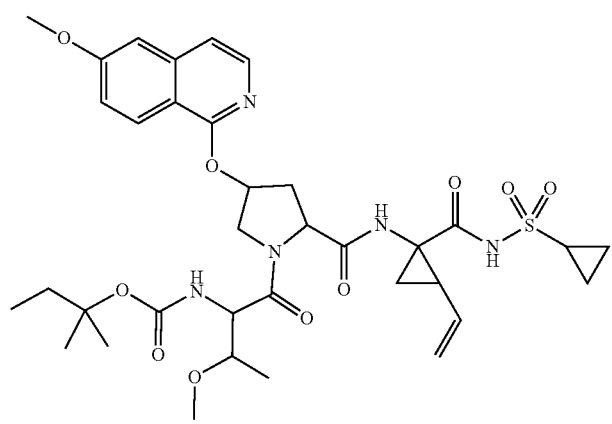 [SMILES: C=CC1CC1(NC(=O)C1CC(Oc2nccc3cc(OC)ccc23)CN1C(=O)C(NC(=O)OC(C)(C)CC)C(C)OC)C(=O)NS(=O)(=O)C1CC1]
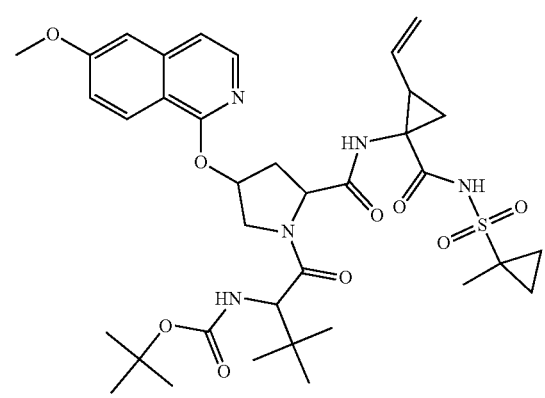 [SMILES: C=CC1CC1(NC(=O)C1CC(Oc2nccc3cc(OC)ccc23)CN1C(=O)C(NC(=O)OC(C)(C)C)C(C)(C)C)C(=O)NS(=O)(=O)C1(C)CC1]

TABLE 4-continued
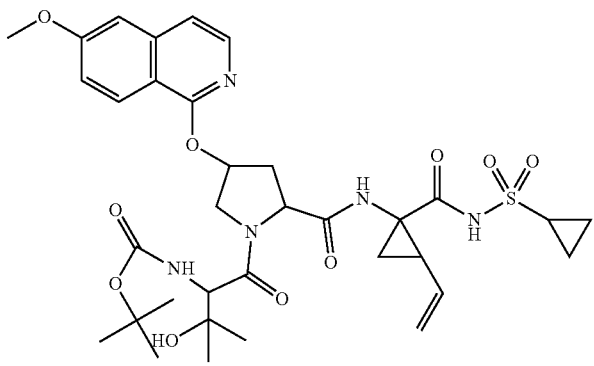 [SMILES: C=CC1CC1(NC(=O)C1CC(Oc2nccc3cc(OC)ccc23)CN1C(=O)C(NC(=O)OC(C)(C)C)C(C)(C)O)C(=O)NS(=O)(=O)C1CC1]
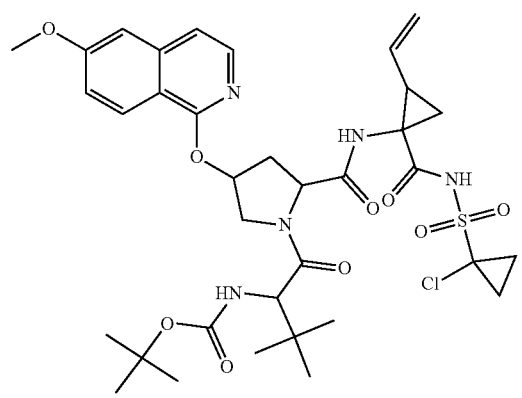 [SMILES: C=CC1CC1(NC(=O)C1CC(Oc2nccc3cc(OC)ccc23)CN1C(=O)C(NC(=O)OC(C)(C)C)C(C)(C)C)C(=O)NS(=O)(=O)C1(Cl)CC1]
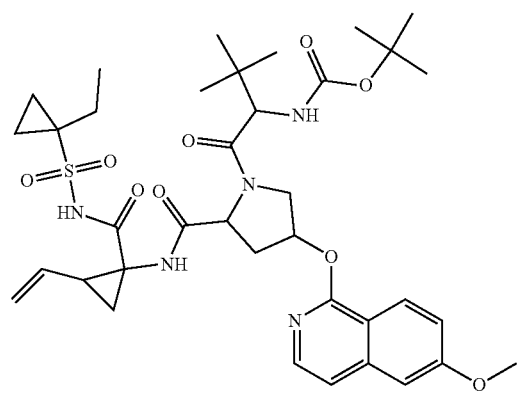 [SMILES: C=CC1CC1(NC(=O)C1CC(Oc2nccc3cc(OC)ccc23)CN1C(=O)C(NC(=O)OC(C)(C)C)C(C)(C)C)C(=O)NS(=O)(=O)C1(CC)CC1]
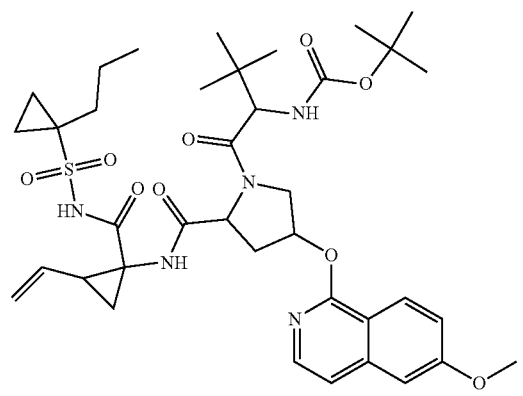 [SMILES: C=CC1CC1(NC(=O)C1CC(Oc2nccc3cc(OC)ccc23)CN1C(=O)C(NC(=O)OC(C)(C)C)C(C)(C)C)C(=O)NS(=O)(=O)C1(CCC)CC1]

TABLE 4-continued
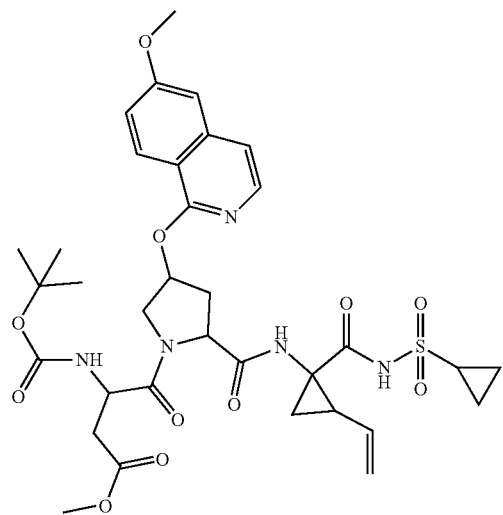 [SMILES: C=CC1CC1(NC(=O)C1CC(Oc2nccc3cc(OC)ccc23)CN1C(=O)C(CC(=O)OC)NC(=O)OC(C)(C)C)C(=O)NS(=O)(=O)C1CC1]
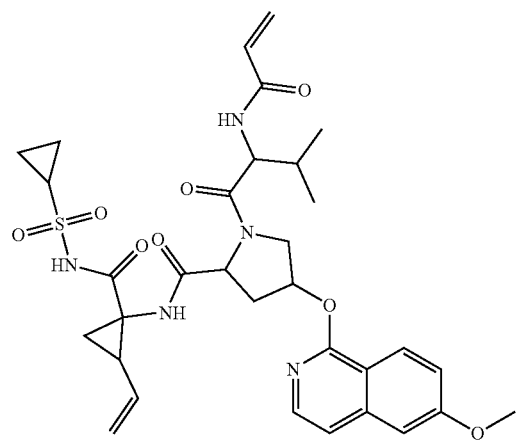 [SMILES: C=CC(=O)NC(C(=O)N1CC(Oc2nccc3cc(OC)ccc23)CC1C(=O)NC1(C(=O)NS(=O)(=O)C2CC2)CC1C=C)C(C)C]
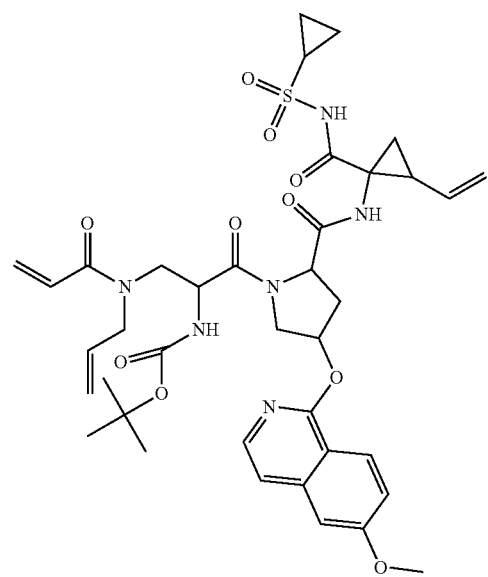 [SMILES: C=CCN(CC(NC(=O)OC(C)(C)C)C(=O)N1CC(Oc2nccc3cc(OC)ccc23)CC1C(=O)NC1(C(=O)NS(=O)(=O)C2CC2)CC1C=C)C(=O)C=C]

TABLE 4-continued
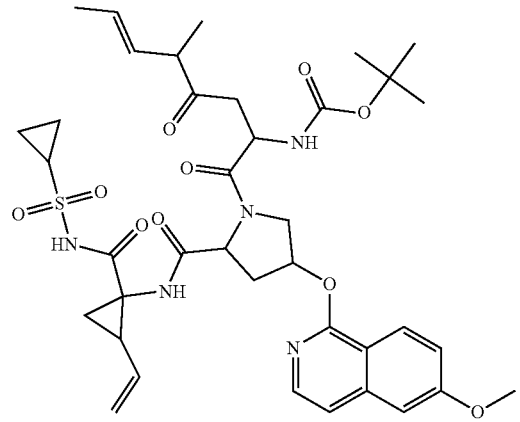 [SMILES: C=CC1CC1(NC(=O)C1CC(Oc2nccc3cc(OC)ccc23)CN1C(=O)C(CC(=O)C(C)/C=C/C)NC(=O)OC(C)(C)C)C(=O)NS(=O)(=O)C1CC1]
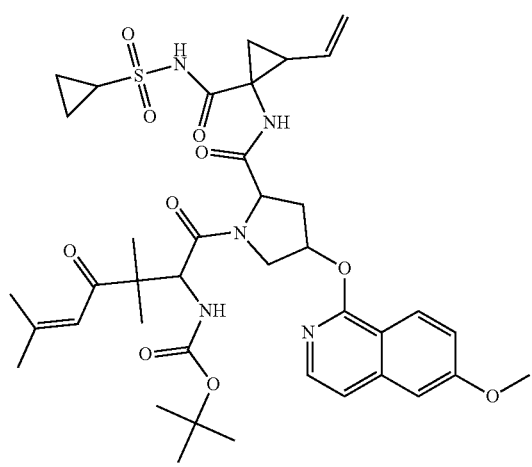 [SMILES: C=CC1CC1(NC(=O)C1CC(Oc2nccc3cc(OC)ccc23)CN1C(=O)C(NC(=O)OC(C)(C)C)C(C)(C)C(=O)C=C(C)C)C(=O)NS(=O)(=O)C1CC1]
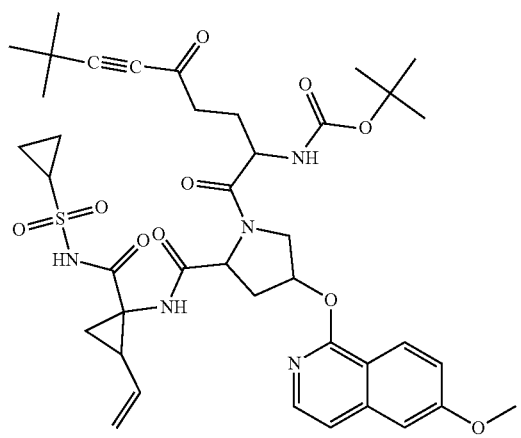 [SMILES: C=CC1CC1(NC(=O)C1CC(Oc2nccc3cc(OC)ccc23)CN1C(=O)C(CCC(=O)C#CC(C)(C)C)NC(=O)OC(C)(C)C)C(=O)NS(=O)(=O)C1CC1]

TABLE 4-continued
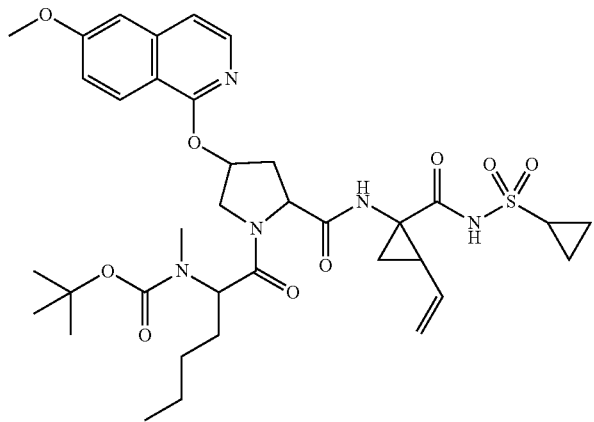 [SMILES: C=CC1CC1(NC(=O)C1CC(Oc2nccc3cc(OC)ccc23)CN1C(=O)C(CCCC)N(C)C(=O)OC(C)(C)C)C(=O)NS(=O)(=O)C1CC1]
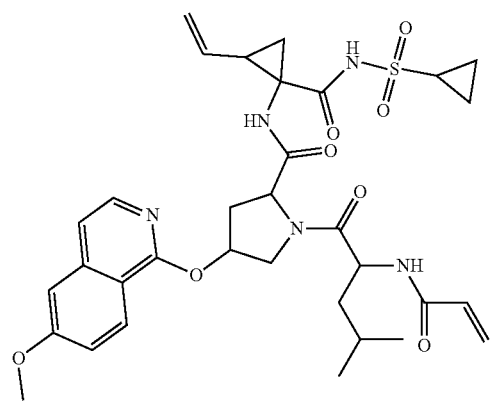 [SMILES: C=CC(=O)NC(CC(C)C)C(=O)N1CC(Oc2nccc3cc(OC)ccc23)CC1C(=O)NC1(C(=O)NS(=O)(=O)C2CC2)CC1C=C]
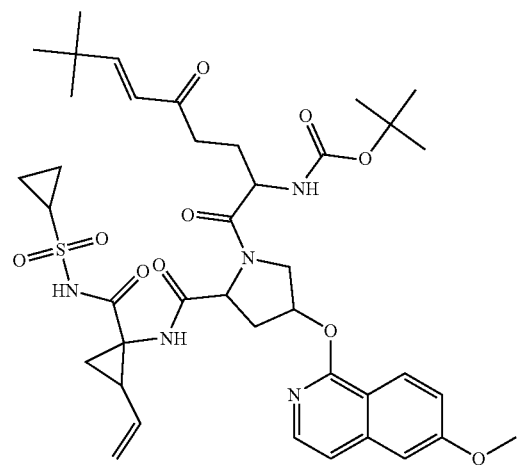 [SMILES: C=CC1CC1(NC(=O)C1CC(Oc2nccc3cc(OC)ccc23)CN1C(=O)C(CCC(=O)/C=C/C(C)(C)C)NC(=O)OC(C)(C)C)C(=O)NS(=O)(=O)C1CC1]

TABLE 4-continued
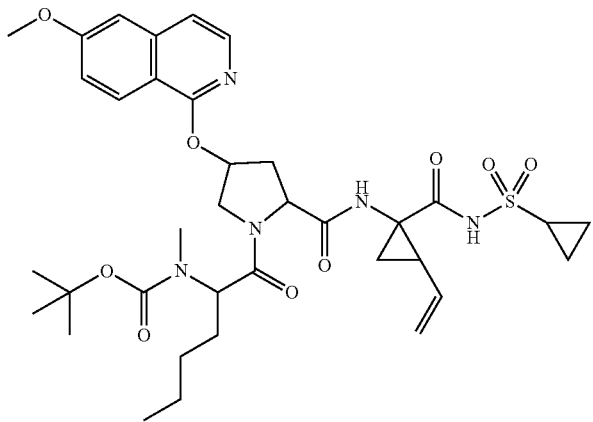 [SMILES: C=CC1CC1(NC(=O)C1CC(Oc2nccc3cc(OC)ccc23)CN1C(=O)C(CCCC)N(C)C(=O)OC(C)(C)C)C(=O)NS(=O)(=O)C1CC1]
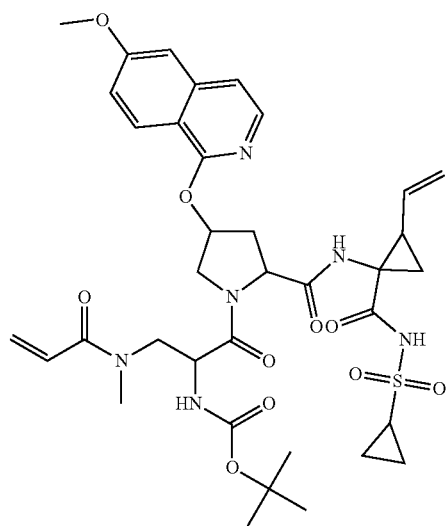 [SMILES: C=CC(=O)N(C)CC(NC(=O)OC(C)(C)C)C(=O)N1CC(Oc2nccc3cc(OC)ccc23)CC1C(=O)NC1(C(=O)NS(=O)(=O)C2CC2)CC1C=C]
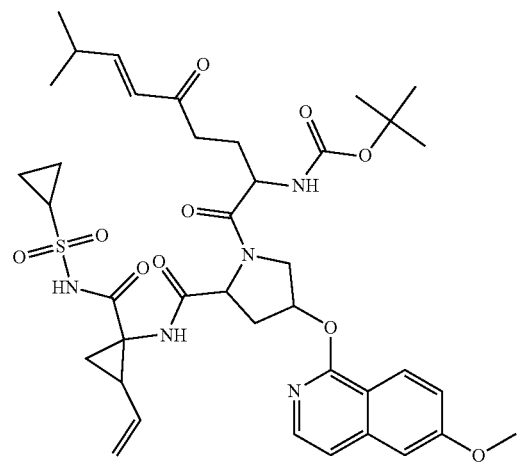 [SMILES: C=CC1CC1(NC(=O)C1CC(Oc2nccc3cc(OC)ccc23)CN1C(=O)C(CCC(=O)/C=C/C(C)C)NC(=O)OC(C)(C)C)C(=O)NS(=O)(=O)C1CC1]

TABLE 4-continued
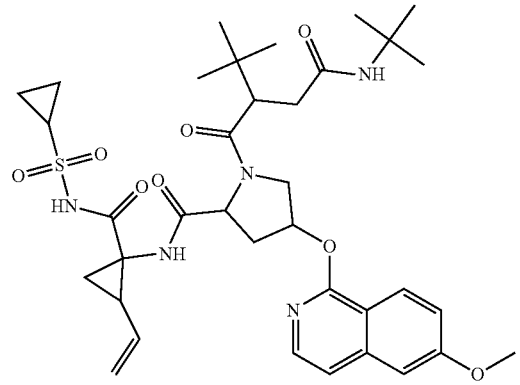 [SMILES: C=CC1CC1(NC(=O)C1CC(Oc2nccc3cc(OC)ccc23)CN1C(=O)C(CC(=O)NC(C)(C)C)C(C)(C)C)C(=O)NS(=O)(=O)C1CC1]
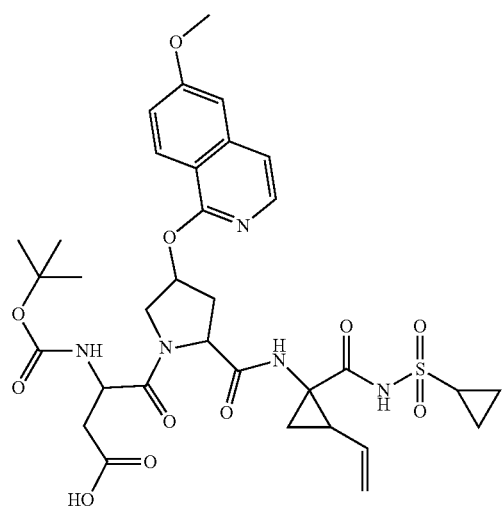 [SMILES: C=CC1CC1(NC(=O)C1CC(Oc2nccc3cc(OC)ccc23)CN1C(=O)C(CC(=O)O)NC(=O)OC(C)(C)C)C(=O)NS(=O)(=O)C1CC1]
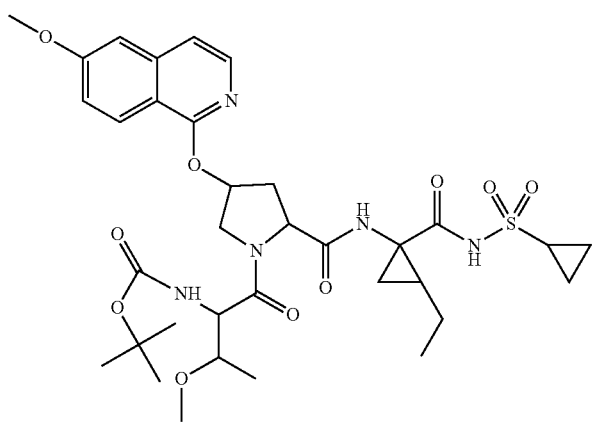 [SMILES: CCC1CC1(NC(=O)C1CC(Oc2nccc3cc(OC)ccc23)CN1C(=O)C(NC(=O)OC(C)(C)C)C(C)OC)C(=O)NS(=O)(=O)C1CC1]

TABLE 4-continued
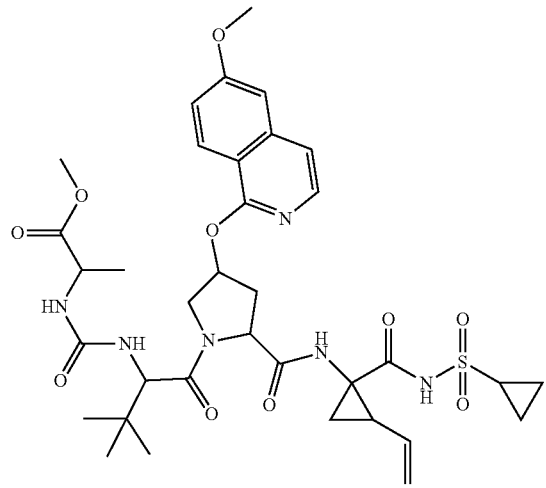 [SMILES: C=CC1CC1(NC(=O)C1CC(Oc2nccc3cc(OC)ccc23)CN1C(=O)C(NC(=O)NC(C)C(=O)OC)C(C)(C)C)C(=O)NS(=O)(=O)C1CC1]
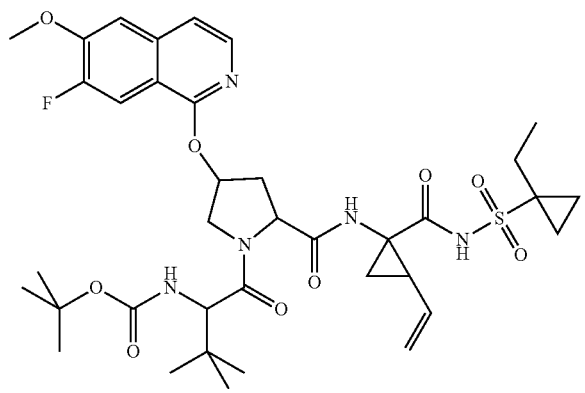 [SMILES: C=CC1CC1(NC(=O)C1CC(Oc2nccc3cc(OC)c(F)cc23)CN1C(=O)C(NC(=O)OC(C)(C)C)C(C)(C)C)C(=O)NS(=O)(=O)C1(CC)CC1]
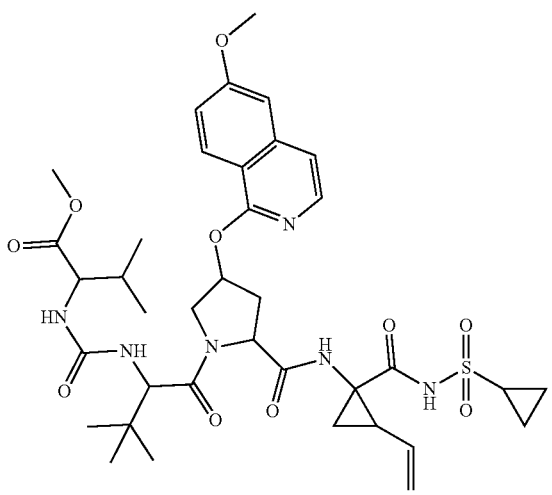 [SMILES: C=CC1CC1(NC(=O)C1CC(Oc2nccc3cc(OC)ccc23)CN1C(=O)C(NC(=O)NC(C(=O)OC)C(C)C)C(C)(C)C)C(=O)NS(=O)(=O)C1CC1]

TABLE 4-continued
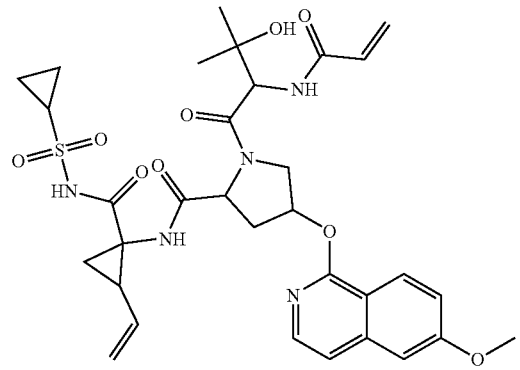 [SMILES: C=CC(=O)NC(C(=O)N1CC(Oc2nccc3cc(OC)ccc23)CC1C(=O)NC1(C(=O)NS(=O)(=O)C2CC2)CC1C=C)C(C)(C)O]
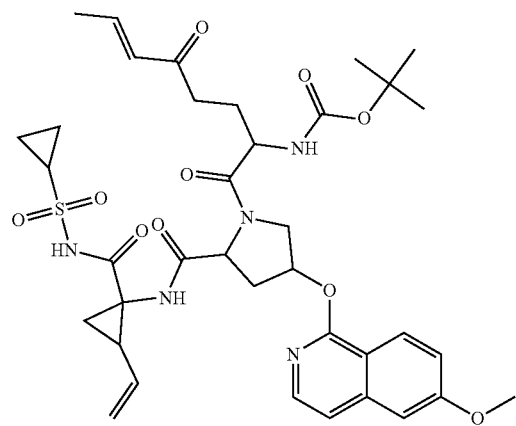 [SMILES: C=CC1CC1(NC(=O)C1CC(Oc2nccc3cc(OC)ccc23)CN1C(=O)C(CCC(=O)/C=C/C)NC(=O)OC(C)(C)C)C(=O)NS(=O)(=O)C1CC1]
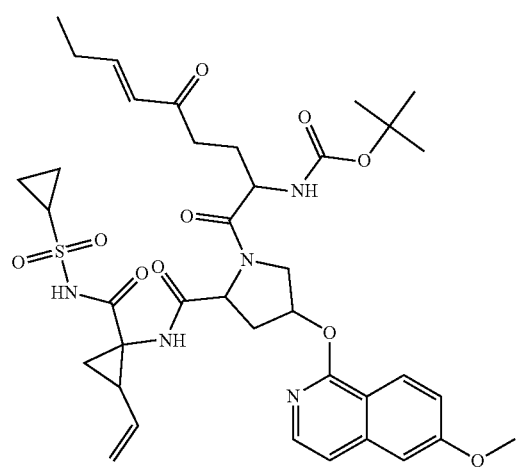 [SMILES: C=CC1CC1(NC(=O)C1CC(Oc2nccc3cc(OC)ccc23)CN1C(=O)C(CCC(=O)/C=C/CC)NC(=O)OC(C)(C)C)C(=O)NS(=O)(=O)C1CC1]

TABLE 4-continued
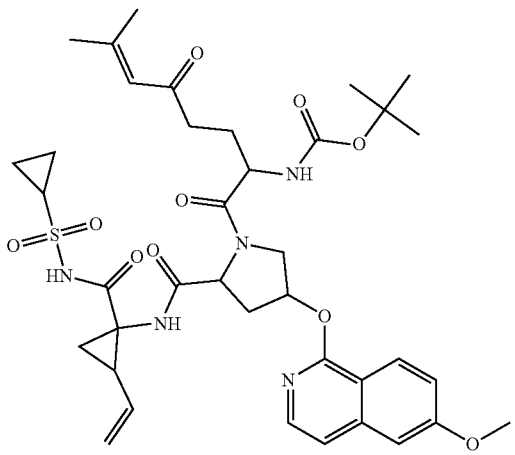 [SMILES: C=CC1CC1(NC(=O)C1CC(Oc2nccc3cc(OC)ccc23)CN1C(=O)C(CCC(=O)C=C(C)C)NC(=O)OC(C)(C)C)C(=O)NS(=O)(=O)C1CC1]
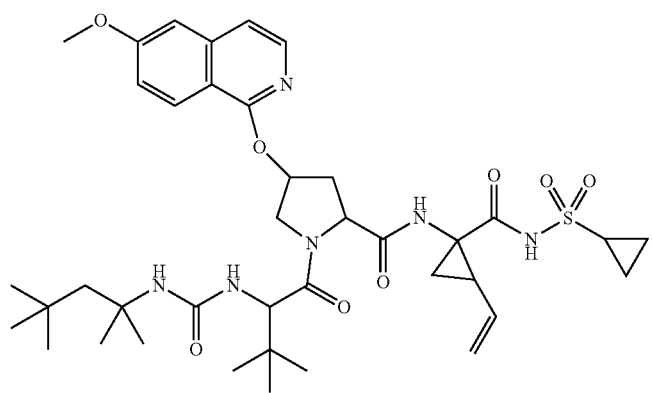 [SMILES: C=CC1CC1(NC(=O)C1CC(Oc2nccc3cc(OC)ccc23)CN1C(=O)C(NC(=O)NC(C)(C)CC(C)(C)C)C(C)(C)C)C(=O)NS(=O)(=O)C1CC1]
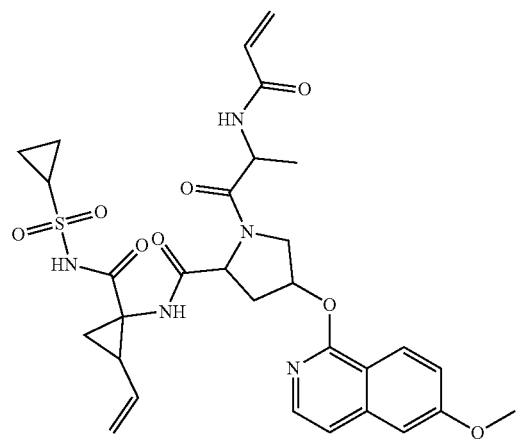 [SMILES: C=CC(=O)NC(C)C(=O)N1CC(Oc2nccc3cc(OC)ccc23)CC1C(=O)NC1(C(=O)NS(=O)(=O)C2CC2)CC1C=C]

TABLE 4-continued
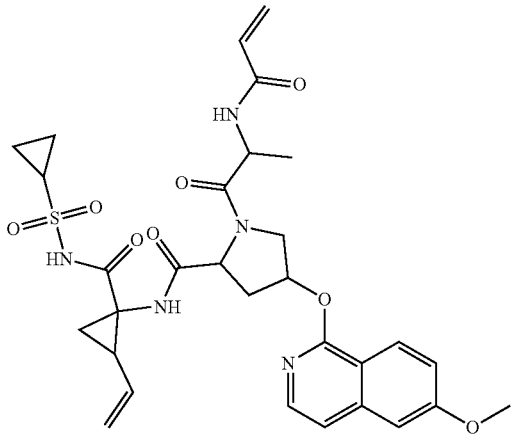 [SMILES: C=CC(=O)NC(C)C(=O)N1CC(Oc2nccc3cc(OC)ccc23)CC1C(=O)NC1(C(=O)NS(=O)(=O)C2CC2)CC1C=C]
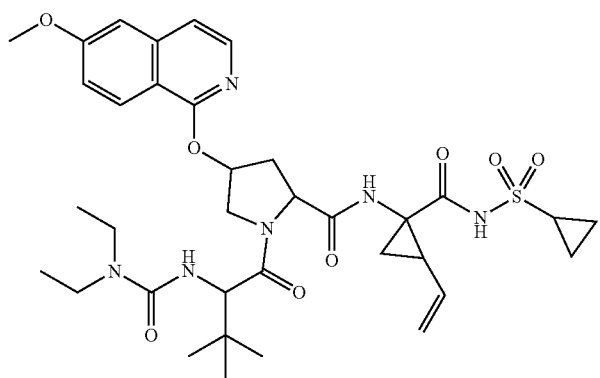 [SMILES: C=CC1CC1(NC(=O)C1CC(Oc2nccc3cc(OC)ccc23)CN1C(=O)C(NC(=O)N(CC)CC)C(C)(C)C)C(=O)NS(=O)(=O)C1CC1]
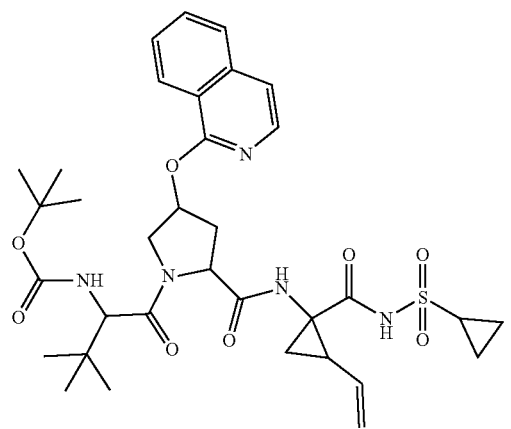 [SMILES: C=CC1CC1(NC(=O)C1CC(Oc2nccc3ccccc23)CN1C(=O)C(NC(=O)OC(C)(C)C)C(C)(C)C)C(=O)NS(=O)(=O)C1CC1]

TABLE 4-continued
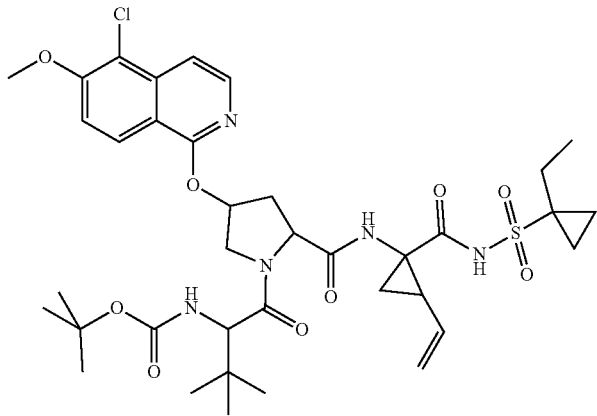 [SMILES: C=CC1CC1(NC(=O)C1CC(Oc2nccc3c(Cl)c(OC)ccc23)CN1C(=O)C(NC(=O)OC(C)(C)C)C(C)(C)C)C(=O)NS(=O)(=O)C1(CC)CC1]
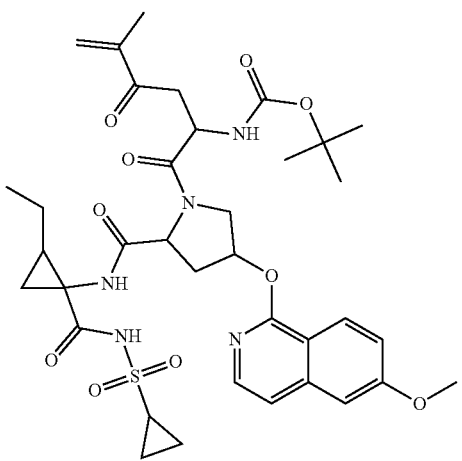 [SMILES: C=C(C)C(=O)CC(NC(=O)OC(C)(C)C)C(=O)N1CC(Oc2nccc3cc(OC)ccc23)CC1C(=O)NC1(C(=O)NS(=O)(=O)C2CC2)CC1CC]
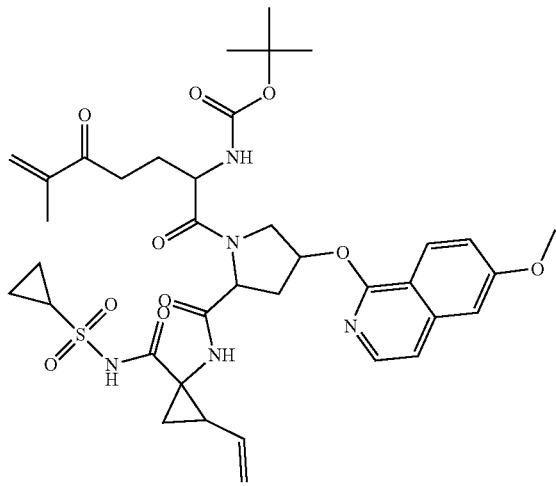 [SMILES: C=CC1CC1(NC(=O)C1CC(Oc2nccc3cc(OC)ccc23)CN1C(=O)C(CCC(=O)C(=C)C)NC(=O)OC(C)(C)C)C(=O)NS(=O)(=O)C1CC1]

TABLE 4-continued
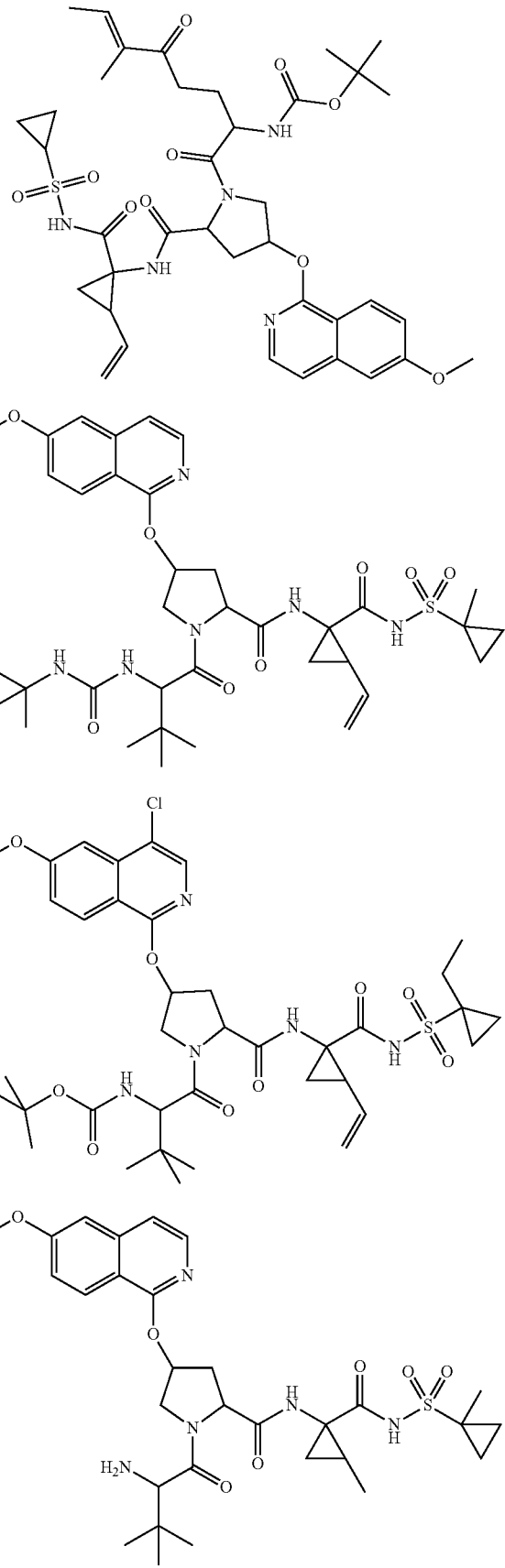

TABLE 4-continued
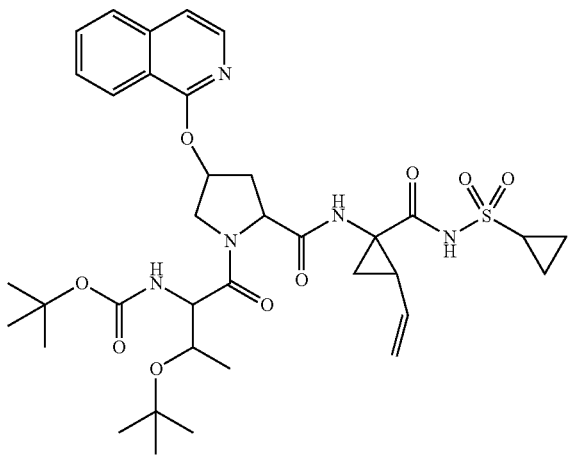 [SMILES: C=CC1CC1(NC(=O)C1CC(Oc2nccc3ccccc23)CN1C(=O)C(NC(=O)OC(C)(C)C)C(C)OC(C)(C)C)C(=O)NS(=O)(=O)C1CC1]
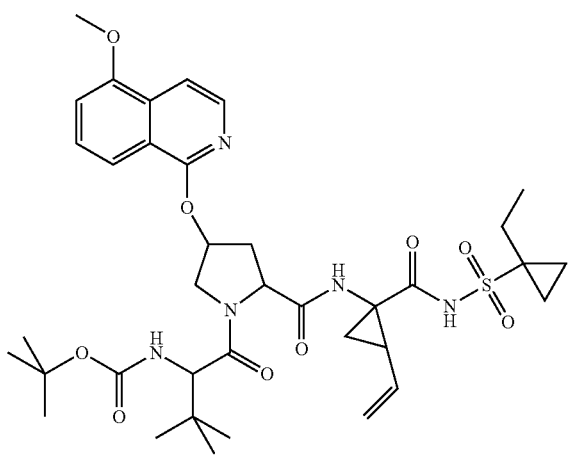 [SMILES: C=CC1CC1(NC(=O)C1CC(Oc2nccc3c(OC)cccc23)CN1C(=O)C(NC(=O)OC(C)(C)C)C(C)(C)C)C(=O)NS(=O)(=O)C1(CC)CC1]
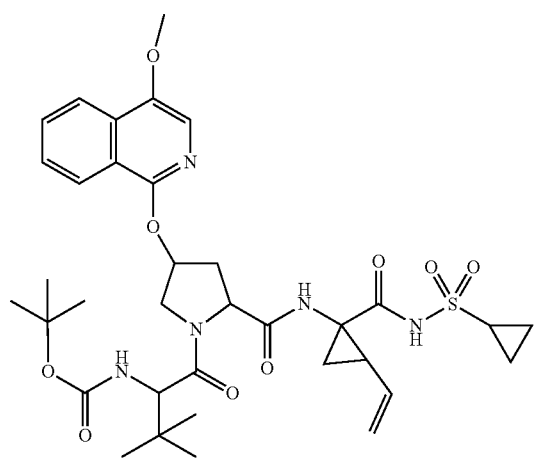

TABLE 4-continued
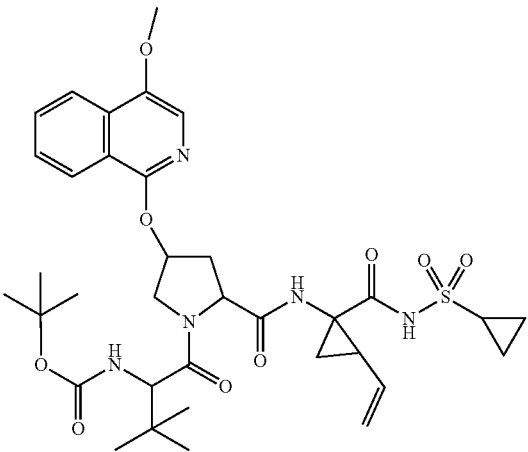
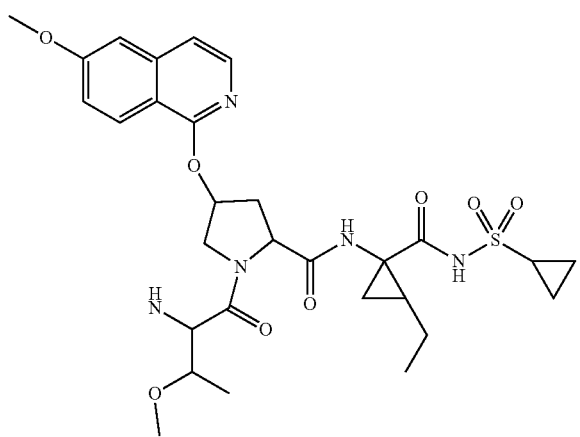
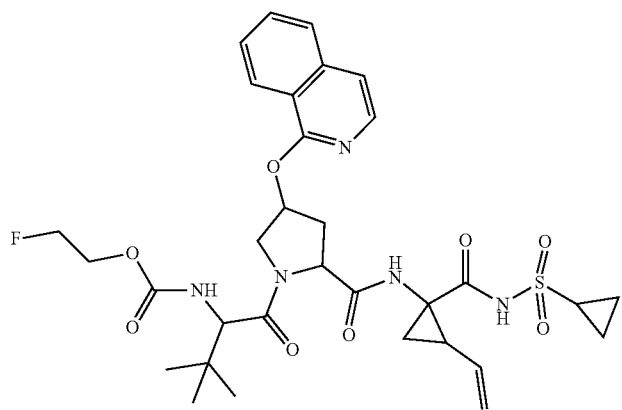 [SMILES: C=CC1CC1(NC(=O)C1CC(Oc2nccc3ccccc23)CN1C(=O)C(NC(=O)OCCF)C(C)(C)C)C(=O)NS(=O)(=O)C1CC1]

TABLE 4-continued
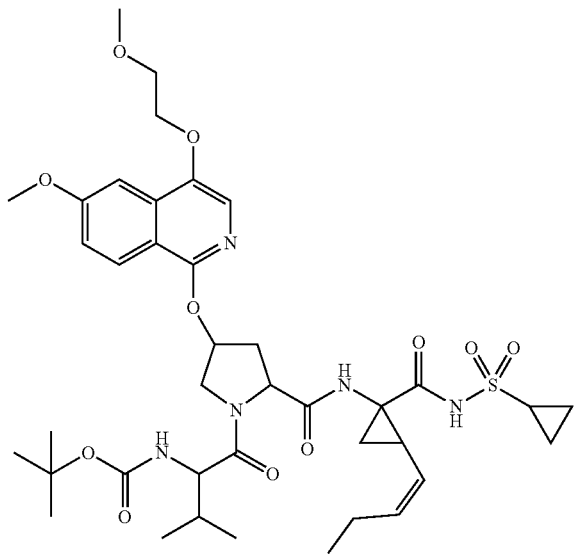 [SMILES: CC/C=C\C1CC1(NC(=O)C1CC(Oc2ncc(OCCOC)c3cc(OC)ccc23)CN1C(=O)C(NC(=O)OC(C)(C)C)C(C)C)C(=O)NS(=O)(=O)C1CC1]
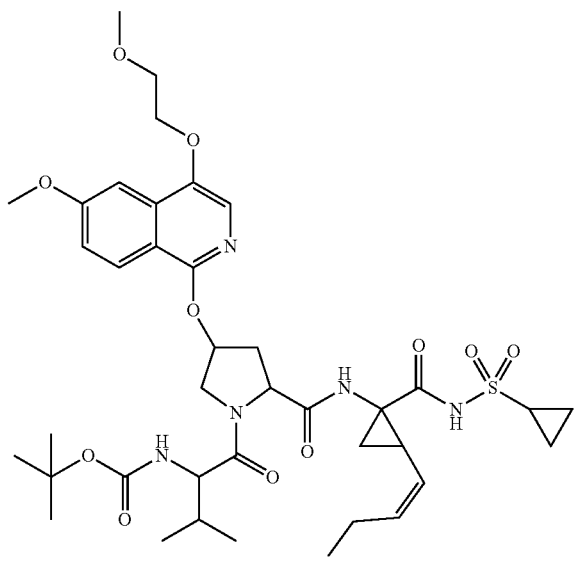 [SMILES: CC/C=C\C1CC1(NC(=O)C1CC(Oc2ncc(OCCOC)c3cc(OC)ccc23)CN1C(=O)C(NC(=O)OC(C)(C)C)C(C)C)C(=O)NS(=O)(=O)C1CC1]
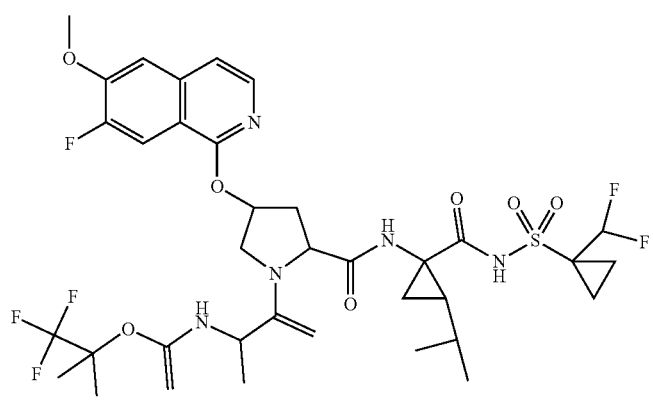 [SMILES: C=C(NC(C)C(=C)N1CC(Oc2nccc3cc(OC)c(F)cc23)CC1C(=O)NC1(C(=O)NS(=O)(=O)C2(C(F)F)CC2)CC1C(C)C)OC(C)(C)C(F)(F)F]

TABLE 4-continued
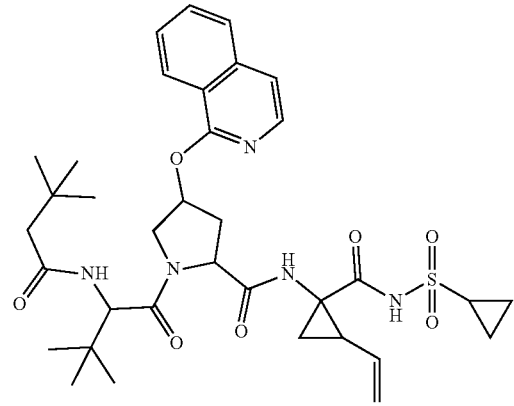 [SMILES: C=CC1CC1(NC(=O)C1CC(Oc2nccc3ccccc23)CN1C(=O)C(NC(=O)CC(C)(C)C)C(C)(C)C)C(=O)NS(=O)(=O)C1CC1]
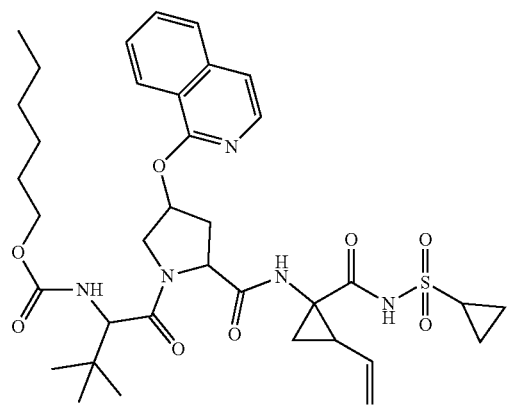 [SMILES: C=CC1CC1(NC(=O)C1CC(Oc2nccc3ccccc23)CN1C(=O)C(NC(=O)OCCCCCC)C(C)(C)C)C(=O)NS(=O)(=O)C1CC1]
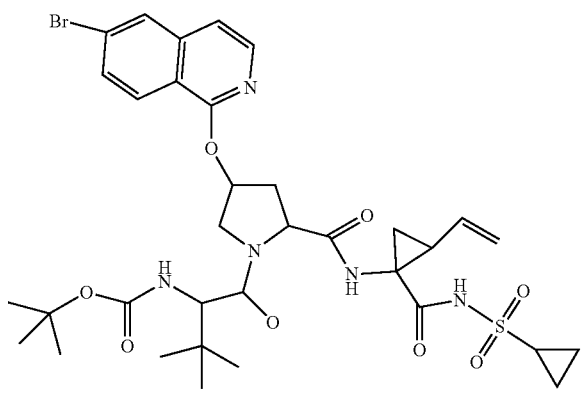 [SMILES: C=CC1CC1(NC(=O)C1CC(Oc2nccc3cc(Br)ccc23)CN1C(O)C(NC(=O)OC(C)(C)C)C(C)(C)C)C(=O)NS(=O)(=O)C1CC1]

TABLE 4-continued
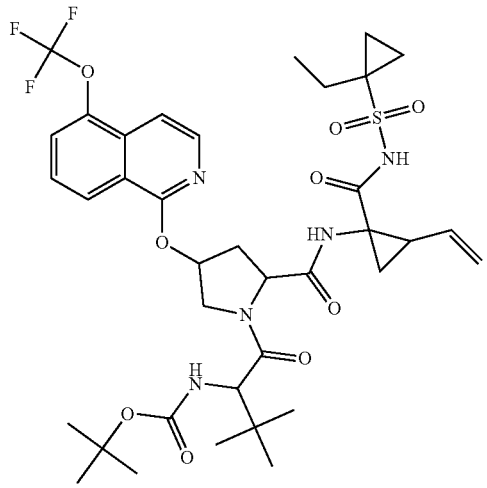 [SMILES: C=CC1CC1(NC(=O)C1CC(Oc2nccc3c(OC(F)(F)F)cccc23)CN1C(=O)C(NC(=O)OC(C)(C)C)C(C)(C)C)C(=O)NS(=O)(=O)C1(CC)CC1]
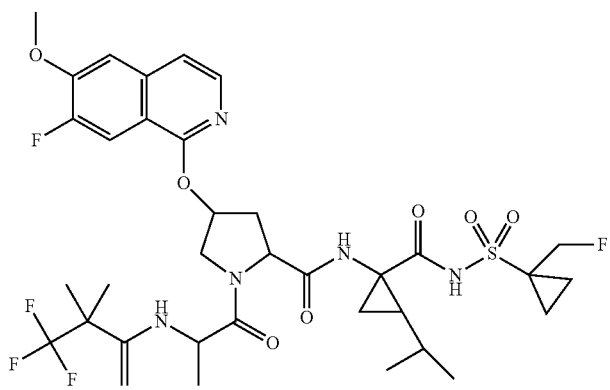 [SMILES: C=C(NC(C)C(=O)N1CC(Oc2nccc3cc(OC)c(F)cc23)CC1C(=O)NC1(C(=O)NS(=O)(=O)C2(CF)CC2)CC1C(C)C)C(C)(C)C(F)(F)F]
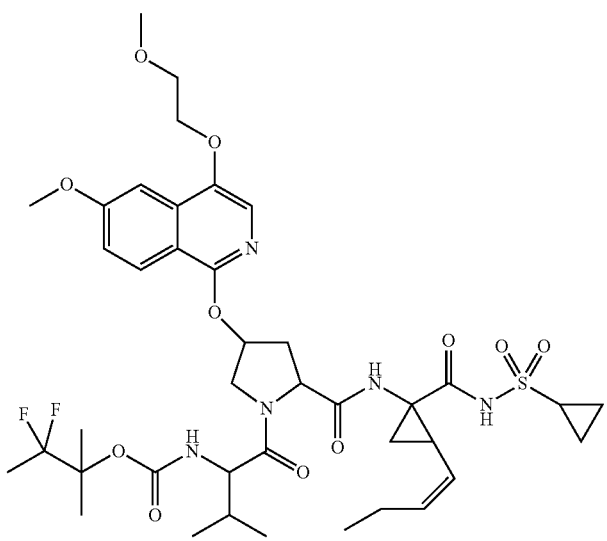 [SMILES: CC/C=C\C1CC1(NC(=O)C1CC(Oc2ncc(OCCOC)c3cc(OC)ccc23)CN1C(=O)C(NC(=O)OC(C)(C)C(C)(F)F)C(C)C)C(=O)NS(=O)(=O)C1CC1]

TABLE 4-continued
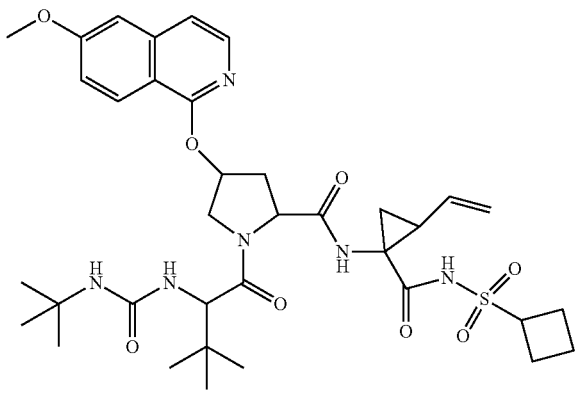 [SMILES: C=CC1CC1(NC(=O)C1CC(Oc2nccc3cc(OC)ccc23)CN1C(=O)C(NC(=O)NC(C)(C)C)C(C)(C)C)C(=O)NS(=O)(=O)C1CCC1]
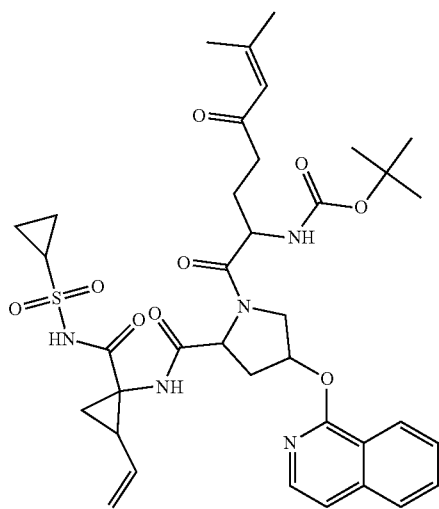 [SMILES: C=CC1CC1(NC(=O)C1CC(Oc2nccc3ccccc23)CN1C(=O)C(CCC(=O)C=C(C)C)NC(=O)OC(C)(C)C)C(=O)NS(=O)(=O)C1CC1]
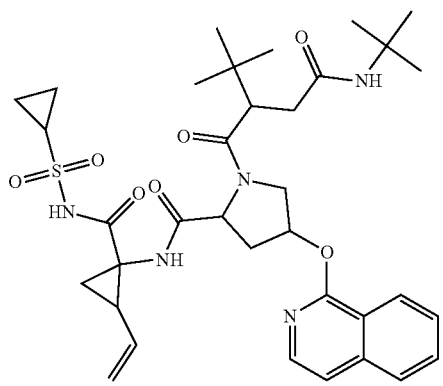 [SMILES: C=CC1CC1(NC(=O)C1CC(Oc2nccc3ccccc23)CN1C(=O)C(CC(=O)NC(C)(C)C)C(C)(C)C)C(=O)NS(=O)(=O)C1CC1]

TABLE 4-continued
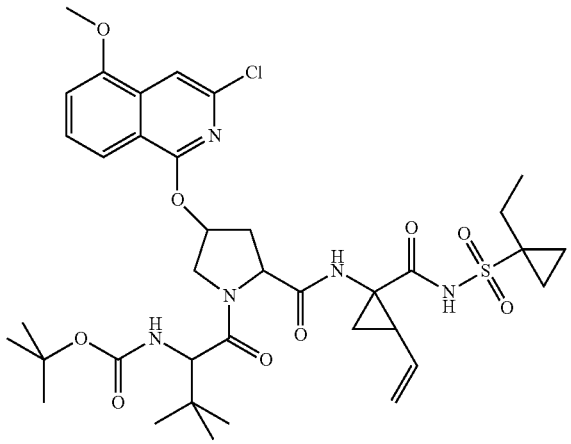 [SMILES: C=CC1CC1(NC(=O)C1CC(Oc2nc(Cl)cc3c(OC)cccc23)CN1C(=O)C(NC(=O)OC(C)(C)C)C(C)(C)C)C(=O)NS(=O)(=O)C1(CC)CC1]
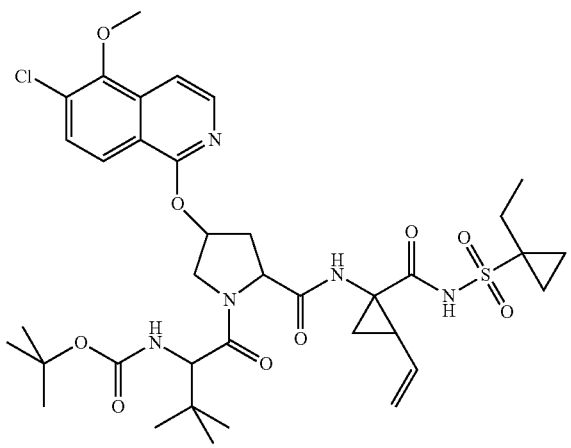 [SMILES: C=CC1CC1(NC(=O)C1CC(Oc2nccc3c(OC)c(Cl)ccc23)CN1C(=O)C(NC(=O)OC(C)(C)C)C(C)(C)C)C(=O)NS(=O)(=O)C1(CC)CC1]
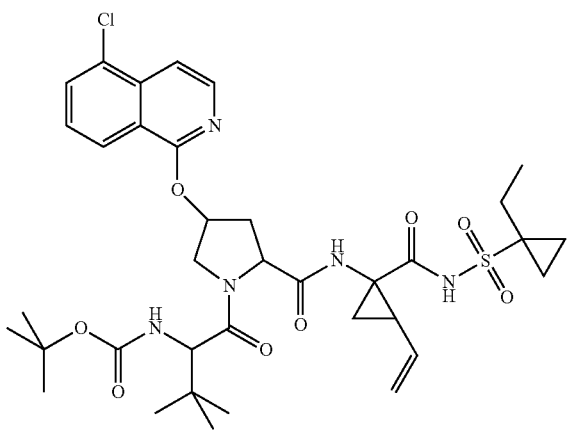 [SMILES: C=CC1CC1(NC(=O)C1CC(Oc2nccc3c(Cl)cccc23)CN1C(=O)C(NC(=O)OC(C)(C)C)C(C)(C)C)C(=O)NS(=O)(=O)C1(CC)CC1]

TABLE 4-continued
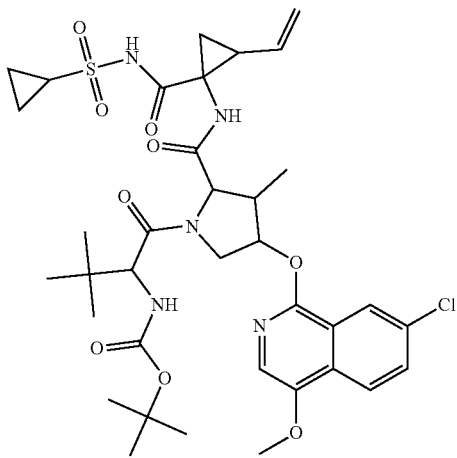 [SMILES: C=CC1CC1(NC(=O)C1C(C)C(Oc2ncc(OC)c3ccc(Cl)cc23)CN1C(=O)C(NC(=O)OC(C)(C)C)C(C)(C)C)C(=O)NS(=O)(=O)C1CC1]
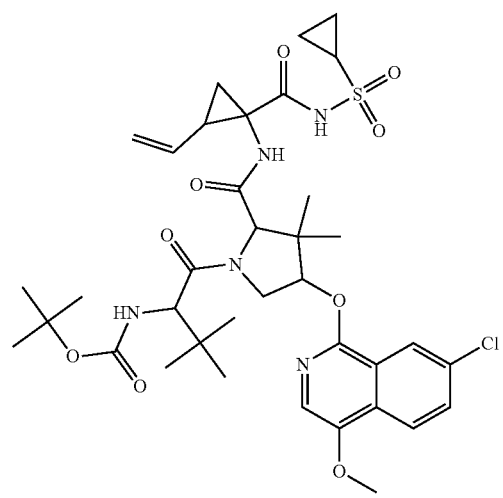 [SMILES: C=CC1CC1(NC(=O)C1N(C(=O)C(NC(=O)OC(C)(C)C)C(C)(C)C)CC(Oc2ncc(OC)c3ccc(Cl)cc23)C1(C)C)C(=O)NS(=O)(=O)C1CC1]
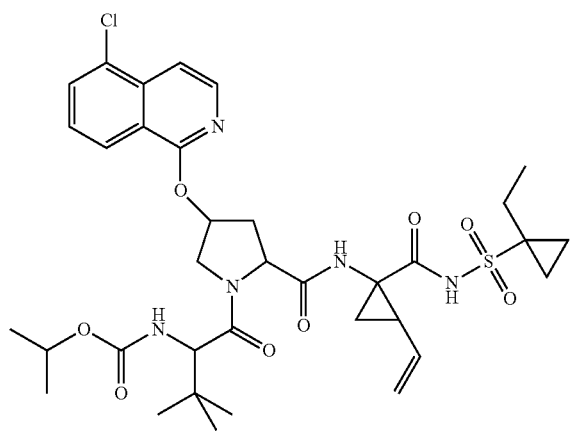 [SMILES: C=CC1CC1(NC(=O)C1CC(Oc2nccc3c(Cl)cccc23)CN1C(=O)C(NC(=O)OC(C)C)C(C)(C)C)C(=O)NS(=O)(=O)C1(CC)CC1]

TABLE 4-continued
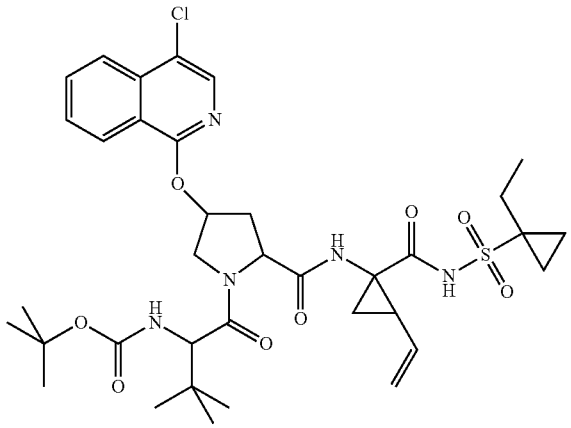 [SMILES: C=CC1CC1(NC(=O)C1CC(Oc2ncc(Cl)c3ccccc23)CN1C(=O)C(NC(=O)OC(C)(C)C)C(C)(C)C)C(=O)NS(=O)(=O)C1(CC)CC1]
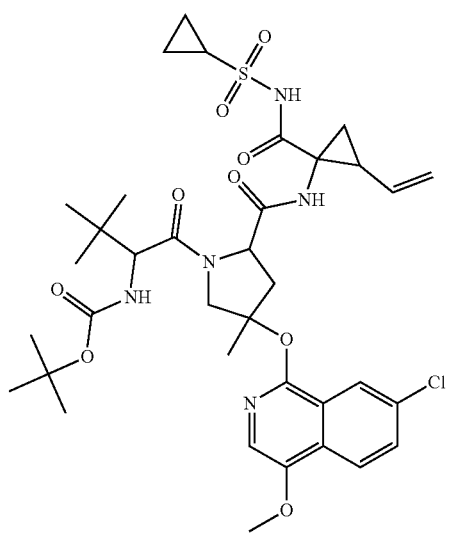 [SMILES: C=CC1CC1(NC(=O)C1CC(C)(Oc2ncc(OC)c3ccc(Cl)cc23)CN1C(=O)C(NC(=O)OC(C)(C)C)C(C)(C)C)C(=O)NS(=O)(=O)C1CC1]
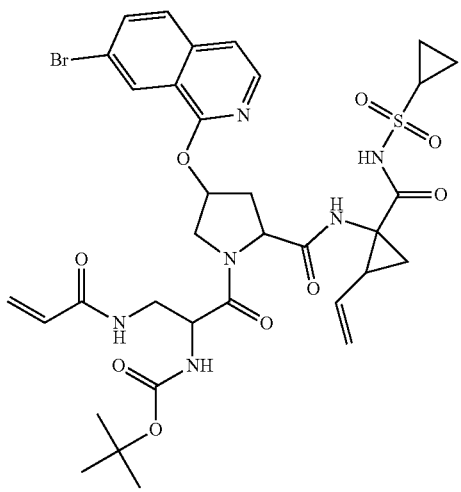 [SMILES: C=CC(=O)NCC(NC(=O)OC(C)(C)C)C(=O)N1CC(Oc2nccc3ccc(Br)cc23)CC1C(=O)NC1(C(=O)NS(=O)(=O)C2CC2)CC1C=C]

TABLE 4-continued
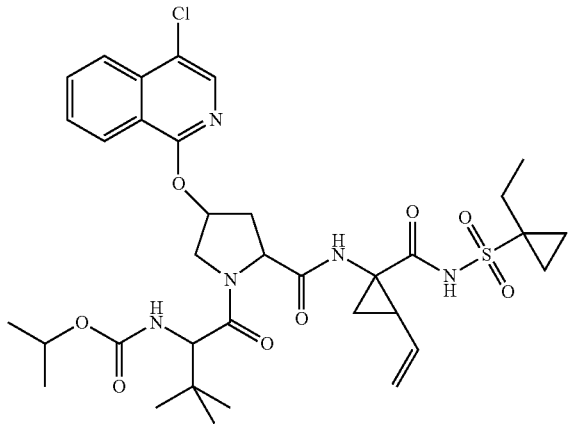
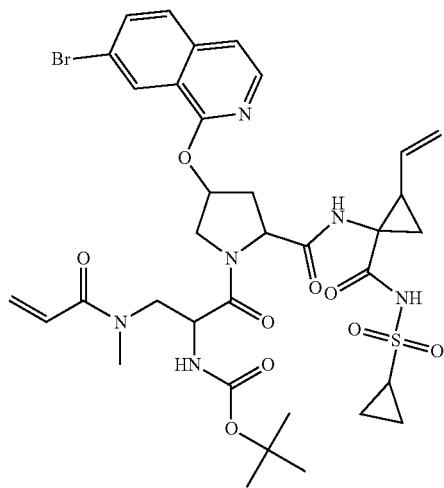 [SMILES: C=CC(=O)N(C)CC(NC(=O)OC(C)(C)C)C(=O)N1CC(Oc2nccc3ccc(Br)cc23)CC1C(=O)NC1(C(=O)NS(=O)(=O)C2CC2)CC1C=C]
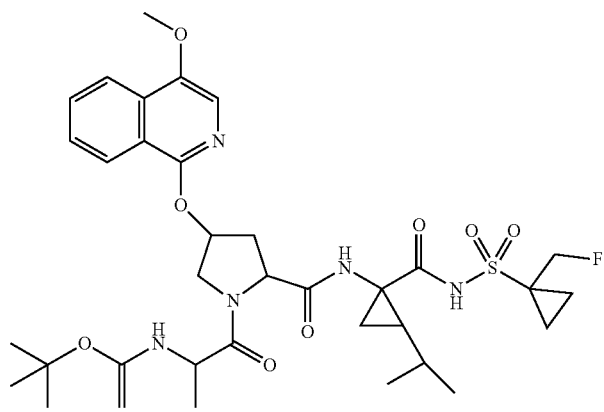 [SMILES: C=C(NC(C)C(=O)N1CC(Oc2ncc(OC)c3ccccc23)CC1C(=O)NC1(C(=O)NS(=O)(=O)C2(CF)CC2)CC1C(C)C)OC(C)(C)C]

TABLE 4-continued
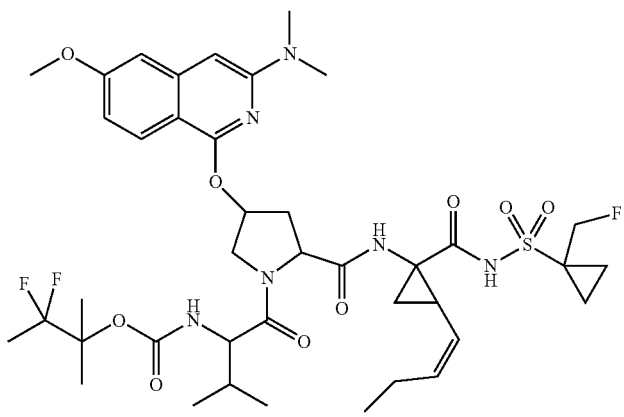 [SMILES: CC/C=C\C1CC1(NC(=O)C1CC(Oc2nc(N(C)C)cc3cc(OC)ccc23)CN1C(=O)C(NC(=O)OC(C)(C)C(C)(F)F)C(C)C)C(=O)NS(=O)(=O)C1(CF)CC1]
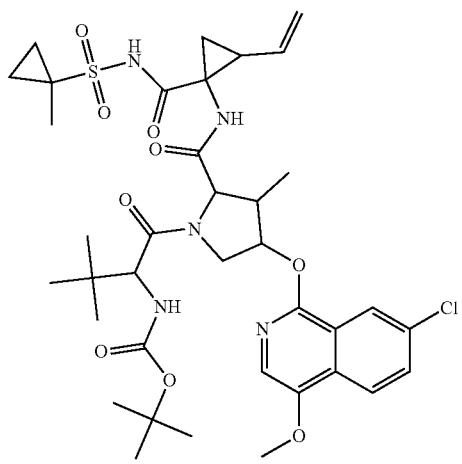 [SMILES: C=CC1CC1(NC(=O)C1C(C)C(Oc2ncc(OC)c3ccc(Cl)cc23)CN1C(=O)C(NC(=O)OC(C)(C)C)C(C)(C)C)C(=O)NS(=O)(=O)C1(C)CC1]
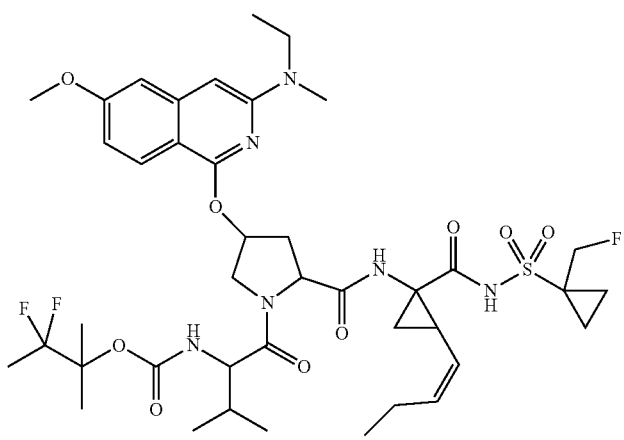 [SMILES: CC/C=C\C1CC1(NC(=O)C1CC(Oc2nc(N(C)CC)cc3cc(OC)ccc23)CN1C(=O)C(NC(=O)OC(C)(C)C(C)(F)F)C(C)C)C(=O)NS(=O)(=O)C1(CF)CC1]

TABLE 4-continued
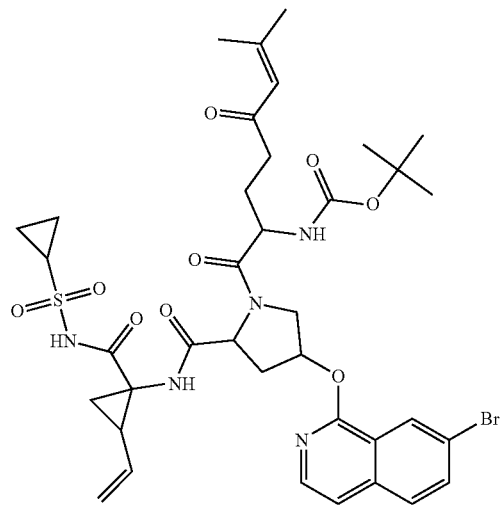 [SMILES: C=CC1CC1(NC(=O)C1CC(Oc2nccc3ccc(Br)cc23)CN1C(=O)C(CCC(=O)C=C(C)C)NC(=O)OC(C)(C)C)C(=O)NS(=O)(=O)C1CC1]
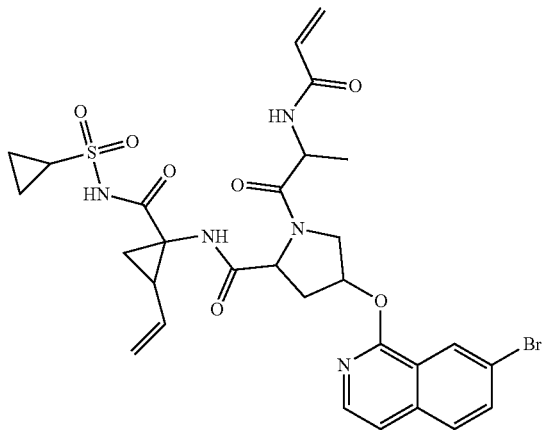 [SMILES: C=CC(=O)NC(C)C(=O)N1CC(Oc2nccc3ccc(Br)cc23)CC1C(=O)NC1(C(=O)NS(=O)(=O)C2CC2)CC1C=C]
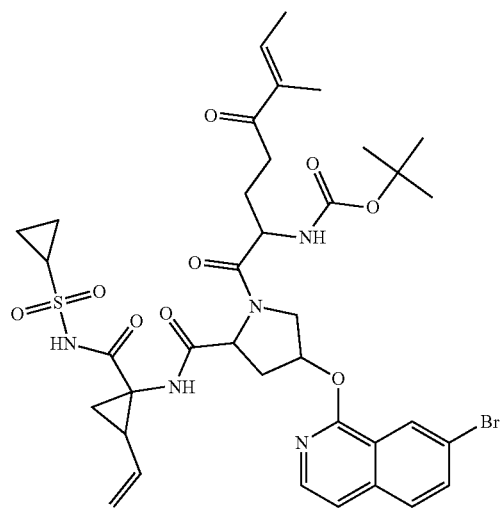 [SMILES: C=CC1CC1(NC(=O)C1CC(Oc2nccc3ccc(Br)cc23)CN1C(=O)C(CCC(=O)/C(C)=C/C)NC(=O)OC(C)(C)C)C(=O)NS(=O)(=O)C1CC1]

TABLE 4-continued

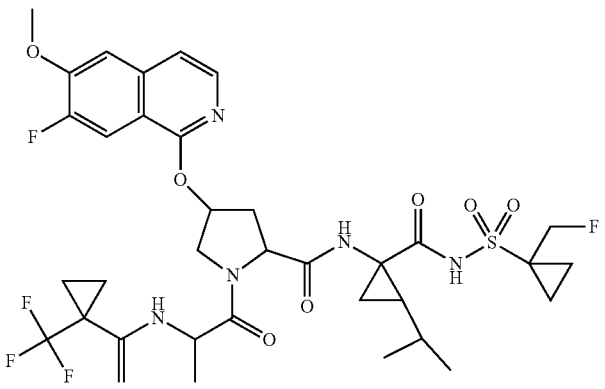 [SMILES: C=C(NC(C)C(=O)N1CC(Oc2nccc3cc(OC)c(F)cc23)CC1C(=O)NC1(C(=O)NS(=O)(=O)C2(CF)CC2)CC1C(C)C)C1(C(F)(F)F)CC1]

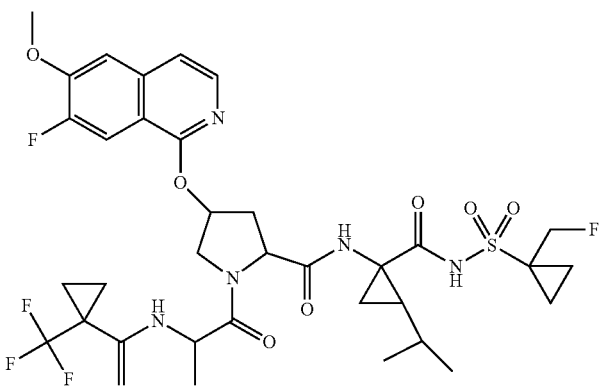 [SMILES: C=C(NC(C)C(=O)N1CC(Oc2nccc3cc(OC)c(F)cc23)CC1C(=O)NC1(C(=O)NS(=O)(=O)C2(CF)CC2)CC1C(C)C)C1(C(F)(F)F)CC1]

In one implementation, the compound is BZF (1-benzofuran)-961 having the formula:

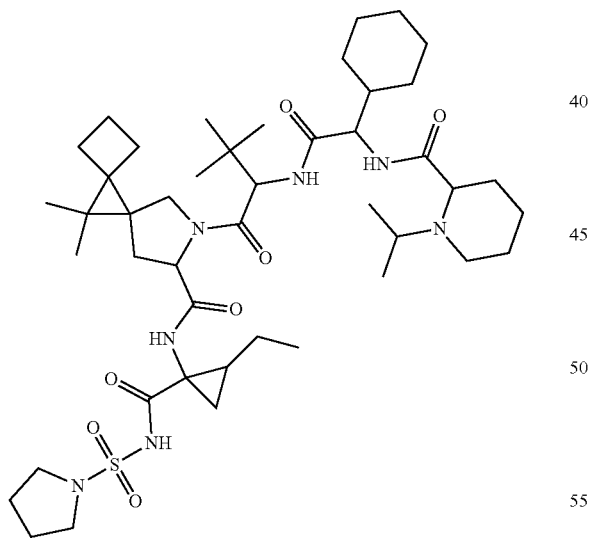

and understood as a compound clinically investigated as a NS3 protease inhibitor. In one particular implementation, the compound, or variations and permutations thereof, is described in WO2010116248 the contents of which are hereby incorporated by reference for all purposes and the specific purposes identified herein. In some embodiments, such compounds are represented by any one or more of the structures shown in Table 7. Any one of the compounds depicted in Table 7 is suitable for use in the methods of the present disclosure.

TABLE 5
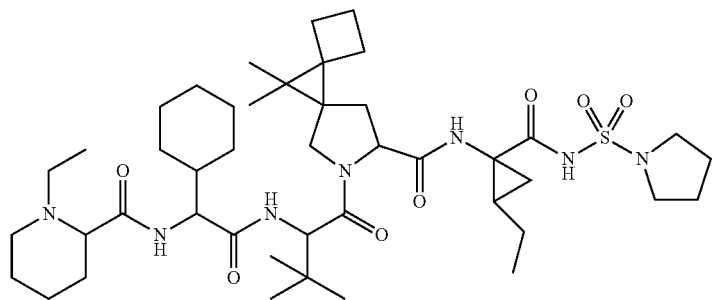 [SMILES: CCC1CC1(NC(=O)C1CC2(CN1C(=O)C(NC(=O)C(NC(=O)C1CCCCN1CC)C1CCCCC1)C(C)(C)C)C(C)(C)C21CCC1)C(=O)NS(=O)(=O)N1CCCC1]
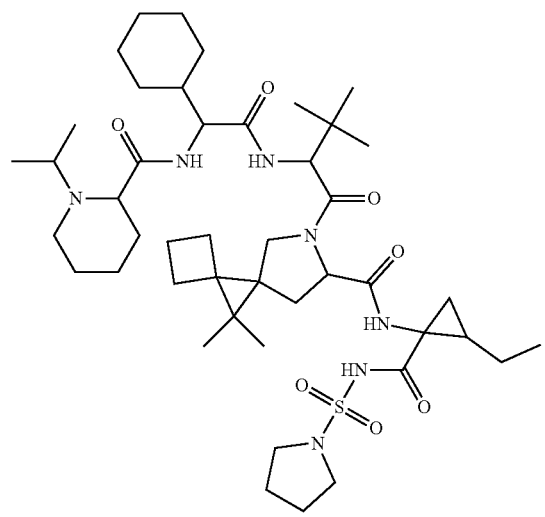 [SMILES: CCC1CC1(NC(=O)C1CC2(CN1C(=O)C(NC(=O)C(NC(=O)C1CCCCN1C(C)C)C1CCCCC1)C(C)(C)C)C(C)(C)C21CCC1)C(=O)NS(=O)(=O)N1CCCC1]
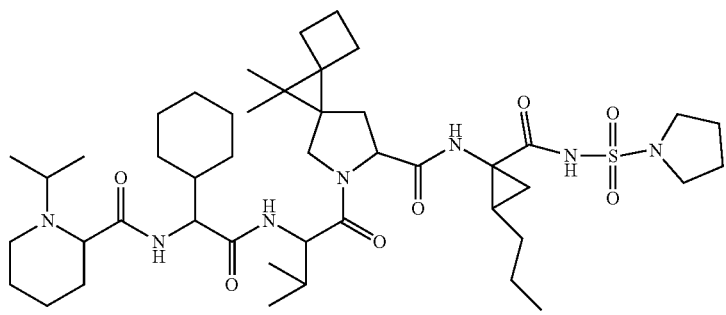 [SMILES: CCCC1CC1(NC(=O)C1CC2(CN1C(=O)C(NC(=O)C(NC(=O)C1CCCCN1C(C)C)C1CCCCC1)C(C)C)C(C)(C)C21CCC1)C(=O)NS(=O)(=O)N1CCCC1]
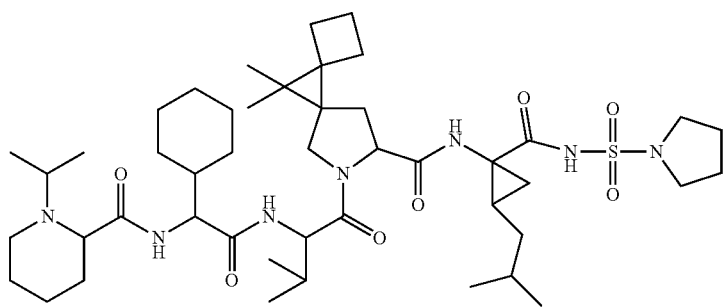 [SMILES: CC(C)CC1CC1(NC(=O)C1CC2(CN1C(=O)C(NC(=O)C(NC(=O)C1CCCCN1C(C)C)C1CCCCC1)C(C)C)C(C)(C)C21CCC1)C(=O)NS(=O)(=O)N1CCCC1]

TABLE 5-continued
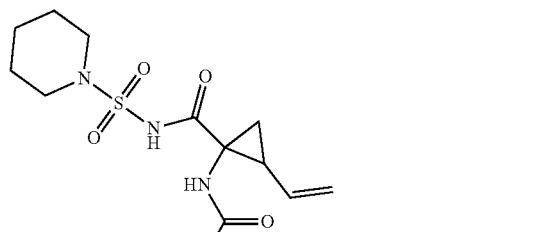
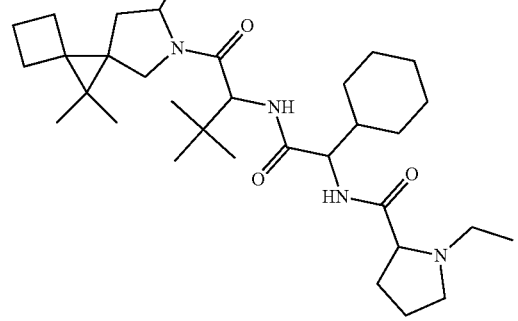
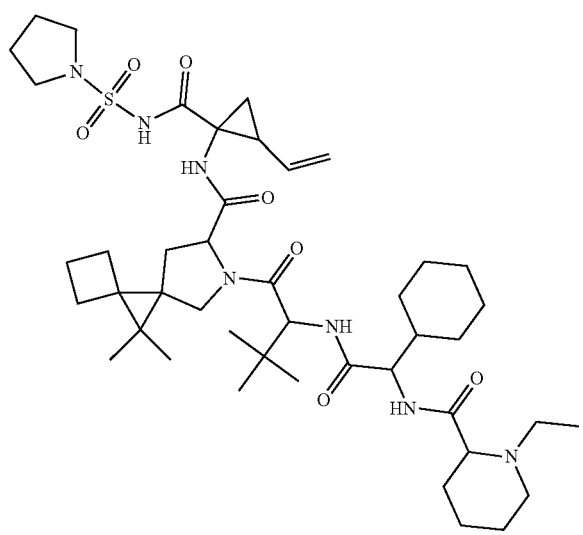 [SMILES: C=CC1CC1(NC(=O)C1CC2(CN1C(=O)C(NC(=O)C(NC(=O)C1CCCCN1CC)C1CCCCC1)C(C)(C)C)C(C)(C)C21CCC1)C(=O)NS(=O)(=O)N1CCCC1]
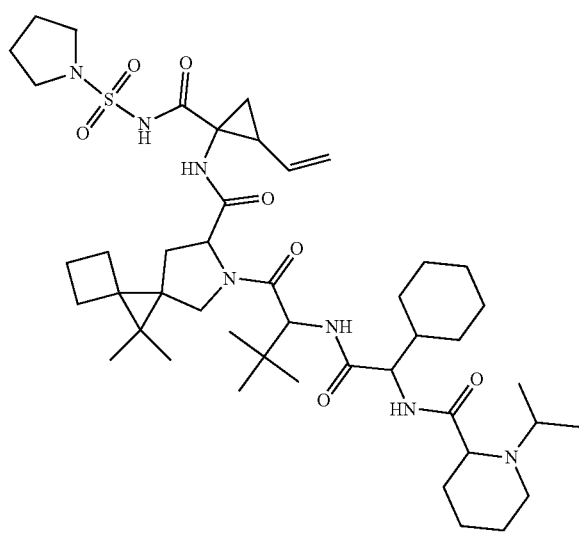 [SMILES: C=CC1CC1(NC(=O)C1CC2(CN1C(=O)C(NC(=O)C(NC(=O)C1CCCCN1C(C)C)C1CCCCC1)C(C)(C)C)C(C)(C)C21CCC1)C(=O)NS(=O)(=O)N1CCCC1]

TABLE 5-continued
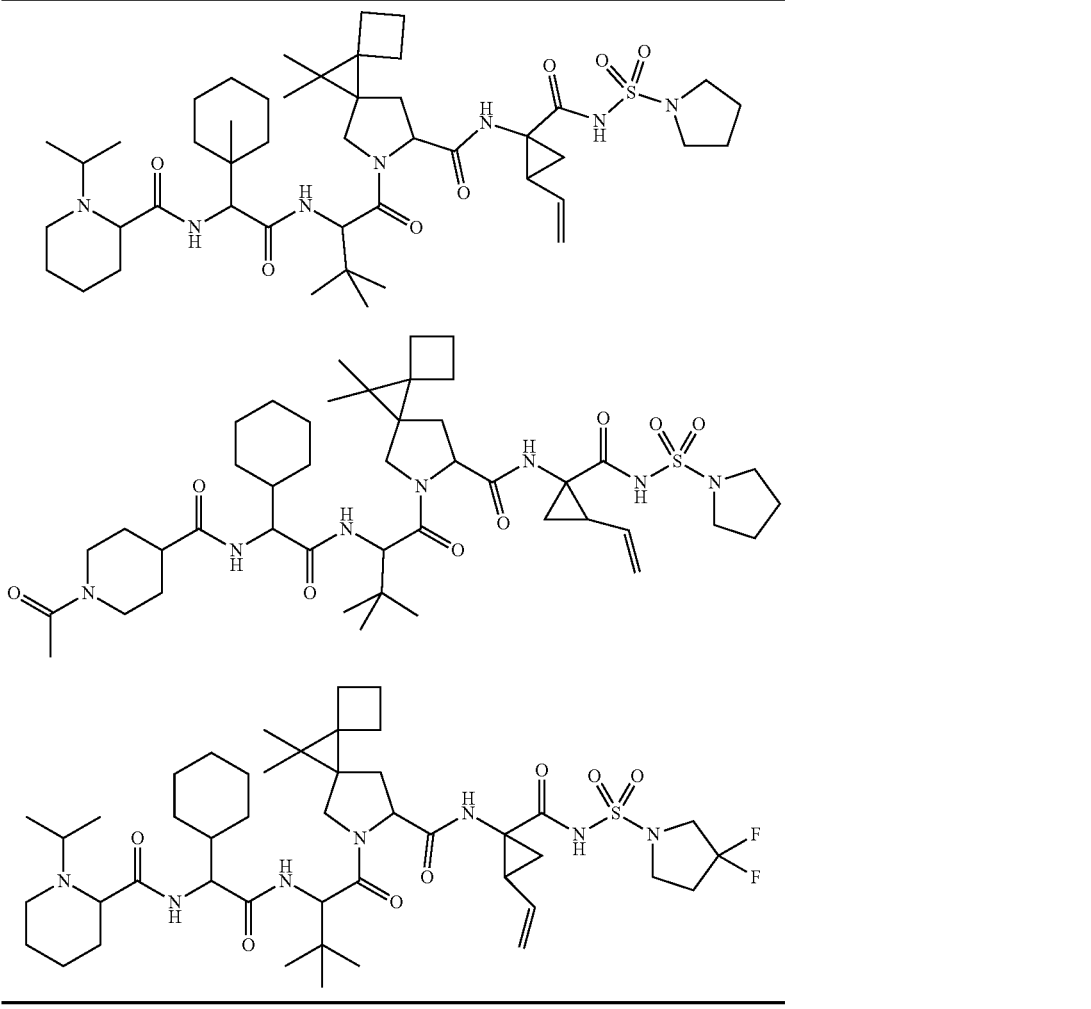
In one implementation, the compound is a CCR1 antagonists or chemokine having the formula:
In a particular arrangement the compound is
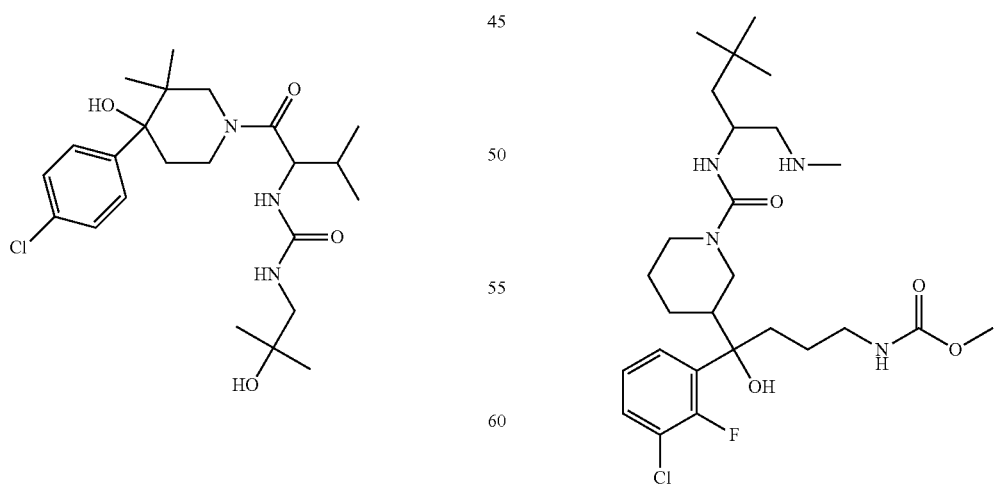
as further described in WO2007070201 the contents of which are hereby incorporated by reference for all purposes and the specific purposes identified herein.

In one arrangement, the compound is the drug Almirall, a cyclooxygenase 2 inhibitor having the formula:

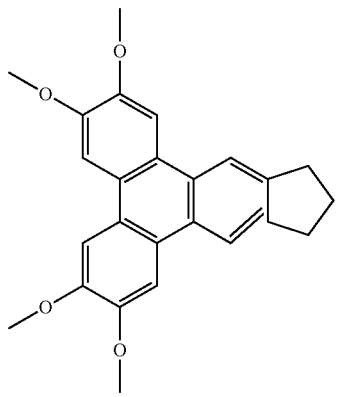 [SMILES: C=Cc1c(C=C2CCCC2)c2cc(OC)c(OC)cc2c2cc(OC)c(OC)cc12]

In one or more implementations the compound is

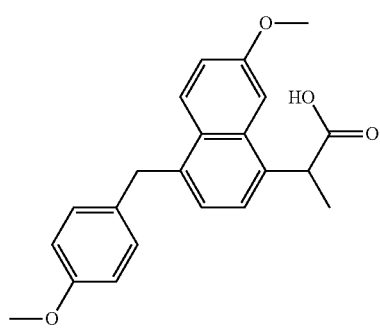 [SMILES: COc1ccc(Cc2ccc(C(C)C(=O)O)c3cc(OC)ccc23)cc1]

or a variation thereof as described in U.S. Pat. No. 8,440,649, herein incorporated by reference in its entirety. In one implementation, the compound is DPC-684 (N-[4-[(4-aminophenyl)sulfonyl-(2-methylpropyl)amino]-3-hydroxy-1-phenylbutan-2-yl]-2-[[2-[(3-fluorophenyl)methylamino]acetyl]amino]-3,3-dimethylbutanamide), a clinically investigated HIV-1 protease inhibitor. In one particular implementation, the compound, or variations and permutations thereof, is further described in U.S. Pat. No. 6,391,919; WO2004043355; WO2002006292; WO2004043355; WO2005061450; WO2004043911 the contents of which are hereby incorporated by reference for all purposes and the specific purposes identified herein.

In one implementation, the compound is E-5050 (3-[4-(2,6-dimethylheptyl)phenyl]-N-(2-hydroxyethyl)butanamide), a clinically investigated protease inhibitor compound. In one particular implementation, the compound, or variations and permutations thereof, is described in WO1999050229 the contents of which are hereby incorporated by reference for all purposes and the specific purposes identified herein. In some embodiments, such compounds are represented by any one or more of the structures shown in Table 9. Any one of the compounds depicted in Table 9 is suitable for use in the methods of the present disclosure.

TABLE 6

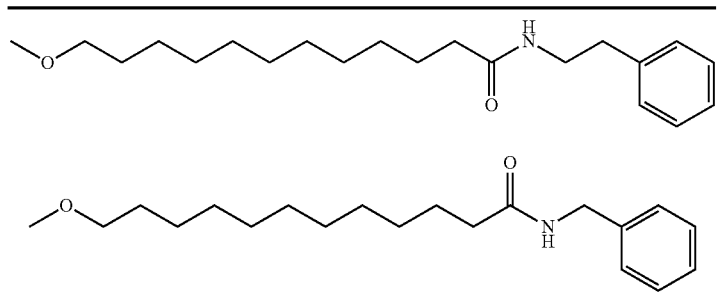

In one implementation, the compound is GPI-1485, (2S)-1-(3,3-Dimethyl-2-oxopentanoyl)pyrrolidine-2-carboxylic acid), a clinically investigated compound operating as a FK506 binding protein modulator. In one particular implementation, the compound, or variations and permutations thereof, is described in WO02100844 the contents of which are hereby incorporated by reference for all purposes and the specific purposes identified herein. In some embodiments, such compounds are represented by any one or more of the structures shown in Table 10. Any one of the compounds depicted in Table 10 is suitable for use in the methods of the present disclosure.

TABLE 7

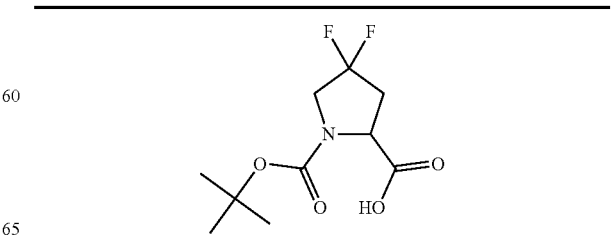

TABLE 7-continued

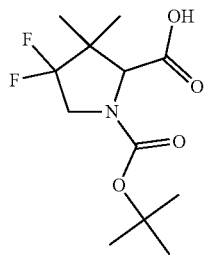 [SMILES: CC(C)(C)OC(=O)N1CC(F)(F)C(C)(C)C1C(=O)O]

In one implementation, the compound is GSK-2485852, (4-((N-(5-cyclopropyl-2-(4-fluorophenyl)-3-(methylcarbamoyl)benzofuran-6-yl)methylsulfonamido)methyl)-2-fluorophenyl)boronic acid, a clinically investigated compound functioning as a Hepatitis C virus NS5B polymerase inhibitor or RNA polymerase inhibitor. In one particular implementation, the compound, or variations and permutations thereof, is described in WO2011103063 the contents of which are hereby incorporated by reference for all purposes and the specific purposes identified herein. In some embodiments, such compounds are represented by any one or more of the structures shown in Table 11. Any one of the compounds depicted in Table 11 is suitable for use in the methods of the present disclosure.

TABLE 8

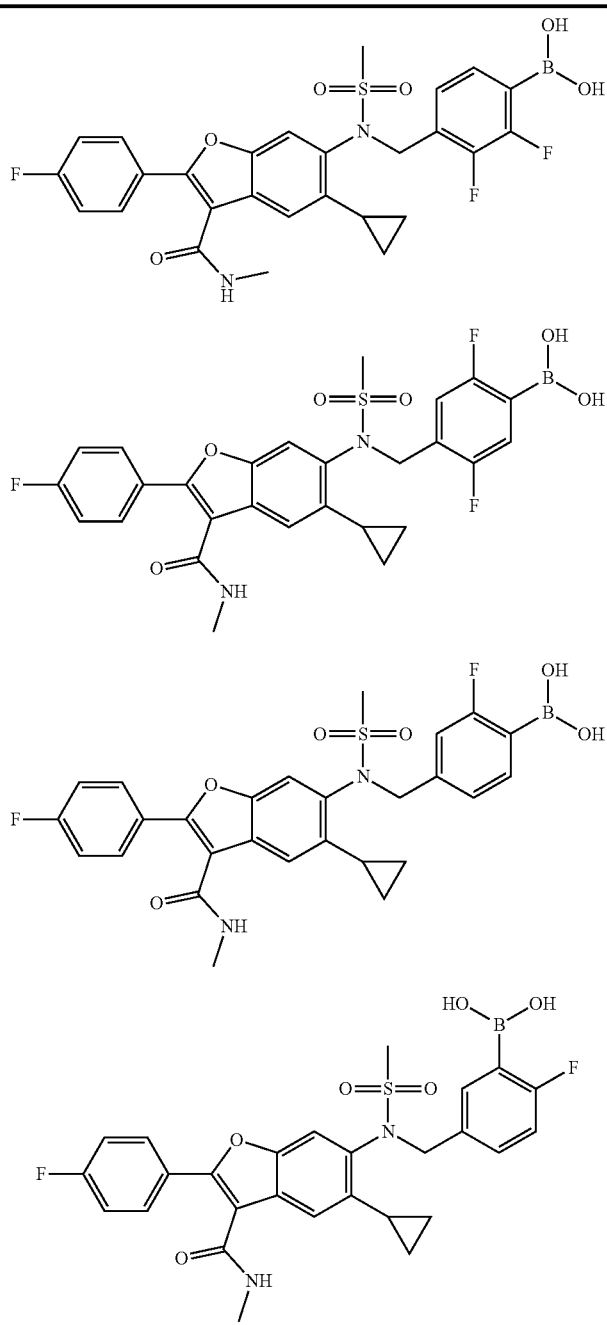

TABLE 8-continued
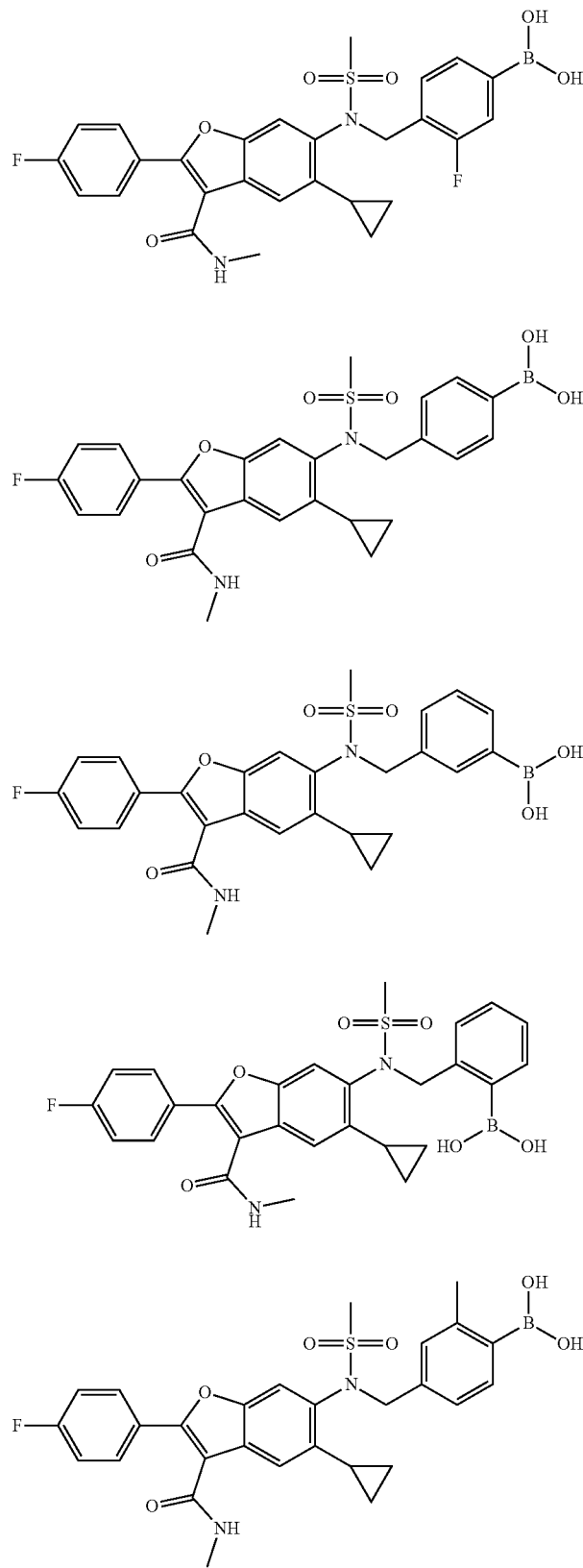

TABLE 8-continued
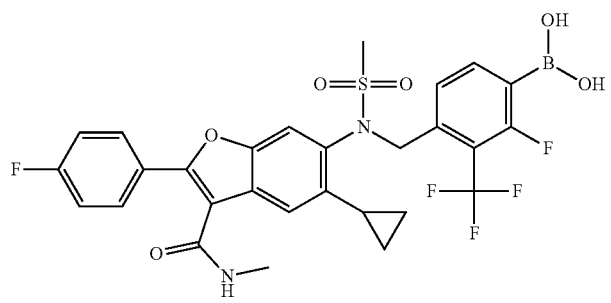 [SMILES: CNC(=O)c1c(-c2ccc(F)cc2)oc2cc(N(Cc3ccc(B(O)O)c(F)c3C(F)(F)F)S(C)(=O)=O)c(C3CC3)cc12]
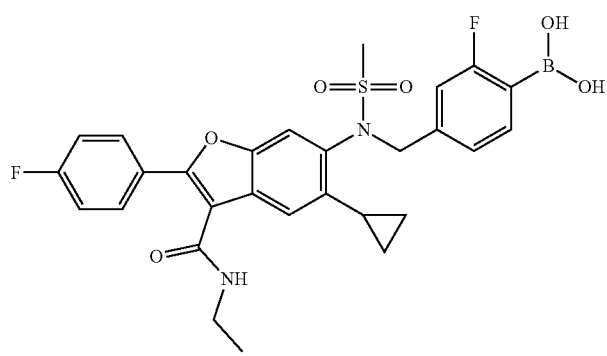 [SMILES: CCNC(=O)c1c(-c2ccc(F)cc2)oc2cc(N(Cc3ccc(B(O)O)c(F)c3)S(C)(=O)=O)c(C3CC3)cc12]
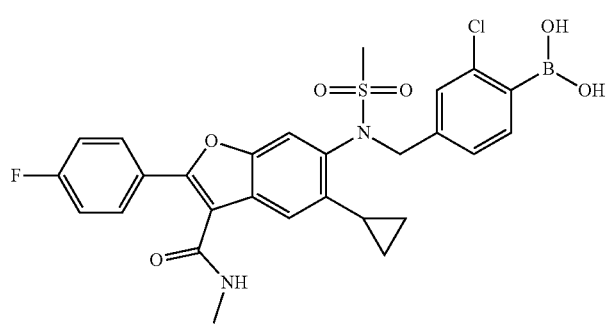
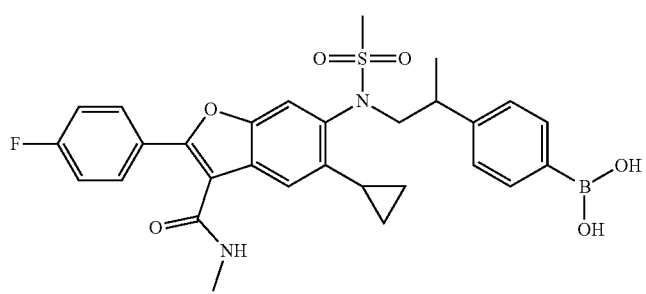 [SMILES: CNC(=O)c1c(-c2ccc(F)cc2)oc2cc(N(CC(C)c3ccc(B(O)O)cc3)S(C)(=O)=O)c(C3CC3)cc12]

TABLE 8-continued
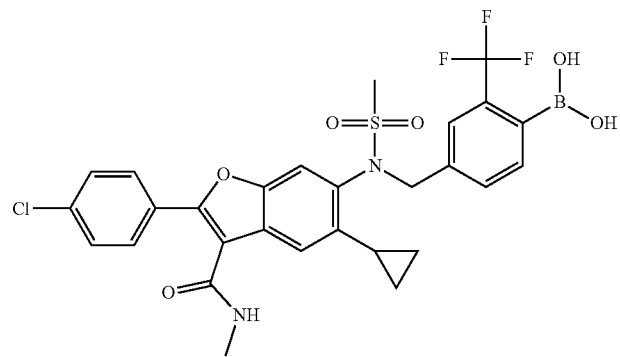 [SMILES: CNC(=O)c1c(-c2ccc(Cl)cc2)oc2cc(N(Cc3ccc(B(O)O)c(C(F)(F)F)c3)S(C)(=O)=O)c(C3CC3)cc12]
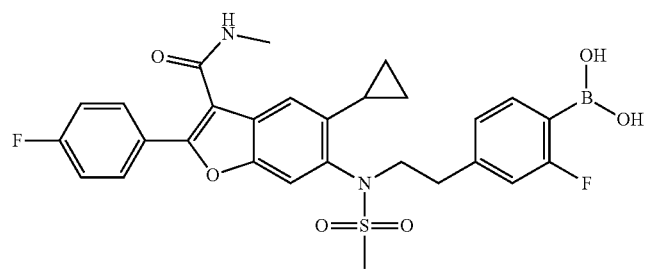 [SMILES: CNC(=O)c1c(-c2ccc(F)cc2)oc2cc(N(CCc3ccc(B(O)O)c(F)c3)S(C)(=O)=O)c(C3CC3)cc12]
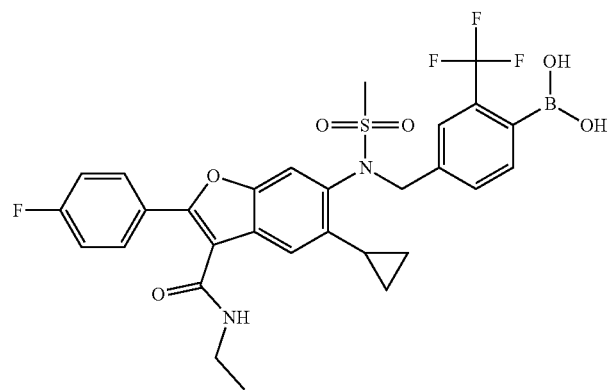 [SMILES: CCNC(=O)c1c(-c2ccc(F)cc2)oc2cc(N(Cc3ccc(B(O)O)c(C(F)(F)F)c3)S(C)(=O)=O)c(C3CC3)cc12]
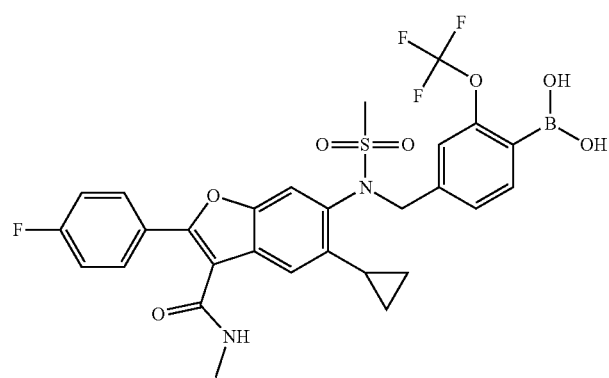 [SMILES: CNC(=O)c1c(-c2ccc(F)cc2)oc2cc(N(Cc3ccc(B(O)O)c(OC(F)(F)F)c3)S(C)(=O)=O)c(C3CC3)cc12]

TABLE 8-continued
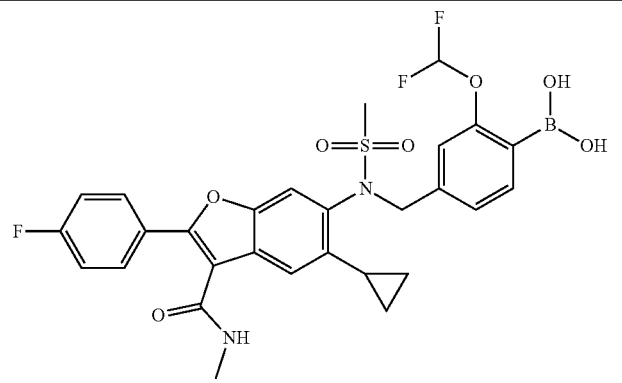
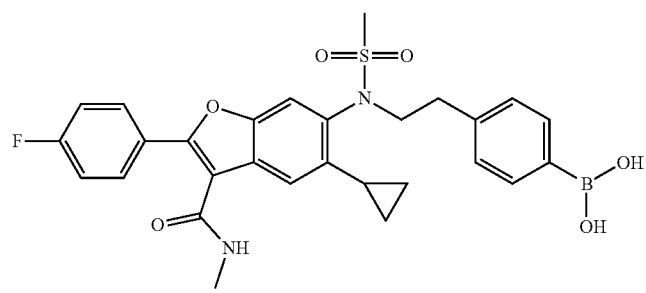 [SMILES: CNC(=O)c1c(-c2ccc(F)cc2)oc2cc(N(CCc3ccc(B(O)O)cc3)S(C)(=O)=O)c(C3CC3)cc12]
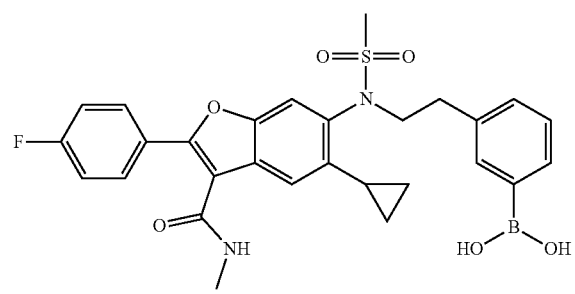 [SMILES: CNC(=O)c1c(-c2ccc(F)cc2)oc2cc(N(CCc3cccc(B(O)O)c3)S(C)(=O)=O)c(C3CC3)cc12]
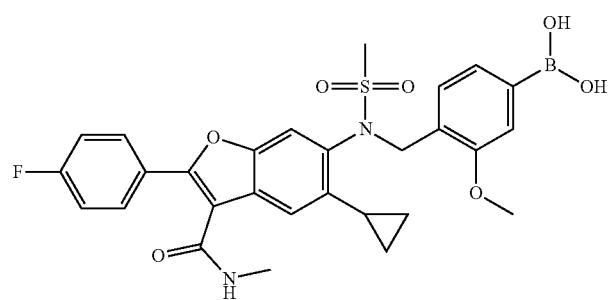 [SMILES: CNC(=O)c1c(-c2ccc(F)cc2)oc2cc(N(Cc3ccc(B(O)O)cc3OC)S(C)(=O)=O)c(C3CC3)cc12]
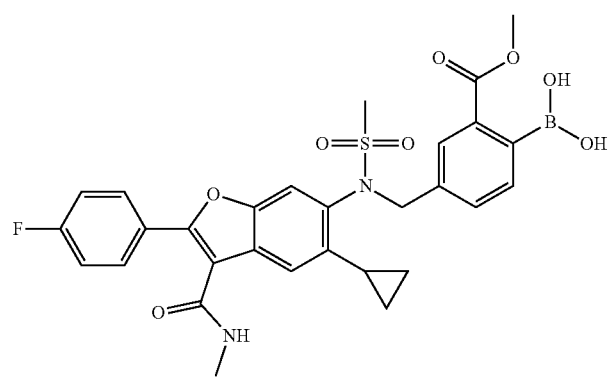 [SMILES: CNC(=O)c1c(-c2ccc(F)cc2)oc2cc(N(Cc3ccc(B(O)O)c(C(=O)OC)c3)S(C)(=O)=O)c(C3CC3)cc12]

TABLE 8-continued
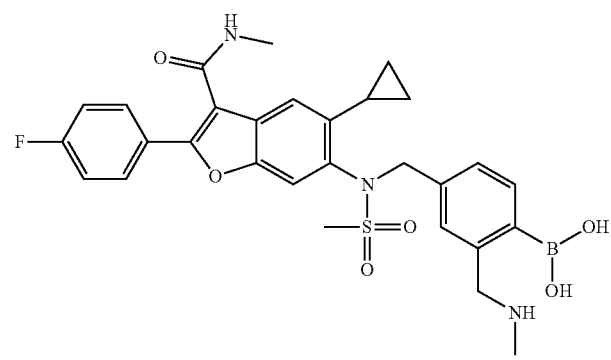 [SMILES: CNCc1cc(CN(c2cc3oc(-c4ccc(F)cc4)c(C(=O)NC)c3cc2C2CC2)S(C)(=O)=O)ccc1B(O)O]
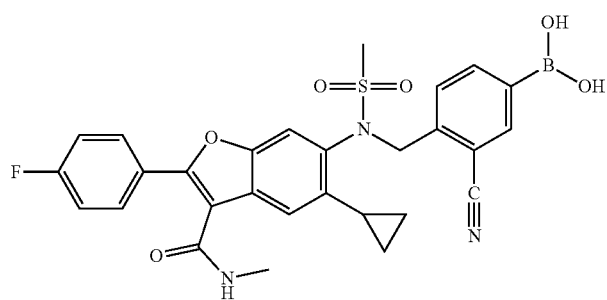 [SMILES: CNC(=O)c1c(-c2ccc(F)cc2)oc2cc(N(Cc3ccc(B(O)O)cc3C#N)S(C)(=O)=O)c(C3CC3)cc12]
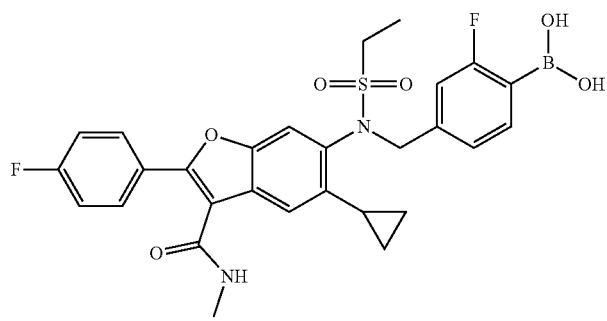 [SMILES: CCS(=O)(=O)N(Cc1ccc(B(O)O)c(F)c1)c1cc2oc(-c3ccc(F)cc3)c(C(=O)NC)c2cc1C1CC1]
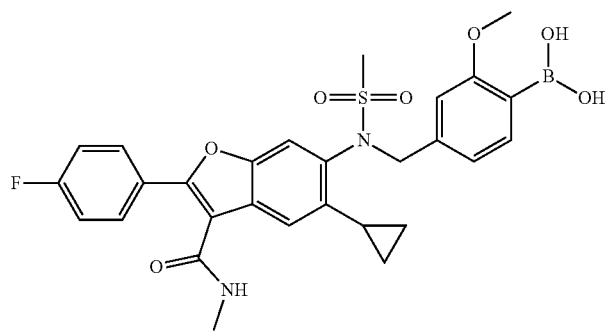 [SMILES: CNC(=O)c1c(-c2ccc(F)cc2)oc2cc(N(Cc3ccc(B(O)O)c(OC)c3)S(C)(=O)=O)c(C3CC3)cc12]
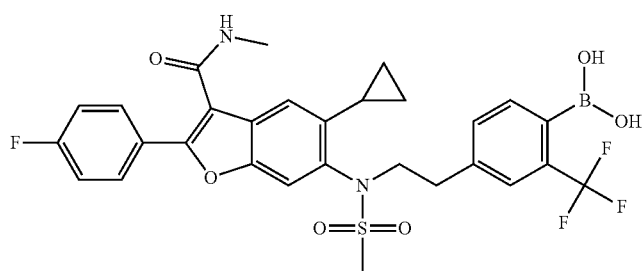 [SMILES: CNC(=O)c1c(-c2ccc(F)cc2)oc2cc(N(CCc3ccc(B(O)O)c(C(F)(F)F)c3)S(C)(=O)=O)c(C3CC3)cc12]

TABLE 8-continued
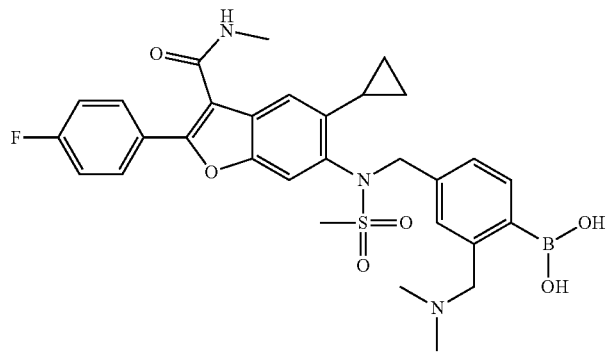 [SMILES: CNC(=O)c1c(-c2ccc(F)cc2)oc2cc(N(Cc3ccc(B(O)O)c(CN(C)C)c3)S(C)(=O)=O)c(C3CC3)cc12]
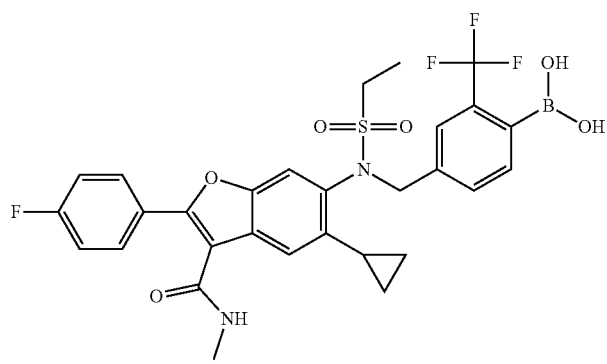 [SMILES: CCS(=O)(=O)N(Cc1ccc(B(O)O)c(C(F)(F)F)c1)c1cc2oc(-c3ccc(F)cc3)c(C(=O)NC)c2cc1C1CC1]
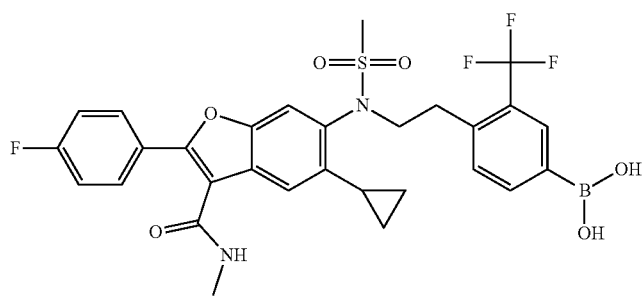 [SMILES: CNC(=O)c1c(-c2ccc(F)cc2)oc2cc(N(CCc3ccc(B(O)O)cc3C(F)(F)F)S(C)(=O)=O)c(C3CC3)cc12]
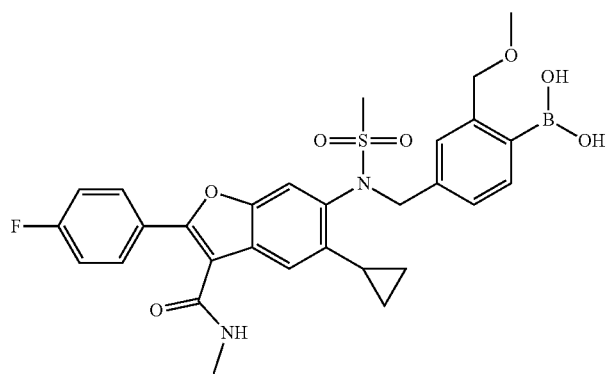 [SMILES: CNC(=O)c1c(-c2ccc(F)cc2)oc2cc(N(Cc3ccc(B(O)O)c(COC)c3)S(C)(=O)=O)c(C3CC3)cc12]

TABLE 8-continued

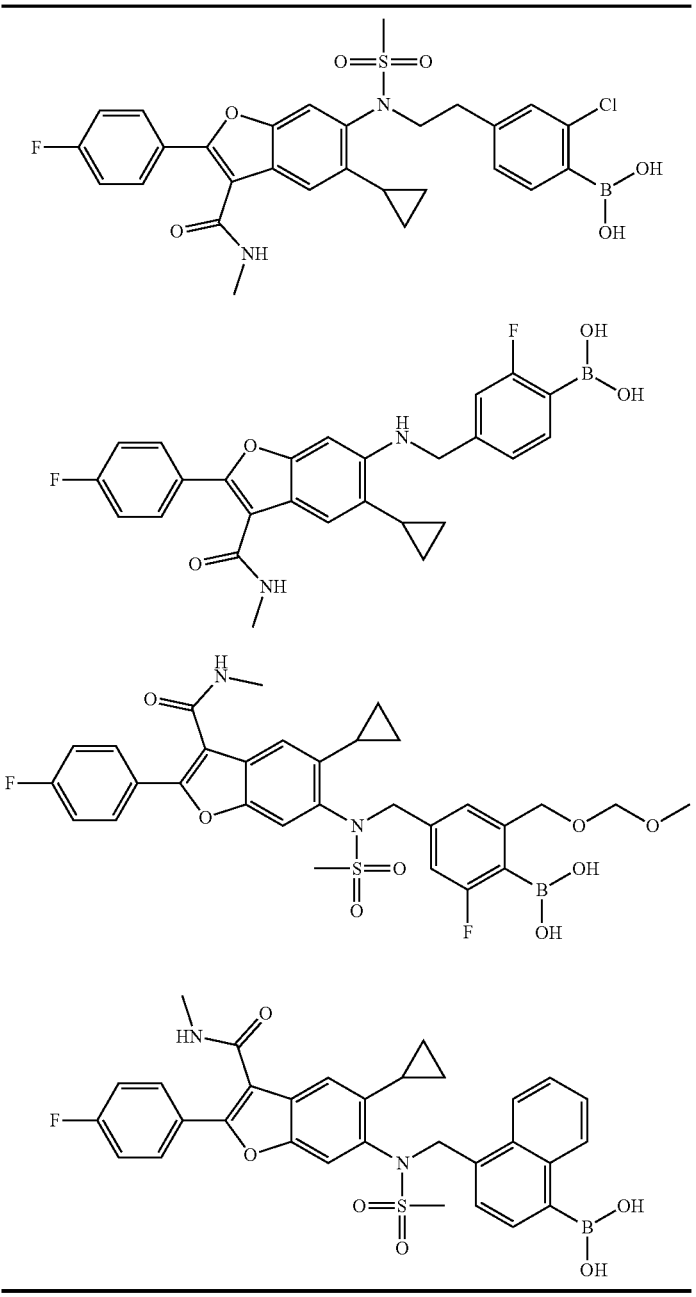

In one implementation, the compound is Hoe-065((E)-but-2-enedioic acid;octyl (2S,3aS,6aS)-1[(2S)-2-[[(2S)-1-ethoxy-1-oxo-4-phenylbutan-2-yl]amino]propanoyl]-3,3a,4,5,6,6a-hexahydro-2H-cyclopenta[b]pyrrole-2-carboxylate), a clinically investigated acetylcholine receptor agonist or acetylcholinesterase inhibitor. In one particular implementation, the compound, or variations and permutations thereof, is described in WO2007117560 the contents of which are hereby incorporated by reference for all purposes and the specific purposes identified herein. In some embodiments, such compounds are represented by any one or more of the structures shown in Table 12. Any one of the compounds depicted in Table 12 is suitable for use in the methods of the present disclosure.

TABLE 9

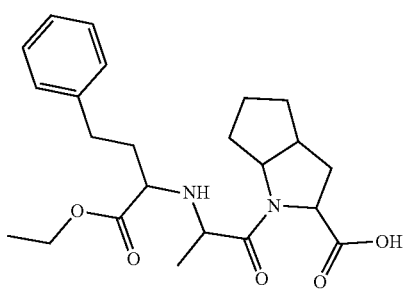 [SMILES: CCOC(=O)C(CCc1ccccc1)NC(C)C(=O)N1C(C(=O)O)CC2CCCC21]

TABLE 9-continued

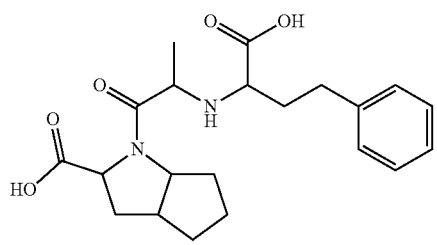 [SMILES: CC(NC(CCc1ccccc1)C(=O)O)C(=O)N1C(C(=O)O)CC2CCCC21]

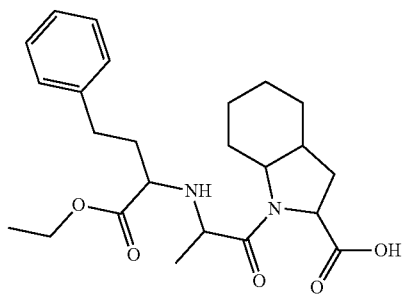 [SMILES: CCOC(=O)C(CCc1ccccc1)NC(C)C(=O)N1C(C(=O)O)CC2CCCCC21]

In one implementation, the compound is IDX-320 ((1S, 4R,6S,7Z,18S)-18-[7-methoxy-8-methyl-2-[4-(trifluoromethyl)-1,3-thiazol-2-yl]quinolin-4-yl]oxy-13-methyl-N-(1-methylcyclopropyl)sulfonyl-2,14-dioxo-3,13,15-triazatricyclo[13.4.0.04,6]nonadec-7-ene-4-carboxamide) a clinically investigated NS3 protease inhibitor. In one particular implementation, the compound, or variations and permutations thereof, is described in WO2009014730 the contents of which are hereby incorporated by reference for all purposes and the specific purposes identified herein. In some embodiments, such compounds are represented by any one or more of the structures shown in Table 13. Any one of the compounds depicted in Table 13 is suitable for use in the methods of the present disclosure.

TABLE 10

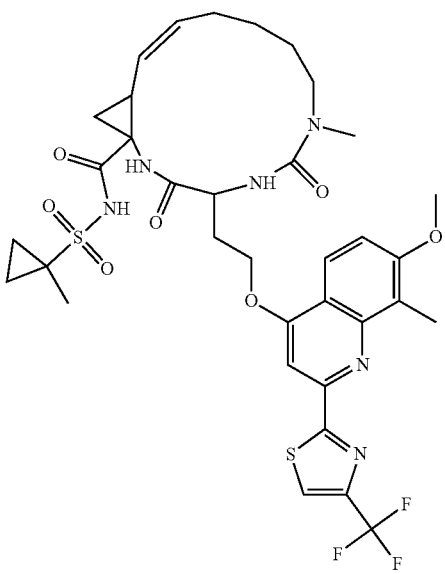 [SMILES: COc1ccc2c(OCCC3NC(=O)N(C)CCCC/C=C\C4CC4(C(=O)NS(=O)(=O)C4(C)CC4)NC3=O)cc(-c3nc(C(F)(F)F)cs3)nc2c1C]

TABLE 10-continued

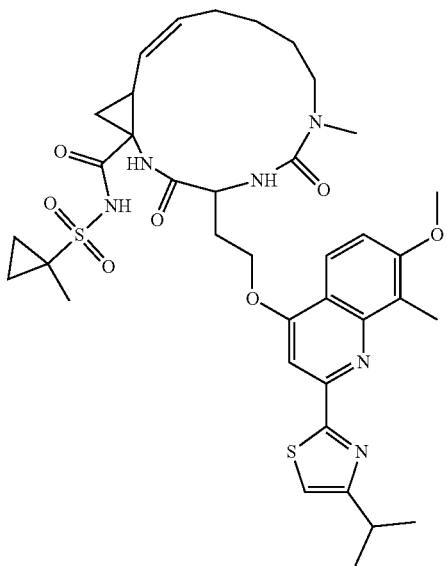 [SMILES: COc1ccc2c(OCCC3NC(=O)N(C)CCCC/C=C\C4CC4(C(=O)NS(=O)(=O)C4(C)CC4)NC3=O)cc(-c3nc(C(C)C)cs3)nc2c1C]

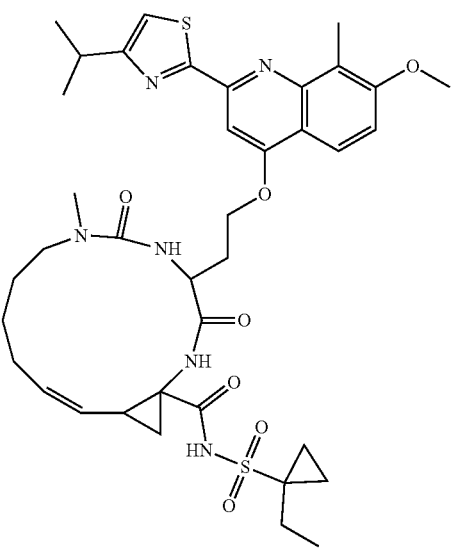 [SMILES: CCC1(S(=O)(=O)NC(=O)C23CC2/C=C\CCCCN(C)C(=O)NC(CCOc2cc(-c4nc(C(C)C)cs4)nc4c(C)c(OC)ccc24)C(=O)N3)CC1]

In one implementation, the compound is L-653328 ((S)-4-(3-(tert-butylamino)-2-hydroxypropoxy)phenethyl acetate). In one particular implementation, the compound, or variations and permutations thereof, is described in WO2007117560 the contents of which are hereby incorporated by reference for all purposes and the specific purposes identified herein. In some embodiments, such compounds are represented by any one or more of the structures shown in Table 14. Any one of the compounds depicted in Table 14 is suitable for use in the methods of the present disclosure.

TABLE 11

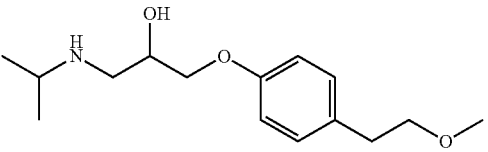 [SMILES: COCCc1ccc(OCC(O)CNC(C)C)cc1]

TABLE 11-continued

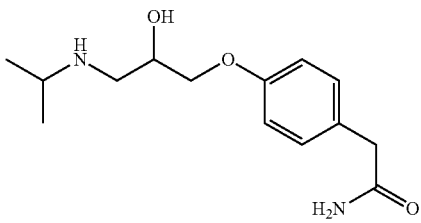 [SMILES: CC(C)NCC(O)COc1ccc(CC(N)=O)cc1]

In one implementation, the compound is MK-1220 ((3R, 5S,8S)-8-cyclohexyl-N-[(1R,2S)-1-(cyclopropylsulfonyl-carbamoyl)-2-ethenylcyclopropyl]-18-methoxy-13,13-dimethyl-7,10-dioxo-2,11-dioxa-6,9,23-triazatetracyclo [15.6.2.13,6.020,24]hexacosa-1(23), 17,19,21,24-pentaene-5-carboxamide), a clinically investigated NS5B polymerase inhibitor. In one particular implementation, the compound, or variations and permutations thereof, is further described in WO2007016441; WO2008057208 the contents of which are hereby incorporated by reference for all purposes and the specific purposes identified herein. In some embodiments, such compounds are represented by any one or more of the structures shown in Table 15. Any one of the compounds depicted in Table 15 is suitable for use in the methods of the present disclosure.

TABLE 12

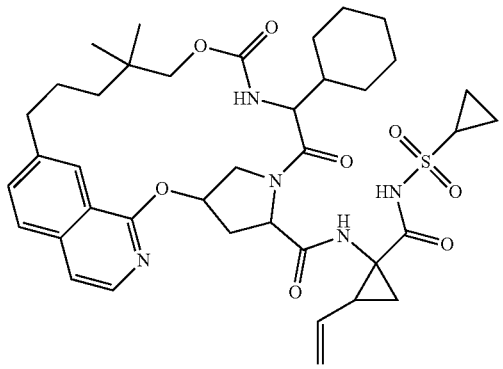 [SMILES: C=CC1CC1(NC(=O)C1CC2CN1C(=O)C(C1CCCCC1)NC(=O)OCC(C)(C)CCCc1ccc3ccnc(c3c1)O2)C(=O)NS(=O)(=O)C1CC1]

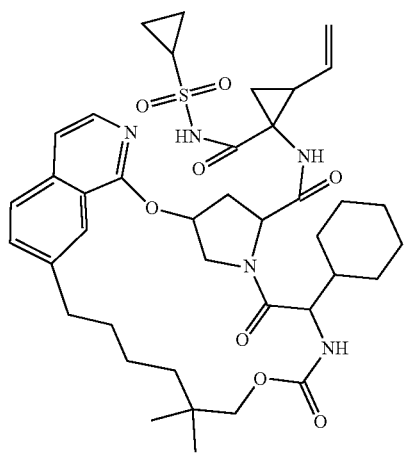 [SMILES: C=CC1CC1(NC(=O)C1CC2CN1C(=O)C(C1CCCCC1)NC(=O)OCC(C)(C)CCCCc1ccc3ccnc(c3c1)O2)C(=O)NS(=O)(=O)C1CC1]

TABLE 12-continued

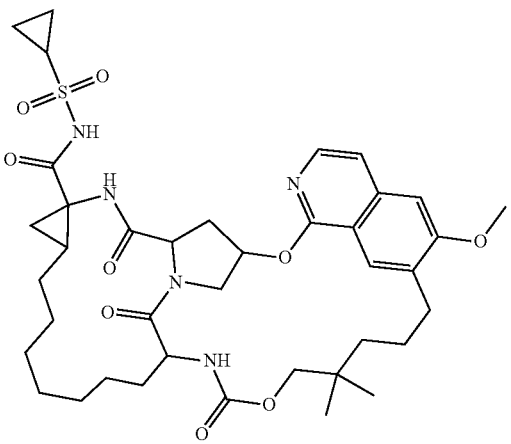 [SMILES: COc1cc2ccnc3c2cc1CCCC(C)(C)COC(=O)NC1CCCCCCCC2CC2(C(=O)NS(=O)(=O)C2CC2)NC(=O)C2CC(CN2C1=O)O3]

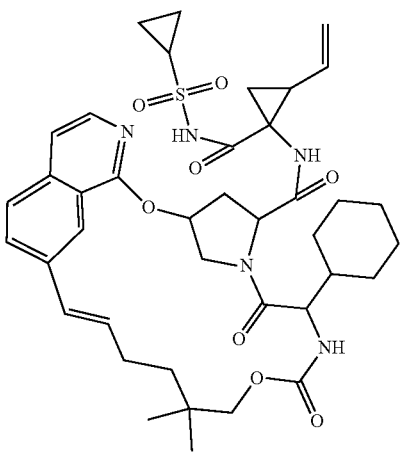 [SMILES: C=CC1CC1(NC(=O)C1CC2CN1C(=O)C(C1CCCCC1)NC(=O)OCC(C)(C)CC/C=C/c1ccc3ccnc(c3c1)O2)C(=O)NS(=O)(=O)C1CC1]

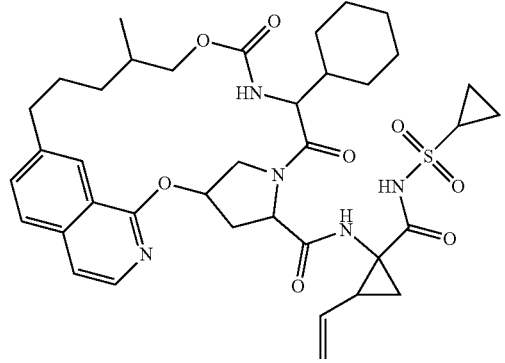 [SMILES: C=CC1CC1(NC(=O)C1CC2CN1C(=O)C(C1CCCCC1)NC(=O)OCC(C)CCCc1ccc3ccnc(c3c1)O2)C(=O)NS(=O)(=O)C1CC1]

TABLE 12-continued
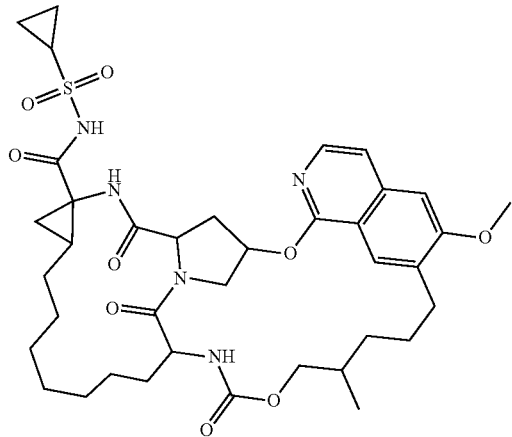 [SMILES: COc1cc2ccnc3c2cc1CCCC(C)COC(=O)NC1CCCCCCCC2CC2(C(=O)NS(=O)(=O)C2CC2)NC(=O)C2CC(CN2C1=O)O3]
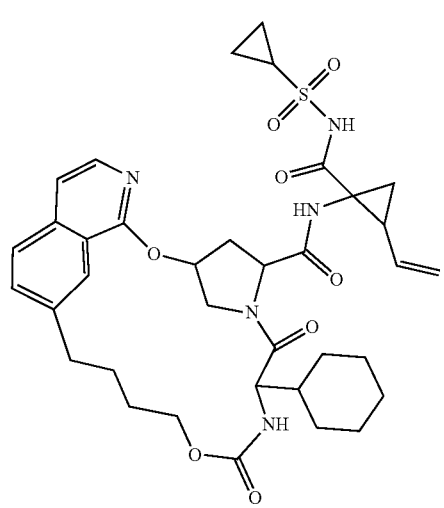 [SMILES: C=CC1CC1(NC(=O)C1CC2CN1C(=O)C(C1CCCCC1)NC(=O)OCCCCc1ccc3ccnc(c3c1)O2)C(=O)NS(=O)(=O)C1CC1]
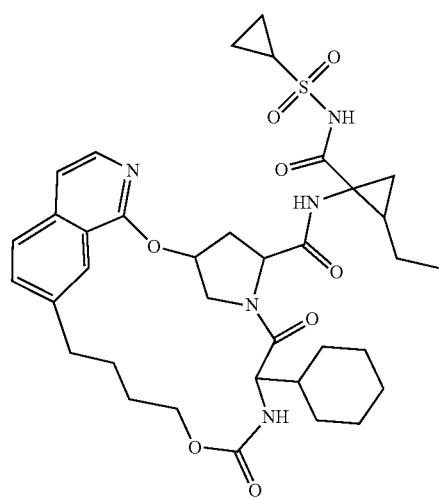 [SMILES: CCC1CC1(NC(=O)C1CC2CN1C(=O)C(C1CCCCC1)NC(=O)OCCCCc1ccc3ccnc(c3c1)O2)C(=O)NS(=O)(=O)C1CC1]
TABLE 12-continued
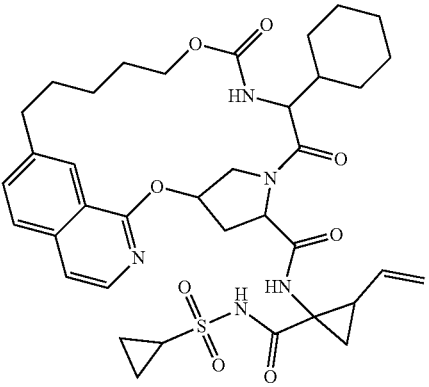 [SMILES: C=CC1CC1(NC(=O)C1CC2CN1C(=O)C(C1CCCCC1)NC(=O)OCCCCCc1ccc3ccnc(c3c1)O2)C(=O)NS(=O)(=O)C1CC1]
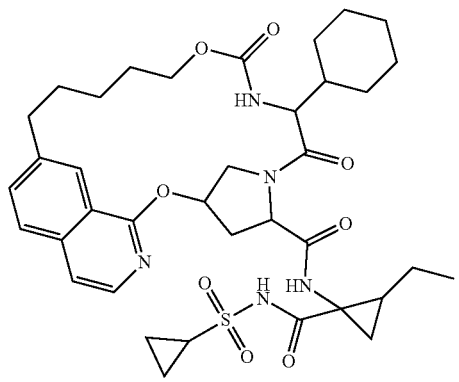 [SMILES: CCC1CC1(NC(=O)C1CC2CN1C(=O)C(C1CCCCC1)NC(=O)OCCCCCc1ccc3ccnc(c3c1)O2)C(=O)NS(=O)(=O)C1CC1]
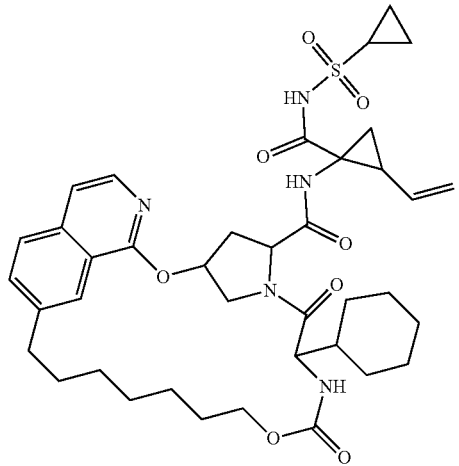 [SMILES: C=CC1CC1(NC(=O)C1CC2CN1C(=O)C(C1CCCCC1)NC(=O)OCCCCCCCc1ccc3ccnc(c3c1)O2)C(=O)NS(=O)(=O)C1CC1]

TABLE 12-continued
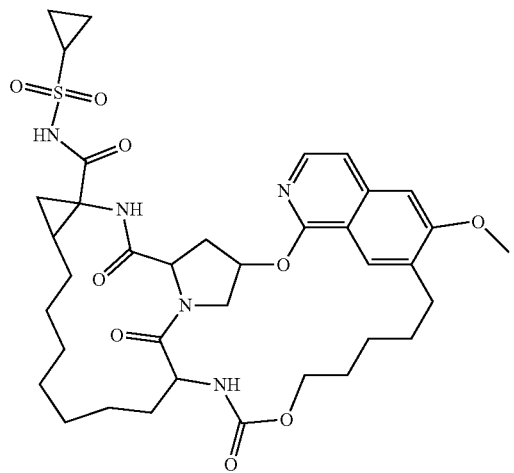 [SMILES: COc1cc2ccnc3c2cc1CCCCCOC(=O)NC1CCCCCCCC2CC2(C(=O)NS(=O)(=O)C2CC2)NC(=O)C2CC(CN2C1=O)O3]
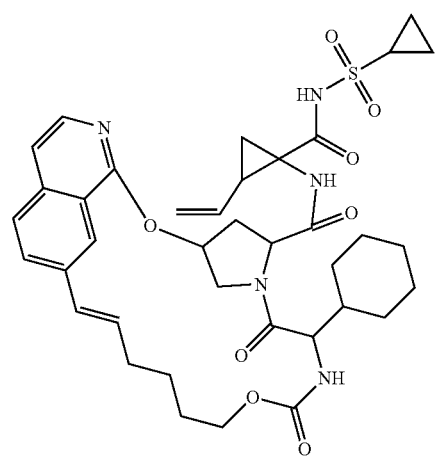 [SMILES: C=CC1CC1(NC(=O)C1CC2CN1C(=O)C(C1CCCCC1)NC(=O)OCCCC/C=C/c1ccc3ccnc(c3c1)O2)C(=O)NS(=O)(=O)C1CC1]
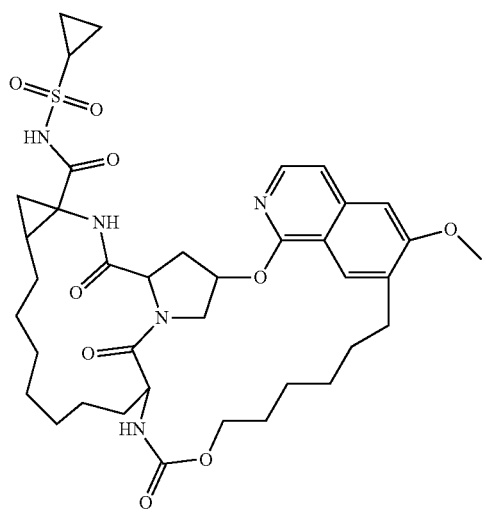 [SMILES: COc1cc2ccnc3c2cc1CCCCCCOC(=O)NC1CCCCCCCC2CC2(C(=O)NS(=O)(=O)C2CC2)NC(=O)C2CC(CN2C1=O)O3]
TABLE 12-continued
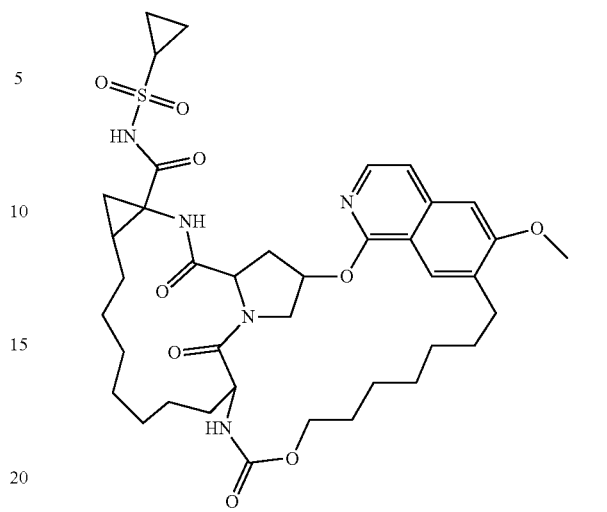
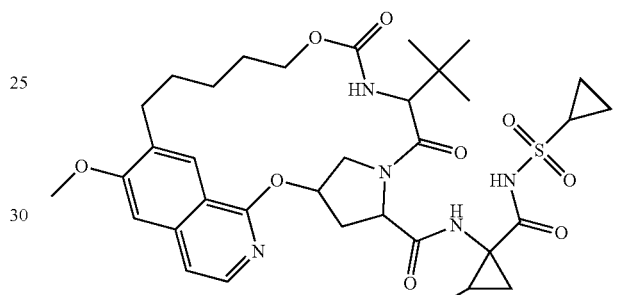
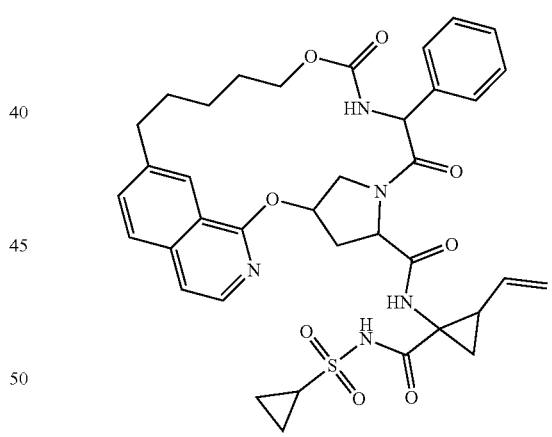
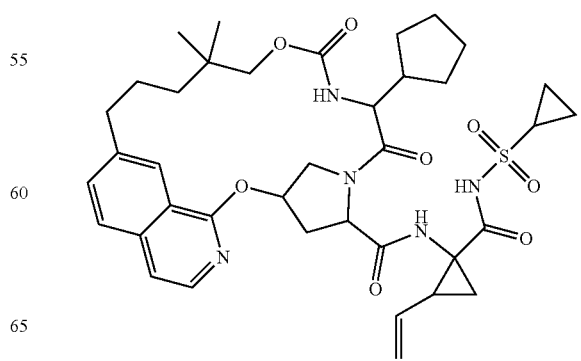

TABLE 12-continued

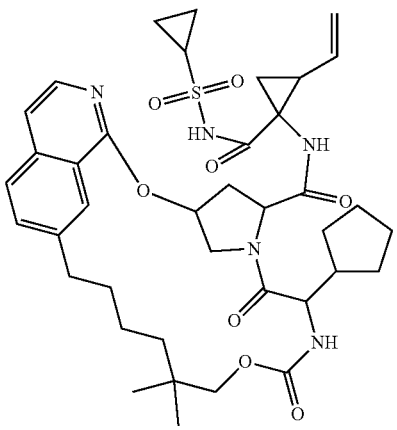 [SMILES: C=CC1CC1(NC(=O)C1CC2CN1C(=O)C(C1CCCC1)NC(=O)OCC(C)(C)CCCCc1ccc3ccnc(c3c1)O2)C(=O)NS(=O)(=O)C1CC1]

TABLE 12-continued

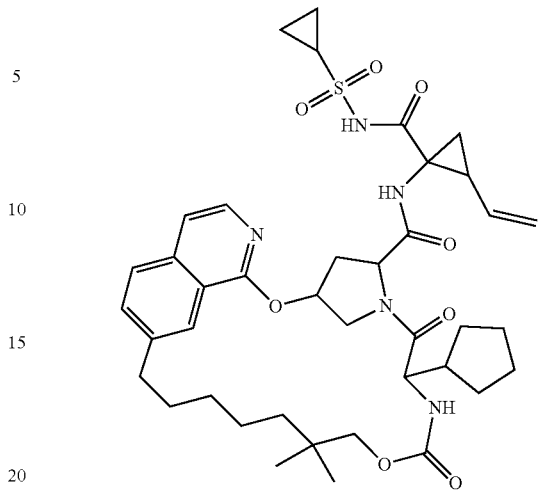

In one implementation, the compound is MR-708 (2-acetamido-3-phenylpropanoic acid;adamantan-1-amine) a clinically investigated protease Inhibitor. In one particular implementation, the compound, or variations and permutations thereof, is further described in JP2000159746 and WO2007002172 the contents of which are hereby incorporated by reference for all purposes and the specific purposes identified herein. In some embodiments, such compounds are represented by any one or more of the structures shown in Table 16. Any one of the compounds depicted in Table 16 is suitable for use in the methods of the present disclosure.

TABLE 13

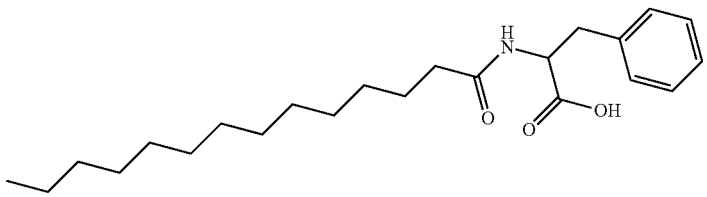 [SMILES: CCCCCCCCCCCCCC(=O)NC(Cc1ccccc1)C(=O)O]

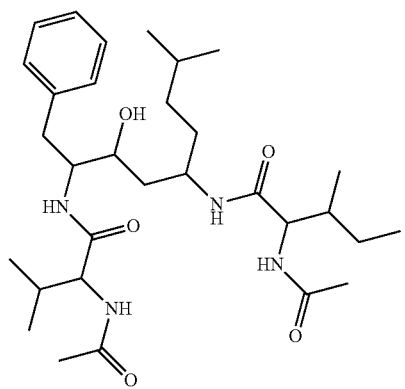 [SMILES: CCC(C)C(NC(C)=O)C(=O)NC(CCC(C)C)CC(O)C(Cc1ccccc1)NC(=O)C(NC(C)=O)C(C)C]

TABLE 13-continued
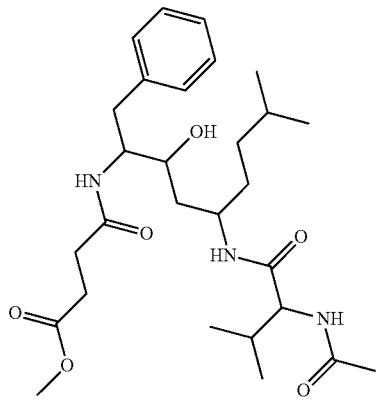 [SMILES: COC(=O)CCC(=O)NC(Cc1ccccc1)C(O)CC(CCC(C)C)NC(=O)C(NC(C)=O)C(C)C]
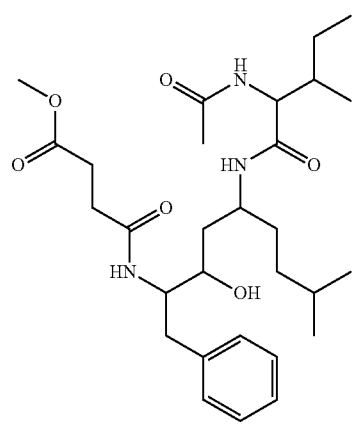 [SMILES: CCC(C)C(NC(C)=O)C(=O)NC(CCC(C)C)CC(O)C(Cc1ccccc1)NC(=O)CCC(=O)OC]
In one implementation, the compound is MSI-469, having the formula
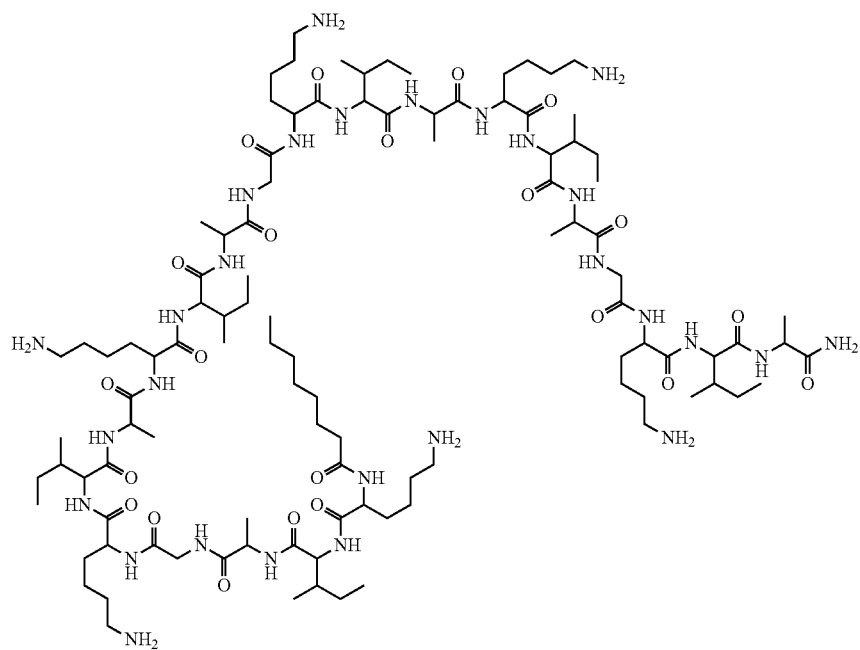 [SMILES: CCCCCCCC(=O)NC(CCCCN)C(=O)NC(C(=O)NC(C)C(=O)NCC(=O)NC(CCCCN)C(=O)NC(C(=O)NC(C)C(=O)NC(CCCCN)C(=O)NC(C(=O)NC(C)C(=O)NCC(=O)NC(CCCCN)C(=O)NC(C(=O)NC(C)C(=O)NC(CCCCN)C(=O)NC(C(=O)NC(C)C(=O)NCC(=O)NC(CCCCN)C(=O)NC(C(=O)NC(C)C(N)=O)C(C)CC)C(C)CC)C(C)CC)C(C)CC)C(C)CC)C(C)CC]

a clinically investigated Peptidomimetic inhibitor of the human cytomegalovirus protease. In a particular arrangement the compound is further described in WO1998029435 the contents of which are hereby incorporated by reference for all purposes and the specific purposes identified herein. In some embodiments, such compounds are represented by any one or more of the structures shown in Table 17. Any one of the compounds depicted in Table 17 is suitable for use in the methods of the present disclosure.

TABLE 14

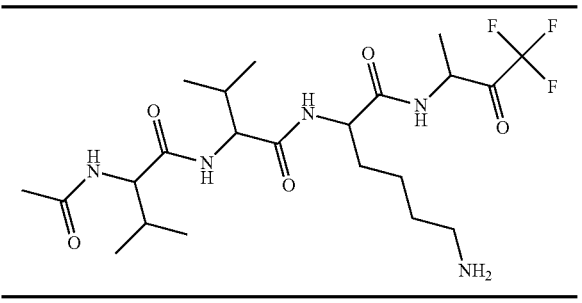

In one implementation, the compound is N30-201, having the formula

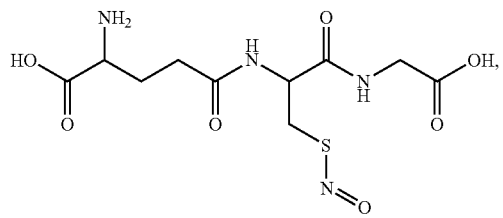 [SMILES: NC(CCC(=O)NC(CSN=O)C(=O)NCC(=O)O)C(=O)O]

a clinically investigated alcohol dehydrogenase 5 modulator. In one particular implementation, the compound, or variations and permutations thereof, is further described in WO2003051910 the contents of which are hereby incorporated by reference for all purposes and the specific purposes identified herein. In some embodiments, such compounds are represented by any one or more of the structures shown in Table 18. Any one of the compounds depicted in Table 18 is suitable for use in the methods of the present disclosure.

TABLE 15

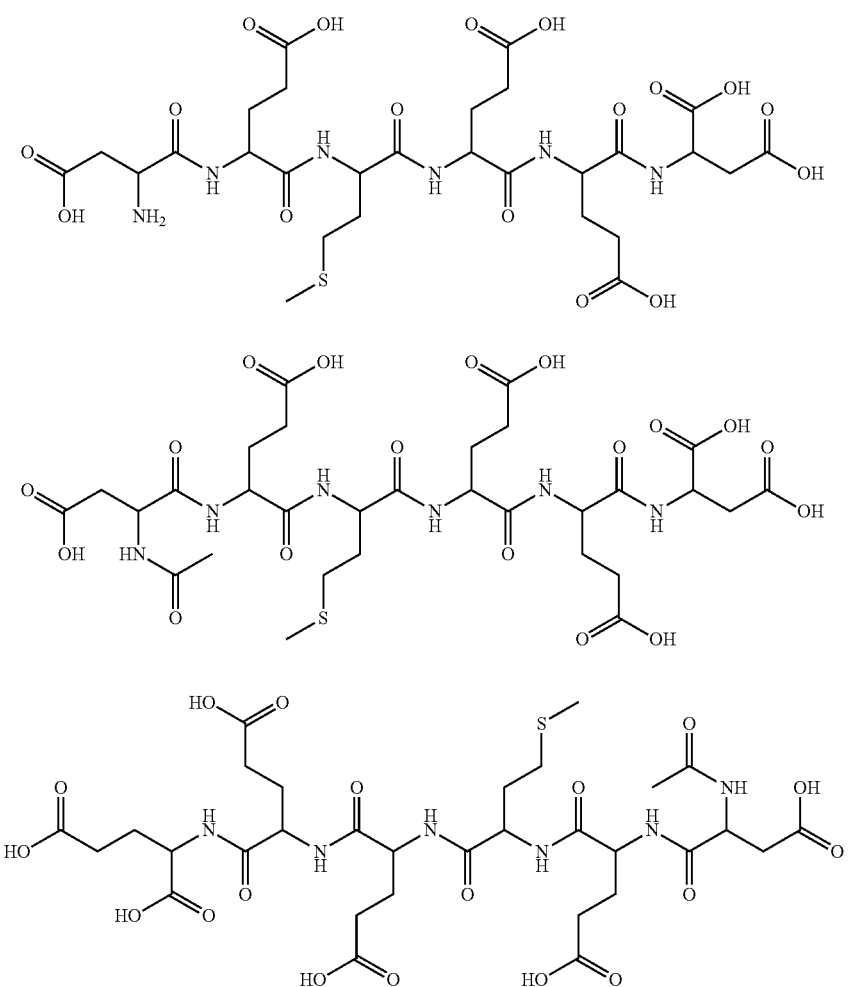

In one implementation, the compound is a NO-antihypertensives, for example having the formula

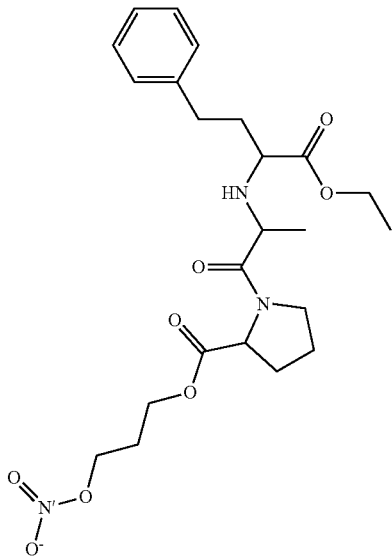

and being clinically investigated ACE inhibitor. In one particular implementation, the compound, or variations and permutations thereof, is further described in WO2007117560 the contents of which are hereby incorporated by reference for all purposes and the specific purposes identified herein. In some embodiments, such compounds are represented by any one or more of the structures shown in Table 19. Any one of the compounds depicted in Table 19 is suitable for use in the methods of the present disclosure.

TABLE 16

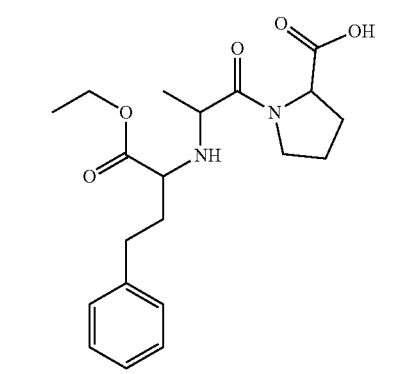 [SMILES: CCOC(=O)C(CCc1ccccc1)NC(C)C(=O)N1CCCC1C(=O)O]

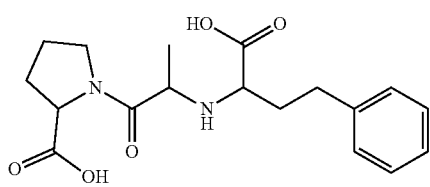 [SMILES: CC(NC(CCc1ccccc1)C(=O)O)C(=O)N1CCCC1C(=O)O]

TABLE 16-continued

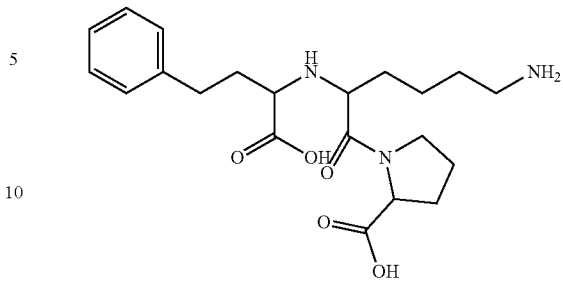

In one implementation, the compound is NPC-15199 ((2S)-2-(9H-fluoren-9-ylmethoxycarbonylamino)-4-methylpentanoic acid), a clinically investigated NS3 protease inhibitor. In one particular implementation, the compound, or variations and permutations thereof, is further described in WO1999064442 the contents of which are hereby incorporated by reference for all purposes and the specific purposes identified herein.

In one implementation, the compound is ONO-405, having the formula

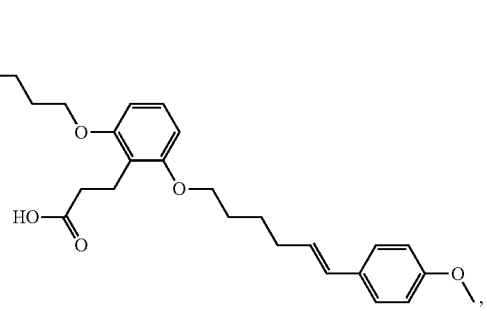

and clinically investigated as a leukotriene BLT receptor antagonist. In one particular implementation, the compound, or variations and permutations thereof, is further described in WO1998019997 the contents of which are hereby incorporated by reference for all purposes and the specific purposes identified herein. In some embodiments, such compounds are represented by any one or more of the structures shown in Table 20. Any one of the compounds depicted in Table 20 is suitable for use in the methods of the present disclosure.

TABLE 17

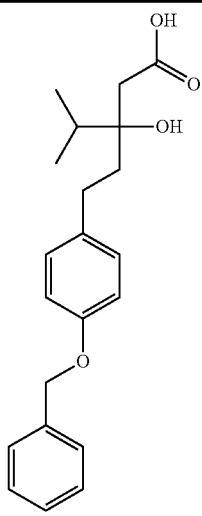

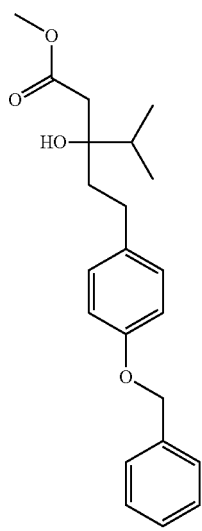 [SMILES: COC(=O)CC(O)(CCc1ccc(OCc2ccccc2)cc1)C(C)C]

TABLE 17-continued

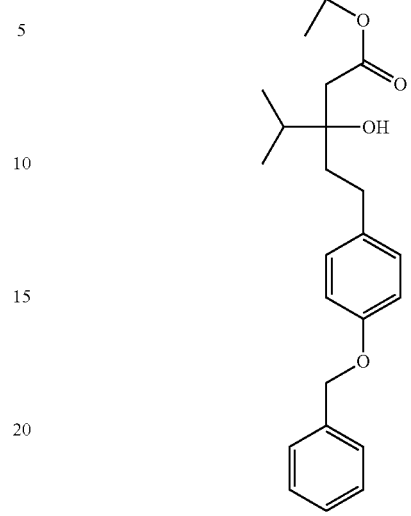

In one implementation, the compound is PBI-4050 (2-(3-pentylphenyl)acetic acid), a clinically investigated connective tissue growth factor ligand inhibitor; free fatty acid receptor 1 agonist; and G-protein coupled receptor 84 antagonist. In one particular implementation, the compound, or variations and permutations thereof, is further described in WO2000015634 the contents of which are hereby incorporated by reference for all purposes and the specific purposes identified herein. In some embodiments, such compounds are represented by any one or more of the structures shown in Table 21. Any one of the compounds depicted in Table 21 is suitable for use in the methods of the present disclosure.

TABLE 18

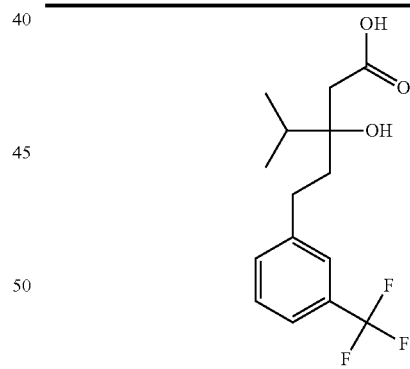

In one implementation, the compound is PL-37 (1-ethoxycarbonyloxyethyl 2-[[(2S)-2-[[[(2S)-2-amino-4-methylsulfanylbutyl]disulfanyl]methyl]-3-phenylpropanoyl]amino]acetate), a clinically investigated aminopeptidase N inhibitor; Neutral endopeptidase inhibitor. In one particular implementation, the compound, or variations and permutations thereof, is further described in WO1999050229 the contents of which are hereby incorporated by reference for all purposes and the specific purposes identified herein. In some embodiments, such compounds are represented by any one or more of the structures shown in Table 22. Any one of the compounds depicted in Table 22 is suitable for use in the methods of the present disclosure.

TABLE 19

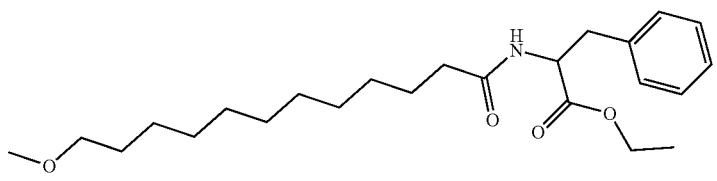 [SMILES: CCOC(=O)C(Cc1ccccc1)NC(=O)CCCCCCCCCCCOC]

In one implementation, the compound is PZ-128 (N-[(2S)-6-amino-1-[[(2S)-6-amino-1-[[(2S)-1-[(2S)-1-[[(2S)-1-[[(2S)-1-amino-1-oxo-3-phenylpropan-2-yl]amino]-4-methyl-1-oxopentan-2-yl]amino]-1-oxopropan-2-yl]amino]-5-(diaminomethylideneamino)-1-oxopentan-2-yl]amino]-3-hydroxy-1-oxopropan-2-yl]amino]-1-oxohexan-2-yl]amino]-1-oxohexan-2-yl]hexadecanamide), a clinically investigated protease-activated receptor-1 antagonist. In one particular implementation, the compound, or variations and permutations thereof, is further described in WO2007002172 the contents of which are hereby incorporated by reference for all purposes and the specific purposes identified herein. In some embodiments, such compounds are represented by any one or more of the structures shown in Table 23. Any one of the compounds depicted in Table 23 is suitable for use in the methods of the present disclosure.

TABLE 20

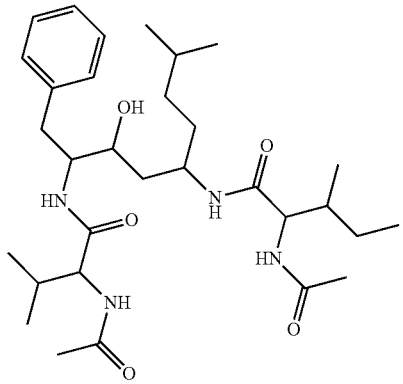 [SMILES: CCC(C)C(NC(C)=O)C(=O)NC(CCC(C)C)CC(O)C(Cc1ccccc1)NC(=O)C(NC(C)=O)C(C)C]

In one implementation, the compound is R-944 having a formula

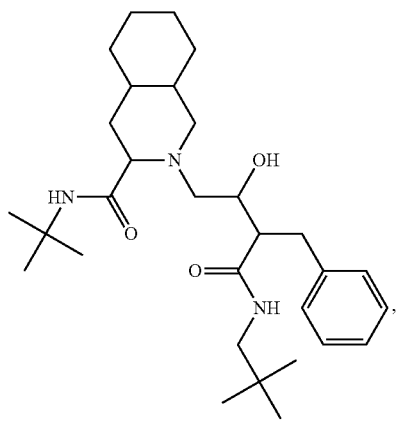 [SMILES: CC(C)(C)CNC(=O)C(Cc1ccccc1)C(O)CN1CC2CCCCC2CC1C(=O)NC(C)(C)C]

and used as a clinically investigated HIV protease inhibitor. In one particular implementation, the compound, or variations and permutations thereof, is further described in WO1993023379 and WO2002042277 the contents of which are hereby incorporated by reference for all purposes and the specific purposes identified herein. In some embodiments, such compounds are represented by any one or more of the structures shown in Table 24. Any one of the compounds depicted in Table 24 is suitable for use in the methods of the present disclosure.

TABLE 21

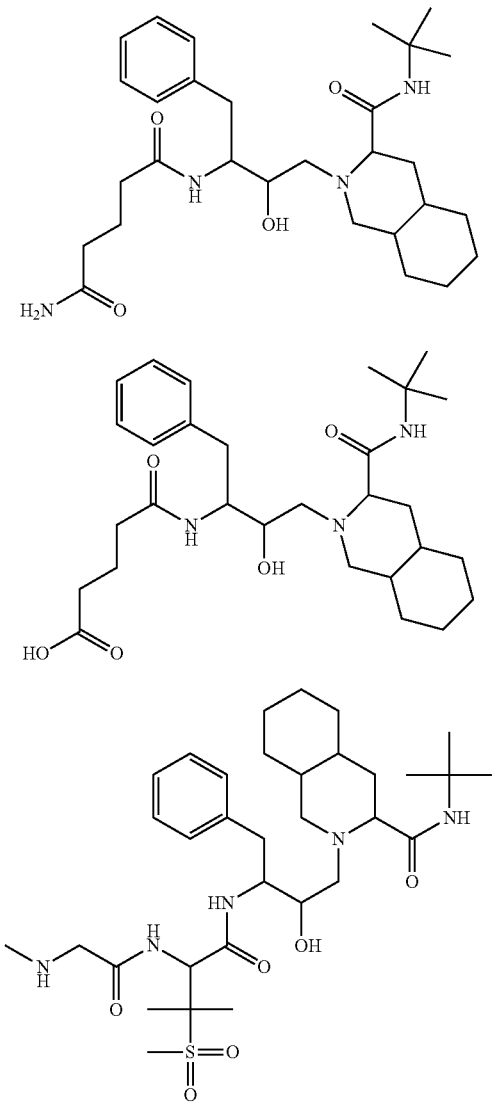

TABLE 21-continued
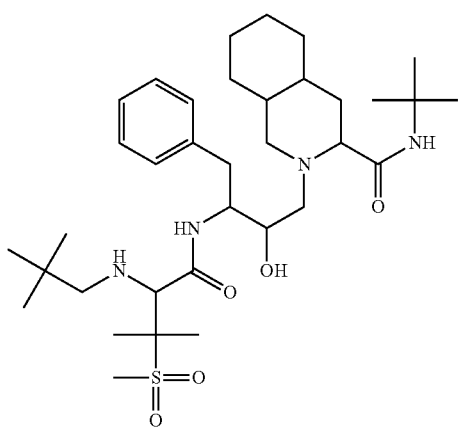 [SMILES: CC(C)(C)CNC(C(=O)NC(Cc1ccccc1)C(O)CN1CC2CCCCC2CC1C(=O)NC(C)(C)C)C(C)(C)S(C)(=O)=O]
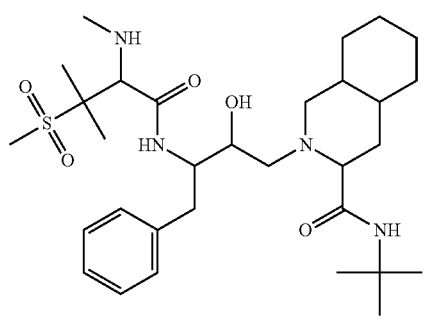 [SMILES: CNC(C(=O)NC(Cc1ccccc1)C(O)CN1CC2CCCCC2CC1C(=O)NC(C)(C)C)C(C)(C)S(C)(=O)=O]
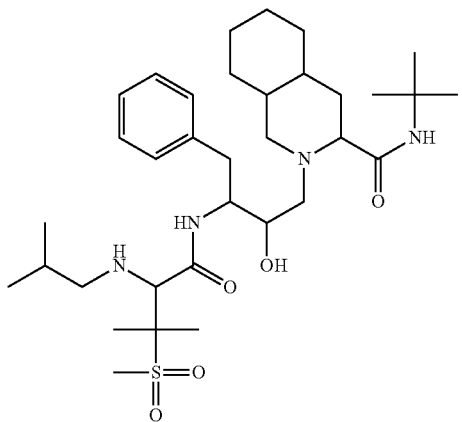 [SMILES: CC(C)CNC(C(=O)NC(Cc1ccccc1)C(O)CN1CC2CCCCC2CC1C(=O)NC(C)(C)C)C(C)(C)S(C)(=O)=O]
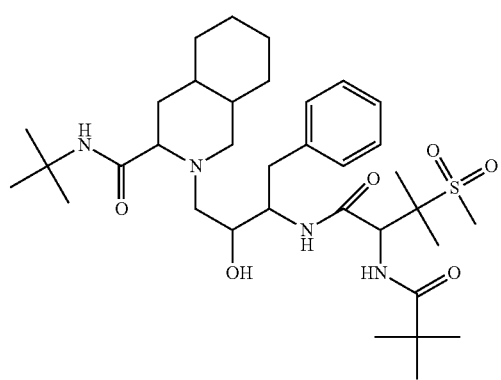 [SMILES: CC(C)(C)NC(=O)C1CC2CCCCC2CN1CC(O)C(Cc1ccccc1)NC(=O)C(NC(=O)C(C)(C)C)C(C)(C)S(C)(=O)=O]
TABLE 21-continued
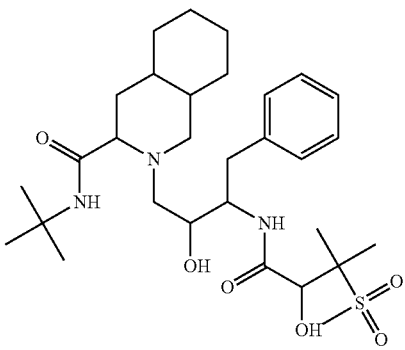 [SMILES: CC(C)(C)NC(=O)C1CC2CCCCC2CN1CC(O)C(Cc1ccccc1)NC(=O)C(O)C(C)(C)S(C)(=O)=O]
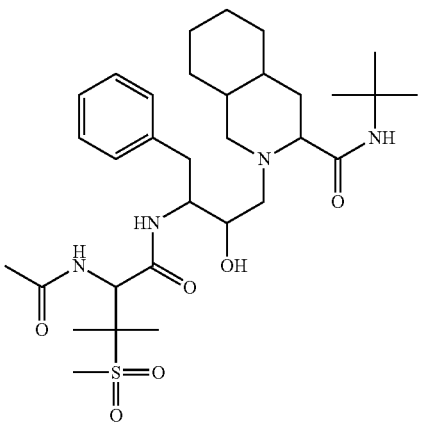 [SMILES: CC(=O)NC(C(=O)NC(Cc1ccccc1)C(O)CN1CC2CCCCC2CC1C(=O)NC(C)(C)C)C(C)(C)S(C)(=O)=O]
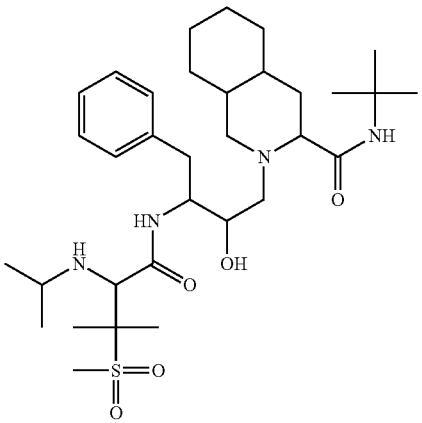 [SMILES: CC(C)NC(C(=O)NC(Cc1ccccc1)C(O)CN1CC2CCCCC2CC1C(=O)NC(C)(C)C)C(C)(C)S(C)(=O)=O]
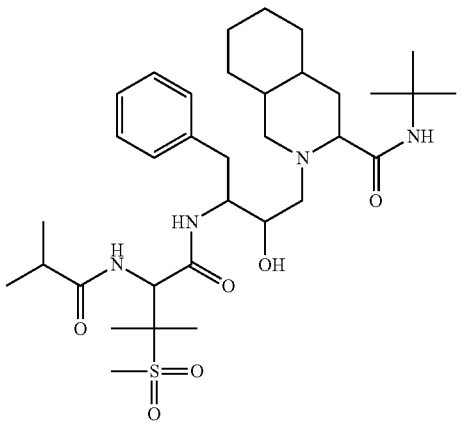

TABLE 21-continued
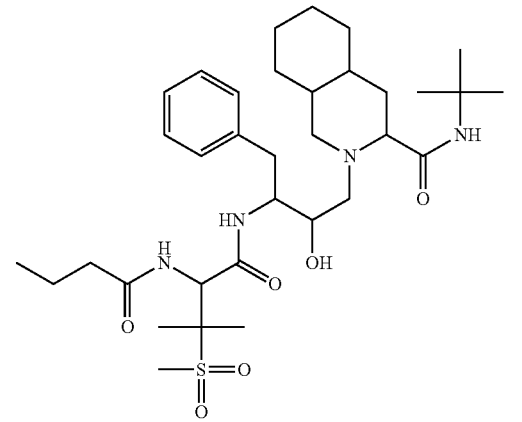 [SMILES: CCCC(=O)NC(C(=O)NC(Cc1ccccc1)C(O)CN1CC2CCCCC2CC1C(=O)NC(C)(C)C)C(C)(C)S(C)(=O)=O]
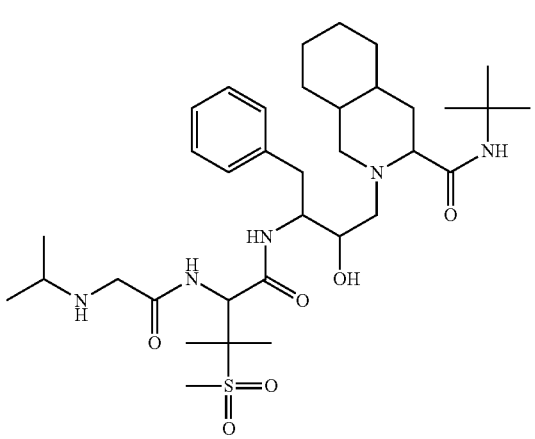 [SMILES: CC(C)NCC(=O)NC(C(=O)NC(Cc1ccccc1)C(O)CN1CC2CCCCC2CC1C(=O)NC(C)(C)C)C(C)(C)S(C)(=O)=O]
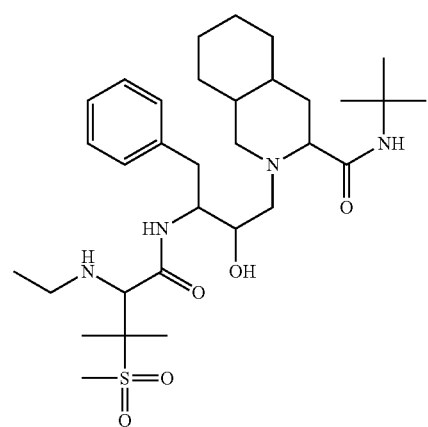 [SMILES: CCNC(C(=O)NC(Cc1ccccc1)C(O)CN1CC2CCCCC2CC1C(=O)NC(C)(C)C)C(C)(C)S(C)(=O)=O]
TABLE 21-continued
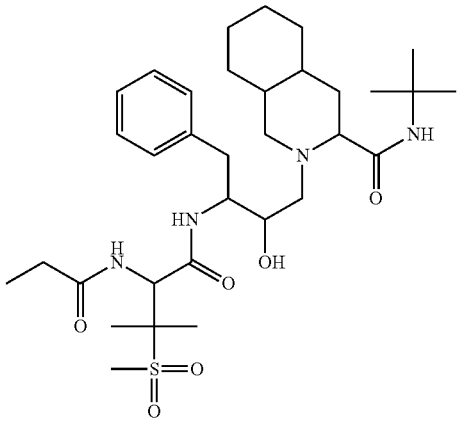
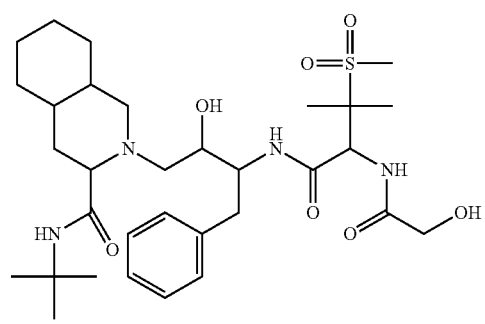 [SMILES: CC(C)(C)NC(=O)C1CC2CCCCC2CN1CC(O)C(Cc1ccccc1)NC(=O)C(NC(=O)CO)C(C)(C)S(C)(=O)=O]
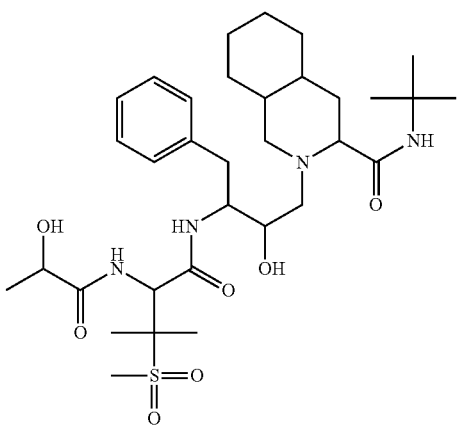 [SMILES: CC(O)C(=O)NC(C(=O)NC(Cc1ccccc1)C(O)CN1CC2CCCCC2CC1C(=O)NC(C)(C)C)C(C)(C)S(C)(=O)=O]
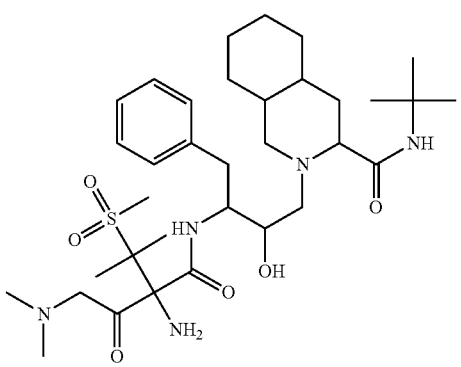 [SMILES: CN(C)CC(=O)C(N)(C(=O)NC(Cc1ccccc1)C(O)CN1CC2CCCCC2CC1C(=O)NC(C)(C)C)C(C)(C)S(C)(=O)=O]

TABLE 21-continued
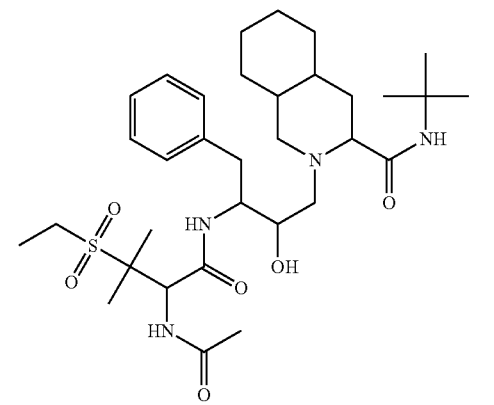 [SMILES: CCS(=O)(=O)C(C)(C)C(NC(C)=O)C(=O)NC(Cc1ccccc1)C(O)CN1CC2CCCCC2CC1C(=O)NC(C)(C)C]
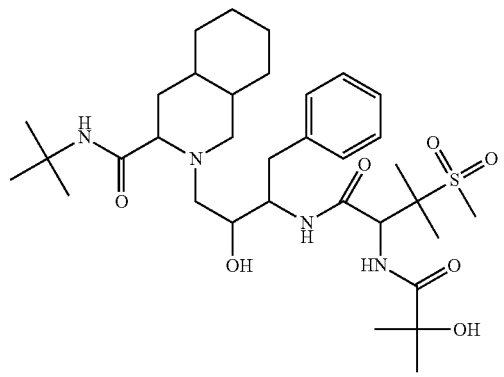 [SMILES: CC(C)(C)NC(=O)C1CC2CCCCC2CN1CC(O)C(Cc1ccccc1)NC(=O)C(NC(=O)C(C)(C)O)C(C)(C)S(C)(=O)=O]
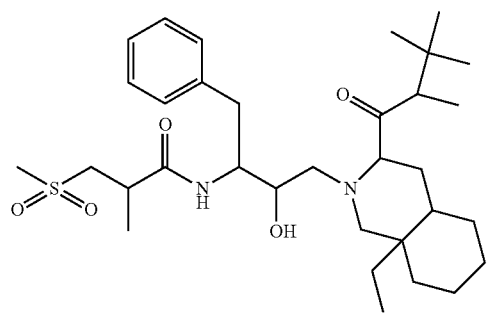 [SMILES: CCC12CCCCC1CC(C(=O)C(C)C(C)(C)C)N(CC(O)C(Cc1ccccc1)NC(=O)C(C)CS(C)(=O)=O)C2]
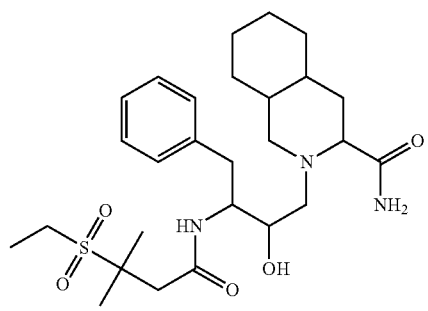 [SMILES: CCS(=O)(=O)C(C)(C)CC(=O)NC(Cc1ccccc1)C(O)CN1CC2CCCCC2CC1C(N)=O]
TABLE 21-continued
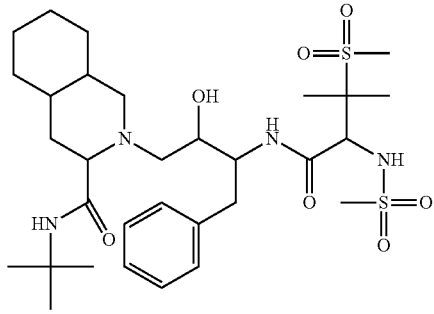 [SMILES: CC(C)(C)NC(=O)C1CC2CCCCC2CN1CC(O)C(Cc1ccccc1)NC(=O)C(NS(C)(=O)=O)C(C)(C)S(C)(=O)=O]
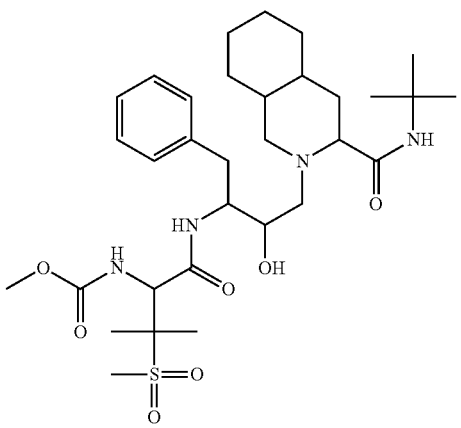
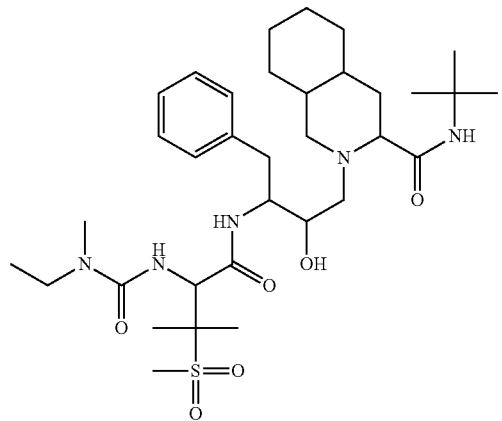 [SMILES: CCN(C)C(=O)NC(C(=O)NC(Cc1ccccc1)C(O)CN1CC2CCCCC2CC1C(=O)NC(C)(C)C)C(C)(C)S(C)(=O)=O]
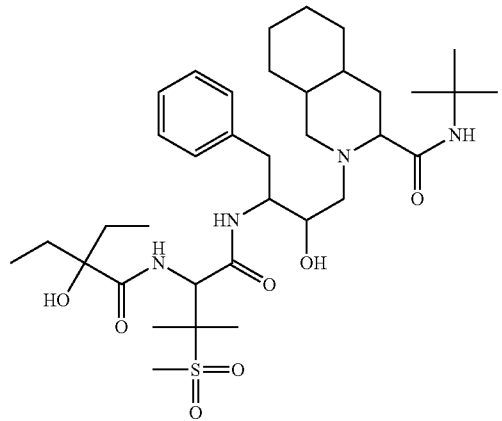 [SMILES: CCC(O)(CC)C(=O)NC(C(=O)NC(Cc1ccccc1)C(O)CN1CC2CCCCC2CC1C(=O)NC(C)(C)C)C(C)(C)S(C)(=O)=O]

TABLE 21-continued

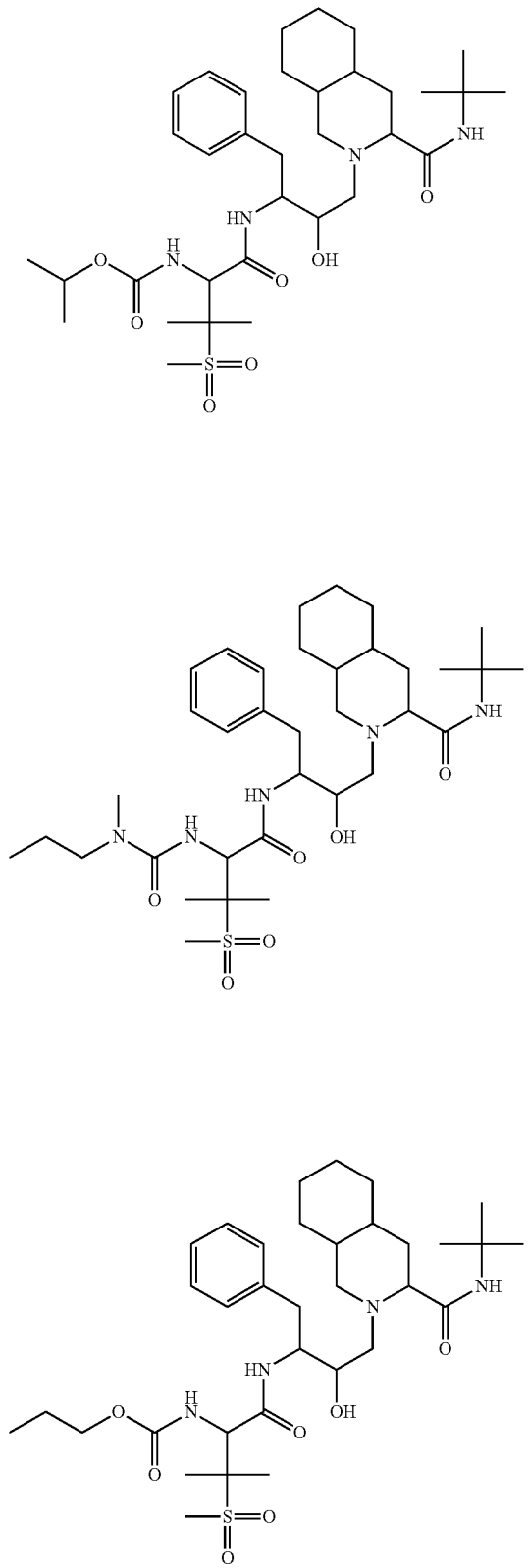

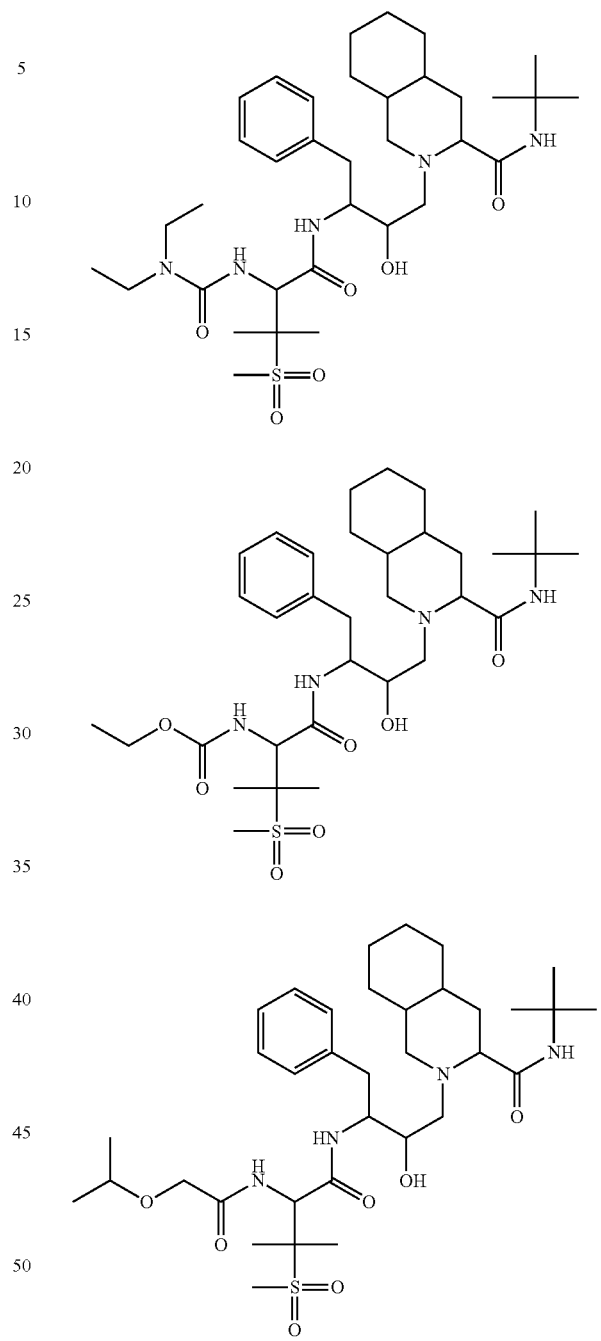

In one implementation, the compound is SC-49483([(2R, 3R,4R,5S)-3,4,5-tri(butanoyloxy)-1-butylpiperidin-2-yl] methyl butanoate), a clinically investigated alpha-glucosidase inhibitor. In one particular implementation, the compound, or variations and permutations thereof, is further described in WO2006073456 the contents of which are hereby incorporated by reference for all purposes and the specific purposes identified herein. In some embodiments, such compounds are represented by any one or more of the structures shown in Table 25. Any one of the compounds depicted in Table 25 is suitable for use in the methods of the present disclosure.

TABLE 22

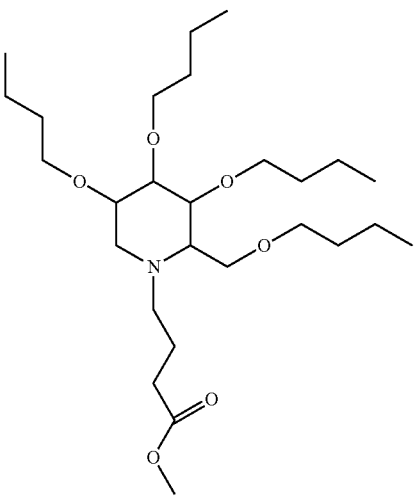 [SMILES: CCCCOCC1C(OCCCC)C(OCCCC)C(OCCCC)CN1CCCC(=O)OC]

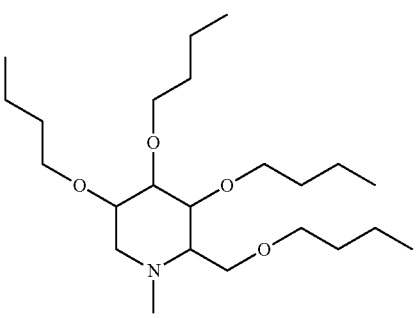 [SMILES: CCCCOCC1C(OCCCC)C(OCCCC)C(OCCCC)CN1C]

In one implementation, the compound is SC-49992 ((3S)-4-[(1S)-1-carboxy-2-phenylethyl]amino]-3-[8-(diaminomethylideneamino)octanoylamino]-4-oxobutanoic acid), a clinically investigated GP IIb IIIa antagonist and described according to:

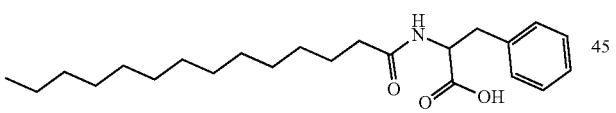

In one particular implementation, the compound, or variations and permutations thereof, is further described in JP2000159746 the contents of which are hereby incorporated by reference for all purposes and the specific purposes identified herein.

In one implementation, the compound is SM-8849 (4-[1-(3-fluoro-4-phenylphenyl)ethyl]-N-methyl-1,3-thiazol-2-amine), a clinically investigated 2-Aminothiazole compounds useful as aspartyl protease inhibitors. In one particular implementation, the compound, or variations and permutations thereof, is further described in WO2005097767 the contents of which are hereby incorporated by reference for all purposes and the specific purposes identified herein. In some embodiments, such compounds are represented by any one or more of the structures shown in Table 26. Any one of the compounds depicted in Table 26 is suitable for use in the methods of the present disclosure.

TABLE 23

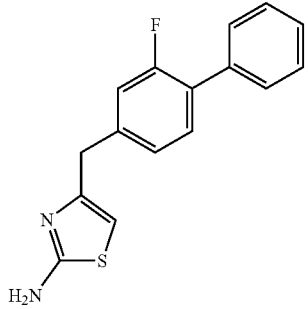 [SMILES: Nc1nc(Cc2ccc(-c3ccccc3)c(F)c2)cs1]

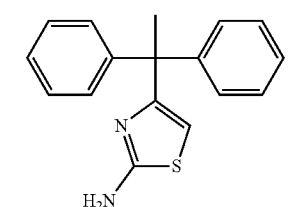

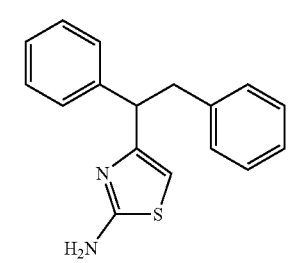 [SMILES: Nc1nc(C(Cc2ccccc2)c2ccccc2)cs1]

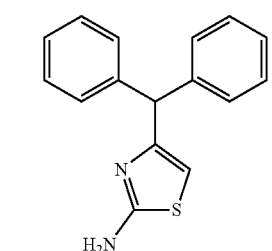

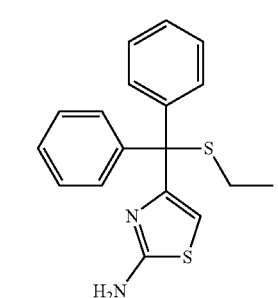

In one implementation, the compound is Sch-42495 (ethyl (2S)-2-[[(2S)-2-(acetylsulfanylmethyl)-3-(2-methylphenyl)propanoyl]amino]-4-methylsulfanylbutanoate) a clinically investigated endopeptidase inhibitor, In one particular implementation, the compound, or variations and permutations thereof, is further described in WO1999050229 the contents of which are hereby incorporated by reference for all purposes and the specific purposes identified herein In one further implementation, the compound has the formula:

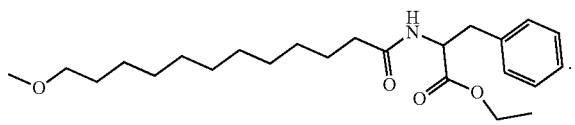 [SMILES: CCOC(=O)C(Cc1ccccc1)NC(=O)CCCCCCCCCCCOC]

In one implementation, the compound is TMB-607 (methyl N-[(2S)-1-[[(5S)-5-[(4-aminophenyl) sulfonyl-(2-methylpropyl)amino]-6-hydroxyhexyl]amino]-1-oxo-3,3-diphenylpropan-2-yl]carbamate), a clinically investigated HIV protease inhibitor. In one particular implementation, the compound, or variations and permutations thereof, is further described in PE20091208; SG00129185; WO2004056764; WO2008078200; WO2009042093; WO2012055031 the contents of which are hereby incorporated by reference for all purposes and the specific purposes identified herein. In some embodiments, such compounds are represented by any one or more of the structures shown in Table 27. Any one of the compounds depicted in Table 27 is suitable for use in the methods of the present disclosure.

TABLE 24

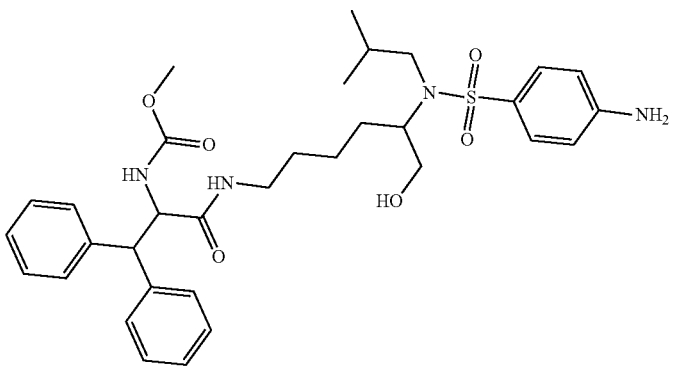 [SMILES: COC(=O)NC(C(=O)NCCCCC(CO)N(CC(C)C)S(=O)(=O)c1ccc(N)cc1)C(c1ccccc1)c1ccccc1]

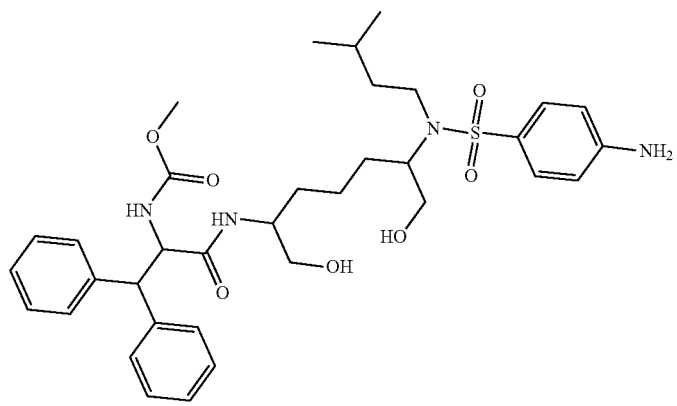 [SMILES: COC(=O)NC(C(=O)NC(CO)CCCC(CO)N(CCC(C)C)S(=O)(=O)c1ccc(N)cc1)C(c1ccccc1)c1ccccc1]

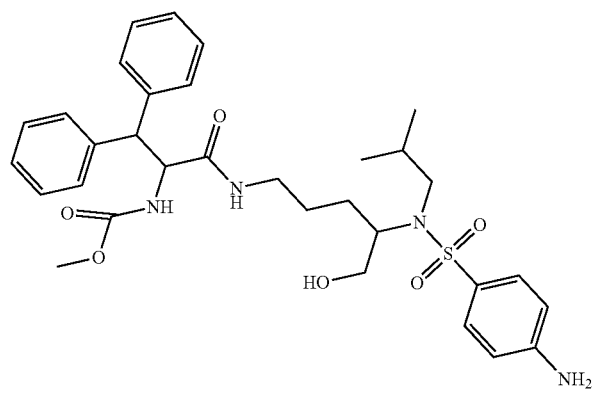 [SMILES: COC(=O)NC(C(=O)NCCCC(CO)N(CC(C)C)S(=O)(=O)c1ccc(N)cc1)C(c1ccccc1)c1ccccc1]

TABLE 24-continued
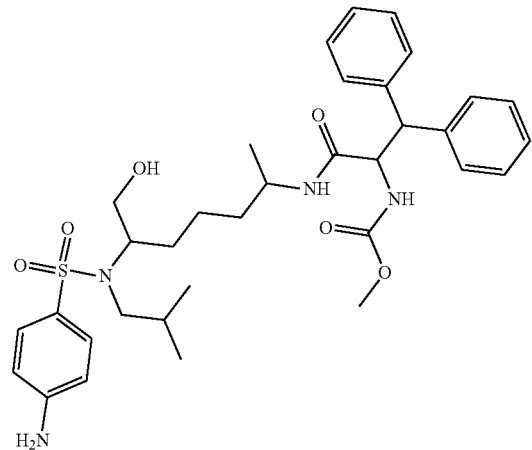 [SMILES: COC(=O)NC(C(=O)NC(C)CCCC(CO)N(CC(C)C)S(=O)(=O)c1ccc(N)cc1)C(c1ccccc1)c1ccccc1]
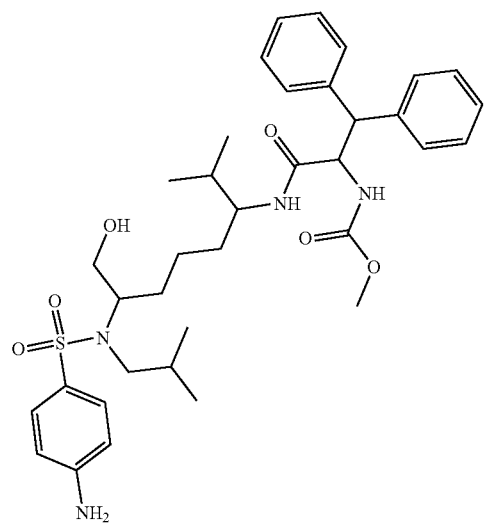 [SMILES: COC(=O)NC(C(=O)NC(CCCC(CO)N(CC(C)C)S(=O)(=O)c1ccc(N)cc1)C(C)C)C(c1ccccc1)c1ccccc1]
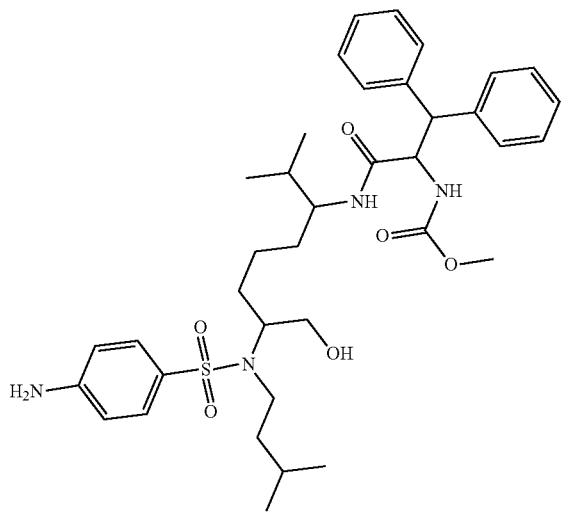 [SMILES: COC(=O)NC(C(=O)NC(CCCC(CO)N(CCC(C)C)S(=O)(=O)c1ccc(N)cc1)C(C)C)C(c1ccccc1)c1ccccc1]

TABLE 24-continued
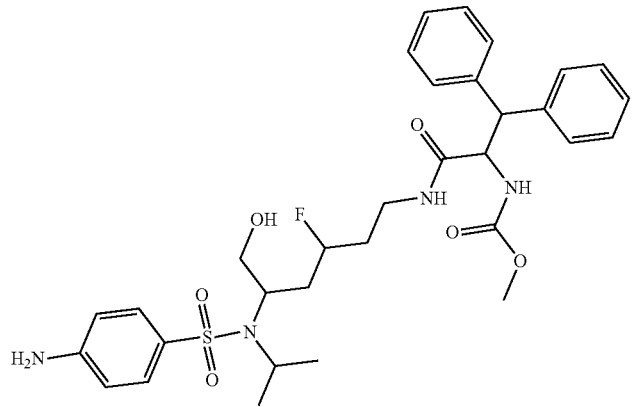 [SMILES: COC(=O)NC(C(=O)NCCC(F)CC(CO)N(C(C)C)S(=O)(=O)c1ccc(N)cc1)C(c1ccccc1)c1ccccc1]
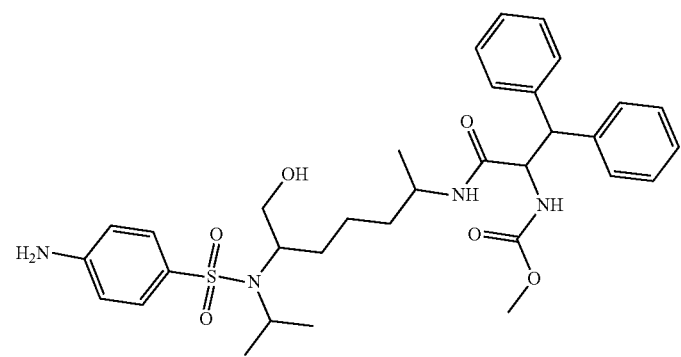 [SMILES: COC(=O)NC(C(=O)NC(C)CCCC(CO)N(C(C)C)S(=O)(=O)c1ccc(N)cc1)C(c1ccccc1)c1ccccc1]
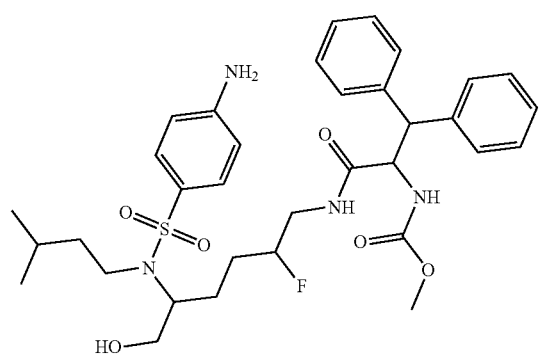 [SMILES: COC(=O)NC(C(=O)NCC(F)CCC(CO)N(CCC(C)C)S(=O)(=O)c1ccc(N)cc1)C(c1ccccc1)c1ccccc1]

TABLE 24-continued
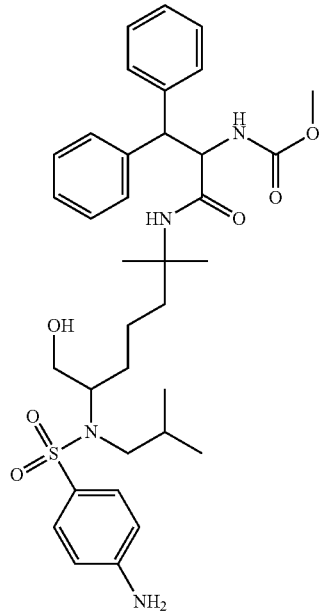 [SMILES: COC(=O)NC(C(=O)NC(C)(C)CCCC(CO)N(CC(C)C)S(=O)(=O)c1ccc(N)cc1)C(c1ccccc1)c1ccccc1]
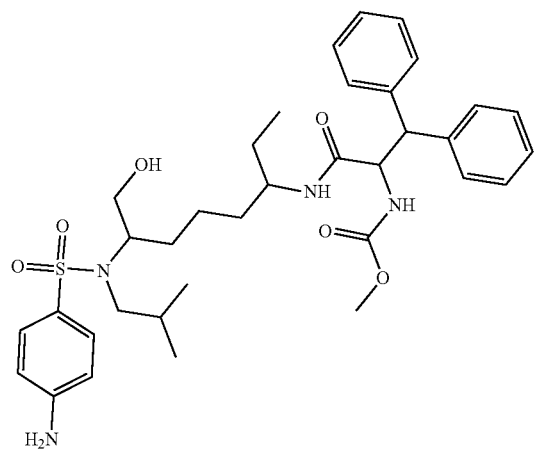 [SMILES: CCC(CCCC(CO)N(CC(C)C)S(=O)(=O)c1ccc(N)cc1)NC(=O)C(NC(=O)OC)C(c1ccccc1)c1ccccc1]
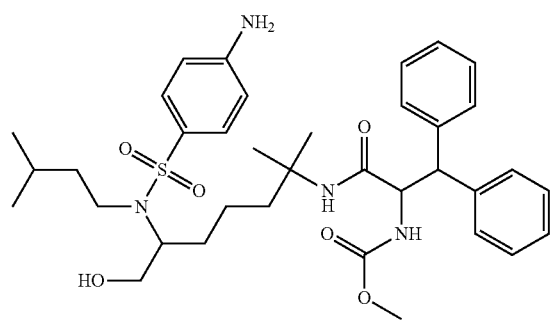 [SMILES: COC(=O)NC(C(=O)NC(C)(C)CCCC(CO)N(CCC(C)C)S(=O)(=O)c1ccc(N)cc1)C(c1ccccc1)c1ccccc1]

TABLE 24-continued
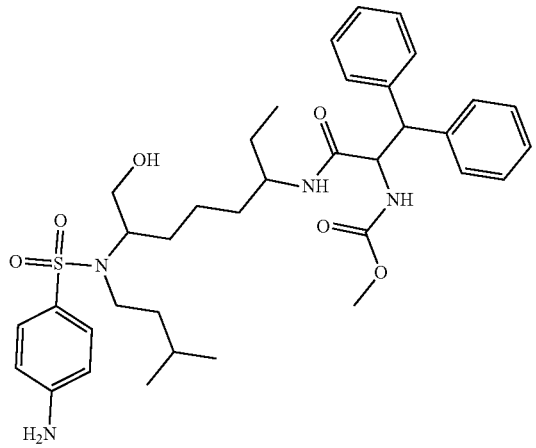 [SMILES: CCC(CCCC(CO)N(CCC(C)C)S(=O)(=O)c1ccc(N)cc1)NC(=O)C(NC(=O)OC)C(c1ccccc1)c1ccccc1]
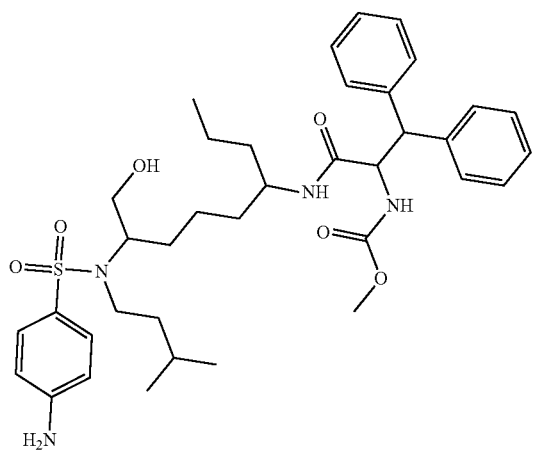 [SMILES: CCCC(CCCC(CO)N(CCC(C)C)S(=O)(=O)c1ccc(N)cc1)NC(=O)C(NC(=O)OC)C(c1ccccc1)c1ccccc1]
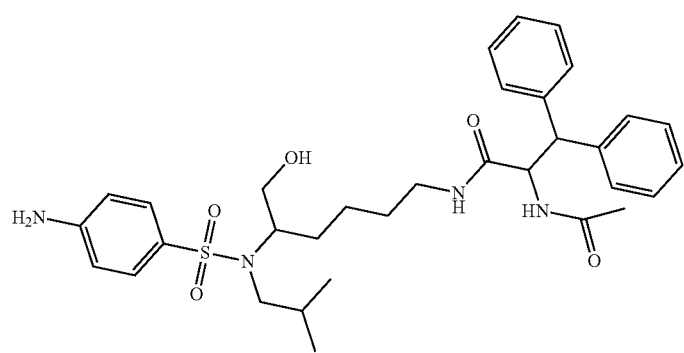 [SMILES: CC(=O)NC(C(=O)NCCCCC(CO)N(CC(C)C)S(=O)(=O)c1ccc(N)cc1)C(c1ccccc1)c1ccccc1]

TABLE 24-continued
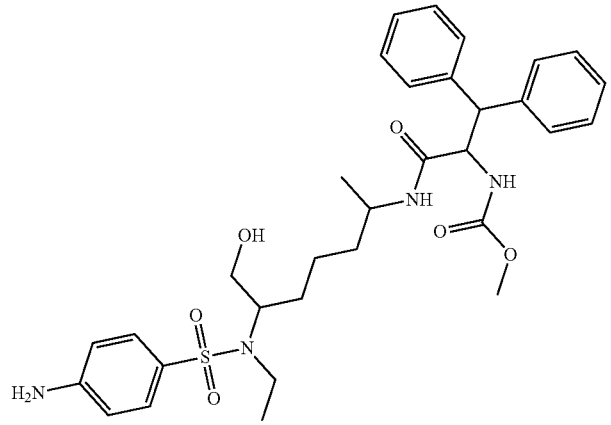 [SMILES: CCN(C(CO)CCCC(C)NC(=O)C(NC(=O)OC)C(c1ccccc1)c1ccccc1)S(=O)(=O)c1ccc(N)cc1]
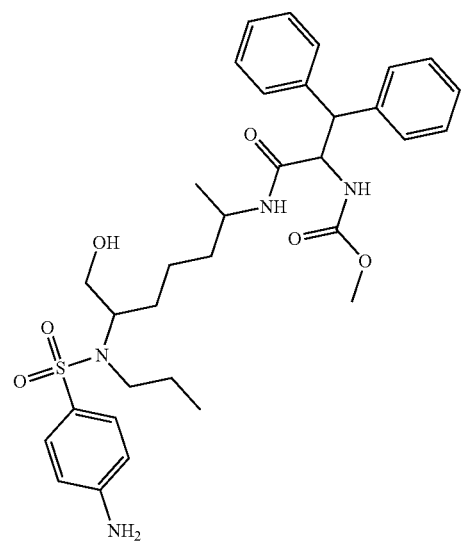 [SMILES: CCCN(C(CO)CCCC(C)NC(=O)C(NC(=O)OC)C(c1ccccc1)c1ccccc1)S(=O)(=O)c1ccc(N)cc1]
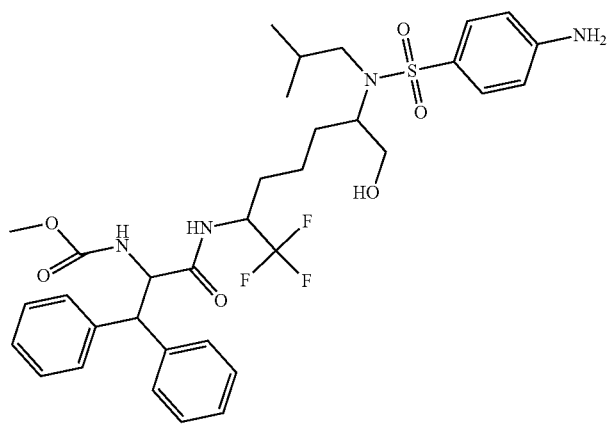 [SMILES: COC(=O)NC(C(=O)NC(CCCC(CO)N(CC(C)C)S(=O)(=O)c1ccc(N)cc1)C(F)(F)F)C(c1ccccc1)c1ccccc1]

TABLE 24-continued
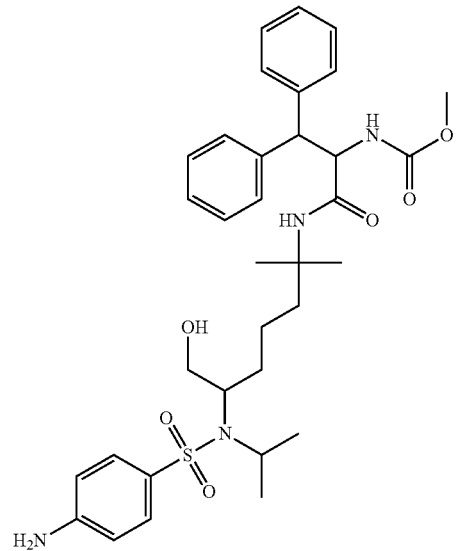 [SMILES: COC(=O)NC(C(=O)NC(C)(C)CCCC(CO)N(C(C)C)S(=O)(=O)c1ccc(N)cc1)C(c1ccccc1)c1ccccc1]
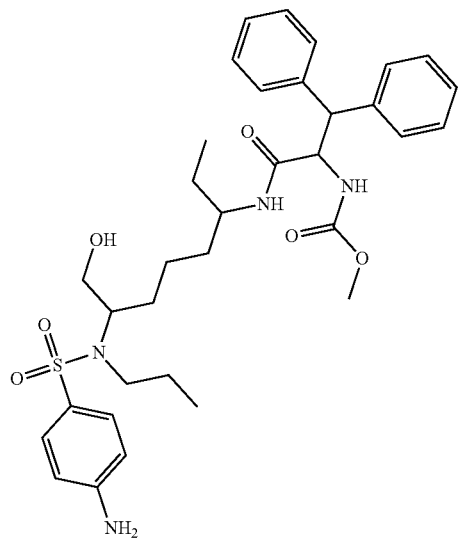 [SMILES: CCCN(C(CO)CCCC(CC)NC(=O)C(NC(=O)OC)C(c1ccccc1)c1ccccc1)S(=O)(=O)c1ccc(N)cc1]
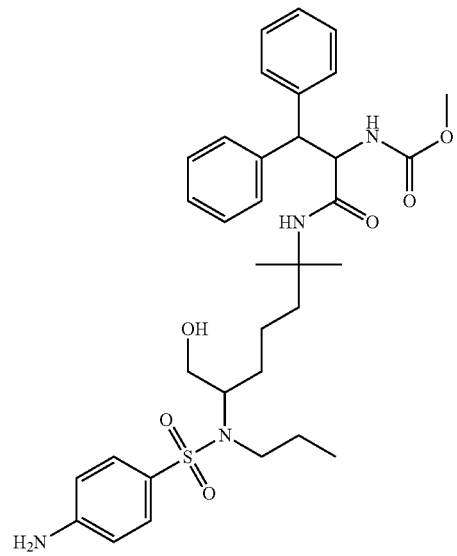 [SMILES: CCCN(C(CO)CCCC(C)(C)NC(=O)C(NC(=O)OC)C(c1ccccc1)c1ccccc1)S(=O)(=O)c1ccc(N)cc1]

TABLE 24-continued
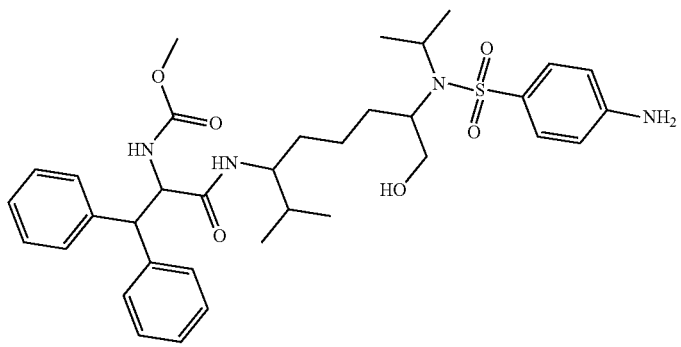 [SMILES: COC(=O)NC(C(=O)NC(CCCC(CO)N(C(C)C)S(=O)(=O)c1ccc(N)cc1)C(C)C)C(c1ccccc1)c1ccccc1]
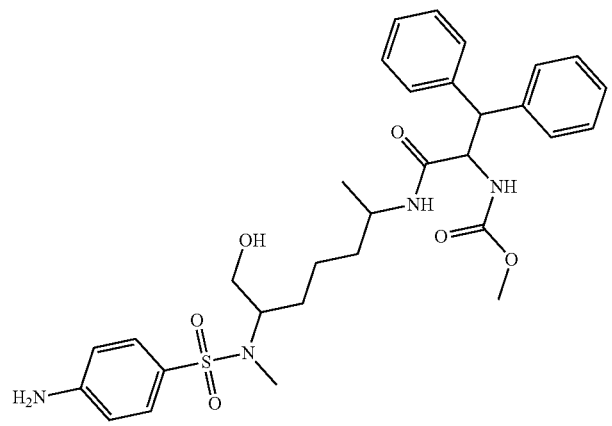 [SMILES: COC(=O)NC(C(=O)NC(C)CCCC(CO)N(C)S(=O)(=O)c1ccc(N)cc1)C(c1ccccc1)c1ccccc1]
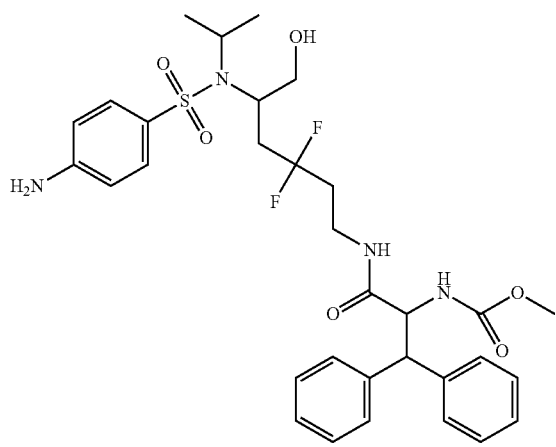 [SMILES: COC(=O)NC(C(=O)NCCC(F)(F)CC(CO)N(C(C)C)S(=O)(=O)c1ccc(N)cc1)C(c1ccccc1)c1ccccc1]

TABLE 24-continued
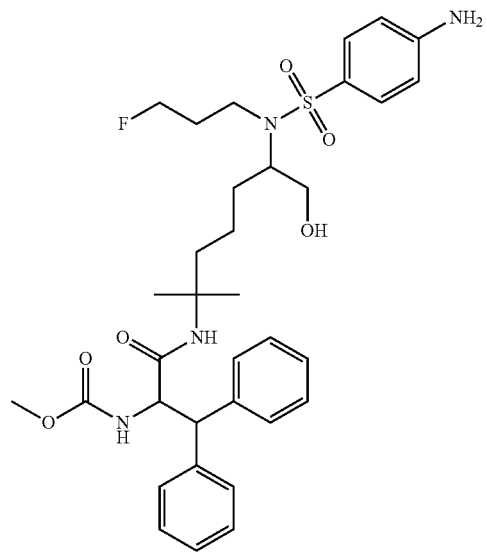 [SMILES: COC(=O)NC(C(=O)NC(C)(C)CCCC(CO)N(CCCF)S(=O)(=O)c1ccc(N)cc1)C(c1ccccc1)c1ccccc1]
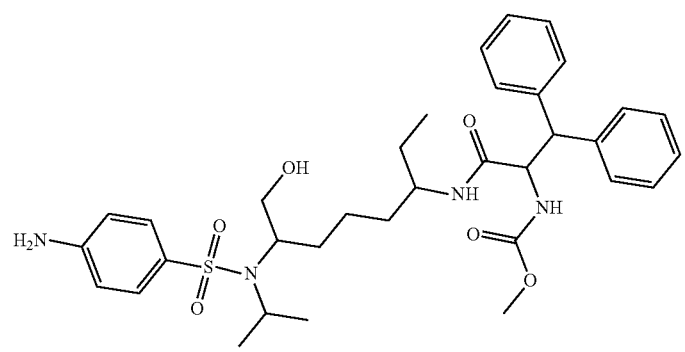 [SMILES: CCC(CCCC(CO)N(C(C)C)S(=O)(=O)c1ccc(N)cc1)NC(=O)C(NC(=O)OC)C(c1ccccc1)c1ccccc1]
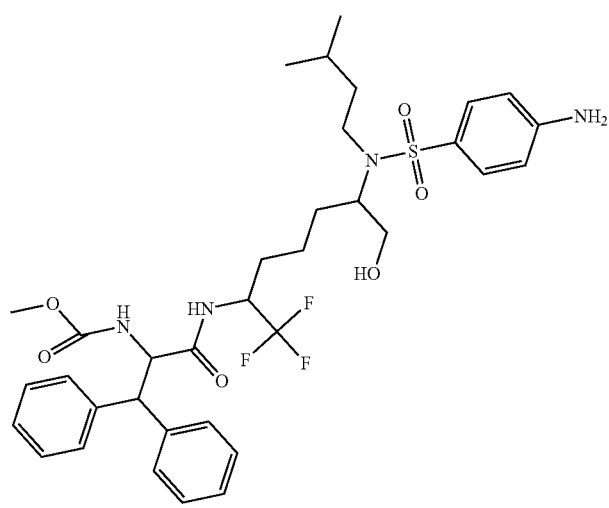 [SMILES: COC(=O)NC(C(=O)NC(CCCC(CO)N(CCC(C)C)S(=O)(=O)c1ccc(N)cc1)C(F)(F)F)C(c1ccccc1)c1ccccc1]

TABLE 24-continued
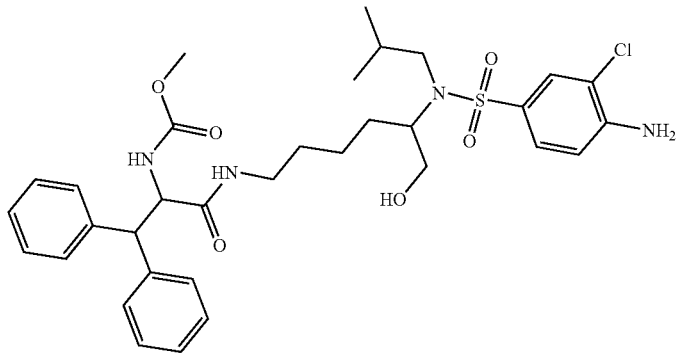 [SMILES: COC(=O)NC(C(=O)NCCCCC(CO)N(CC(C)C)S(=O)(=O)c1ccc(N)c(Cl)c1)C(c1ccccc1)c1ccccc1]
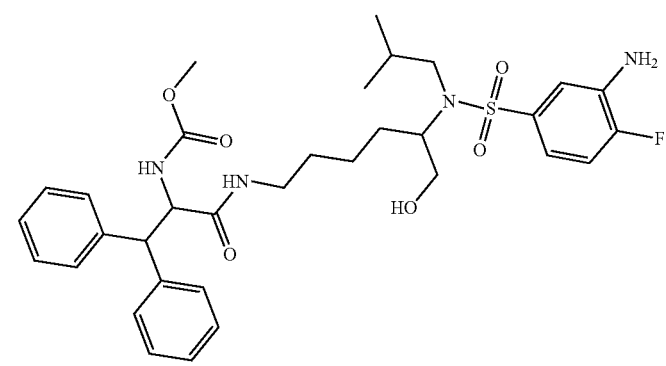 [SMILES: COC(=O)NC(C(=O)NCCCCC(CO)N(CC(C)C)S(=O)(=O)c1ccc(F)c(N)c1)C(c1ccccc1)c1ccccc1]
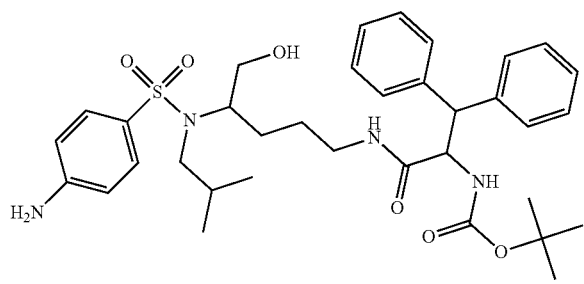 [SMILES: CC(C)CN(C(CO)CCCNC(=O)C(NC(=O)OC(C)(C)C)C(c1ccccc1)c1ccccc1)S(=O)(=O)c1ccc(N)cc1]
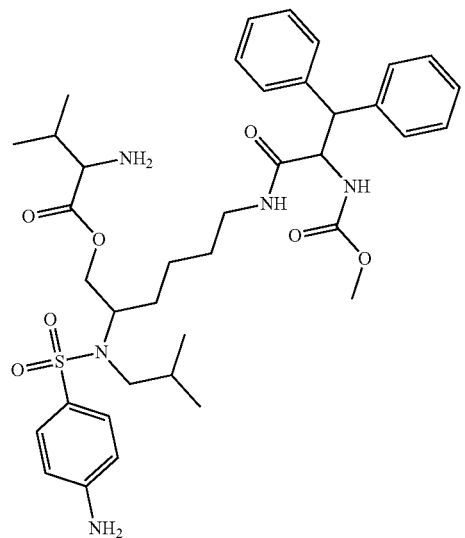 [SMILES: COC(=O)NC(C(=O)NCCCCC(COC(=O)C(N)C(C)C)N(CC(C)C)S(=O)(=O)c1ccc(N)cc1)C(c1ccccc1)c1ccccc1]

TABLE 24-continued
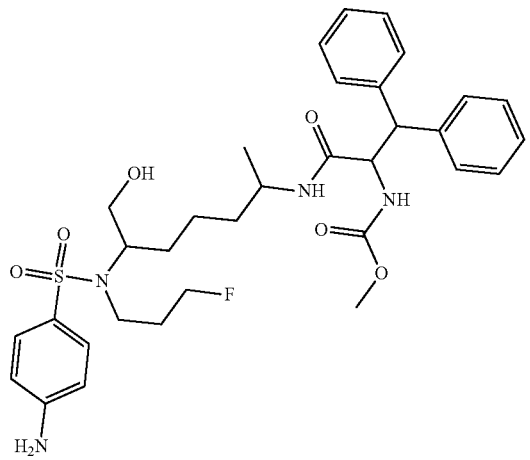 [SMILES: COC(=O)NC(C(=O)NC(C)CCCC(CO)N(CCCF)S(=O)(=O)c1ccc(N)cc1)C(c1ccccc1)c1ccccc1]
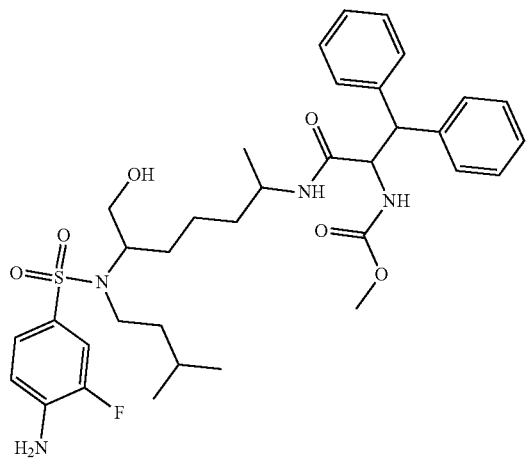 [SMILES: COC(=O)NC(C(=O)NC(C)CCCC(CO)N(CCC(C)C)S(=O)(=O)c1ccc(N)c(F)c1)C(c1ccccc1)c1ccccc1]
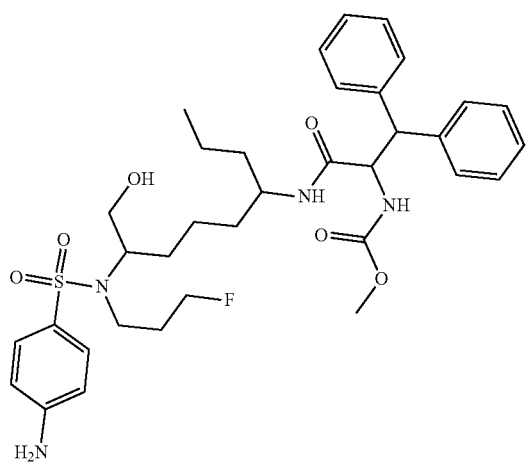 [SMILES: CCCC(CCCC(CO)N(CCCF)S(=O)(=O)c1ccc(N)cc1)NC(=O)C(NC(=O)OC)C(c1ccccc1)c1ccccc1]

TABLE 24-continued
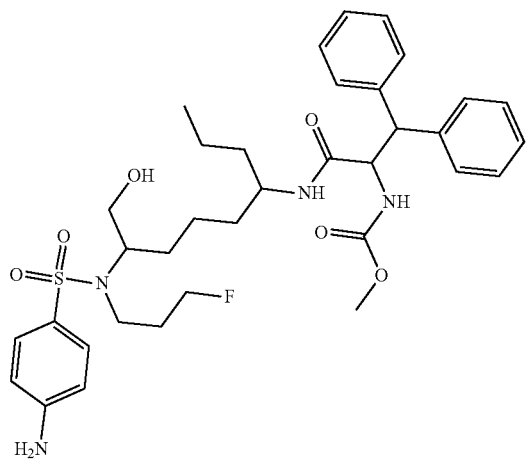 [SMILES: CCCC(CCCC(CO)N(CCCF)S(=O)(=O)c1ccc(N)cc1)NC(=O)C(NC(=O)OC)C(c1ccccc1)c1ccccc1]
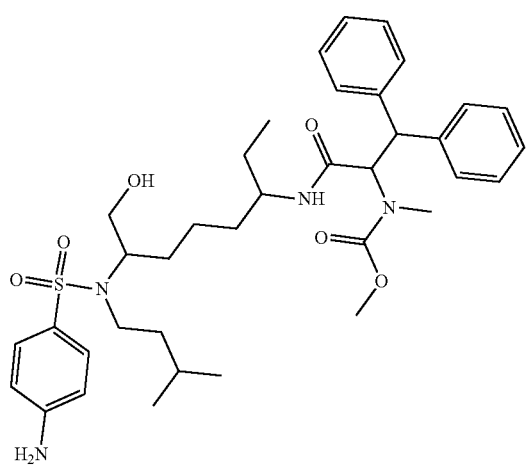 [SMILES: CCC(CCCC(CO)N(CCC(C)C)S(=O)(=O)c1ccc(N)cc1)NC(=O)C(C(c1ccccc1)c1ccccc1)N(C)C(=O)OC]
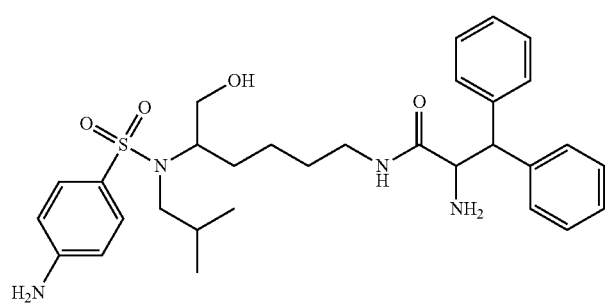 [SMILES: CC(C)CN(C(CO)CCCCNC(=O)C(N)C(c1ccccc1)c1ccccc1)S(=O)(=O)c1ccc(N)cc1]

TABLE 24-continued
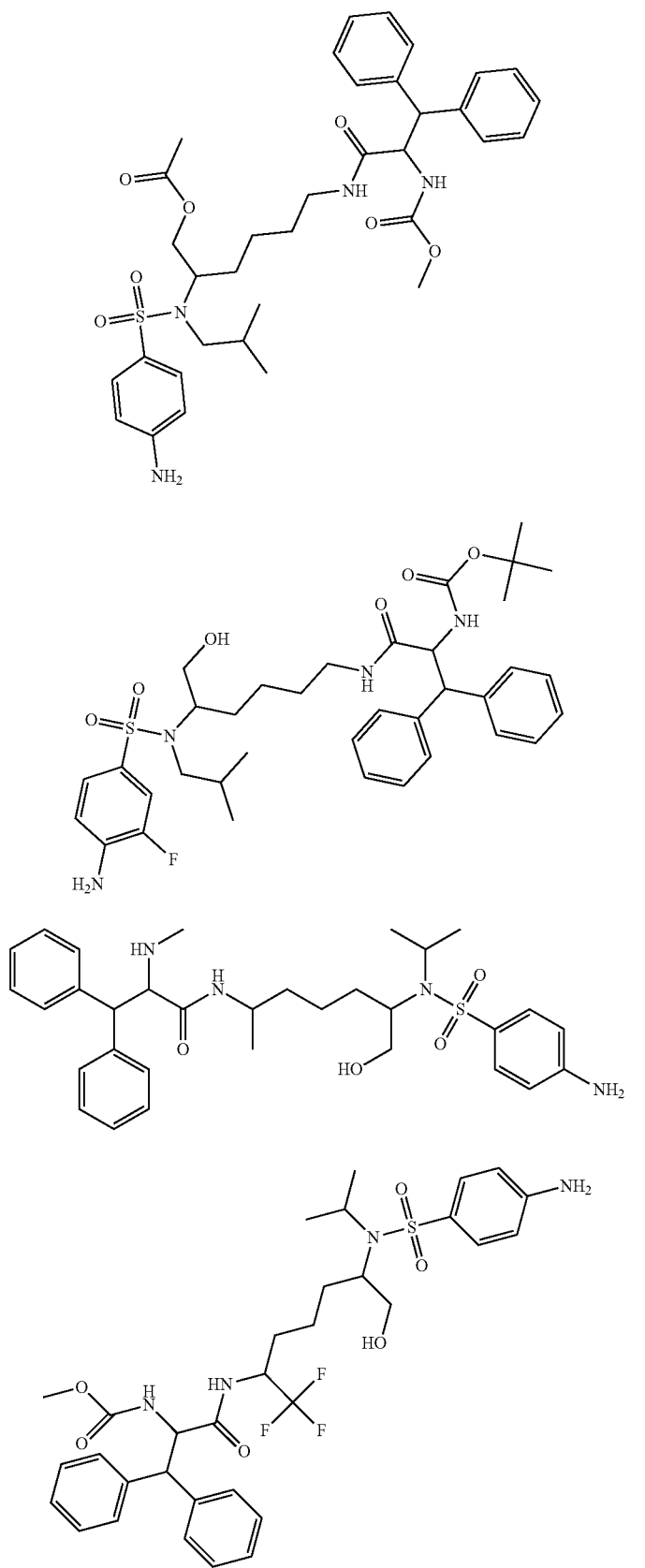

TABLE 24-continued
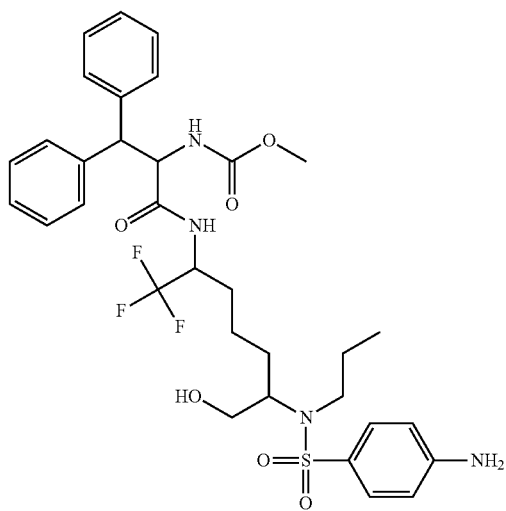 [SMILES: CCCN(C(CO)CCCC(NC(=O)C(NC(=O)OC)C(c1ccccc1)c1ccccc1)C(F)(F)F)S(=O)(=O)c1ccc(N)cc1]
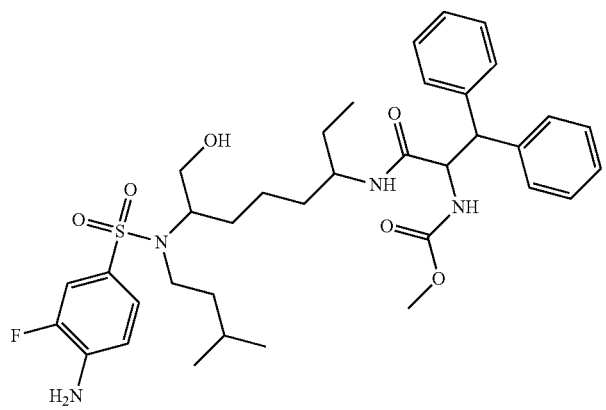 [SMILES: CCC(CCCC(CO)N(CCC(C)C)S(=O)(=O)c1ccc(N)c(F)c1)NC(=O)C(NC(=O)OC)C(c1ccccc1)c1ccccc1]
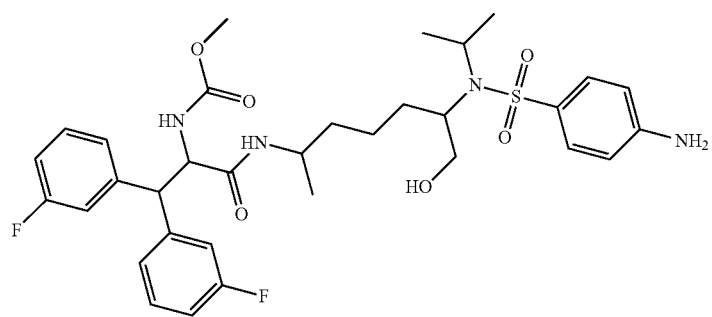 [SMILES: COC(=O)NC(C(=O)NC(C)CCCC(CO)N(C(C)C)S(=O)(=O)c1ccc(N)cc1)C(c1cccc(F)c1)c1cccc(F)c1]

TABLE 24-continued
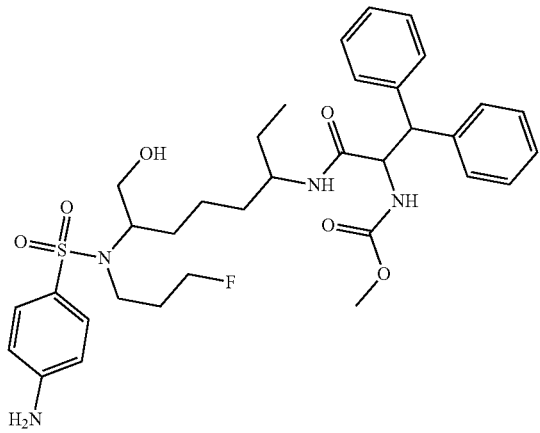 [SMILES: CCC(CCCC(CO)N(CCCF)S(=O)(=O)c1ccc(N)cc1)NC(=O)C(NC(=O)OC)C(c1ccccc1)c1ccccc1]
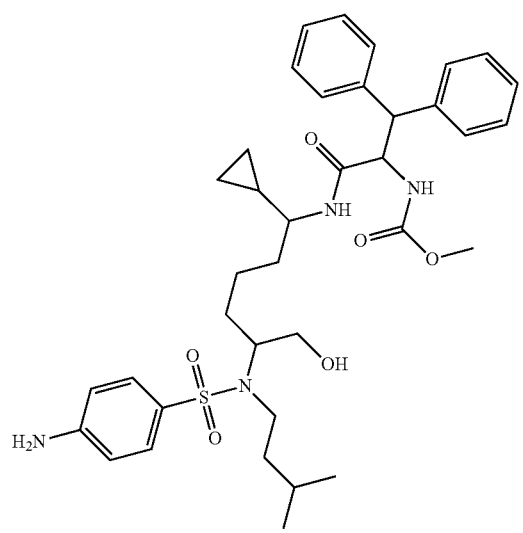 [SMILES: COC(=O)NC(C(=O)NC(CCCC(CO)N(CCC(C)C)S(=O)(=O)c1ccc(N)cc1)C1CC1)C(c1ccccc1)c1ccccc1]
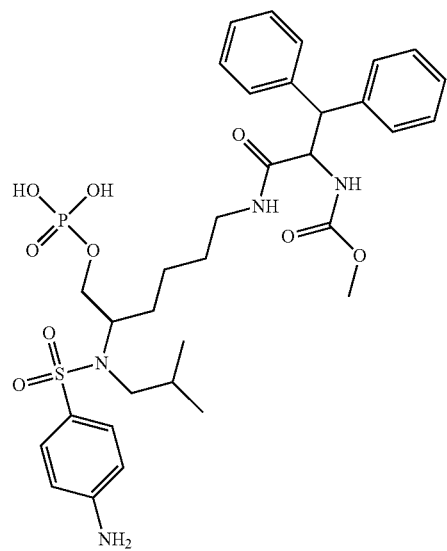 [SMILES: COC(=O)NC(C(=O)NCCCCC(COP(=O)(O)O)N(CC(C)C)S(=O)(=O)c1ccc(N)cc1)C(c1ccccc1)c1ccccc1]

TABLE 24-continued
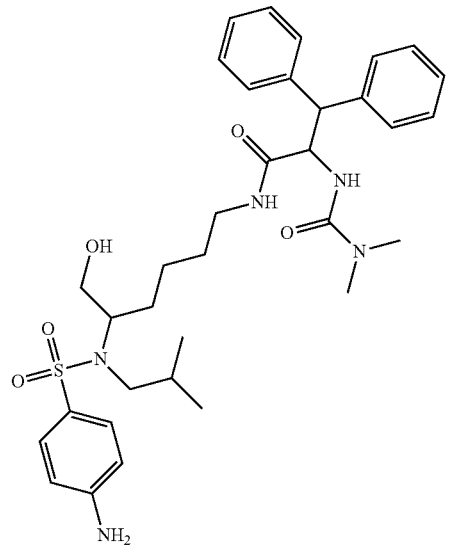 [SMILES: CC(C)CN(C(CO)CCCCNC(=O)C(NC(=O)N(C)C)C(c1ccccc1)c1ccccc1)S(=O)(=O)c1ccc(N)cc1]
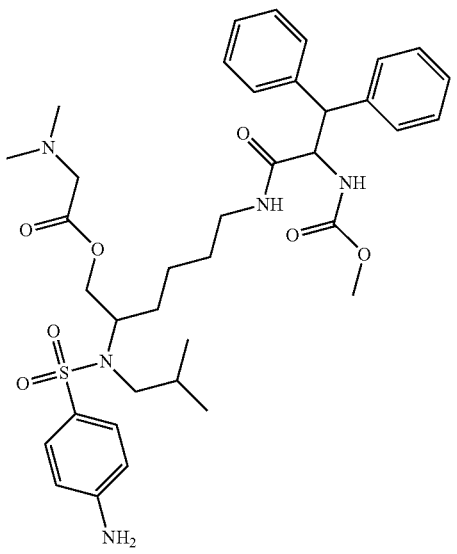 [SMILES: COC(=O)NC(C(=O)NCCCCC(COC(=O)CN(C)C)N(CC(C)C)S(=O)(=O)c1ccc(N)cc1)C(c1ccccc1)c1ccccc1]
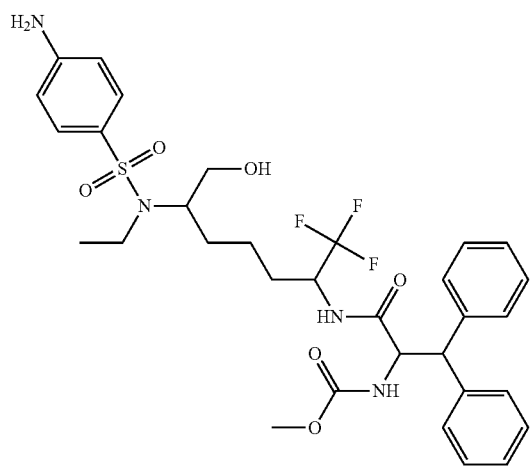 [SMILES: CCN(C(CO)CCCC(NC(=O)C(NC(=O)OC)C(c1ccccc1)c1ccccc1)C(F)(F)F)S(=O)(=O)c1ccc(N)cc1]

TABLE 24-continued
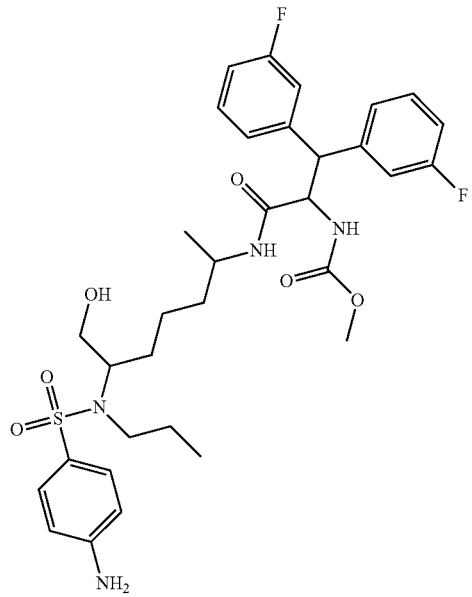 [SMILES: CCCN(C(CO)CCCC(C)NC(=O)C(NC(=O)OC)C(c1cccc(F)c1)c1cccc(F)c1)S(=O)(=O)c1ccc(N)cc1]
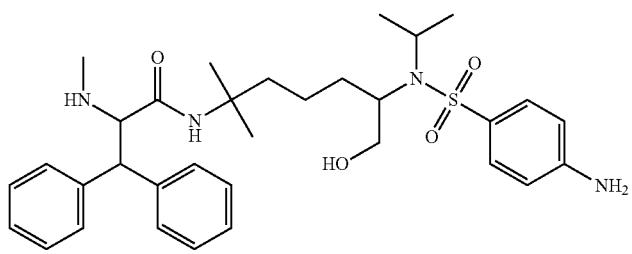 [SMILES: CNC(C(=O)NC(C)(C)CCCC(CO)N(C(C)C)S(=O)(=O)c1ccc(N)cc1)C(c1ccccc1)c1ccccc1]
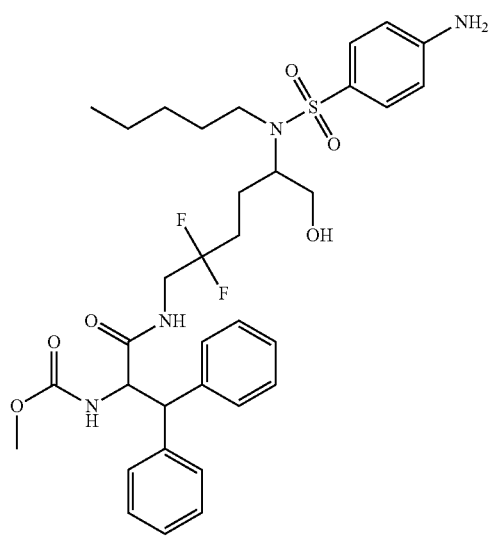 [SMILES: CCCCCN(C(CO)CCC(F)(F)CNC(=O)C(NC(=O)OC)C(c1ccccc1)c1ccccc1)S(=O)(=O)c1ccc(N)cc1]

TABLE 24-continued
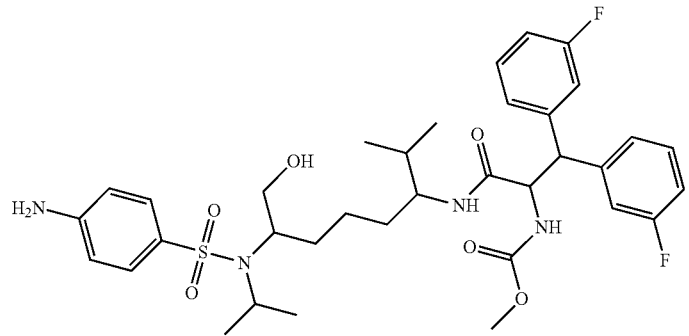 [SMILES: COC(=O)NC(C(=O)NC(CCCC(CO)N(C(C)C)S(=O)(=O)c1ccc(N)cc1)C(C)C)C(c1cccc(F)c1)c1cccc(F)c1]
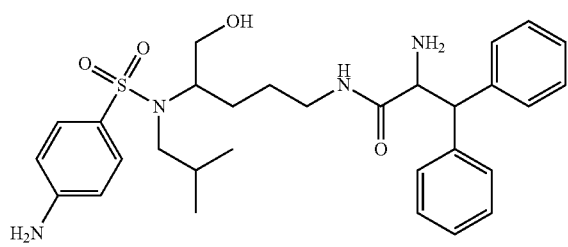 [SMILES: CC(C)CN(C(CO)CCCNC(=O)C(N)C(c1ccccc1)c1ccccc1)S(=O)(=O)c1ccc(N)cc1]
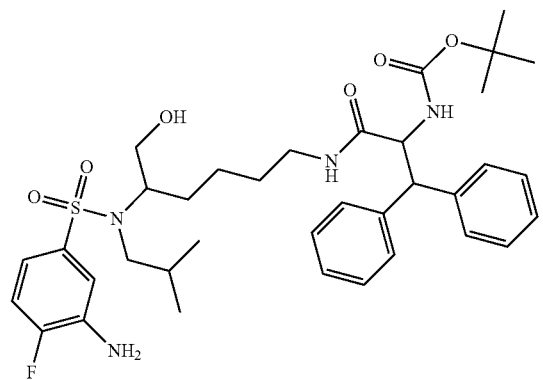 [SMILES: CC(C)CN(C(CO)CCCCNC(=O)C(NC(=O)OC(C)(C)C)C(c1ccccc1)c1ccccc1)S(=O)(=O)c1ccc(F)c(N)c1]
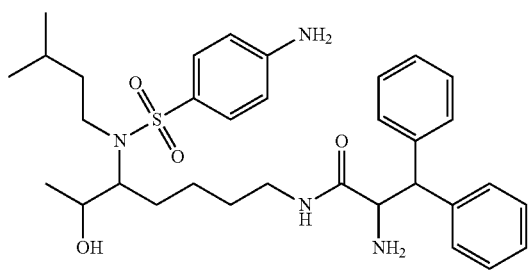 [SMILES: CC(C)CCN(C(CCCCNC(=O)C(N)C(c1ccccc1)c1ccccc1)C(C)O)S(=O)(=O)c1ccc(N)cc1]

TABLE 24-continued
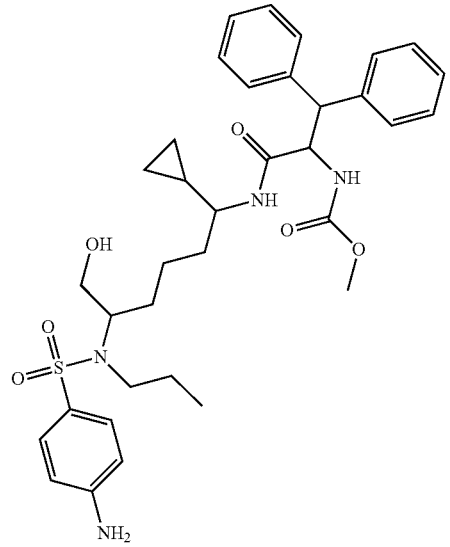 [SMILES: CCCN(C(CO)CCCC(NC(=O)C(NC(=O)OC)C(c1ccccc1)c1ccccc1)C1CC1)S(=O)(=O)c1ccc(N)cc1]
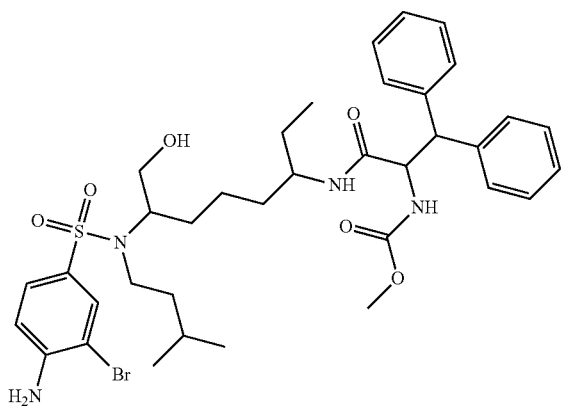 [SMILES: CCC(CCCC(CO)N(CCC(C)C)S(=O)(=O)c1ccc(N)c(Br)c1)NC(=O)C(NC(=O)OC)C(c1ccccc1)c1ccccc1]
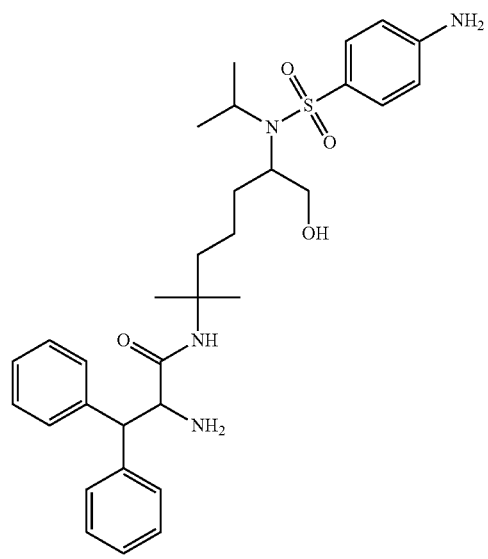 [SMILES: CC(C)N(C(CO)CCCC(C)(C)NC(=O)C(N)C(c1ccccc1)c1ccccc1)S(=O)(=O)c1ccc(N)cc1]

TABLE 24-continued
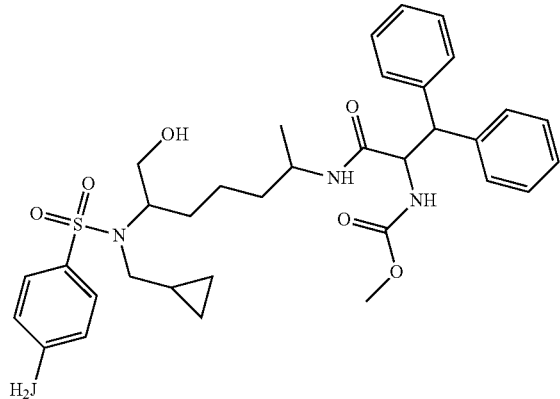
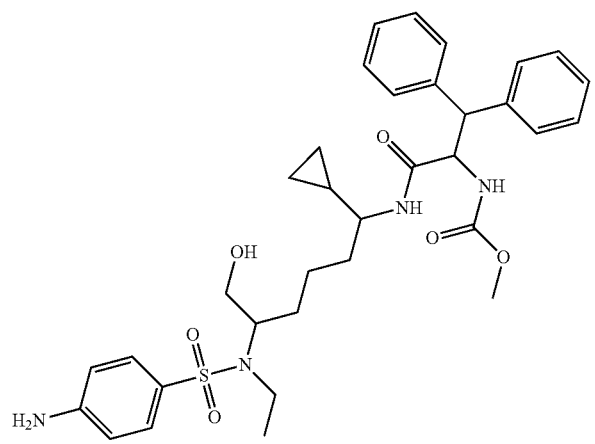 [SMILES: CCN(C(CO)CCCC(NC(=O)C(NC(=O)OC)C(c1ccccc1)c1ccccc1)C1CC1)S(=O)(=O)c1ccc(N)cc1]
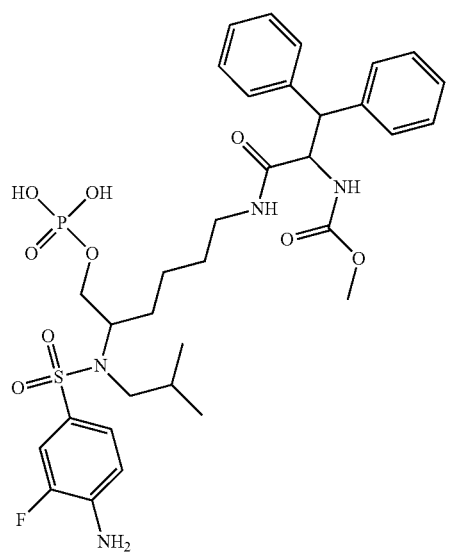 [SMILES: COC(=O)NC(C(=O)NCCCCC(COP(=O)(O)O)N(CC(C)C)S(=O)(=O)c1ccc(N)c(F)c1)C(c1ccccc1)c1ccccc1]

TABLE 24-continued
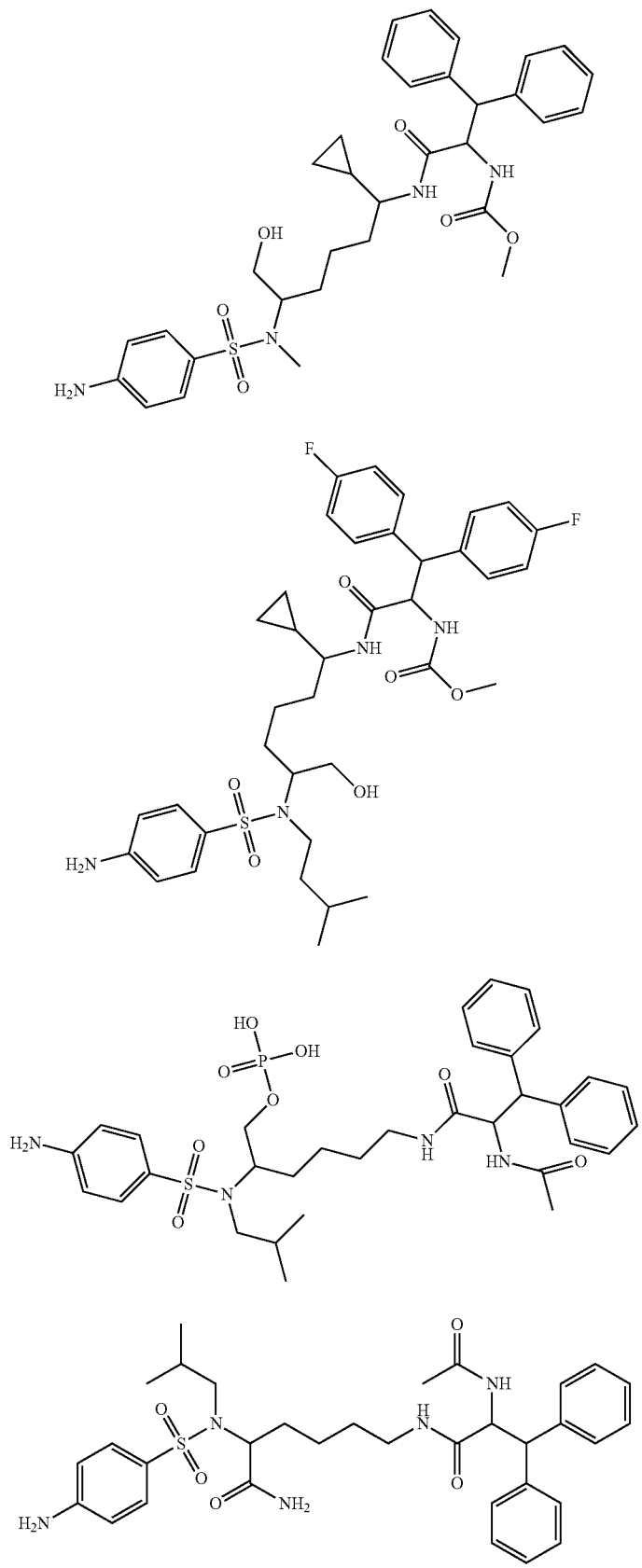

TABLE 24-continued
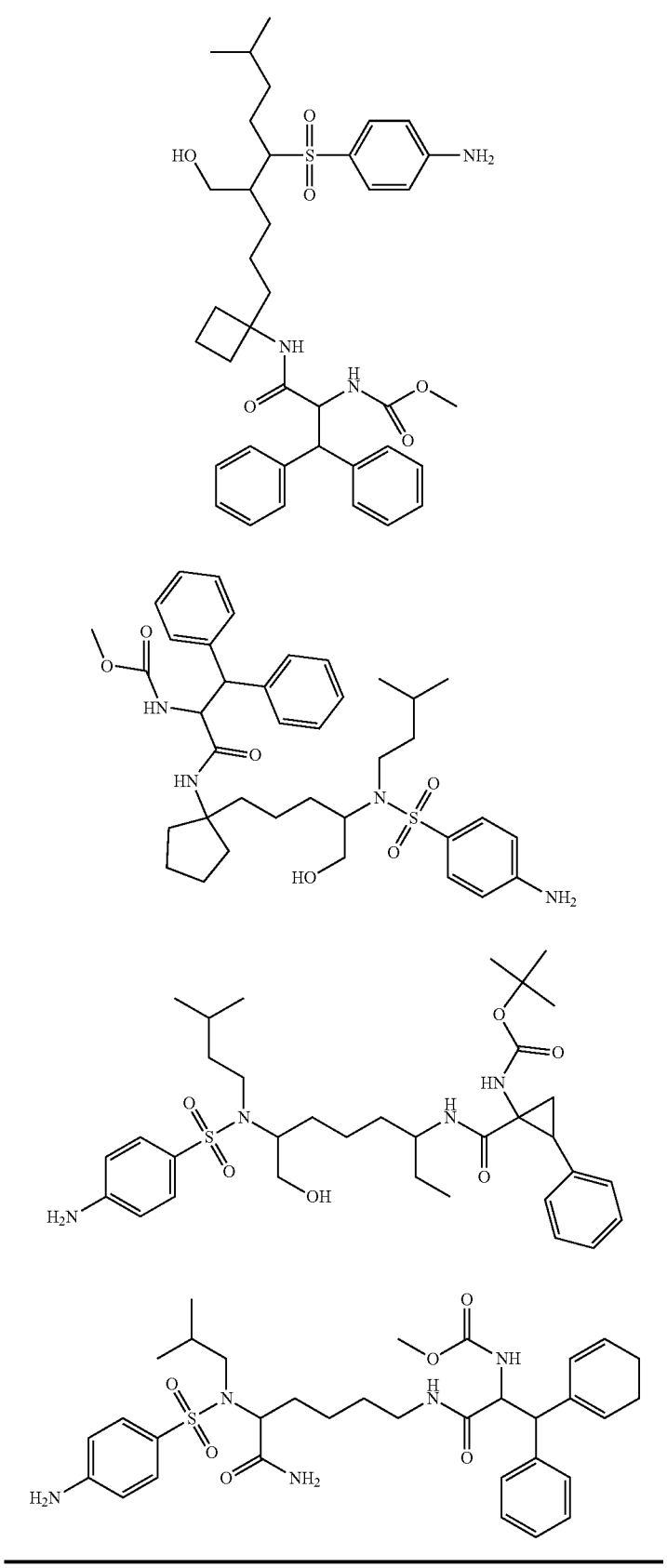

In one implementation, the compound is TMC-310911 ([(3aS,4R,6aR)-2,3,3a,4,5,6a-hexahydrofuro[2,3-b]furan-4-yl] N-[(2S,3R)-4-[2-[(1-cyclopentylpiperidin-4-yl)amino]-1,3-benzothiazol-6-yl]sulfonyl-(2-methylpropyl)amino]-3-hydroxy-1-phenylbutan-2-yl]carbamate), a clinically investigated HIV-1 protease inhibitor. In one particular implementation, the compound, or variations and permutations thereof, is further described in WO2007147884; U.S. Pat. No. 9,346,820; WO2017031220 the contents of which are hereby incorporated by reference for all purposes and the specific purposes identified herein.

In one implementation, the compound is Thymotrinan, (2S)-2-[[(2S)-6-amino-2-[[(2S)-2-amino-5-(diaminomethylideneamino)pentanoyl]amino]hexanoyl]amino]butanedioic acid. In one particular implementation, the compound, or variations and permutations thereof, is further described in WO2003051910 the contents of which are hereby incorporated by reference for all purposes and the specific purposes identified herein. In some embodiments, such compounds are represented by any one or more of the structures shown in Table 29. Any one of the compounds depicted in Table 29 is suitable for use in the methods of the present disclosure.

TABLE 25

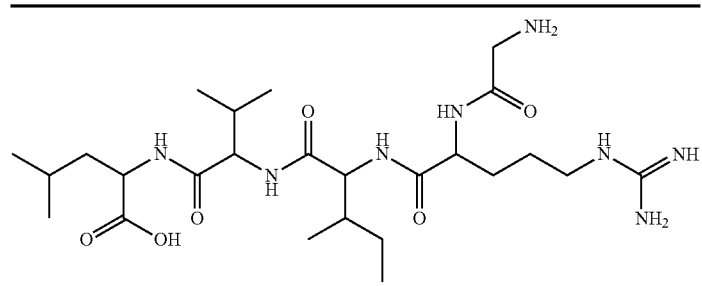

In one implementation, the compound is U-96988 (4-hydroxy-6-(1-phenylbutan-2-yl)-3-(1-phenylpropyl)pyran-2-one), a clinically investigated HIV protease inhibitor. In one particular implementation, the compound, or variations and permutations thereof, is further described in WO1994011361 the contents of which are hereby incorporated by reference for all purposes and the specific purposes identified herein. In some embodiments, such compounds are represented by any one or more of the structures shown in Table 30. Any one of the compounds depicted in Table 30 is suitable for use in the methods of the present disclosure.

TABLE 26

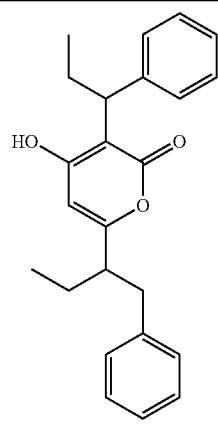

TABLE 26-continued

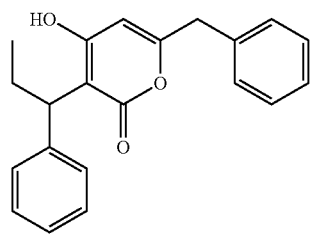 [SMILES: CCC(c1ccccc1)c1c(O)cc(Cc2ccccc2)oc1=O]

TABLE 26-continued

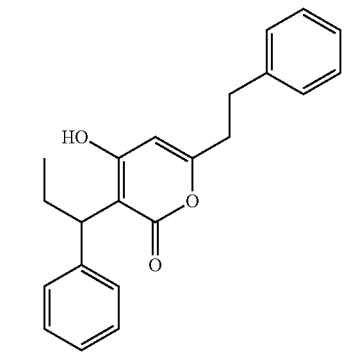 [SMILES: CCC(c1ccccc1)c1c(O)cc(CCc2ccccc2)oc1=O]

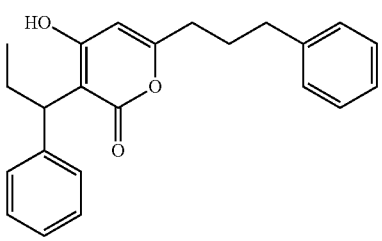 [SMILES: CCC(c1ccccc1)c1c(O)cc(CCCc2ccccc2)oc1=O]

TABLE 26-continued
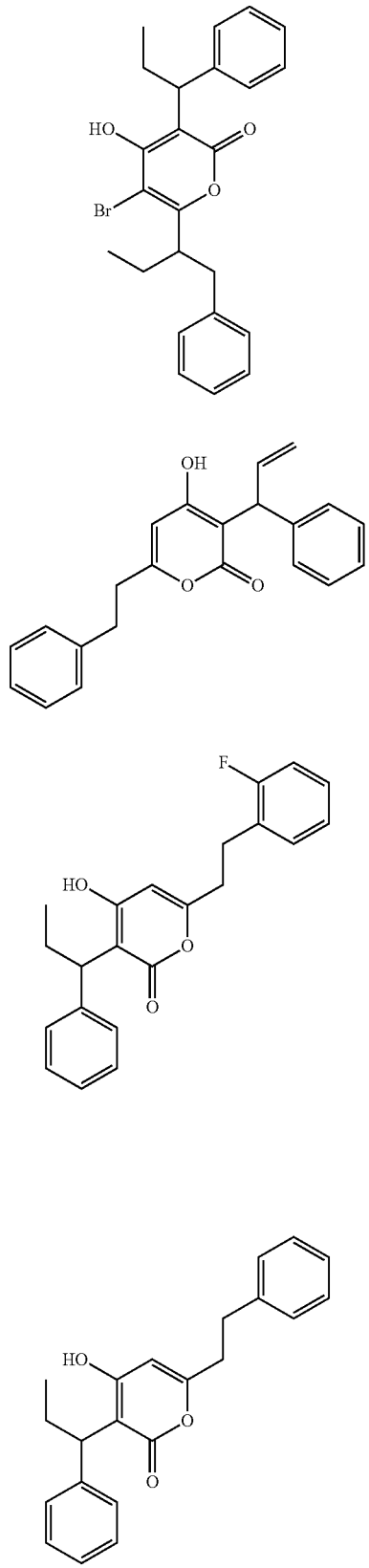
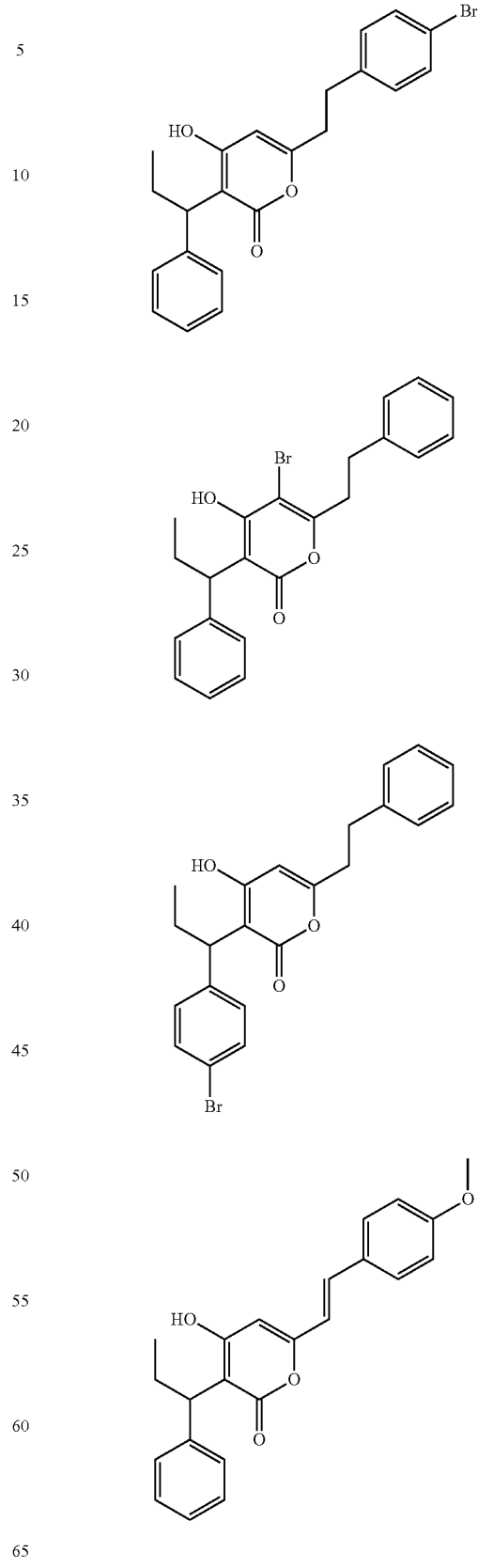

TABLE 26-continued

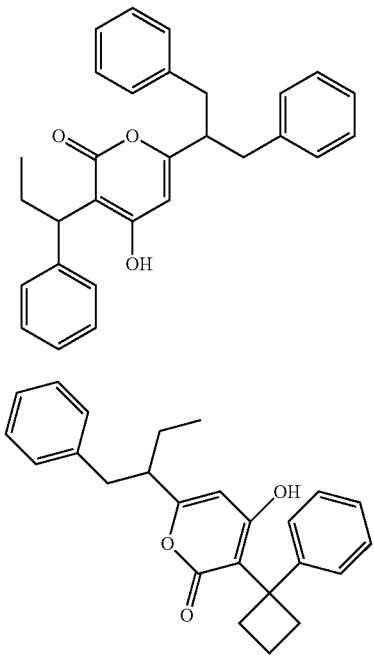

TABLE 26-continued

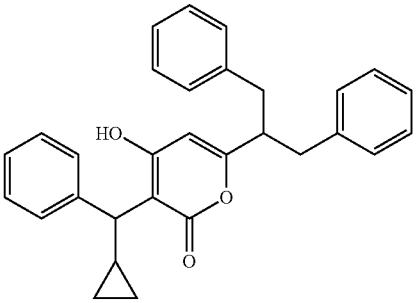 [SMILES: O=c1oc(C(Cc2ccccc2)Cc2ccccc2)cc(O)c1C(c1ccccc1)C1CC1]

In one implementation, the compound is VTP-27999 (Methyl N-[2-[(R)-(3-Chlorophenyl)[(3R)-1-[[[(2S)-2-(methylamino)-3-[(3R)-tetrahydro-2H-pyran-3-yl]propyl]amino]carbonyl]-3-piperidinyl]methoxy]ethyl]carbamate trifluoroacetate) a clinically investigated selective renin inhibitor. In one particular implementation, the compound, or variations and permutations thereof, is further described in WO2007070201 the contents of which are hereby incorporated by reference for all purposes and the specific purposes identified herein. In some embodiments, such compounds are represented by any one or more of the structures shown in Table 31. Any one of the compounds depicted in Table 31 is suitable for use in the methods of the present disclosure.

TABLE 27

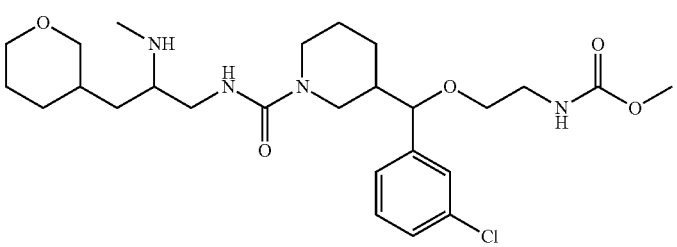 [SMILES: CNC(CNC(=O)N1CCCC(C(OCCNC(=O)OC)c2cccc(Cl)c2)C1)CC1CCCOC1]

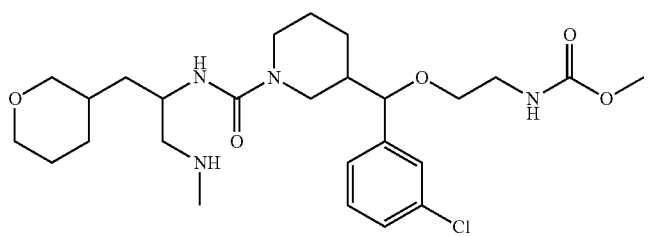

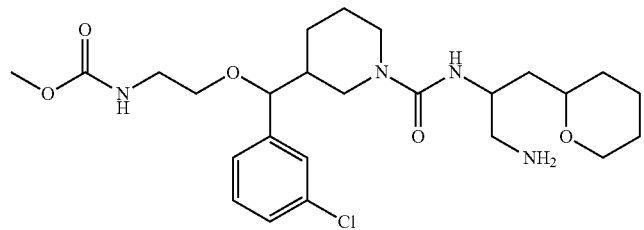 [SMILES: COC(=O)NCCOC(c1cccc(Cl)c1)C1CCCN(C(=O)NC(CN)CC2CCCCO2)C1]

TABLE 27-continued
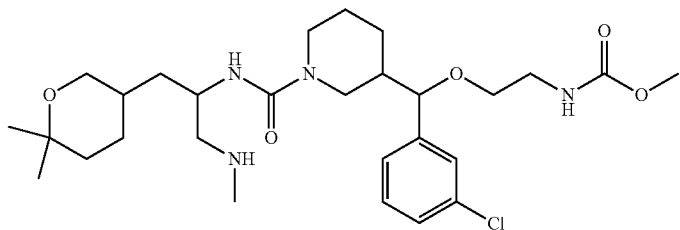
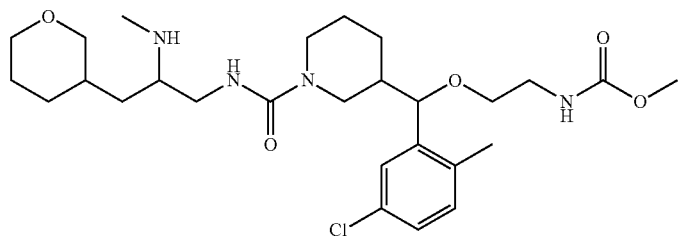 [SMILES: CNC(CNC(=O)N1CCCC(C(OCCNC(=O)OC)c2cc(Cl)ccc2C)C1)CC1CCCOC1]
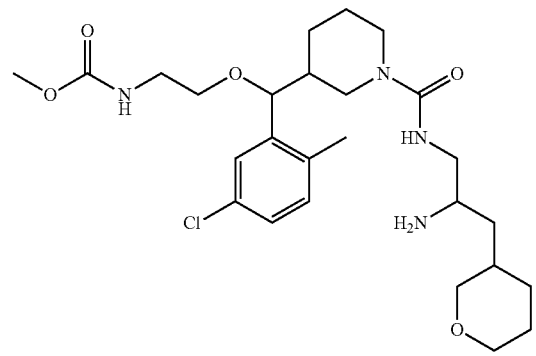 [SMILES: COC(=O)NCCOC(c1cc(Cl)ccc1C)C1CCCN(C(=O)NCC(N)CC2CCCOC2)C1]
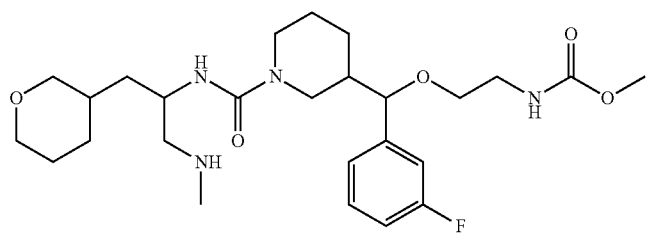 [SMILES: CNCC(CC1CCCOC1)NC(=O)N1CCCC(C(OCCNC(=O)OC)c2cccc(F)c2)C1]
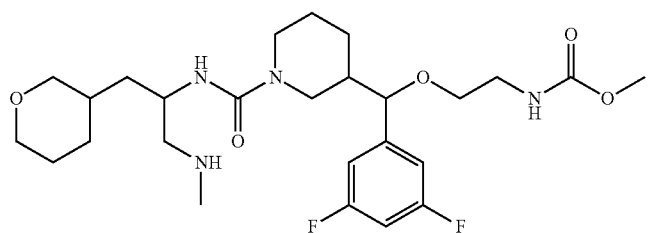 [SMILES: CNCC(CC1CCCOC1)NC(=O)N1CCCC(C(OCCNC(=O)OC)c2cc(F)cc(F)c2)C1]
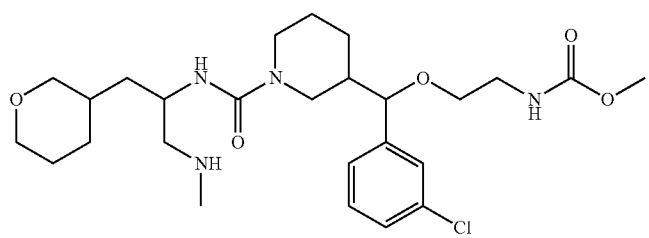 [SMILES: CNCC(CC1CCCOC1)NC(=O)N1CCCC(C(OCCNC(=O)OC)c2cccc(Cl)c2)C1]

TABLE 27-continued
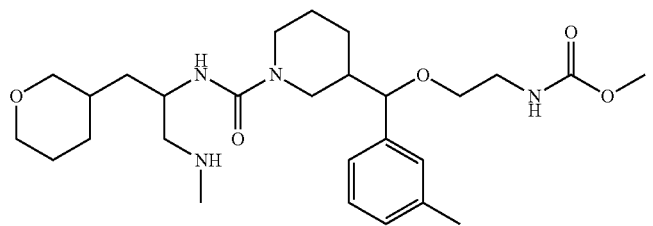 [SMILES: CNCC(CC1CCCOC1)NC(=O)N1CCCC(C(OCCNC(=O)OC)c2cccc(C)c2)C1]
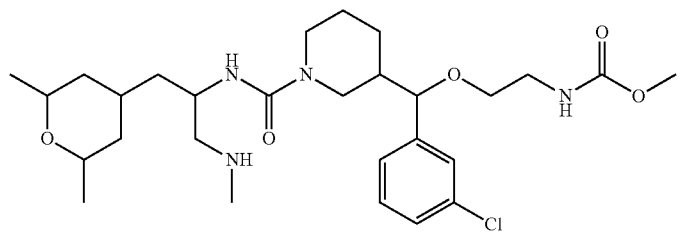
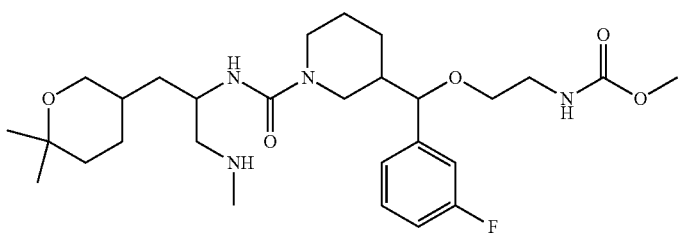
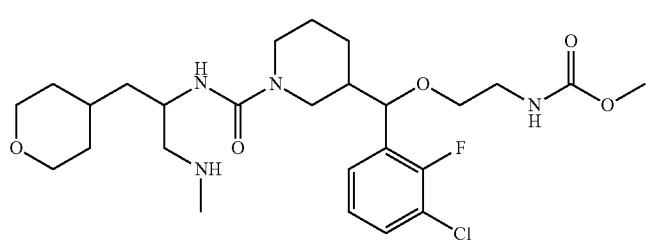 [SMILES: CNCC(CC1CCOCC1)NC(=O)N1CCCC(C(OCCNC(=O)OC)c2cccc(Cl)c2F)C1]
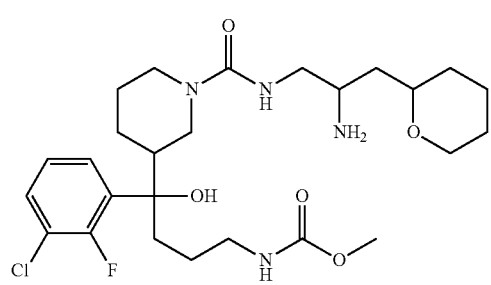 [SMILES: COC(=O)NCCCC(O)(c1cccc(Cl)c1F)C1CCCN(C(=O)NCC(N)CC2CCCCO2)C1]
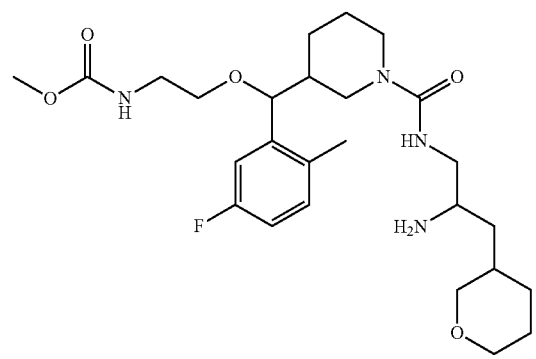

TABLE 27-continued
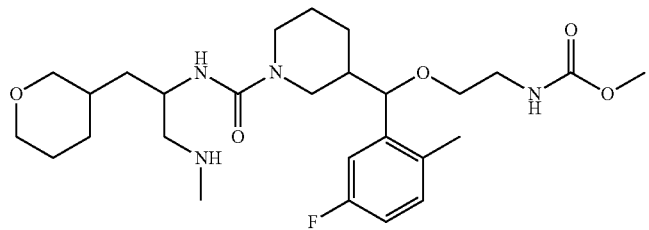
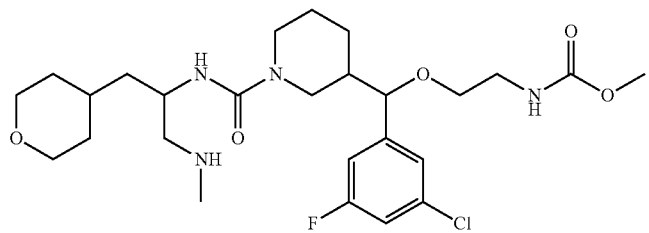 [SMILES: CNCC(CC1CCOCC1)NC(=O)N1CCCC(C(OCCNC(=O)OC)c2cc(F)cc(Cl)c2)C1]
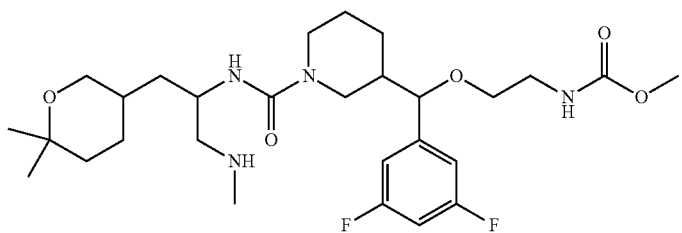
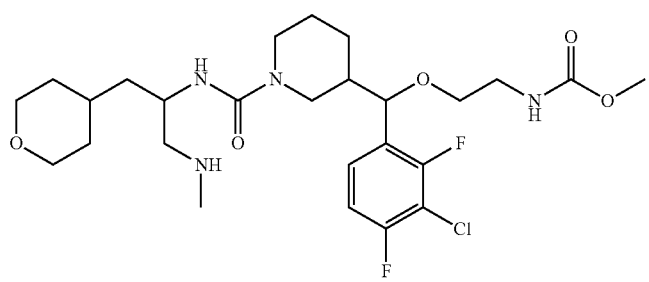 [SMILES: CNCC(CC1CCOCC1)NC(=O)N1CCCC(C(OCCNC(=O)OC)c2ccc(F)c(Cl)c2F)C1]
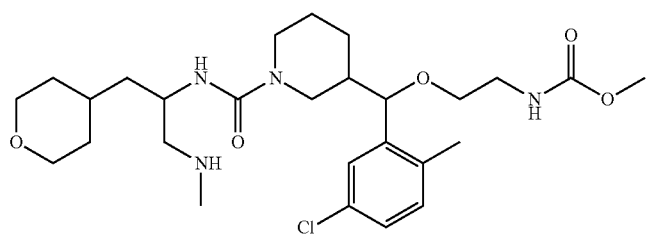 [SMILES: CNCC(CC1CCOCC1)NC(=O)N1CCCC(C(OCCNC(=O)OC)c2cc(Cl)ccc2C)C1]

TABLE 27-continued
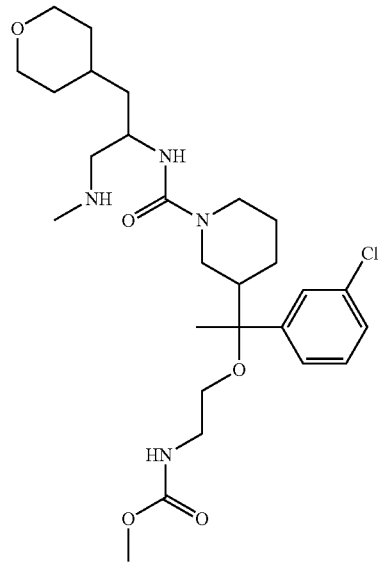 [SMILES: CNCC(CC1CCOCC1)NC(=O)N1CCCC(C(C)(OCCNC(=O)OC)c2cccc(Cl)c2)C1]
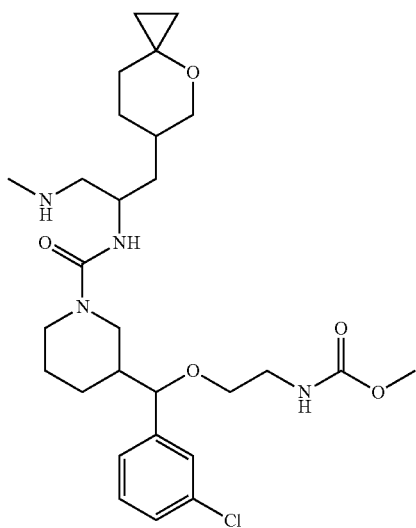
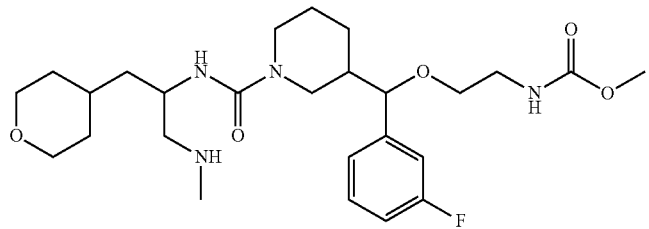 [SMILES: CNCC(CC1CCOCC1)NC(=O)N1CCCC(C(OCCNC(=O)OC)c2cccc(F)c2)C1]
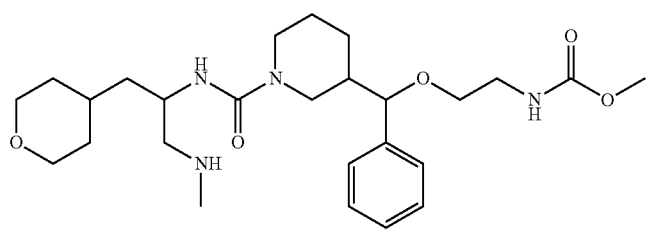 [SMILES: CNCC(CC1CCOCC1)NC(=O)N1CCCC(C(OCCNC(=O)OC)c2ccccc2)C1]

TABLE 27-continued
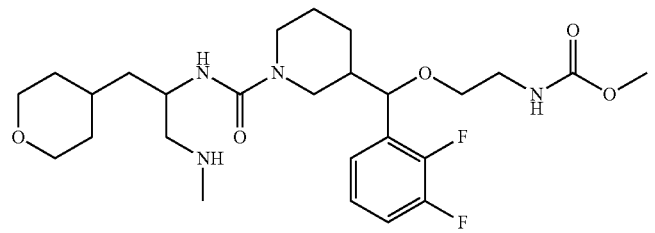 [SMILES: CNCC(CC1CCOCC1)NC(=O)N1CCCC(C(OCCNC(=O)OC)c2cccc(F)c2F)C1]
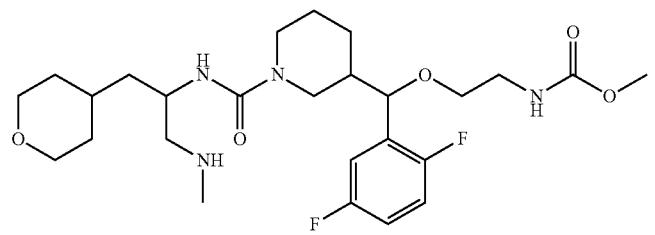 [SMILES: CNCC(CC1CCOCC1)NC(=O)N1CCCC(C(OCCNC(=O)OC)c2cc(F)ccc2F)C1]
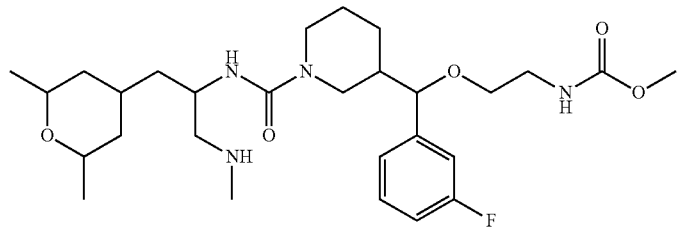
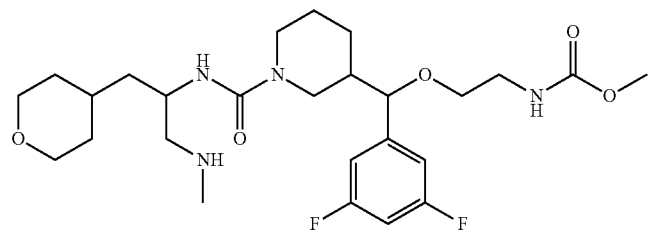 [SMILES: CNCC(CC1CCOCC1)NC(=O)N1CCCC(C(OCCNC(=O)OC)c2cc(F)cc(F)c2)C1]
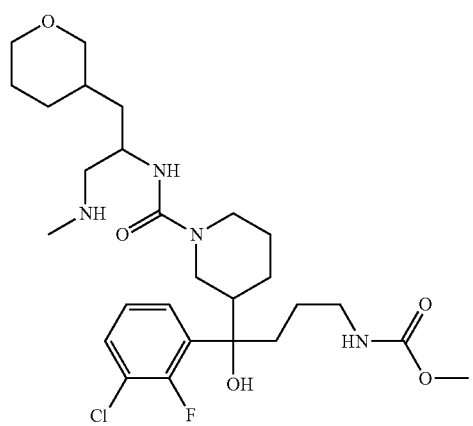 [SMILES: CNCC(CC1CCCOC1)NC(=O)N1CCCC(C(O)(CCCNC(=O)OC)c2cccc(Cl)c2F)C1]
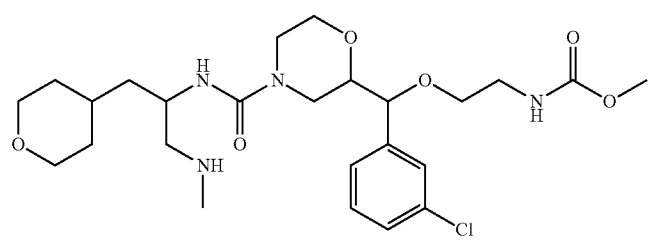 [SMILES: CNCC(CC1CCOCC1)NC(=O)N1CCOC(C(OCCNC(=O)OC)c2cccc(Cl)c2)C1]

TABLE 27-continued
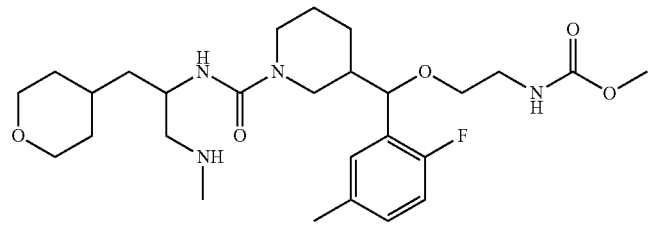 [SMILES: CNCC(CC1CCOCC1)NC(=O)N1CCCC(C(OCCNC(=O)OC)c2cc(C)ccc2F)C1]
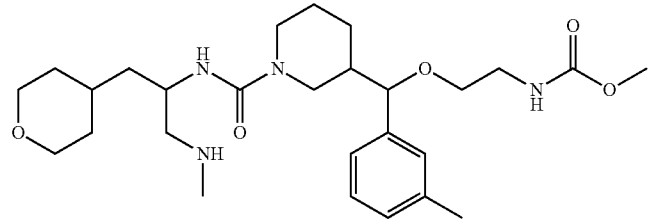 [SMILES: CNCC(CC1CCOCC1)NC(=O)N1CCCC(C(OCCNC(=O)OC)c2cccc(C)c2)C1]
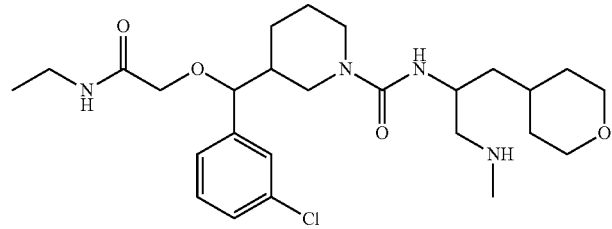 [SMILES: CCNC(=O)COC(c1cccc(Cl)c1)C1CCCN(C(=O)NC(CNC)CC2CCOCC2)C1]
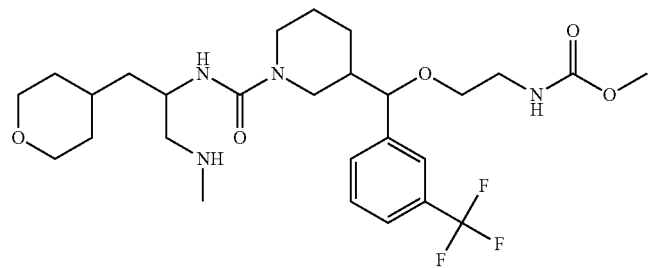 [SMILES: CNCC(CC1CCOCC1)NC(=O)N1CCCC(C(OCCNC(=O)OC)c2cccc(C(F)(F)F)c2)C1]
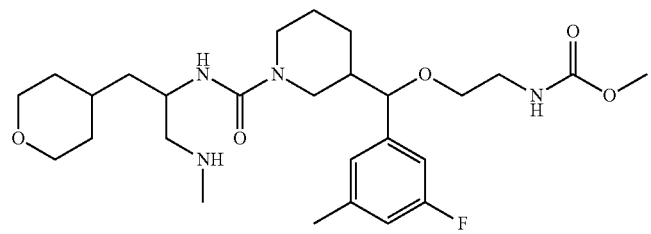 [SMILES: CNCC(CC1CCOCC1)NC(=O)N1CCCC(C(OCCNC(=O)OC)c2cc(C)cc(F)c2)C1]
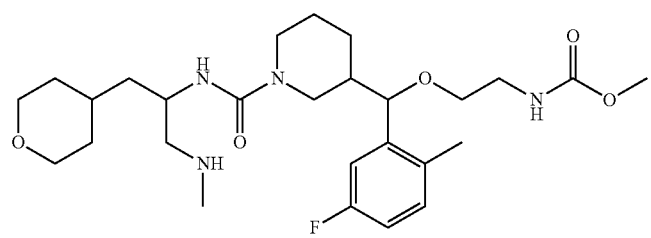 [SMILES: CNCC(CC1CCOCC1)NC(=O)N1CCCC(C(OCCNC(=O)OC)c2cc(F)ccc2C)C1]

TABLE 27-continued
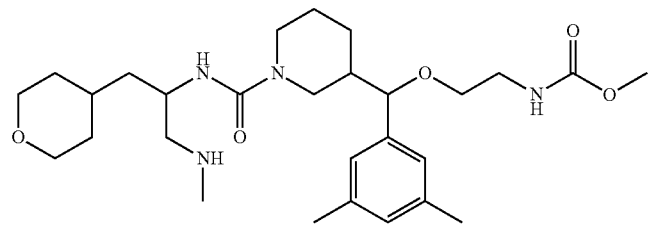 [SMILES: CNCC(CC1CCOCC1)NC(=O)N1CCCC(C(OCCNC(=O)OC)c2cc(C)cc(C)c2)C1]
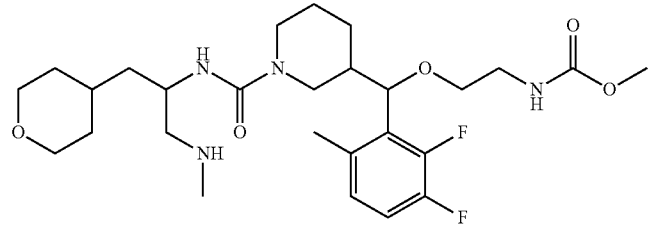 [SMILES: CNCC(CC1CCOCC1)NC(=O)N1CCCC(C(OCCNC(=O)OC)c2c(C)ccc(F)c2F)C1]
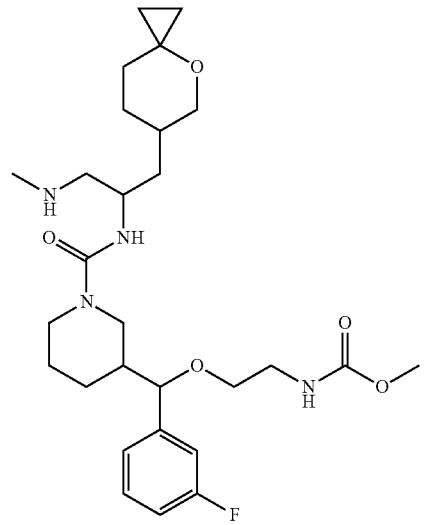
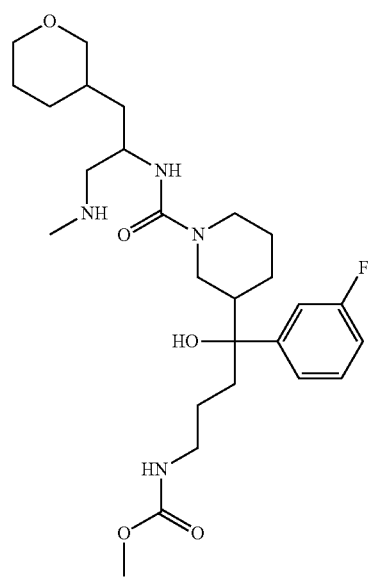 [SMILES: CNCC(CC1CCCOC1)NC(=O)N1CCCC(C(O)(CCCNC(=O)OC)c2cccc(F)c2)C1]

TABLE 27-continued
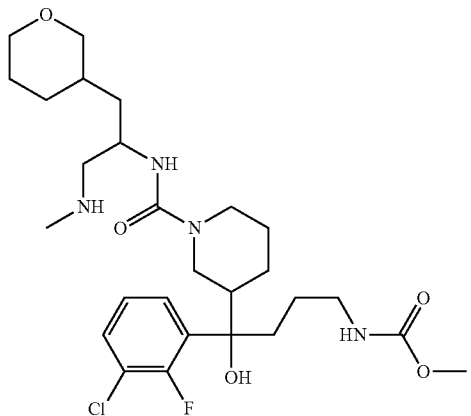 [SMILES: CNCC(CC1CCCOC1)NC(=O)N1CCCC(C(O)(CCCNC(=O)OC)c2cccc(Cl)c2F)C1]
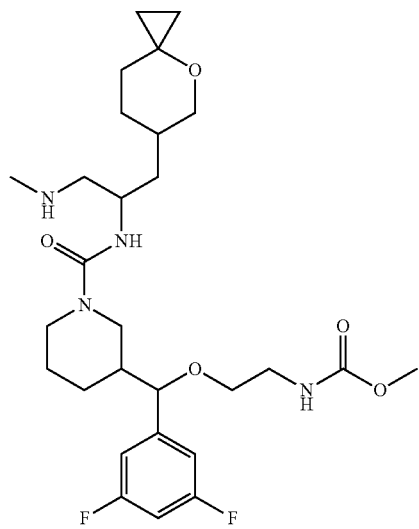
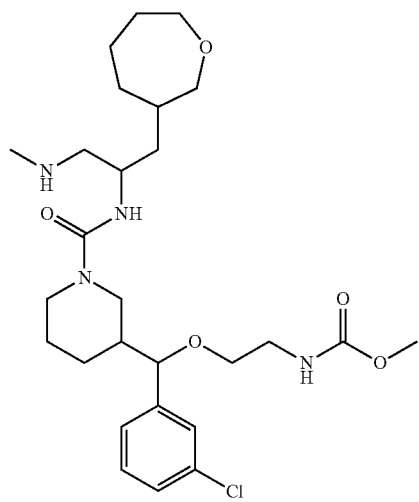

TABLE 27-continued
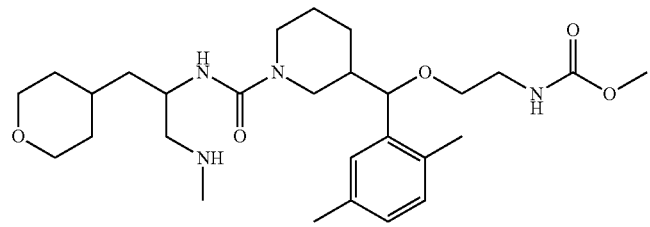 [SMILES: CNCC(CC1CCOCC1)NC(=O)N1CCCC(C(OCCNC(=O)OC)c2cc(C)ccc2C)C1]
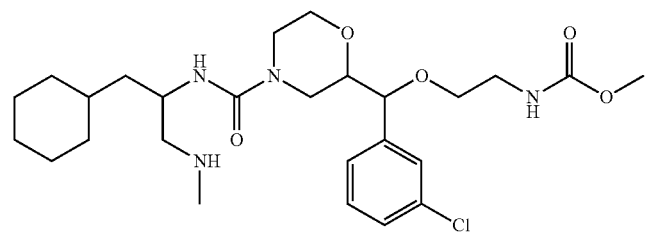 [SMILES: CNCC(CC1CCCCC1)NC(=O)N1CCOC(C(OCCNC(=O)OC)c2cccc(Cl)c2)C1]
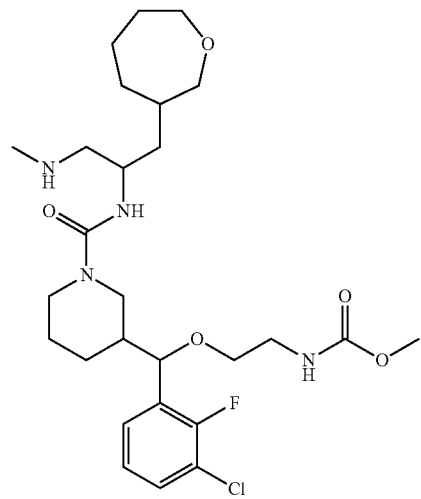
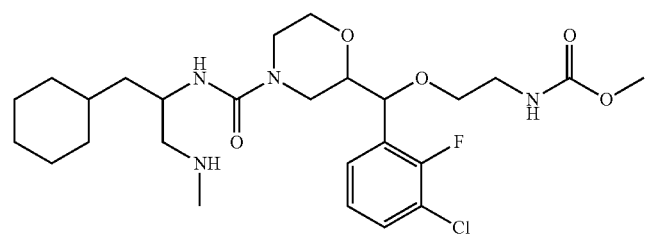 [SMILES: CNCC(CC1CCCCC1)NC(=O)N1CCOC(C(OCCNC(=O)OC)c2cccc(Cl)c2F)C1]
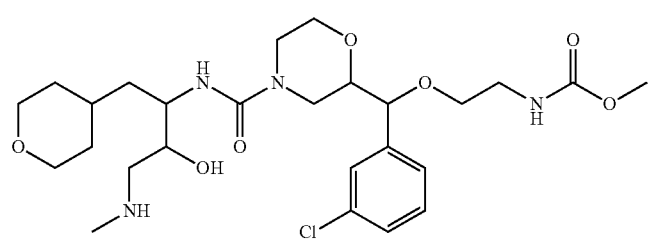 [SMILES: CNCC(O)C(CC1CCOCC1)NC(=O)N1CCOC(C(OCCNC(=O)OC)c2cccc(Cl)c2)C1]

TABLE 27-continued
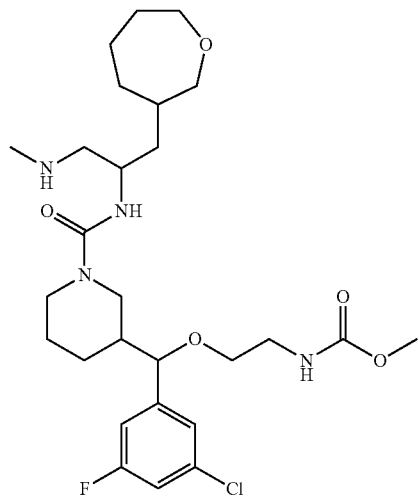
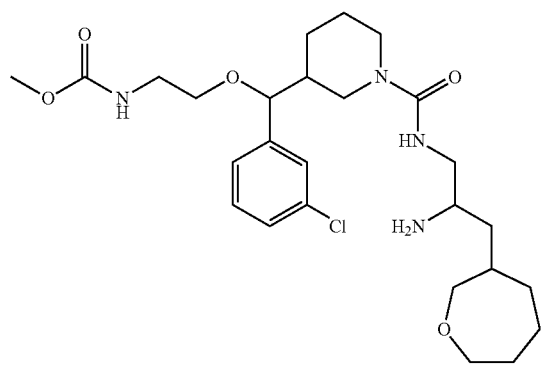 [SMILES: COC(=O)NCCOC(c1cccc(Cl)c1)C1CCCN(C(=O)NCC(N)CC2CCCCOC2)C1]
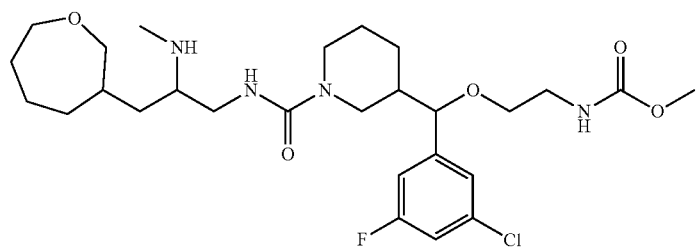 [SMILES: CNC(CNC(=O)N1CCCC(C(OCCNC(=O)OC)c2cc(F)cc(Cl)c2)C1)CC1CCCCOC1]
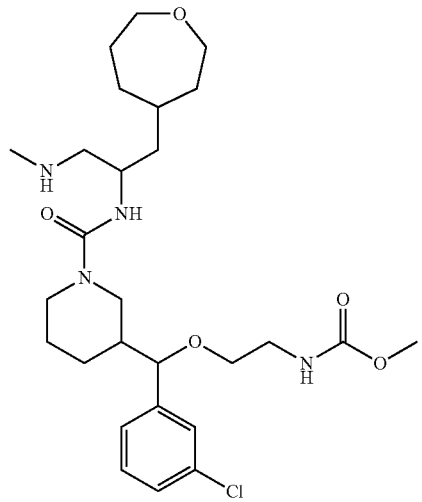

TABLE 27-continued
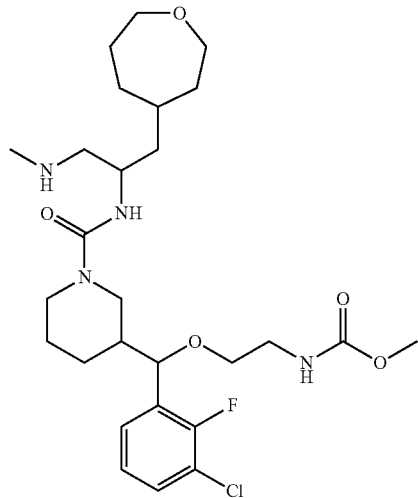
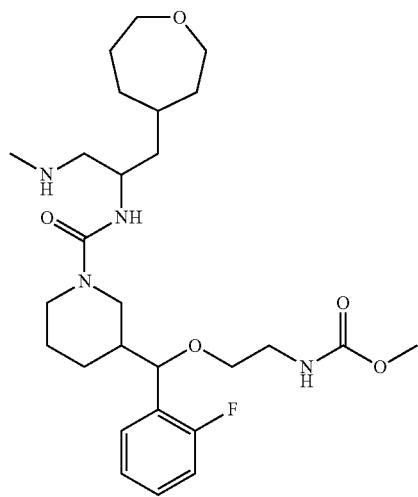
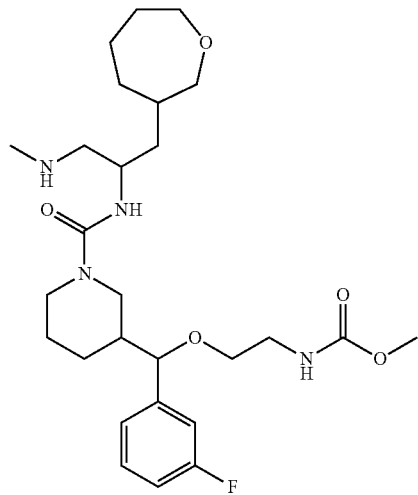

TABLE 27-continued
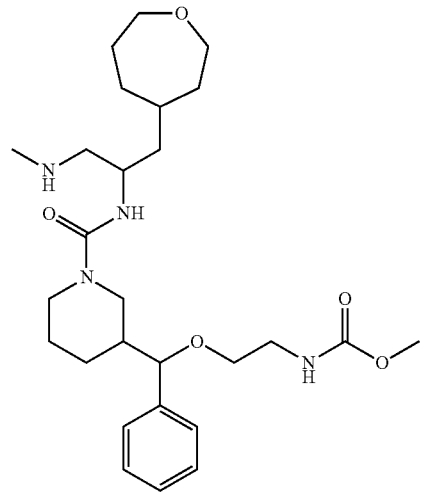
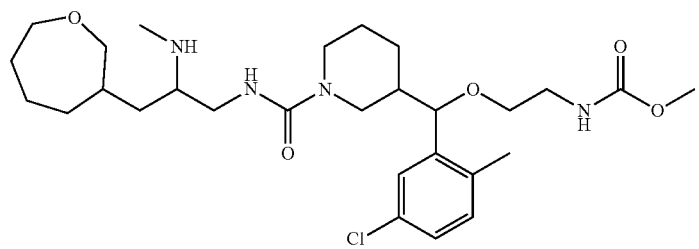 [SMILES: CNC(CNC(=O)N1CCCC(C(OCCNC(=O)OC)c2cc(Cl)ccc2C)C1)CC1CCCCOC1]
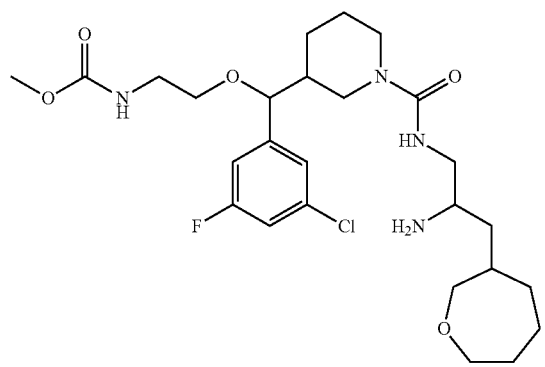 [SMILES: COC(=O)NCCOC(c1cc(F)cc(Cl)c1)C1CCCN(C(=O)NCC(N)CC2CCCCOC2)C1]
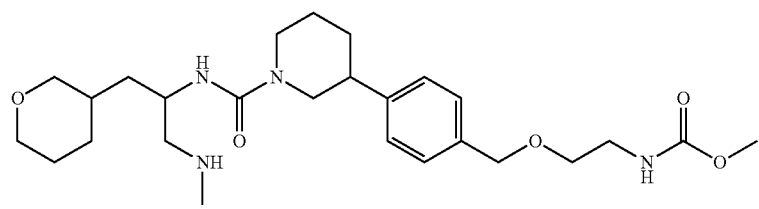 [SMILES: CNCC(CC1CCCOC1)NC(=O)N1CCCC(c2ccc(COCCNC(=O)OC)cc2)C1]

TABLE 27-continued

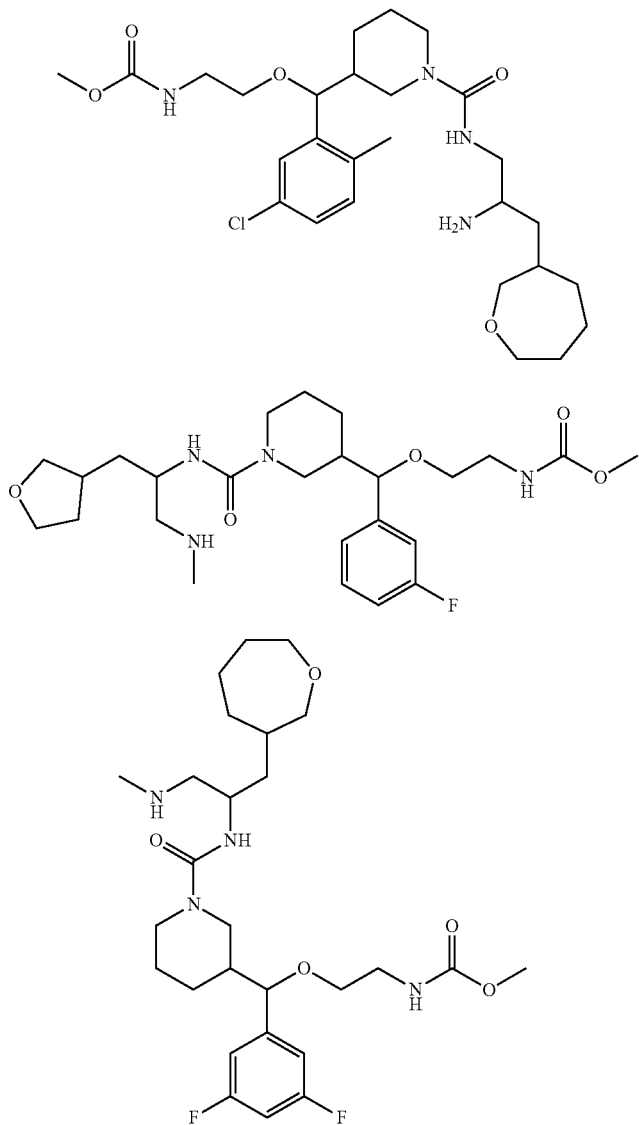

In one implementation, the compound is Anipamil (2-(3-((m-Methoxyphenethyl)methylamino)propyl)-2-(m-methoxyphenyl)tetradecanenitrile), a clinically investigated calcium channel inhibitor. In one particular implementation, the compound, or variations and permutations thereof, is further described in WO2007117560 the contents of which are hereby incorporated by reference for all purposes and the specific purposes identified herein. In some embodiments, such compounds are represented by any one or more of the structures shown in Table 32. Any one of the compounds depicted in Table 32 is suitable for use in the methods of the present disclosure.

TABLE 28

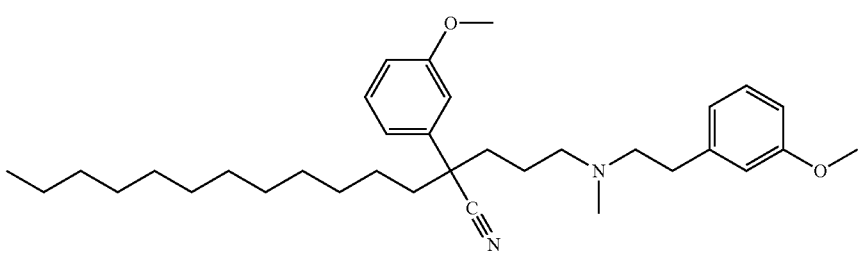 [SMILES: CCCCCCCCCCCCC(C#N)(CCCN(C)CCc1cccc(OC)c1)c1cccc(OC)c1]

TABLE 28-continued

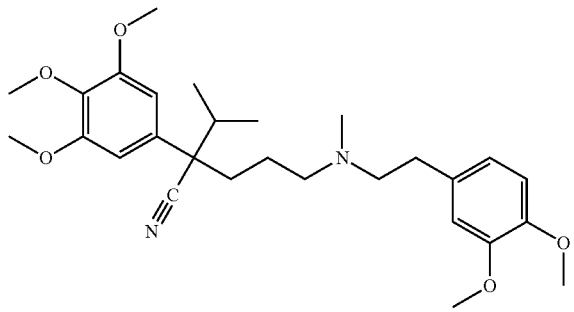

In one implementation, the compound is antineoplaston AS2-1 (sodium (2-phenylacetyl)-L-glutaminate 2-phenylacetate) or antineoplaston AS2-5, a clinically investigated Glutamate receptor modulator. In one particular implementation, the compound, or variations and permutations thereof, is further described in JP2000159746 the contents of which are hereby incorporated by reference for all purposes and the specific purposes identified herein. In some embodiments, such compounds are represented by any one or more of the structures shown in Table 33. Any one of the compounds depicted in Table 33 is suitable for use in the methods of the present disclosure.

TABLE 29

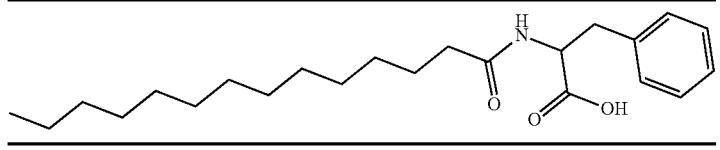

In one implementation, the compound is asunaprevir (1,1-dimethylethyl ((1S)-1-{((2S,4R)-4-(7-chloro-4-methoxyisoquinolin-1-yloxy)-2-({(1R,2S)-1-((cyclopropylsulfonyl)carbamoyl)-2-ethenylcyclopropyl}carbamoyl)pyrrolidin-1-yl)carbonyl}-2,2-dimethylpropyl)carbamate), a clinically investigated NS3 protease inhibitor. In one particular implementation, the compound, or variations and permutations thereof, is further described in WO2012040242 the contents of which are hereby incorporated by reference for all purposes and the specific purposes identified herein. In some embodiments, such compounds are represented by any one or more of the structures shown in Table 34. Any one of the compounds depicted in Table 34 is suitable for use in the methods of the present disclosure.

TABLE 30

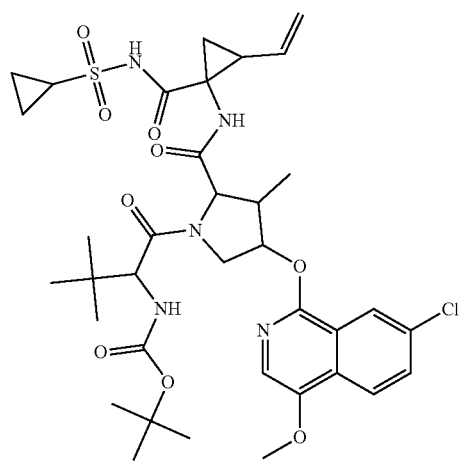 [SMILES: C=CC1CC1(NC(=O)C1C(C)C(Oc2ncc(OC)c3ccc(Cl)cc23)CN1C(=O)C(NC(=O)OC(C)(C)C)C(C)(C)C)C(=O)NS(=O)(=O)C1CC1]

TABLE 30-continued
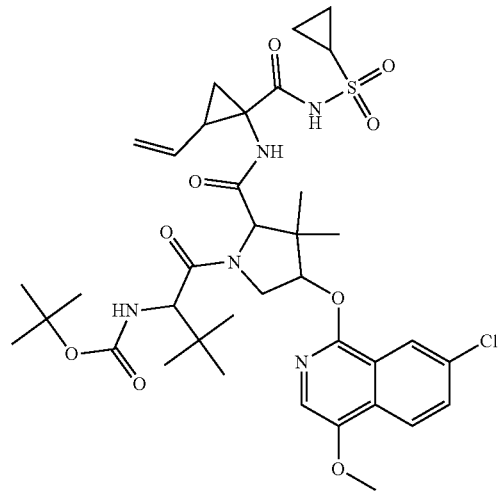 [SMILES: C=CC1CC1(NC(=O)C1N(C(=O)C(NC(=O)OC(C)(C)C)C(C)(C)C)CC(Oc2ncc(OC)c3ccc(Cl)cc23)C1(C)C)C(=O)NS(=O)(=O)C1CC1]
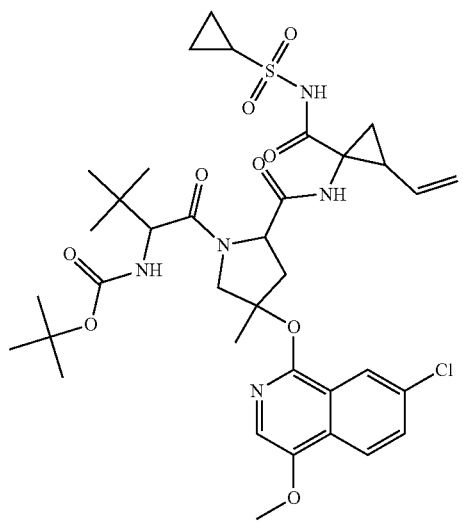 [SMILES: C=CC1CC1(NC(=O)C1CC(C)(Oc2ncc(OC)c3ccc(Cl)cc23)CN1C(=O)C(NC(=O)OC(C)(C)C)C(C)(C)C)C(=O)NS(=O)(=O)C1CC1]
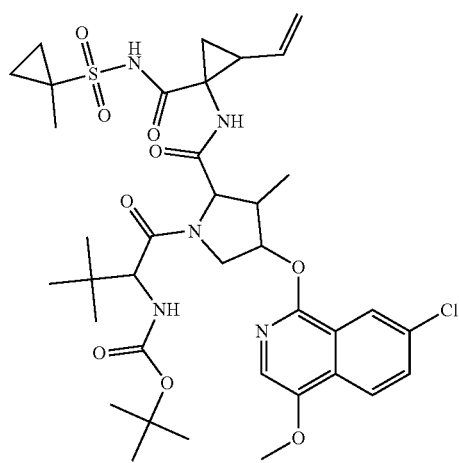 [SMILES: C=CC1CC1(NC(=O)C1C(C)C(Oc2ncc(OC)c3ccc(Cl)cc23)CN1C(=O)C(NC(=O)OC(C)(C)C)C(C)(C)C)C(=O)NS(=O)(=O)C1(C)CC1]

TABLE 30-continued
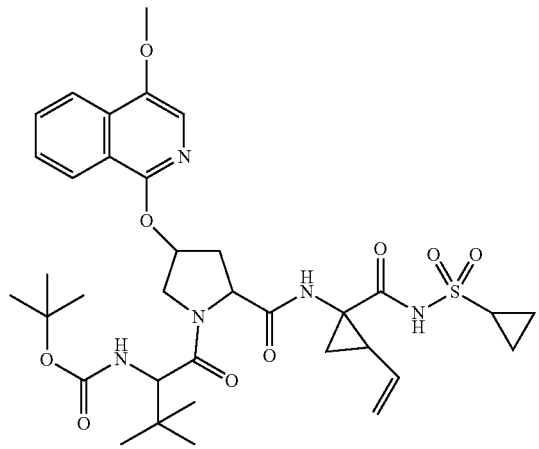 [SMILES: C=CC1CC1(NC(=O)C1CC(Oc2ncc(OC)c3ccccc23)CN1C(=O)C(NC(=O)OC(C)(C)C)C(C)(C)C)C(=O)NS(=O)(=O)C1CC1]
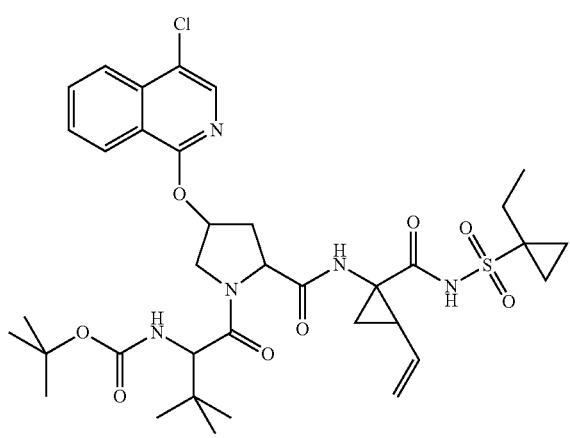 [SMILES: C=CC1CC1(NC(=O)C1CC(Oc2ncc(Cl)c3ccccc23)CN1C(=O)C(NC(=O)OC(C)(C)C)C(C)(C)C)C(=O)NS(=O)(=O)C1(CC)CC1]
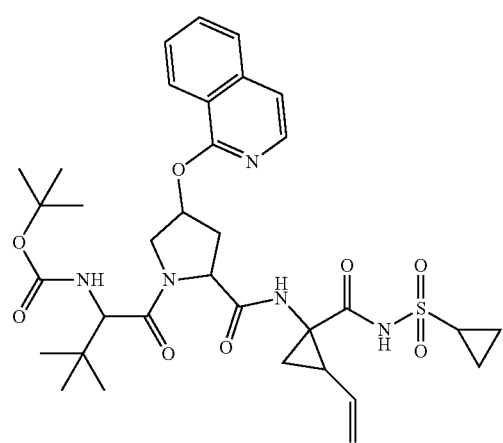 [SMILES: C=CC1CC1(NC(=O)C1CC(Oc2nccc3ccccc23)CN1C(=O)C(NC(=O)OC(C)(C)C)C(C)(C)C)C(=O)NS(=O)(=O)C1CC1]

TABLE 30-continued
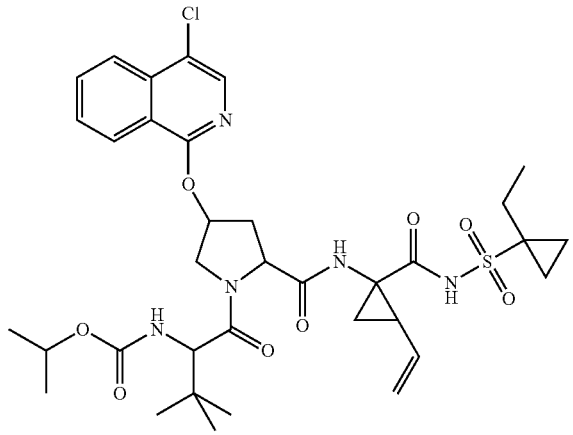 [SMILES: C=CC1CC1(NC(=O)C1CC(Oc2ncc(Cl)c3ccccc23)CN1C(=O)C(NC(=O)OC(C)C)C(C)(C)C)C(=O)NS(=O)(=O)C1(CC)CC1]
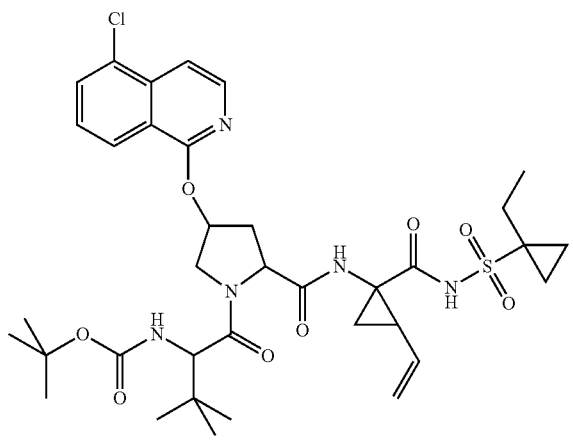 [SMILES: C=CC1CC1(NC(=O)C1CC(Oc2nccc3c(Cl)cccc23)CN1C(=O)C(NC(=O)OC(C)(C)C)C(C)(C)C)C(=O)NS(=O)(=O)C1(CC)CC1]
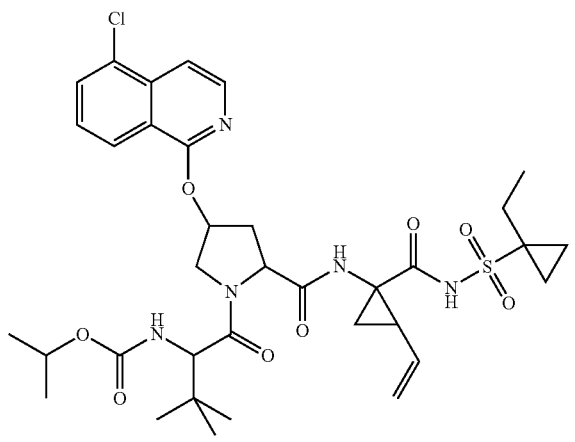 [SMILES: C=CC1CC1(NC(=O)C1CC(Oc2nccc3c(Cl)cccc23)CN1C(=O)C(NC(=O)OC(C)C)C(C)(C)C)C(=O)NS(=O)(=O)C1(CC)CC1]

TABLE 30-continued
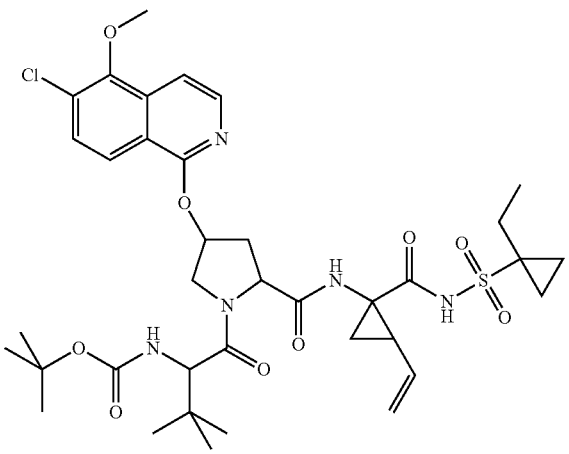 [SMILES: C=CC1CC1(NC(=O)C1CC(Oc2nccc3c(OC)c(Cl)ccc23)CN1C(=O)C(NC(=O)OC(C)(C)C)C(C)(C)C)C(=O)NS(=O)(=O)C1(CC)CC1]
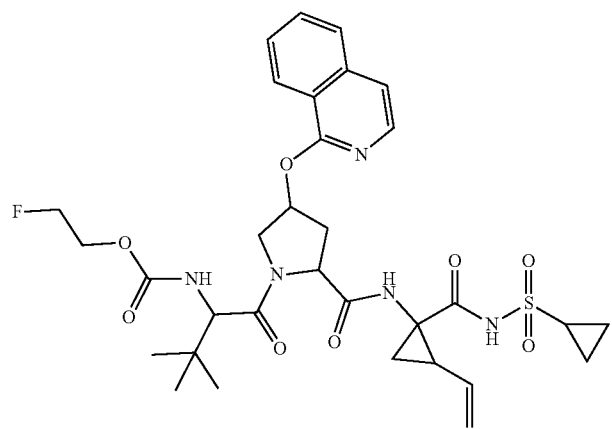 [SMILES: C=CC1CC1(NC(=O)C1CC(Oc2nccc3ccccc23)CN1C(=O)C(NC(=O)OCCF)C(C)(C)C)C(=O)NS(=O)(=O)C1CC1]
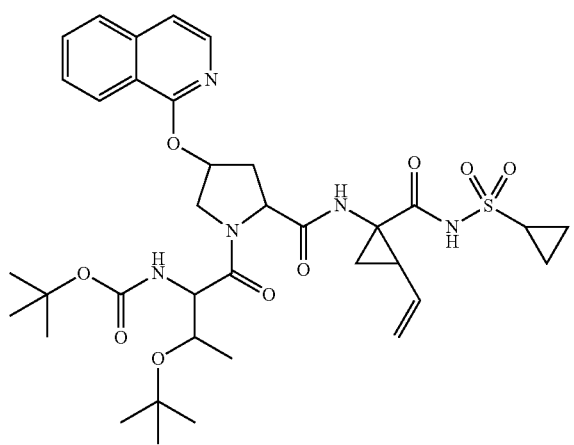 [SMILES: C=CC1CC1(NC(=O)C1CC(Oc2nccc3ccccc23)CN1C(=O)C(NC(=O)OC(C)(C)C)C(C)OC(C)(C)C)C(=O)NS(=O)(=O)C1CC1]

TABLE 30-continued
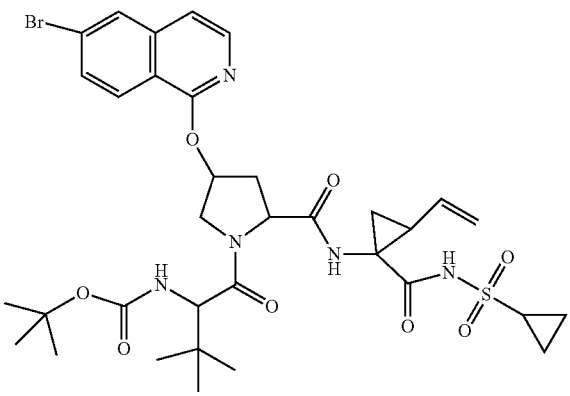 [SMILES: C=CC1CC1(NC(=O)C1CC(Oc2nccc3cc(Br)ccc23)CN1C(=O)C(NC(=O)OC(C)(C)C)C(C)(C)C)C(=O)NS(=O)(=O)C1CC1]
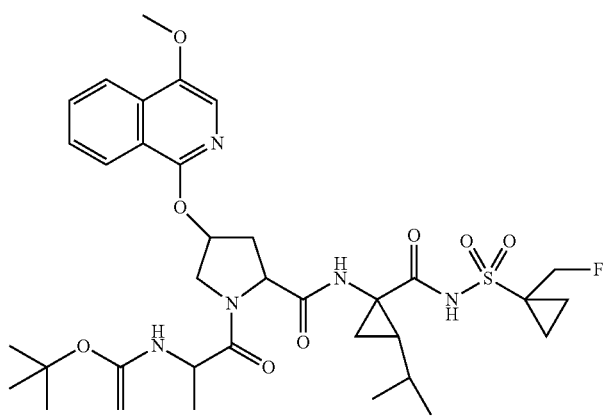 [SMILES: C=C(NC(C)C(=O)N1CC(Oc2ncc(OC)c3ccccc23)CC1C(=O)NC1(C(=O)NS(=O)(=O)C2(CF)CC2)CC1C(C)C)OC(C)(C)C]
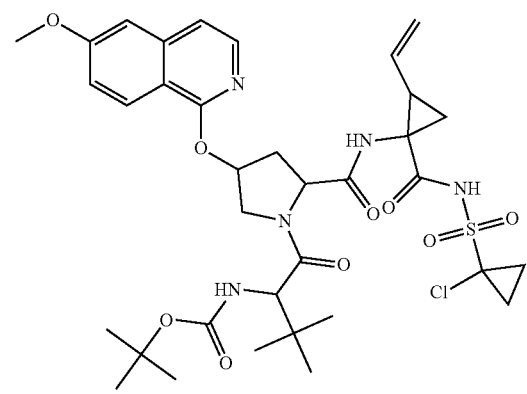 [SMILES: C=CC1CC1(NC(=O)C1CC(Oc2nccc3cc(OC)ccc23)CN1C(=O)C(NC(=O)OC(C)(C)C)C(C)(C)C)C(=O)NS(=O)(=O)C1(Cl)CC1]
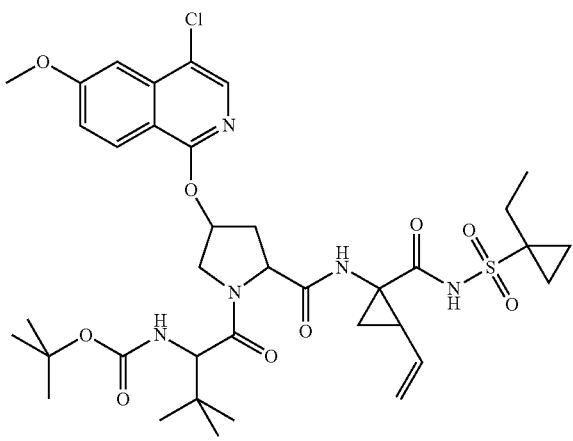 [SMILES: C=CC1CC1(NC(=O)C1CC(Oc2ncc(Cl)c3cc(OC)ccc23)CN1C(=O)C(NC(=O)OC(C)(C)C)C(C)(C)C)C(=O)NS(=O)(=O)C1(CC)CC1]

TABLE 30-continued
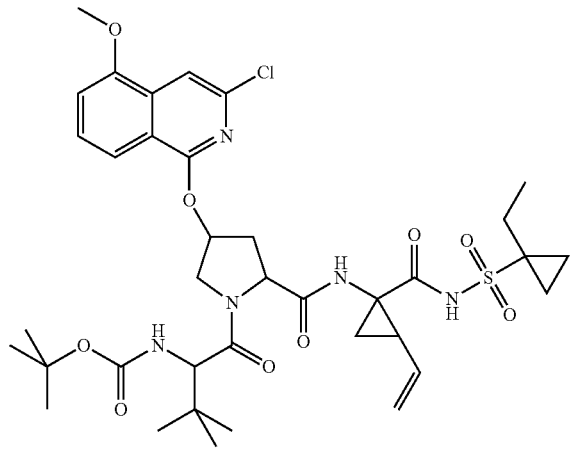 [SMILES: C=CC1CC1(NC(=O)C1CC(Oc2nc(Cl)cc3c(OC)cccc23)CN1C(=O)C(NC(=O)OC(C)(C)C)C(C)(C)C)C(=O)NS(=O)(=O)C1(CC)CC1]
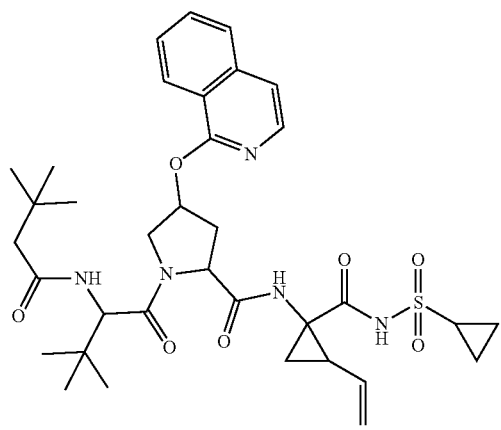 [SMILES: C=CC1CC1(NC(=O)C1CC(Oc2nccc3ccccc23)CN1C(=O)C(NC(=O)CC(C)(C)C)C(C)(C)C)C(=O)NS(=O)(=O)C1CC1]
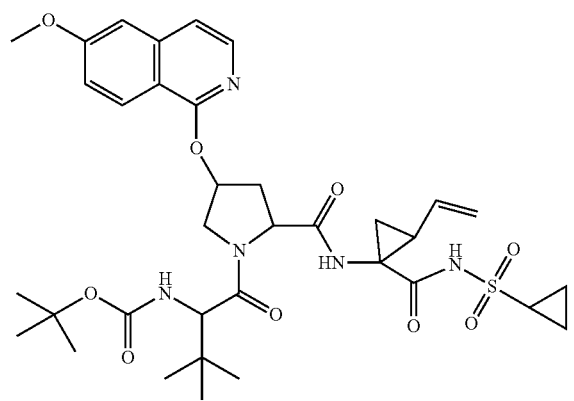 [SMILES: C=CC1CC1(NC(=O)C1CC(Oc2nccc3cc(OC)ccc23)CN1C(=O)C(NC(=O)OC(C)(C)C)C(C)(C)C)C(=O)NS(=O)(=O)C1CC1]

TABLE 30-continued
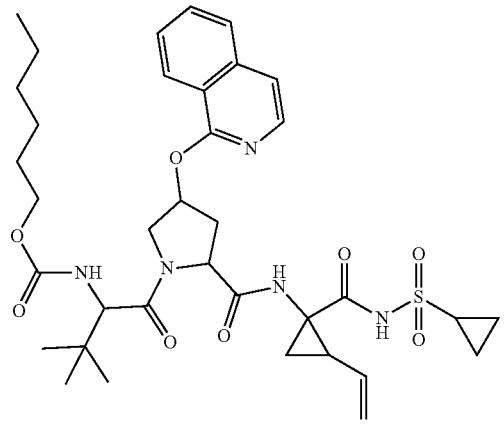 [SMILES: C=CC1CC1(NC(=O)C1CC(Oc2nccc3ccccc23)CN1C(=O)C(NC(=O)OCCCCCC)C(C)(C)C)C(=O)NS(=O)(=O)C1CC1]
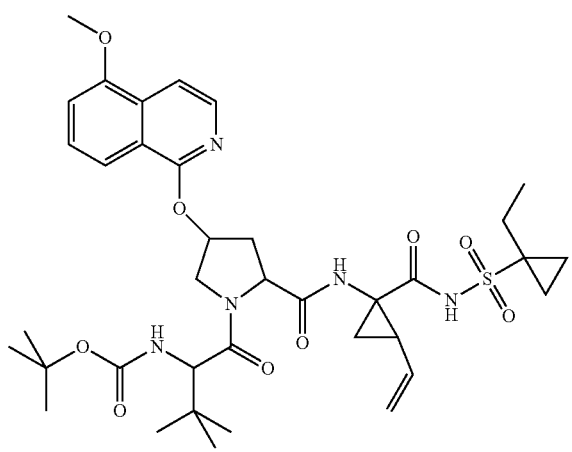 [SMILES: C=CC1CC1(NC(=O)C1CC(Oc2nccc3c(OC)cccc23)CN1C(=O)C(NC(=O)OC(C)(C)C)C(C)(C)C)C(=O)NS(=O)(=O)C1(CC)CC1]
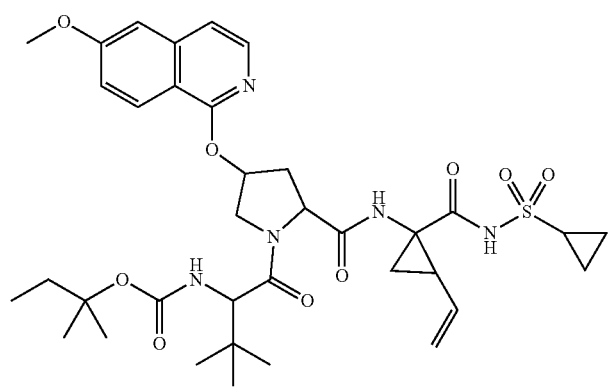 [SMILES: C=CC1CC1(NC(=O)C1CC(Oc2nccc3cc(OC)ccc23)CN1C(=O)C(NC(=O)OC(C)(C)CC)C(C)(C)C)C(=O)NS(=O)(=O)C1CC1]

TABLE 30-continued
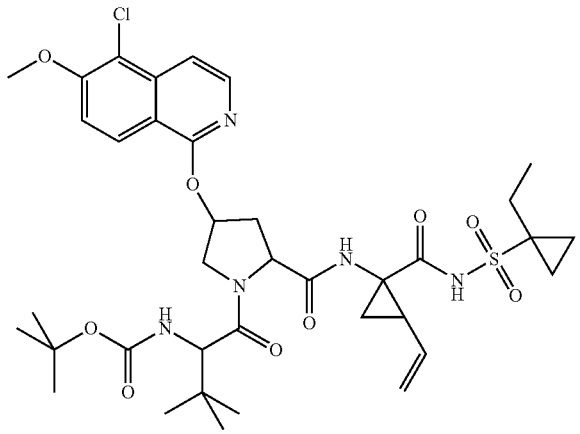 [SMILES: C=CC1CC1(NC(=O)C1CC(Oc2nccc3c(Cl)c(OC)ccc23)CN1C(=O)C(NC(=O)OC(C)(C)C)C(C)(C)C)C(=O)NS(=O)(=O)C1(CC)CC1]
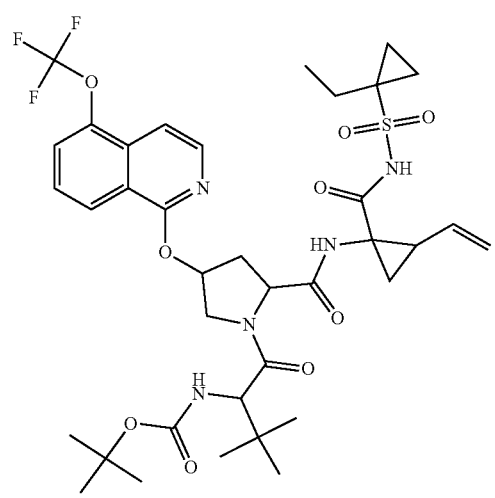 [SMILES: C=CC1CC1(NC(=O)C1CC(Oc2nccc3c(OC(F)(F)F)cccc23)CN1C(=O)C(NC(=O)OC(C)(C)C)C(C)(C)C)C(=O)NS(=O)(=O)C1(CC)CC1]
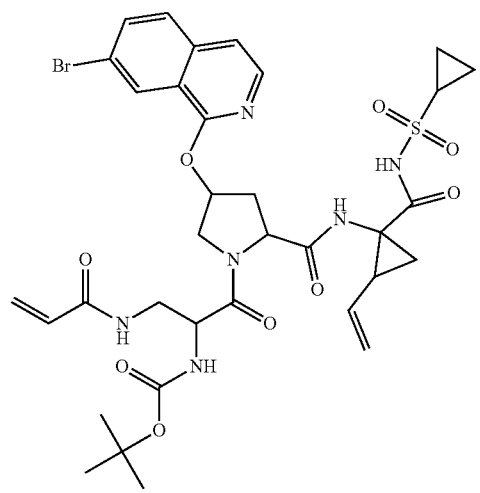 [SMILES: C=CC(=O)NCC(NC(=O)OC(C)(C)C)C(=O)N1CC(Oc2nccc3ccc(Br)cc23)CC1C(=O)NC1(C(=O)NS(=O)(=O)C2CC2)CC1C=C]

TABLE 30-continued
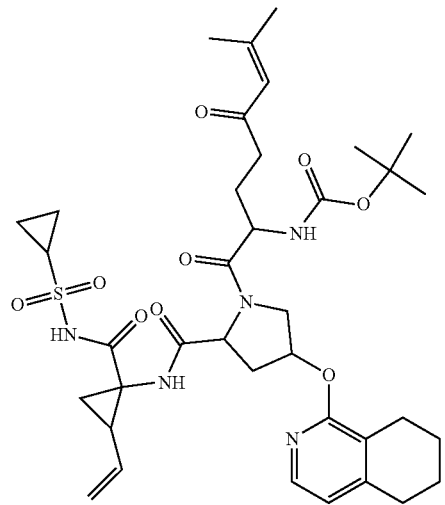 [SMILES: C=CC1CC1(NC(=O)C1CC(Oc2nccc3c2CCCC3)CN1C(=O)C(CCC(=O)C=C(C)C)NC(=O)OC(C)(C)C)C(=O)NS(=O)(=O)C1CC1]
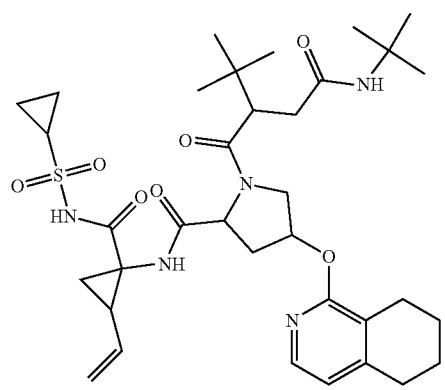 [SMILES: C=CC1CC1(NC(=O)C1CC(Oc2nccc3c2CCCC3)CN1C(=O)C(CC(=O)NC(C)(C)C)C(C)(C)C)C(=O)NS(=O)(=O)C1CC1]
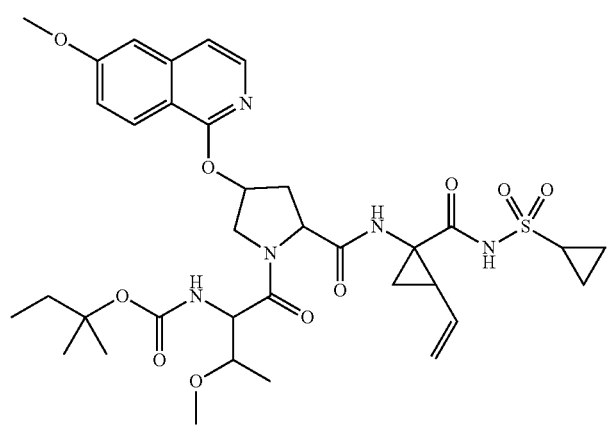 [SMILES: C=CC1CC1(NC(=O)C1CC(Oc2nccc3cc(OC)ccc23)CN1C(=O)C(NC(=O)OC(C)(C)CC)C(C)OC)C(=O)NS(=O)(=O)C1CC1]

TABLE 30-continued
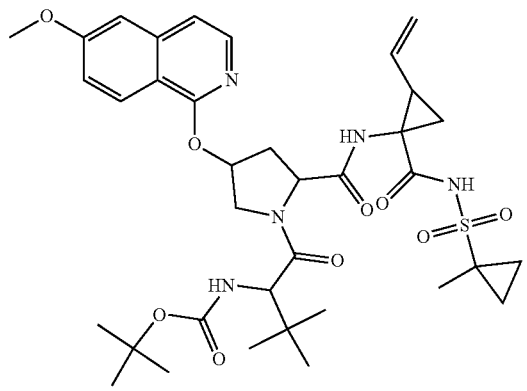 [SMILES: C=CC1CC1(NC(=O)C1CC(Oc2nccc3cc(OC)ccc23)CN1C(=O)C(NC(=O)OC(C)(C)C)C(C)(C)C)C(=O)NS(=O)(=O)C1(C)CC1]
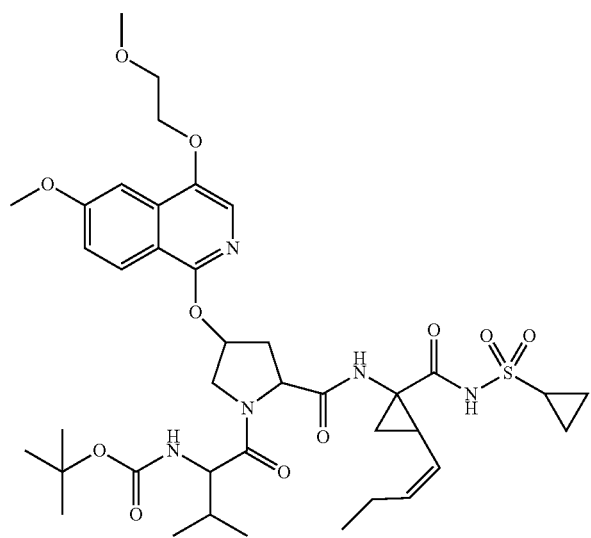 [SMILES: CC/C=C\C1CC1(NC(=O)C1CC(Oc2ncc(OCCOC)c3cc(OC)ccc23)CN1C(=O)C(NC(=O)OC(C)(C)C)C(C)C)C(=O)NS(=O)(=O)C1CC1]
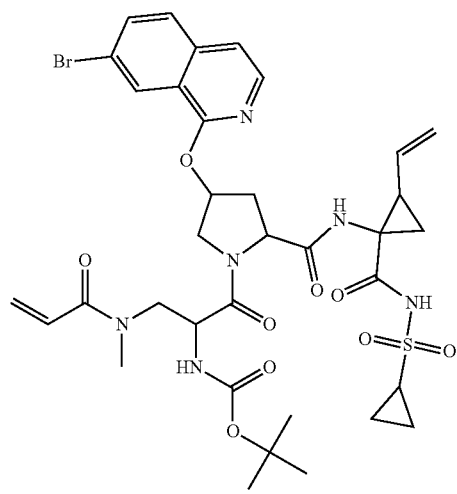 [SMILES: C=CC(=O)N(C)CC(NC(=O)OC(C)(C)C)C(=O)N1CC(Oc2nccc3ccc(Br)cc23)CC1C(=O)NC1(C(=O)NS(=O)(=O)C2CC2)CC1C=C]

TABLE 30-continued
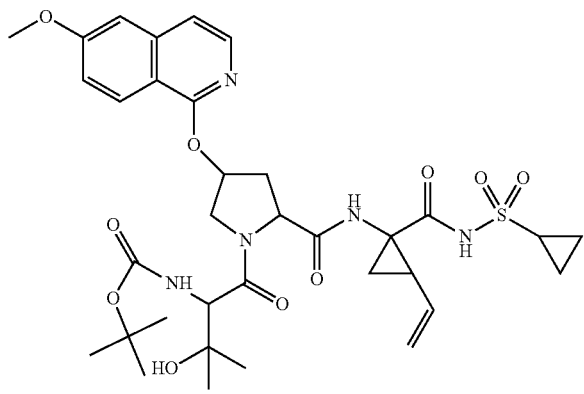 [SMILES: C=CC1CC1(NC(=O)C1CC(Oc2nccc3cc(OC)ccc23)CN1C(=O)C(NC(=O)OC(C)(C)C)C(C)(C)O)C(=O)NS(=O)(=O)C1CC1]
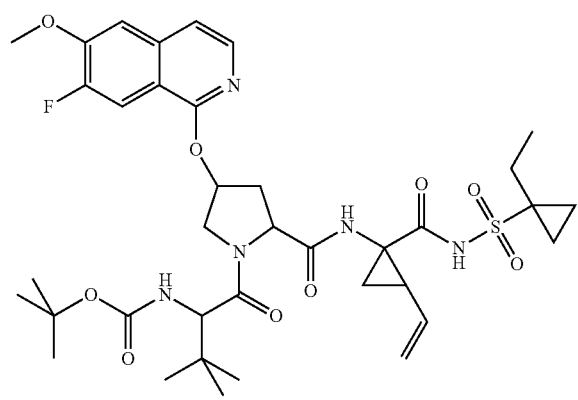 [SMILES: C=CC1CC1(NC(=O)C1CC(Oc2nccc3cc(OC)c(F)cc23)CN1C(=O)C(NC(=O)OC(C)(C)C)C(C)(C)C)C(=O)NS(=O)(=O)C1(CC)CC1]
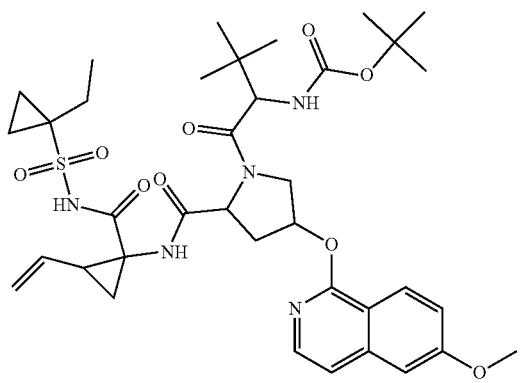 [SMILES: C=CC1CC1(NC(=O)C1CC(Oc2nccc3cc(OC)ccc23)CN1C(=O)C(NC(=O)OC(C)(C)C)C(C)(C)C)C(=O)NS(=O)(=O)C1(CC)CC1]
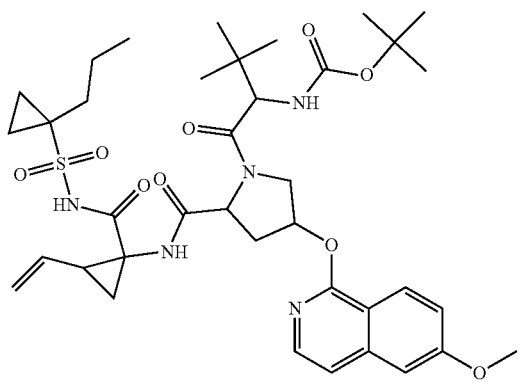 [SMILES: C=CC1CC1(NC(=O)C1CC(Oc2nccc3cc(OC)ccc23)CN1C(=O)C(NC(=O)OC(C)(C)C)C(C)(C)C)C(=O)NS(=O)(=O)C1(CCC)CC1]

TABLE 30-continued
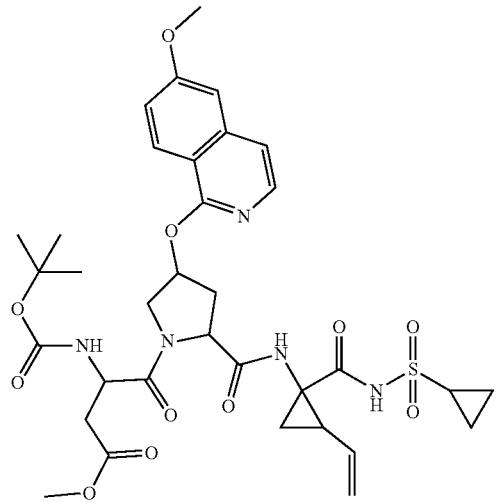 [SMILES: C=CC1CC1(NC(=O)C1CC(Oc2nccc3cc(OC)ccc23)CN1C(=O)C(CC(=O)OC)NC(=O)OC(C)(C)C)C(=O)NS(=O)(=O)C1CC1]
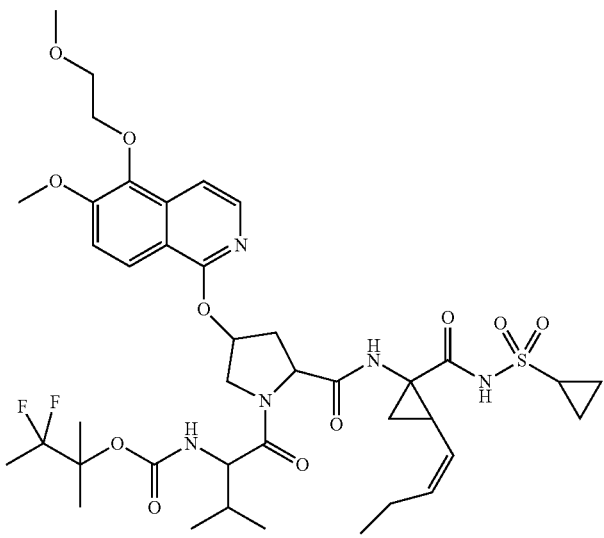 [SMILES: CC/C=C\C1CC1(NC(=O)C1CC(Oc2nccc3c(OCCOC)c(OC)ccc23)CN1C(=O)C(NC(=O)OC(C)(C)C(C)(F)F)C(C)C)C(=O)NS(=O)(=O)C1CC1]
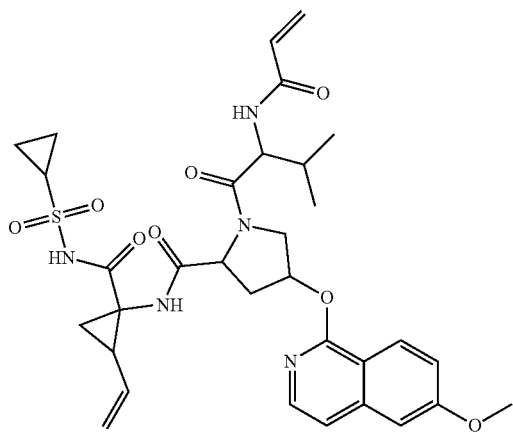 [SMILES: C=CC(=O)NC(C(=O)N1CC(Oc2nccc3cc(OC)ccc23)CC1C(=O)NC1(C(=O)NS(=O)(=O)C2CC2)CC1C=C)C(C)C]

TABLE 30-continued
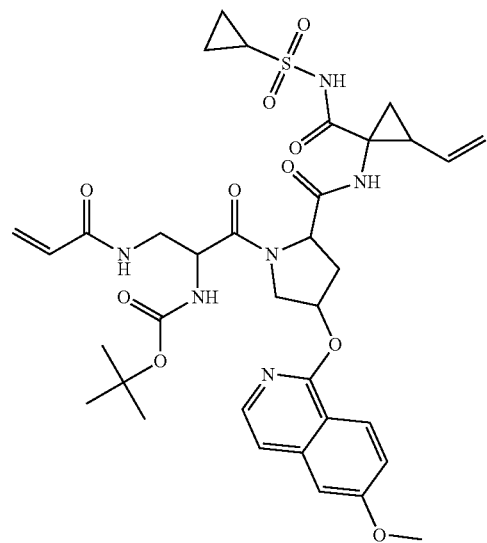 [SMILES: C=CC(=O)NCC(NC(=O)OC(C)(C)C)C(=O)N1CC(Oc2nccc3cc(OC)ccc23)CC1C(=O)NC1(C(=O)NS(=O)(=O)C2CC2)CC1C=C]
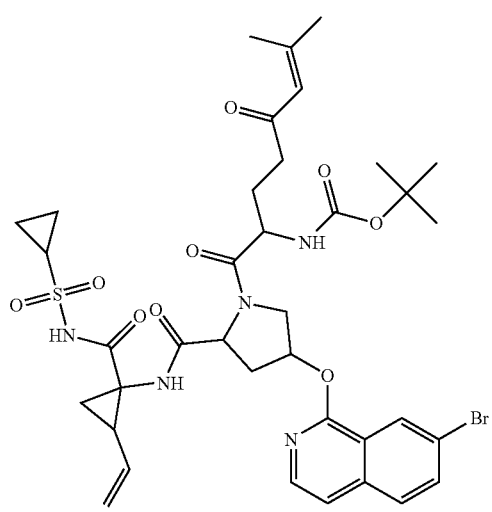 [SMILES: C=CC1CC1(NC(=O)C1CC(Oc2nccc3ccc(Br)cc23)CN1C(=O)C(CCC(=O)C=C(C)C)NC(=O)OC(C)(C)C)C(=O)NS(=O)(=O)C1CC1]
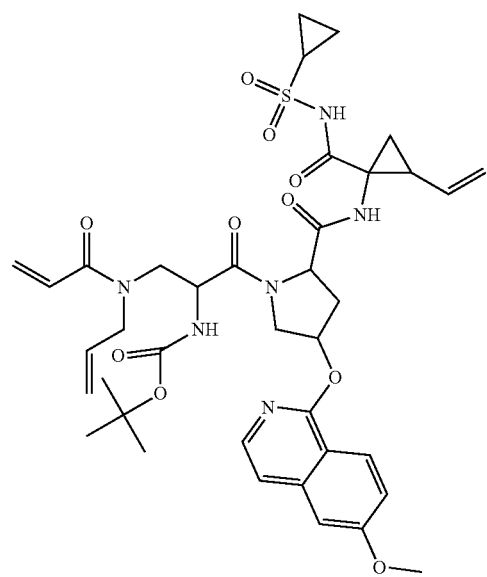 [SMILES: C=CCN(CC(NC(=O)OC(C)(C)C)C(=O)N1CC(Oc2nccc3cc(OC)ccc23)CC1C(=O)NC1(C(=O)NS(=O)(=O)C2CC2)CC1C=C)C(=O)C=C]

TABLE 30-continued
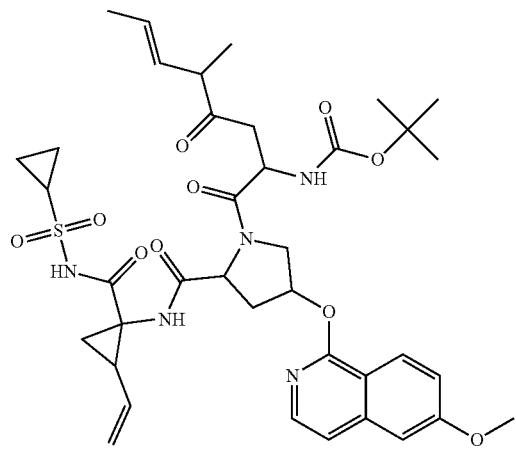 [SMILES: C=CC1CC1(NC(=O)C1CC(Oc2nccc3cc(OC)ccc23)CN1C(=O)C(CC(=O)C(C)/C=C/C)NC(=O)OC(C)(C)C)C(=O)NS(=O)(=O)C1CC1]
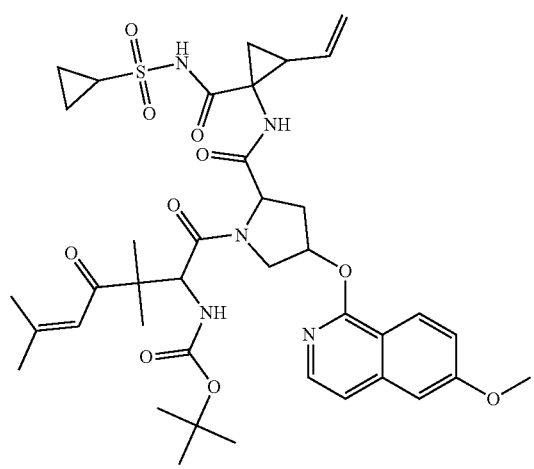 [SMILES: C=CC1CC1(NC(=O)C1CC(Oc2nccc3cc(OC)ccc23)CN1C(=O)C(NC(=O)OC(C)(C)C)C(C)(C)C(=O)C=C(C)C)C(=O)NS(=O)(=O)C1CC1]
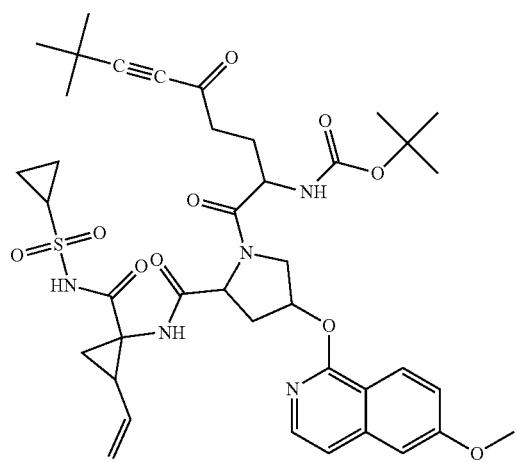 [SMILES: C=CC1CC1(NC(=O)C1CC(Oc2nccc3cc(OC)ccc23)CN1C(=O)C(CCC(=O)C#CC(C)(C)C)NC(=O)OC(C)(C)C)C(=O)NS(=O)(=O)C1CC1]

TABLE 30-continued
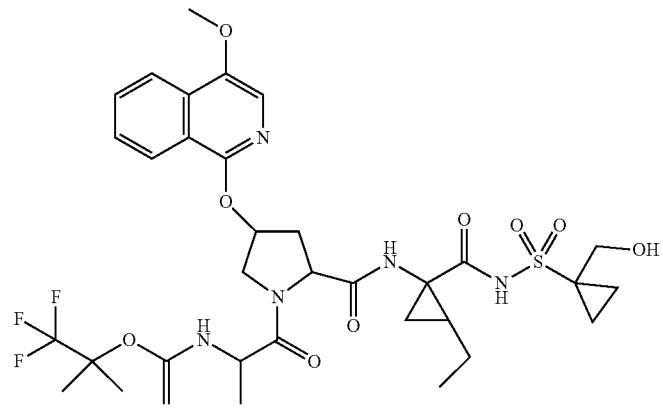 [SMILES: C=C(NC(C)C(=O)N1CC(Oc2ncc(OC)c3ccccc23)CC1C(=O)NC1(C(=O)NS(=O)(=O)C2(CO)CC2)CC1CC)OC(C)(C)C(F)(F)F]
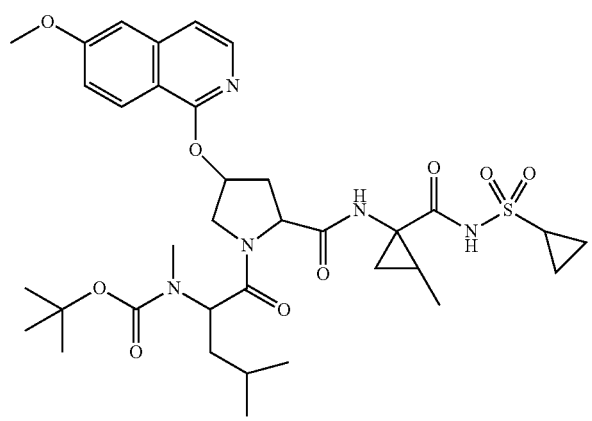 [SMILES: COc1ccc2c(OC3CC(C(=O)NC4(C(=O)NS(=O)(=O)C5CC5)CC4C)N(C(=O)C(CC(C)C)N(C)C(=O)OC(C)(C)C)C3)nccc2c1]
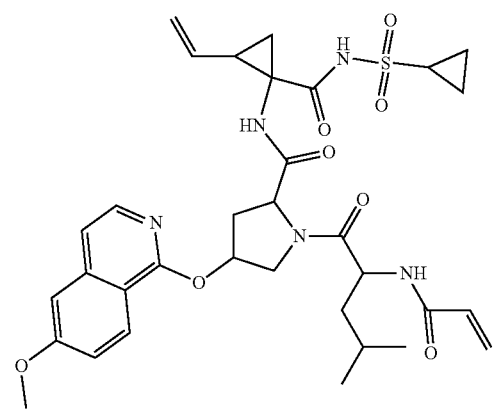 [SMILES: C=CC(=O)NC(CC(C)C)C(=O)N1CC(Oc2nccc3cc(OC)ccc23)CC1C(=O)NC1(C(=O)NS(=O)(=O)C2CC2)CC1C=C]

TABLE 30-continued
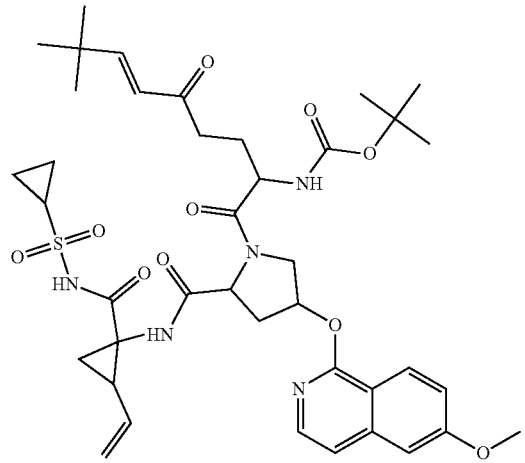 [SMILES: C=CC1CC1(NC(=O)C1CC(Oc2nccc3cc(OC)ccc23)CN1C(=O)C(CCC(=O)/C=C/C(C)(C)C)NC(=O)OC(C)(C)C)C(=O)NS(=O)(=O)C1CC1]
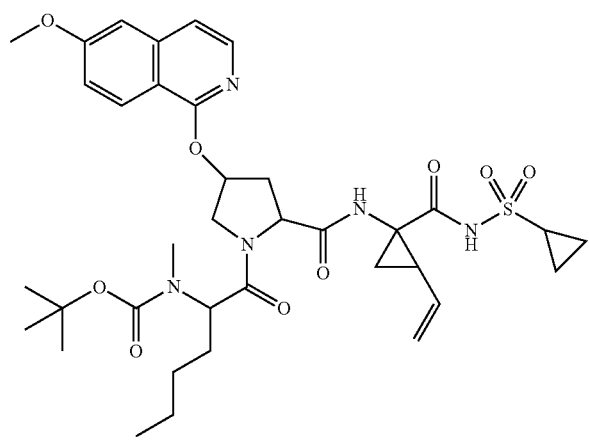 [SMILES: C=CC1CC1(NC(=O)C1CC(Oc2nccc3cc(OC)ccc23)CN1C(=O)C(CCCC)N(C)C(=O)OC(C)(C)C)C(=O)NS(=O)(=O)C1CC1]
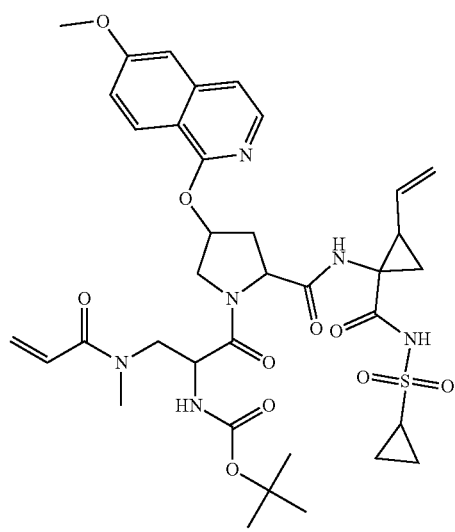 [SMILES: C=CC(=O)N(C)CC(NC(=O)OC(C)(C)C)C(=O)N1CC(Oc2nccc3cc(OC)ccc23)CC1C(=O)NC1(C(=O)NS(=O)(=O)C2CC2)CC1C=C]

TABLE 30-continued
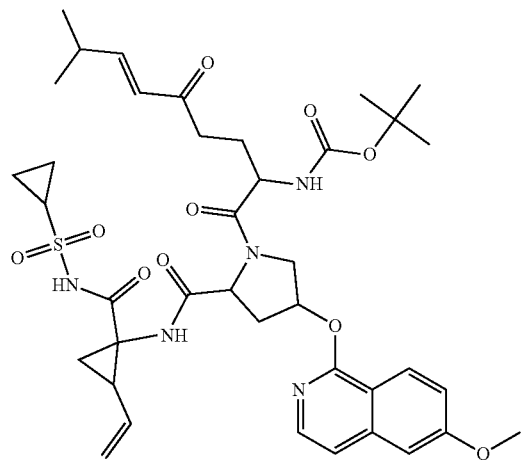 [SMILES: C=CC1CC1(NC(=O)C1CC(Oc2nccc3cc(OC)ccc23)CN1C(=O)C(CCC(=O)/C=C/C(C)C)NC(=O)OC(C)(C)C)C(=O)NS(=O)(=O)C1CC1]
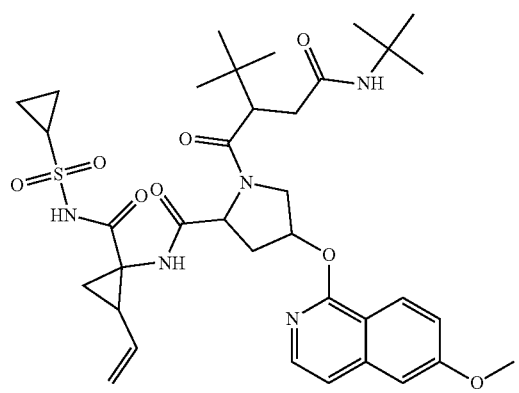 [SMILES: C=CC1CC1(NC(=O)C1CC(Oc2nccc3cc(OC)ccc23)CN1C(=O)C(CC(=O)NC(C)(C)C)C(C)(C)C)C(=O)NS(=O)(=O)C1CC1]
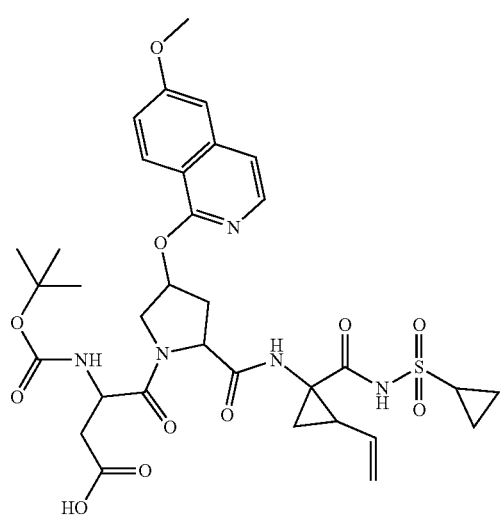 [SMILES: C=CC1CC1(NC(=O)C1CC(Oc2nccc3cc(OC)ccc23)CN1C(=O)C(CC(=O)O)NC(=O)OC(C)(C)C)C(=O)NS(=O)(=O)C1CC1]

TABLE 30-continued
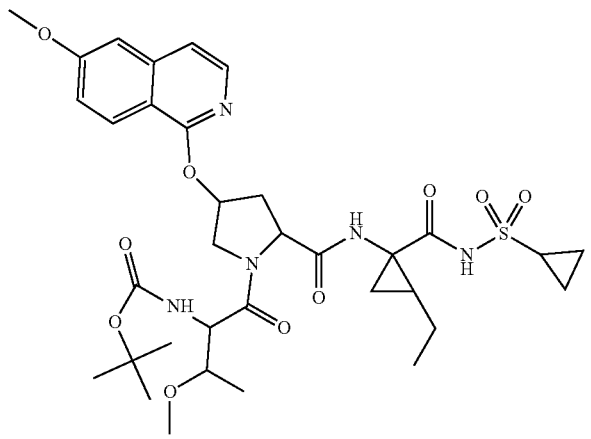 [SMILES: CCC1CC1(NC(=O)C1CC(Oc2nccc3cc(OC)ccc23)CN1C(=O)C(NC(=O)OC(C)(C)C)C(C)OC)C(=O)NS(=O)(=O)C1CC1]
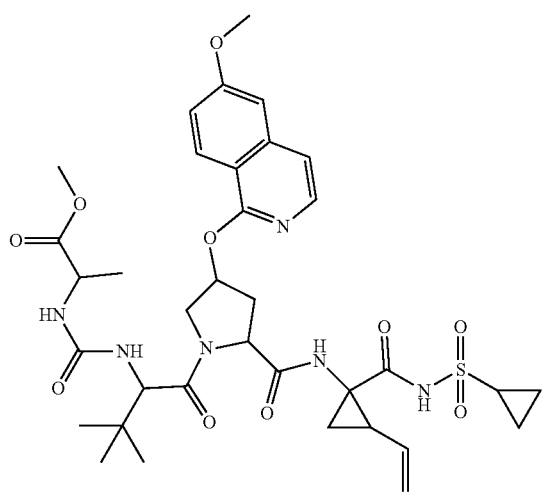 [SMILES: C=CC1CC1(NC(=O)C1CC(Oc2nccc3cc(OC)ccc23)CN1C(=O)C(NC(=O)NC(C)C(=O)OC)C(C)(C)C)C(=O)NS(=O)(=O)C1CC1]
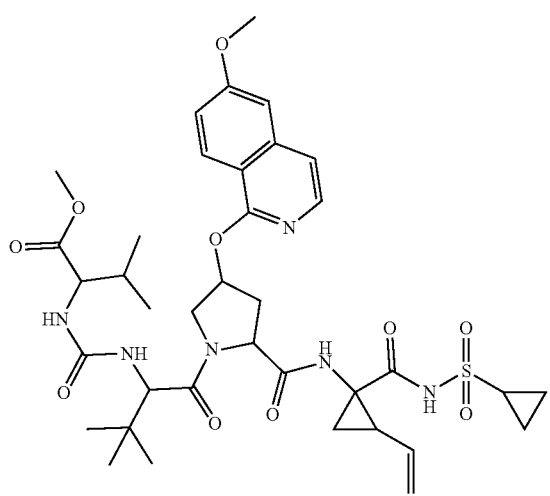 [SMILES: C=CC1CC1(NC(=O)C1CC(Oc2nccc3cc(OC)ccc23)CN1C(=O)C(NC(=O)NC(C(=O)OC)C(C)C)C(C)(C)C)C(=O)NS(=O)(=O)C1CC1]

TABLE 30-continued
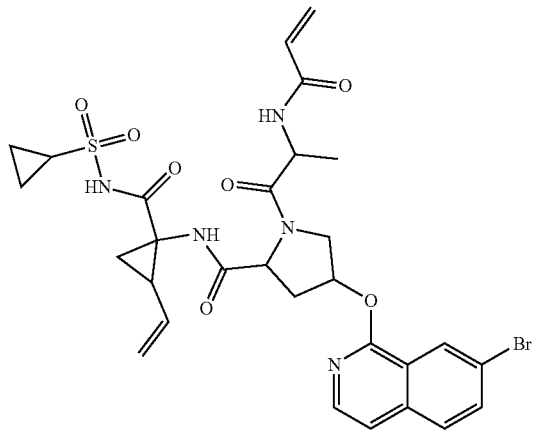 [SMILES: C=CC(=O)NC(C)C(=O)N1CC(Oc2nccc3ccc(Br)cc23)CC1C(=O)NC1(C(=O)NS(=O)(=O)C2CC2)CC1C=C]
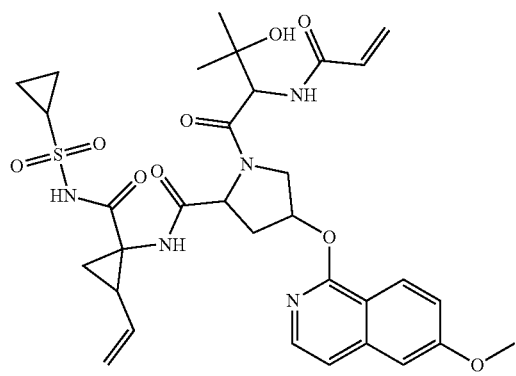 [SMILES: C=CC(=O)NC(C(=O)N1CC(Oc2nccc3cc(OC)ccc23)CC1C(=O)NC1(C(=O)NS(=O)(=O)C2CC2)CC1C=C)C(C)(C)O]
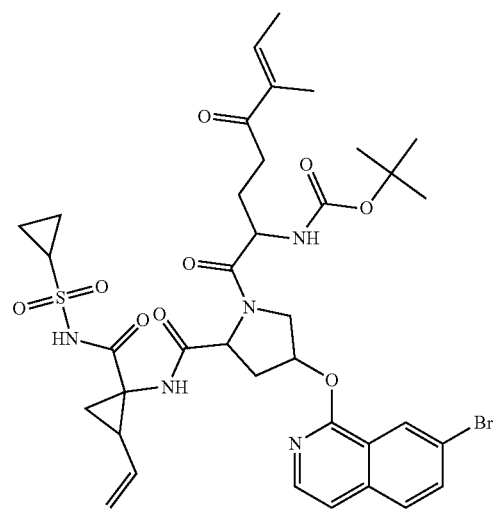 [SMILES: C=CC1CC1(NC(=O)C1CC(Oc2nccc3ccc(Br)cc23)CN1C(=O)C(CCC(=O)/C(C)=C/C)NC(=O)OC(C)(C)C)C(=O)NS(=O)(=O)C1CC1]

TABLE 30-continued
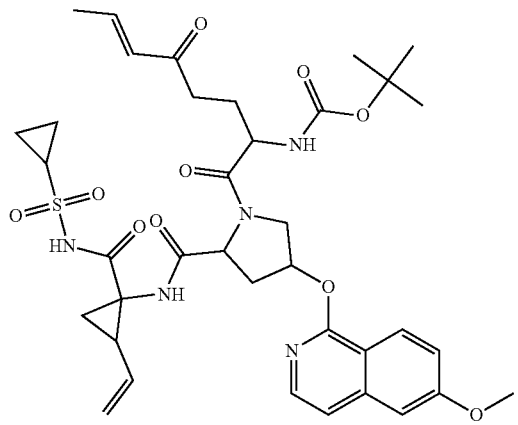 [SMILES: C=CC1CC1(NC(=O)C1CC(Oc2nccc3cc(OC)ccc23)CN1C(=O)C(CCC(=O)/C=C/C)NC(=O)OC(C)(C)C)C(=O)NS(=O)(=O)C1CC1]
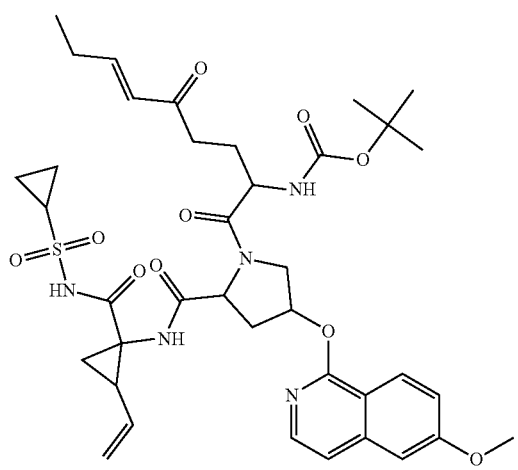 [SMILES: C=CC1CC1(NC(=O)C1CC(Oc2nccc3cc(OC)ccc23)CN1C(=O)C(CCC(=O)/C=C/CC)NC(=O)OC(C)(C)C)C(=O)NS(=O)(=O)C1CC1]
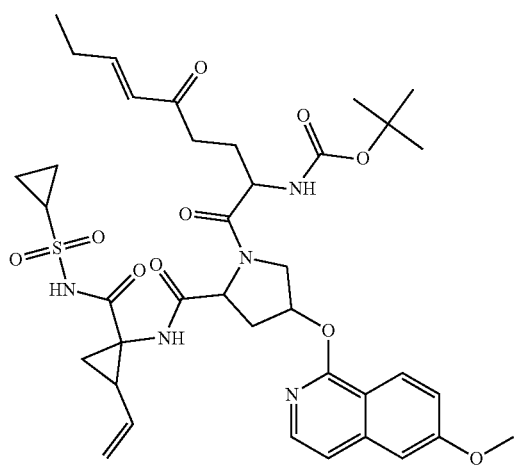 [SMILES: C=CC1CC1(NC(=O)C1CC(Oc2nccc3cc(OC)ccc23)CN1C(=O)C(CCC(=O)/C=C/CC)NC(=O)OC(C)(C)C)C(=O)NS(=O)(=O)C1CC1]

TABLE 30-continued
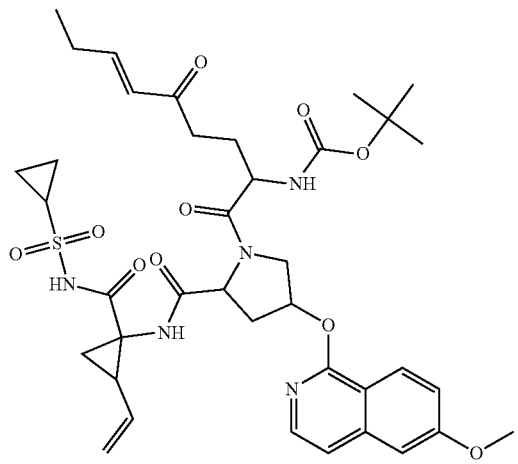 [SMILES: C=CC1CC1(NC(=O)C1CC(Oc2nccc3cc(OC)ccc23)CN1C(=O)C(CCC(=O)/C=C/CC)NC(=O)OC(C)(C)C)C(=O)NS(=O)(=O)C1CC1]
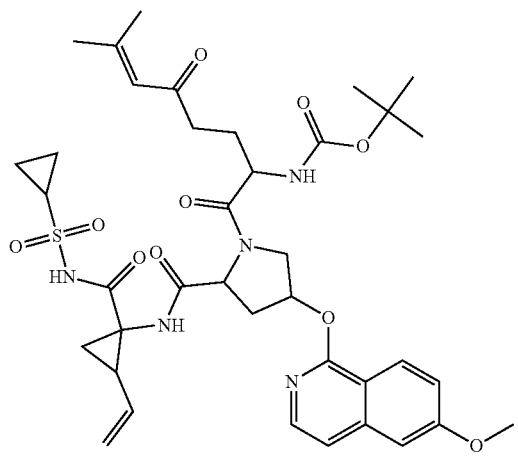 [SMILES: C=CC1CC1(NC(=O)C1CC(Oc2nccc3cc(OC)ccc23)CN1C(=O)C(CCC(=O)C=C(C)C)NC(=O)OC(C)(C)C)C(=O)NS(=O)(=O)C1CC1]
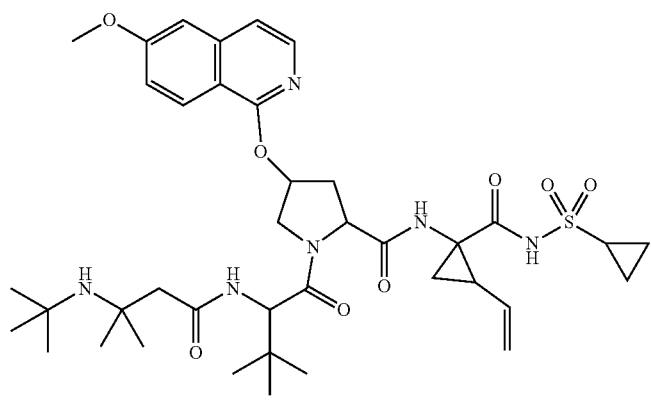 [SMILES: C=CC1CC1(NC(=O)C1CC(Oc2nccc3cc(OC)ccc23)CN1C(=O)C(NC(=O)CC(C)(C)NC(C)(C)C)C(C)(C)C)C(=O)NS(=O)(=O)C1CC1]

TABLE 30-continued
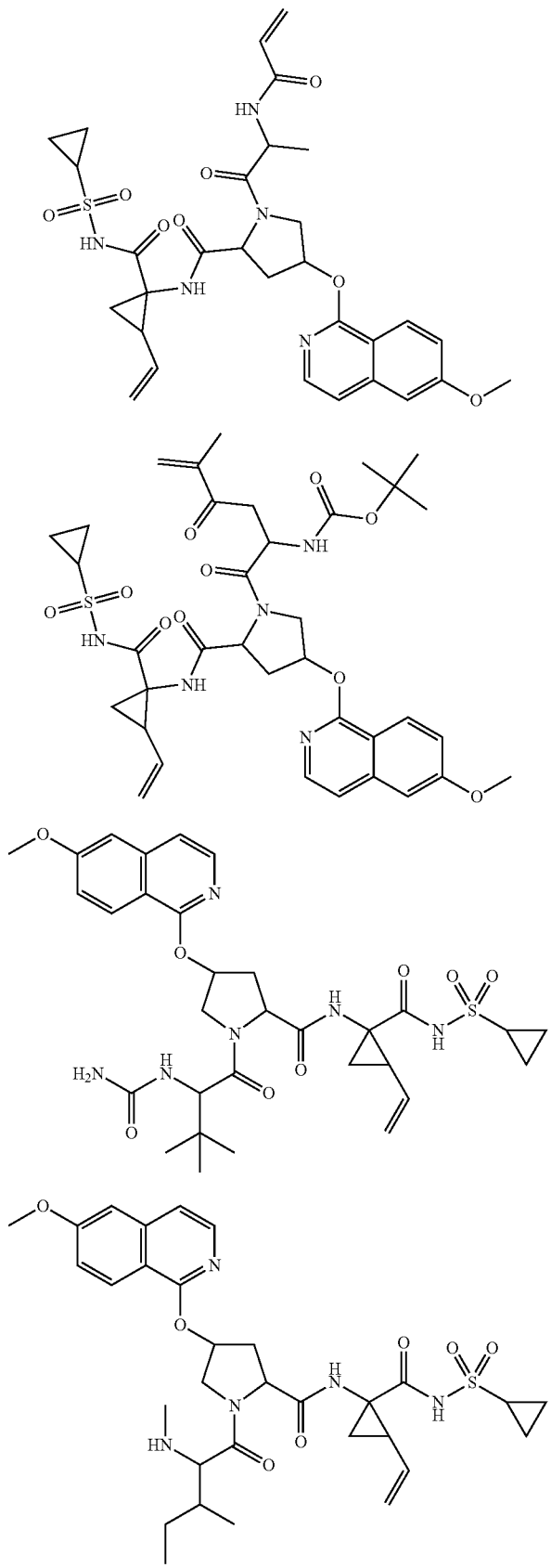

TABLE 30-continued
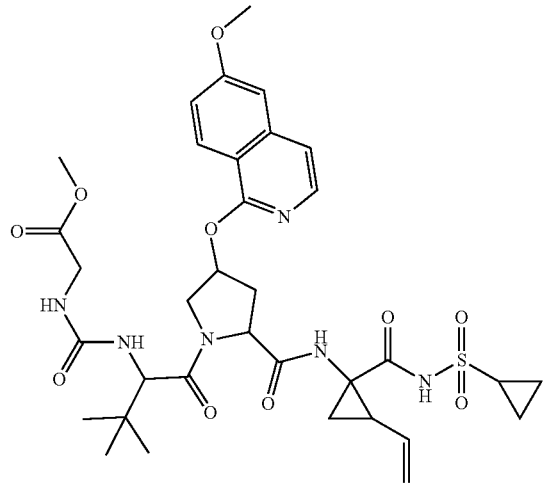 [SMILES: C=CC1CC1(NC(=O)C1CC(Oc2nccc3cc(OC)ccc23)CN1C(=O)C(NC(=O)NCC(=O)OC)C(C)(C)C)C(=O)NS(=O)(=O)C1CC1]
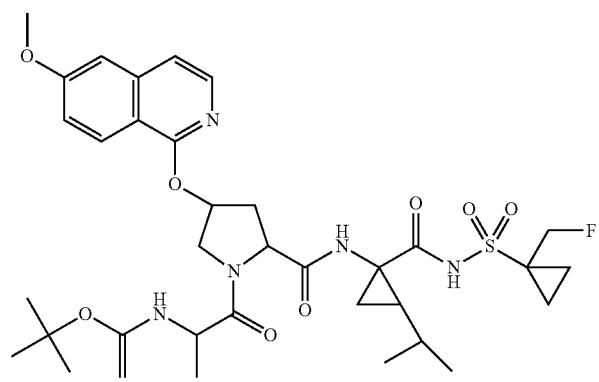 [SMILES: C=C(NC(C)C(=O)N1CC(Oc2nccc3cc(OC)ccc23)CC1C(=O)NC1(C(=O)NS(=O)(=O)C2(CF)CC2)CC1C(C)C)OC(C)(C)C]
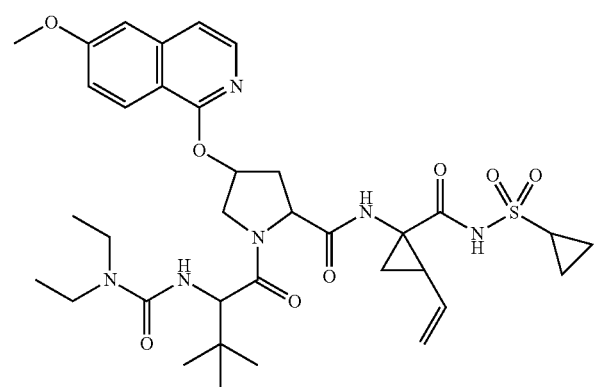 [SMILES: C=CC1CC1(NC(=O)C1CC(Oc2nccc3cc(OC)ccc23)CN1C(=O)C(NC(=O)N(CC)CC)C(C)(C)C)C(=O)NS(=O)(=O)C1CC1]

TABLE 30-continued
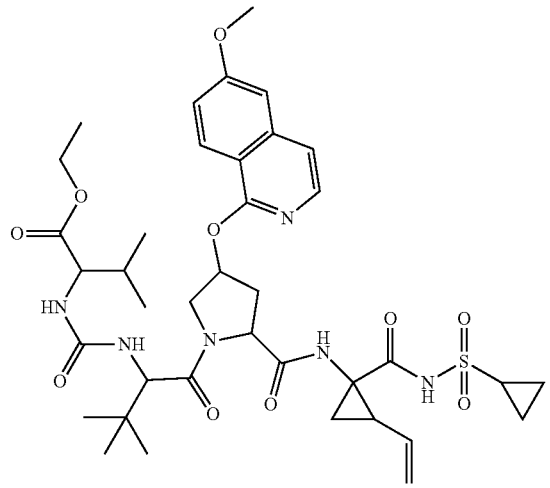 [SMILES: C=CC1CC1(NC(=O)C1CC(Oc2nccc3cc(OC)ccc23)CN1C(=O)C(NC(=O)NC(C(=O)OCC)C(C)C)C(C)(C)C)C(=O)NS(=O)(=O)C1CC1]
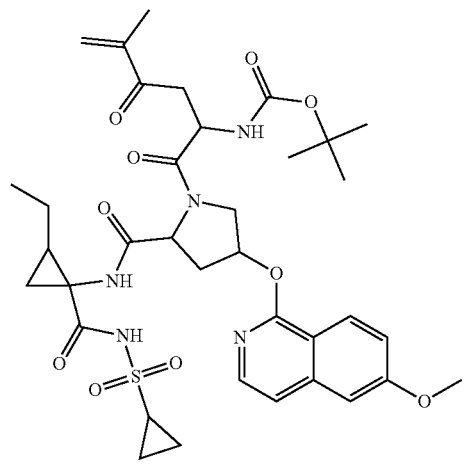 [SMILES: C=C(C)C(=O)CC(NC(=O)OC(C)(C)C)C(=O)N1CC(Oc2nccc3cc(OC)ccc23)CC1C(=O)NC1(C(=O)NS(=O)(=O)C2CC2)CC1CC]
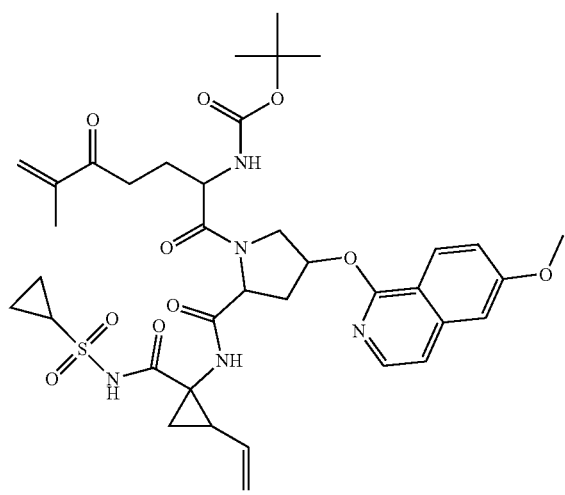 [SMILES: C=CC1CC1(NC(=O)C1CC(Oc2nccc3cc(OC)ccc23)CN1C(=O)C(CCC(=O)C(=C)C)NC(=O)OC(C)(C)C)C(=O)NS(=O)(=O)C1CC1]

TABLE 30-continued
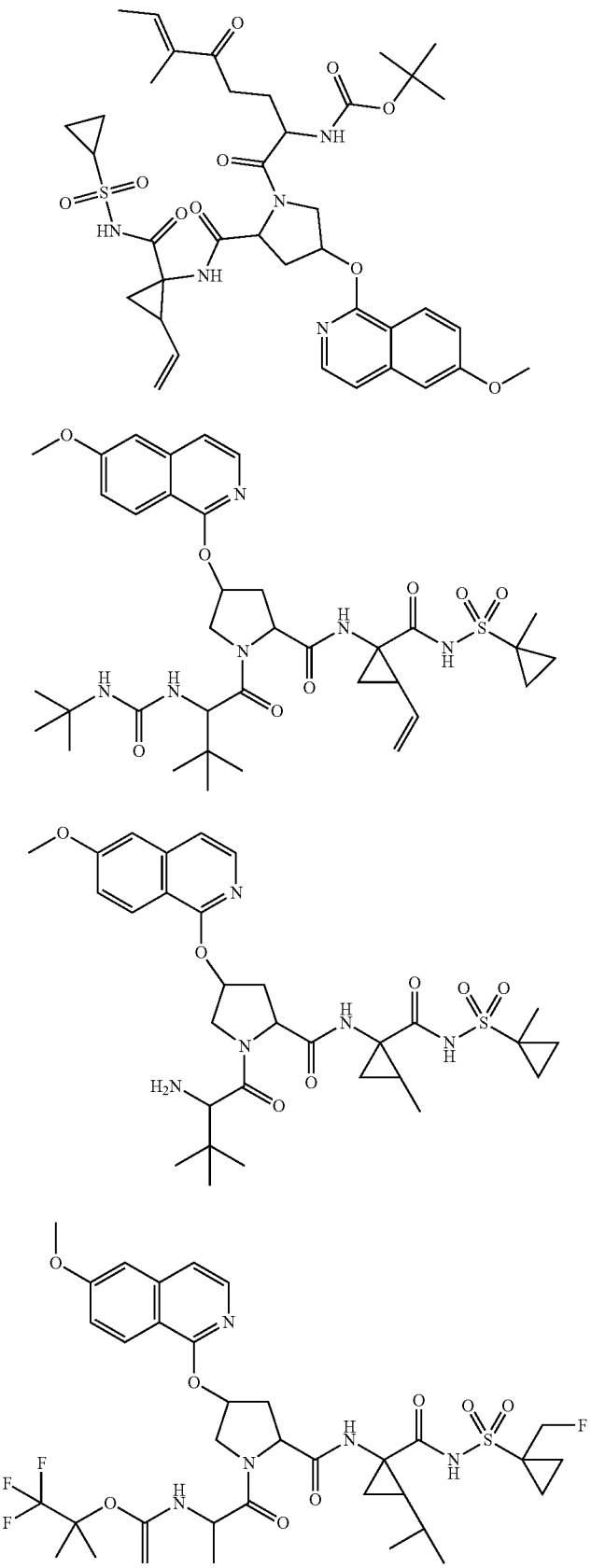

TABLE 30-continued

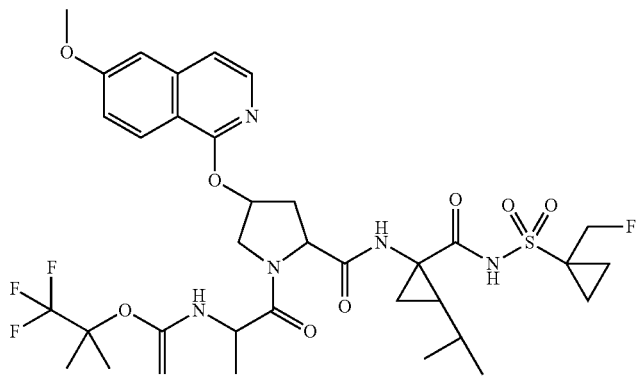 [SMILES: C=C(NC(C)C(=O)N1CC(Oc2nccc3cc(OC)ccc23)CC1C(=O)NC1(C(=O)NS(=O)(=O)C2(CF)CC2)CC1C(C)C)OC(C)(C)C(F)(F)F]

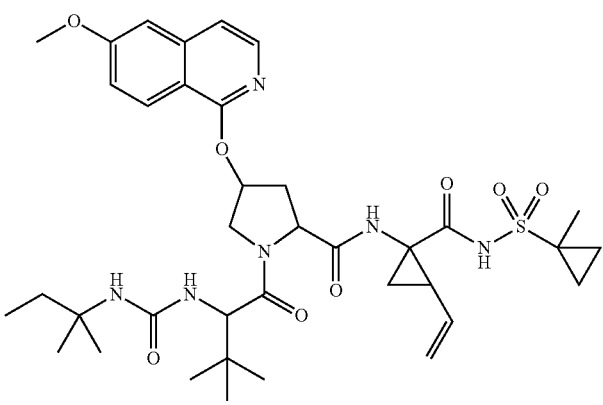 [SMILES: C=CC1CC1(NC(=O)C1CC(Oc2nccc3cc(OC)ccc23)CN1C(=O)C(NC(=O)NC(C)(C)CC)C(C)(C)C)C(=O)NS(=O)(=O)C1(C)CC1]

In one implementation, the compound is Atazanavir (methyl N-[(2S)-1-[2-[(2S,3S)-2-hydroxy-3-[[(2S)-2-(methoxycarbonylamino)-3,3-dimethylbutanoyl]amino]-4-phenylbutyl]-2-[(4-pyridin-2-ylphenyl)methyl]hydrazinyl]-3,3-dimethyl-1-oxobutan-2-yl]carbamate) a clinically investigated HIV GAG POL polyprotein inhibitor; HIV GAG protein inhibitor; and HIV-1 protease inhibitor. In one particular implementation, the compound, or variations and permutations thereof, is further described in WO1999036404; WO2008011117; and WO2005058841 the contents of which are hereby incorporated by reference for all purposes and the specific purposes identified herein. In some embodiments, such compounds are represented by any one or more of the structures shown in Table 35. Any one of the compounds depicted in Table 35 is suitable for use in the methods of the present disclosure.

TABLE 31

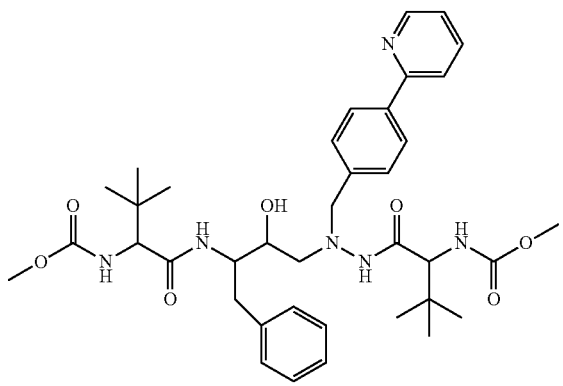

TABLE 31-continued

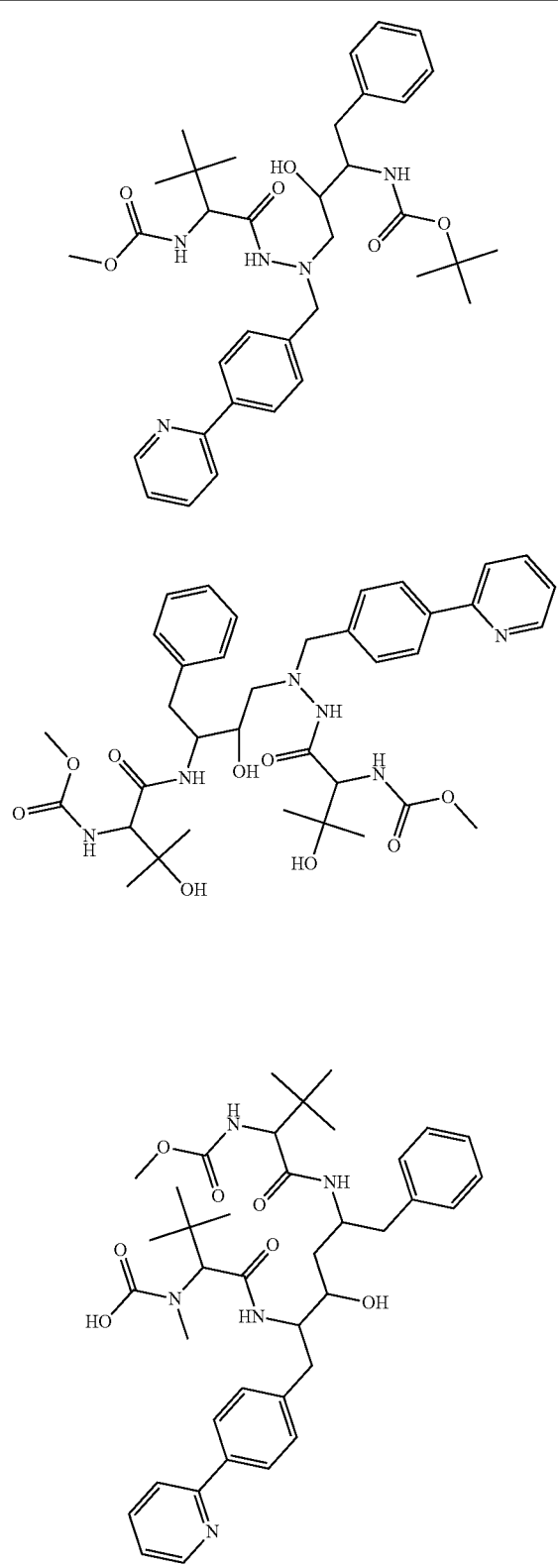

TABLE 31-continued

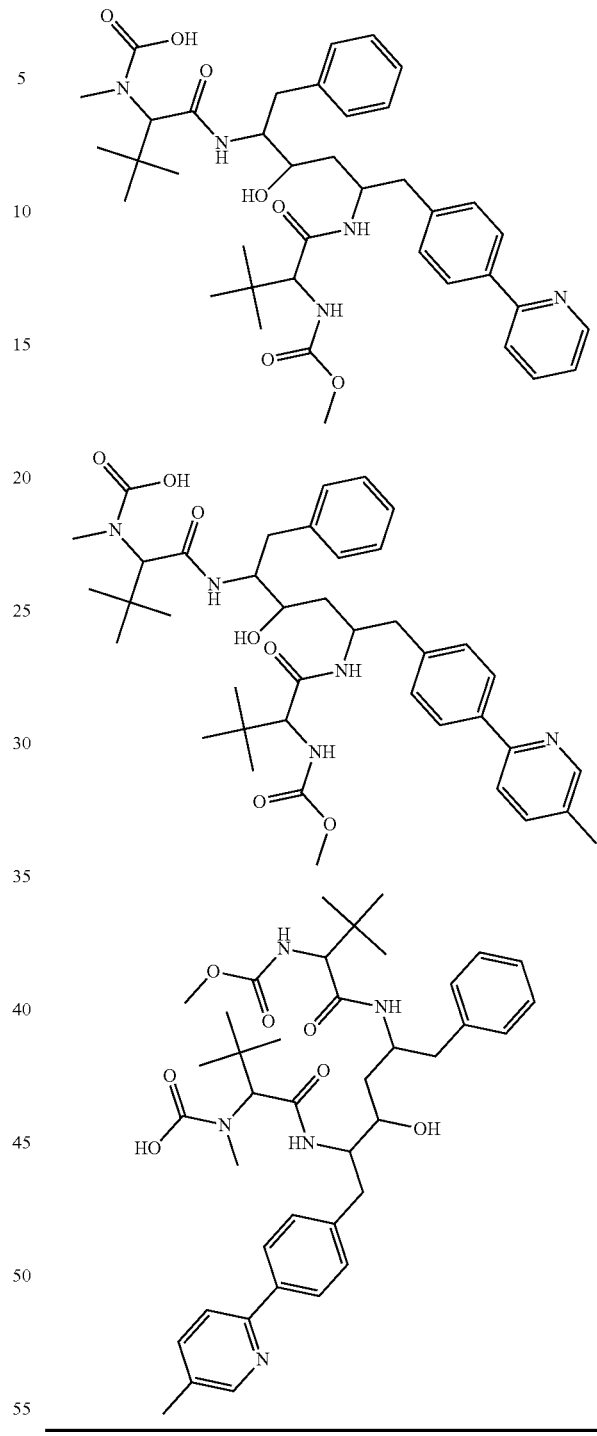

In one implementation, the compound is atenolol, (2-[4-[2-hydroxy-3-(propan-2-ylamino)propoxy]phenyl]acetamide or (s)-atenolol, a clinically investigated Beta 1 adrenoceptor antagonist.

In one particular implementation, the compound, or variations and permutations thereof, is further described in WO2007117560 the contents of which are hereby incorporated by reference for all purposes and the specific purposes identified herein. In some embodiments, such compounds are represented by any one or more of the structures shown

TABLE 32

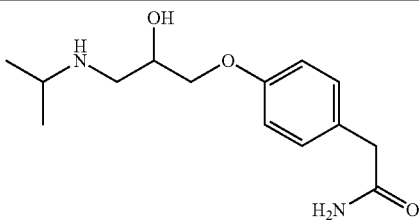

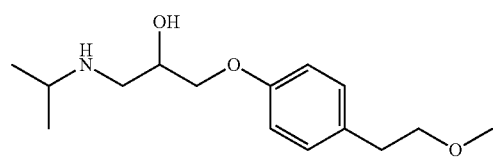 [SMILES: COCCc1ccc(OCC(O)CNC(C)C)cc1]

In one implementation, the compound is beclabuvir (8S, 10R)-19-cyclohexyl-N-(dimethylsulfamoyl)-5-methoxy-10-(3-methyl-3,8-diazabicyclo[3.2.1]octane-8-carbonyl)-12-azapentacyclo[10.7.0.0²,⁷.0⁸,¹⁰.0¹³,¹⁸]nonadeca-1(19), 2(7),3,5,13(18), 14,16-heptaene-15-carboxamide), a clinically investigated hepatitis C virus NS5B polymerase inhibitor. In one particular implementation, the compound, or variations and permutations thereof, is further described in WO2007033175; WO2007136982; and WO2007140109 the contents of which are hereby incorporated by reference for all purposes and the specific purposes identified herein. In some embodiments, such compounds are represented by any one or more of the structures shown in Table 37. Any one of the compounds depicted in Table 37 is suitable for use in the methods of the present disclosure.

TABLE 33

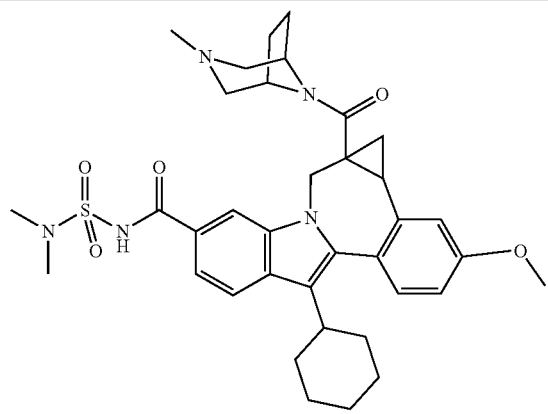

TABLE 33-continued

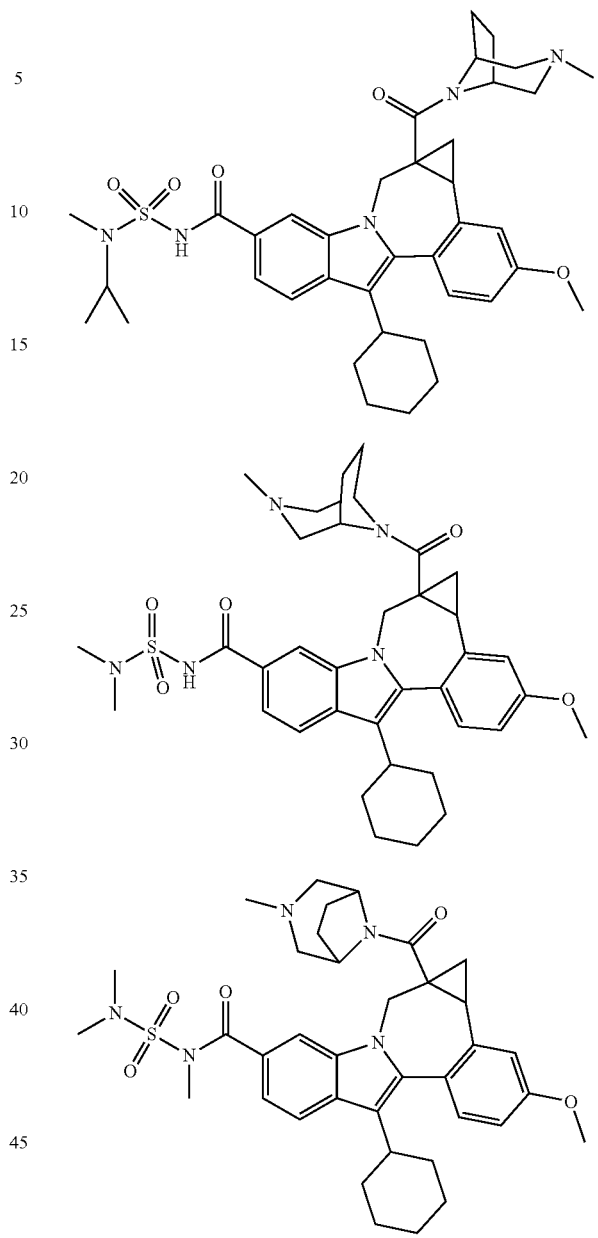

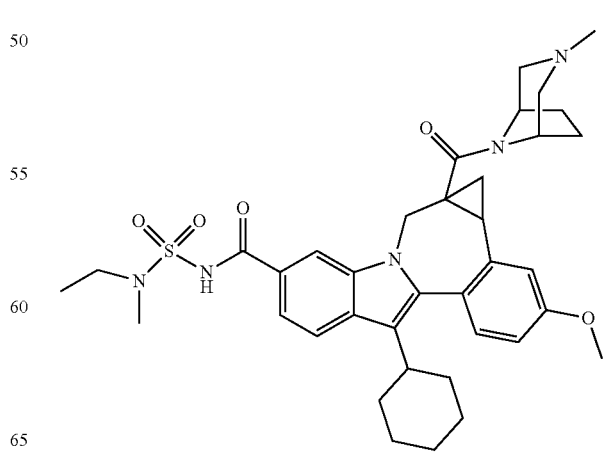

TABLE 33-continued
253
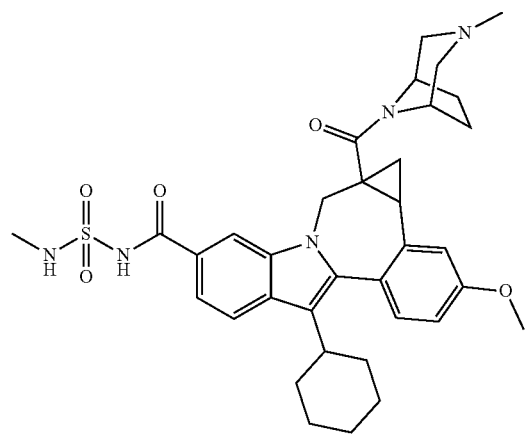
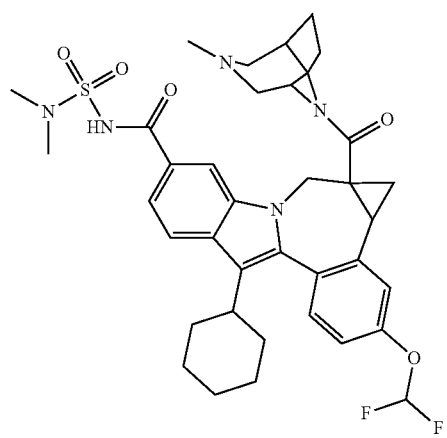 [SMILES: CN1CC2CCC23C(C1)N3C(=O)C12CC1c1cc(OC(F)F)ccc1-c1c(C3CCCCC3)c3ccc(C(=O)NS(=O)(=O)N(C)C)cc3n1C2]
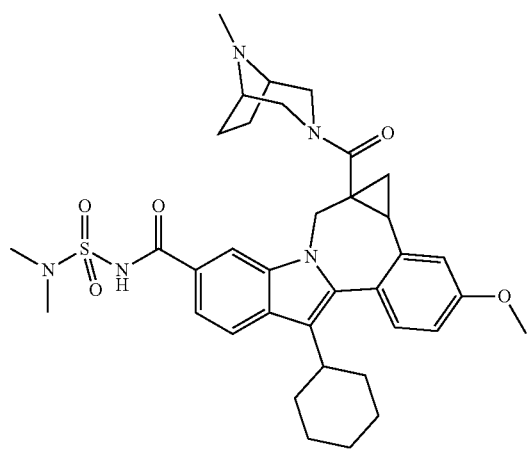
TABLE 33-continued
254
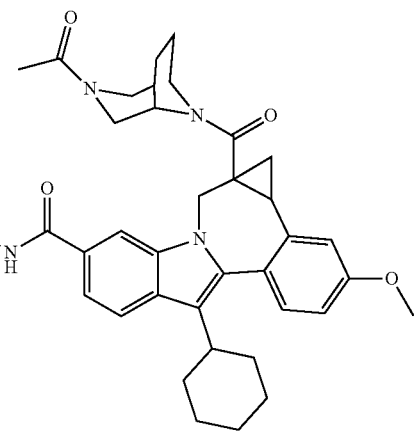
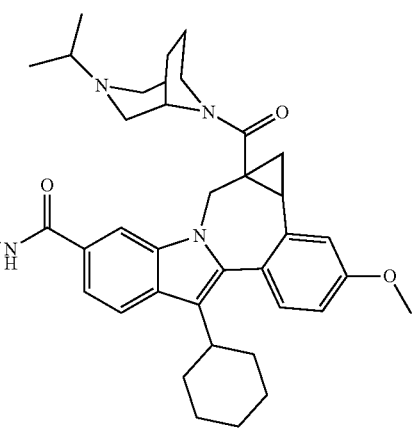
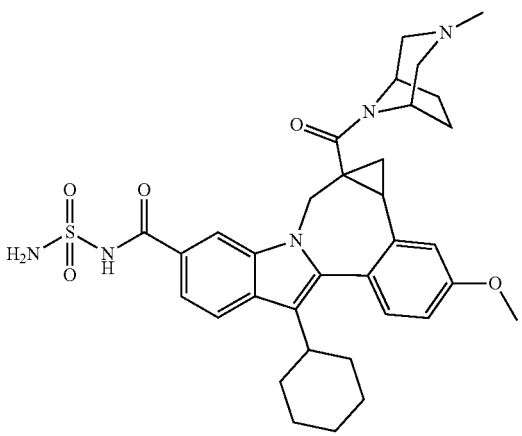 [SMILES: COc1ccc2c(c1)C1CC1(C(=O)N1C3CCC1CN(C)C3)Cn1c-2c(C2CCCCC2)c2ccc(C(=O)NS(N)(=O)=O)cc21]

TABLE 33-continued
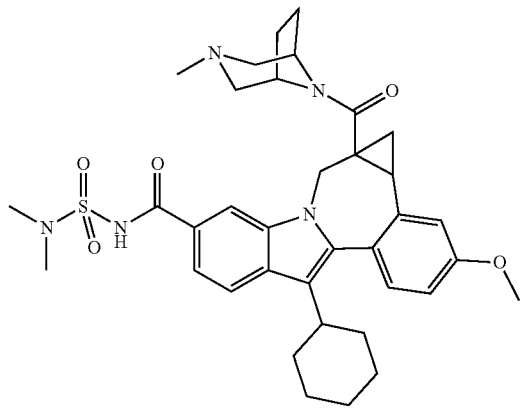
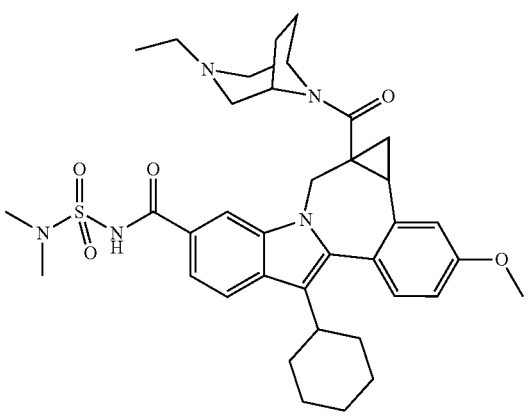
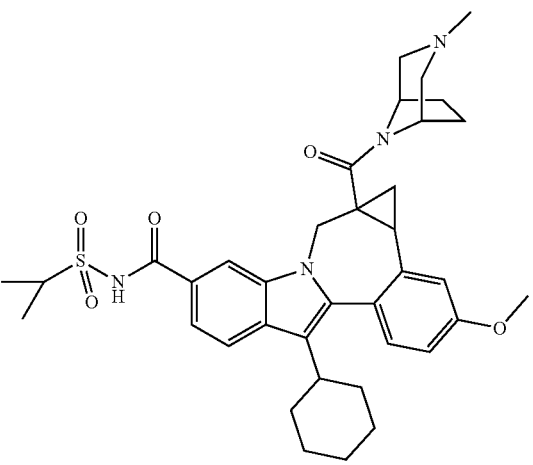 [SMILES: COc1ccc2c(c1)C1CC1(C(=O)N1C3CCC1CN(C)C3)Cn1c-2c(C2CCCCC2)c2ccc(C(=O)NS(=O)(=O)C(C)C)cc21]
TABLE 33-continued
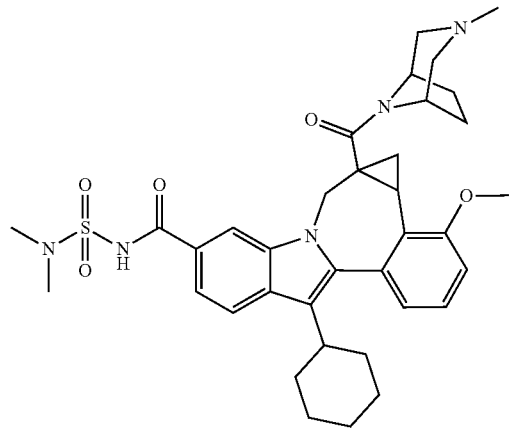
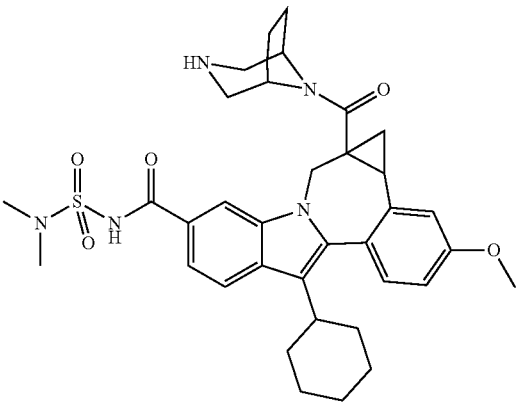
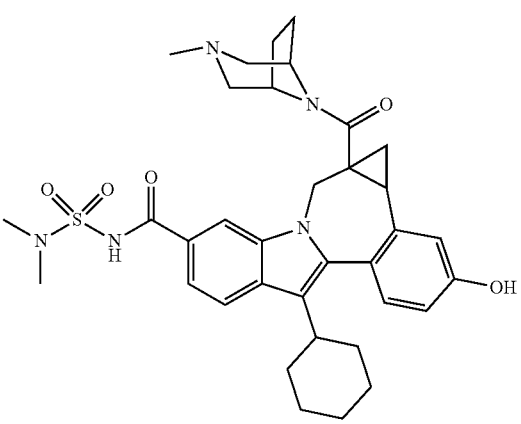 [SMILES: CN1CC2CCC(C1)N2C(=O)C12CC1c1cc(O)ccc1-c1c(C3CCCCC3)c3ccc(C(=O)NS(=O)(=O)N(C)C)cc3n1C2]

TABLE 33-continued
257
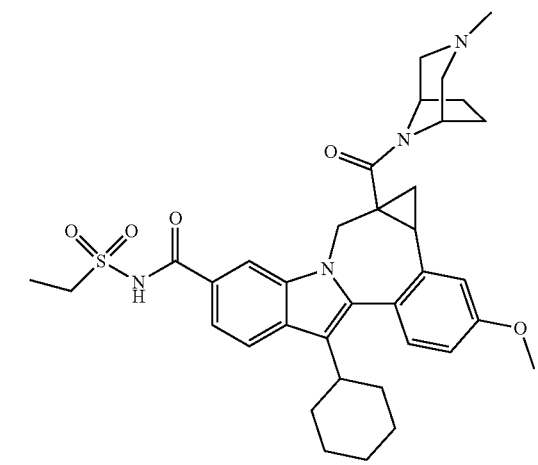 [SMILES: CCS(=O)(=O)NC(=O)c1ccc2c(C3CCCCC3)c3n(c2c1)CC1(C(=O)N2C4CCC2CN(C)C4)CC1c1cc(OC)ccc1-3]
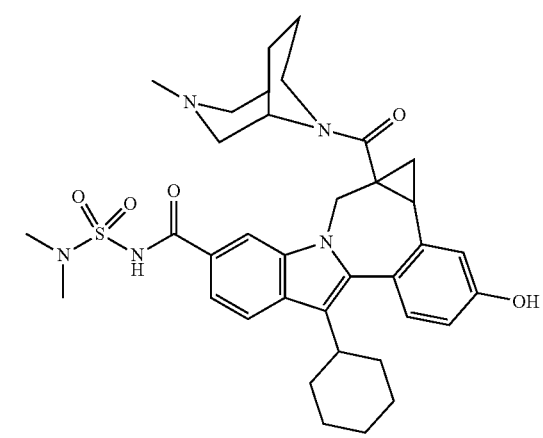 [SMILES: CN1CCC2C(CCCCN2C(=O)C23CC2c2cc(O)ccc2-c2c(C4CCCCC4)c4ccc(C(=O)NS(=O)(=O)N(C)C)cc4n2C3)C1]
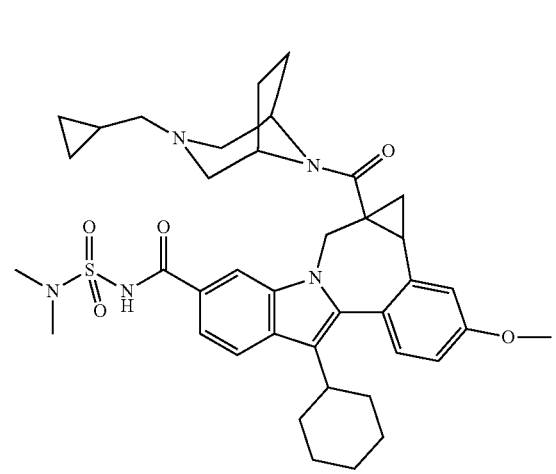
TABLE 33-continued
258
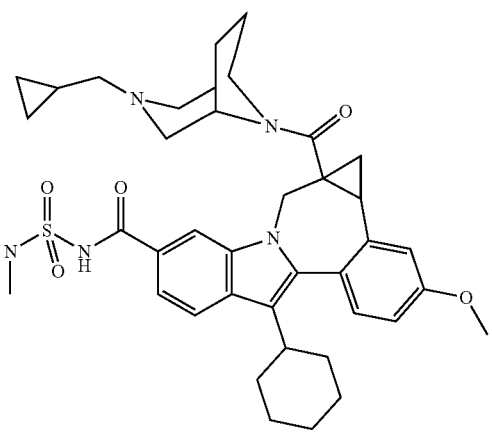
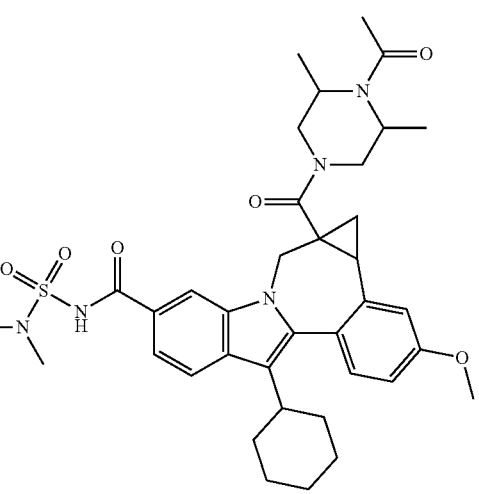
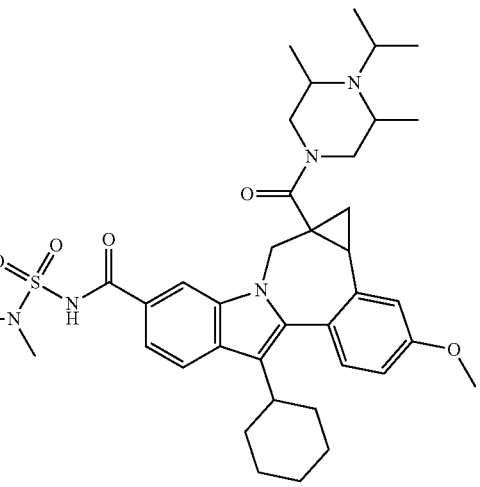

TABLE 33-continued
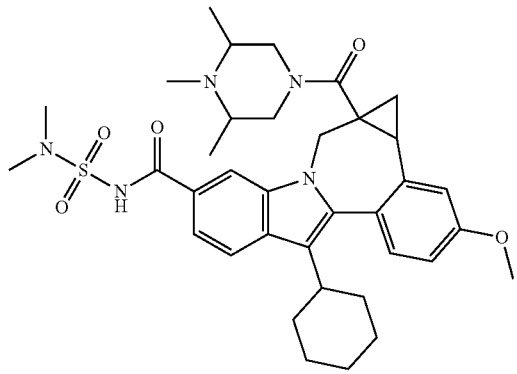
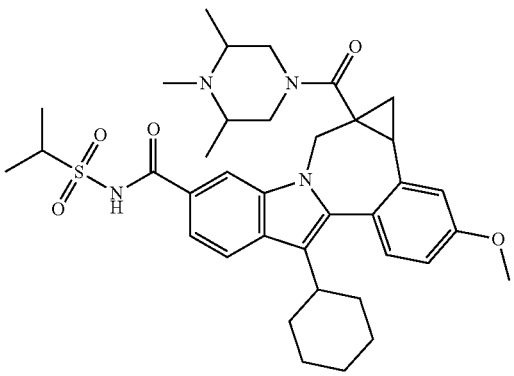
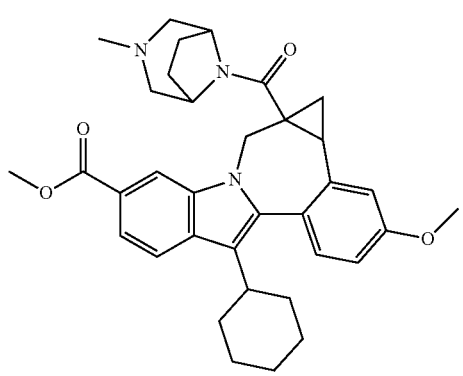
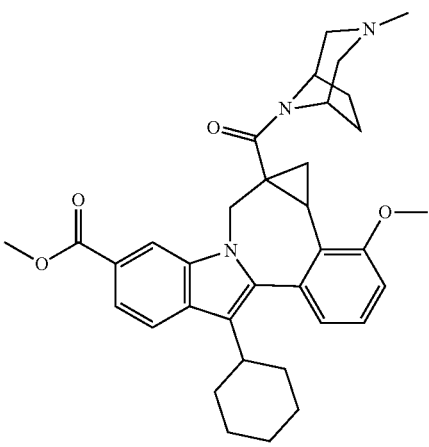
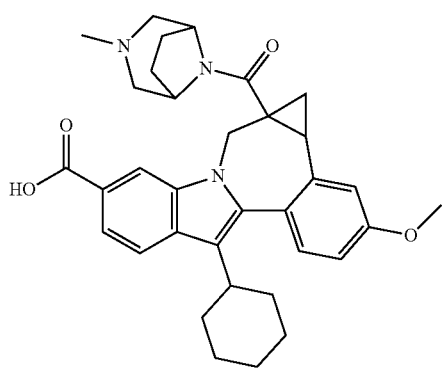 [SMILES: COc1ccc2c(c1)C1CC1(C(=O)N1C3CCC1CN(C)C3)Cn1c-2c(C2CCCCC2)c2ccc(C(=O)O)cc21]
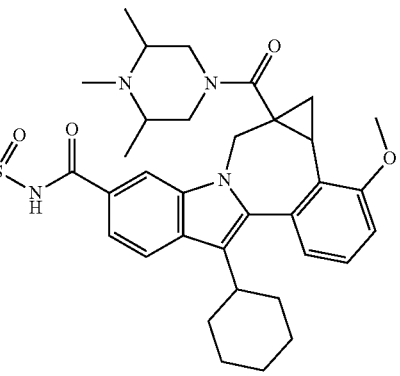
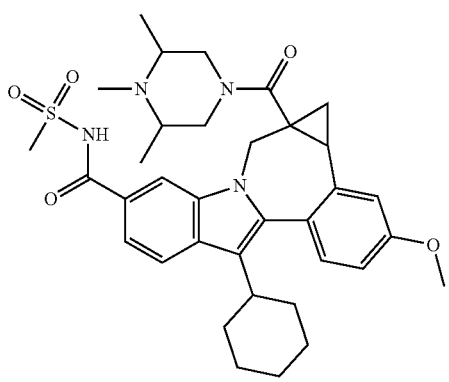 [SMILES: COc1ccc2c(c1)C1CC1(C(=O)N1CC(C)N(C)C(C)C1)Cn1c-2c(C2CCCCC2)c2ccc(C(=O)NS(C)(=O)=O)cc21]
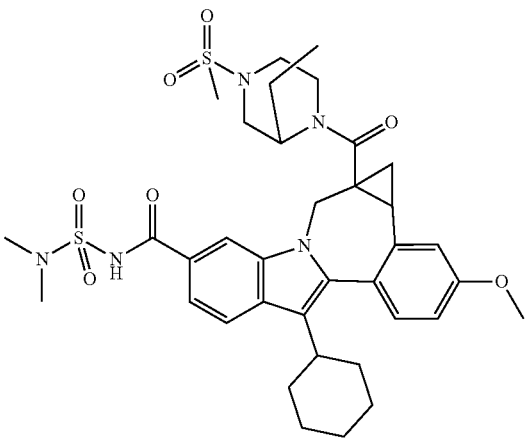

TABLE 33-continued
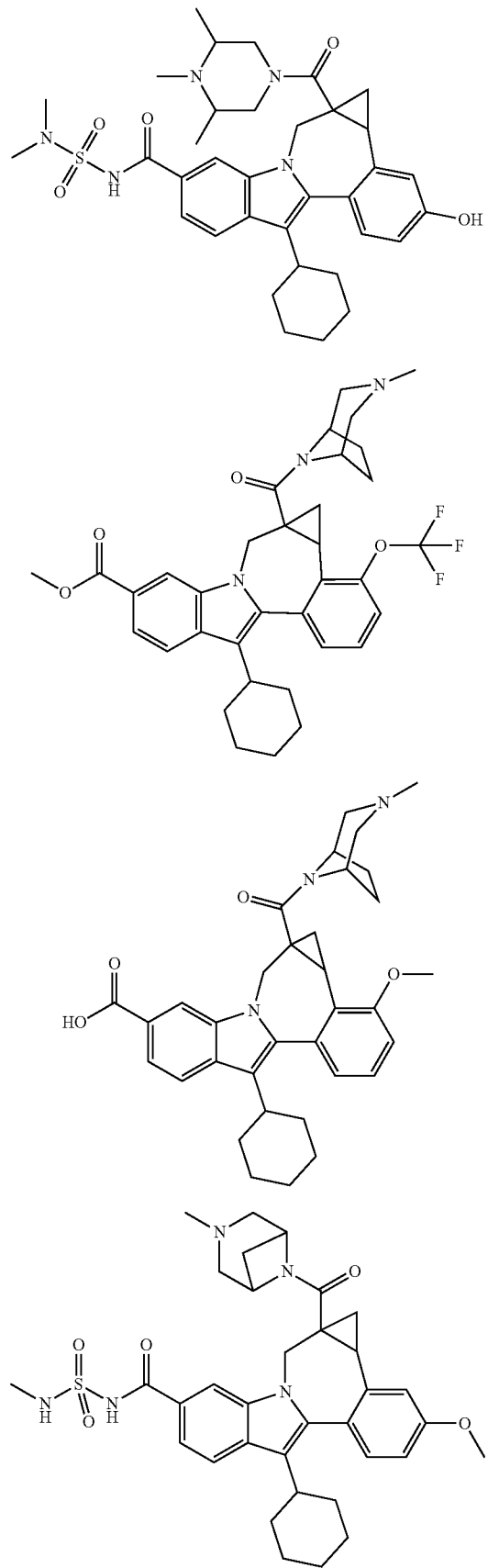
TABLE 33-continued
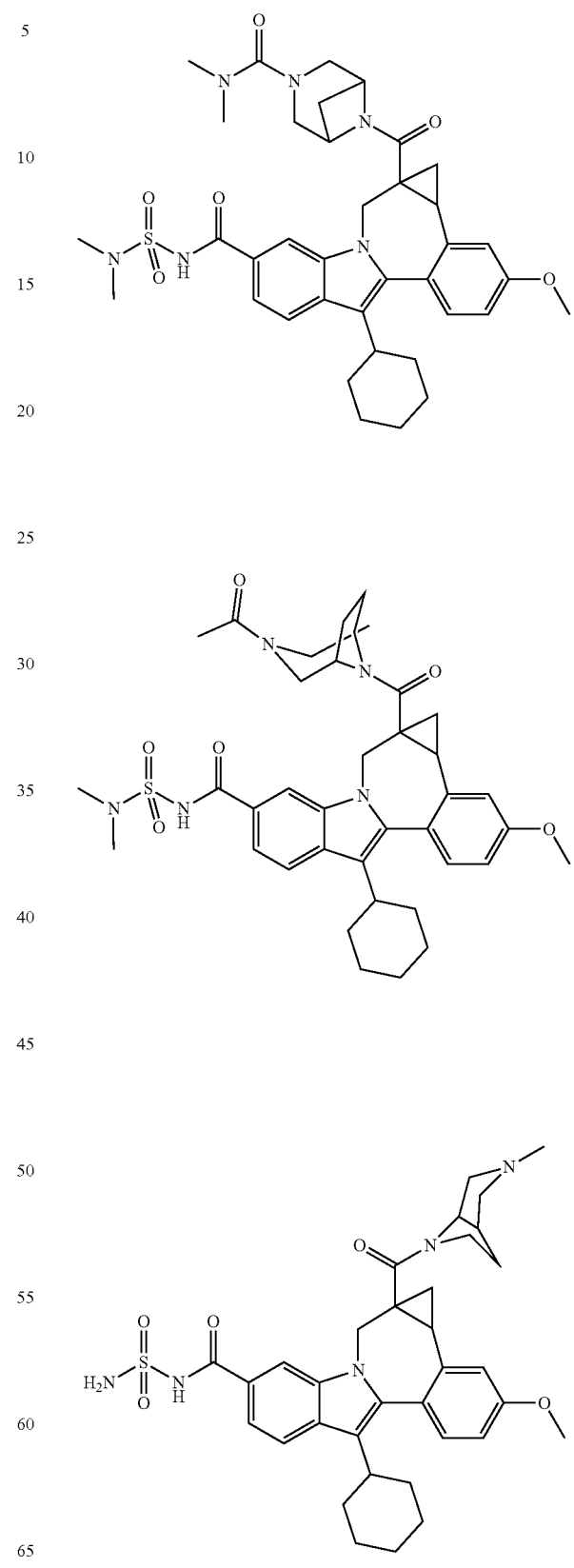

TABLE 33-continued

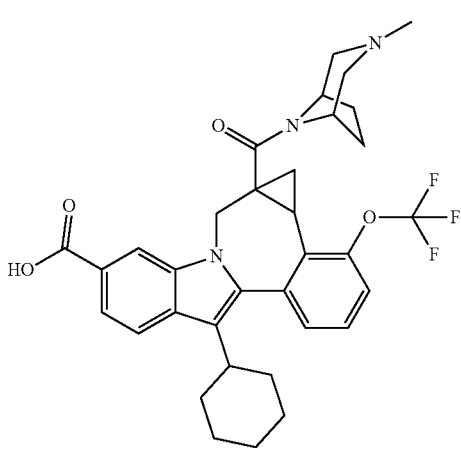 [SMILES: CN1CC2CCC(C1)N2C(=O)C12CC1c1c(OC(F)(F)F)cccc1-c1c(C3CCCCC3)c3ccc(C(=O)O)cc3n1C2]

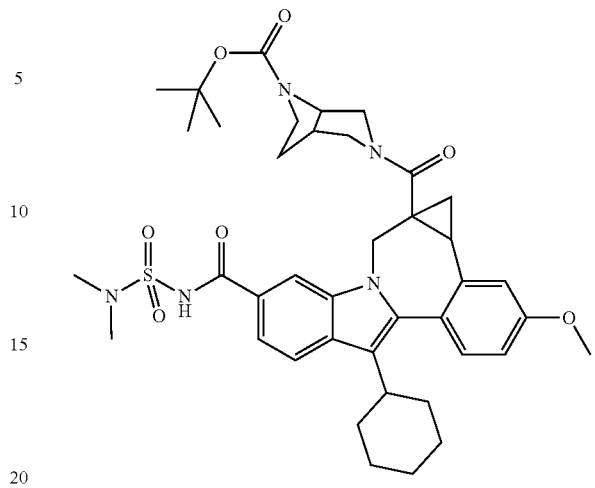

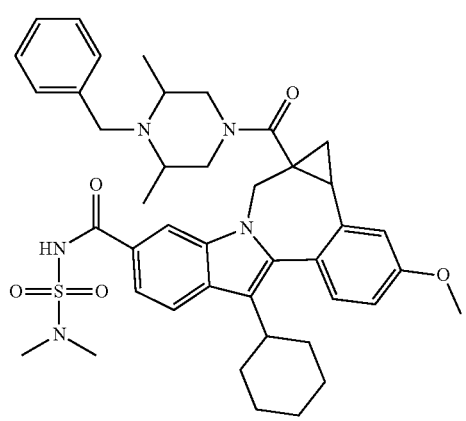 [SMILES: COc1ccc2c(c1)C1CC1(C(=O)N1CC(C)N(Cc3ccccc3)C(C)C1)Cn1c-2c(C2CCCCC2)c2ccc(C(=O)NS(=O)(=O)N(C)C)cc21]

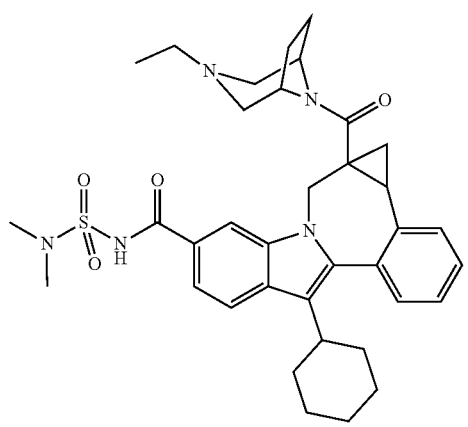 [SMILES: CCN1CC2CCC(C1)N2C(=O)C12CC1c1ccccc1-c1c(C3CCCCC3)c3ccc(C(=O)NS(=O)(=O)N(C)C)cc3n1C2]

In one implementation, the compound is bisoprolol ((E)-but-2-enedioic acid; 1-(propan-2-ylamino)-3-[4-(2-propan-2-yloxyethoxymethyl)phenoxy]propan-2-ol), bisoprolol fumarate, or bisoprolol, a clinically investigated beta adrenoceptor antagonist or beta 1 adrenoceptor antagonist.

In one particular implementation, the compound, or variations and permutations thereof, is further described in WO2007117560 the contents of which are hereby incorporated by reference for all purposes and the specific purposes identified herein. In some embodiments, such compounds are represented by any one or more of the structures shown in Table 39. Any one of the compounds depicted in Table 39 is suitable for use in the methods of the present disclosure.

TABLE 34

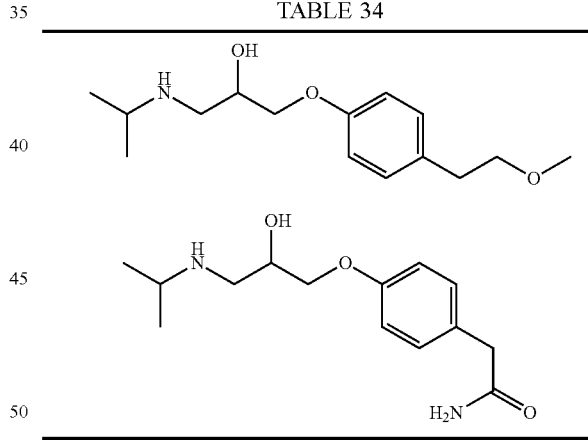

In one implementation, the compound is boceprevir ((1R,2S,5S)—N-(4-amino-1-cyclobutyl-3,4-dioxobutan-2-yl)-3-((S)-2-(3-(tert-butyl)ureido)-3,3-dimethylbutanoyl)-6,6-dimethyl-3-azabicyclo[3.1.0]hexane-2-carboxamide), a clinically investigated hepatitis C virus NS3 protease inhibitor and hepatitis C virus protein NS4B inhibitor. In one particular implementation, the compound, or variations and permutations thereof, is further described in CN101448781; U.S. Pat. No. 8,188,137; WO2002008244; WO2005085275; WO2005087731; WO2005107745; WO2007133865; WO2008124148; and WO201418727 the contents of which are hereby incorporated by reference for all purposes and the specific purposes identified herein. In some embodiments, such compounds are represented by any one or more of the structures shown in Table 40. Any one of the compounds depicted in Table 40 is suitable for use in the methods of the present disclosure.

TABLE 35
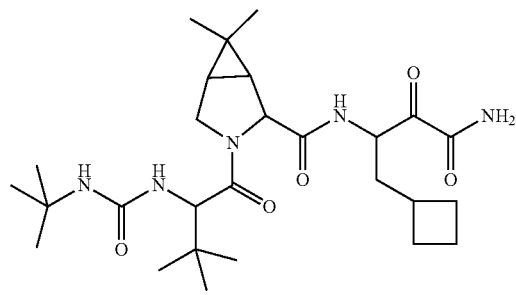 [SMILES: CC(C)(C)NC(=O)NC(C(=O)N1CC2C(C1C(=O)NC(CC1CCC1)C(=O)C(N)=O)C2(C)C)C(C)(C)C]
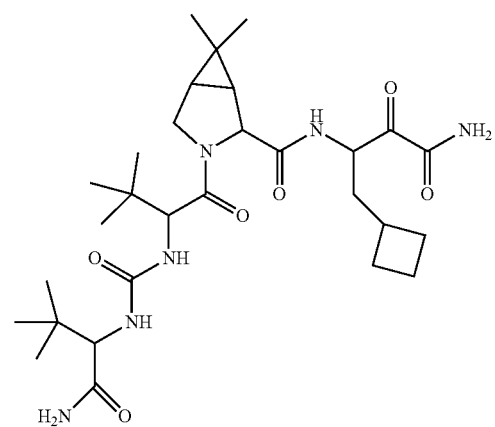 [SMILES: CC(C)(C)C(NC(=O)NC(C(=O)N1CC2C(C1C(=O)NC(CC1CCC1)C(=O)C(N)=O)C2(C)C)C(C)(C)C)C(N)=O]
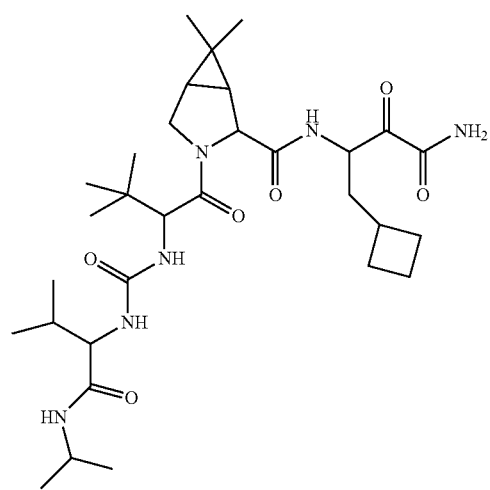 [SMILES: CC(C)NC(=O)C(NC(=O)NC(C(=O)N1CC2C(C1C(=O)NC(CC1CCC1)C(=O)C(N)=O)C2(C)C)C(C)(C)C)C(C)C]

TABLE 35-continued
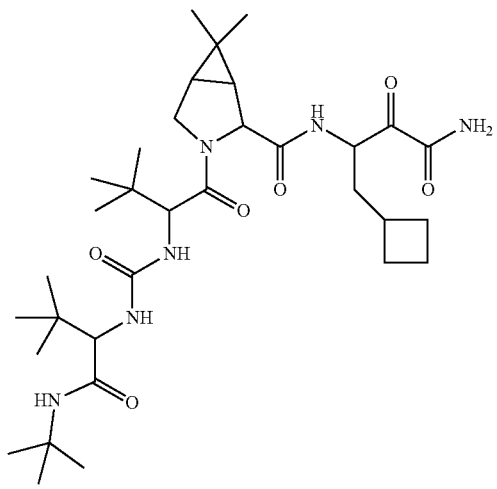 [SMILES: CC(C)(C)NC(=O)C(NC(=O)NC(C(=O)N1CC2C(C1C(=O)NC(CC1CCC1)C(=O)C(N)=O)C2(C)C)C(C)(C)C)C(C)(C)C]
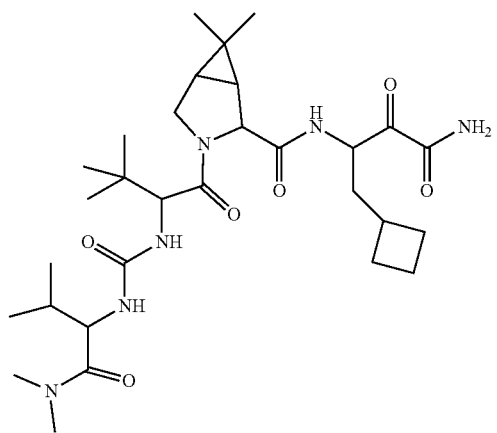 [SMILES: CC(C)C(NC(=O)NC(C(=O)N1CC2C(C1C(=O)NC(CC1CCC1)C(=O)C(N)=O)C2(C)C)C(C)(C)C)C(=O)N(C)C]
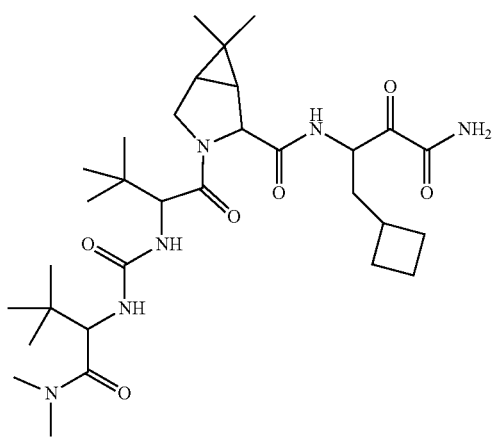 [SMILES: CN(C)C(=O)C(NC(=O)NC(C(=O)N1CC2C(C1C(=O)NC(CC1CCC1)C(=O)C(N)=O)C2(C)C)C(C)(C)C)C(C)(C)C]

TABLE 35-continued
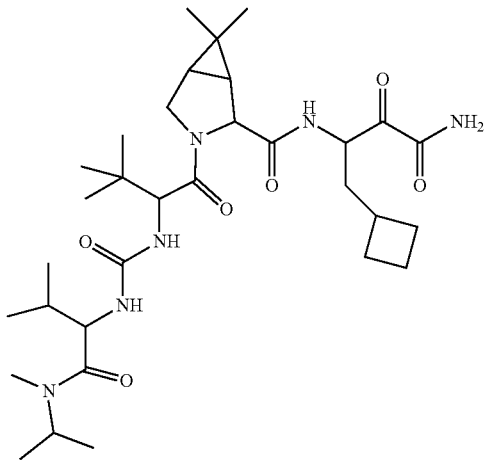 [SMILES: CC(C)C(NC(=O)NC(C(=O)N1CC2C(C1C(=O)NC(CC1CCC1)C(=O)C(N)=O)C2(C)C)C(C)(C)C)C(=O)N(C)C(C)C]
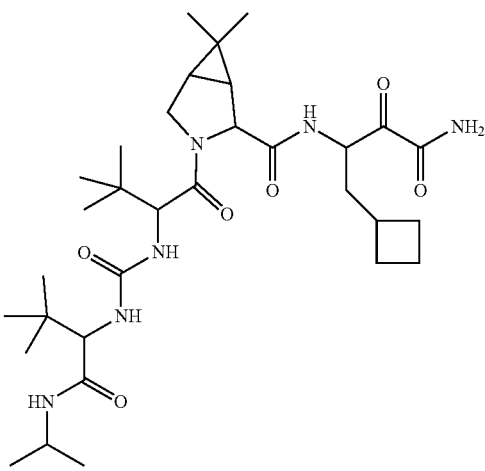 [SMILES: CC(C)NC(=O)C(NC(=O)NC(C(=O)N1CC2C(C1C(=O)NC(CC1CCC1)C(=O)C(N)=O)C2(C)C)C(C)(C)C)C(C)(C)C]
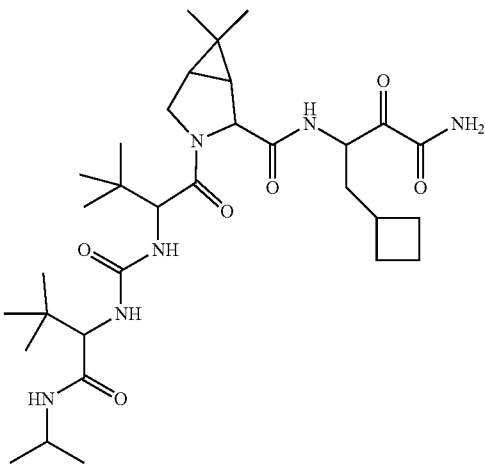 [SMILES: CC(C)NC(=O)C(NC(=O)NC(C(=O)N1CC2C(C1C(=O)NC(CC1CCC1)C(=O)C(N)=O)C2(C)C)C(C)(C)C)C(C)(C)C]

TABLE 35-continued
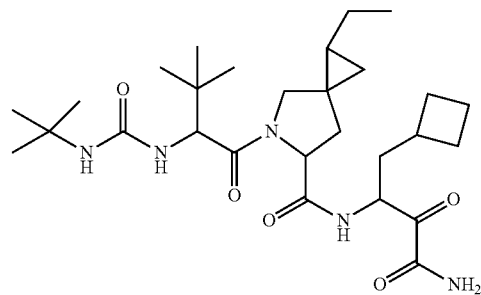 [SMILES: CCC1CC12CC(C(=O)NC(CC1CCC1)C(=O)C(N)=O)N(C(=O)C(NC(=O)NC(C)(C)C)C(C)(C)C)C2]
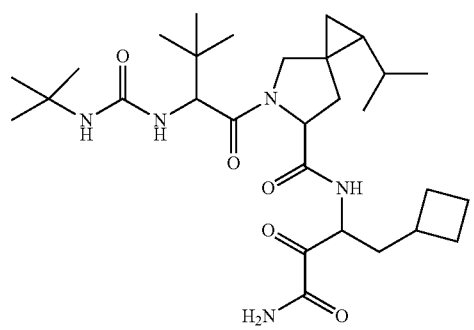 [SMILES: CC(C)C1CC12CC(C(=O)NC(CC1CCC1)C(=O)C(N)=O)N(C(=O)C(NC(=O)NC(C)(C)C)C(C)(C)C)C2]
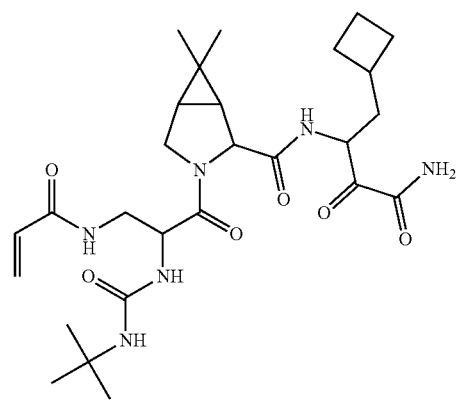 [SMILES: C=CC(=O)NCC(NC(=O)NC(C)(C)C)C(=O)N1CC2C(C1C(=O)NC(CC1CCC1)C(=O)C(N)=O)C2(C)C]
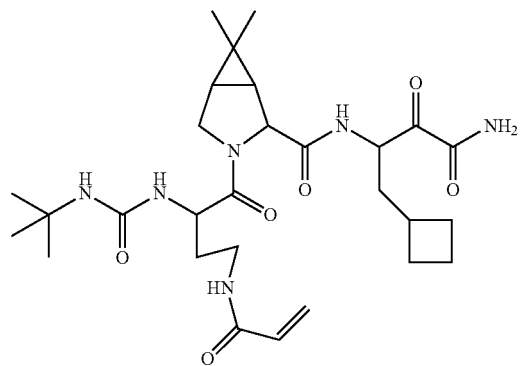 [SMILES: C=CC(=O)NCCC(NC(=O)NC(C)(C)C)C(=O)N1CC2C(C1C(=O)NC(CC1CCC1)C(=O)C(N)=O)C2(C)C]

TABLE 35-continued
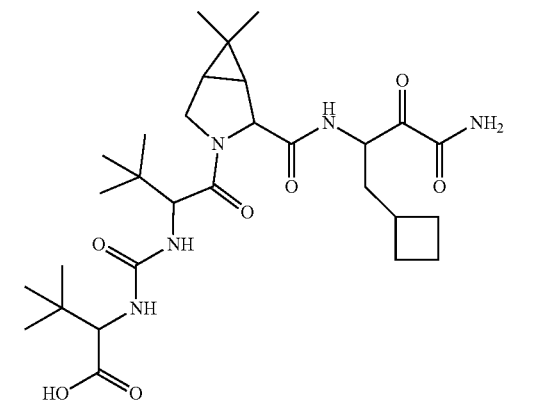 [SMILES: CC(C)(C)C(NC(=O)NC(C(=O)N1CC2C(C1C(=O)NC(CC1CCC1)C(=O)C(N)=O)C2(C)C)C(C)(C)C)C(=O)O]
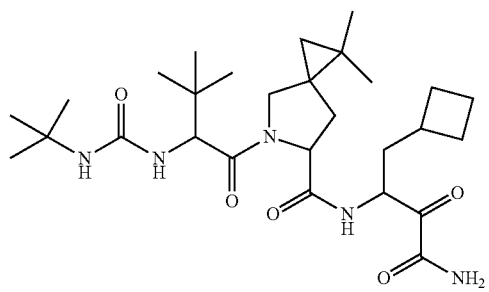 [SMILES: CC(C)(C)NC(=O)NC(C(=O)N1CC2(CC1C(=O)NC(CC1CCC1)C(=O)C(N)=O)CC2(C)C)C(C)(C)C]
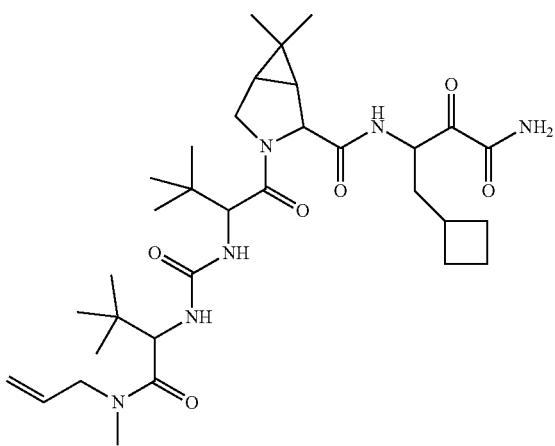 [SMILES: C=CCN(C)C(=O)C(NC(=O)NC(C(=O)N1CC2C(C1C(=O)NC(CC1CCC1)C(=O)C(N)=O)C2(C)C)C(C)(C)C)C(C)(C)C]
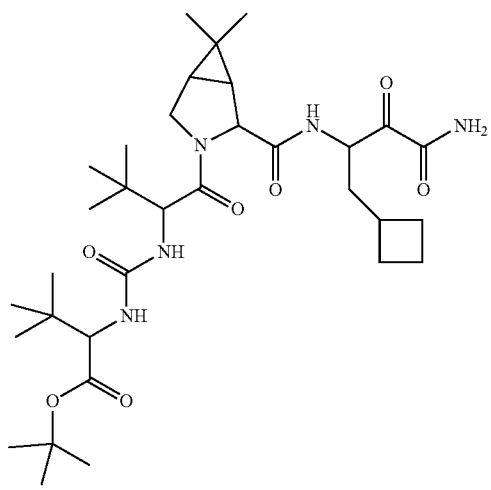 [SMILES: CC(C)(C)OC(=O)C(NC(=O)NC(C(=O)N1CC2C(C1C(=O)NC(CC1CCC1)C(=O)C(N)=O)C2(C)C)C(C)(C)C)C(C)(C)C]

TABLE 35-continued
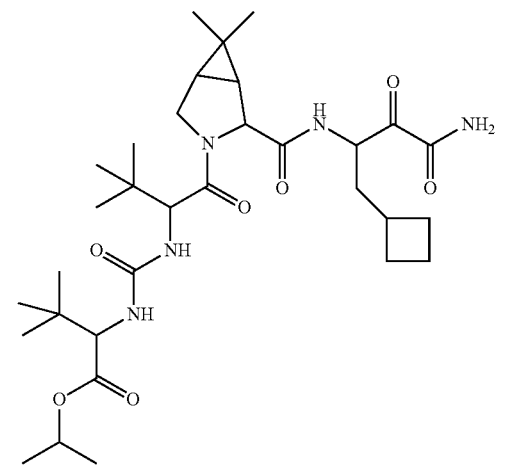 [SMILES: CC(C)OC(=O)C(NC(=O)NC(C(=O)N1CC2C(C1C(=O)NC(CC1CCC1)C(=O)C(N)=O)C2(C)C)C(C)(C)C)C(C)(C)C]
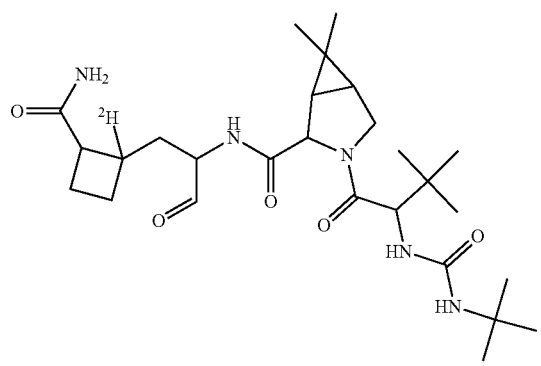 [SMILES: [2H]C1(CC(C=O)NC(=O)C2C3C(CN2C(=O)C(NC(=O)NC(C)(C)C)C(C)(C)C)C3(C)C)CCC1C(N)=O]
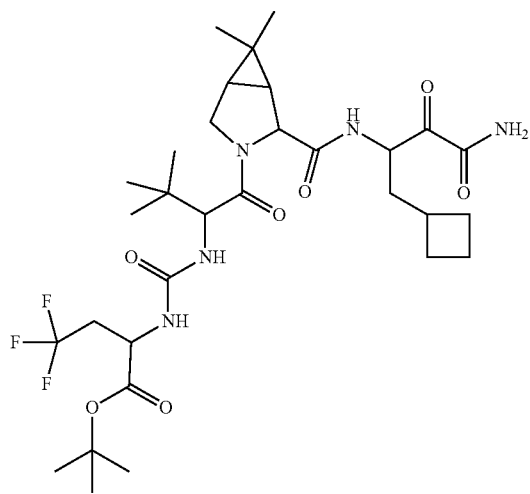 [SMILES: CC(C)(C)OC(=O)C(CC(F)(F)F)NC(=O)NC(C(=O)N1CC2C(C1C(=O)NC(CC1CCC1)C(=O)C(N)=O)C2(C)C)C(C)(C)C]
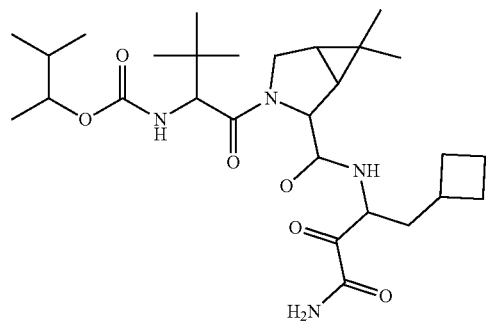 [SMILES: CC(C)C(C)OC(=O)NC(C(=O)N1CC2C(C1C(O)NC(CC1CCC1)C(=O)C(N)=O)C2(C)C)C(C)(C)C]

TABLE 35-continued
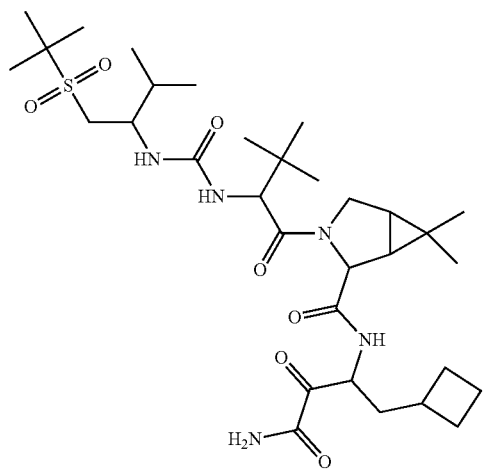 [SMILES: CC(C)C(CS(=O)(=O)C(C)(C)C)NC(=O)NC(C(=O)N1CC2C(C1C(=O)NC(CC1CCC1)C(=O)C(N)=O)C2(C)C)C(C)(C)C]
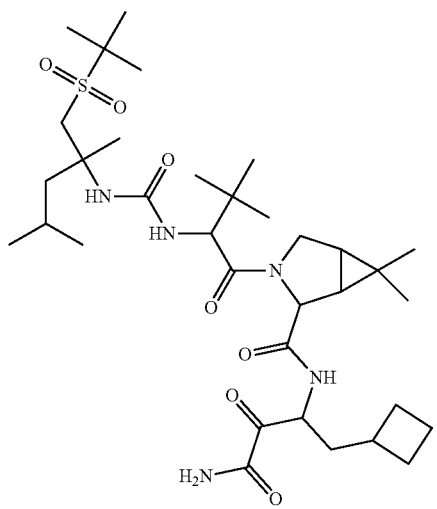 [SMILES: CC(C)CC(C)(CS(=O)(=O)C(C)(C)C)NC(=O)NC(C(=O)N1CC2C(C1C(=O)NC(CC1CCC1)C(=O)C(N)=O)C2(C)C)C(C)(C)C]
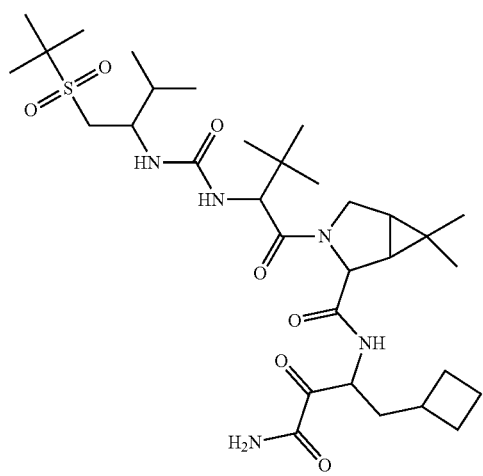 [SMILES: CC(C)C(CS(=O)(=O)C(C)(C)C)NC(=O)NC(C(=O)N1CC2C(C1C(=O)NC(CC1CCC1)C(=O)C(N)=O)C2(C)C)C(C)(C)C]

TABLE 35-continued
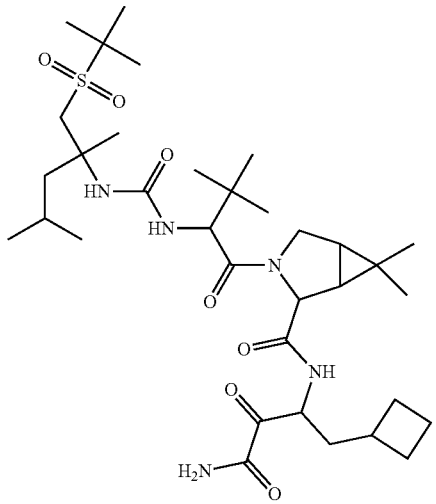 [SMILES: CC(C)CC(C)(CS(=O)(=O)C(C)(C)C)NC(=O)NC(C(=O)N1CC2C(C1C(=O)NC(CC1CCC1)C(=O)C(N)=O)C2(C)C)C(C)(C)C]
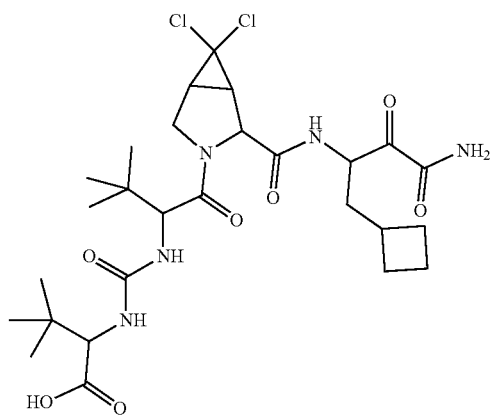 [SMILES: CC(C)(C)C(NC(=O)NC(C(=O)N1CC2C(C1C(=O)NC(CC1CCC1)C(=O)C(N)=O)C2(Cl)Cl)C(C)(C)C)C(=O)O]
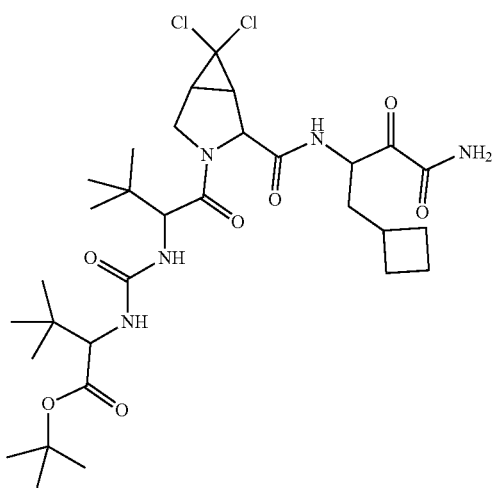 [SMILES: CC(C)(C)OC(=O)C(NC(=O)NC(C(=O)N1CC2C(C1C(=O)NC(CC1CCC1)C(=O)C(N)=O)C2(Cl)Cl)C(C)(C)C)C(C)(C)C]

TABLE 35-continued
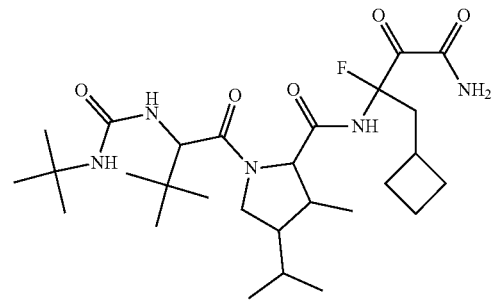 [SMILES: CC(C)C1CN(C(=O)C(NC(=O)NC(C)(C)C)C(C)(C)C)C(C(=O)NC(F)(CC2CCC2)C(=O)C(N)=O)C1C]
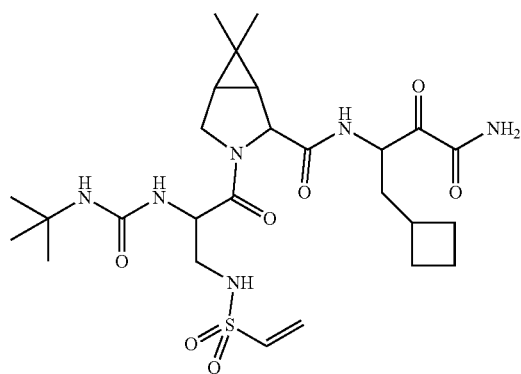 [SMILES: C=CS(=O)(=O)NCC(NC(=O)NC(C)(C)C)C(=O)N1CC2C(C1C(=O)NC(CC1CCC1)C(=O)C(N)=O)C2(C)C]
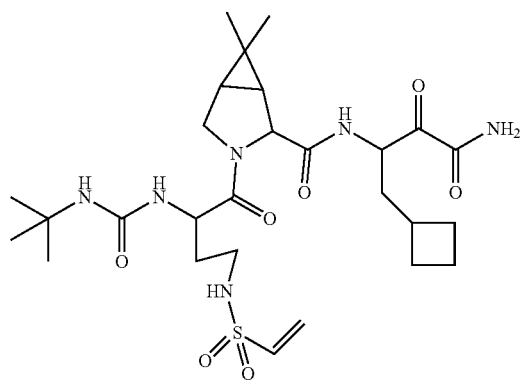 [SMILES: C=CS(=O)(=O)NCCC(NC(=O)NC(C)(C)C)C(=O)N1CC2C(C1C(=O)NC(CC1CCC1)C(=O)C(N)=O)C2(C)C]
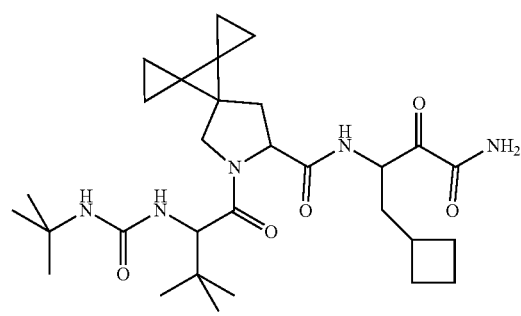 [SMILES: CC(C)(C)NC(=O)NC(C(=O)N1CC2(CC1C(=O)NC(CC1CCC1)C(=O)C(N)=O)C1(CC1)C21CC1)C(C)(C)C]

TABLE 35-continued
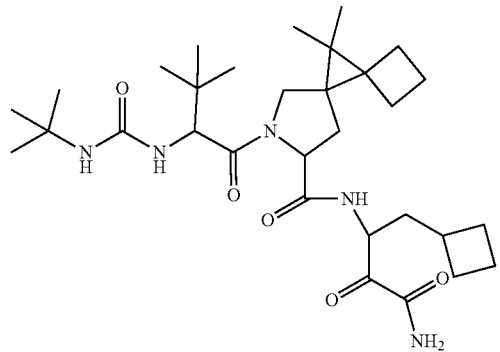 [SMILES: CC(C)(C)NC(=O)NC(C(=O)N1CC2(CC1C(=O)NC(CC1CCC1)C(=O)C(N)=O)C(C)(C)C21CCC1)C(C)(C)C]
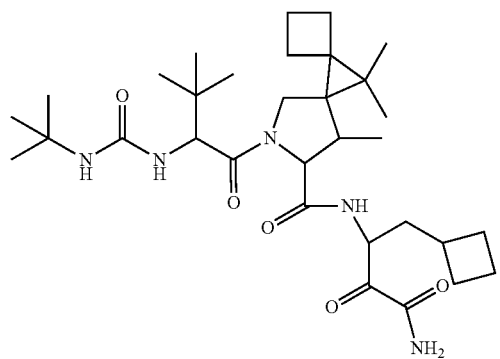 [SMILES: CC1C(C(=O)NC(CC2CCC2)C(=O)C(N)=O)N(C(=O)C(NC(=O)NC(C)(C)C)C(C)(C)C)CC12C(C)(C)C21CCC1]
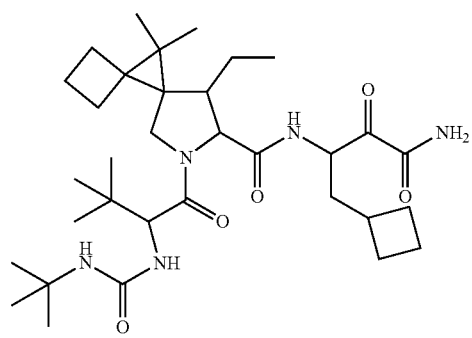 [SMILES: CCC1C(C(=O)NC(CC2CCC2)C(=O)C(N)=O)N(C(=O)C(NC(=O)NC(C)(C)C)C(C)(C)C)CC12C(C)(C)C21CCC1]
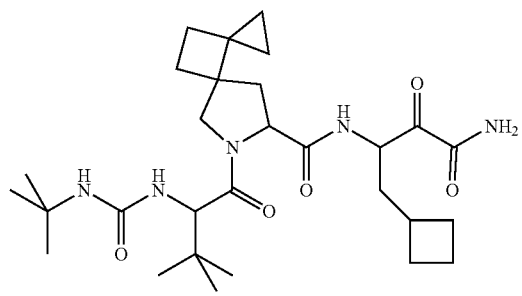 [SMILES: CC(C)(C)NC(=O)NC(C(=O)N1CC2(CCC23CC3)CC1C(=O)NC(CC1CCC1)C(=O)C(N)=O)C(C)(C)C]

TABLE 35-continued
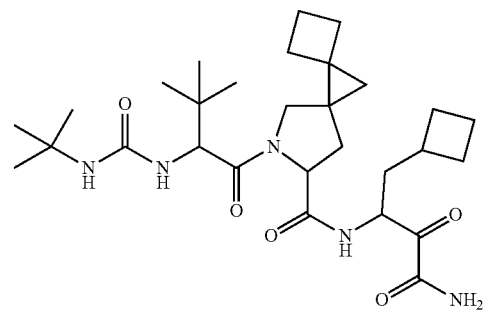 [SMILES: CC(C)(C)NC(=O)NC(C(=O)N1CC2(CC1C(=O)NC(CC1CCC1)C(=O)C(N)=O)CC21CCC1)C(C)(C)C]
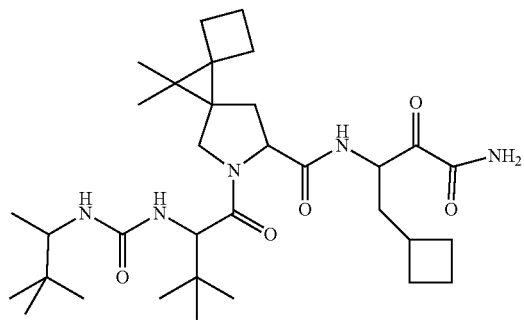 [SMILES: CC(NC(=O)NC(C(=O)N1CC2(CC1C(=O)NC(CC1CCC1)C(=O)C(N)=O)C(C)(C)C21CCC1)C(C)(C)C)C(C)(C)C]
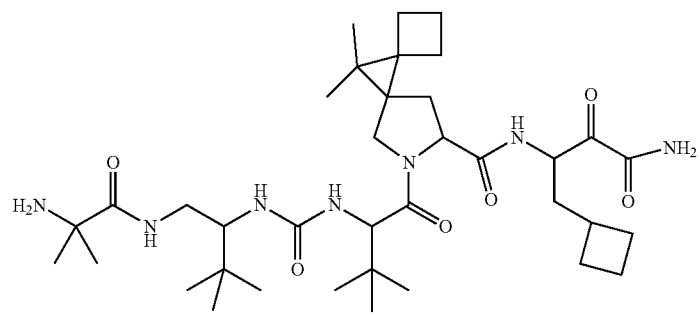 [SMILES: CC(C)(N)C(=O)NCC(NC(=O)NC(C(=O)N1CC2(CC1C(=O)NC(CC1CCC1)C(=O)C(N)=O)C(C)(C)C21CCC1)C(C)(C)C)C(C)(C)C]
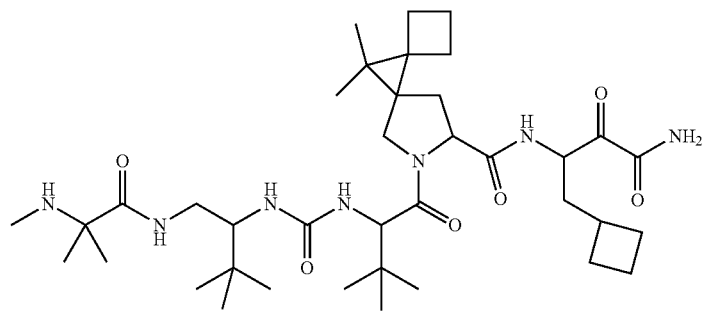 [SMILES: CNC(C)(C)C(=O)NCC(NC(=O)NC(C(=O)N1CC2(CC1C(=O)NC(CC1CCC1)C(=O)C(N)=O)C(C)(C)C21CCC1)C(C)(C)C)C(C)(C)C]

TABLE 35-continued

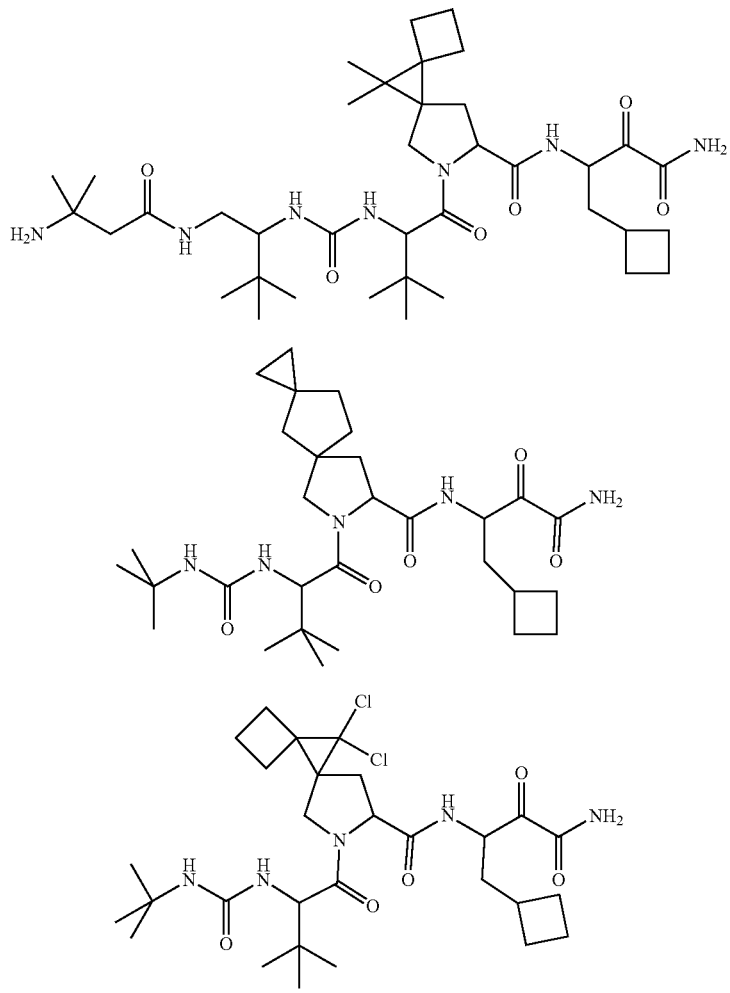

In one implementation, the compound is Brecanavir ([(3aS,4R,6aR)-2,3,3a,4,5,6a-hexahydrofuro[2,3-b]furan-4-yl] N-[(2S,3R)-4-[1,3-benzodioxol-5-ylsulfonyl(2-methylpropyl)amino]-3-hydroxy-1-[4-[(2-methyl-1,3-thiazol-4-yl)methoxy]phenyl]butan-2-yl]carbamate), a clinically investigated aspartic protease inhibitor and HIV protease inhibitor. In one particular implementation, the compound, or variations and permutations thereof, is further described in WO2010135424; WO2008115894; WO2006104646; and WO2000076961 the contents of which are hereby incorporated by reference for all purposes and the specific purposes identified herein.

In one implementation, the compound is celiprolol (3-(3-acetyl-4-(3-(tert-butylamino)-2-hydroxypropoxy)phenyl)-1,1-diethylurea) a clinically investigated beta adrenoceptor antagonist. In one particular implementation, the compound, or variations and permutations thereof, is further described in WO2007117560 the contents of which are hereby incorporated by reference for all purposes and the specific purposes identified herein. In some embodiments, such compounds are represented by any one or more of the structures shown in Table 42. Any one of the compounds depicted in Table 42 is suitable for use in the methods of the present disclosure.

TABLE 36

In one implementation, the compound is ciluprevir ((2R,6S,13aS,14aR, 16aS,Z)-6-(((cyclopentyloxy)carbonyl)amino)-2-((2-(2-(isopropylamino)thiazol-4-yl)-7-methoxyquinolin-4-yl)oxy)-5,16-dioxo-1,2,3,6,7,8,9,10,11,13a,14,15,16,16a-tetradecahydrocyclopropa[e]pyrrolo[1,2-a]), a clinically investigated Hepatitis C virus NS3 protease inhibitor. In one particular implementation, the compound, or variations and permutations thereof, is further described in US20080267917; WO2003064416; WO2003064455; WO2003064456; WO2004037855; WO2004101605; WO2004103996; WO2005028501; WO2007001406; WO2009005676; WO2009053828; WO2009076173; and WO2012040242 the contents of which are hereby incorporated by reference for all purposes and the specific purposes identified herein. In some embodiments, such compounds are represented by any one or more of the structures shown in Table 43. Any one of the compounds depicted in Table 43 is suitable for use in the methods of the present disclosure.
TABLE 37
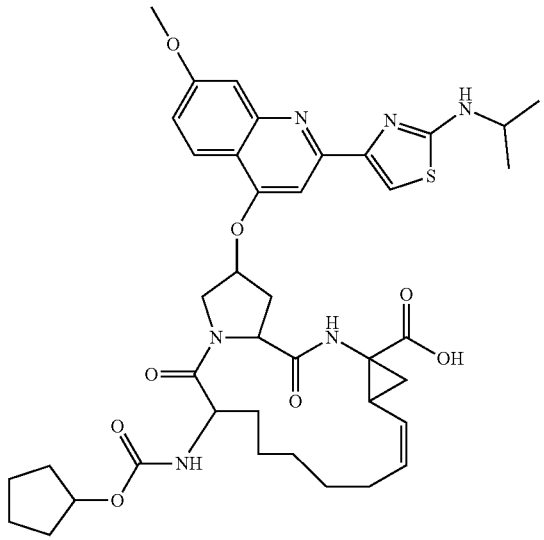 [SMILES: COc1ccc2c(OC3CC4C(=O)NC5(C(=O)O)CC5/C=C\CCCCCC(NC(=O)OC5CCCC5)C(=O)N4C3)cc(-c3csc(NC(C)C)n3)nc2c1]
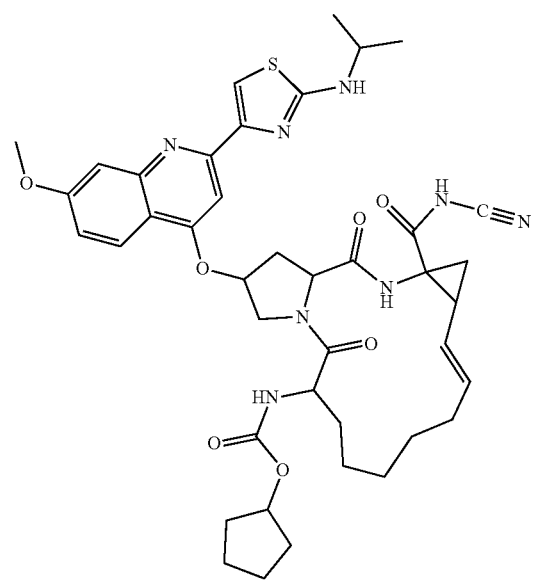 [SMILES: COc1ccc2c(OC3CC4C(=O)NC5(C(=O)NC#N)CC5/C=C/CCCCCC(NC(=O)OC5CCCC5)C(=O)N4C3)cc(-c3csc(NC(C)C)n3)nc2c1]

TABLE 37-continued
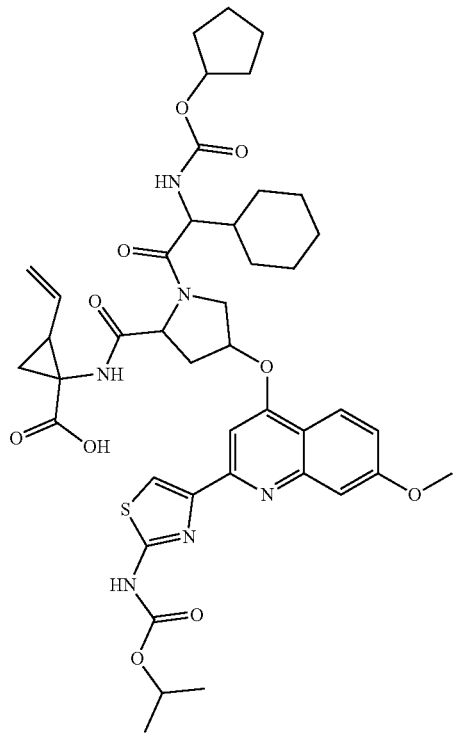 [SMILES: C=CC1CC1(NC(=O)C1CC(Oc2cc(-c3csc(NC(=O)OC(C)C)n3)nc3cc(OC)ccc23)CN1C(=O)C(NC(=O)OC1CCCC1)C1CCCCC1)C(=O)O]
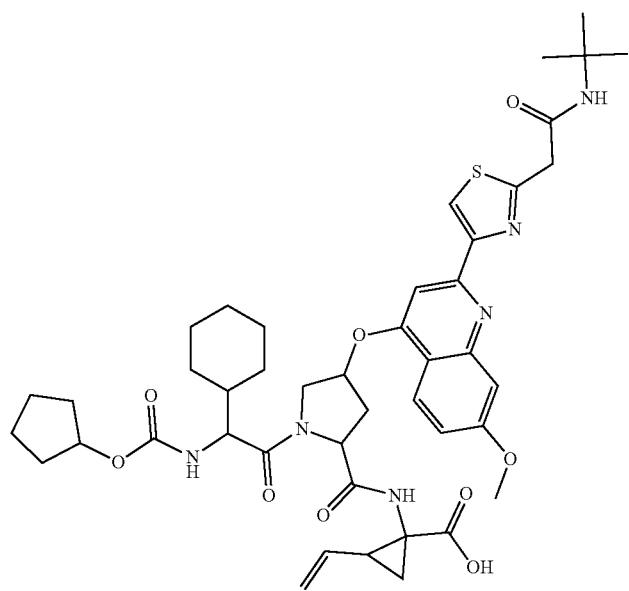 [SMILES: C=CC1CC1(NC(=O)C1CC(Oc2cc(-c3csc(CC(=O)NC(C)(C)C)n3)nc3cc(OC)ccc23)CN1C(=O)C(NC(=O)OC1CCCC1)C1CCCCC1)C(=O)O]

TABLE 37-continued
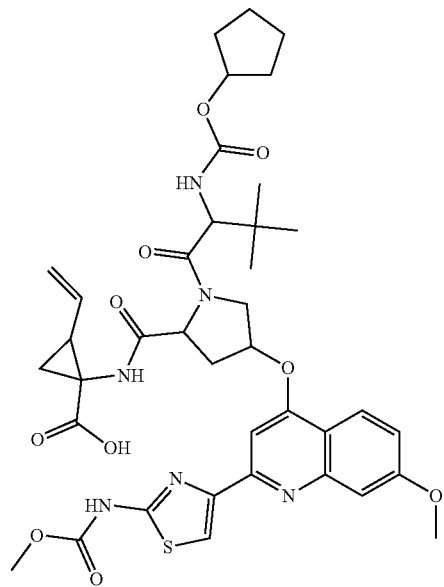
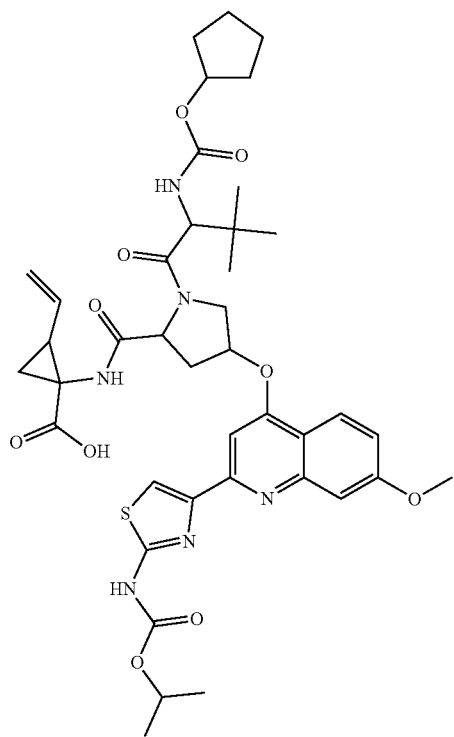 [SMILES: C=CC1CC1(NC(=O)C1CC(Oc2cc(-c3csc(NC(=O)OC(C)C)n3)nc3cc(OC)ccc23)CN1C(=O)C(NC(=O)OC1CCCC1)C(C)(C)C)C(=O)O]

TABLE 37-continued
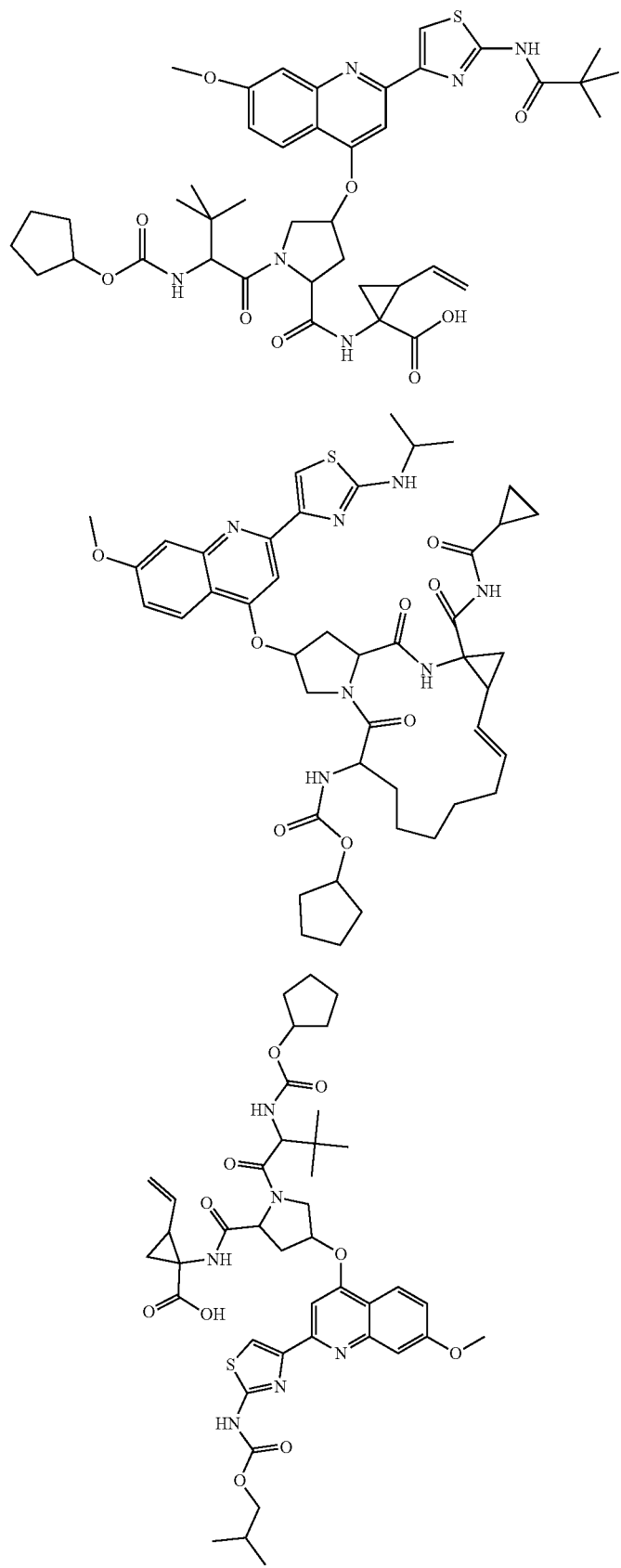

TABLE 37-continued
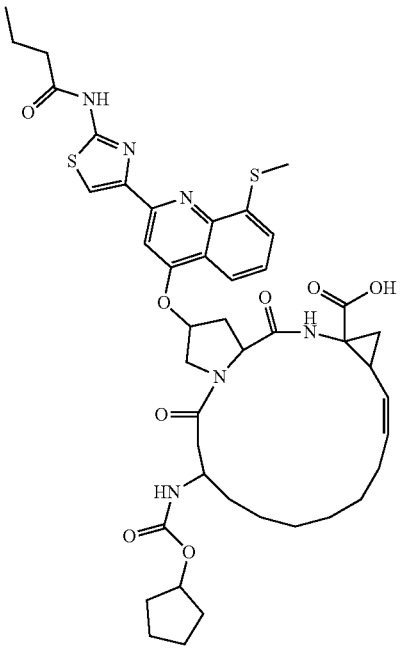 [SMILES: CCCC(=O)Nc1nc(-c2cc(OC3CC4C(=O)NC5(C(=O)O)CC5/C=C\CCCCCCC(NC(=O)OC5CCCC5)CC(=O)N4C3)c3cccc(SC)c3n2)cs1]
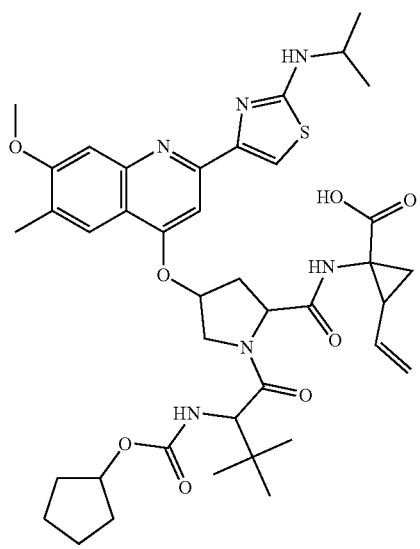 [SMILES: C=CC1CC1(NC(=O)C1CC(Oc2cc(-c3csc(NC(C)C)n3)nc3cc(OC)c(C)cc23)CN1C(=O)C(NC(=O)OC1CCCC1)C(C)(C)C)C(=O)O]

TABLE 37-continued
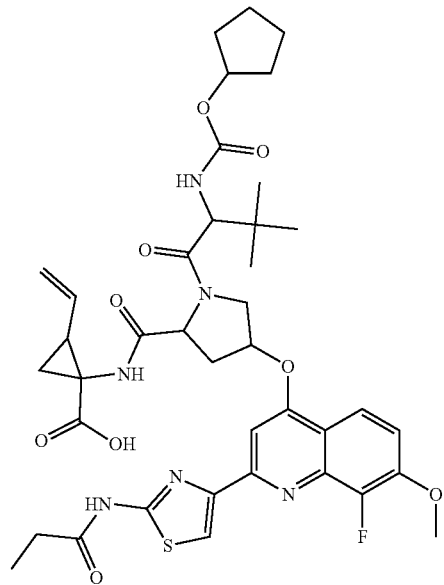 [SMILES: C=CC1CC1(NC(=O)C1CC(Oc2cc(-c3csc(NC(=O)CC)n3)nc3c(F)c(OC)ccc23)CN1C(=O)C(NC(=O)OC1CCCC1)C(C)(C)C)C(=O)O]
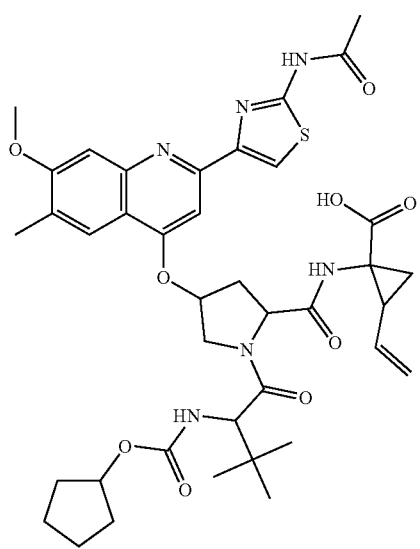 [SMILES: C=CC1CC1(NC(=O)C1CC(Oc2cc(-c3csc(NC(C)=O)n3)nc3cc(OC)c(C)cc23)CN1C(=O)C(NC(=O)OC1CCCC1)C(C)(C)C)C(=O)O]

TABLE 37-continued
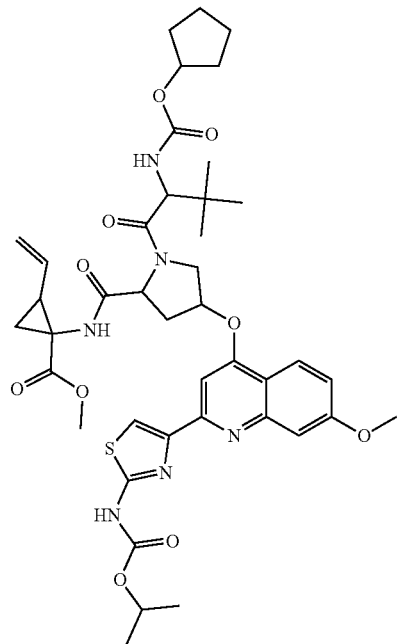 [SMILES: C=CC1CC1(NC(=O)C1CC(Oc2cc(-c3csc(NC(=O)OC(C)C)n3)nc3cc(OC)ccc23)CN1C(=O)C(NC(=O)OC1CCCC1)C(C)(C)C)C(=O)OC]
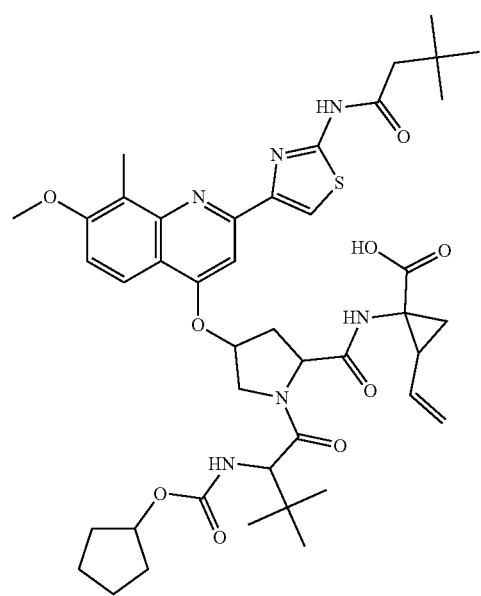 [SMILES: C=CC1CC1(NC(=O)C1CC(Oc2cc(-c3csc(NC(=O)CC(C)(C)C)n3)nc3c(C)c(OC)ccc23)CN1C(=O)C(NC(=O)OC1CCCC1)C(C)(C)C)C(=O)O]

TABLE 37-continued
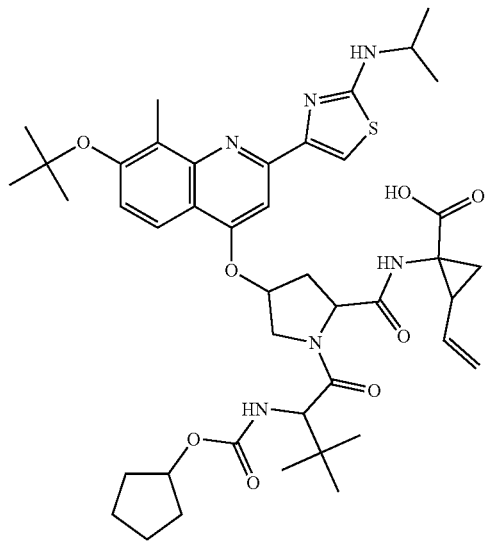 [SMILES: C=CC1CC1(NC(=O)C1CC(Oc2cc(-c3csc(NC(C)C)n3)nc3c(C)c(OC(C)(C)C)ccc23)CN1C(=O)C(NC(=O)OC1CCCC1)C(C)(C)C)C(=O)O]
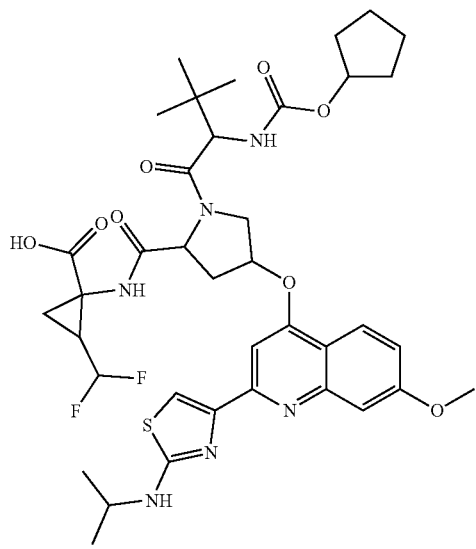 [SMILES: COc1ccc2c(OC3CC(C(=O)NC4(C(=O)O)CC4C(F)F)N(C(=O)C(NC(=O)OC4CCCC4)C(C)(C)C)C3)cc(-c3csc(NC(C)C)n3)nc2c1]
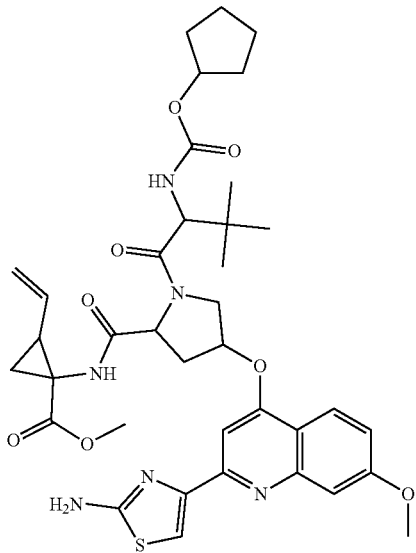 [SMILES: C=CC1CC1(NC(=O)C1CC(Oc2cc(-c3csc(N)n3)nc3cc(OC)ccc23)CN1C(=O)C(NC(=O)OC1CCCC1)C(C)(C)C)C(=O)OC]

TABLE 37-continued
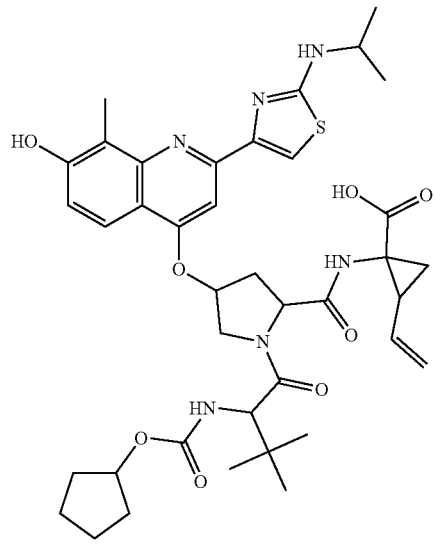 [SMILES: C=CC1CC1(NC(=O)C1CC(Oc2cc(-c3csc(NC(C)C)n3)nc3c(C)c(O)ccc23)CN1C(=O)C(NC(=O)OC1CCCC1)C(C)(C)C)C(=O)O]
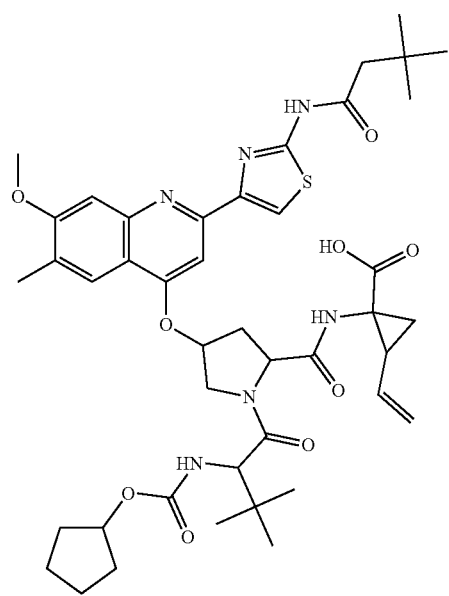 [SMILES: C=CC1CC1(NC(=O)C1CC(Oc2cc(-c3csc(NC(=O)CC(C)(C)C)n3)nc3cc(OC)c(C)cc23)CN1C(=O)C(NC(=O)OC1CCCC1)C(C)(C)C)C(=O)O]

TABLE 37-continued
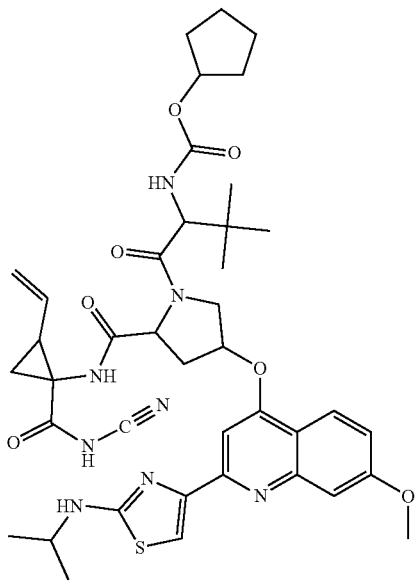 [SMILES: C=CC1CC1(NC(=O)C1CC(Oc2cc(-c3csc(NC(C)C)n3)nc3cc(OC)ccc23)CN1C(=O)C(NC(=O)OC1CCCC1)C(C)(C)C)C(=O)NC#N]
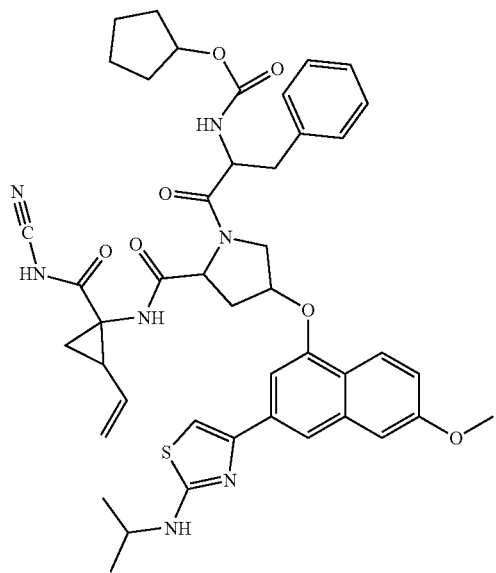 [SMILES: C=CC1CC1(NC(=O)C1CC(Oc2cc(-c3csc(NC(C)C)n3)cc3cc(OC)ccc23)CN1C(=O)C(Cc1ccccc1)NC(=O)OC1CCCC1)C(=O)NC#N]
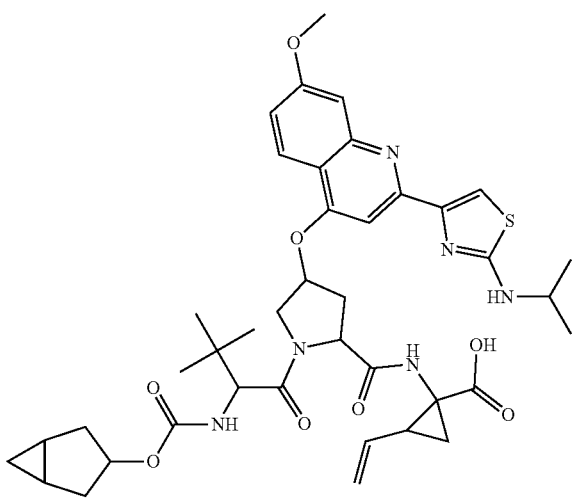 [SMILES: C=CC1CC1(NC(=O)C1CC(Oc2cc(-c3csc(NC(C)C)n3)nc3cc(OC)ccc23)CN1C(=O)C(NC(=O)OC1CC2CC2C1)C(C)(C)C)C(=O)O]

TABLE 37-continued
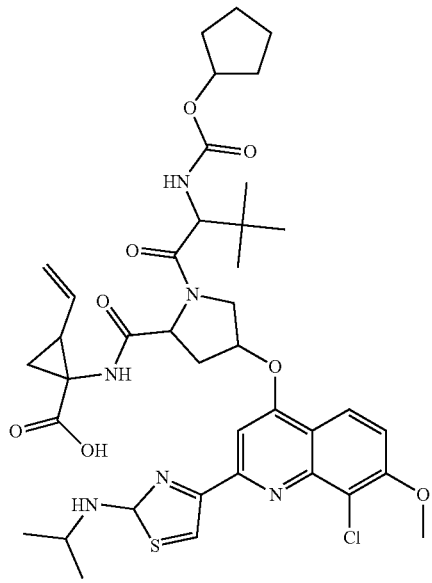
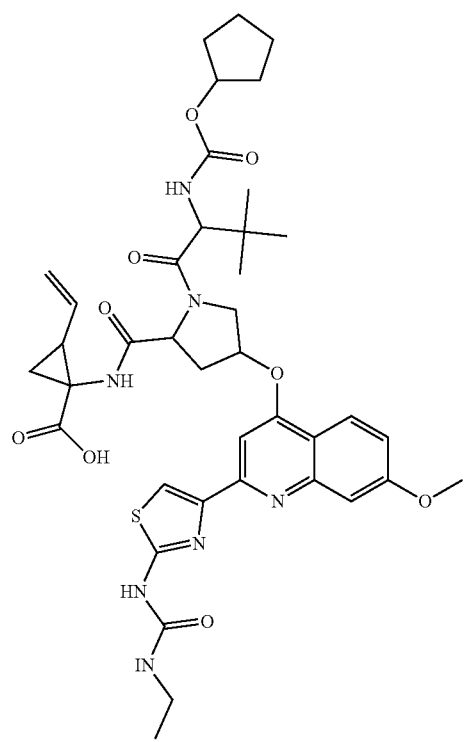

TABLE 37-continued
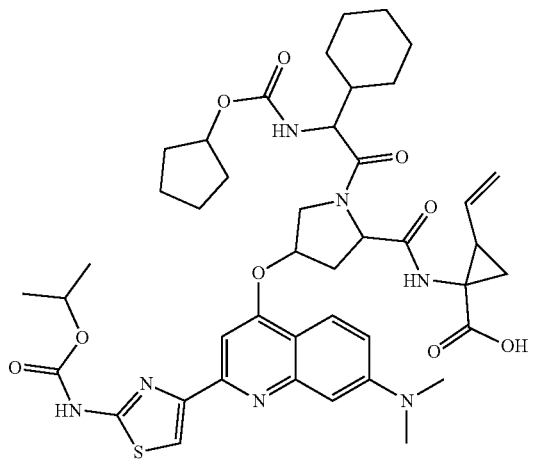 [SMILES: C=CC1CC1(NC(=O)C1CC(Oc2cc(-c3csc(NC(=O)OC(C)C)n3)nc3cc(N(C)C)ccc23)CN1C(=O)C(NC(=O)OC1CCCC1)C1CCCCC1)C(=O)O]
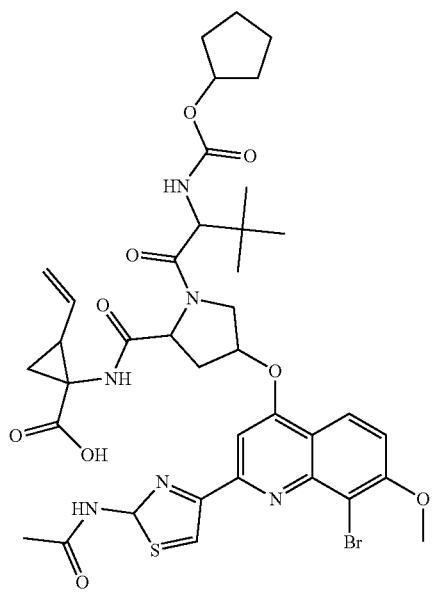
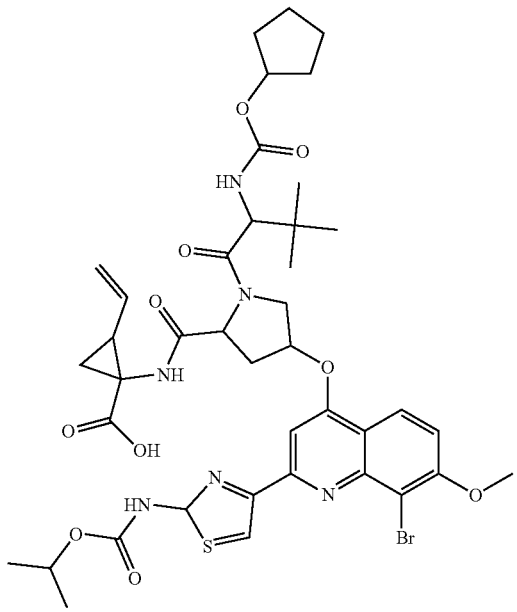

TABLE 37-continued
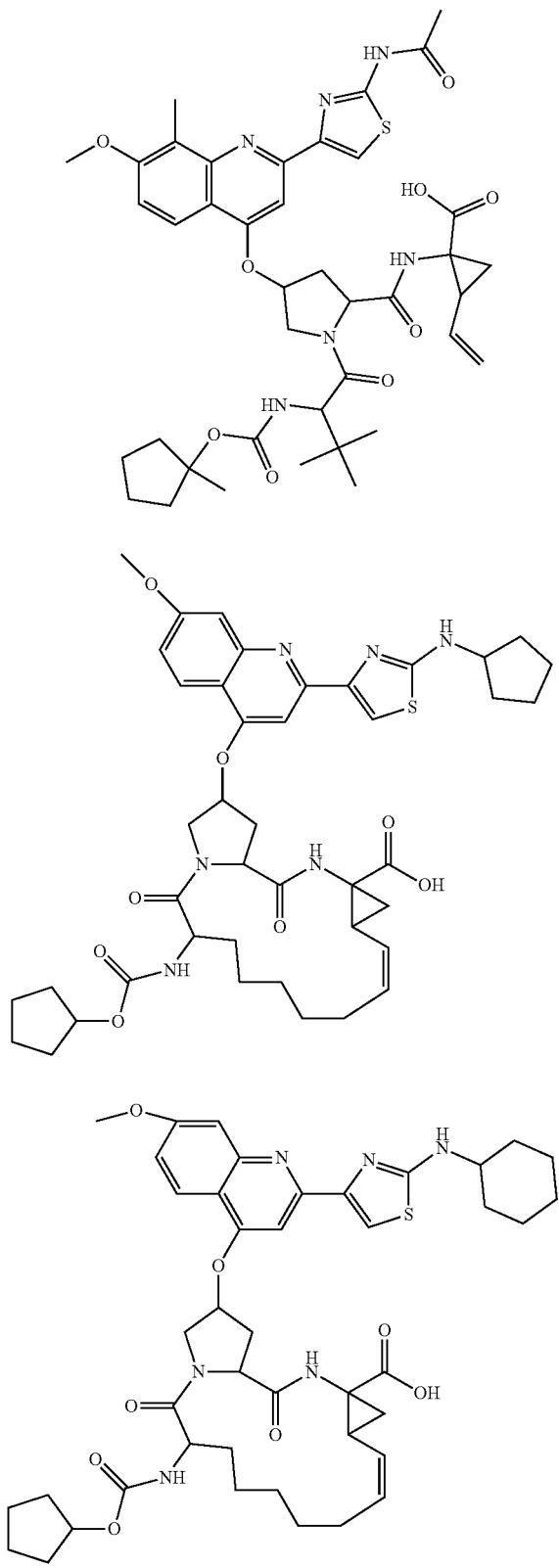

TABLE 37-continued
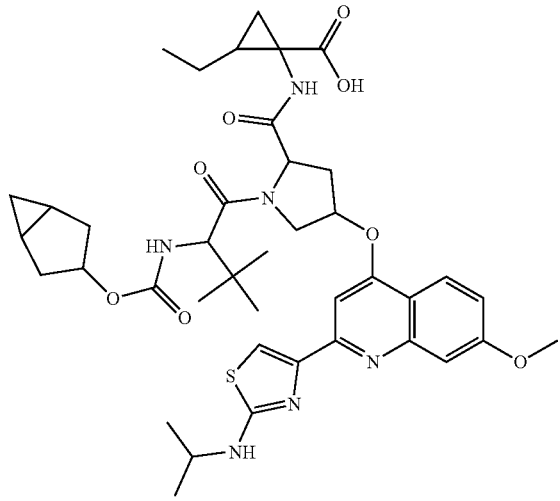 [SMILES: CCC1CC1(NC(=O)C1CC(Oc2cc(-c3csc(NC(C)C)n3)nc3cc(OC)ccc23)CN1C(=O)C(NC(=O)OC1CC2CC2C1)C(C)(C)C)C(=O)O]
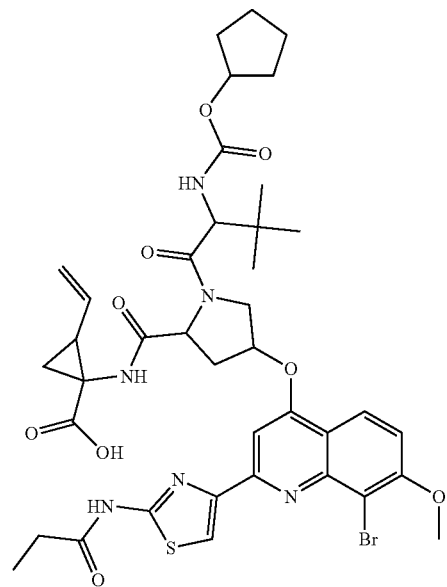 [SMILES: C=CC1CC1(NC(=O)C1CC(Oc2cc(-c3csc(NC(=O)CC)n3)nc3c(Br)c(OC)ccc23)CN1C(=O)C(NC(=O)OC1CCCC1)C(C)(C)C)C(=O)O]

TABLE 37-continued
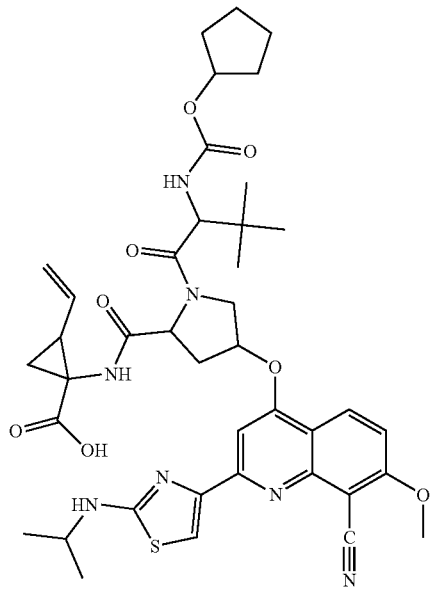 [SMILES: C=CC1CC1(NC(=O)C1CC(Oc2cc(-c3csc(NC(C)C)n3)nc3c(C#N)c(OC)ccc23)CN1C(=O)C(NC(=O)OC1CCCC1)C(C)(C)C)C(=O)O]
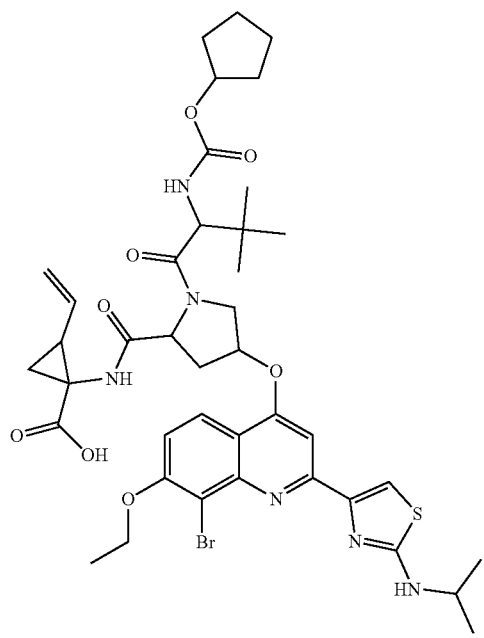 [SMILES: C=CC1CC1(NC(=O)C1CC(Oc2cc(-c3csc(NC(C)C)n3)nc3c(Br)c(OCC)ccc23)CN1C(=O)C(NC(=O)OC1CCCC1)C(C)(C)C)C(=O)O]

TABLE 37-continued
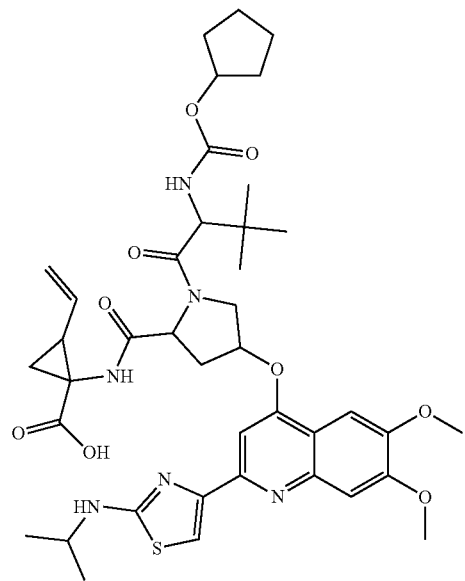 [SMILES: C=CC1CC1(NC(=O)C1CC(Oc2cc(-c3csc(NC(C)C)n3)nc3cc(OC)c(OC)cc23)CN1C(=O)C(NC(=O)OC1CCCC1)C(C)(C)C)C(=O)O]
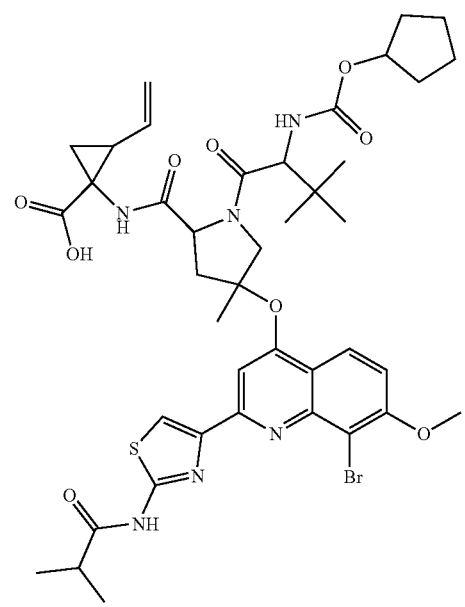 [SMILES: C=CC1CC1(NC(=O)C1CC(C)(Oc2cc(-c3csc(NC(=O)C(C)C)n3)nc3c(Br)c(OC)ccc23)CN1C(=O)C(NC(=O)OC1CCCC1)C(C)(C)C)C(=O)O]

TABLE 37-continued
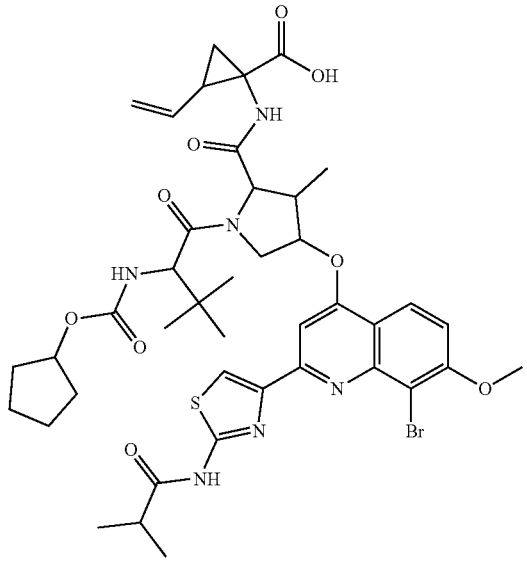 [SMILES: C=CC1CC1(NC(=O)C1C(C)C(Oc2cc(-c3csc(NC(=O)C(C)C)n3)nc3c(Br)c(OC)ccc23)CN1C(=O)C(NC(=O)OC1CCCC1)C(C)(C)C)C(=O)O]
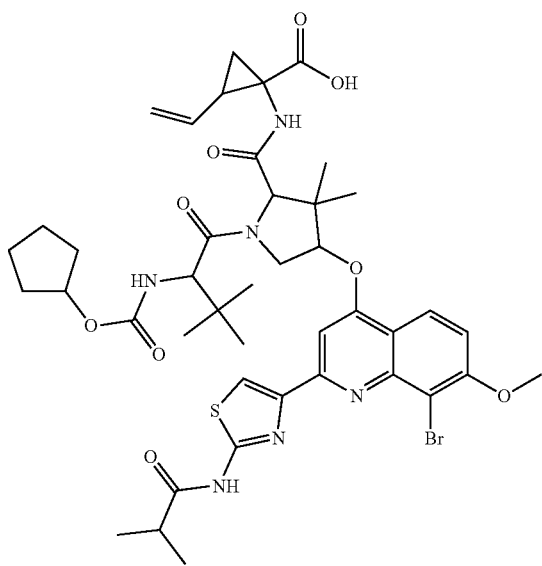 [SMILES: C=CC1CC1(NC(=O)C1N(C(=O)C(NC(=O)OC2CCCC2)C(C)(C)C)CC(Oc2cc(-c3csc(NC(=O)C(C)C)n3)nc3c(Br)c(OC)ccc23)C1(C)C)C(=O)O]

TABLE 37-continued
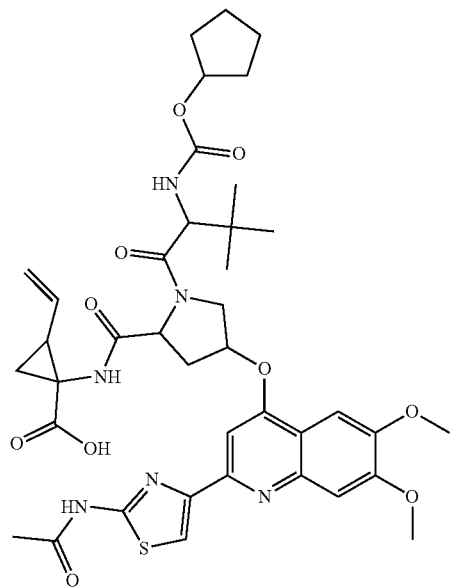 [SMILES: C=CC1CC1(NC(=O)C1CC(Oc2cc(-c3csc(NC(C)=O)n3)nc3cc(OC)c(OC)cc23)CN1C(=O)C(NC(=O)OC1CCCC1)C(C)(C)C)C(=O)O]
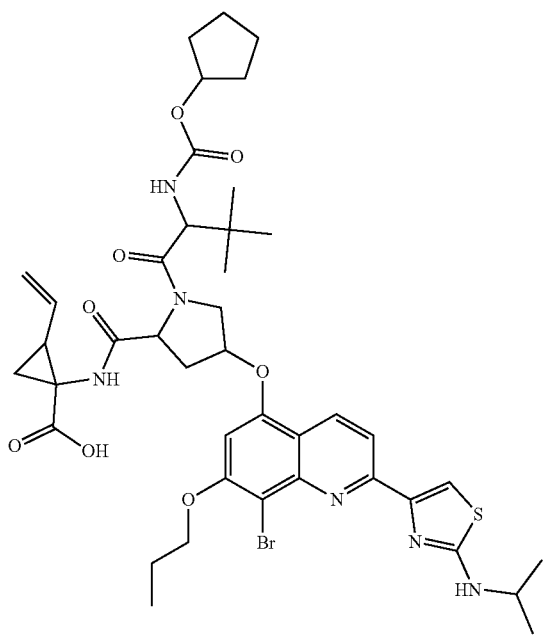 [SMILES: C=CC1CC1(NC(=O)C1CC(Oc2cc(OCCC)c(Br)c3nc(-c4csc(NC(C)C)n4)ccc23)CN1C(=O)C(NC(=O)OC1CCCC1)C(C)(C)C)C(=O)O]

TABLE 37-continued
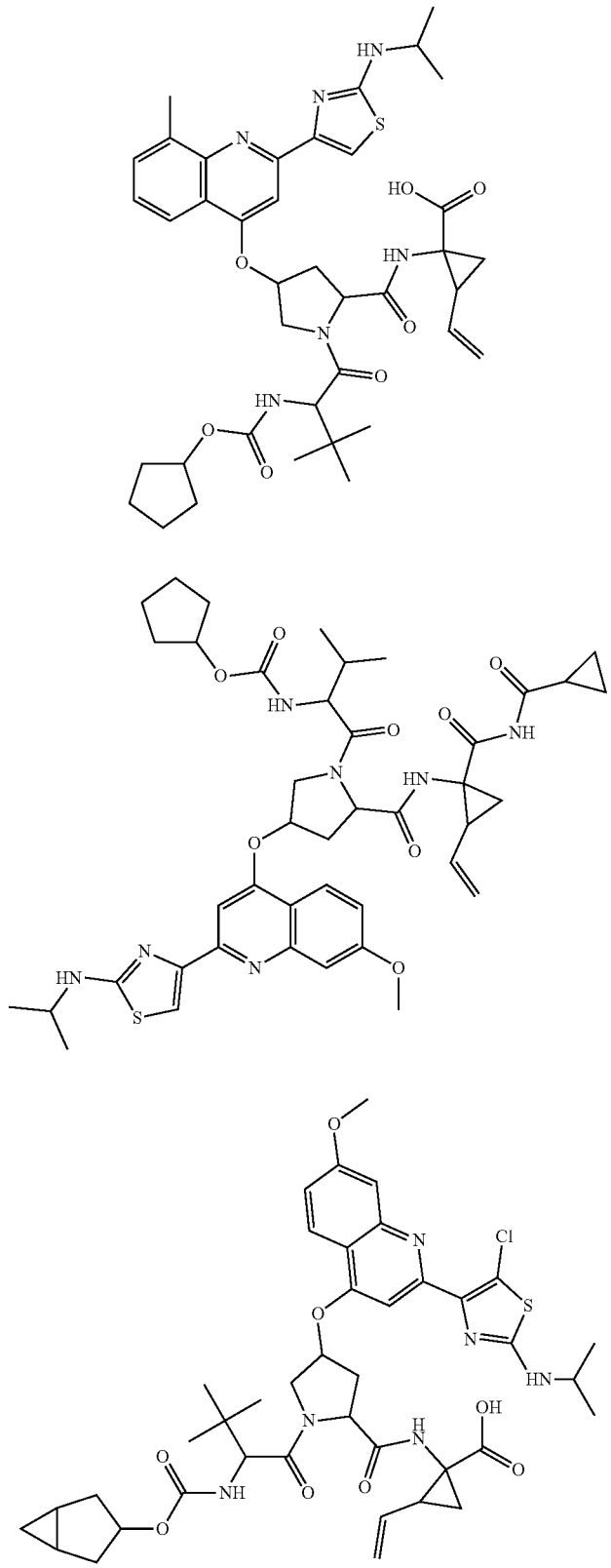

TABLE 37-continued
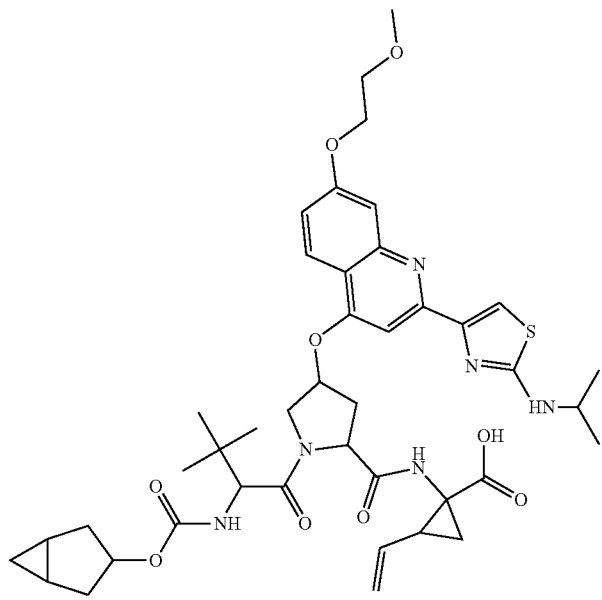 [SMILES: C=CC1CC1(NC(=O)C1CC(Oc2cc(-c3csc(NC(C)C)n3)nc3cc(OCCOC)ccc23)CN1C(=O)C(NC(=O)OC1CC2CC2C1)C(C)(C)C)C(=O)O]
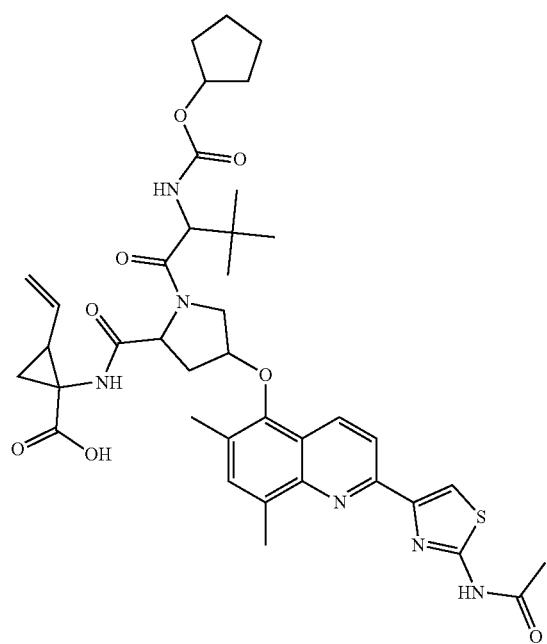 [SMILES: C=CC1CC1(NC(=O)C1CC(Oc2c(C)cc(C)c3nc(-c4csc(NC(C)=O)n4)ccc23)CN1C(=O)C(NC(=O)OC1CCCC1)C(C)(C)C)C(=O)O]

TABLE 37-continued
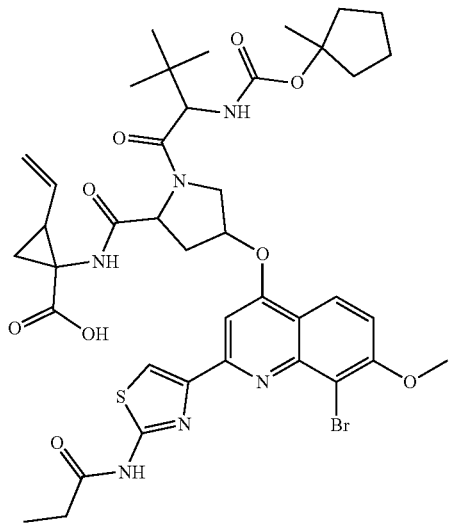 [SMILES: C=CC1CC1(NC(=O)C1CC(Oc2cc(-c3csc(NC(=O)CC)n3)nc3c(Br)c(OC)ccc23)CN1C(=O)C(NC(=O)OC1(C)CCCC1)C(C)(C)C)C(=O)O]
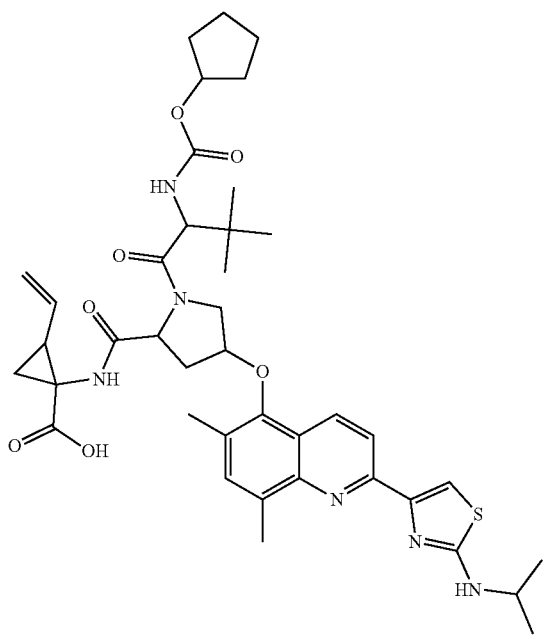 [SMILES: C=CC1CC1(NC(=O)C1CC(Oc2c(C)cc(C)c3nc(-c4csc(NC(C)C)n4)ccc23)CN1C(=O)C(NC(=O)OC1CCCC1)C(C)(C)C)C(=O)O]

TABLE 37-continued
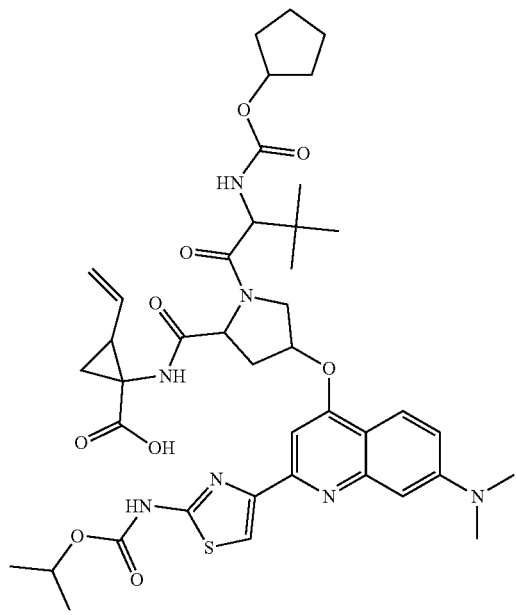 [SMILES: C=CC1CC1(NC(=O)C1CC(Oc2cc(-c3csc(NC(=O)OC(C)C)n3)nc3cc(N(C)C)ccc23)CN1C(=O)C(NC(=O)OC1CCCC1)C(C)(C)C)C(=O)O]
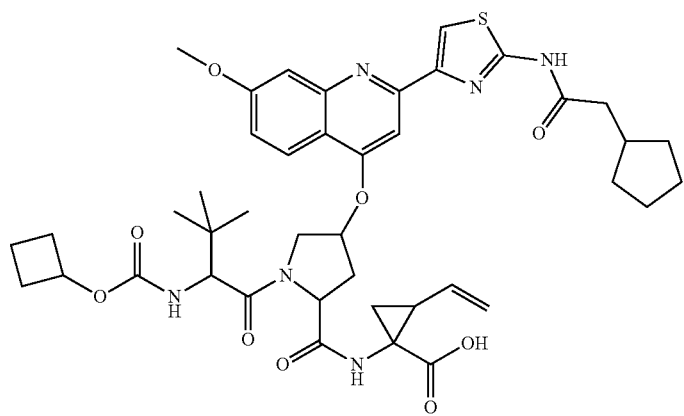 [SMILES: C=CC1CC1(NC(=O)C1CC(Oc2cc(-c3csc(NC(=O)CC4CCCC4)n3)nc3cc(OC)ccc23)CN1C(=O)C(NC(=O)OC1CCC1)C(C)(C)C)C(=O)O]
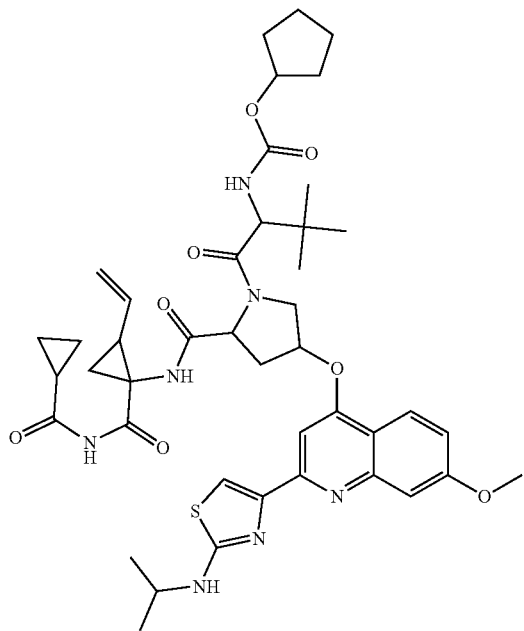 [SMILES: C=CC1CC1(NC(=O)C1CC(Oc2cc(-c3csc(NC(C)C)n3)nc3cc(OC)ccc23)CN1C(=O)C(NC(=O)OC1CCCC1)C(C)(C)C)C(=O)NC(=O)C1CC1]

TABLE 37-continued
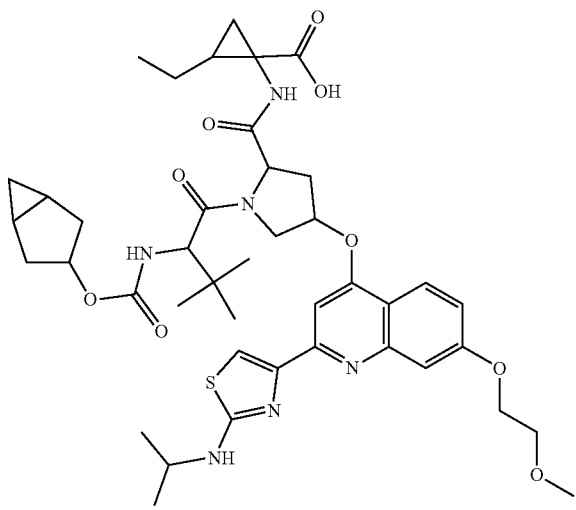 [SMILES: CCC1CC1(NC(=O)C1CC(Oc2cc(-c3csc(NC(C)C)n3)nc3cc(OCCOC)ccc23)CN1C(=O)C(NC(=O)OC1CC2CC2C1)C(C)(C)C)C(=O)O]
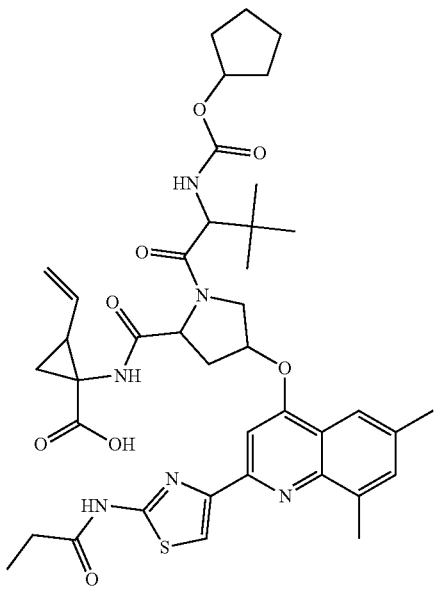 [SMILES: C=CC1CC1(NC(=O)C1CC(Oc2cc(-c3csc(NC(=O)CC)n3)nc3c(C)cc(C)cc23)CN1C(=O)C(NC(=O)OC1CCCC1)C(C)(C)C)C(=O)O]
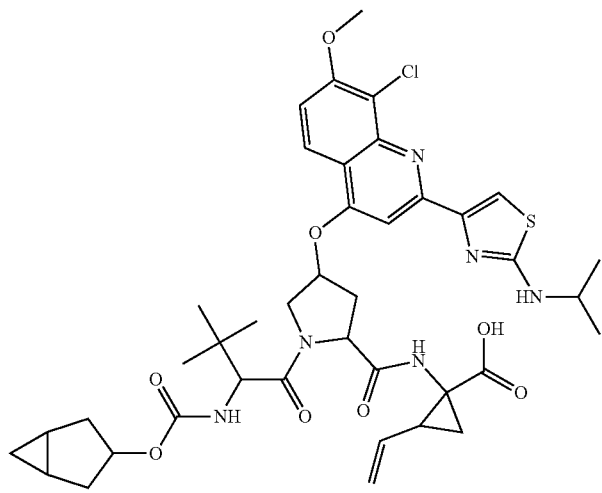 [SMILES: C=CC1CC1(NC(=O)C1CC(Oc2cc(-c3csc(NC(C)C)n3)nc3c(Cl)c(OC)ccc23)CN1C(=O)C(NC(=O)OC1CC2CC2C1)C(C)(C)C)C(=O)O]

TABLE 37-continued
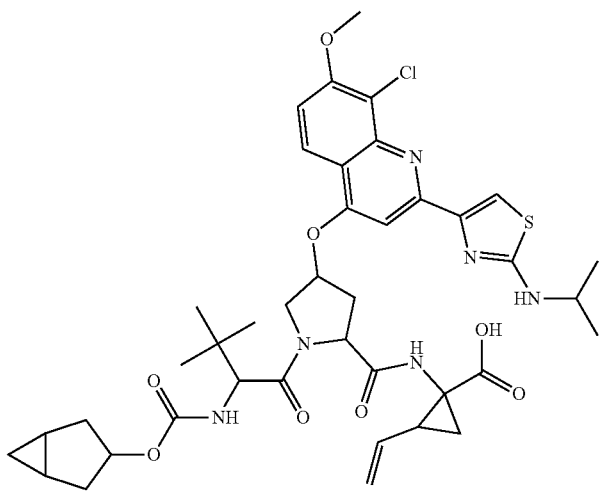 [SMILES: C=CC1CC1(NC(=O)C1CC(Oc2cc(-c3csc(NC(C)C)n3)nc3c(Cl)c(OC)ccc23)CN1C(=O)C(NC(=O)OC1CC2CC2C1)C(C)(C)C)C(=O)O]
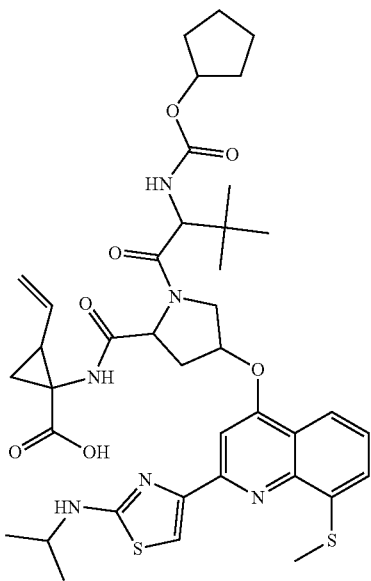 [SMILES: C=CC1CC1(NC(=O)C1CC(Oc2cc(-c3csc(NC(C)C)n3)nc3c(SC)cccc23)CN1C(=O)C(NC(=O)OC1CCCC1)C(C)(C)C)C(=O)O]
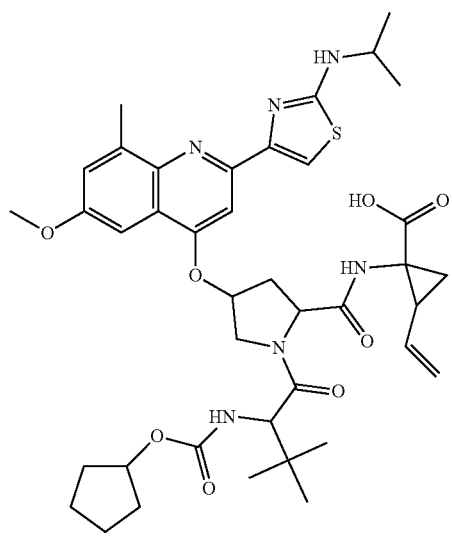 [SMILES: C=CC1CC1(NC(=O)C1CC(Oc2cc(-c3csc(NC(C)C)n3)nc3c(C)cc(OC)cc23)CN1C(=O)C(NC(=O)OC1CCCC1)C(C)(C)C)C(=O)O]

TABLE 37-continued
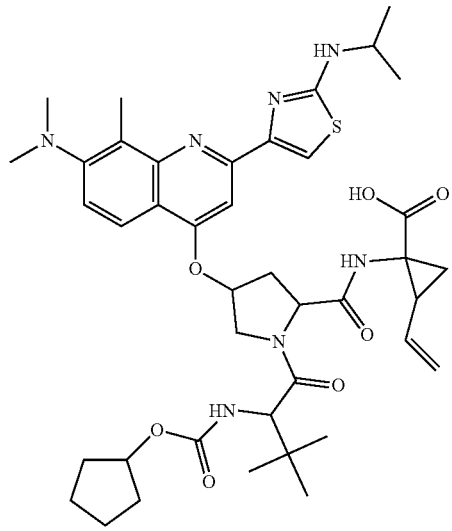 [SMILES: C=CC1CC1(NC(=O)C1CC(Oc2cc(-c3csc(NC(C)C)n3)nc3c(C)c(N(C)C)ccc23)CN1C(=O)C(NC(=O)OC1CCCC1)C(C)(C)C)C(=O)O]
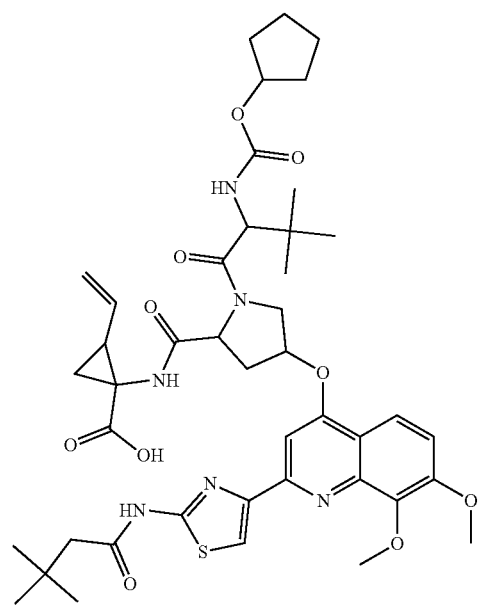 [SMILES: C=CC1CC1(NC(=O)C1CC(Oc2cc(-c3csc(NC(=O)CC(C)(C)C)n3)nc3c(OC)c(OC)ccc23)CN1C(=O)C(NC(=O)OC1CCCC1)C(C)(C)C)C(=O)O]

TABLE 37-continued
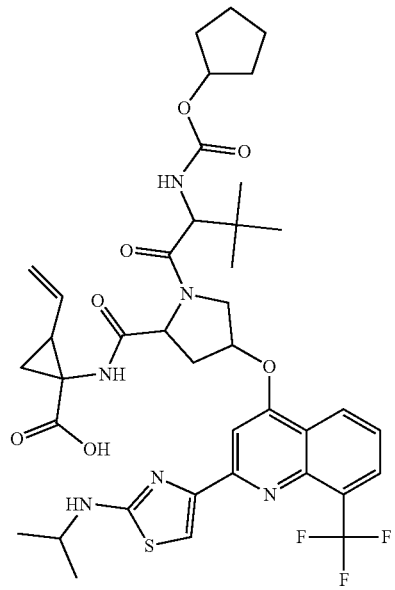 [SMILES: C=CC1CC1(NC(=O)C1CC(Oc2cc(-c3csc(NC(C)C)n3)nc3c(C(F)(F)F)cccc23)CN1C(=O)C(NC(=O)OC1CCCC1)C(C)(C)C)C(=O)O]
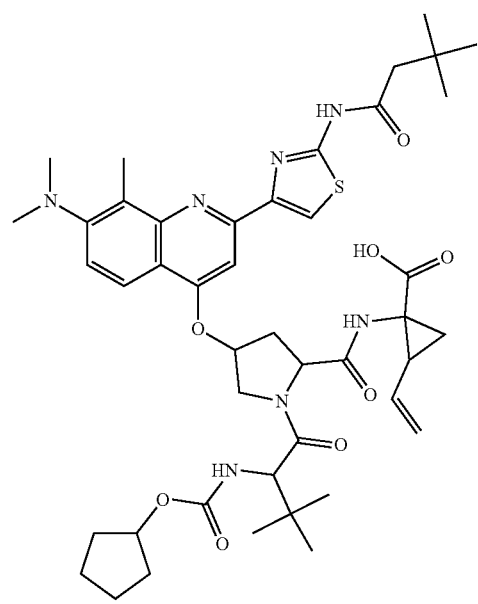 [SMILES: C=CC1CC1(NC(=O)C1CC(Oc2cc(-c3csc(NC(=O)CC(C)(C)C)n3)nc3c(C)c(N(C)C)ccc23)CN1C(=O)C(NC(=O)OC1CCCC1)C(C)(C)C)C(=O)O]

TABLE 37-continued
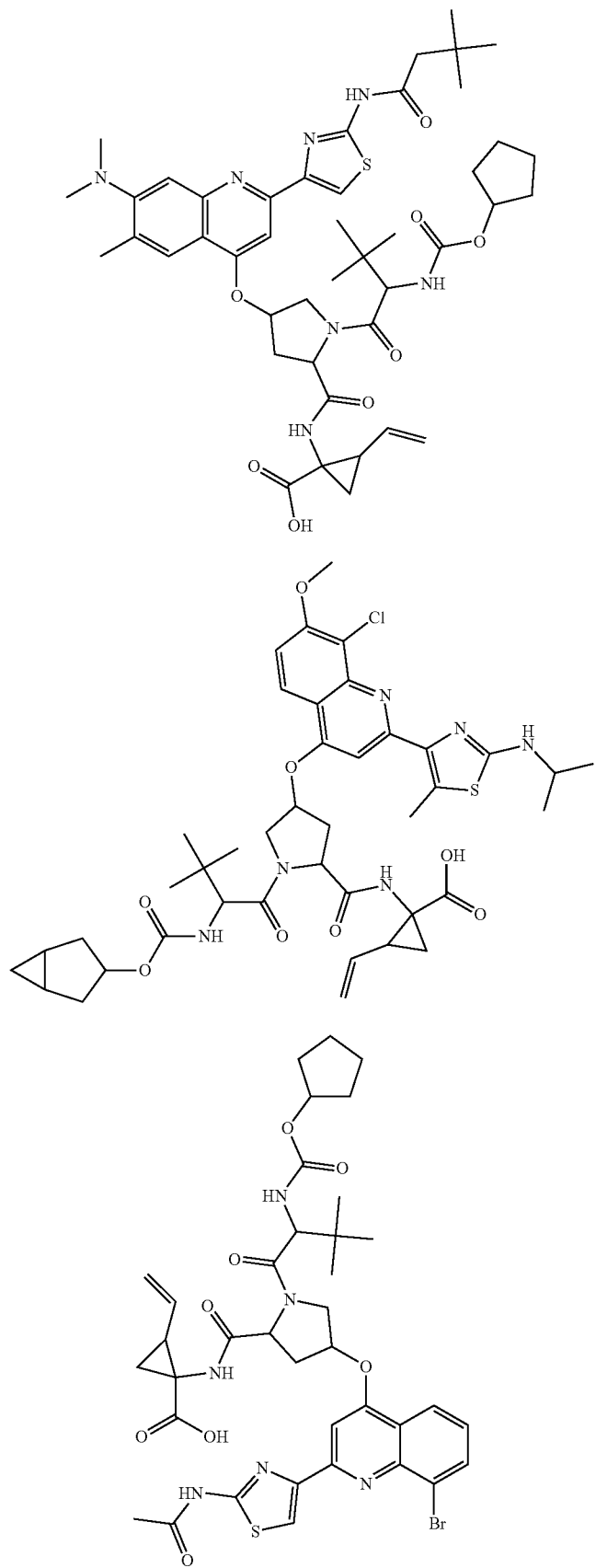

TABLE 37-continued
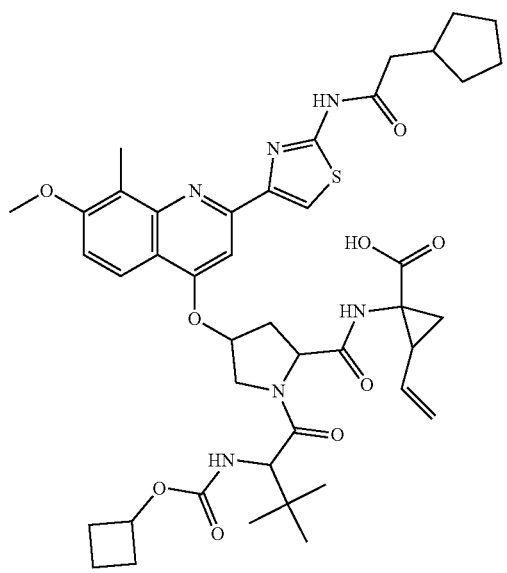 [SMILES: C=CC1CC1(NC(=O)C1CC(Oc2cc(-c3csc(NC(=O)CC4CCCC4)n3)nc3c(C)c(OC)ccc23)CN1C(=O)C(NC(=O)OC1CCC1)C(C)(C)C)C(=O)O]
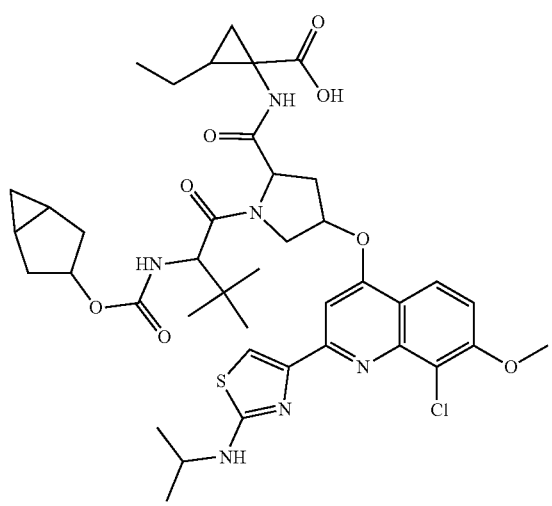 [SMILES: CCC1CC1(NC(=O)C1CC(Oc2cc(-c3csc(NC(C)C)n3)nc3c(Cl)c(OC)ccc23)CN1C(=O)C(NC(=O)OC1CC2CC2C1)C(C)(C)C)C(=O)O]
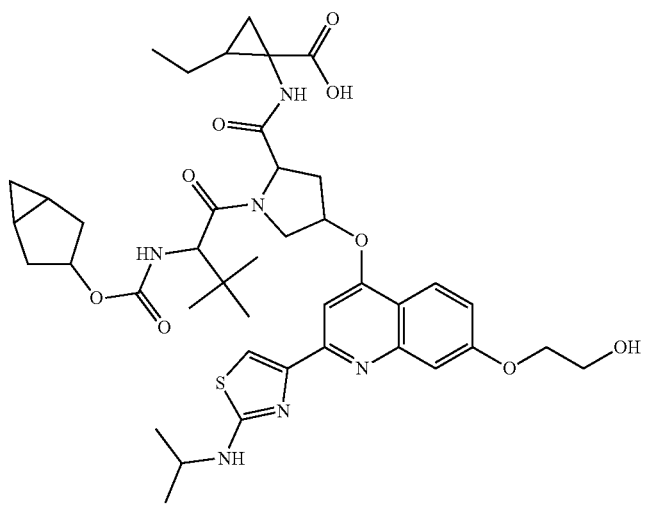 [SMILES: CCC1CC1(NC(=O)C1CC(Oc2cc(-c3csc(NC(C)C)n3)nc3cc(OCCO)ccc23)CN1C(=O)C(NC(=O)OC1CC2CC2C1)C(C)(C)C)C(=O)O]

TABLE 37-continued
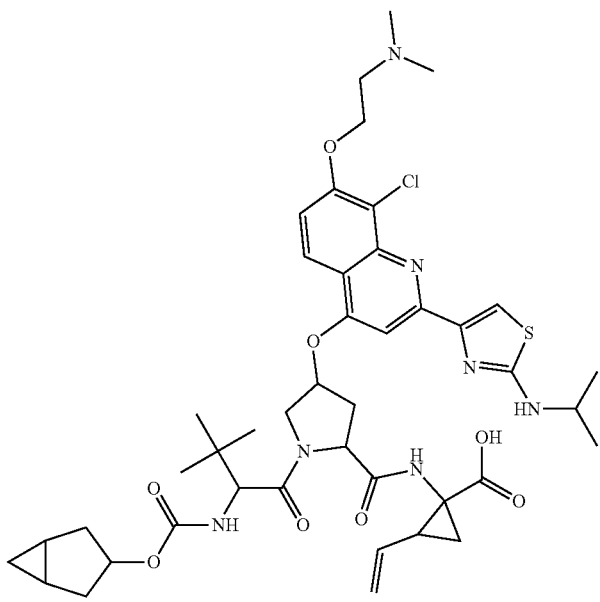 [SMILES: C=CC1CC1(NC(=O)C1CC(Oc2cc(-c3csc(NC(C)C)n3)nc3c(Cl)c(OCCN(C)C)ccc23)CN1C(=O)C(NC(=O)OC1CC2CC2C1)C(C)(C)C)C(=O)O]
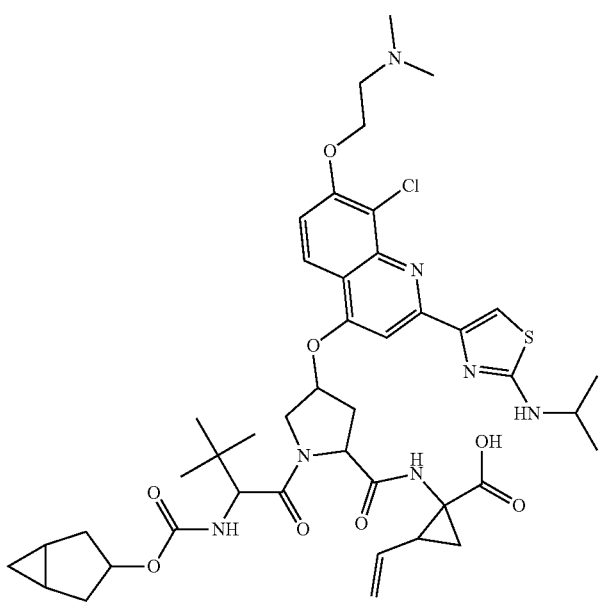 [SMILES: C=CC1CC1(NC(=O)C1CC(Oc2cc(-c3csc(NC(C)C)n3)nc3c(Cl)c(OCCN(C)C)ccc23)CN1C(=O)C(NC(=O)OC1CC2CC2C1)C(C)(C)C)C(=O)O]
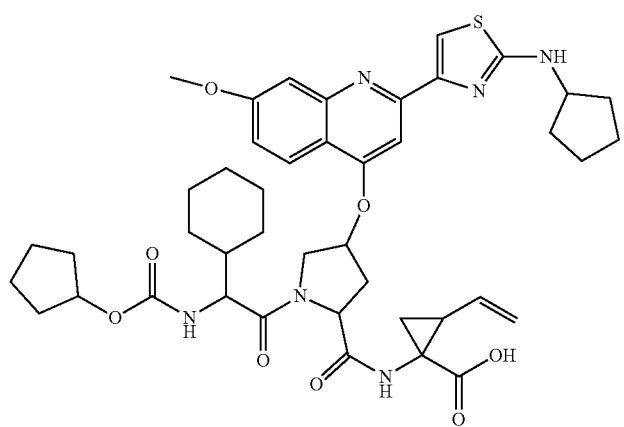 [SMILES: C=CC1CC1(NC(=O)C1CC(Oc2cc(-c3csc(NC4CCCC4)n3)nc3cc(OC)ccc23)CN1C(=O)C(NC(=O)OC1CCCC1)C1CCCCC1)C(=O)O]

TABLE 37-continued
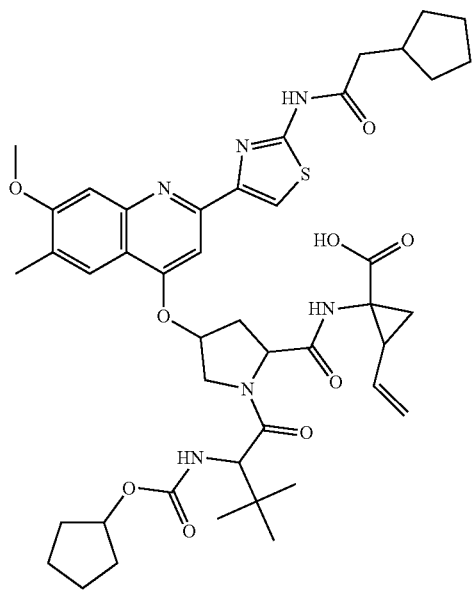 [SMILES: C=CC1CC1(NC(=O)C1CC(Oc2cc(-c3csc(NC(=O)CC4CCCC4)n3)nc3cc(OC)c(C)cc23)CN1C(=O)C(NC(=O)OC1CCCC1)C(C)(C)C)C(=O)O]
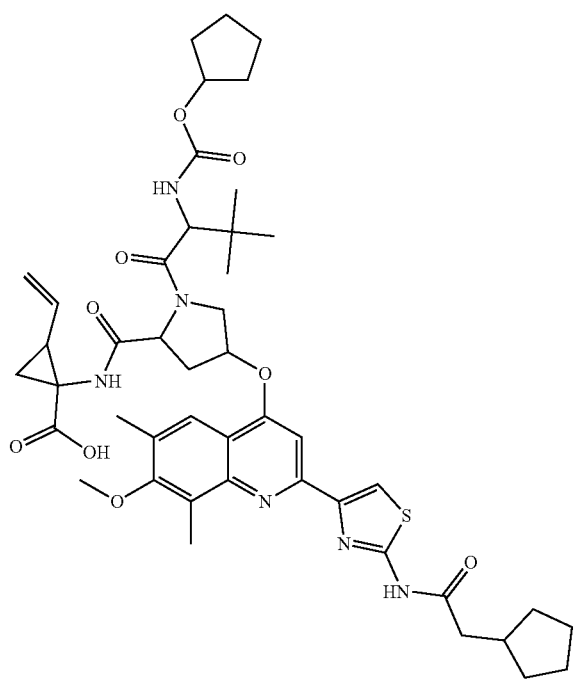 [SMILES: C=CC1CC1(NC(=O)C1CC(Oc2cc(-c3csc(NC(=O)CC4CCCC4)n3)nc3c(C)c(OC)c(C)cc23)CN1C(=O)C(NC(=O)OC1CCCC1)C(C)(C)C)C(=O)O]

TABLE 37-continued
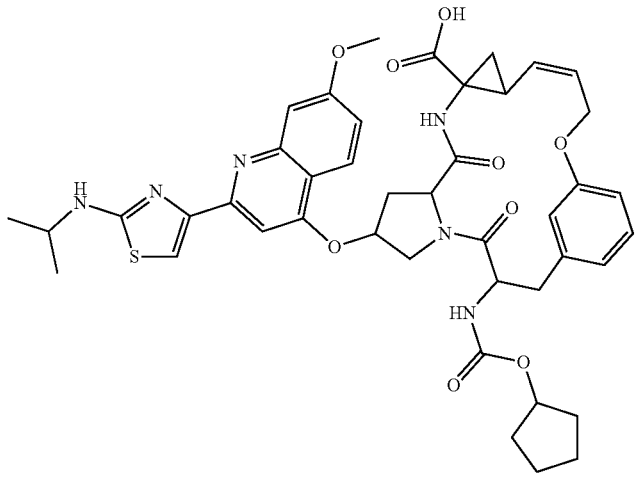 [SMILES: COc1ccc2c(OC3CC4C(=O)NC5(C(=O)O)CC5/C=C\COc5cccc(c5)CC(NC(=O)OC5CCCC5)C(=O)N4C3)cc(-c3csc(NC(C)C)n3)nc2c1]
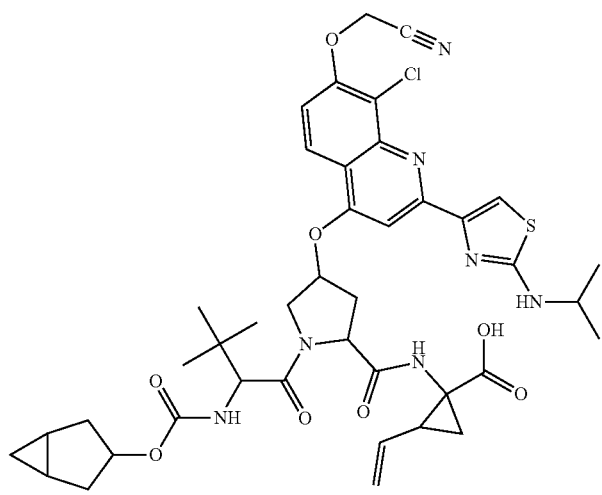 [SMILES: C=CC1CC1(NC(=O)C1CC(Oc2cc(-c3csc(NC(C)C)n3)nc3c(Cl)c(OCC#N)ccc23)CN1C(=O)C(NC(=O)OC1CC2CC2C1)C(C)(C)C)C(=O)O]
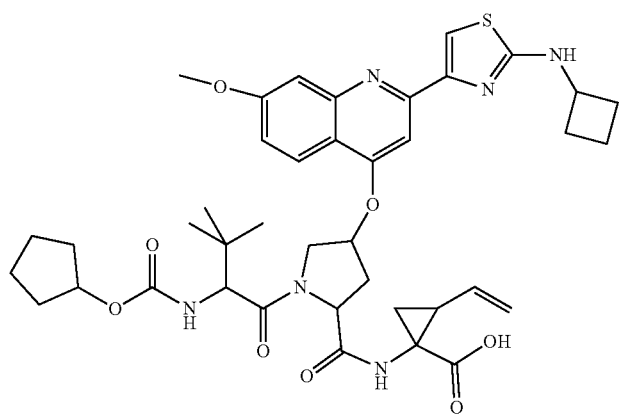 [SMILES: C=CC1CC1(NC(=O)C1CC(Oc2cc(-c3csc(NC4CCC4)n3)nc3cc(OC)ccc23)CN1C(=O)C(NC(=O)OC1CCCC1)C(C)(C)C)C(=O)O]

TABLE 37-continued
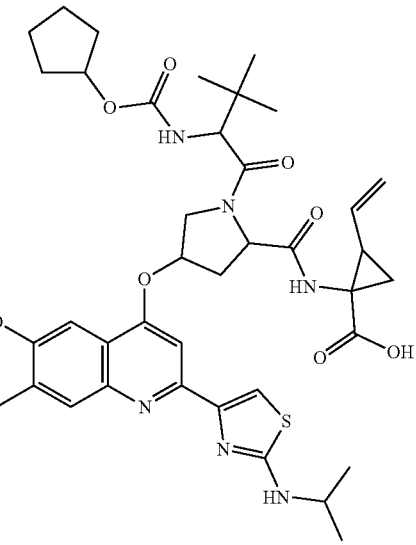
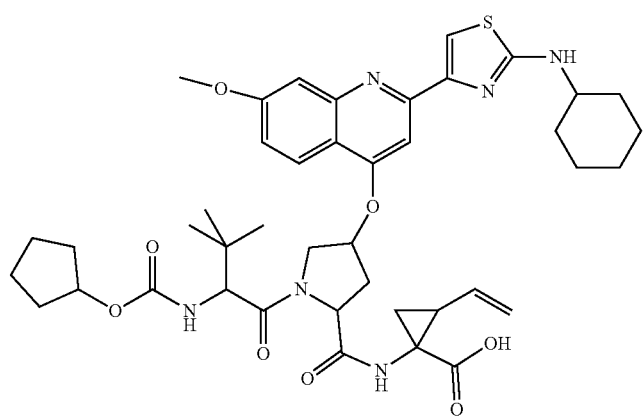 [SMILES: C=CC1CC1(NC(=O)C1CC(Oc2cc(-c3csc(NC4CCCCC4)n3)nc3cc(OC)ccc23)CN1C(=O)C(NC(=O)OC1CCCC1)C(C)(C)C)C(=O)O]
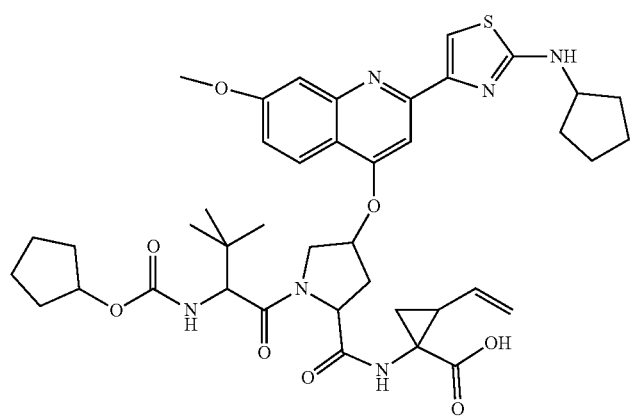 [SMILES: C=CC1CC1(NC(=O)C1CC(Oc2cc(-c3csc(NC4CCCC4)n3)nc3cc(OC)ccc23)CN1C(=O)C(NC(=O)OC1CCCC1)C(C)(C)C)C(=O)O]

TABLE 37-continued
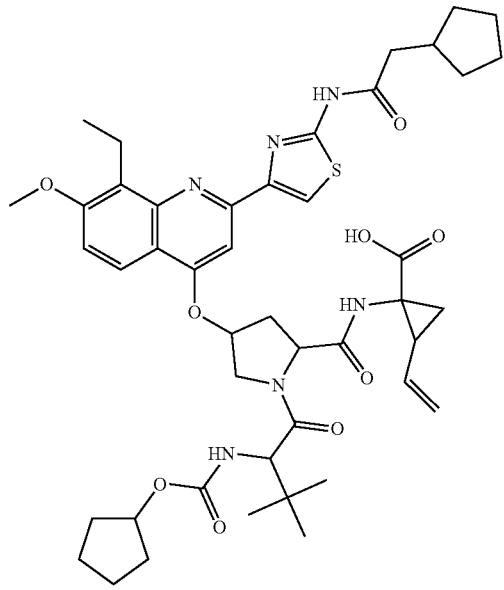 [SMILES: C=CC1CC1(NC(=O)C1CC(Oc2cc(-c3csc(NC(=O)CC4CCCC4)n3)nc3c(CC)c(OC)ccc23)CN1C(=O)C(NC(=O)OC1CCCC1)C(C)(C)C)C(=O)O]
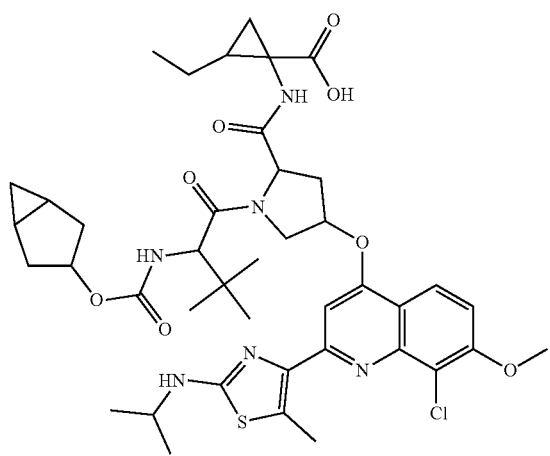 [SMILES: CCC1CC1(NC(=O)C1CC(Oc2cc(-c3nc(NC(C)C)sc3C)nc3c(Cl)c(OC)ccc23)CN1C(=O)C(NC(=O)OC1CC2CC2C1)C(C)(C)C)C(=O)O]
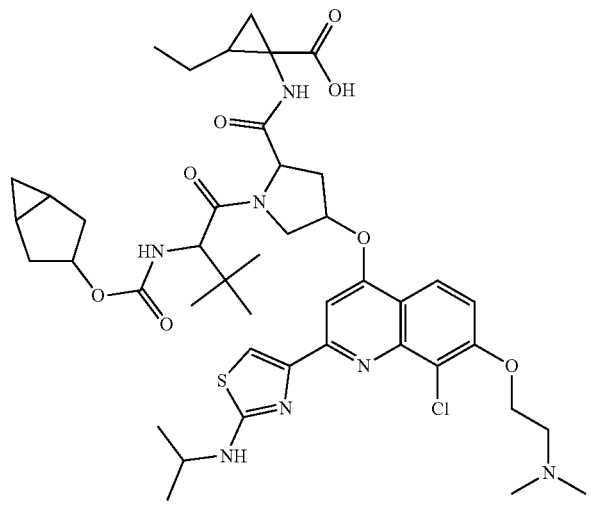 [SMILES: CCC1CC1(NC(=O)C1CC(Oc2cc(-c3csc(NC(C)C)n3)nc3c(Cl)c(OCCN(C)C)ccc23)CN1C(=O)C(NC(=O)OC1CC2CC2C1)C(C)(C)C)C(=O)O]

In one implementation, the compound is cyclizine (1-benzhydryl-4-methylpiperazine) lactate, a clinically investigated histimine H1 antagonist. In one particular implementation, the compound, or variations and permutations thereof, is further described in WO2007117560 the contents of which are hereby incorporated by reference for all purposes and the specific purposes identified herein.

In some embodiments, such compounds are represented by any one or more of the structures shown in Table 44. Any one of the compounds depicted in Table 44 is suitable for use in the methods of the present disclosure.

TABLE 38

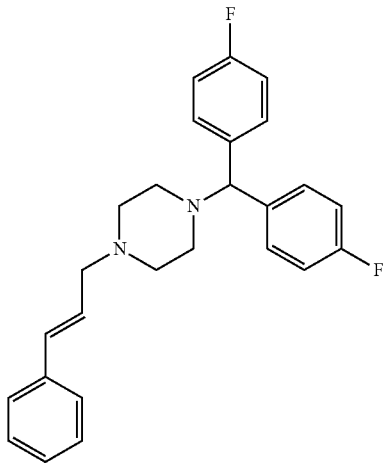 [SMILES: Fc1ccc(C(c2ccc(F)cc2)N2CCN(C/C=C/c3ccccc3)CC2)cc1]

In one implementation, the compound is danoprevir, 2R,13aS,14aR,16aS,Z)-6-((tert-butoxycarbonyl)amino)-14a-((cyclopropylsulfonyl)carbamoyl)-5,16-dioxo-1,2,3,5,6,7,8,9,10,11,13a, 14,14a,15,16,16a-hexadecahydrocyclopropa[e]pyrrolo[1,2-a][1,4]diazacyclopentadecin-2-yl 4-fluoroisoindoline-2-carboxylate, a clinically investigated NS3/4A protease inhibitor. In one particular implementation, the compound, or variations and permutations thereof, is further described in WO2005037214; WO2007015824; WO2007044893; WO2008134395; WO2008137779; WO2009053828; WO2009070689; WO2009070692; WO2009082697; WO2011038283; WO2011091757; WO2011150190; WO2012040242; and WO2014070974 the contents of which are hereby incorporated by reference for all purposes and the specific purposes identified herein.

In one implementation, the compound is darinaparsin ((S)-2-amino-5-(((R)-1-((carboxymethyl)amino)-3-((dimethylarsino)thio)-1-oxopropan-2-yl)amino)-5-oxopentanoic acid), a clinically investigated viral protease inhibitor. In one particular implementation, the compound, or variations and permutations thereof, is further described in WO2003051910 the contents of which are hereby incorporated by reference for all purposes and the specific purposes identified herein.

In one implementation, the compound is darunavir ((3R, 3aS,6aR)-hexahydrofuro[2,3-b]furan-3-yl ((2S,3R)-4-(4-amino-N-isobutylphenylsulfonamido)-3-hydroxy-1-phenylbutan-2-yl)carbamate), a clinically investigated HIV-1 protease inhibitor. In one particular implementation, the compound, or variations and permutations thereof, is further described in U.S. Pat. No. 9,346,820; WO1999067254; WO2000047551; WO2000076961; WO2003078438; WO2008013834; WO2012031237; WO2012092168; WO2016069955; and WO2017031220 the contents of which are hereby incorporated by reference for all purposes and the specific purposes identified herein. In some embodiments, such compounds are represented by any one or more of the structures shown in Table 47. Any one of the compounds depicted in Table 47 is suitable for use in the methods of the present disclosure.

TABLE 39

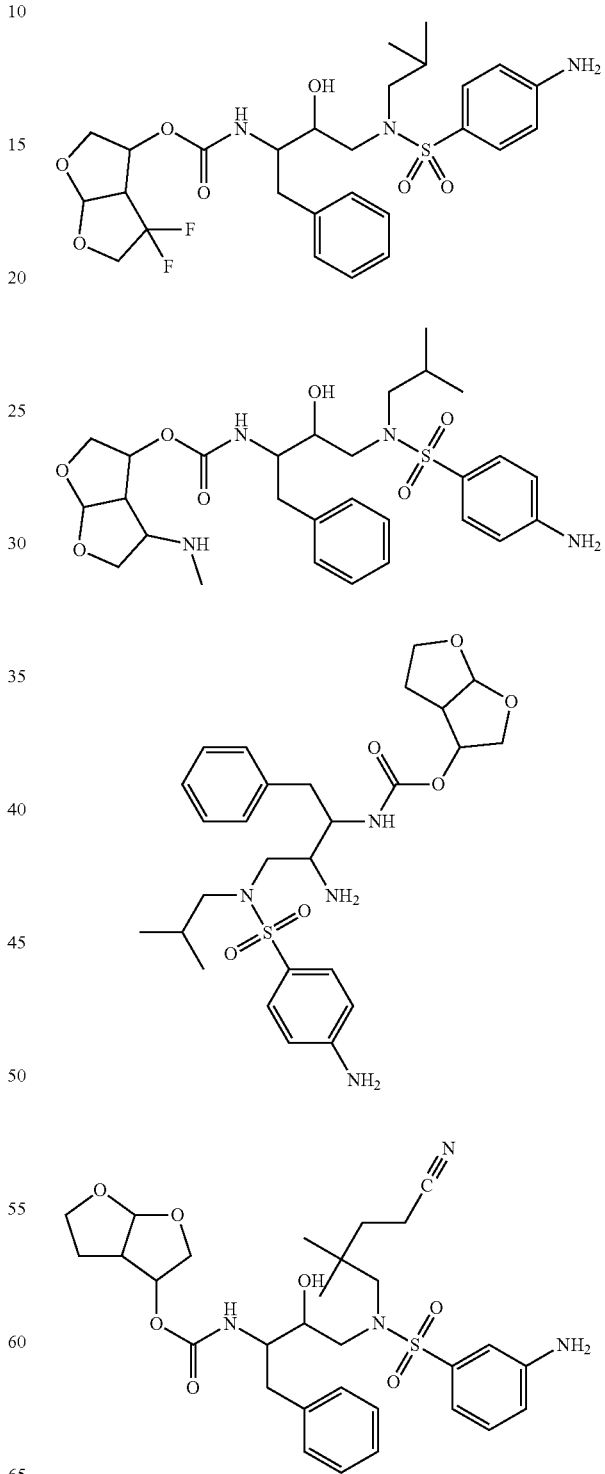

TABLE 39-continued
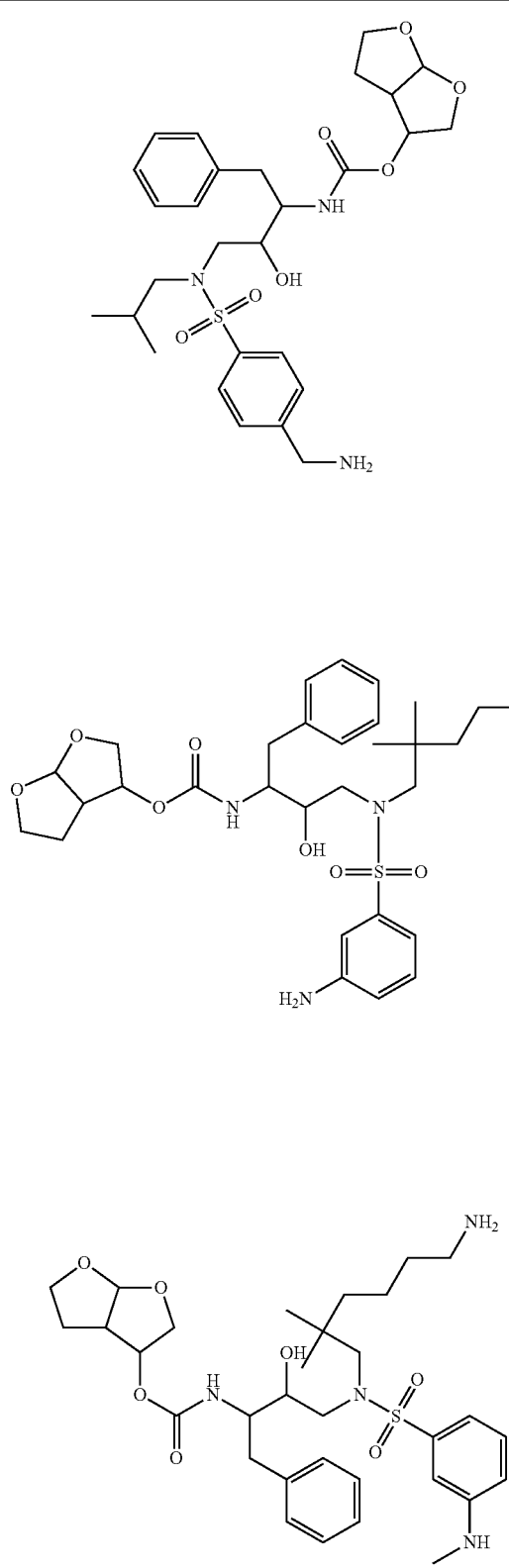
TABLE 39-continued
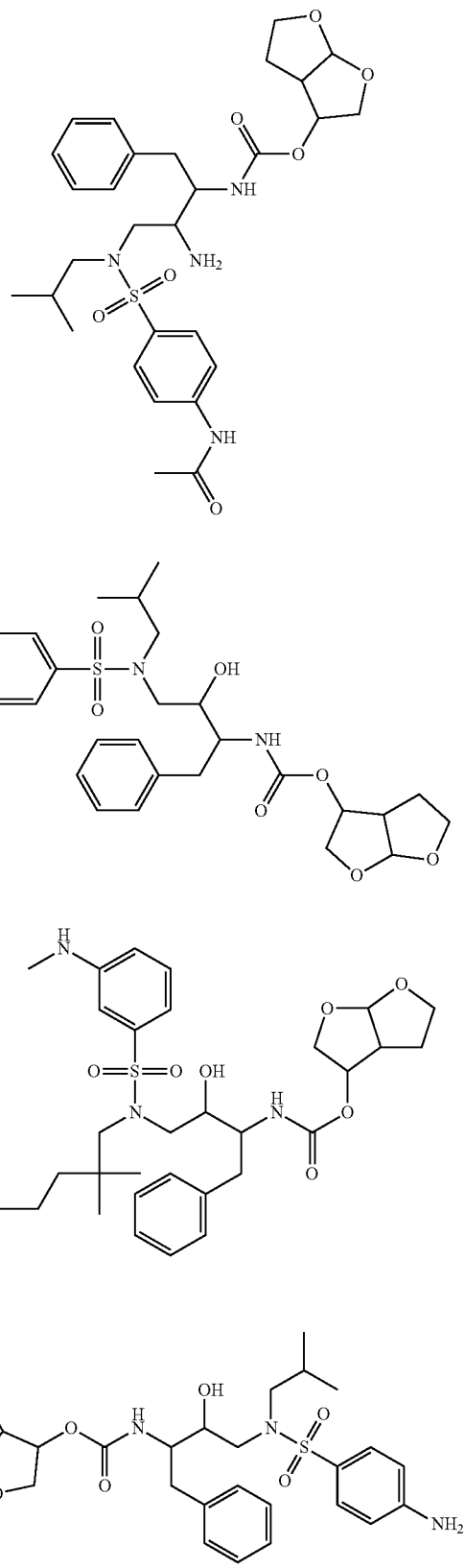

TABLE 39-continued
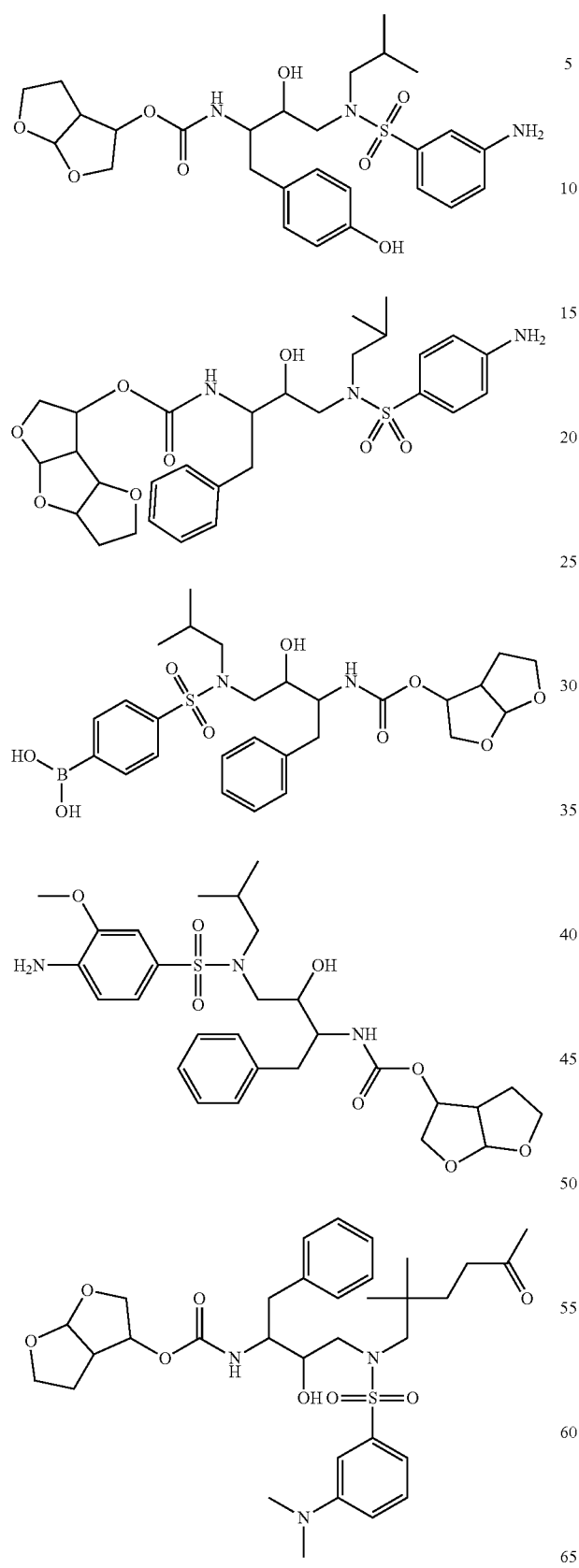
TABLE 39-continued
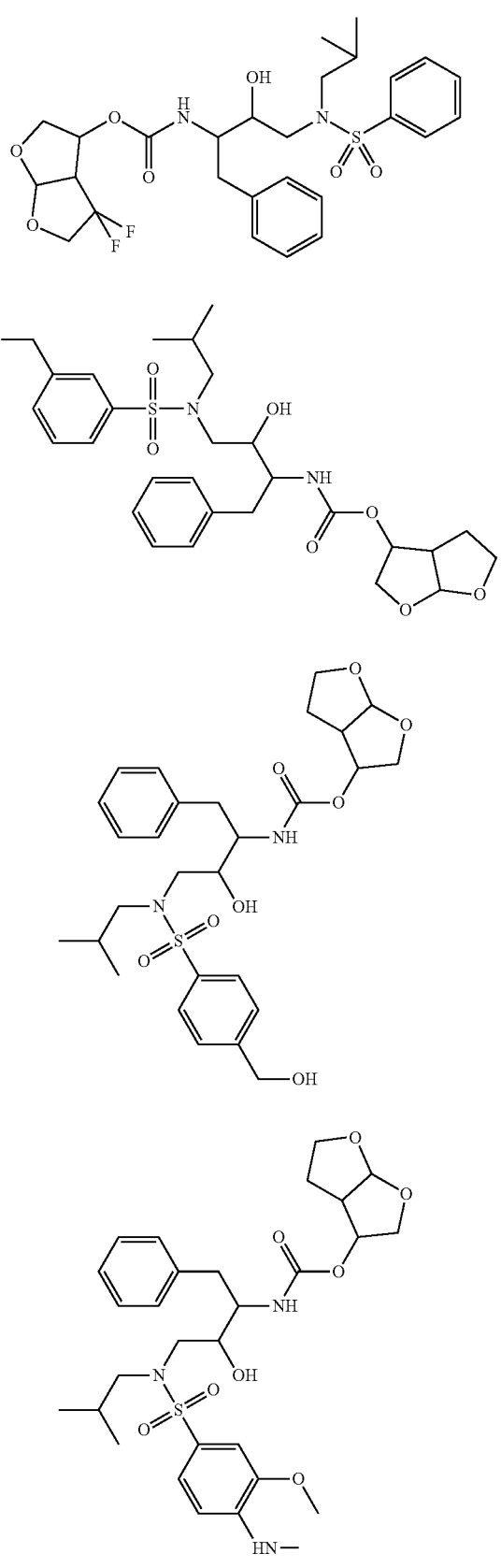

TABLE 39-continued

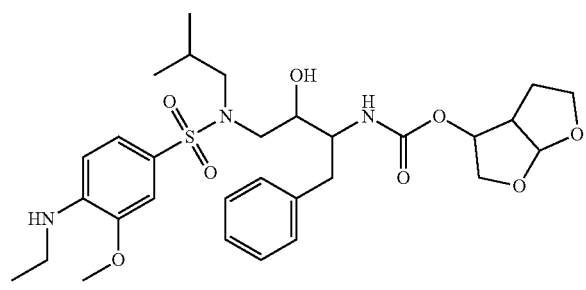 [SMILES: CCNc1ccc(S(=O)(=O)N(CC(C)C)CC(O)C(Cc2ccccc2)NC(=O)OC2COC3OCCC23)cc1OC]

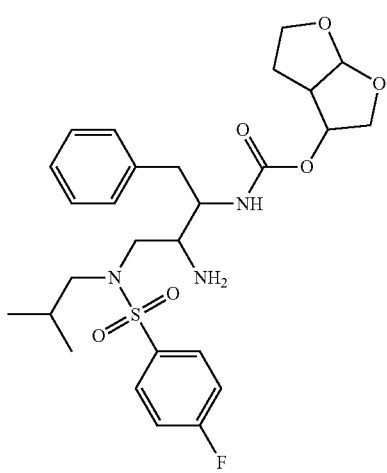 [SMILES: CC(C)CN(CC(N)C(Cc1ccccc1)NC(=O)OC1COC2OCCC12)S(=O)(=O)c1ccc(F)cc1]

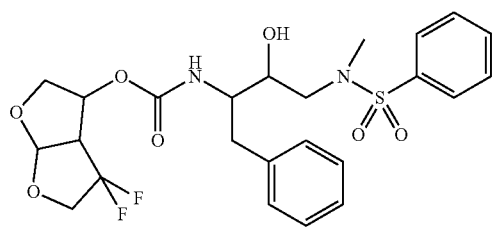 [SMILES: CN(CC(O)C(Cc1ccccc1)NC(=O)OC1COC2OCC(F)(F)C12)S(=O)(=O)c1ccccc1]

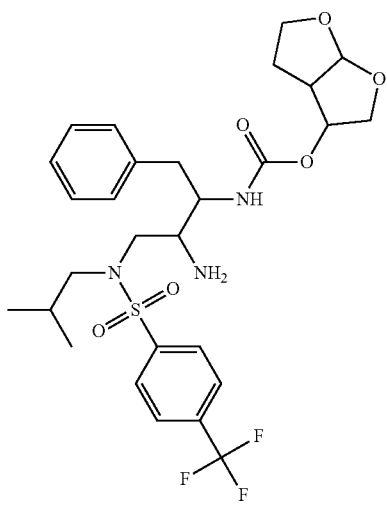 [SMILES: CC(C)CN(CC(N)C(Cc1ccccc1)NC(=O)OC1COC2OCCC12)S(=O)(=O)c1ccc(C(F)(F)F)cc1]

TABLE 39-continued

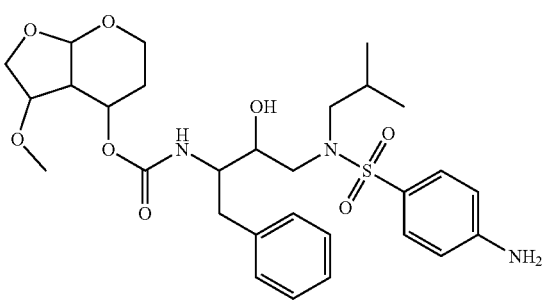 [SMILES: COC1COC2OCCC(OC(=O)NC(Cc3ccccc3)C(O)CN(CC(C)C)S(=O)(=O)c3ccc(N)cc3)C12]

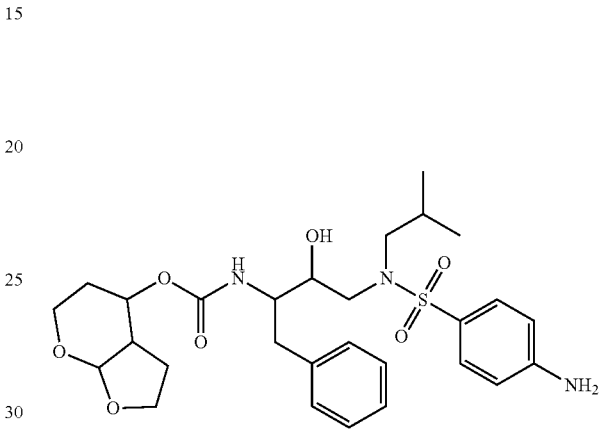

In one implementation, the compound is dasabuvir (N-(6-(3-(tert-butyl)-5-(2,4-dioxo-3,4-dihydropyrimidin-1(2H)-yl)-2-methoxyphenyl)naphthalen-2-yl)methanesulfonamide), a clinically investigated hepatitis C virus NS5B polymerase inhibitor. In one particular implementation, the compound, or variations and permutations thereof, is further described in WO2015197028 the contents of which are hereby incorporated by reference for all purposes and the specific purposes identified herein. In some embodiments, such compounds are represented by any one or more of the structures shown in Table 48. Any one of the compounds depicted in Table 48 is suitable for use in the methods of the present disclosure.

TABLE 40

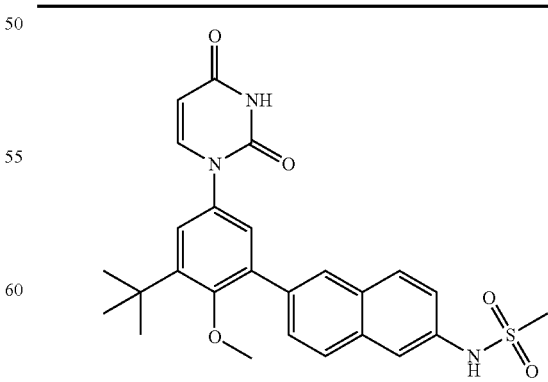

TABLE 40-continued
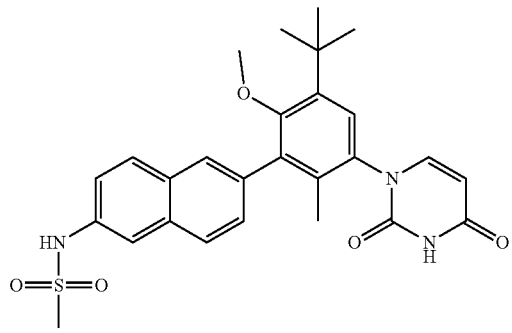 [SMILES: COc1c(C(C)(C)C)cc(-n2ccc(=O)[nH]c2=O)c(C)c1-c1ccc2cc(NS(C)(=O)=O)ccc2c1]
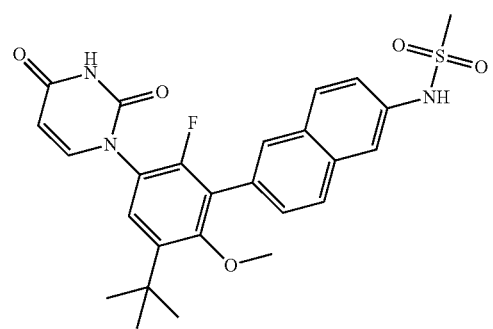 [SMILES: COc1c(C(C)(C)C)cc(-n2ccc(=O)[nH]c2=O)c(F)c1-c1ccc2cc(NS(C)(=O)=O)ccc2c1]
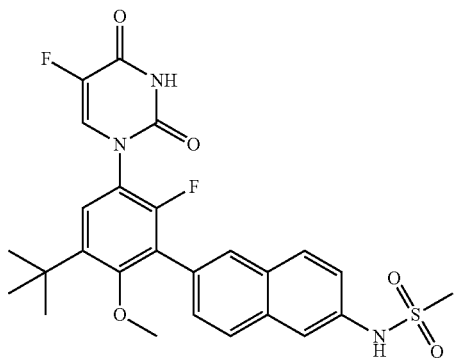 [SMILES: COc1c(C(C)(C)C)cc(-n2cc(F)c(=O)[nH]c2=O)c(F)c1-c1ccc2cc(NS(C)(=O)=O)ccc2c1]
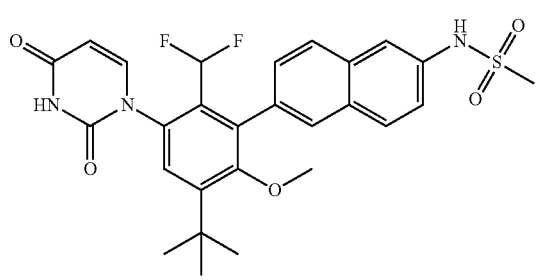 [SMILES: COc1c(C(C)(C)C)cc(-n2ccc(=O)[nH]c2=O)c(C(F)F)c1-c1ccc2cc(NS(C)(=O)=O)ccc2c1]
TABLE 40-continued
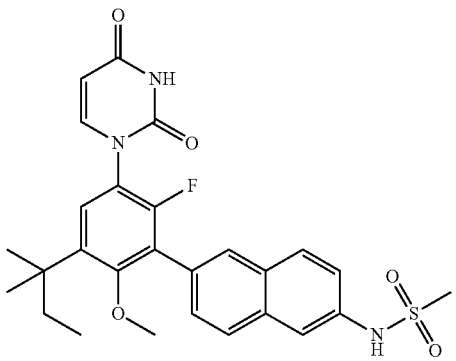 [SMILES: CCC(C)(C)c1cc(-n2ccc(=O)[nH]c2=O)c(F)c(-c2ccc3cc(NS(C)(=O)=O)ccc3c2)c1OC]
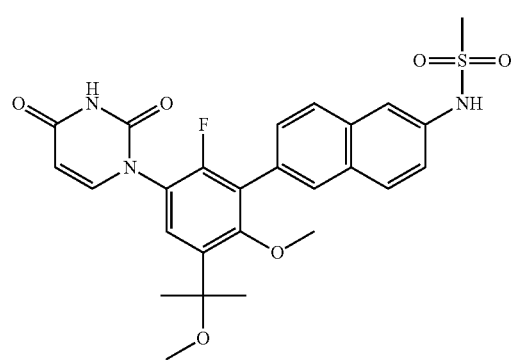 [SMILES: COc1c(C(C)(C)OC)cc(-n2ccc(=O)[nH]c2=O)c(F)c1-c1ccc2cc(NS(C)(=O)=O)ccc2c1]
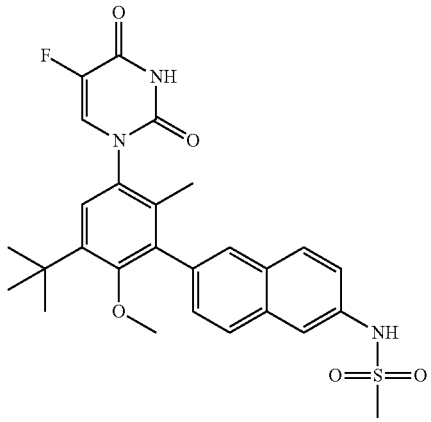 [SMILES: COc1c(C(C)(C)C)cc(-n2cc(F)c(=O)[nH]c2=O)c(C)c1-c1ccc2cc(NS(C)(=O)=O)ccc2c1]
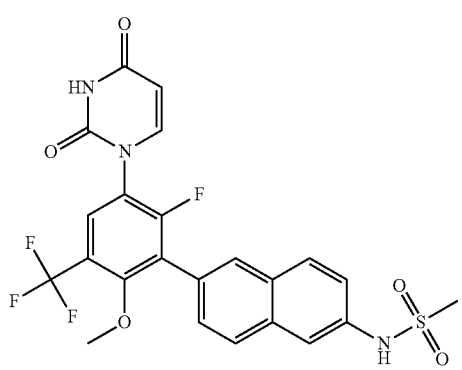 [SMILES: COc1c(C(F)(F)F)cc(-n2ccc(=O)[nH]c2=O)c(F)c1-c1ccc2cc(NS(C)(=O)=O)ccc2c1]

TABLE 40-continued

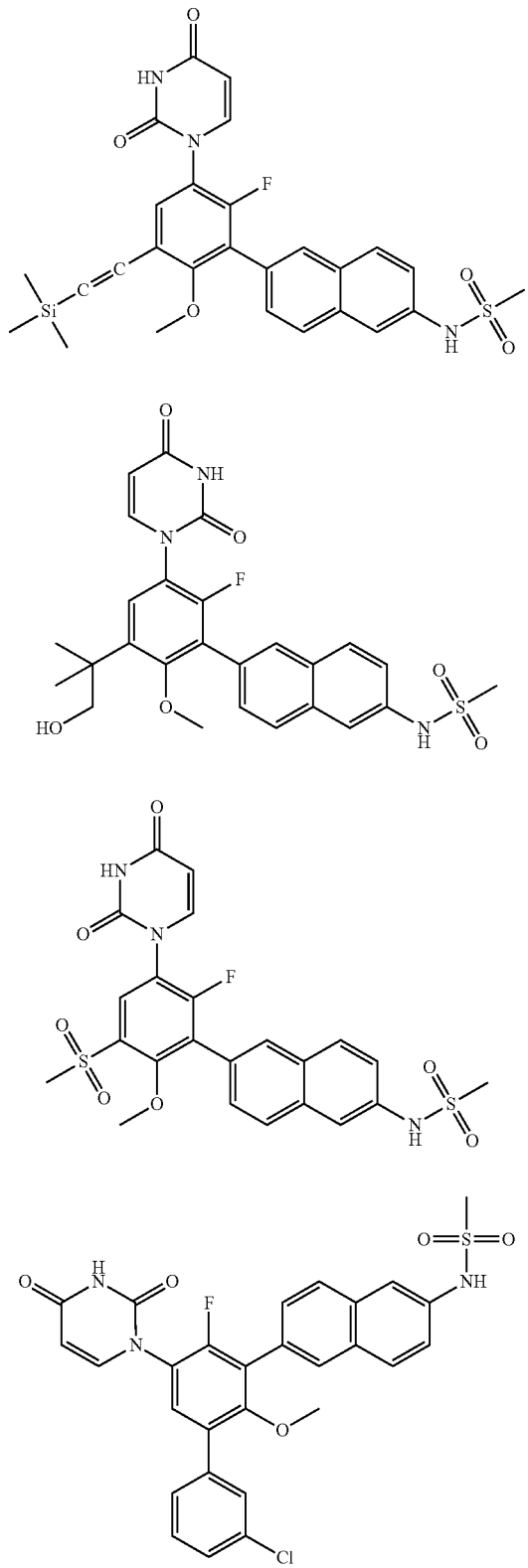

TABLE 40-continued

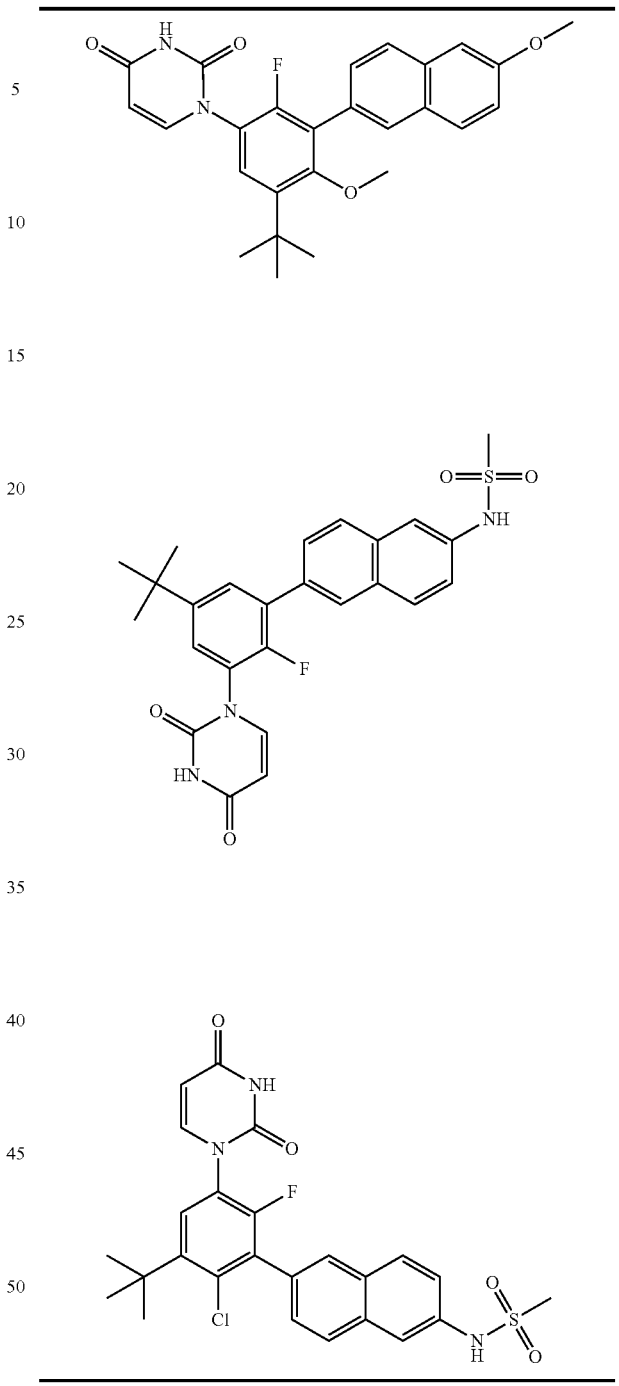

In one implementation, the compound is a dexamfetamine prodrug, or Lisdexamphetamine ((S)-6-amino-2-(((S)-1-phenylpropan-2-yl)amino)hexanamide, dimesylate), clinically investigated as an adrenergic receptor agonist. In one particular implementation, the compound, or variations and permutations thereof, is further described in WO1998029435 the contents of which are hereby incorporated by reference for all purposes and the specific purposes identified herein. In some embodiments, such compounds are represented by any one or more of the structures shown in Table 49. Any one of the compounds depicted in Table 49 is suitable for use in the methods of the present disclosure.

TABLE 41

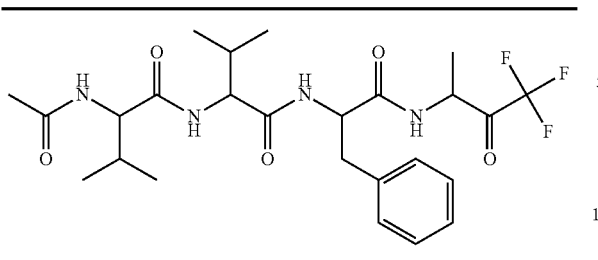

In one implementation, the compound is di-PHPB (potassium 2-(1-hydroxypentyl)benzoate) a clinically investigated HIV protease inhibitor. In one particular implementation, the compound, or variations and permutations thereof, is further described in WO2000015634 the contents of which are hereby incorporated by reference for all purposes and the specific purposes identified herein.

In some embodiments, such compounds are represented by any one or more of the structures shown in Table 50. Any one of the compounds depicted in Table 50 is suitable for use in the methods of the present disclosure.

TABLE 42

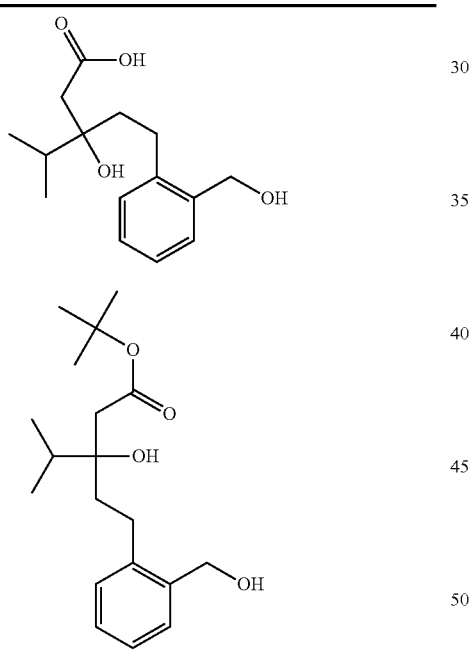

In one implementation, the compound is emivirine (1-(Ethoxymethyl)-5-(1-methylethyl)-6-(phenylmethyl)-2,4 (1H,3H)-pyrimidinedione) a clinically investigated HIV-1 reverse transcriptase inhibitor and non-nucleoside reverse transcriptase inhibitor. In one particular implementation, the compound, or variations and permutations thereof, is further described in WO2009005674 the contents of which are hereby incorporated by reference for all purposes and the specific purposes identified herein. In some embodiments, such compounds are represented by any one or more of the structures shown in Table 51. Any one of the compounds depicted in Table 51 is suitable for use in the methods of the present disclosure.

TABLE 43

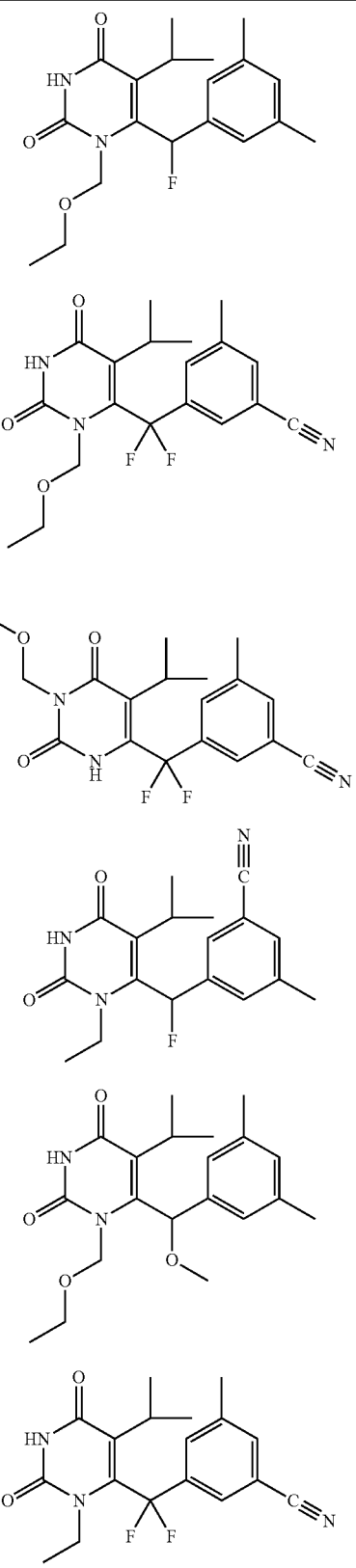

In one implementation, the compound is enalapril maleate (Z)-but-2-enedioic acid; (2S)-1-[(2S)-2-[(2S)-1-ethoxy-1-oxo-4-phenylbutan-2-yl]amino]propanoyl]pyrrolidine-2- carboxylic acid), a clinically investigated ACE inhibitor. In one particular implementation, the compound, or variations and permutations thereof, is further described in WO2007117560 the contents of which are hereby incorporated by reference for all purposes and the specific purposes identified herein. In some embodiments, such compounds are represented by any one or more of the structures shown in Table 52. Any one of the compounds depicted in Table 52 is suitable for use in the methods of the present disclosure.

TABLE 44

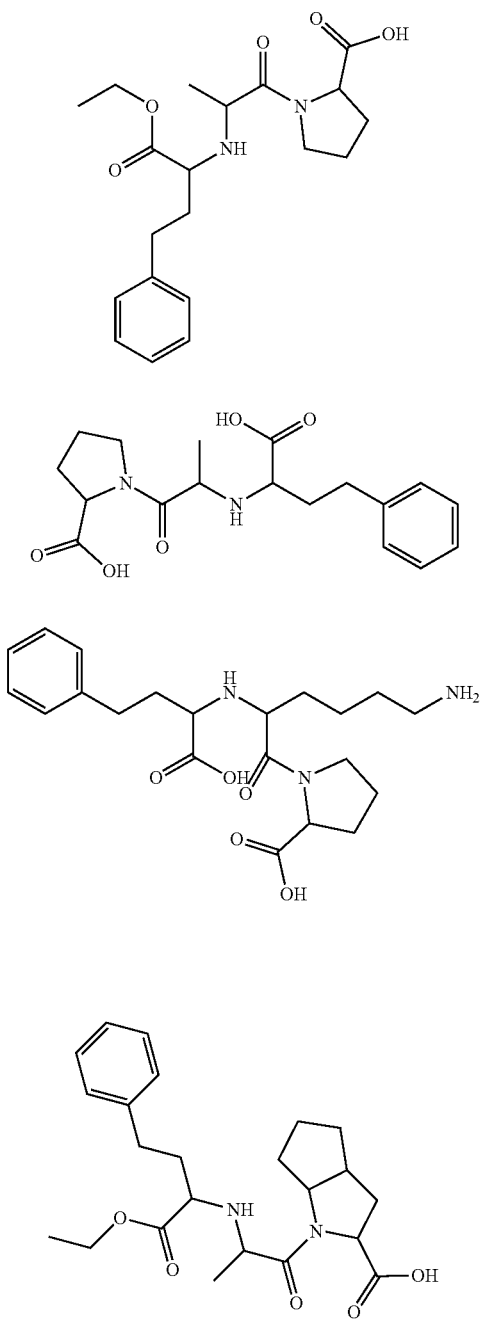

TABLE 44-continued

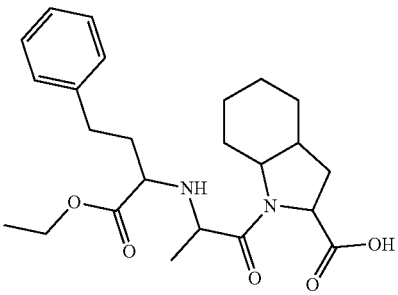 [SMILES: CCOC(=O)C(CCc1ccccc1)NC(C)C(=O)N1C(C(=O)O)CC2CCCCC21]

In one implementation, the compound is entacapone ((E)-2-cyano-3-(3,4-dihydroxy-5-nitrophenyl)-N,N-diethyl-acrylamide), a clinically investigated catechol O-methyltransferase inhibitor. In one particular implementation, the compound, or variations and permutations thereof, is further described in WO2014164667 the contents of which are hereby incorporated by reference for all purposes and the specific purposes identified herein. In some embodiments, such compounds are represented by any one or more of the structures shown in Table 53. Any one of the compounds depicted in Table 53 is suitable for use in the methods of the present disclosure.

TABLE 45

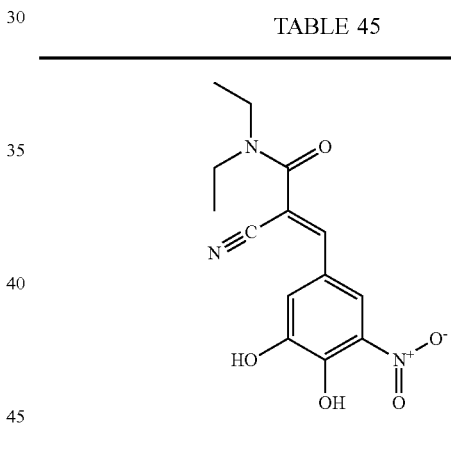

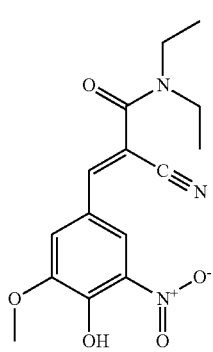

TABLE 45-continued

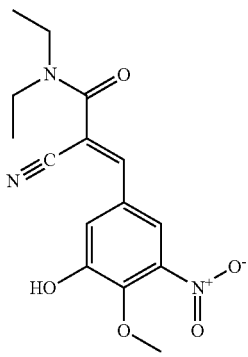 [SMILES: CCN(CC)C(=O)/C(C#N)=C/c1cc(O)c(OC)c([N+](=O)[O-])c1]

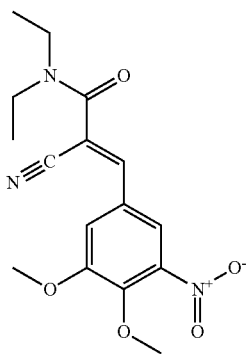 [SMILES: CCN(CC)C(=O)/C(C#N)=C/c1cc(OC)c(OC)c([N+](=O)[O-])c1]

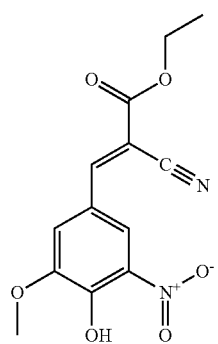 [SMILES: CCOC(=O)/C(C#N)=C/c1cc(OC)c(O)c([N+](=O)[O-])c1]

In one implementation, the compound is esprolol (ethyl (S)-3-(2-(2-hydroxy-3-(isopropylamino)propoxy)phenyl) propanoate hydrochloride), a clinically investigated beta adrenoceptor antagonist. In one particular implementation, the compound, or variations and permutations thereof, is further described in WO2007117560 the contents of which are hereby incorporated by reference for all purposes and the specific purposes identified herein. In some embodiments, such compounds are represented by any one or more of the structures shown in Table 54. Any one of the compounds depicted in Table 54 is suitable for use in the methods of the present disclosure.

TABLE 46

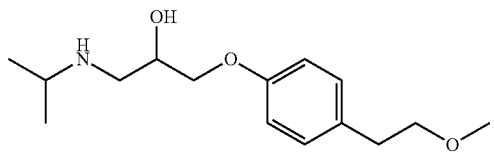 [SMILES: COCCc1ccc(OCC(O)CNC(C)C)cc1]

TABLE 46-continued

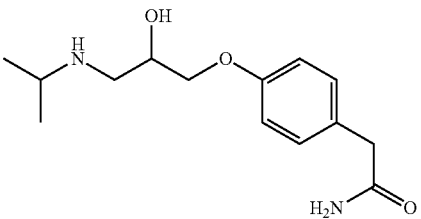 [SMILES: CC(C)NCC(O)COc1ccc(CC(N)=O)cc1]

In one implementation, the compound is faldaprevir (1R, 2S)-1-((2S,4R)-4-((8-bromo-2-(2-isobutyramidothiazol-4-yl)-7-methoxyquinolin-4-yl)oxy)-1-((S)-2-(((cyclopentyloxy)carbonyl)amino)-3,3-dimethylbutanoyl)pyrrolidine-2-carboxamido)-2-vinylcyclopropane-1-carboxylic acid), a clinically investigated hepatitis C virus NS3 protease inhibitor. In one particular implementation, the compound, or variations and permutations thereof, is further described in US20080267917; WO2003064416; WO2003064456; WO2004037855; WO2004101605; WO2004103996; WO2005028501; WO2009005676; WO2009053828; WO2009076173; WO2012040242; and WO2012040242 the contents of which are hereby incorporated by reference for all purposes and the specific purposes identified herein In one implementation, the compound is felbinac (2-([1, 1'-biphenyl]-4-yl)acetic acid) or felbinac trometamol, a clinically investigated cyclooxygenase inhibitor. In one particular implementation, the compound, or variations and permutations thereof, is further described in WO1998019997 the contents of which are hereby incorporated by reference for all purposes and the specific purposes identified herein. In some embodiments, such compounds are represented by any one or more of the structures shown in Table 56. Any one of the compounds depicted in Table 56 is suitable for use in the methods of the present disclosure.

TABLE 47

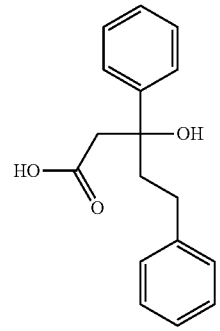 [SMILES: O=C(O)CC(O)(CCc1ccccc1)c1ccccc1]

In one implementation, the compound is fosamprenavir or calcium; [(2R,3S)-1-[(4-aminophenyl)sulfonyl-(2-methylpropyl)amino]-3-[(3S)-oxolan-3-yl]oxycarbonylamino]-4-phenylbutan-2-yl] phosphate, a clinically investigated HIV protease inhibitor. In one particular implementation, the compound, or variations and permutations thereof, is further described in WO1994005639; WO1999033815; WO2000047551; WO2001000635; WO2008013834; WO2008118849; and WO2016069955 the contents of which are hereby incorporated by reference for all purposes and the specific purposes identified herein. In some embodiments, such compounds are represented by any one or more of the structures shown in Table 57. Any one of the compounds depicted in Table 57 is suitable for use in the methods of the present disclosure.
TABLE 48
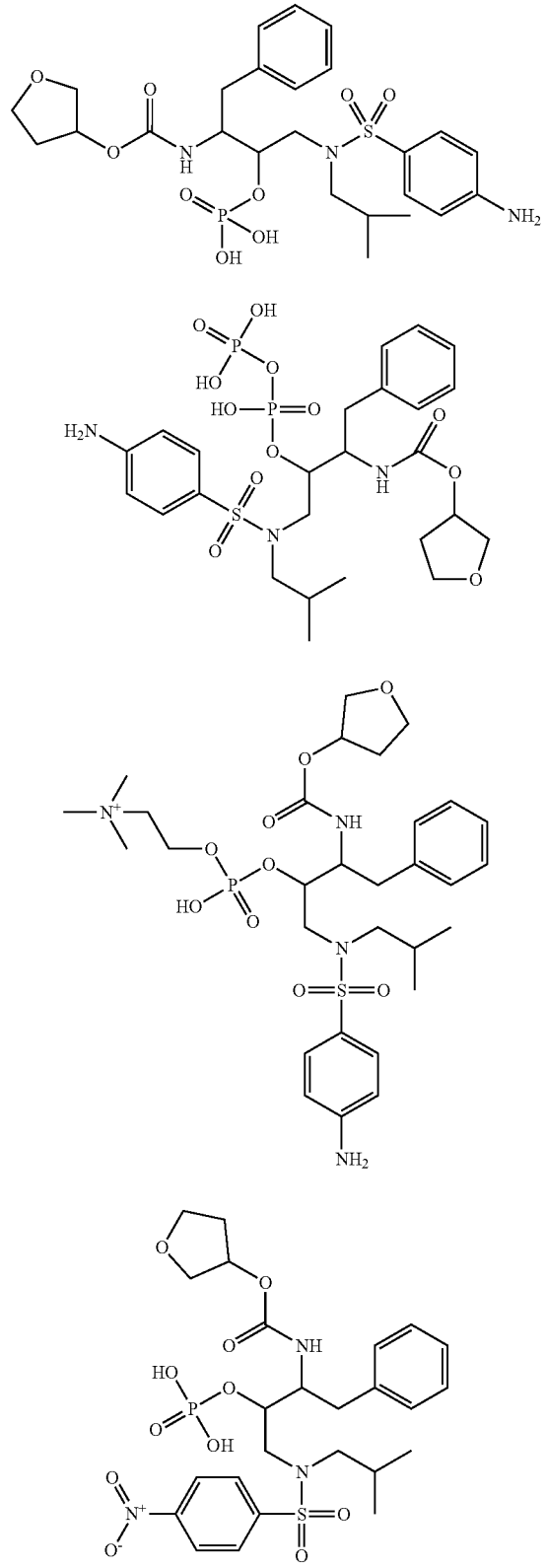
TABLE 48-continued
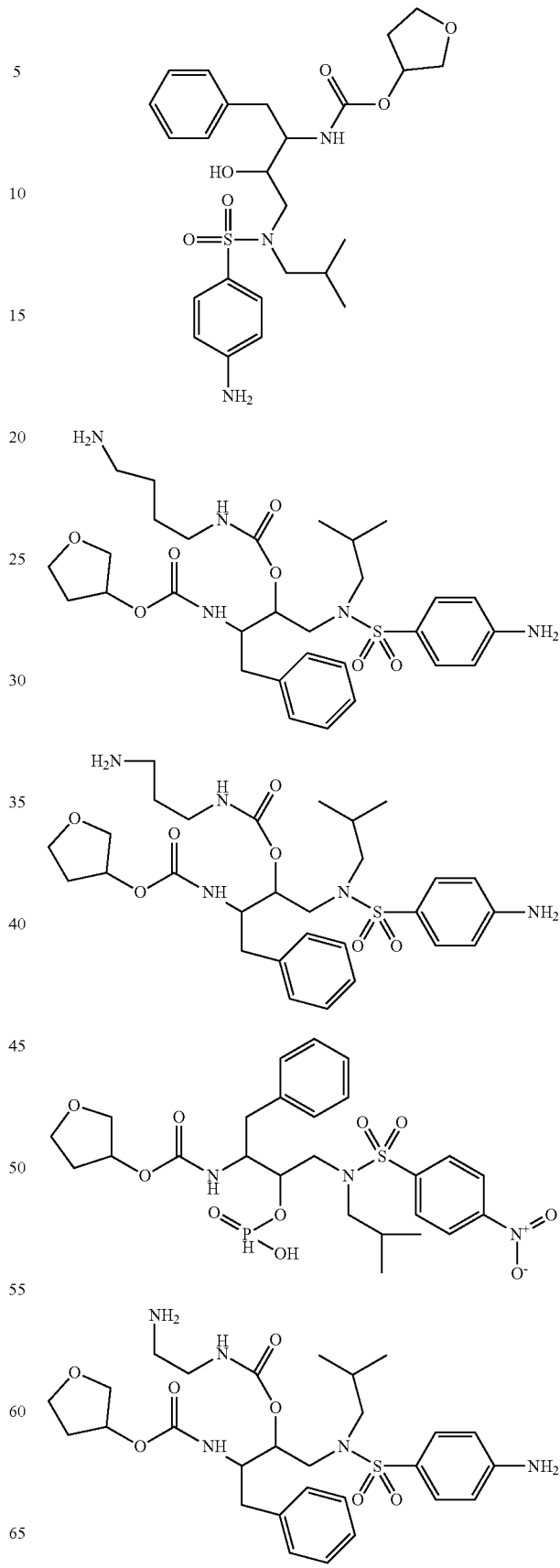

TABLE 48-continued
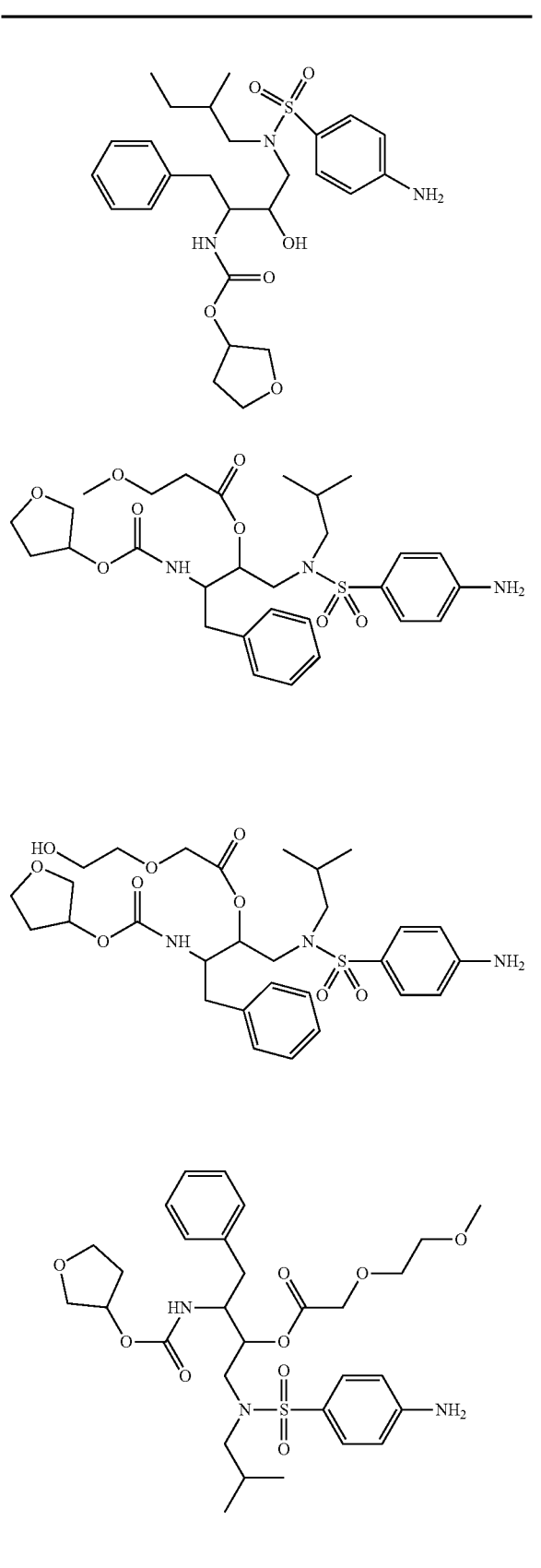
TABLE 48-continued
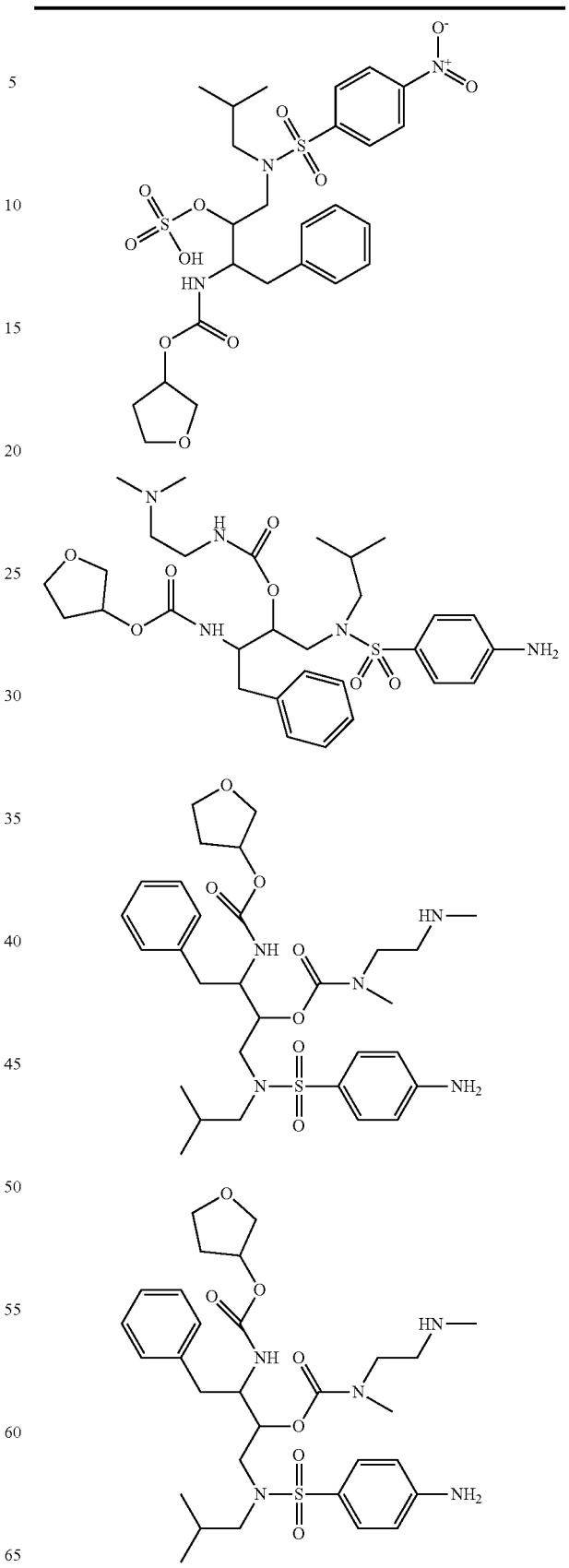

TABLE 48-continued
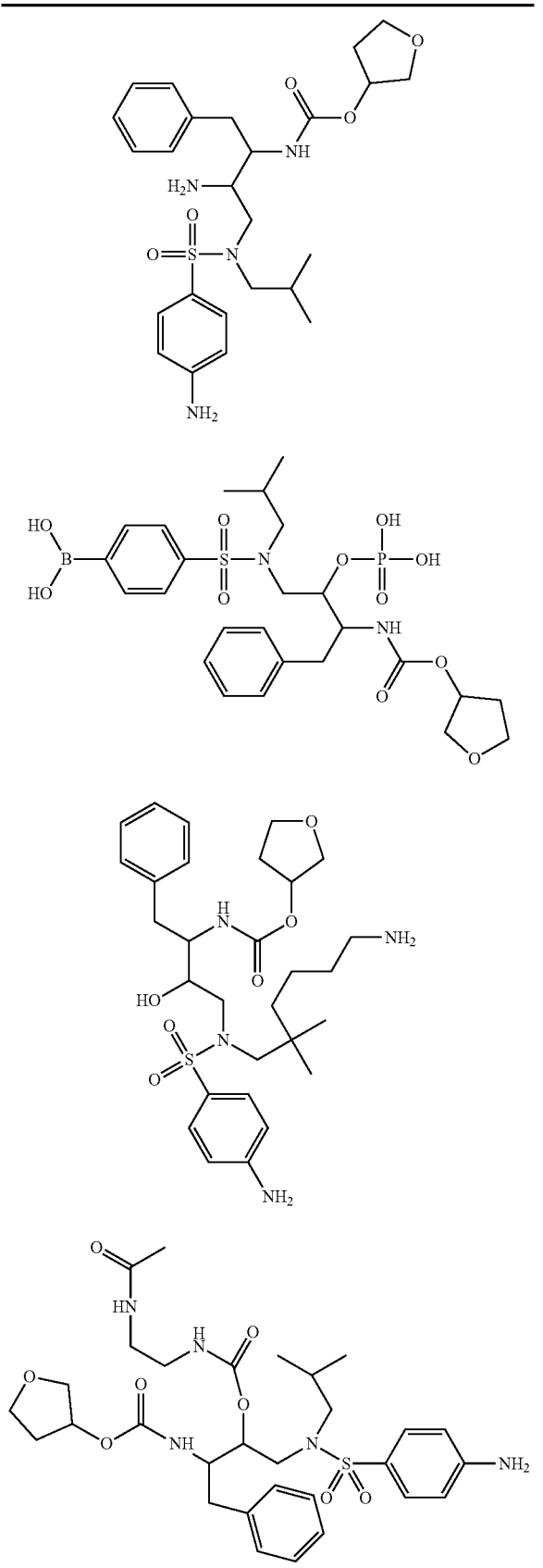
TABLE 48-continued
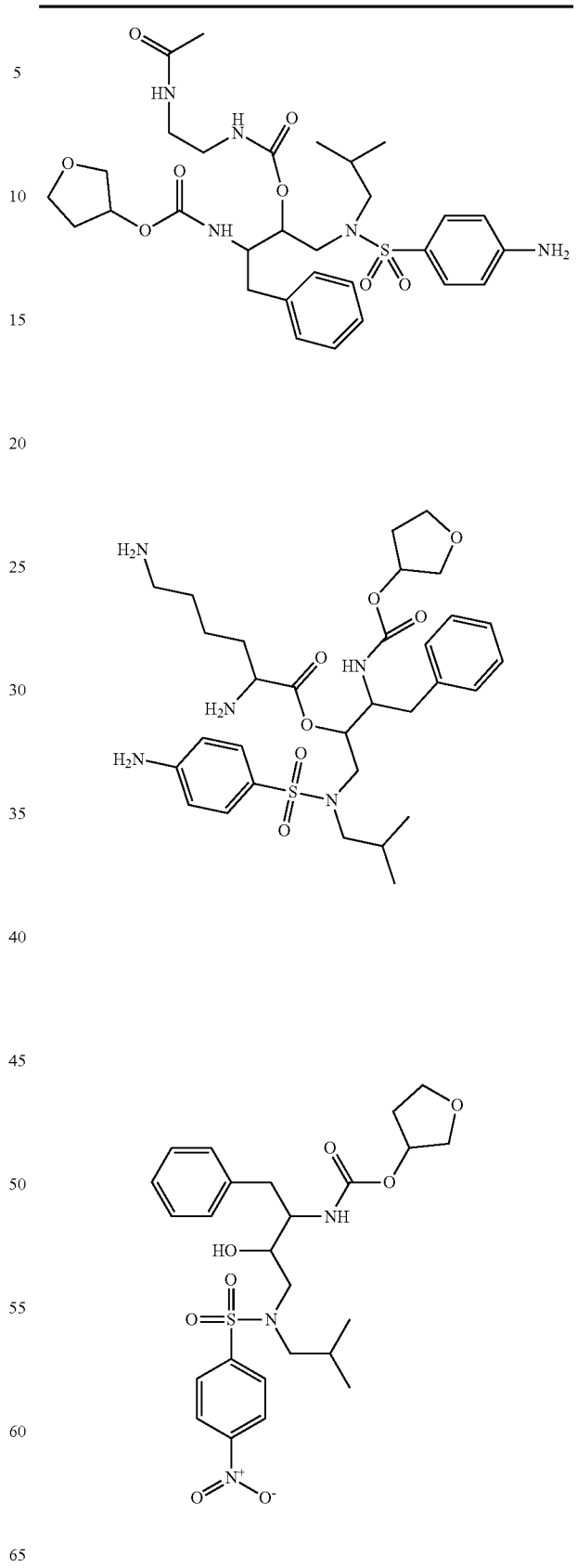

TABLE 48-continued
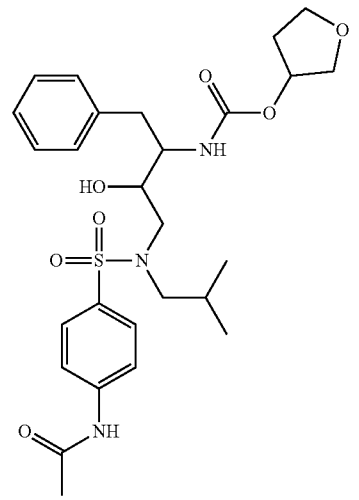 [SMILES: CC(=O)Nc1ccc(S(=O)(=O)N(CC(C)C)CC(O)C(Cc2ccccc2)NC(=O)OC2CCOC2)cc1]
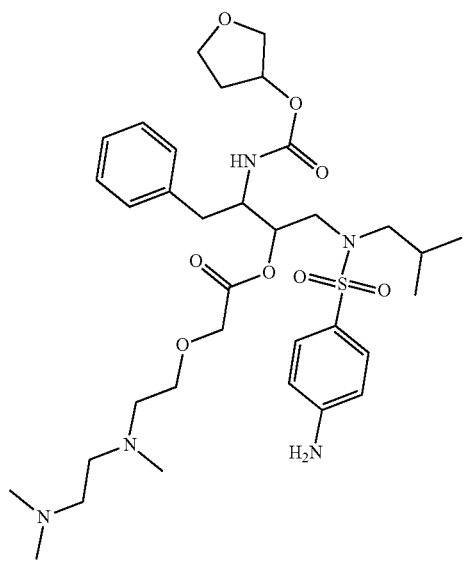 [SMILES: CC(C)CN(CC(OC(=O)COCCN(C)CCN(C)C)C(Cc1ccccc1)NC(=O)OC1CCOC1)S(=O)(=O)c1ccc(N)cc1]
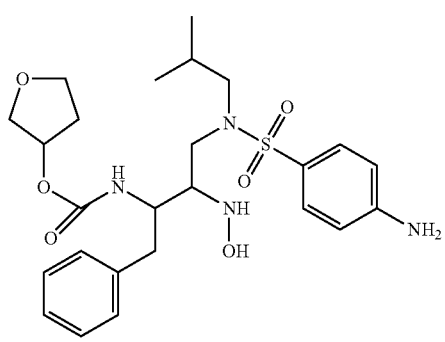 [SMILES: CC(C)CN(CC(NO)C(Cc1ccccc1)NC(=O)OC1CCOC1)S(=O)(=O)c1ccc(N)cc1]
TABLE 48-continued
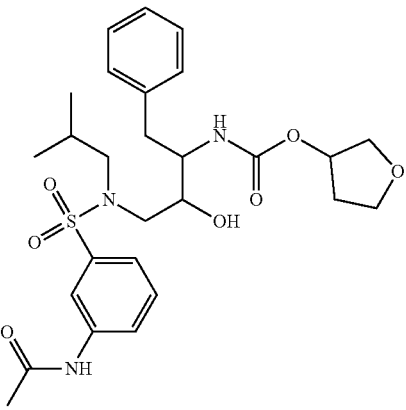 [SMILES: CC(=O)Nc1cccc(S(=O)(=O)N(CC(C)C)CC(O)C(Cc2ccccc2)NC(=O)OC2CCOC2)c1]
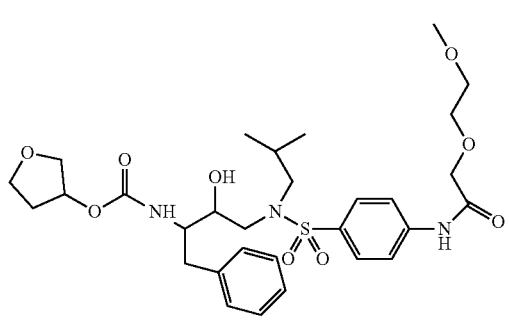
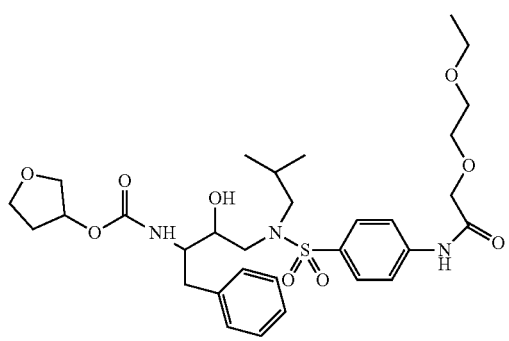
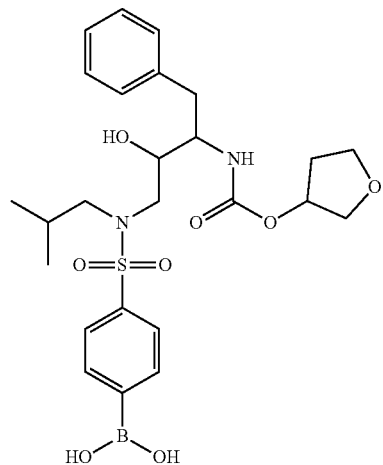 [SMILES: CC(C)CN(CC(O)C(Cc1ccccc1)NC(=O)OC1CCOC1)S(=O)(=O)c1ccc(B(O)O)cc1]

TABLE 48-continued

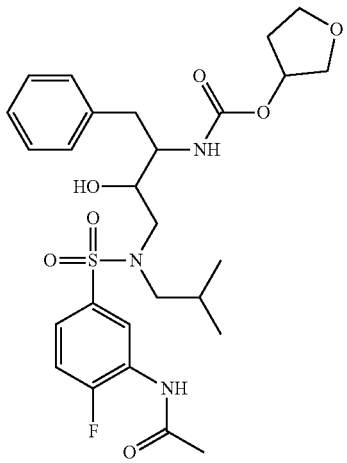 [SMILES: CC(=O)Nc1cc(S(=O)(=O)N(CC(C)C)CC(O)C(Cc2ccccc2)NC(=O)OC2CCOC2)ccc1F]

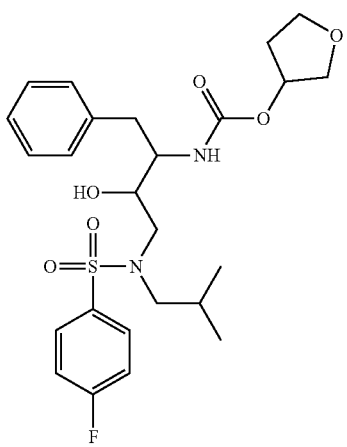 [SMILES: CC(C)CN(CC(O)C(Cc1ccccc1)NC(=O)OC1CCOC1)S(=O)(=O)c1ccc(F)cc1]

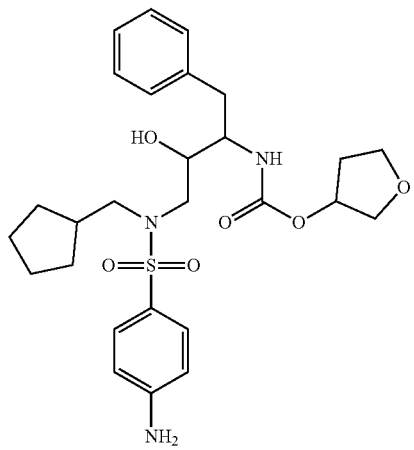 [SMILES: Nc1ccc(S(=O)(=O)N(CC2CCCC2)CC(O)C(Cc2ccccc2)NC(=O)OC2CCOC2)cc1]

In one implementation, the compound is frovatriptan (1H-Carbazole-6-carboxamide, 2,3,4,9-tetrahydro-3-(methylamino)-, (3R)-), a clinically investigated 5-HT 1b receptor agonist and 5-HT 1d receptor agonist. In one particular implementation, the compound, or variations and permutations thereof, is further described in WO2005037791 the contents of which are hereby incorporated by reference for all purposes and the specific purposes identified herein. In some embodiments, such compounds are represented by any one or more of the structures shown in Table 58. Any one of the compounds depicted in Table 58 is suitable for use in the methods of the present disclosure.

TABLE 49

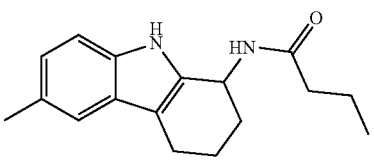 [SMILES: CCCC(=O)NC1CCCc2c1[nH]c1ccc(C)cc21]

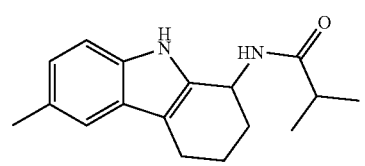 [SMILES: Cc1ccc2[nH]c3c(c2c1)CCCC3NC(=O)C(C)C]

In one implementation, the compound is furaprevir (cyclopentyl N-[(1S,4R,6S,7Z,14S,18R)-4-[(1-methylcyclopropyl)sulfonylcarbamoyl]-2,15-dioxo-18-[2-(4-propan-2-yloxyphenyl)-[1]benzofuro[3,2-d]pyrimidin-4-yl]oxy]-3,16-diazatricyclo[14.3.0.04,6]nonadec-7-en-14-yl] carbamate), a clinically investigated hepatitis C virus NS3 protease inhibitor. In one particular implementation, the compound, or variations and permutations thereof, is further described in WO2009139792; WO2011034518; and WO2016127859 the contents of which are hereby incorporated by reference for all purposes and the specific purposes identified herein. In some embodiments, such compounds are represented by any one or more of the structures shown in Table 59. Any one of the compounds depicted in Table 59 is suitable for use in the methods of the present disclosure.

TABLE 50

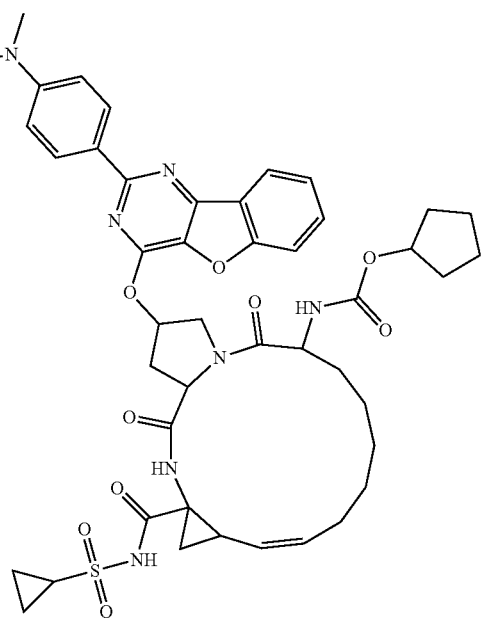

383
TABLE 50-continued
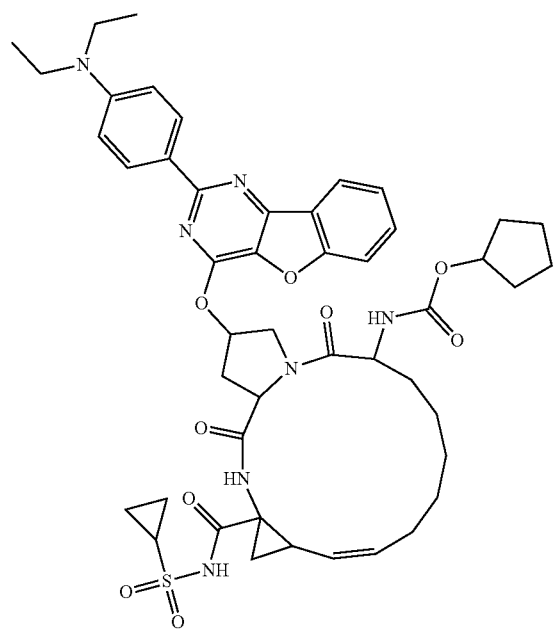 [SMILES: CCN(CC)c1ccc(-c2nc(OC3CC4C(=O)NC5(C(=O)NS(=O)(=O)C6CC6)CC5/C=C\CCCCCC(NC(=O)OC5CCCC5)C(=O)N4C3)c3oc4ccccc4c3n2)cc1]
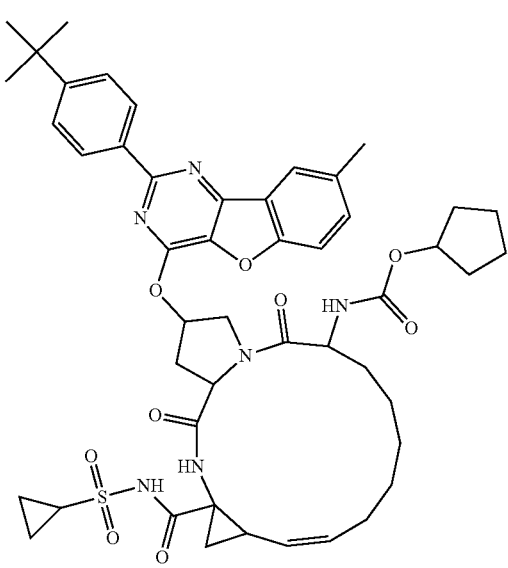 [SMILES: Cc1ccc2oc3c(OC4CC5C(=O)NC6(C(=O)NS(=O)(=O)C7CC7)CC6/C=C\CCCCCC(NC(=O)OC6CCCC6)C(=O)N5C4)nc(-c4ccc(C(C)(C)C)cc4)nc3c2c1]
384
TABLE 50-continued
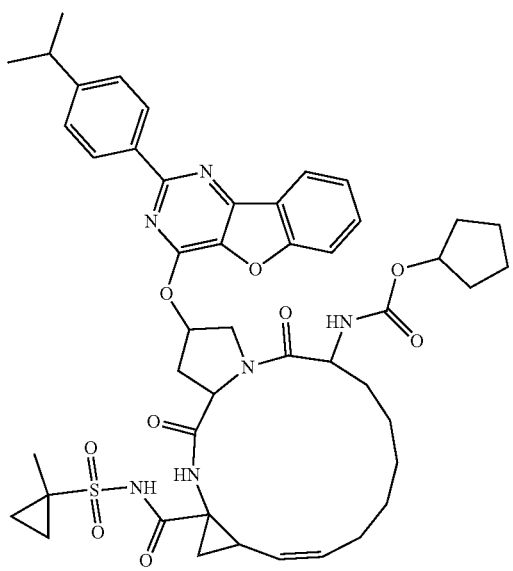 [SMILES: CC(C)c1ccc(-c2nc(OC3CC4C(=O)NC5(C(=O)NS(=O)(=O)C6(C)CC6)CC5/C=C\CCCCCC(NC(=O)OC5CCCC5)C(=O)N4C3)c3oc4ccccc4c3n2)cc1]

385
TABLE 50-continued
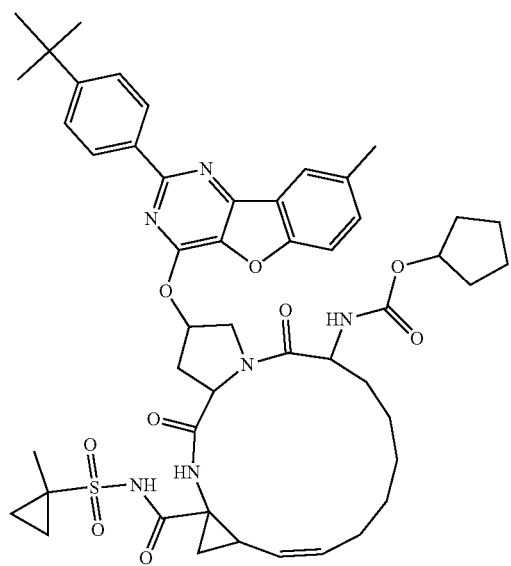 [SMILES: Cc1ccc2oc3c(OC4CC5C(=O)NC6(C(=O)NS(=O)(=O)C7(C)CC7)CC6/C=C\CCCCCC(NC(=O)OC6CCCC6)C(=O)N5C4)nc(-c4ccc(C(C)(C)C)cc4)nc3c2c1]
386
TABLE 50-continued
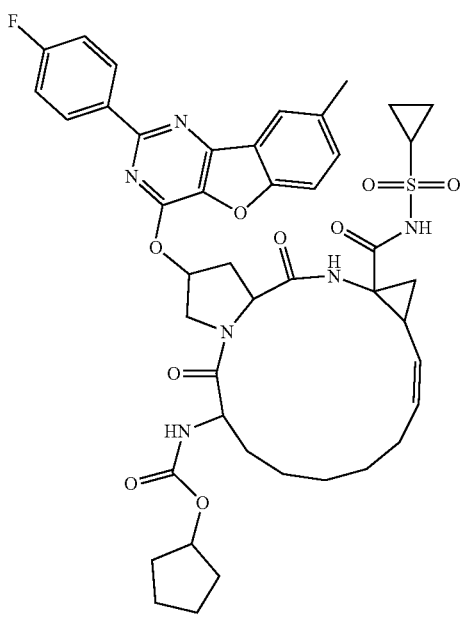
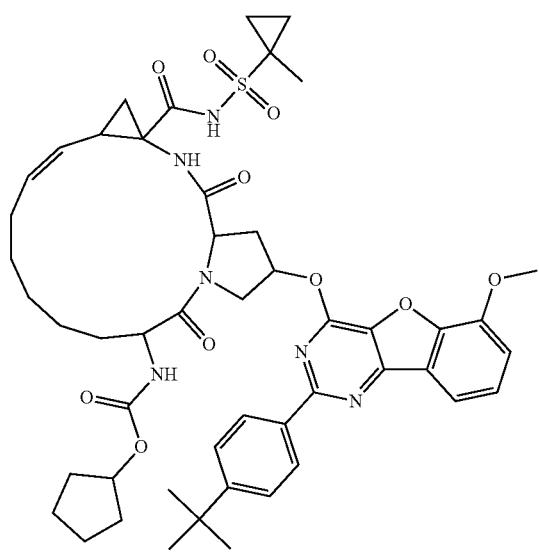 [SMILES: COc1cccc2c1oc1c(OC3CC4C(=O)NC5(C(=O)NS(=O)(=O)C6(C)CC6)CC5/C=C\CCCCCC(NC(=O)OC5CCCC5)C(=O)N4C3)nc(-c3ccc(C(C)(C)C)cc3)nc12]
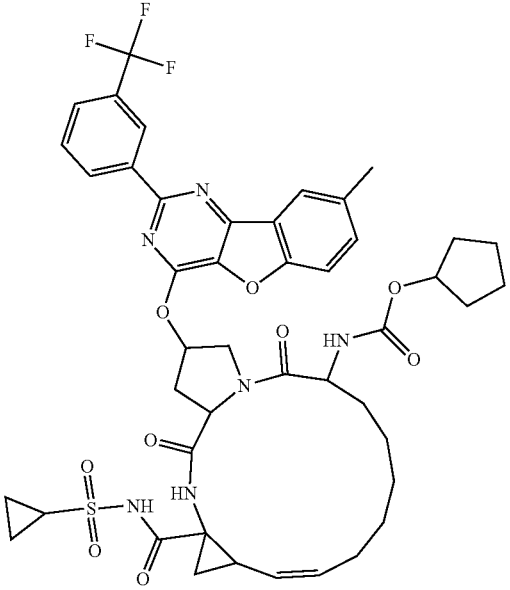 [SMILES: Cc1ccc2oc3c(OC4CC5C(=O)NC6(C(=O)NS(=O)(=O)C7CC7)CC6/C=C\CCCCCC(NC(=O)OC6CCCC6)C(=O)N5C4)nc(-c4cccc(C(F)(F)F)c4)nc3c2c1]

387
TABLE 50-continued
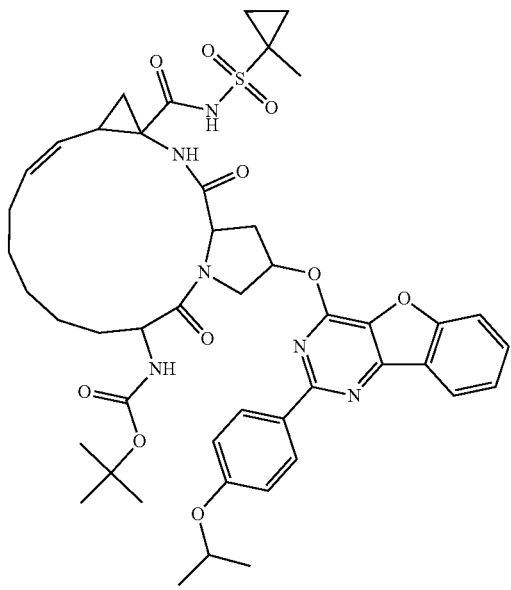 [SMILES: CC(C)Oc1ccc(-c2nc(OC3CC4C(=O)NC5(C(=O)NS(=O)(=O)C6(C)CC6)CC5/C=C\CCCCCC(NC(=O)OC(C)(C)C)C(=O)N4C3)c3oc4ccccc4c3n2)cc1]
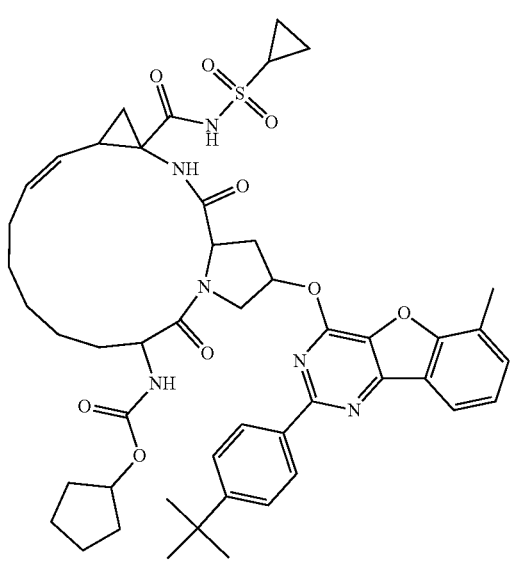 [SMILES: Cc1cccc2c1oc1c(OC3CC4C(=O)NC5(C(=O)NS(=O)(=O)C6CC6)CC5/C=C\CCCCCC(NC(=O)OC5CCCC5)C(=O)N4C3)nc(-c3ccc(C(C)(C)C)cc3)nc12]
388
TABLE 50-continued
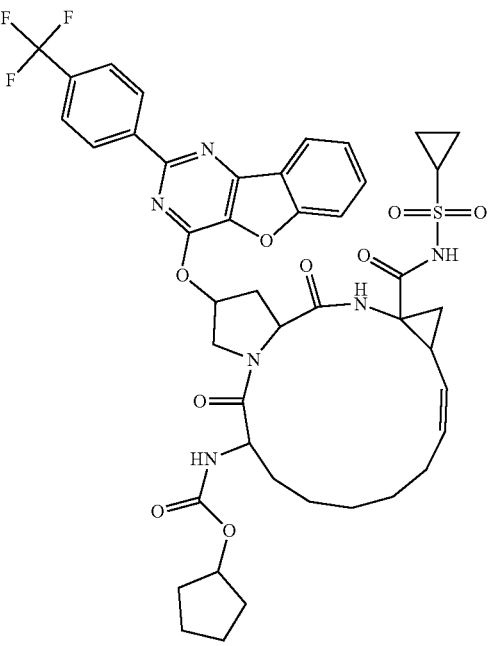 [SMILES: O=C(NC1CCCCC/C=C\C2CC2(C(=O)NS(=O)(=O)C2CC2)NC(=O)C2CC(Oc3nc(-c4ccc(C(F)(F)F)cc4)nc4c3oc3ccccc34)CN2C1=O)OC1CCCC1]
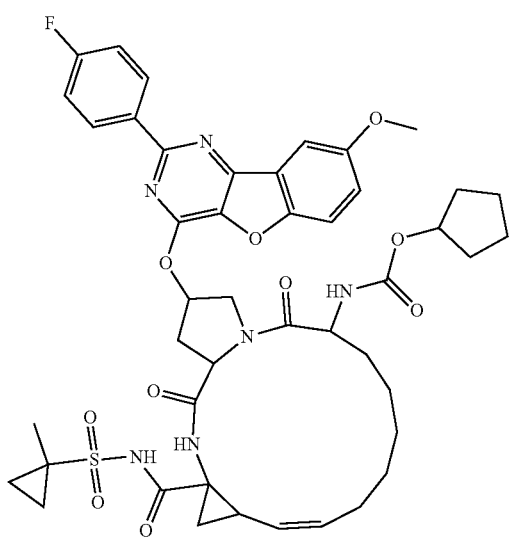 [SMILES: COc1ccc2oc3c(OC4CC5C(=O)NC6(C(=O)NS(=O)(=O)C7(C)CC7)CC6/C=C\CCCCCC(NC(=O)OC6CCCC6)C(=O)N5C4)nc(-c4ccc(F)cc4)nc3c2c1]

389
TABLE 50-continued
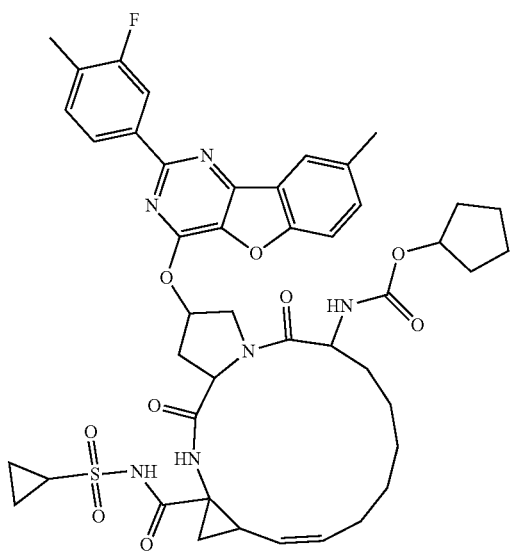 [SMILES: Cc1ccc2oc3c(OC4CC5C(=O)NC6(C(=O)NS(=O)(=O)C7CC7)CC6/C=C\CCCCCC(NC(=O)OC6CCCC6)C(=O)N5C4)nc(-c4ccc(C)c(F)c4)nc3c2c1]
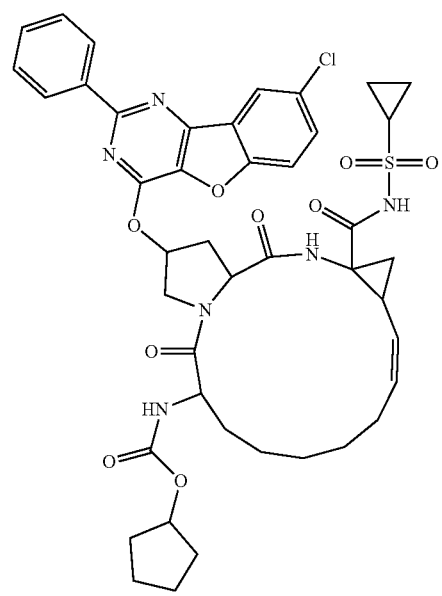 [SMILES: O=C(NC1CCCCC/C=C\C2CC2(C(=O)NS(=O)(=O)C2CC2)NC(=O)C2CC(Oc3nc(-c4ccccc4)nc4c3oc3ccc(Cl)cc34)CN2C1=O)OC1CCCC1]
390
TABLE 50-continued
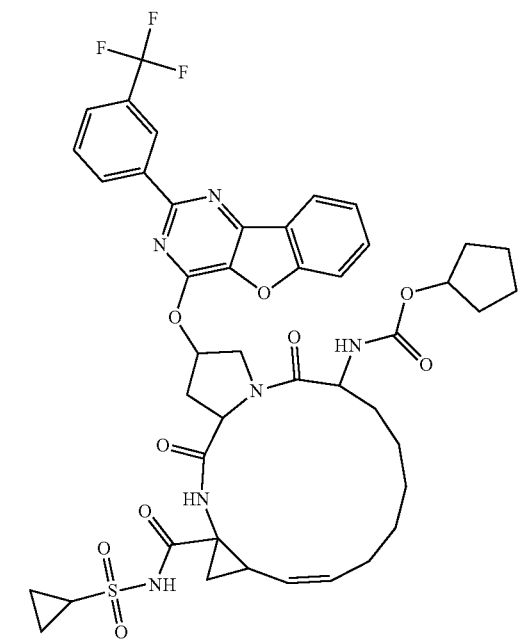 [SMILES: O=C(NC1CCCCC/C=C\C2CC2(C(=O)NS(=O)(=O)C2CC2)NC(=O)C2CC(Oc3nc(-c4cccc(C(F)(F)F)c4)nc4c3oc3ccccc34)CN2C1=O)OC1CCCC1]

TABLE 50-continued
391
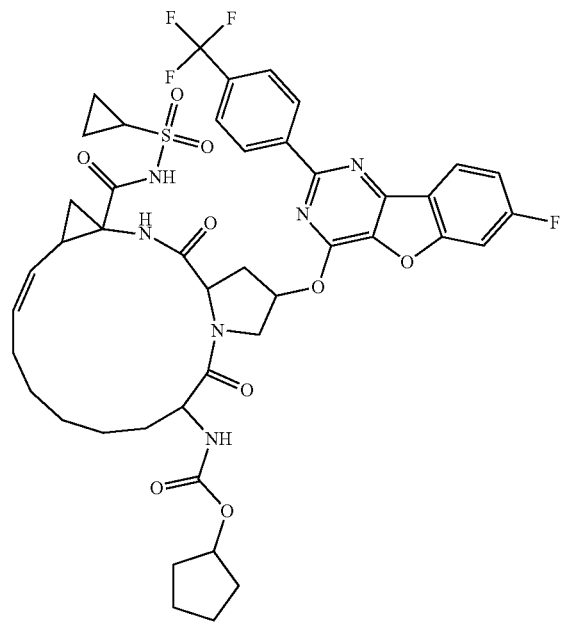 [SMILES: O=C(NC1CCCCC/C=C\C2CC2(C(=O)NS(=O)(=O)C2CC2)NC(=O)C2CC(Oc3nc(-c4ccc(C(F)(F)F)cc4)nc4c3oc3cc(F)ccc34)CN2C1=O)OC1CCCC1]
392
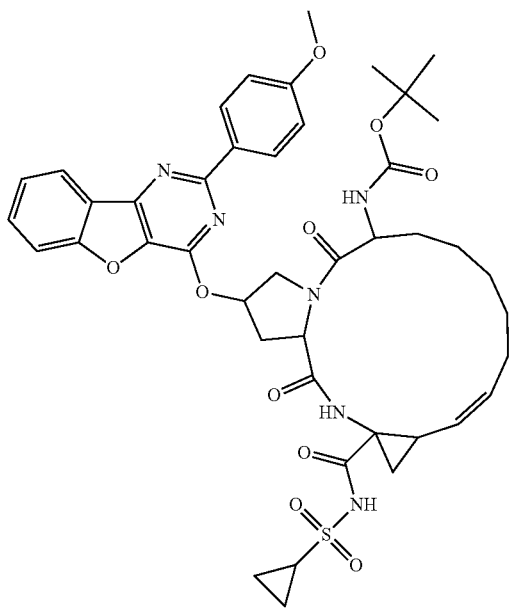 [SMILES: COc1ccc(-c2nc(OC3CC4C(=O)NC5(C(=O)NS(=O)(=O)C6CC6)CC5/C=C\CCCCCC(NC(=O)OC(C)(C)C)C(=O)N4C3)c3oc4ccccc4c3n2)cc1]
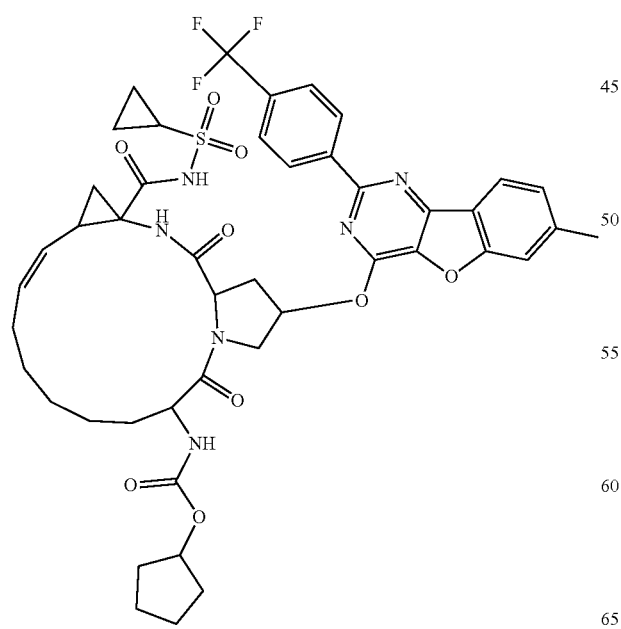
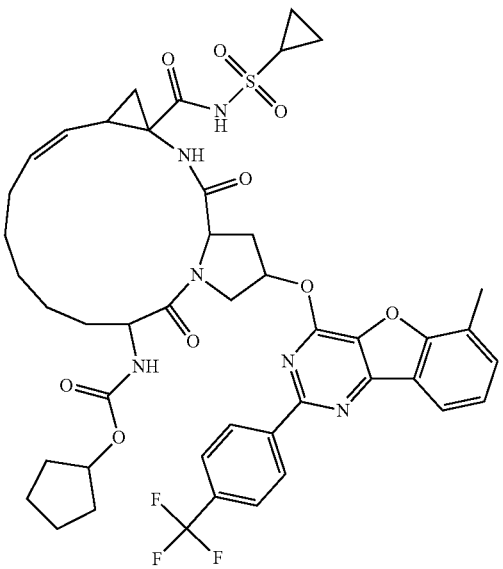 [SMILES: Cc1cccc2c1oc1c(OC3CC4C(=O)NC5(C(=O)NS(=O)(=O)C6CC6)CC5/C=C\CCCCCC(NC(=O)OC5CCCC5)C(=O)N4C3)nc(-c3ccc(C(F)(F)F)cc3)nc12]

TABLE 50-continued
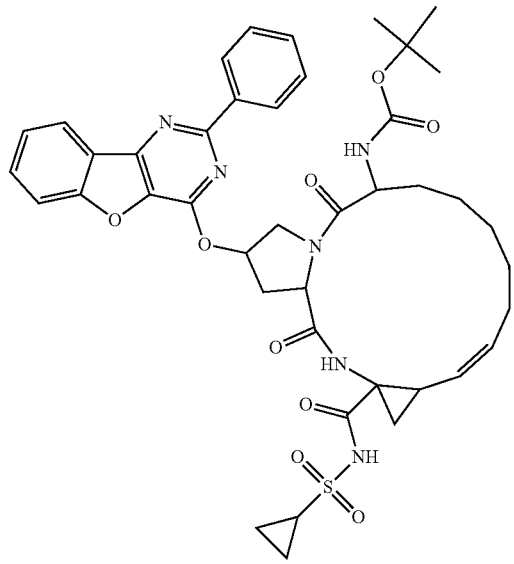 [SMILES: CC(C)(C)OC(=O)NC1CCCCC/C=C\C2CC2(C(=O)NS(=O)(=O)C2CC2)NC(=O)C2CC(Oc3nc(-c4ccccc4)nc4c3oc3ccccc34)CN2C1=O]
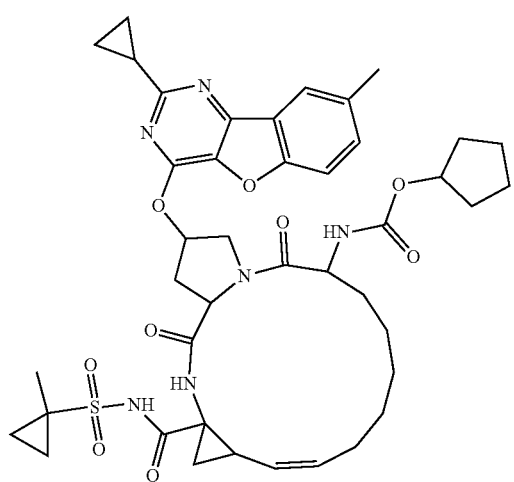 [SMILES: Cc1ccc2oc3c(OC4CC5C(=O)NC6(C(=O)NS(=O)(=O)C7(C)CC7)CC6/C=C\CCCCCC(NC(=O)OC6CCCC6)C(=O)N5C4)nc(C4CC4)nc3c2c1]
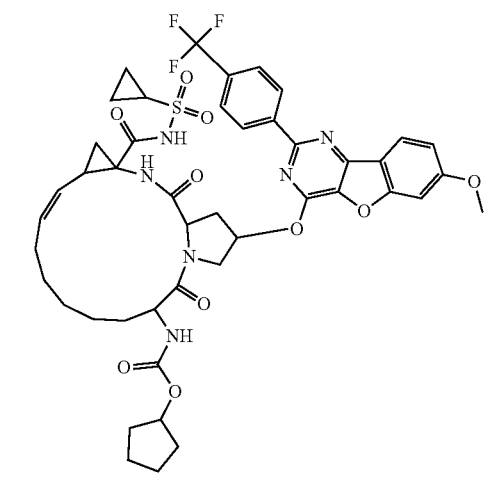 [SMILES: COc1ccc2c(c1)oc1c(OC3CC4C(=O)NC5(C(=O)NS(=O)(=O)C6CC6)CC5/C=C\CCCCCC(NC(=O)OC5CCCC5)C(=O)N4C3)nc(-c3ccc(C(F)(F)F)cc3)nc12]
TABLE 50-continued
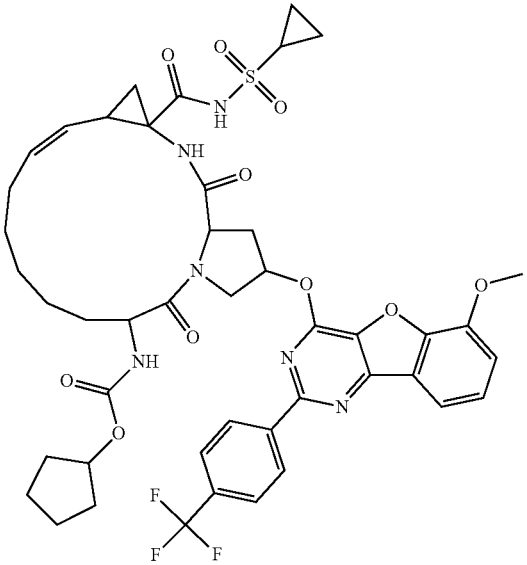 [SMILES: COc1cccc2c1oc1c(OC3CC4C(=O)NC5(C(=O)NS(=O)(=O)C6CC6)CC5/C=C\CCCCCC(NC(=O)OC5CCCC5)C(=O)N4C3)nc(-c3ccc(C(F)(F)F)cc3)nc12]
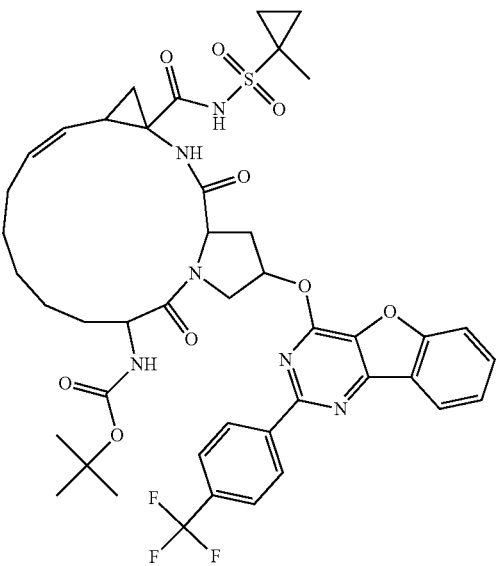 [SMILES: CC(C)(C)OC(=O)NC1CCCCC/C=C\C2CC2(C(=O)NS(=O)(=O)C2(C)CC2)NC(=O)C2CC(Oc3nc(-c4ccc(C(F)(F)F)cc4)nc4c3oc3ccccc34)CN2C1=O]

TABLE 50-continued
395
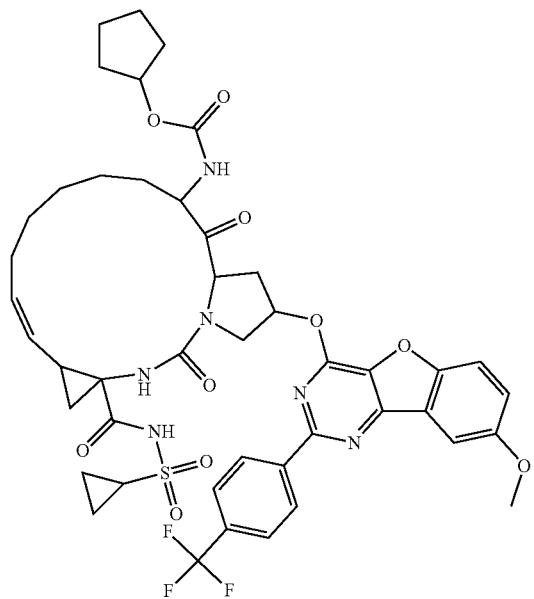 [SMILES: COc1ccc2oc3c(OC4CC5C(=O)C(NC(=O)OC6CCCC6)CCCCC/C=C\C6CC6(C(=O)NS(=O)(=O)C6CC6)NC(=O)N5C4)nc(-c4ccc(C(F)(F)F)cc4)nc3c2c1]
396
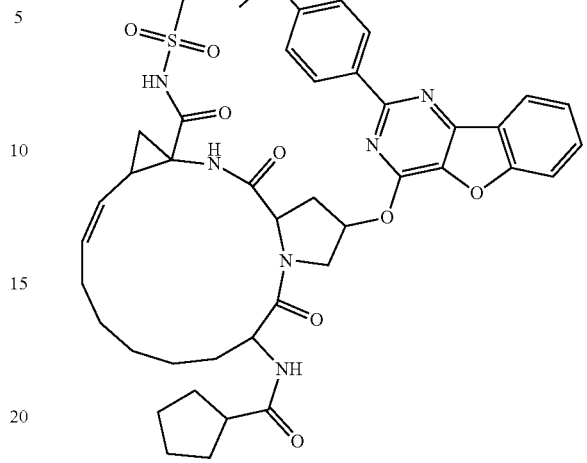
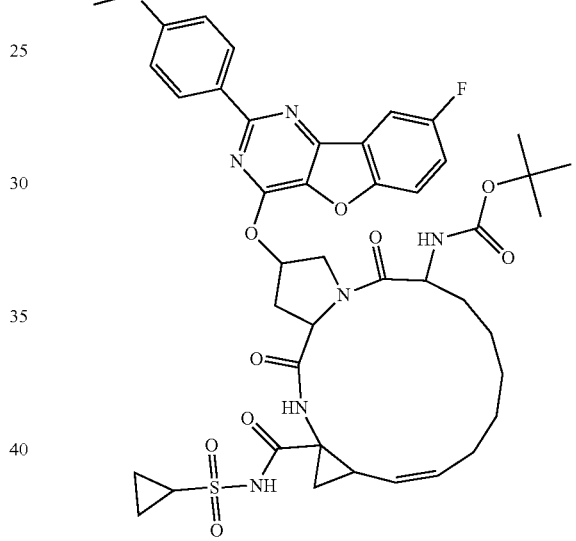
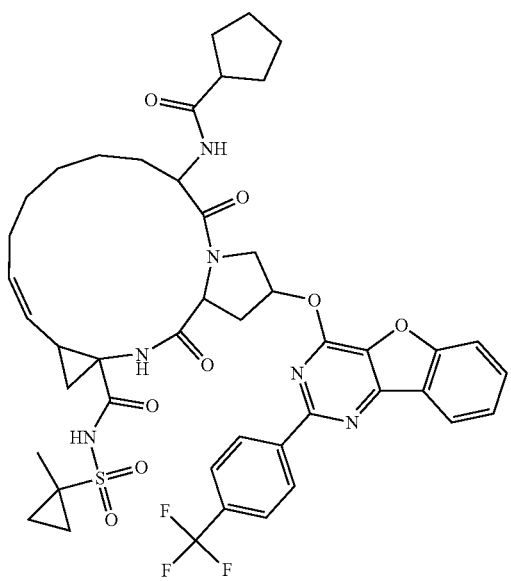 [SMILES: CC1(S(=O)(=O)NC(=O)C23CC2/C=C\CCCCCC(NC(=O)C2CCCC2)C(=O)N2CC(Oc4nc(-c5ccc(C(F)(F)F)cc5)nc5c4oc4ccccc45)CC2C(=O)N3)CC1]
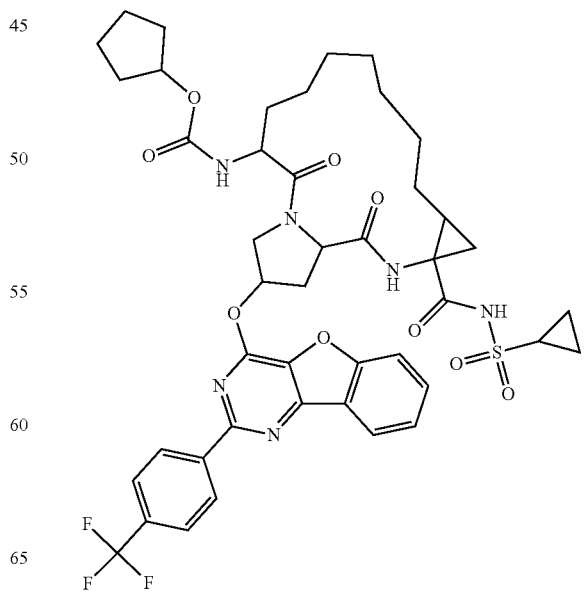

397
TABLE 50-continued
398
TABLE 50-continued
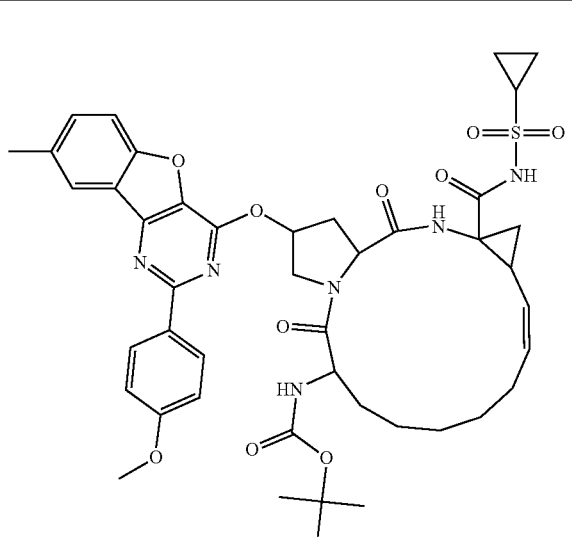
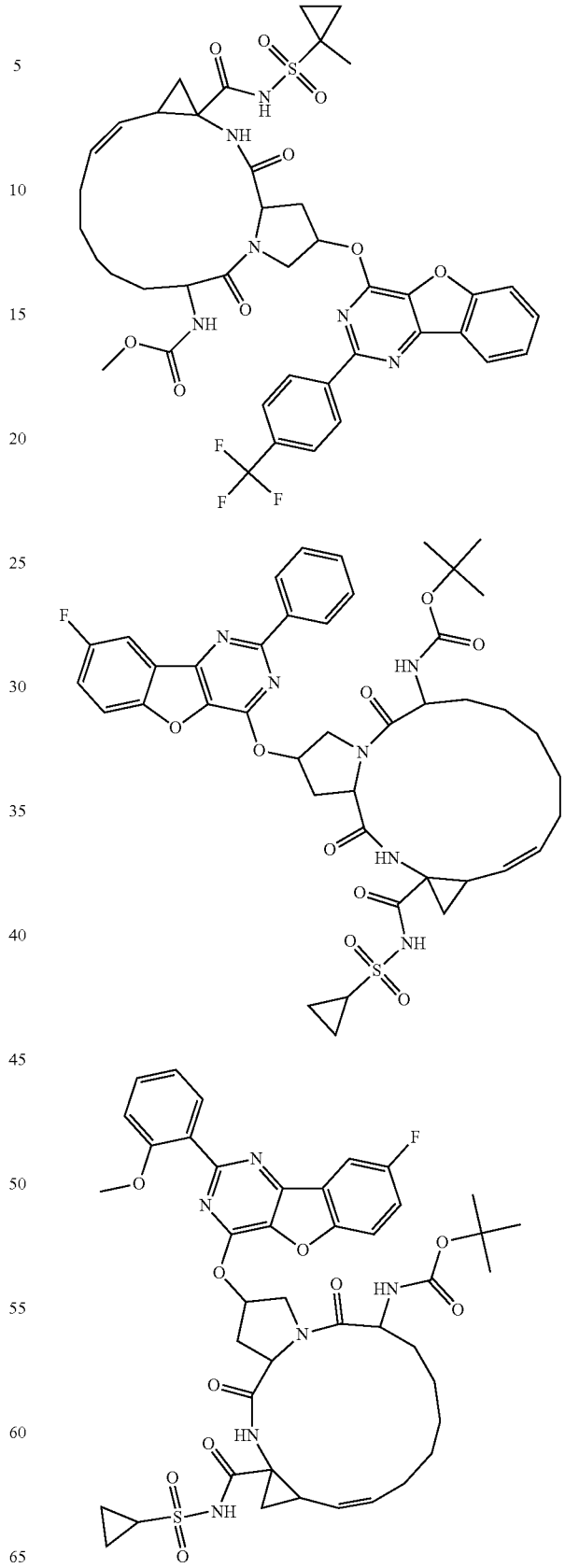

TABLE 50-continued
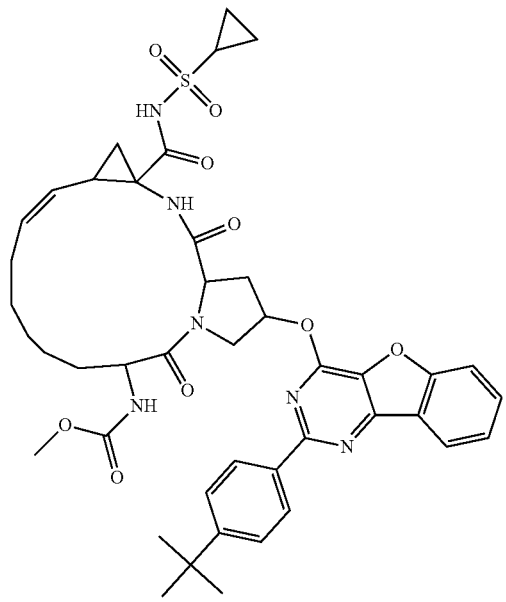 [SMILES: COC(=O)NC1CCCCC/C=C\C2CC2(C(=O)NS(=O)(=O)C2CC2)NC(=O)C2CC(Oc3nc(-c4ccc(C(C)(C)C)cc4)nc4c3oc3ccccc34)CN2C1=O]
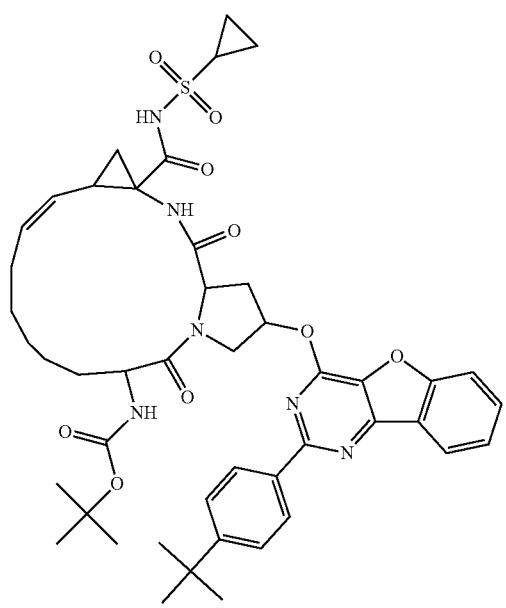 [SMILES: CC(C)(C)OC(=O)NC1CCCCC/C=C\C2CC2(C(=O)NS(=O)(=O)C2CC2)NC(=O)C2CC(Oc3nc(-c4ccc(C(C)(C)C)cc4)nc4c3oc3ccccc34)CN2C1=O]
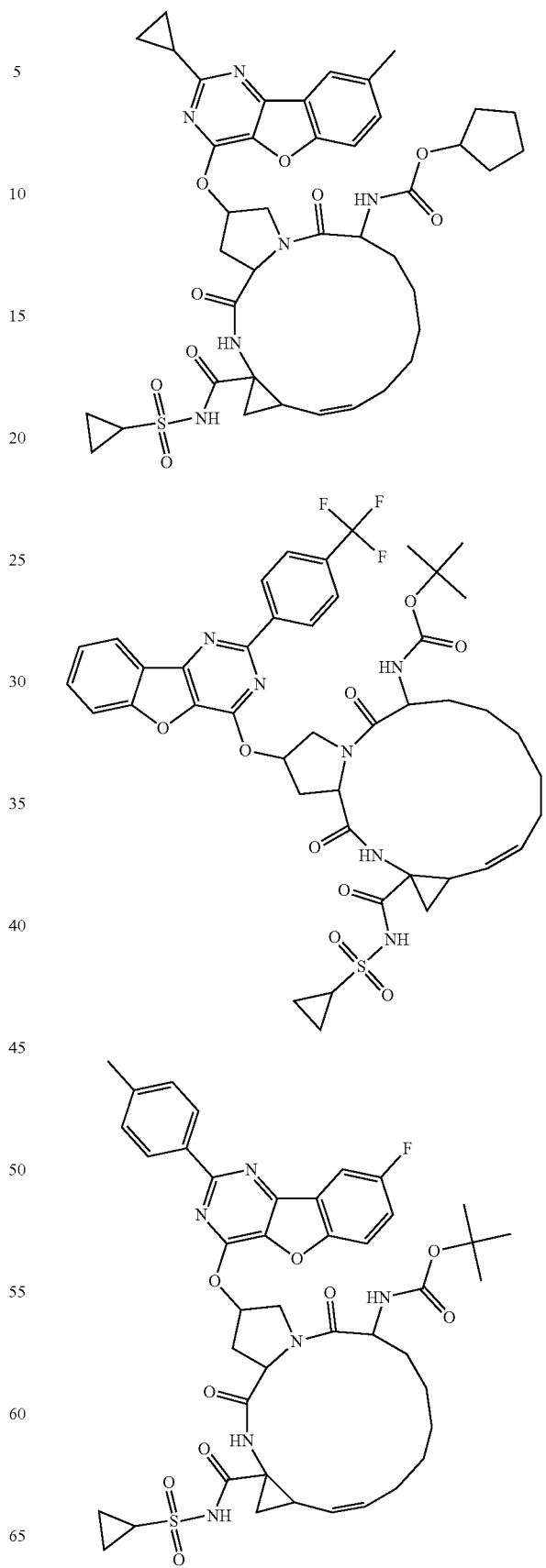

TABLE 50-continued
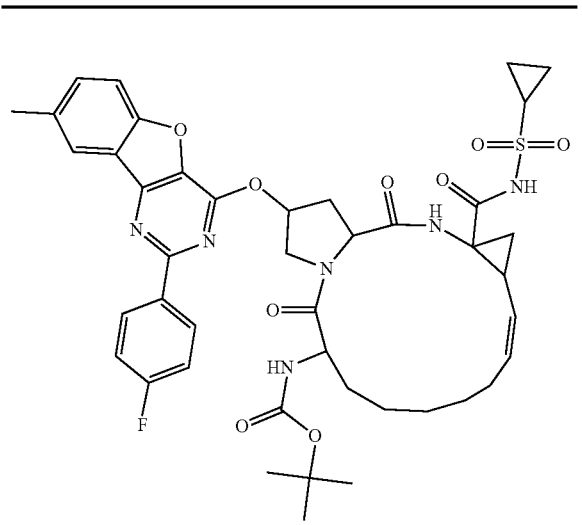
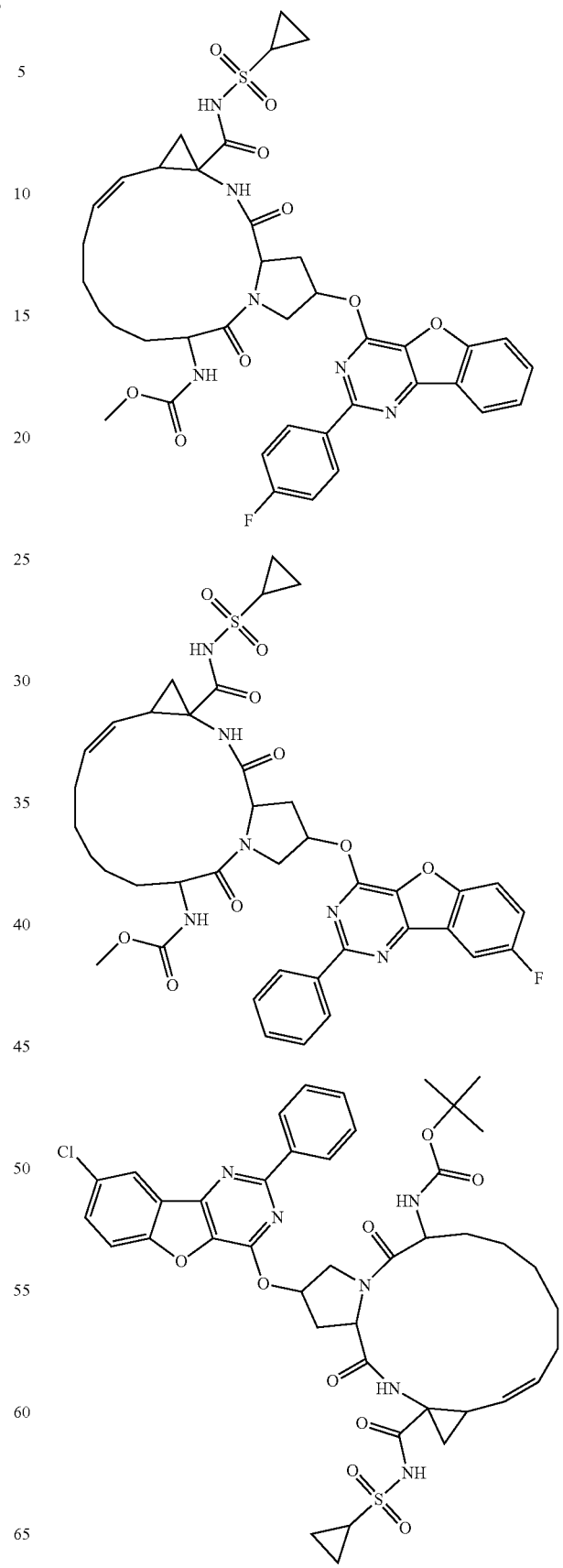

TABLE 50-continued
403
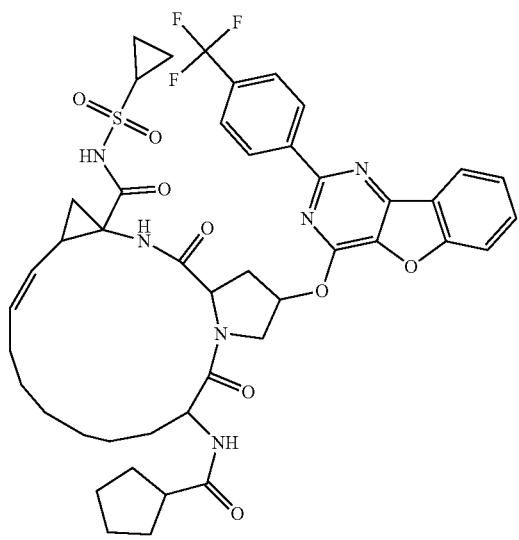 [SMILES: O=C(NC1CCCCCC/C=C\C2CC2(C(=O)NS(=O)(=O)C2CC2)NC(=O)C2CC(Oc3nc(-c4ccc(C(F)(F)F)cc4)nc4c3oc3ccccc34)CN2C1=O)C1CCCC1]
404
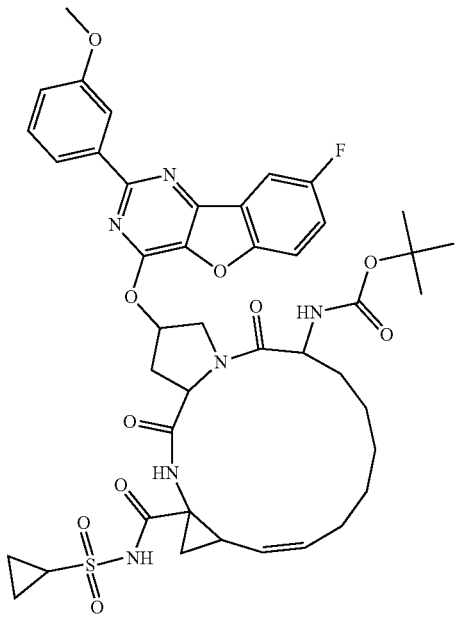
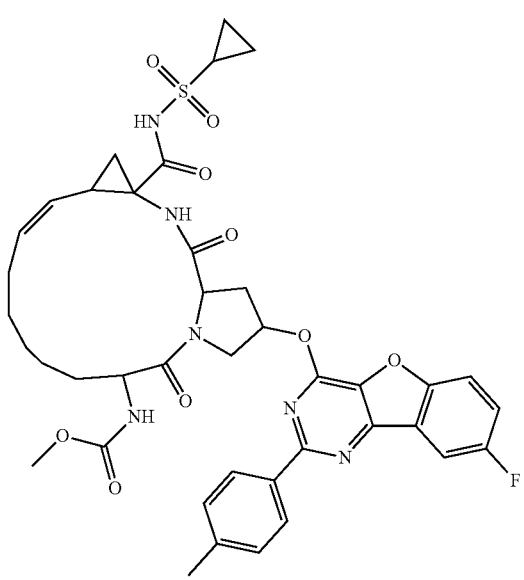 [SMILES: COC(=O)NC1CCCCC/C=C\C2CC2(C(=O)NS(=O)(=O)C2CC2)NC(=O)C2CC(Oc3nc(-c4ccc(C)cc4)nc4c3oc3ccc(F)cc34)CN2C1=O]
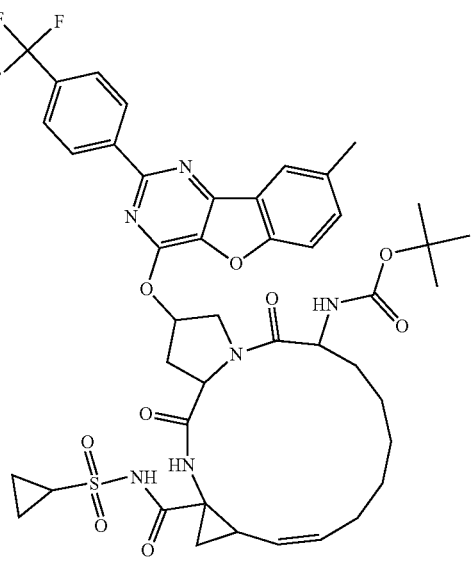

| 405 | 406 |
|---|---|
| TABLE 50-continued | TABLE 50-continued |
| 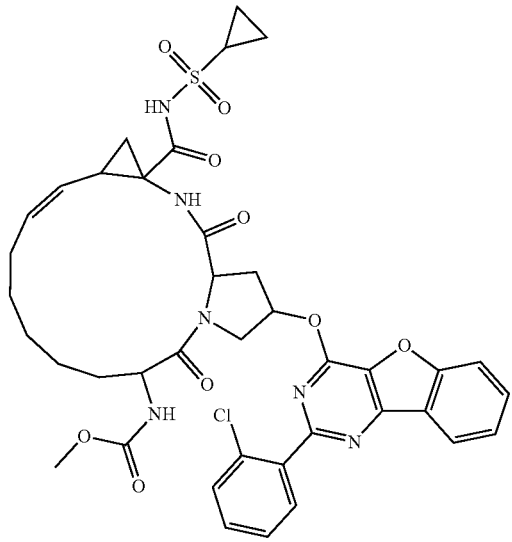 [SMILES: COC(=O)NC1CCCCC/C=C\C2CC2(C(=O)NS(=O)(=O)C2CC2)NC(=O)C2CC(Oc3nc(-c4ccccc4Cl)nc4c3oc3ccccc34)CN2C1=O] | 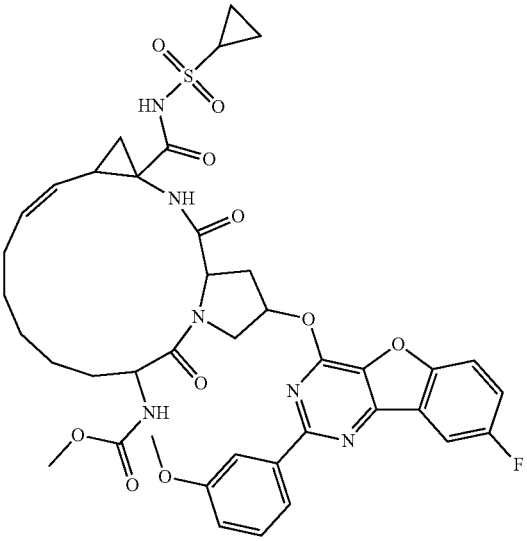 |
| 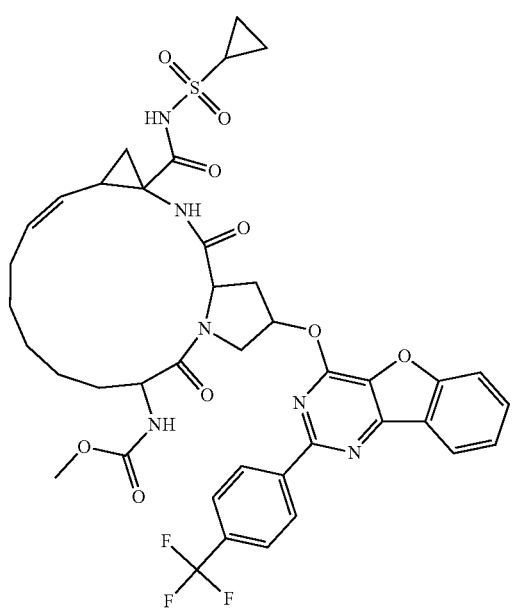 [SMILES: COC(=O)NC1CCCCC/C=C\C2CC2(C(=O)NS(=O)(=O)C2CC2)NC(=O)C2CC(Oc3nc(-c4ccc(C(F)(F)F)cc4)nc4c3oc3ccccc34)CN2C1=O] | 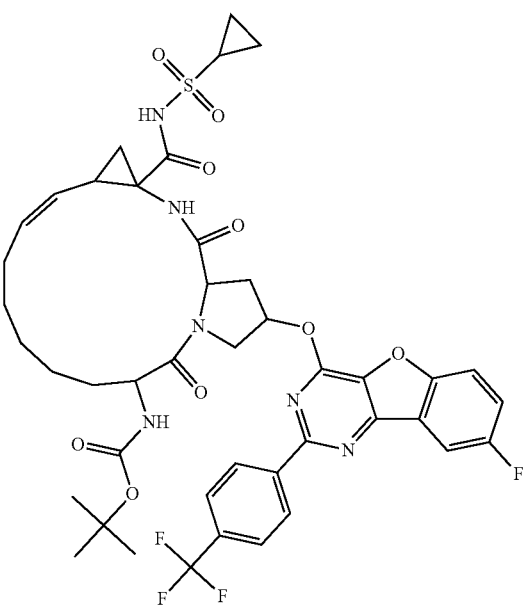 [SMILES: CC(C)(C)OC(=O)NC1CCCCC/C=C\C2CC2(C(=O)NS(=O)(=O)C2CC2)NC(=O)C2CC(Oc3nc(-c4ccc(C(F)(F)F)cc4)nc4c3oc3ccc(F)cc34)CN2C1=O] |

407
TABLE 50-continued
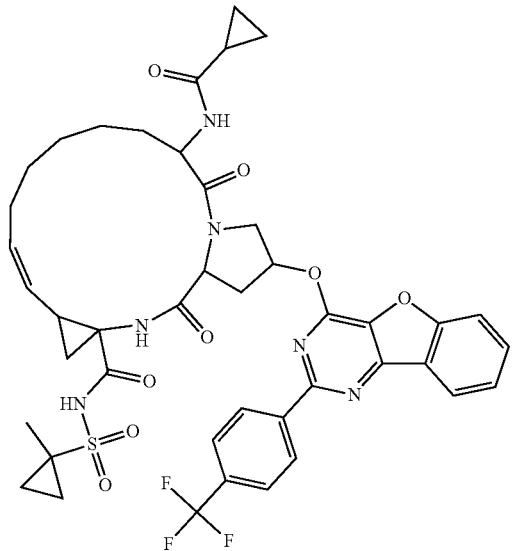 [SMILES: CC1(S(=O)(=O)NC(=O)C23CC2/C=C\CCCCCC(NC(=O)C2CC2)C(=O)N2CC(Oc4nc(-c5ccc(C(F)(F)F)cc5)nc5c4oc4ccccc45)CC2C(=O)N3)CC1]
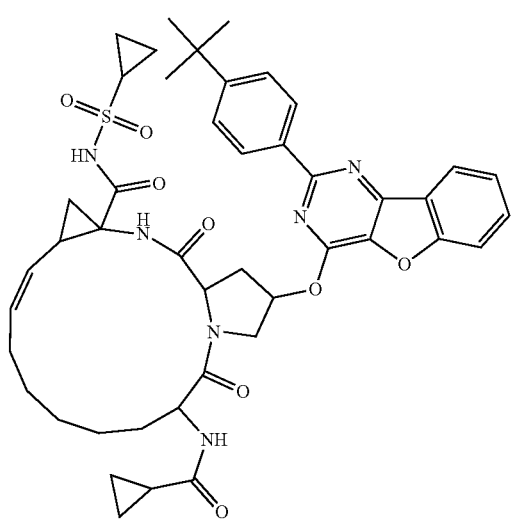 [SMILES: CC(C)(C)c1ccc(-c2nc(OC3CC4C(=O)NC5(C(=O)NS(=O)(=O)C6CC6)CC5/C=C\CCCCCC(NC(=O)C5CC5)C(=O)N4C3)c3oc4ccccc4c3n2)cc1]
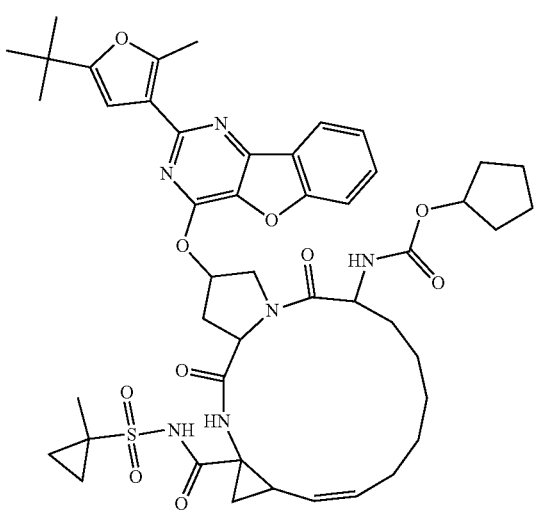 [SMILES: Cc1oc(C(C)(C)C)cc1-c1nc(OC2CC3C(=O)NC4(C(=O)NS(=O)(=O)C5(C)CC5)CC4/C=C\CCCCCC(NC(=O)OC4CCCC4)C(=O)N3C2)c2oc3ccccc3c2n1]
408
TABLE 50-continued
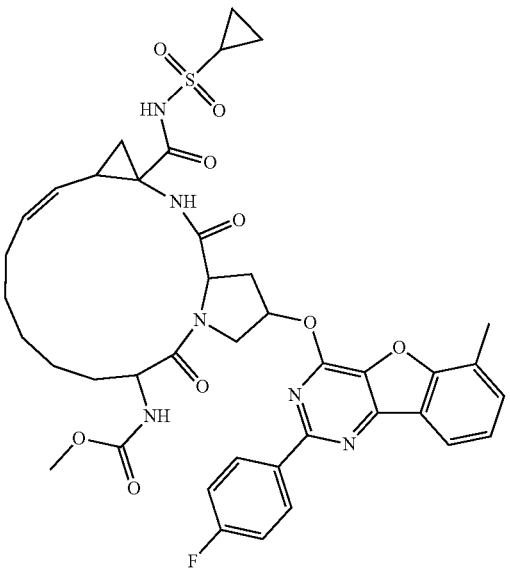 [SMILES: COC(=O)NC1CCCCC/C=C\C2CC2(C(=O)NS(=O)(=O)C2CC2)NC(=O)C2CC(Oc3nc(-c4ccc(F)cc4)nc4c3oc3c(C)cccc34)CN2C1=O]
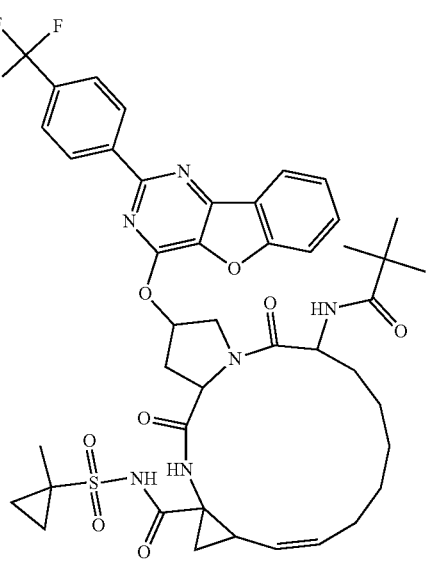
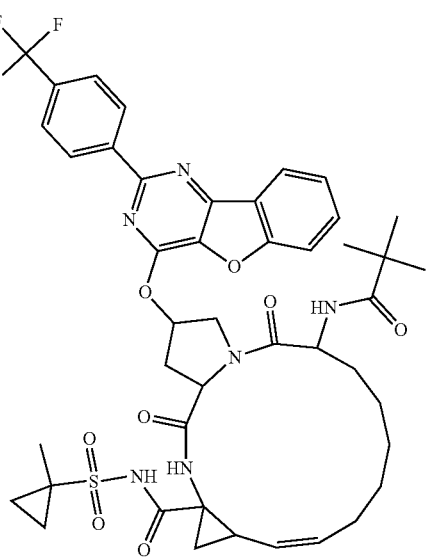

409
TABLE 50-continued
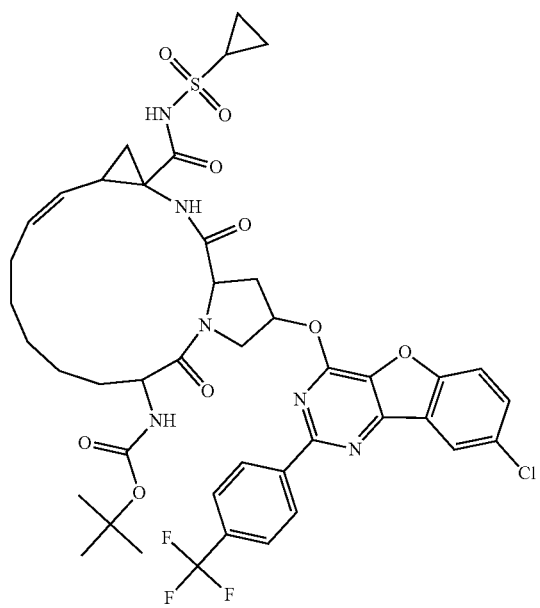 [SMILES: CC(C)(C)OC(=O)NC1CCCCC/C=C\C2CC2(C(=O)NS(=O)(=O)C2CC2)NC(=O)C2CC(Oc3nc(-c4ccc(C(F)(F)F)cc4)nc4c3oc3ccc(Cl)cc34)CN2C1=O]
410
TABLE 50-continued
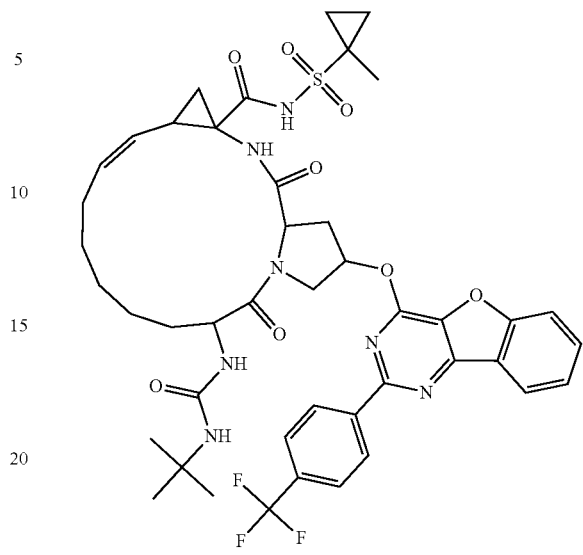
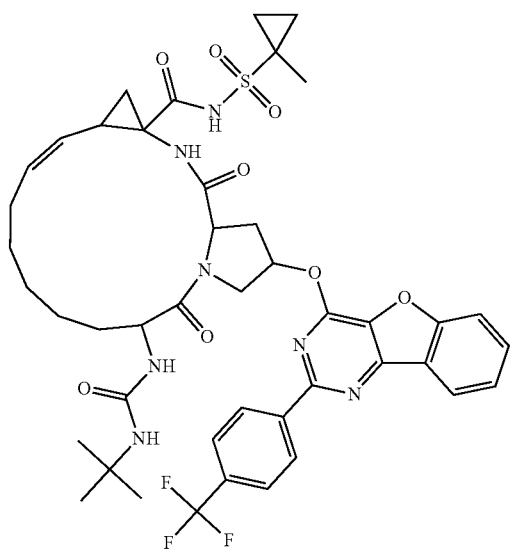 [SMILES: CC(C)(C)NC(=O)NC1CCCCC/C=C\C2CC2(C(=O)NS(=O)(=O)C2(C)CC2)NC(=O)C2CC(Oc3nc(-c4ccc(C(F)(F)F)cc4)nc4c3oc3ccccc34)CN2C1=O]
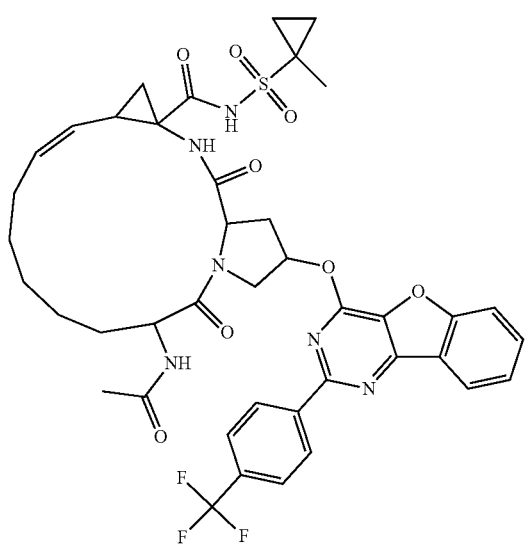 [SMILES: CC(=O)NC1CCCCC/C=C\C2CC2(C(=O)NS(=O)(=O)C2(C)CC2)NC(=O)C2CC(Oc3nc(-c4ccc(C(F)(F)F)cc4)nc4c3oc3ccccc34)CN2C1=O]

| 411 | 412 |
|---|---|
| TABLE 50-continued | TABLE 50-continued |
| 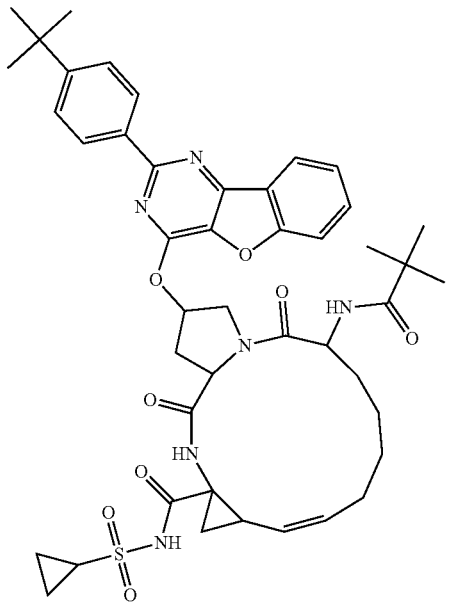 [SMILES: CC(C)(C)C(=O)NC1CCCC/C=C\C2CC2(C(=O)NS(=O)(=O)C2CC2)NC(=O)C2CC(Oc3nc(-c4ccc(C(C)(C)C)cc4)nc4c3oc3ccccc34)CN2C1=O] | 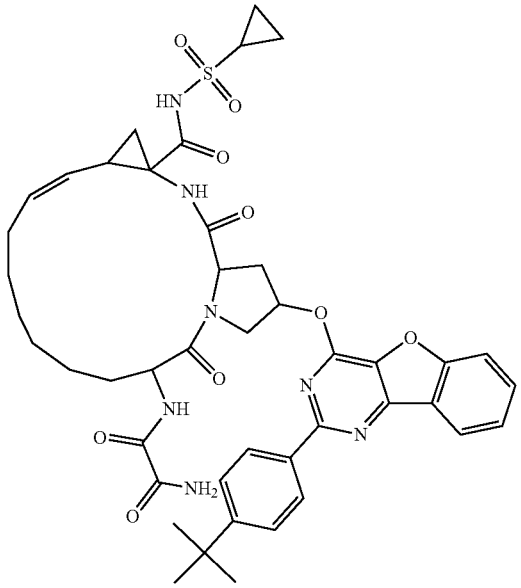 |
| 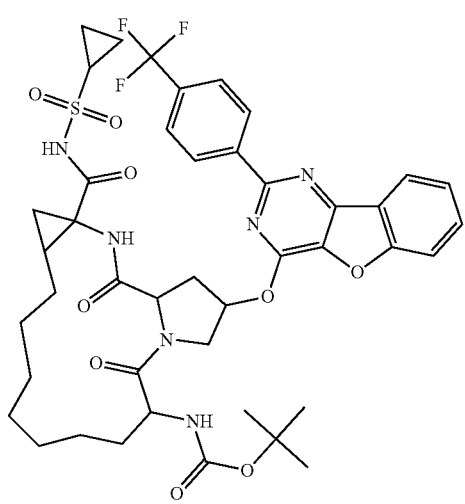 [SMILES: CC(C)(C)OC(=O)NC1CCCCCCCC2CC2(C(=O)NS(=O)(=O)C2CC2)NC(=O)C2CC(Oc3nc(-c4ccc(C(F)(F)F)cc4)nc4c3oc3ccccc34)CN2C1=O] | 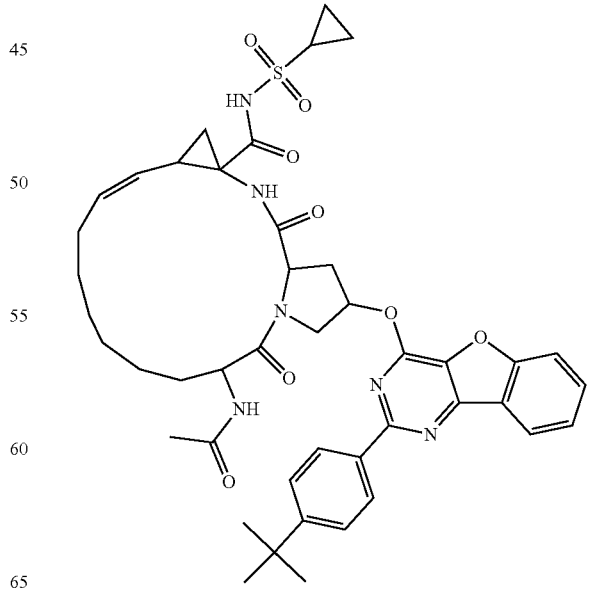 |

TABLE 50-continued

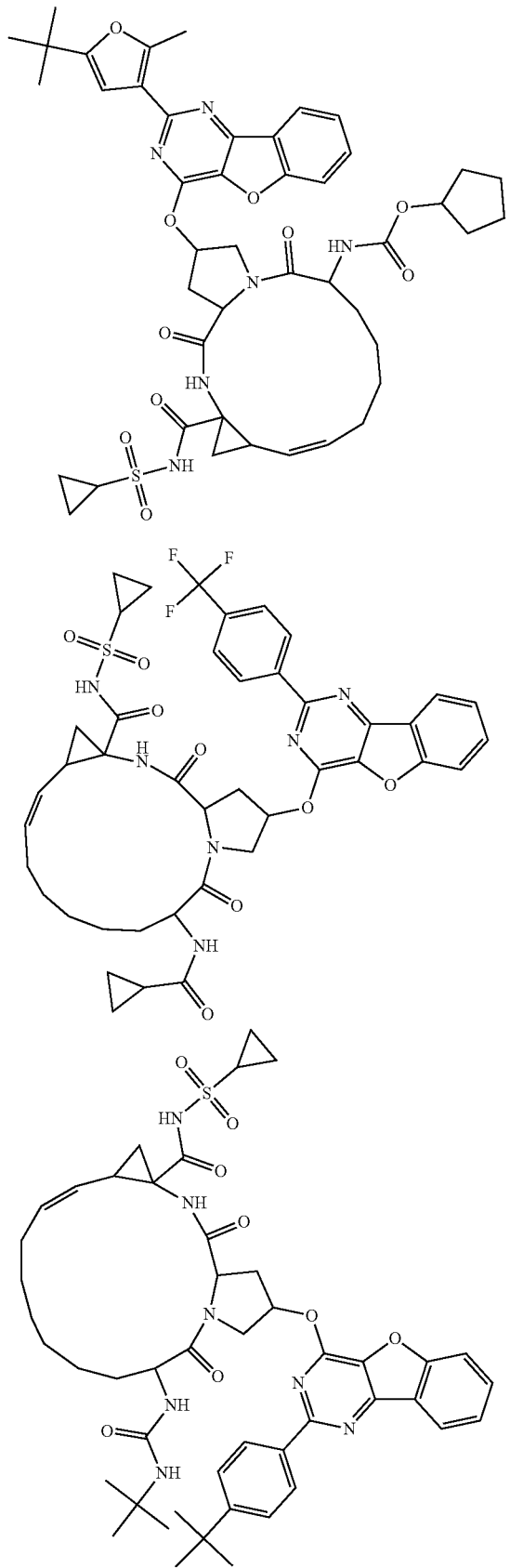

In one implementation, the compound is glecaprevir ((1R,14E,18R,22R,26S,29S)-26-tert-butyl-N-[(1R,2R)-2-(difluoromethyl)-1-[(1-methylcyclopropyl)sulfonylcarbamoyl]cyclopropyl]-13,13-difluoro-24,27-dioxo-2,17,23-trioxa-4,11,25,28-tetrazapentacyclo[26.2.1.03.12.05,10.018,22]hentriaconta-3,5,7,9,11,14-hexaene-29-carboxamide) a clinically investigated hepatitis C virus NS3 protease inhibitor. In one particular implementation, the compound, or variations and permutations thereof, is further described in WO2012040167 and WO2016141890 the contents of which are hereby incorporated by reference for all purposes and the specific purposes identified herein.

In one particular implementation, the compound is glutathione ((2S)-2-amino-5-[(2R)-1-(carboxymethylamino)-1-oxo-3-sulfanylpropan-2-yl]amino]-5-oxopentanoic acid) a clinically investigated nuclear factor kappa B inhibitor. In one particular implementation, the compound, or variations and permutations thereof, is further described in WO2003051910 the contents of which are hereby incorporated by reference for all purposes and the specific purposes identified herein.

In one implementation, the compound is grazoprevir ((1R,18R,20R,24S,27S)-24-tert-butyl-N-[(1R,2S)-1-(cyclopropylsulfonylcarbamoyl)-2-ethenylcyclopropyl]-7-methoxy-22,25-dioxo-2,21-dioxa-4,11,23,26-tetrazapentacyclo[24.2.1.03.12.05.10.018,20]nonacosa-3,5(10),6,8,11-pentaene-27-carboxamide), a clinically investigated hepatitis C virus NS3 protease inhibitor. In one particular implementation, the compound, or variations and permutations thereof, is further described in WO2010011566; WO2011014487; WO2014008285; WO2012040040 and WO2011014487 the contents of which are hereby incorporated by reference for all purposes and the specific purposes identified herein. In some embodiments, such compounds are represented by any one or more of the structures shown in Table 62. Any one of the compounds depicted in Table 62 is suitable for use in the methods of the present disclosure.

TABLE 51

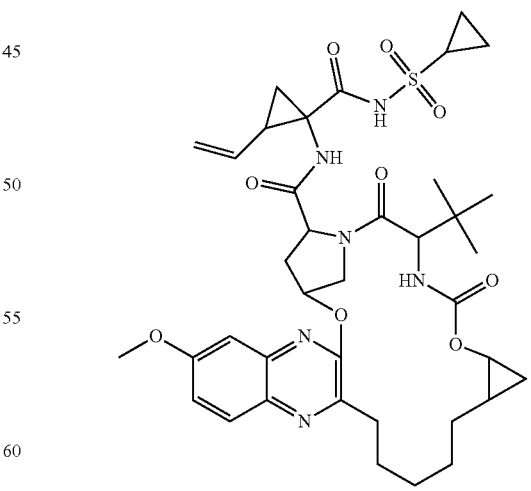

TABLE 51-continued
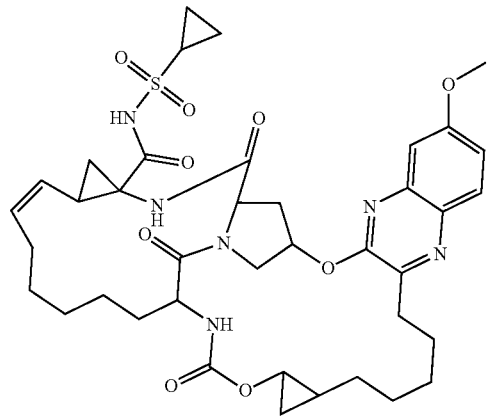 [SMILES: COc1ccc2nc3c(nc2c1)OC1CC2C(=O)NC4(C(=O)NS(=O)(=O)C5CC5)CC4/C=C\CCCCCC(NC(=O)OC4CC4CCCCC3)C(=O)N2C1]
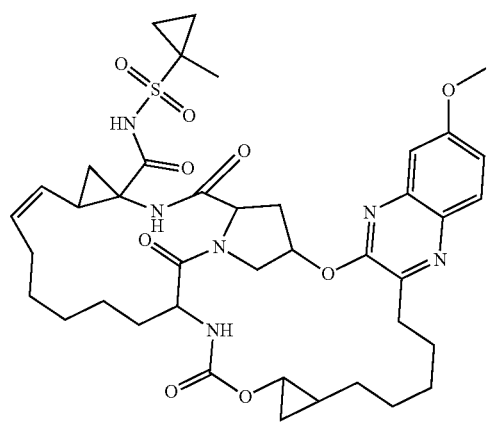 [SMILES: COc1ccc2nc3c(nc2c1)OC1CC2C(=O)NC4(C(=O)NS(=O)(=O)C5(C)CC5)CC4/C=C\CCCCCC(NC(=O)OC4CC4CCCCC3)C(=O)N2C1]
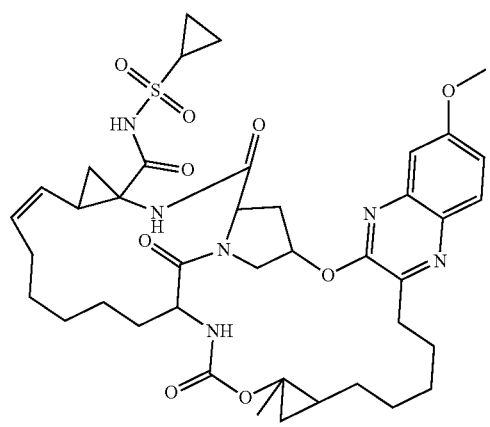 [SMILES: COc1ccc2nc3c(nc2c1)OC1CC2C(=O)NC4(C(=O)NS(=O)(=O)C5CC5)CC4/C=C\CCCCCC(NC(=O)OC4(C)CC4CCCCC3)C(=O)N2C1]
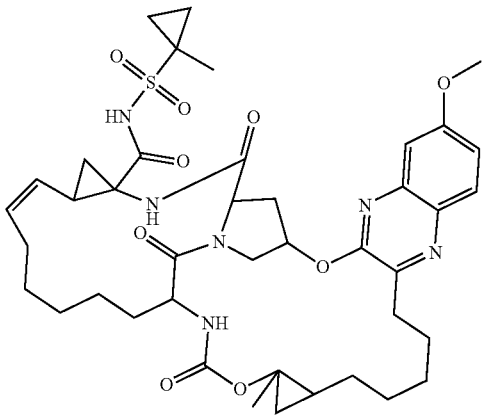 [SMILES: COc1ccc2nc3c(nc2c1)OC1CC2C(=O)NC4(C(=O)NS(=O)(=O)C5(C)CC5)CC4/C=C\CCCCCC(NC(=O)OC4(C)CC4CCCCC3)C(=O)N2C1]
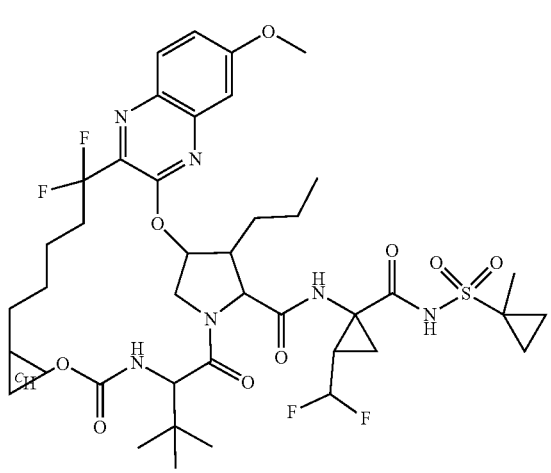
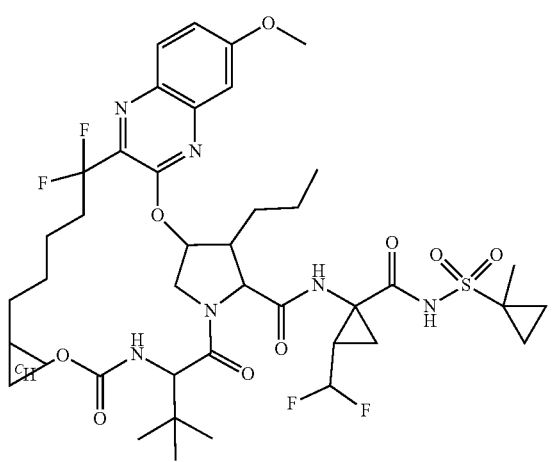

TABLE 51-continued

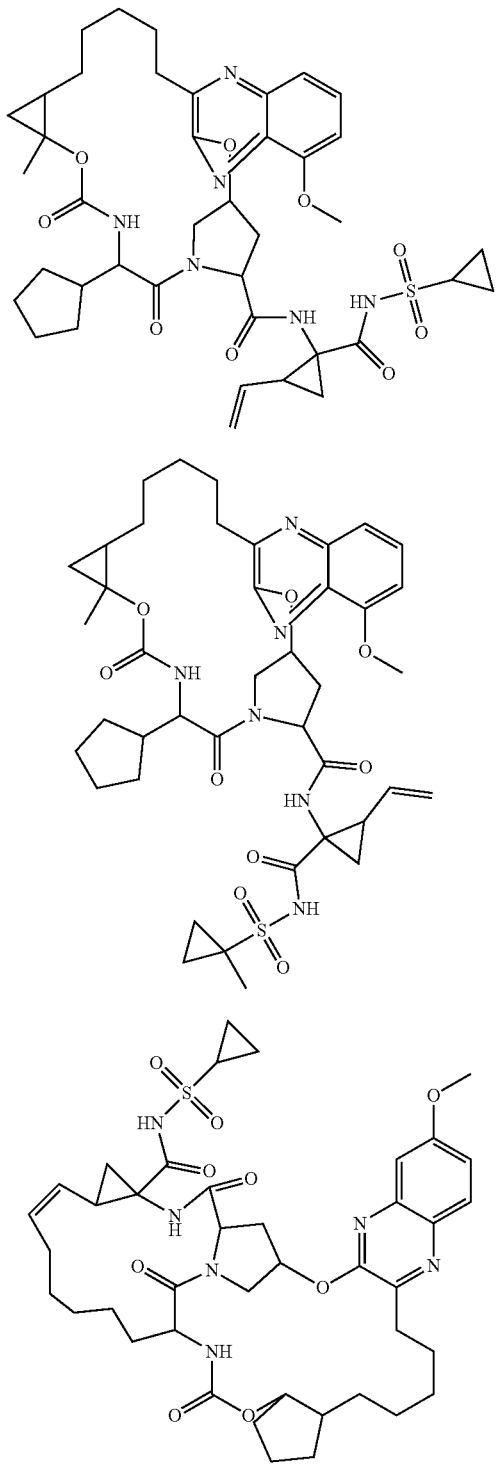

TABLE 52

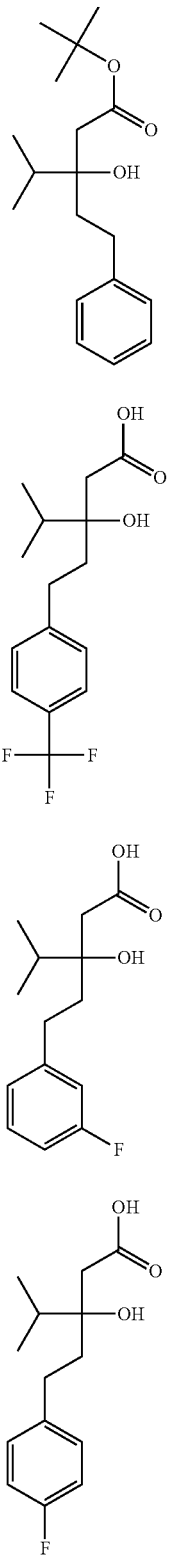

shown in Table 1. Any one of the compounds depicted in Table 1 is suitable for use in the methods of the present disclosure.

In one implementation, the compound is ibuprofen lysine or ibuprofen, a clinically investigated cyclooxygenase inhibitor. In one particular implementation, the compound, or variations and permutations thereof, is further described in WO2000015634 the contents of which are hereby incorporated by reference for all purposes and the specific purposes identified herein. In some embodiments, such compounds are represented by any one or more of the structures TABLE 52-continued
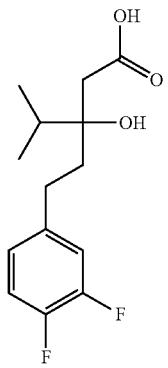 [SMILES: CC(C)C(O)(CCc1ccc(F)c(F)c1)CC(=O)O]
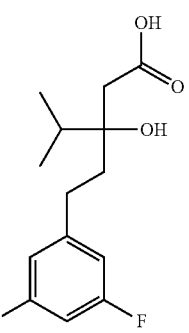
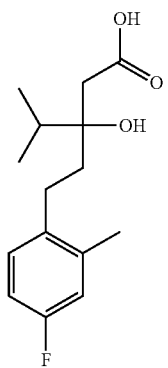 [SMILES: Cc1cc(F)ccc1CCC(O)(CC(=O)O)C(C)C]
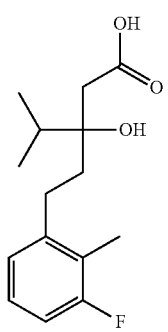 [SMILES: Cc1c(F)cccc1CCC(O)(CC(=O)O)C(C)C]
TABLE 52-continued
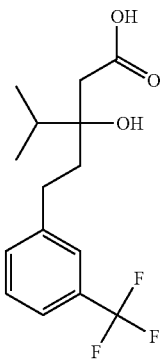 [SMILES: CC(C)C(O)(CCc1cccc(C(F)(F)F)c1)CC(=O)O]
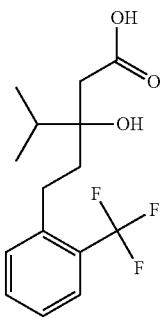 [SMILES: CC(C)C(O)(CCc1ccccc1C(F)(F)F)CC(=O)O]
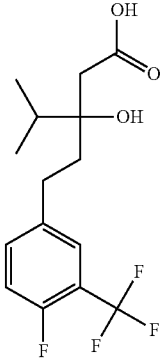 [SMILES: CC(C)C(O)(CCc1ccc(F)c(C(F)(F)F)c1)CC(=O)O]
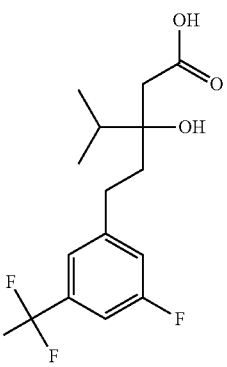

TABLE 52-continued

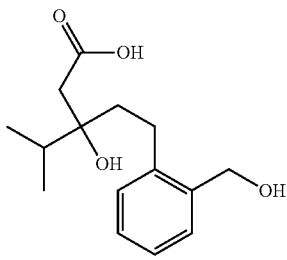 [SMILES: CC(C)C(O)(CCc1ccccc1CO)CC(=O)O]

In one implementation, the compound is imidazole salicylate or salicylic acid, a clinically investigated cyclooxygenase inhibitor and Oxidoreductase inhibitor. In one particular implementation, the compound, or variations and permutations thereof, is further described in WO1998019997 the contents of which are hereby incorporated by reference for all purposes and the specific purposes identified herein. In some embodiments, such compounds are represented by any one or more of the structures shown in Table 64. Any one of the compounds depicted in Table 64 is suitable for use in the methods of the present disclosure.

TABLE 53

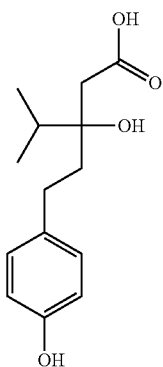

In one implementation, the compound is indinavir ((2S)-1-[(2S,4R)-4-benzyl-2-hydroxy-5-[[(1S,2R)-2-hydroxy-2,3-dihydro-1H-inden-1-yl]amino]-5-oxopentyl]-N-tert-butyl-4-(pyridin-3-ylmethyl)piperazine-2-carboxamide), a clinically investigated HIV protease inhibitor. In one particular implementation, the compound, or variations and permutations thereof, is further described in WO2001038332 the contents of which are hereby incorporated by reference for all purposes and the specific purposes identified herein. In some embodiments, such compounds are represented by any one or more of the structures shown in Table 65. Any one of the compounds depicted in Table 1 is suitable for use in the methods of the present disclosure.

TABLE 54

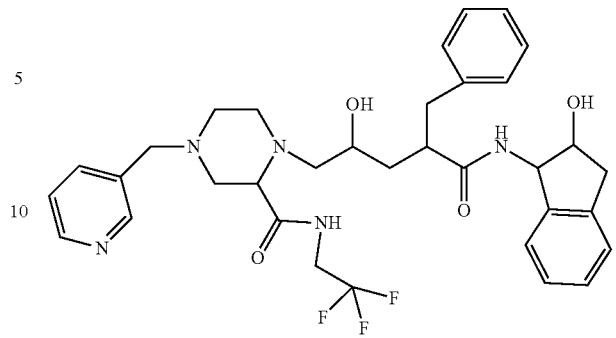

In one implementation, the compound is iofolastat I 123 ((2S)-2-[[(1S)-1-carboxy-5-[(4-($^{123}$I)iodanylphenyl)methylamino]pentyl]carbamoylamino]pentanedioic acid), a clinically investigated glutamate carboxypeptidase II inhibitor. In one particular implementation, the compound, or variations and permutations thereof, is further described in JP2000159746 the contents of which are hereby incorporated by reference for all purposes and the specific purposes identified herein. In some embodiments, such compounds are represented by any one or more of the structures shown in Table 66. Any one of the compounds depicted in Table 66 is suitable for use in the methods of the present disclosure.

TABLE 55

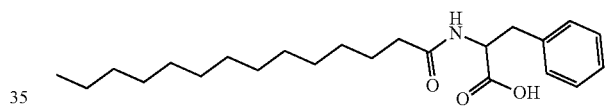

In one implementation, the compound is lacosamide ((2R)-2-acetamido-N-benzyl-3-methoxypropanamide), a dihydropyrimidinase related protein 2 modulator and Sodium channel modulator. In one particular implementation, the compound, or variations and permutations thereof, is further described in WO2006084688, the contents of which are hereby incorporated by reference for all purposes and the specific purposes identified herein. In some embodiments, such compounds are represented by any one or more of the structures shown in Table 67. Any one of the compounds depicted in Table 67 is suitable for use in the methods of the present disclosure.

TABLE 56

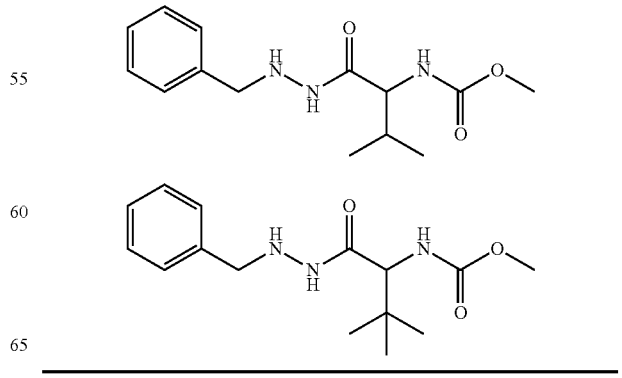

In one implementation, the compound is lisdexamfetamine ((2S)-2,6-diamino-N-[(2S)-1-phenylpropan-2-yl]hexanamide), a clinically investigated Cytomegalovirus protease inhibitor. In one particular implementation, the compound, or variations and permutations thereof, is further described in WO1998029435 and JP2000159746, the contents of which are hereby incorporated by reference for all purposes and the specific purposes identified herein. In some embodiments, such compounds are represented by any one or more of the structures shown in Table 1. Any one of the compounds depicted in Table 1 is suitable for use in the methods of the present disclosure.

TABLE 57

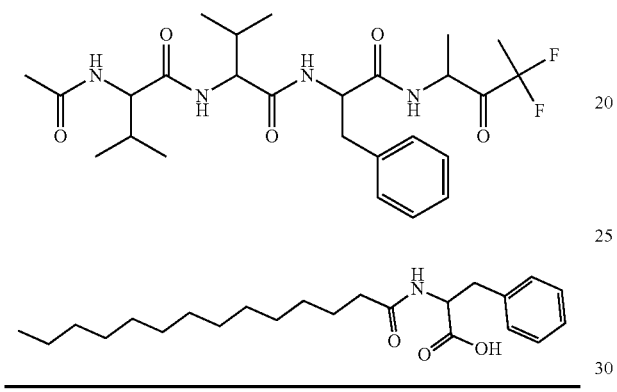

In one implementation, the compound is lisinopril ((2S)-1-[(2S)-6-amino-2-[[(1S)-1-carboxy-3-phenylpropyl]amino]hexanoyl]pyrrolidine-2-carboxylic acid), a clinically investigated ACE inhibitor. In one particular implementation, the compound, or variations and permutations thereof, is further described in WO2007117560 the contents of which are hereby incorporated by reference for all purposes and the specific purposes identified herein. In some embodiments, such compounds are represented by any one or more of the structures shown in Table 69. Any one of the compounds depicted in Table 69 is suitable for use in the methods of the present disclosure.

TABLE 58

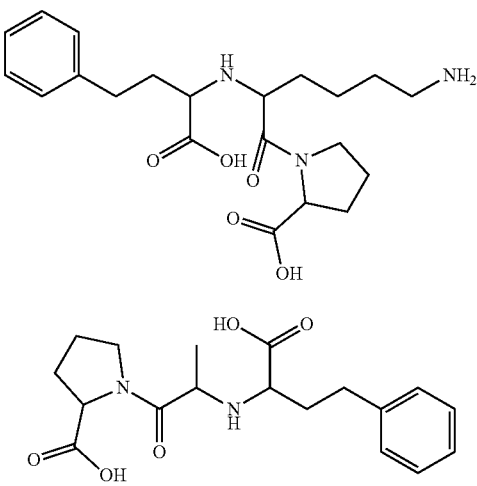

TABLE 58-continued

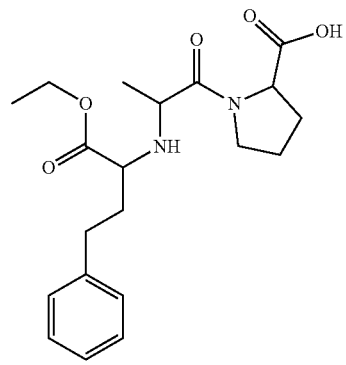 [SMILES: CCOC(=O)C(CCc1ccccc1)NC(C)C(=O)N1CCCC1C(=O)O]

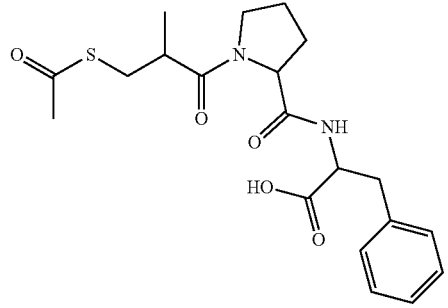 [SMILES: CC(=O)SCC(C)C(=O)N1CCCC1C(=O)NC(Cc1ccccc1)C(=O)O]

In one implementation, the compound is lucerastat ((2R,3S,4R,5S)-1-butyl-2-(hydroxymethyl)piperidine-3,4,5-triol) or miglustat, a clinically investigated glucosylceramide synthase inhibitor. In one particular implementation, the compound, or variations and permutations thereof, is further described in the contents of WO2006073456 which are hereby incorporated by reference for all purposes and the specific purposes identified herein. In some embodiments, such compounds are represented by any one or more of the structures shown in Table 70. Any one of the compounds depicted in Table 70 is suitable for use in the methods of the present disclosure.

TABLE 59

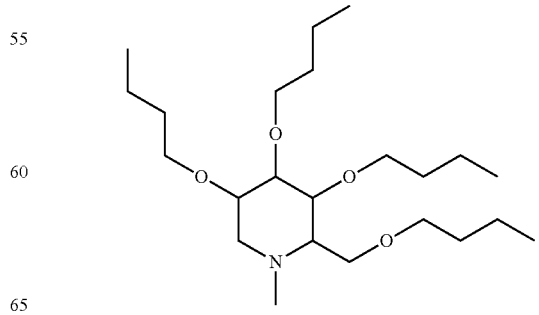

In one implementation, the compound is masoprocol (4-[(2S,3R)-4-(3,4-dihydroxyphenyl)-2,3-dimethylbutyl]benzene-1,2-diol), a clinically investigated erbb2 tyrosine kinase receptor inhibitor; Insulin-like growth factor 1 receptor antagonist; and Lipase inhibitor. In one particular implementation, the compound, or variations and permutations thereof, is further described in the contents of WO2005073195 which are hereby incorporated by reference for all purposes and the specific purposes identified herein. In some embodiments, such compounds are represented by any one or more of the structures shown in Table 71. Any one of the compounds depicted in Table 71 is suitable for use in the methods of the present disclosure.

TABLE 60

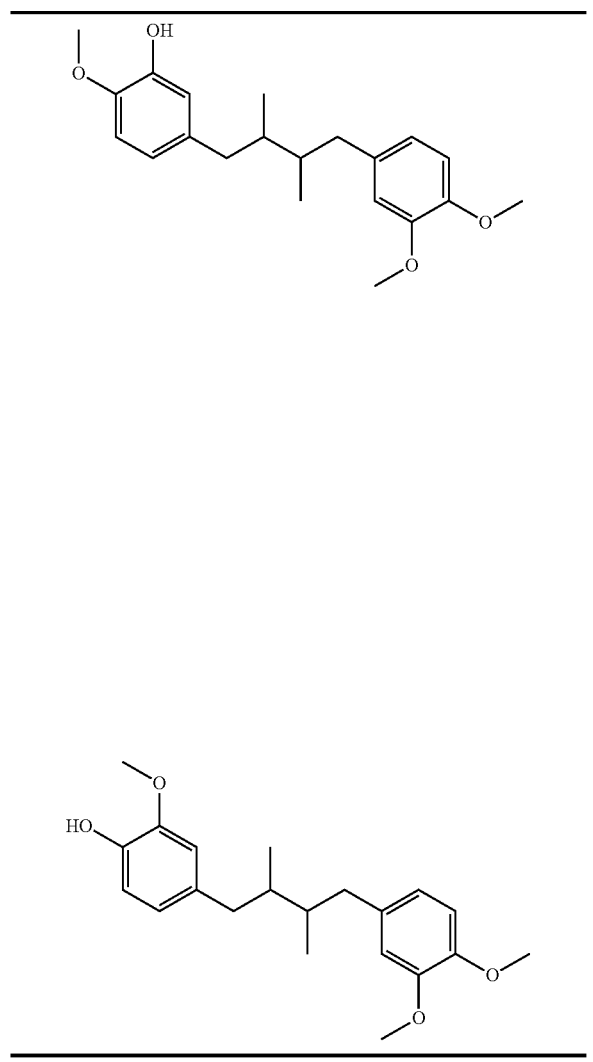

In one implementation, the compound is metoprolol succinate (butanedioic acid; 1-[4-(2-methoxyethyl)phenoxy]-3-(propan-2-ylamino)propan-2-ol), a clinically investigated adrenergic receptor antagonist and Beta 1 adrenoceptor antagonist. In one particular implementation, the compound, or variations and permutations thereof, is further described in WO2007117560 the contents of which are hereby incorporated by reference for all purposes and the specific purposes identified herein. In some embodiments, such compounds are represented by any one or more of the structures shown in Table 72. Any one of the compounds depicted in Table 72 is suitable for use in the methods of the present disclosure.

TABLE 61

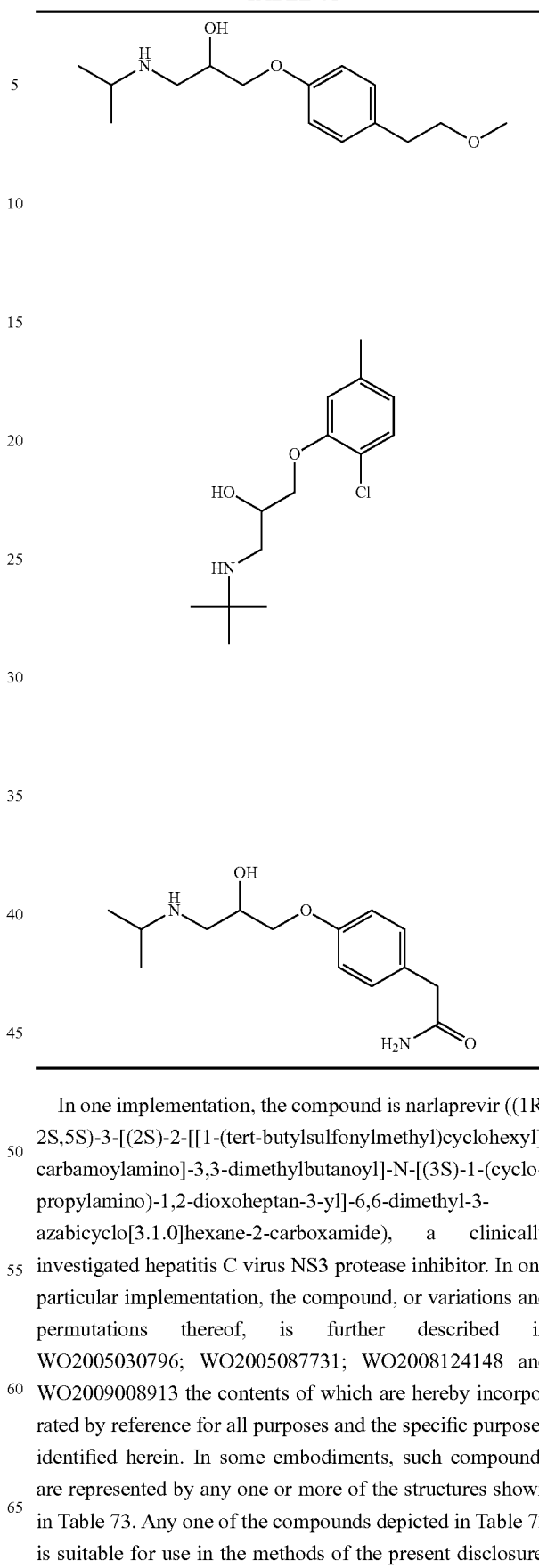

In one implementation, the compound is narlaprevir ((1R, 2S,5S)-3-[(2S)-2-[[1-(tert-butylsulfonylmethyl)cyclohexyl]carbamoylamino]-3,3-dimethylbutanoyl]-N-[(3S)-1-(cyclopropylamino)-1,2-dioxoheptan-3-yl]-6,6-dimethyl-3-azabicyclo[3.1.0]hexane-2-carboxamide), a clinically investigated hepatitis C virus NS3 protease inhibitor. In one particular implementation, the compound, or variations and permutations thereof, is further described in WO2005030796; WO2005087731; WO2008124148 and WO2009008913 the contents of which are hereby incorporated by reference for all purposes and the specific purposes identified herein. In some embodiments, such compounds are represented by any one or more of the structures shown in Table 73. Any one of the compounds depicted in Table 73 is suitable for use in the methods of the present disclosure.

TABLE 62
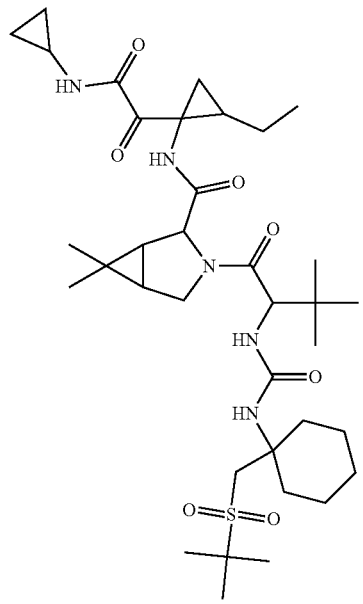 [SMILES: CCC1CC1(NC(=O)C1C2C(CN1C(=O)C(NC(=O)NC1(CS(=O)(=O)C(C)(C)C)CCCCC1)C(C)(C)C)C2(C)C)C(=O)C(=O)NC1CC1]
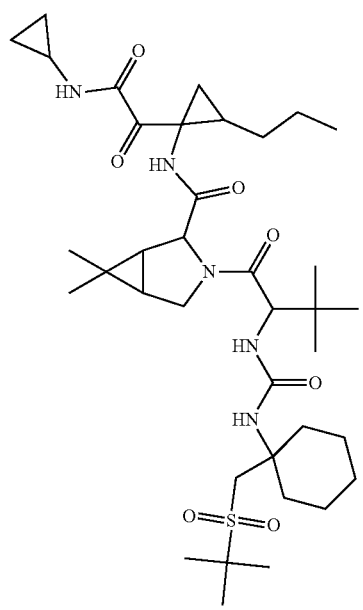 [SMILES: CCCC1CC1(NC(=O)C1C2C(CN1C(=O)C(NC(=O)NC1(CS(=O)(=O)C(C)(C)C)CCCCC1)C(C)(C)C)C2(C)C)C(=O)C(=O)NC1CC1]

TABLE 62-continued
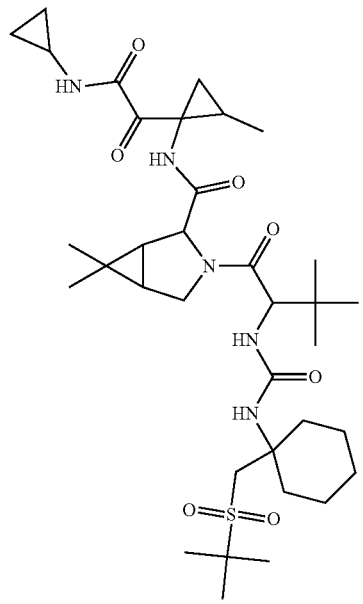 [SMILES: CC1CC1(NC(=O)C1C2C(CN1C(=O)C(NC(=O)NC1(CS(=O)(=O)C(C)(C)C)CCCCC1)C(C)(C)C)C2(C)C)C(=O)C(=O)NC1CC1]
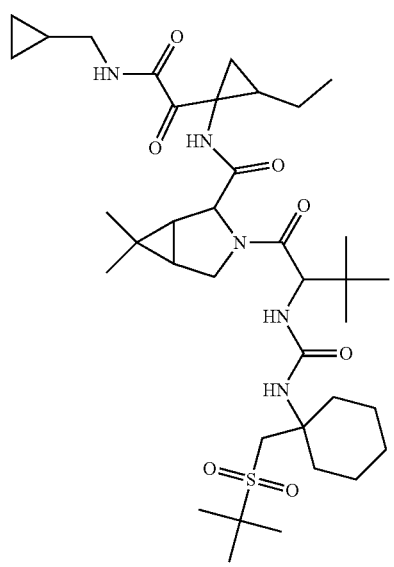 [SMILES: CCC1CC1(NC(=O)C1C2C(CN1C(=O)C(NC(=O)NC1(CS(=O)(=O)C(C)(C)C)CCCCC1)C(C)(C)C)C2(C)C)C(=O)C(=O)NCC1CC1]

TABLE 62-continued
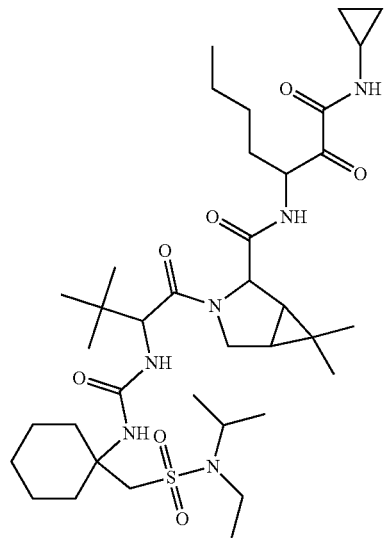 [SMILES: CCCCC(NC(=O)C1C2C(CN1C(=O)C(NC(=O)NC1(CS(=O)(=O)N(CC)C(C)C)CCCCC1)C(C)(C)C)C2(C)C)C(=O)C(=O)NC1CC1]
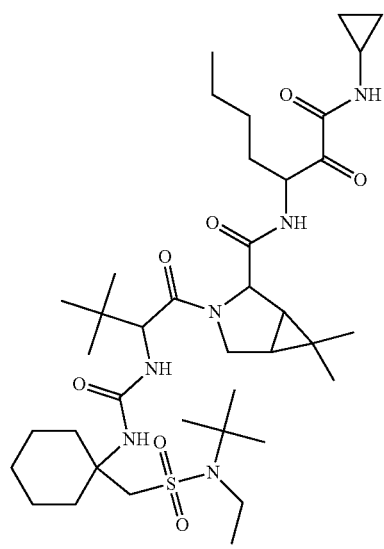 [SMILES: CCCCC(NC(=O)C1C2C(CN1C(=O)C(NC(=O)NC1(CS(=O)(=O)N(CC)C(C)(C)C)CCCCC1)C(C)(C)C)C2(C)C)C(=O)C(=O)NC1CC1]
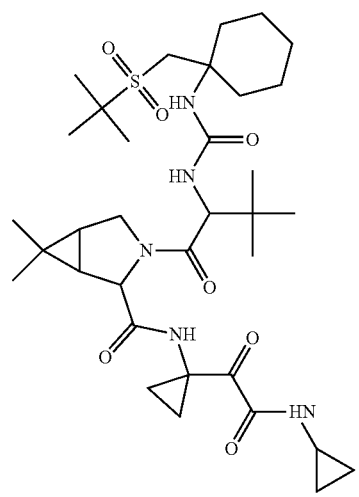 [SMILES: CC(C)(C)C(NC(=O)NC1(CS(=O)(=O)C(C)(C)C)CCCCC1)C(=O)N1CC2C(C1C(=O)NC1(C(=O)C(=O)NC3CC3)CC1)C2(C)C]

TABLE 62-continued
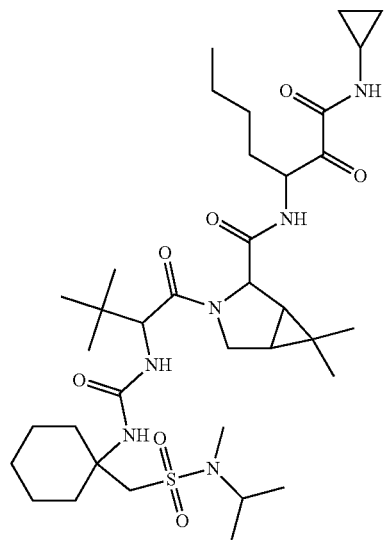 [SMILES: CCCCC(NC(=O)C1C2C(CN1C(=O)C(NC(=O)NC1(CS(=O)(=O)N(C)C(C)C)CCCCC1)C(C)(C)C)C2(C)C)C(=O)C(=O)NC1CC1]
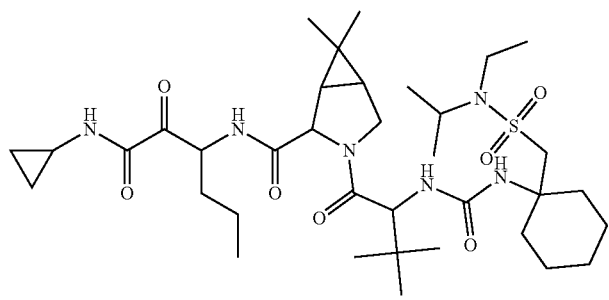 [SMILES: CCCC(NC(=O)C1C2C(CN1C(=O)C(NC(=O)NC1(CS(=O)(=O)N(CC)C(C)C)CCCCC1)C(C)(C)C)C2(C)C)C(=O)C(=O)NC1CC1]
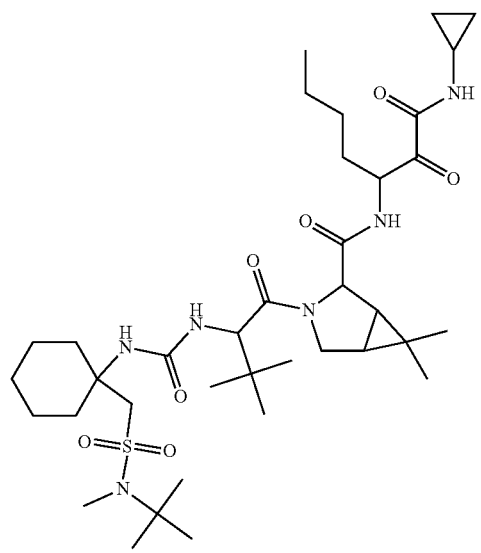 [SMILES: CCCCC(NC(=O)C1C2C(CN1C(=O)C(NC(=O)NC1(CS(=O)(=O)N(C)C(C)(C)C)CCCCC1)C(C)(C)C)C2(C)C)C(=O)C(=O)NC1CC1]

TABLE 62-continued
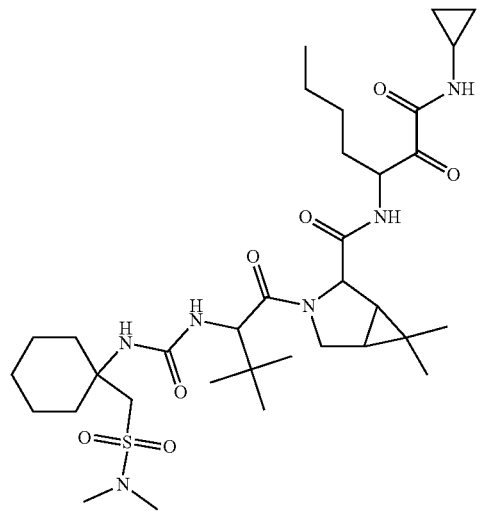 [SMILES: CCCCC(NC(=O)C1C2C(CN1C(=O)C(NC(=O)NC1(CS(=O)(=O)N(C)C)CCCCC1)C(C)(C)C)C2(C)C)C(=O)C(=O)NC1CC1]
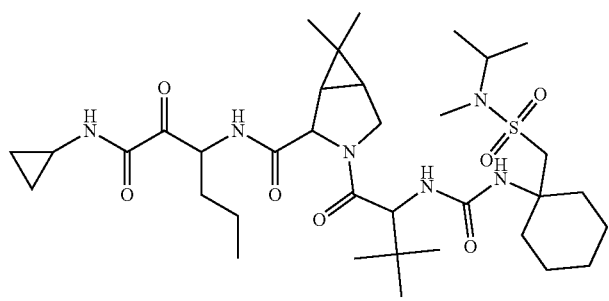 [SMILES: CCCC(NC(=O)C1C2C(CN1C(=O)C(NC(=O)NC1(CS(=O)(=O)N(C)C(C)C)CCCCC1)C(C)(C)C)C2(C)C)C(=O)C(=O)NC1CC1]
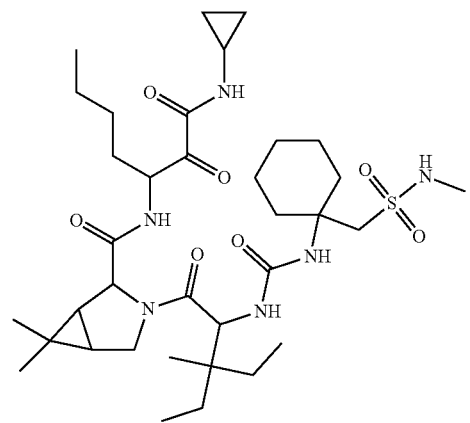

TABLE 62-continued
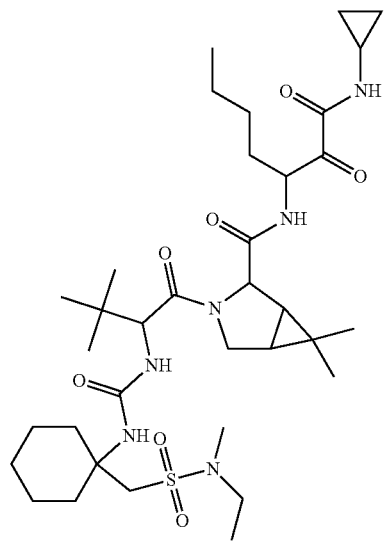 [SMILES: CCCCC(NC(=O)C1C2C(CN1C(=O)C(NC(=O)NC1(CS(=O)(=O)N(C)CC)CCCCC1)C(C)(C)C)C2(C)C)C(=O)C(=O)NC1CC1]
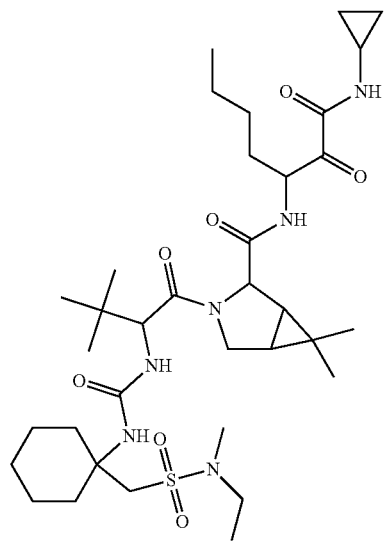 [SMILES: CCCCC(NC(=O)C1C2C(CN1C(=O)C(NC(=O)NC1(CS(=O)(=O)N(C)CC)CCCCC1)C(C)(C)C)C2(C)C)C(=O)C(=O)NC1CC1]
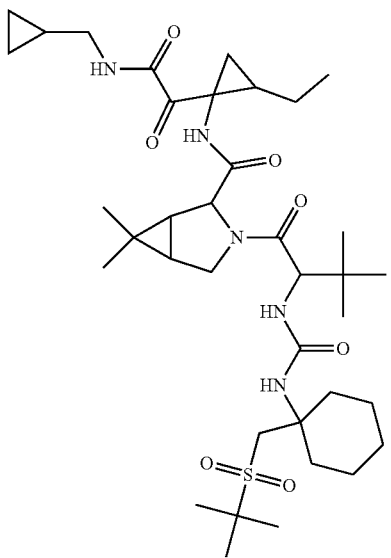 [SMILES: CCC1CC1(NC(=O)C1C2C(CN1C(=O)C(NC(=O)NC1(CS(=O)(=O)C(C)(C)C)CCCCC1)C(C)(C)C)C2(C)C)C(=O)C(=O)NCC1CC1]

TABLE 62-continued
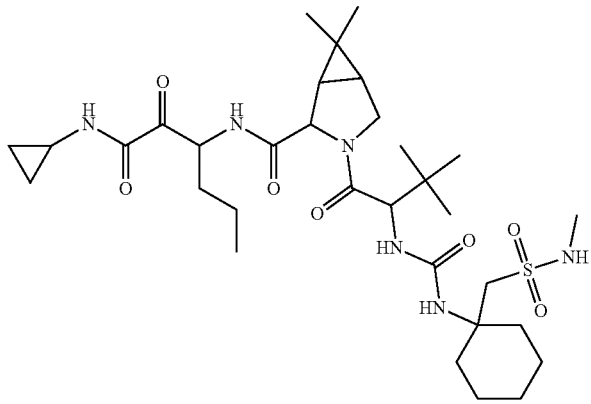 [SMILES: CCCC(NC(=O)C1C2C(CN1C(=O)C(NC(=O)NC1(CS(=O)(=O)NC)CCCCC1)C(C)(C)C)C2(C)C)C(=O)C(=O)NC1CC1]
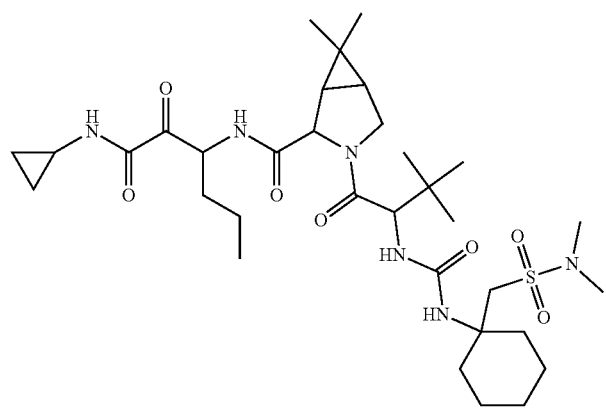 [SMILES: CCCC(NC(=O)C1C2C(CN1C(=O)C(NC(=O)NC1(CS(=O)(=O)N(C)C)CCCCC1)C(C)(C)C)C2(C)C)C(=O)C(=O)NC1CC1]
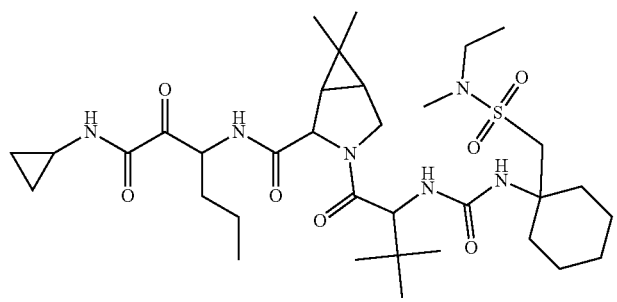 [SMILES: CCCC(NC(=O)C1C2C(CN1C(=O)C(NC(=O)NC1(CS(=O)(=O)N(C)CC)CCCCC1)C(C)(C)C)C2(C)C)C(=O)C(=O)NC1CC1]
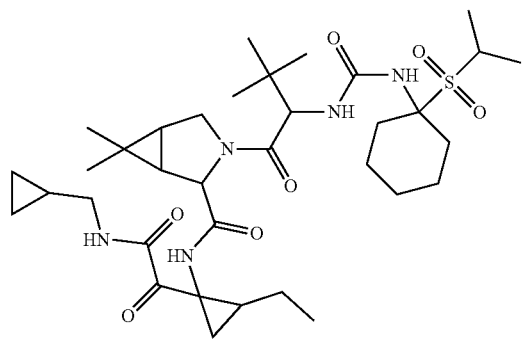 [SMILES: CCC1CC1(NC(=O)C1C2C(CN1C(=O)C(NC(=O)NC1(S(=O)(=O)C(C)C)CCCCC1)C(C)(C)C)C2(C)C)C(=O)C(=O)NCC1CC1]

TABLE 62-continued
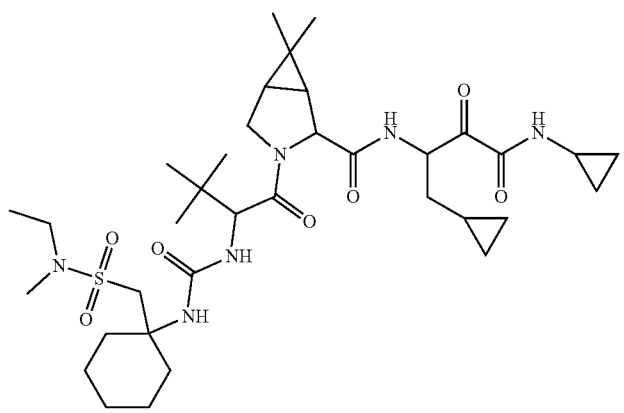 [SMILES: CCN(C)S(=O)(=O)CC1(NC(=O)NC(C(=O)N2CC3C(C2C(=O)NC(CC2CC2)C(=O)C(=O)NC2CC2)C3(C)C)C(C)(C)C)CCCCC1]
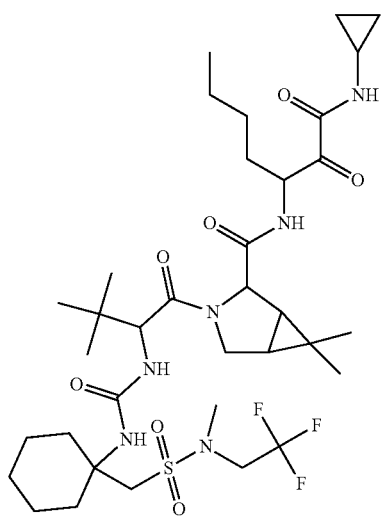 [SMILES: CCCCC(NC(=O)C1C2C(CN1C(=O)C(NC(=O)NC1(CS(=O)(=O)N(C)CC(F)(F)F)CCCCC1)C(C)(C)C)C2(C)C)C(=O)C(=O)NC1CC1]
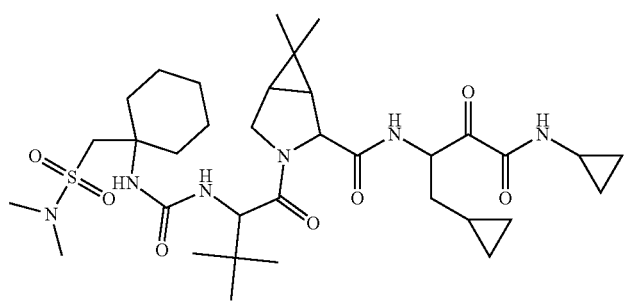 [SMILES: CN(C)S(=O)(=O)CC1(NC(=O)NC(C(=O)N2CC3C(C2C(=O)NC(CC2CC2)C(=O)C(=O)NC2CC2)C3(C)C)C(C)(C)C)CCCCC1]
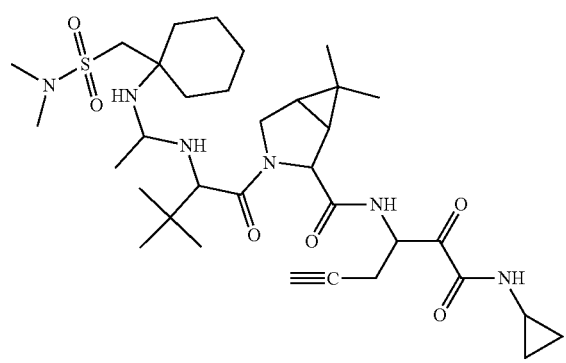 [SMILES: C#CCC(NC(=O)C1C2C(CN1C(=O)C(NC(C)NC1(CS(=O)(=O)N(C)C)CCCCC1)C(C)(C)C)C2(C)C)C(=O)C(=O)NC1CC1]

TABLE 62-continued
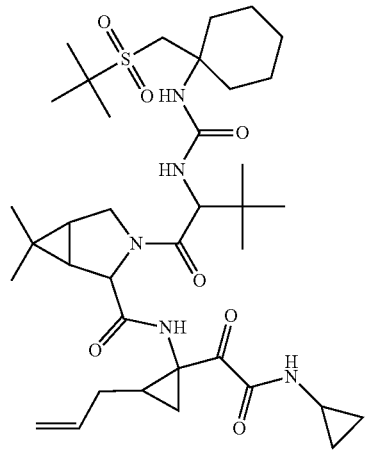 [SMILES: C=CCC1CC1(NC(=O)C1C2C(CN1C(=O)C(NC(=O)NC1(CS(=O)(=O)C(C)(C)C)CCCCC1)C(C)(C)C)C2(C)C)C(=O)C(=O)NC1CC1]
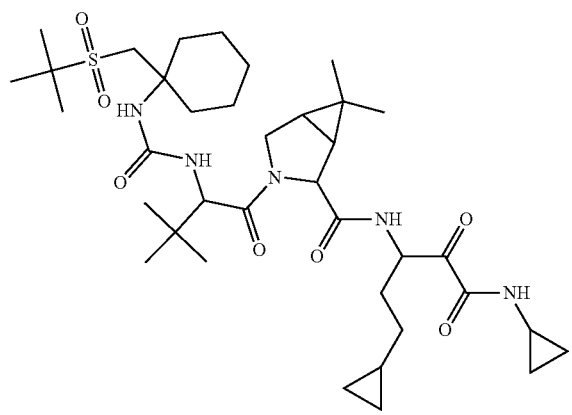 [SMILES: CC(C)(C)C(NC(=O)NC1(CS(=O)(=O)C(C)(C)C)CCCCC1)C(=O)N1CC2C(C1C(=O)NC(CCC1CC1)C(=O)C(=O)NC1CC1)C2(C)C]
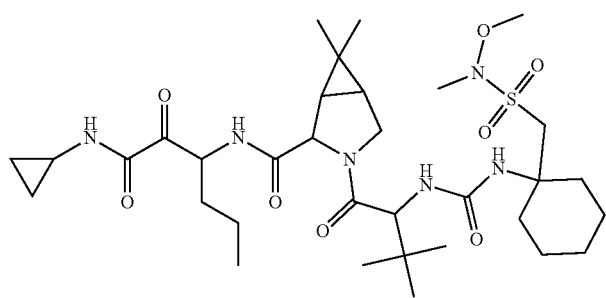 [SMILES: CCCC(NC(=O)C1C2C(CN1C(=O)C(NC(=O)NC1(CS(=O)(=O)N(C)OC)CCCCC1)C(C)(C)C)C2(C)C)C(=O)C(=O)NC1CC1]
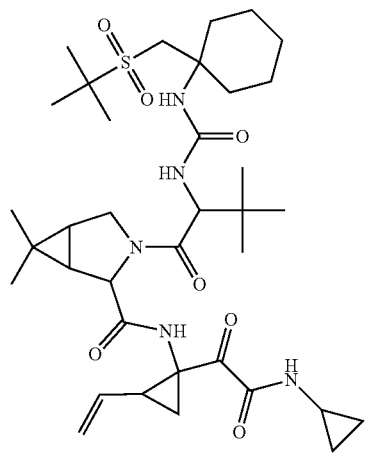 [SMILES: C=CC1CC1(NC(=O)C1C2C(CN1C(=O)C(NC(=O)NC1(CS(=O)(=O)C(C)(C)C)CCCCC1)C(C)(C)C)C2(C)C)C(=O)C(=O)NC1CC1]

TABLE 62-continued
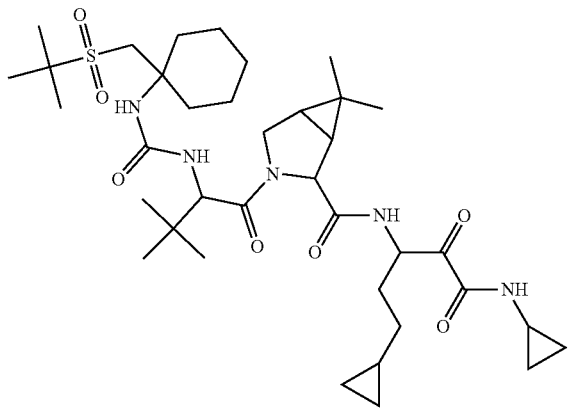 [SMILES: CC(C)(C)C(NC(=O)NC1(CS(=O)(=O)C(C)(C)C)CCCCC1)C(=O)N1CC2C(C1C(=O)NC(CCC1CC1)C(=O)C(=O)NC1CC1)C2(C)C]
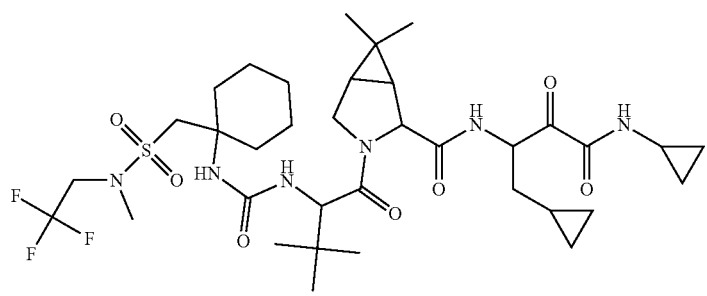 [SMILES: CN(CC(F)(F)F)S(=O)(=O)CC1(NC(=O)NC(C(=O)N2CC3C(C2C(=O)NC(CC2CC2)C(=O)C(=O)NC2CC2)C3(C)C)C(C)(C)C)CCCCC1]
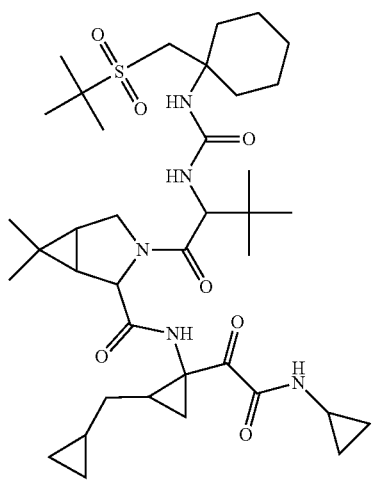 [SMILES: CC(C)(C)C(NC(=O)NC1(CS(=O)(=O)C(C)(C)C)CCCCC1)C(=O)N1CC2C(C1C(=O)NC1(C(=O)C(=O)NC3CC3)CC1CC1CC1)C2(C)C]

TABLE 62-continued
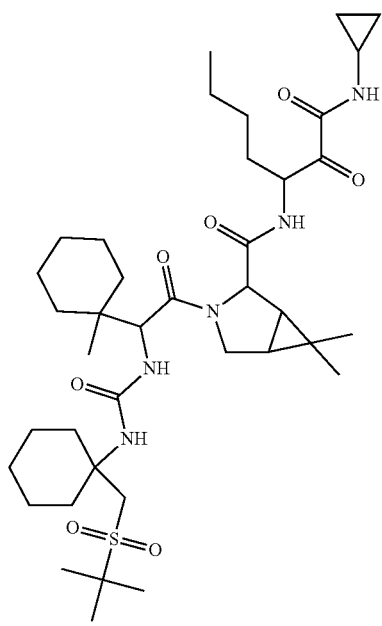 [SMILES: CCCCC(NC(=O)C1C2C(CN1C(=O)C(NC(=O)NC1(CS(=O)(=O)C(C)(C)C)CCCCC1)C1(C)CCCCC1)C2(C)C)C(=O)C(=O)NC1CC1]
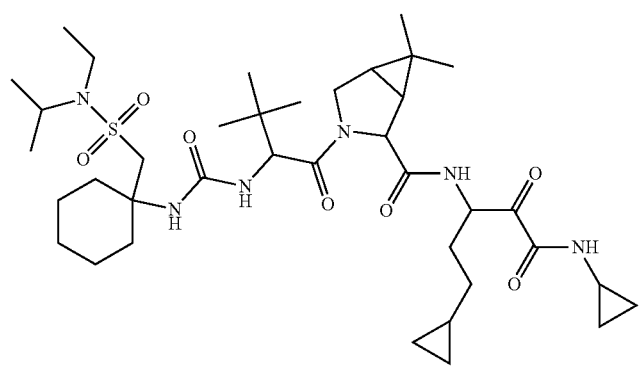 [SMILES: CCN(C(C)C)S(=O)(=O)CC1(NC(=O)NC(C(=O)N2CC3C(C2C(=O)NC(CCC2CC2)C(=O)C(=O)NC2CC2)C3(C)C)C(C)(C)C)CCCCC1]
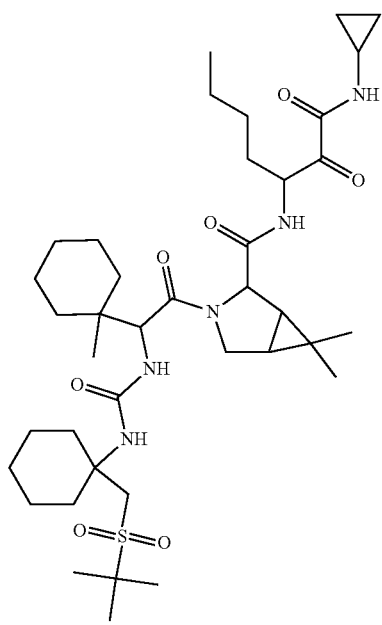 [SMILES: CCCCC(NC(=O)C1C2C(CN1C(=O)C(NC(=O)NC1(CS(=O)(=O)C(C)(C)C)CCCCC1)C1(C)CCCCC1)C2(C)C)C(=O)C(=O)NC1CC1]

TABLE 62-continued
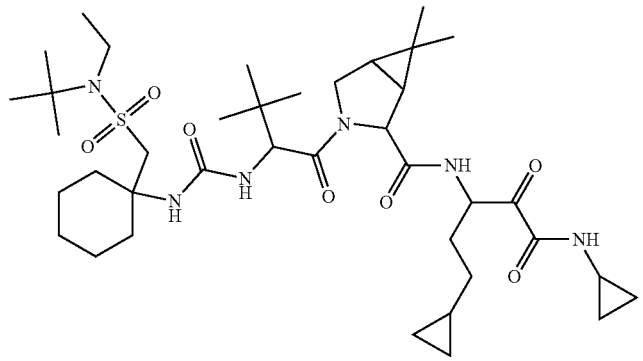 [SMILES: CCN(C(C)(C)C)S(=O)(=O)CC1(NC(=O)NC(C(=O)N2CC3C(C2C(=O)NC(CCC2CC2)C(=O)C(=O)NC2CC2)C3(C)C)C(C)(C)C)CCCCC1]
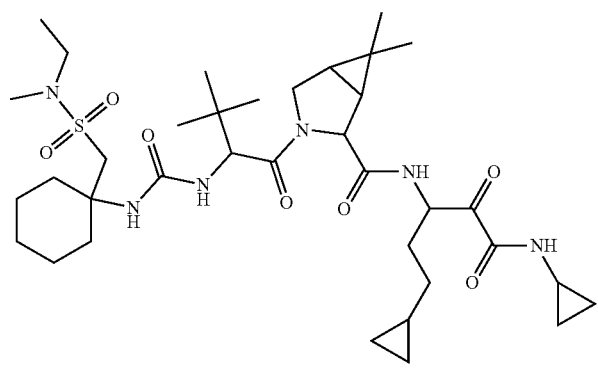 [SMILES: CCN(C)S(=O)(=O)CC1(NC(=O)NC(C(=O)N2CC3C(C2C(=O)NC(CCC2CC2)C(=O)C(=O)NC2CC2)C3(C)C)C(C)(C)C)CCCCC1]
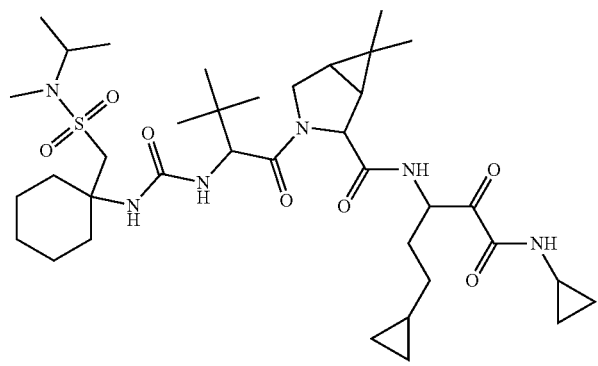 [SMILES: CC(C)N(C)S(=O)(=O)CC1(NC(=O)NC(C(=O)N2CC3C(C2C(=O)NC(CCC2CC2)C(=O)C(=O)NC2CC2)C3(C)C)C(C)(C)C)CCCCC1]

TABLE 62-continued
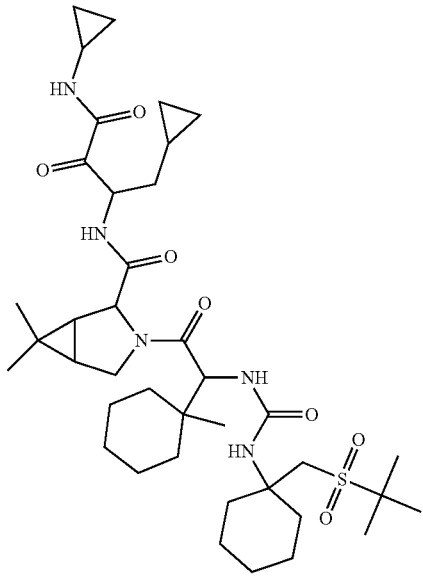 [SMILES: CC1(C(NC(=O)NC2(CS(=O)(=O)C(C)(C)C)CCCCC2)C(=O)N2CC3C(C2C(=O)NC(CC2CC2)C(=O)C(=O)NC2CC2)C3(C)C)CCCCC1]
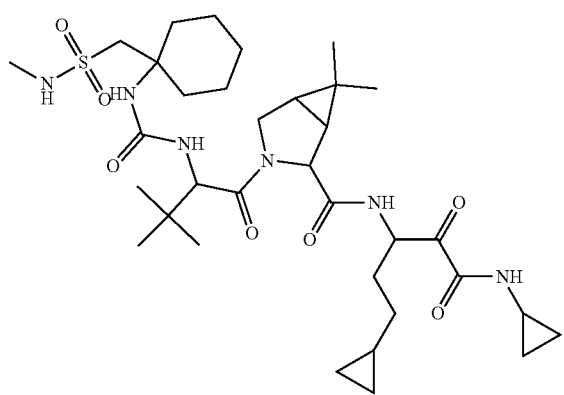 [SMILES: CNS(=O)(=O)CC1(NC(=O)NC(C(=O)N2CC3C(C2C(=O)NC(CCC2CC2)C(=O)C(=O)NC2CC2)C3(C)C)C(C)(C)C)CCCCC1]
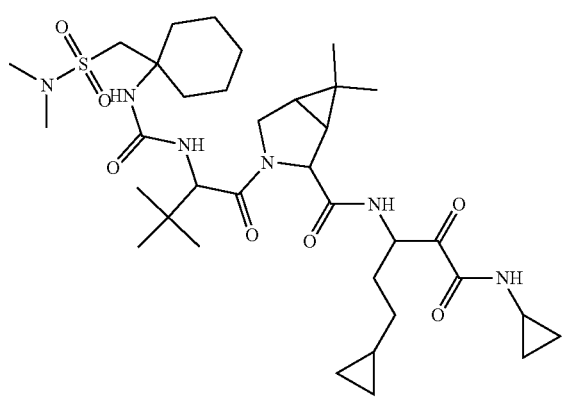 [SMILES: CN(C)S(=O)(=O)CC1(NC(=O)NC(C(=O)N2CC3C(C2C(=O)NC(CCC2CC2)C(=O)C(=O)NC2CC2)C3(C)C)C(C)(C)C)CCCCC1]

TABLE 62-continued
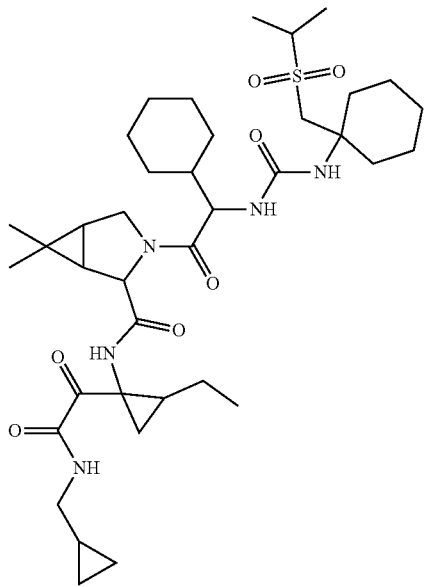 [SMILES: CCC1CC1(NC(=O)C1C2C(CN1C(=O)C(NC(=O)NC1(CS(=O)(=O)C(C)C)CCCCC1)C1CCCCC1)C2(C)C)C(=O)C(=O)NCC1CC1]
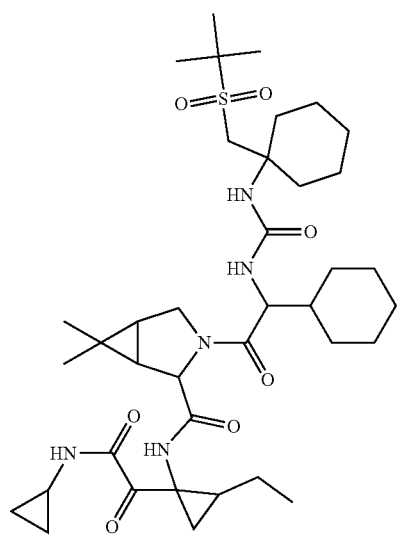 [SMILES: CCC1CC1(NC(=O)C1C2C(CN1C(=O)C(NC(=O)NC1(CS(=O)(=O)C(C)(C)C)CCCCC1)C1CCCCC1)C2(C)C)C(=O)C(=O)NC1CC1]

TABLE 62-continued
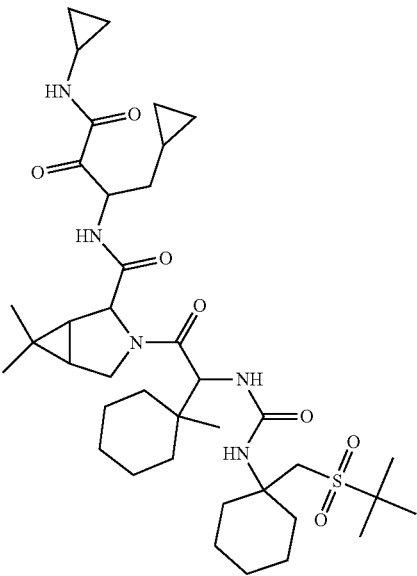 [SMILES: CC1(C(NC(=O)NC2(CS(=O)(=O)C(C)(C)C)CCCCC2)C(=O)N2CC3C(C2C(=O)NC(CC2CC2)C(=O)C(=O)NC2CC2)C3(C)C)CCCCC1]
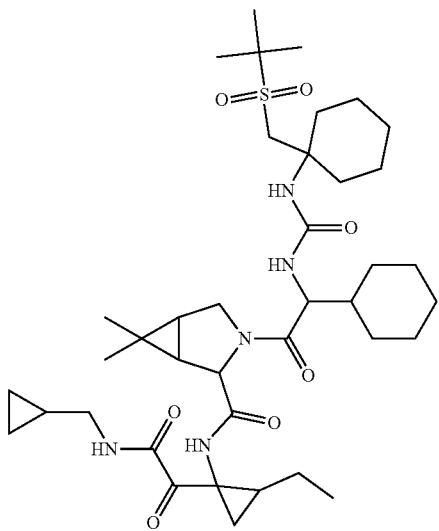 [SMILES: CCC1CC1(NC(=O)C1C2C(CN1C(=O)C(NC(=O)NC1(CS(=O)(=O)C(C)(C)C)CCCCC1)C1CCCCC1)C2(C)C)C(=O)C(=O)NCC1CC1]
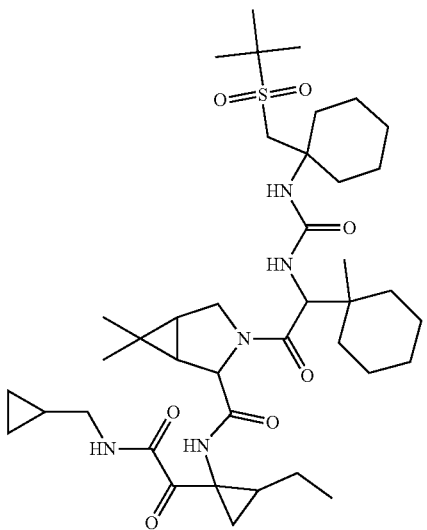 [SMILES: CCC1CC1(NC(=O)C1C2C(CN1C(=O)C(NC(=O)NC1(CS(=O)(=O)C(C)(C)C)CCCCC1)C1(C)CCCCC1)C2(C)C)C(=O)C(=O)NCC1CC1]

TABLE 62-continued
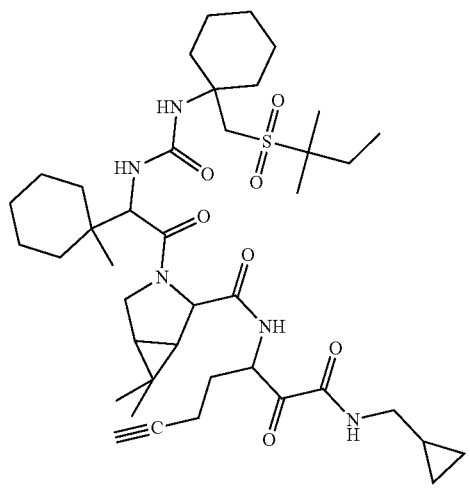 [SMILES: C#CCCC(NC(=O)C1C2C(CN1C(=O)C(NC(=O)NC1(CS(=O)(=O)C(C)(C)CC)CCCCC1)C1(C)CCCCC1)C2(C)C)C(=O)C(=O)NCC1CC1]
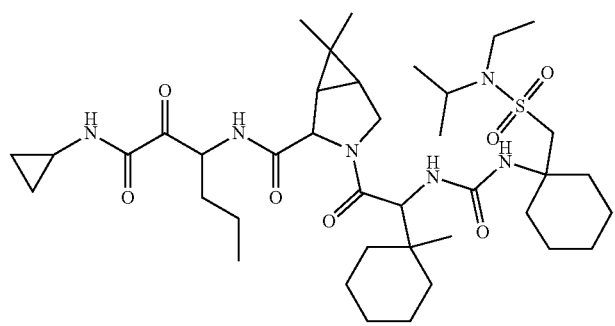 [SMILES: CCCC(NC(=O)C1C2C(CN1C(=O)C(NC(=O)NC1(CS(=O)(=O)N(CC)C(C)C)CCCCC1)C1(C)CCCCC1)C2(C)C)C(=O)C(=O)NC1CC1]
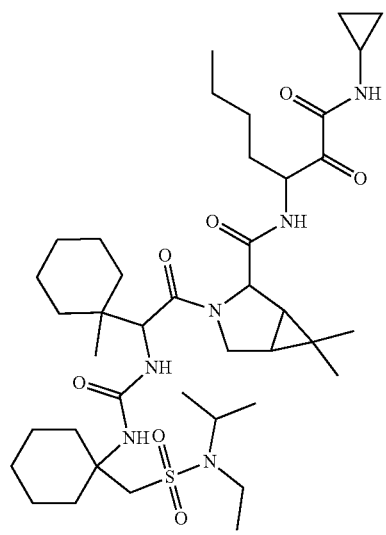 [SMILES: CCCCC(NC(=O)C1C2C(CN1C(=O)C(NC(=O)NC1(CS(=O)(=O)N(CC)C(C)C)CCCCC1)C1(C)CCCCC1)C2(C)C)C(=O)C(=O)NC1CC1]

TABLE 62-continued
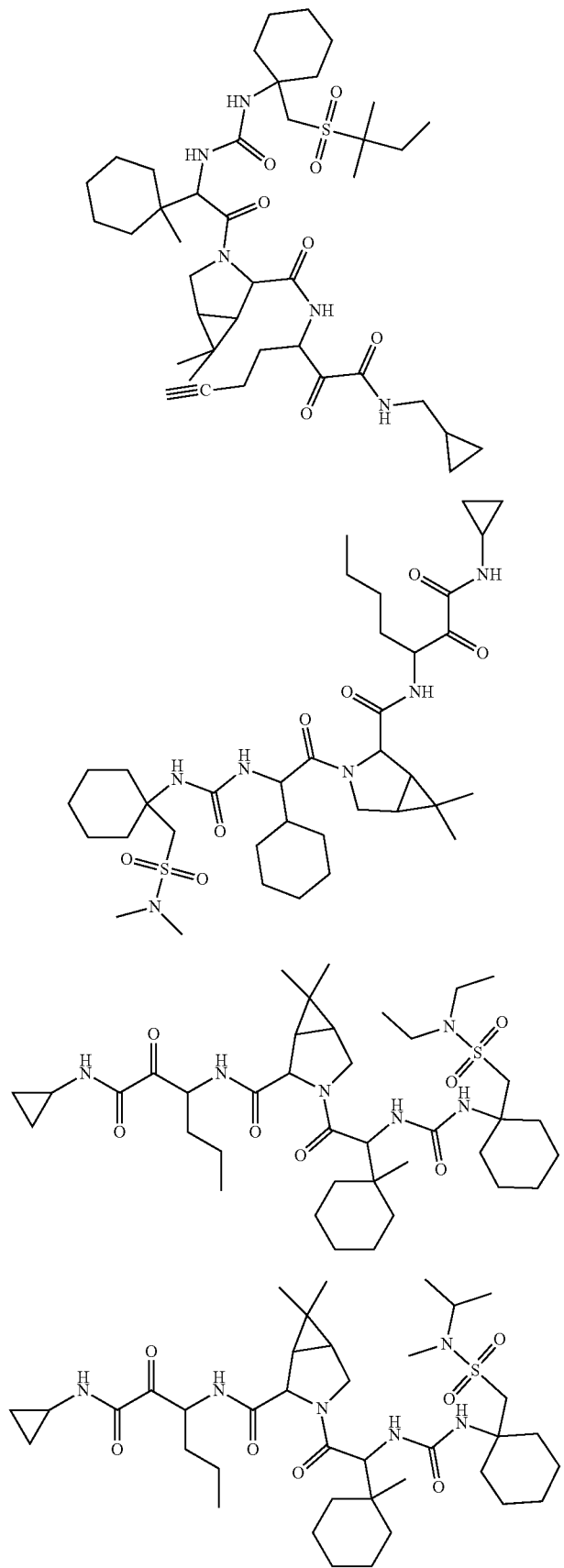

TABLE 62-continued
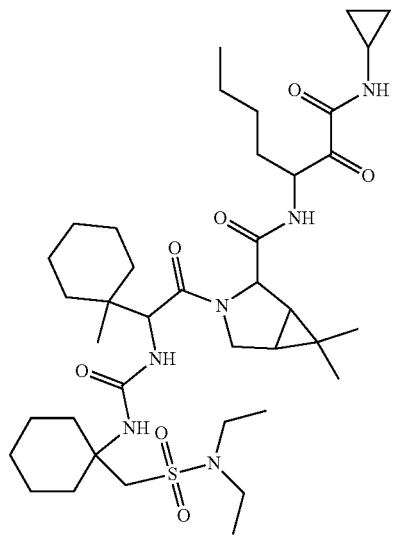 [SMILES: CCCCC(NC(=O)C1C2C(CN1C(=O)C(NC(=O)NC1(CS(=O)(=O)N(CC)CC)CCCCC1)C1(C)CCCCC1)C2(C)C)C(=O)C(=O)NC1CC1]
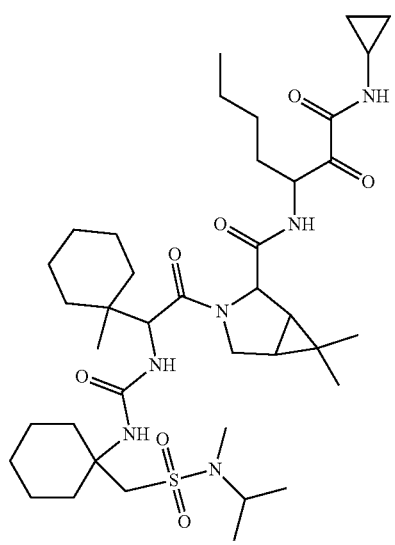 [SMILES: CCCCC(NC(=O)C1C2C(CN1C(=O)C(NC(=O)NC1(CS(=O)(=O)N(C)C(C)C)CCCCC1)C1(C)CCCCC1)C2(C)C)C(=O)C(=O)NC1CC1]
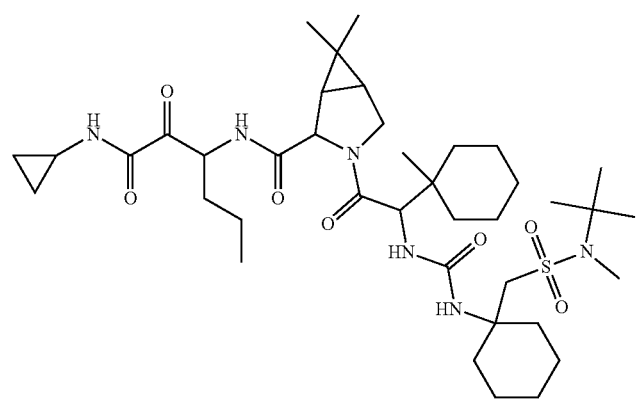 [SMILES: CCCC(NC(=O)C1C2C(CN1C(=O)C(NC(=O)NC1(CS(=O)(=O)N(C)C(C)(C)C)CCCCC1)C1(C)CCCCC1)C2(C)C)C(=O)C(=O)NC1CC1]

TABLE 62-continued
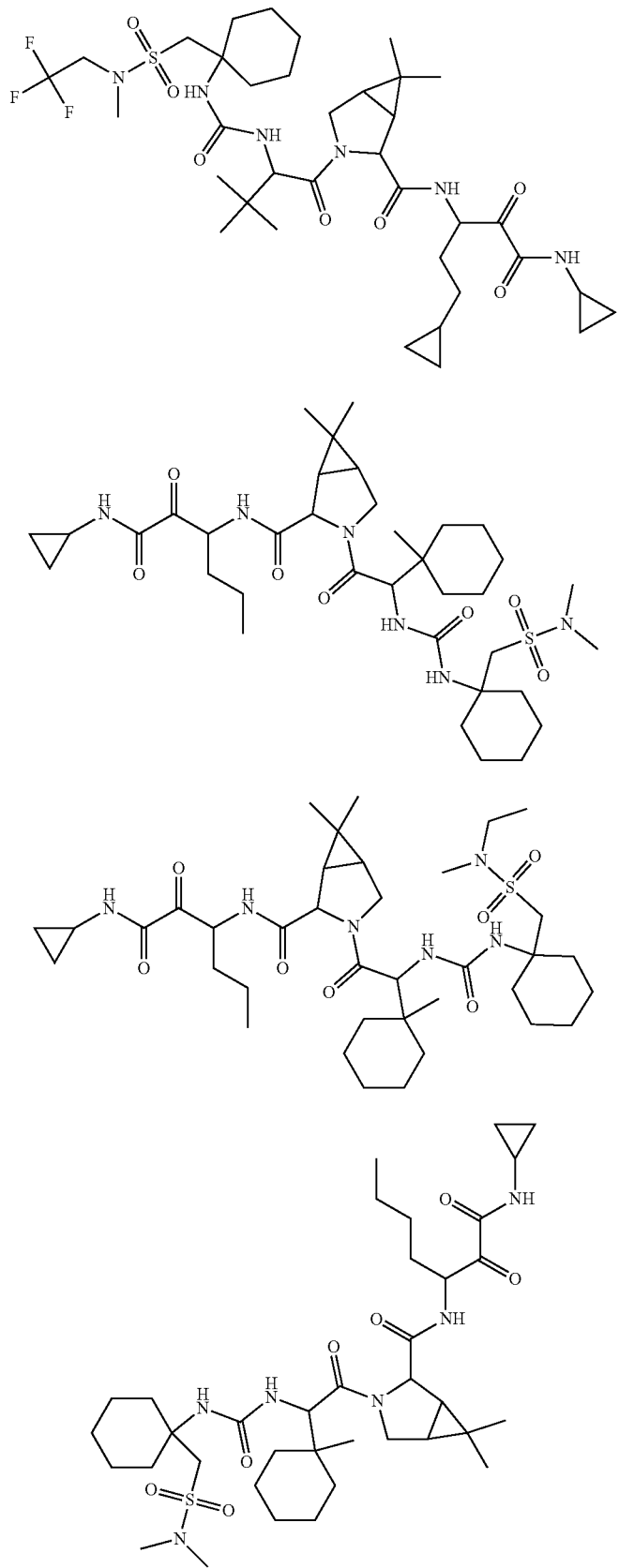

TABLE 62-continued
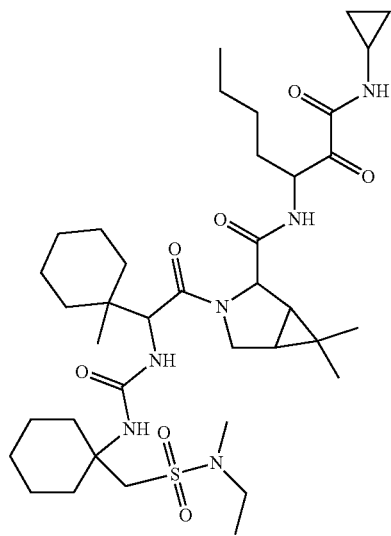 [SMILES: CCCCC(NC(=O)C1C2C(CN1C(=O)C(NC(=O)NC1(CS(=O)(=O)N(C)CC)CCCCC1)C1(C)CCCCC1)C2(C)C)C(=O)C(=O)NC1CC1]
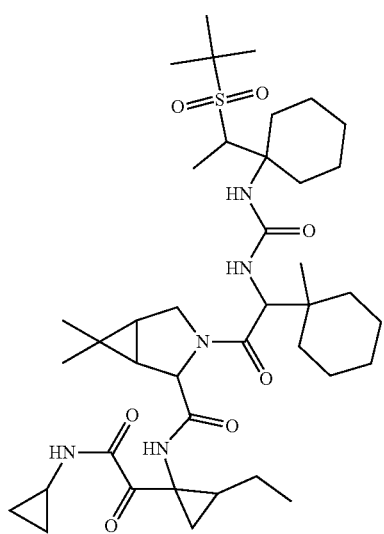 [SMILES: CCC1CC1(NC(=O)C1C2C(CN1C(=O)C(NC(=O)NC1(C(C)S(=O)(=O)C(C)(C)C)CCCCC1)C1(C)CCCCC1)C2(C)C)C(=O)C(=O)NC1CC1]

TABLE 62-continued
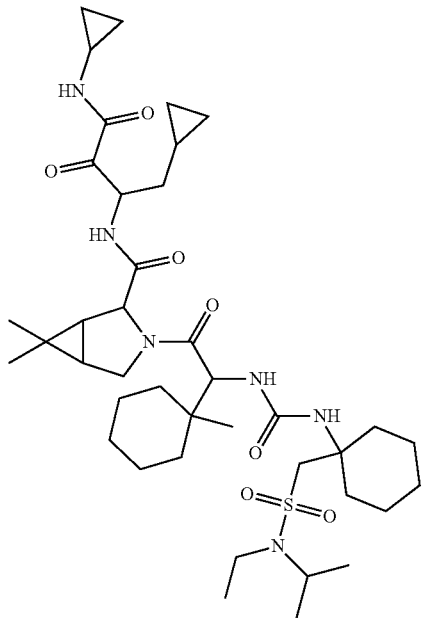 [SMILES: CCN(C(C)C)S(=O)(=O)CC1(NC(=O)NC(C(=O)N2CC3C(C2C(=O)NC(CC2CC2)C(=O)C(=O)NC2CC2)C3(C)C)C2(C)CCCCC2)CCCCC1]
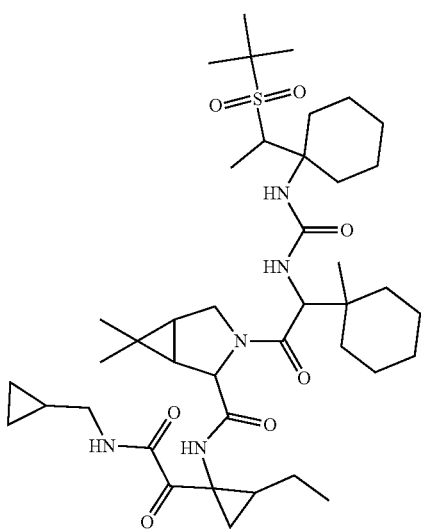 [SMILES: CCC1CC1(NC(=O)C1C2C(CN1C(=O)C(NC(=O)NC1(C(C)S(=O)(=O)C(C)(C)C)CCCCC1)C1(C)CCCCC1)C2(C)C)C(=O)C(=O)NCC1CC1]

TABLE 62-continued
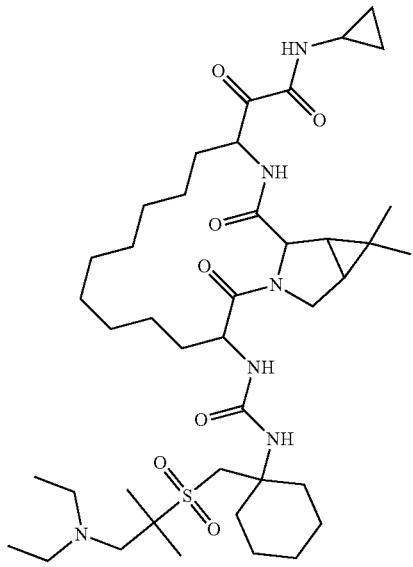 [SMILES: CCN(CC)CC(C)(C)S(=O)(=O)CC1(NC(=O)NC2CCCCCCCCCC(C(=O)C(=O)NC3CC3)NC(=O)C3C4C(CN3C2=O)C4(C)C)CCCCC1]
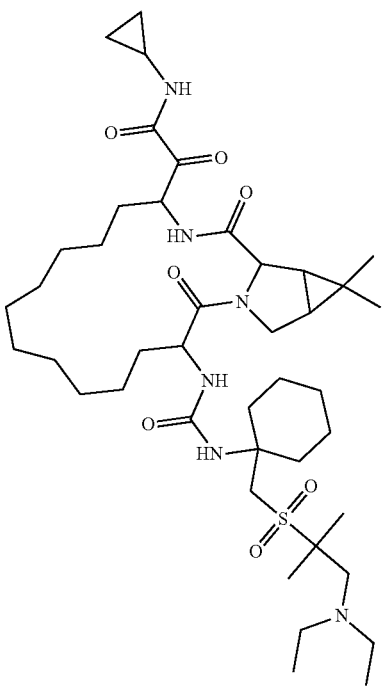 [SMILES: CCN(CC)CC(C)(C)S(=O)(=O)CC1(NC(=O)NC2CCCCCCCCCCC(C(=O)C(=O)NC3CC3)NC(=O)C3C4C(CN3C2=O)C4(C)C)CCCCC1]

TABLE 62-continued
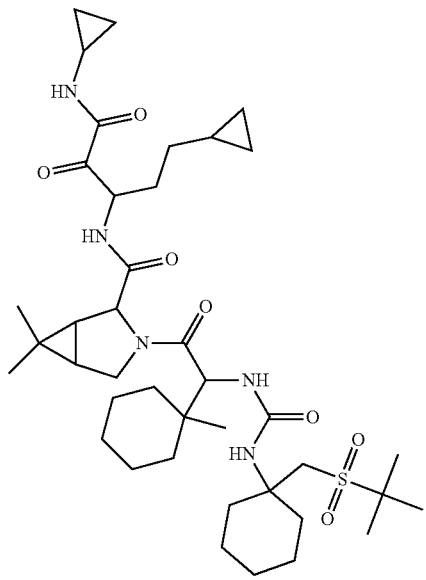 [SMILES: CC1(C(NC(=O)NC2(CS(=O)(=O)C(C)(C)C)CCCCC2)C(=O)N2CC3C(C2C(=O)NC(CCC2CC2)C(=O)C(=O)NC2CC2)C3(C)C)CCCCC1]
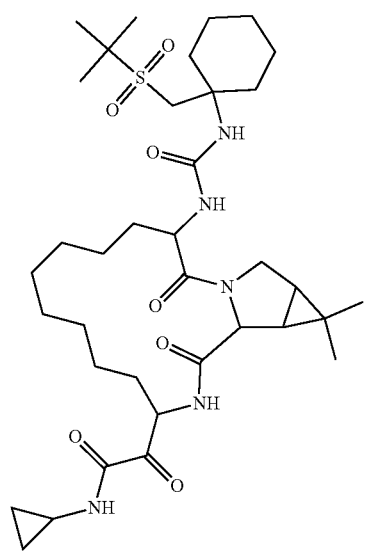 [SMILES: CC1(C)C2CN3C(=O)C(NC(=O)NC4(CS(=O)(=O)C(C)(C)C)CCCCC4)CCCCCCCCC(C(=O)C(=O)NC4CC4)NC(=O)C3C21]

TABLE 62-continued
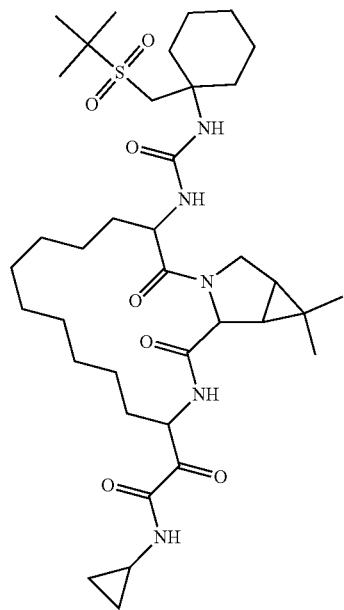 [SMILES: CC1(C)C2CN3C(=O)C(NC(=O)NC4(CS(=O)(=O)C(C)(C)C)CCCCC4)CCCCCCCCCC(C(=O)C(=O)NC4CC4)NC(=O)C3C21]
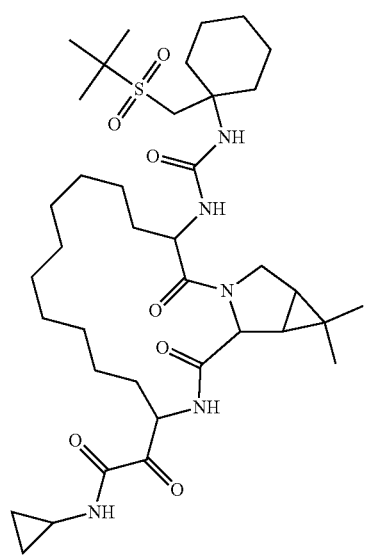 [SMILES: CC1(C)C2CN3C(=O)C(NC(=O)NC4(CS(=O)(=O)C(C)(C)C)CCCCC4)CCCCCCCCCCC(C(=O)C(=O)NC4CC4)NC(=O)C3C21]

TABLE 62-continued
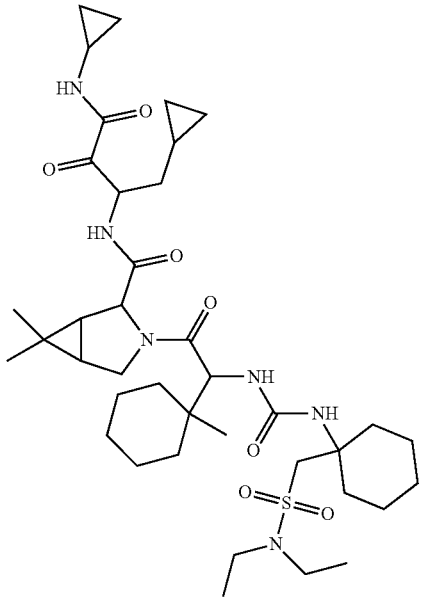 [SMILES: CCN(CC)S(=O)(=O)CC1(NC(=O)NC(C(=O)N2CC3C(C2C(=O)NC(CC2CC2)C(=O)C(=O)NC2CC2)C3(C)C)C2(C)CCCCC2)CCCCC1]
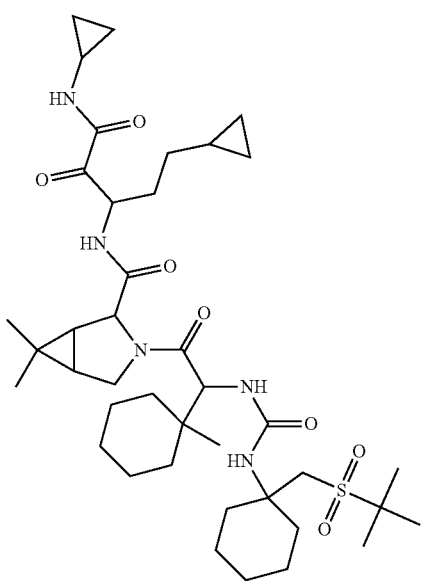 [SMILES: CC1(C(NC(=O)NC2(CS(=O)(=O)C(C)(C)C)CCCCC2)C(=O)N2CC3C(C2C(=O)NC(CCC2CC2)C(=O)C(=O)NC2CC2)C3(C)C)CCCCC1]

TABLE 62-continued
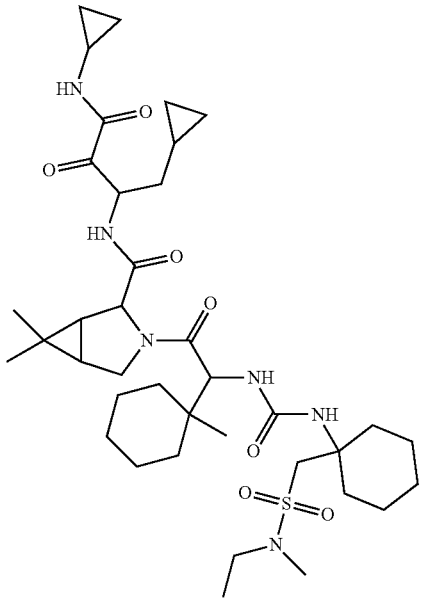 [SMILES: CCN(C)S(=O)(=O)CC1(NC(=O)NC(C(=O)N2CC3C(C2C(=O)NC(CC2CC2)C(=O)C(=O)NC2CC2)C3(C)C)C2(C)CCCCC2)CCCCC1]
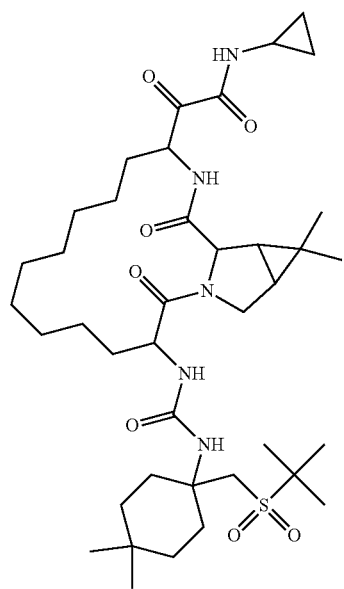 [SMILES: CC1(C)CCC(CS(=O)(=O)C(C)(C)C)(NC(=O)NC2CCCCCCCCCC(C(=O)C(=O)NC3CC3)NC(=O)C3C4C(CN3C2=O)C4(C)C)CC1]

TABLE 62-continued
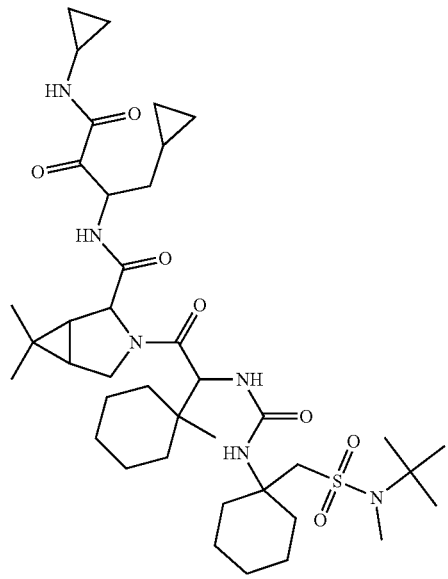 [SMILES: CN(C(C)(C)C)S(=O)(=O)CC1(NC(=O)NC(C(=O)N2CC3C(C2C(=O)NC(CC2CC2)C(=O)C(=O)NC2CC2)C3(C)C)C2(C)CCCCC2)CCCCC1]
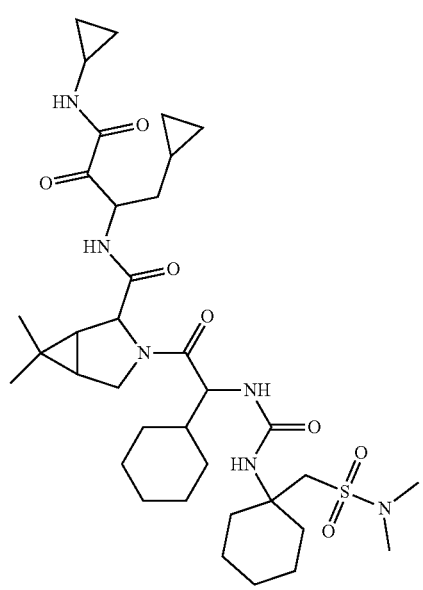

TABLE 62-continued
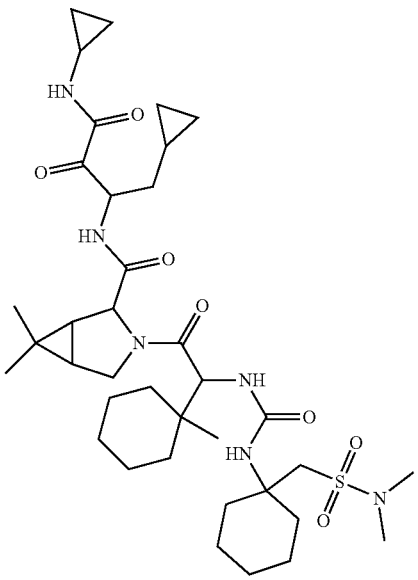
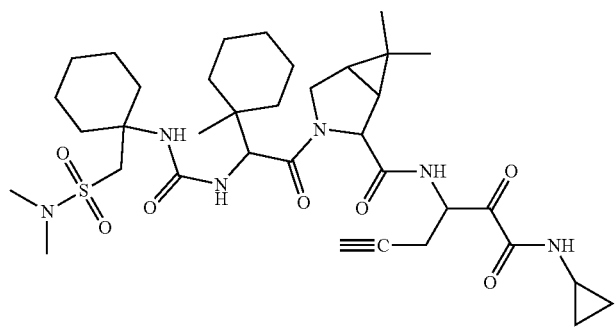 [SMILES: C#CCC(NC(=O)C1C2C(CN1C(=O)C(NC(=O)NC1(CS(=O)(=O)N(C)C)CCCCC1)C1(C)CCCCC1)C2(C)C)C(=O)C(=O)NC1CC1]
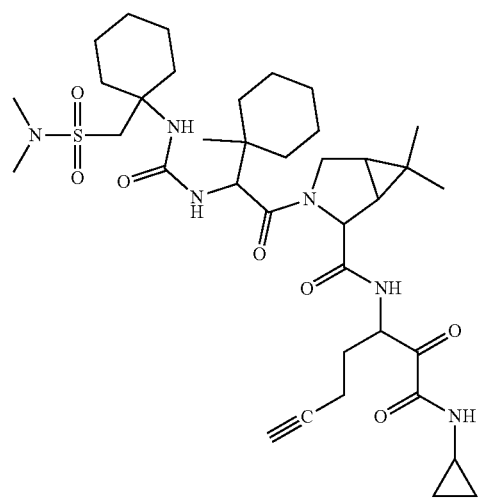 [SMILES: C#CCCC(NC(=O)C1C2C(CN1C(=O)C(NC(=O)NC1(CS(=O)(=O)N(C)C)CCCCC1)C1(C)CCCCC1)C2(C)C)C(=O)C(=O)NC1CC1]

TABLE 62-continued
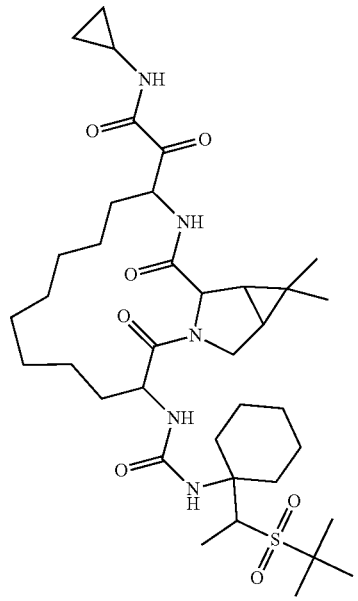 [SMILES: CC(C1(NC(=O)NC2CCCCCCCCC(C(=O)C(=O)NC3CC3)NC(=O)C3C4C(CN3C2=O)C4(C)C)CCCCC1)S(=O)(=O)C(C)(C)C]
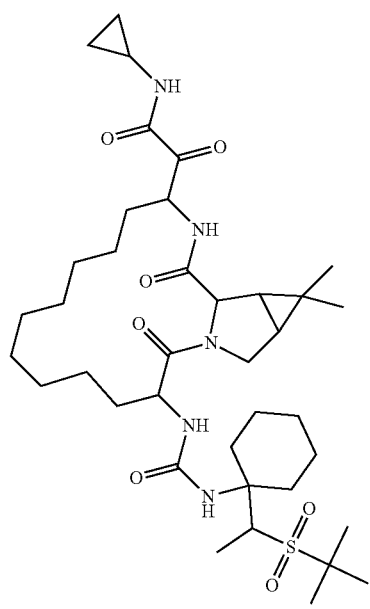 [SMILES: CC(C1(NC(=O)NC2CCCCCCCCCC(C(=O)C(=O)NC3CC3)NC(=O)C3C4C(CN3C2=O)C4(C)C)CCCCC1)S(=O)(=O)C(C)(C)C]

TABLE 62-continued
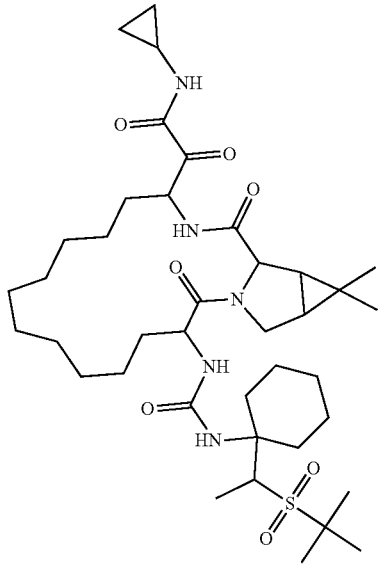 [SMILES: CC(C1(NC(=O)NC2CCCCCCCCCCC(C(=O)C(=O)NC3CC3)NC(=O)C3C4C(CN3C2=O)C4(C)C)CCCCC1)S(=O)(=O)C(C)(C)C]
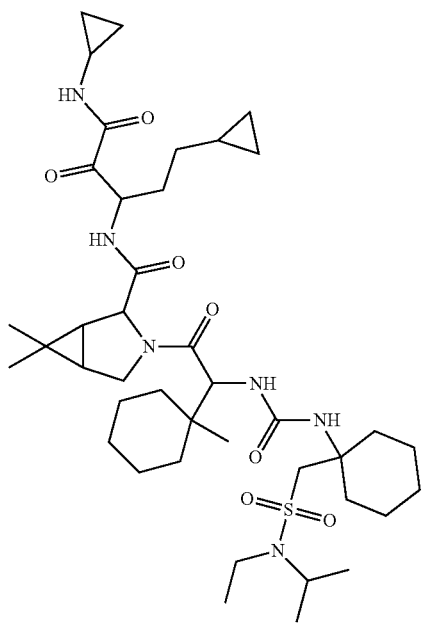 [SMILES: CCN(C(C)C)S(=O)(=O)CC1(NC(=O)NC(C(=O)N2CC3C(C2C(=O)NC(CCC2CC2)C(=O)C(=O)NC2CC2)C3(C)C)C2(C)CCCCC2)CCCCC1]

TABLE 62-continued
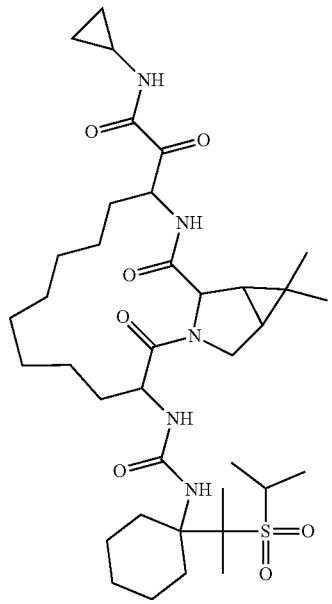 [SMILES: CC(C)S(=O)(=O)C(C)(C)C1(NC(=O)NC2CCCCCCCCC(C(=O)C(=O)NC3CC3)NC(=O)C3C4C(CN3C2=O)C4(C)C)CCCCC1]
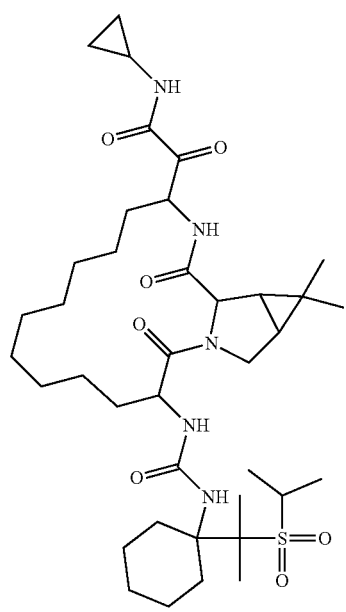 [SMILES: CC(C)S(=O)(=O)C(C)(C)C1(NC(=O)NC2CCCCCCCCCC(C(=O)C(=O)NC3CC3)NC(=O)C3C4C(CN3C2=O)C4(C)C)CCCCC1]

TABLE 62-continued
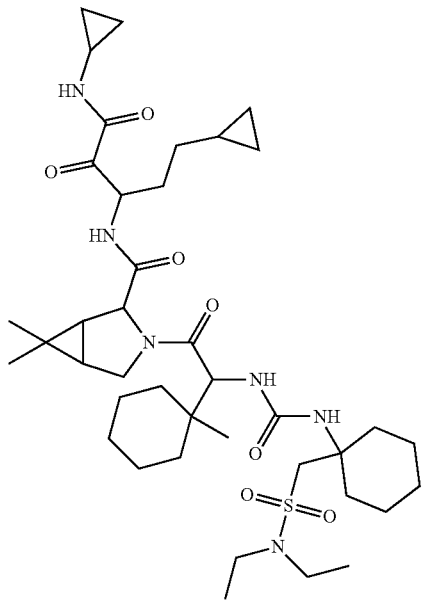 [SMILES: CCN(CC)S(=O)(=O)CC1(NC(=O)NC(C(=O)N2CC3C(C2C(=O)NC(CCC2CC2)C(=O)C(=O)NC2CC2)C3(C)C)C2(C)CCCCC2)CCCCC1]
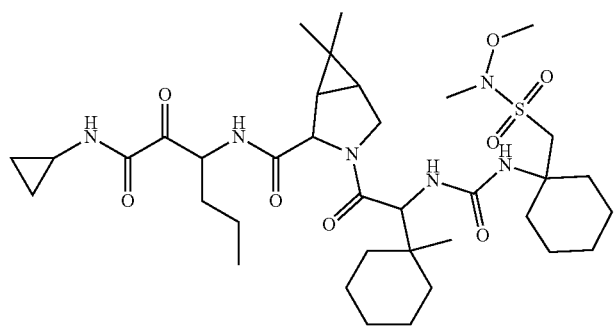 [SMILES: CCCC(NC(=O)C1C2C(CN1C(=O)C(NC(=O)NC1(CS(=O)(=O)N(C)OC)CCCCC1)C1(C)CCCCC1)C2(C)C)C(=O)C(=O)NC1CC1]
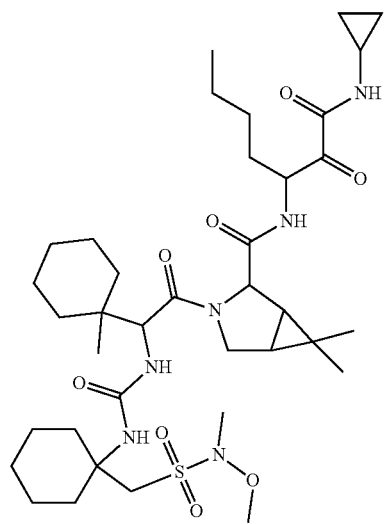 [SMILES: CCCCC(NC(=O)C1C2C(CN1C(=O)C(NC(=O)NC1(CS(=O)(=O)N(C)OC)CCCCC1)C1(C)CCCCC1)C2(C)C)C(=O)C(=O)NC1CC1]

TABLE 62-continued
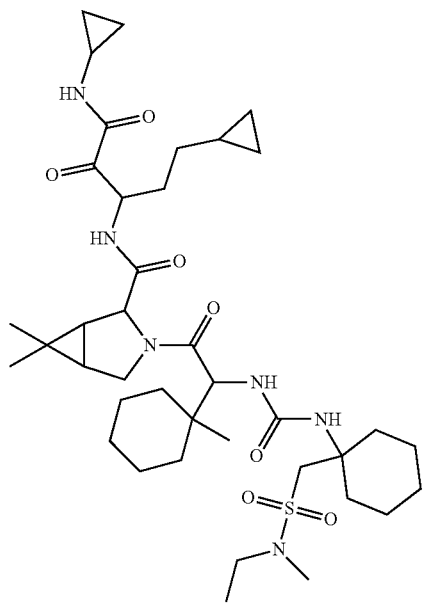 [SMILES: CCN(C)S(=O)(=O)CC1(NC(=O)NC(C(=O)N2CC3C(C2C(=O)NC(CCC2CC2)C(=O)C(=O)NC2CC2)C3(C)C)C2(C)CCCCC2)CCCCC1]
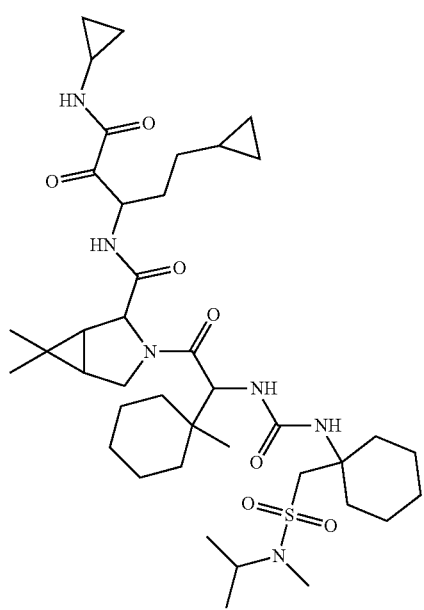 [SMILES: CC(C)N(C)S(=O)(=O)CC1(NC(=O)NC(C(=O)N2CC3C(C2C(=O)NC(CCC2CC2)C(=O)C(=O)NC2CC2)C3(C)C)C2(C)CCCCC2)CCCCC1]

TABLE 62-continued
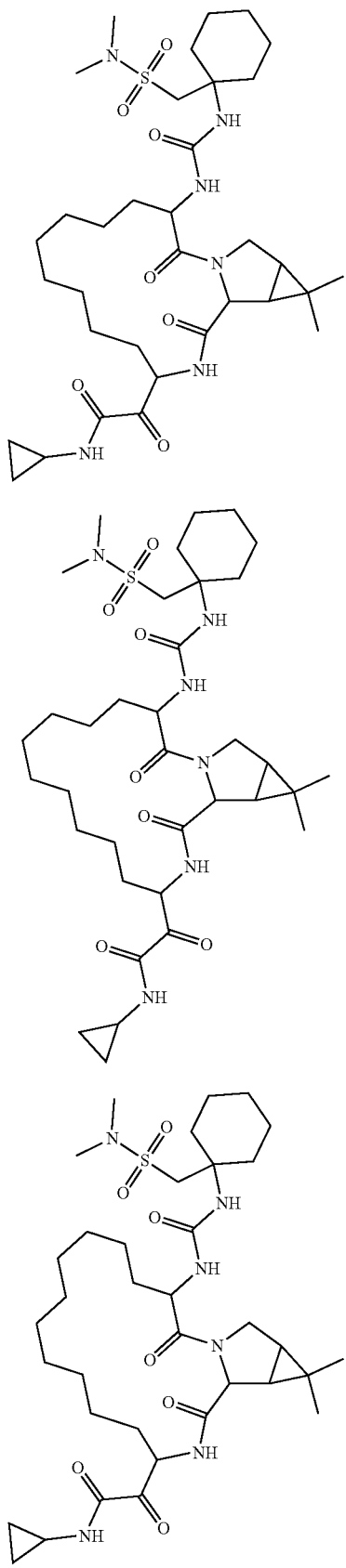

TABLE 62-continued
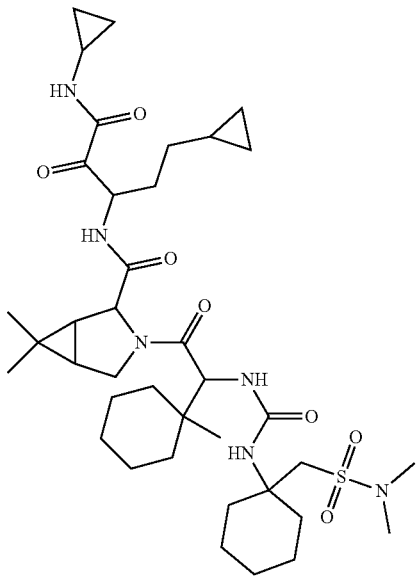
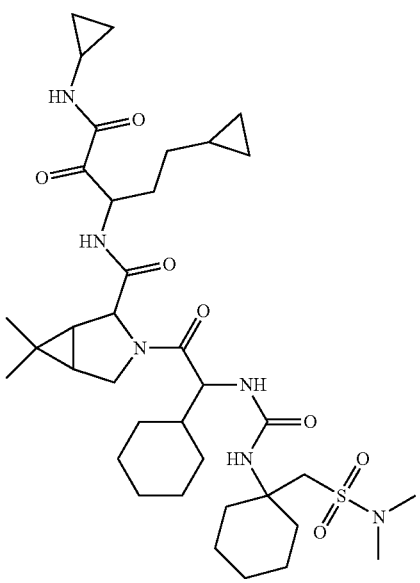

TABLE 62-continued

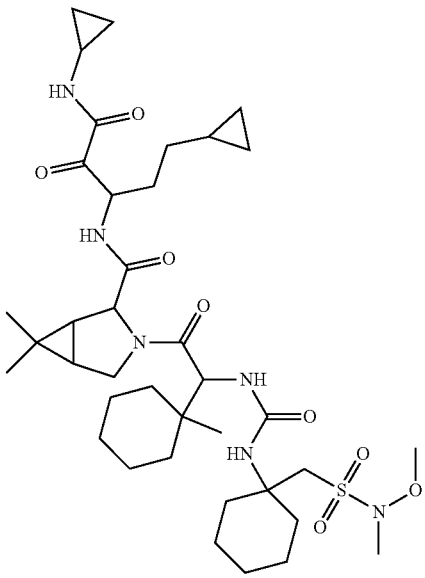

In one or more implementations, Nitecapone (3-(3,4-dihydroxy-5-nitrobenzylidene)pentane-2,4-dione), a clinically investigated catechol O-methyltransferase inhibitor. In one particular implementation, the compound, or variations and permutations thereof, is further described in WO2014164667 the contents of which are hereby incorporated by reference for all purposes and the specific purposes identified herein. In some embodiments, such compounds are represented by any one or more of the structures shown in Table 74. Any one of the compounds depicted in Table 74 is suitable for use in the methods of the present disclosure.

TABLE 63

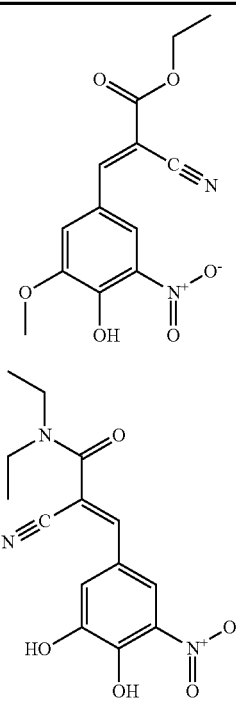

In one or more implementations, the compound is ornithine phenylacetate ((2S)-2,5-diaminopentanoic acid; 2-phenylacetic acid) or MNK-6105, a clinically investigated nuclear factor kappa B modulator or Glutamine synthetase stimulator. In one particular implementation, the compound, or variations and permutations thereof, is further described in WO2000015634 the contents of which are hereby incorporated by reference for all purposes and the specific purposes identified herein. In some embodiments, such compounds are represented by any one or more of the structures shown in Table 1. Any one of the compounds depicted in Table 1 is suitable for use in the methods of the present disclosure.

TABLE 64

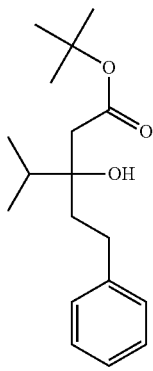 [SMILES: CC(C)C(O)(CCc1ccccc1)CC(=O)OC(C)(C)C]

TABLE 64-continued

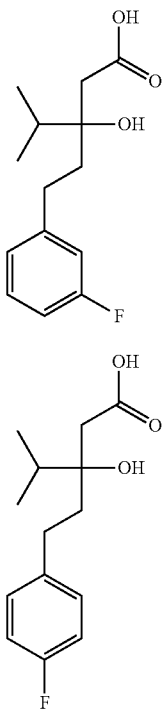

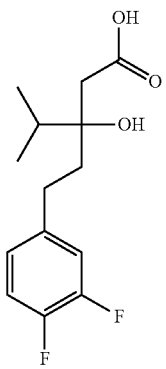

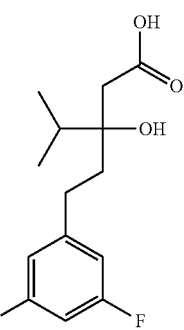

In one or more implementations, the compound is paritaprevir ((1S,4R,6S,7Z,14S,18R)—N-cyclopropylsulfonyl-14-[(5-methylpyrazine-2-carbonyl)amino]-2,15-dioxo-18-phenanthridin-6-yloxy-3,16-diazatricyclo[14.3.0.04,6]nonadec-7-ene-4-carboxamide), is a clinically investigated hepatitis C virus NS3 protease inhibitor. In one particular implementation, the compound, or variations and permutations thereof, is further described in WO2010030359; WO2016127859; and WO2012092409 the contents of which are hereby incorporated by reference for all purposes and the specific purposes identified herein. In some embodiments, such compounds are represented by any one or more of the structures shown in Table 76. Any one of the compounds depicted in Table 76 is suitable for use in the methods of the present disclosure.

TABLE 65

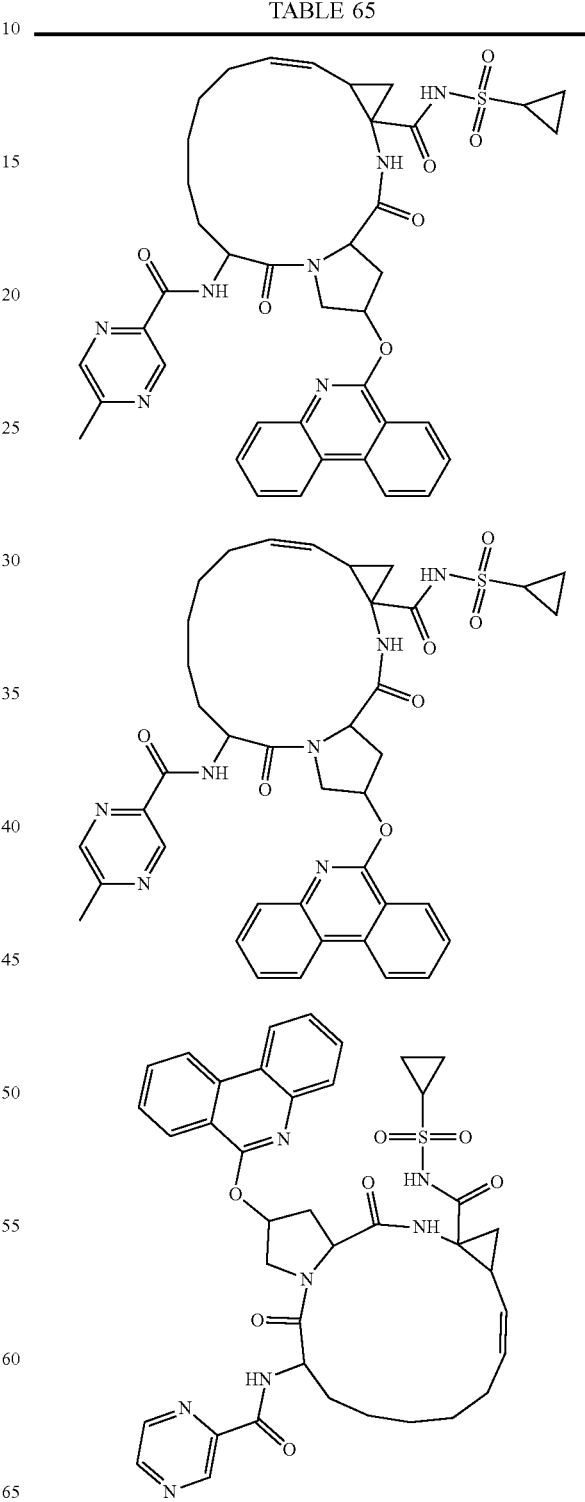

TABLE 65-continued

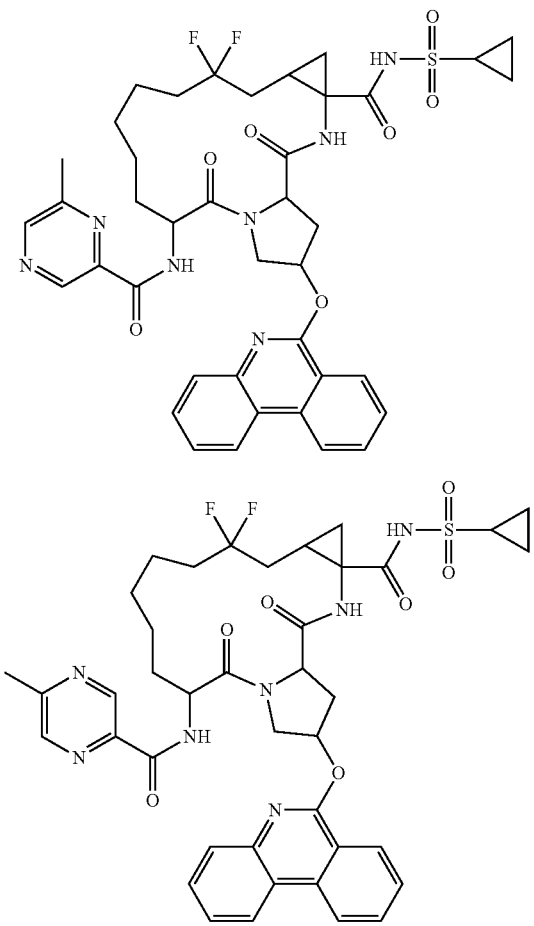

In one or more implementations, the compound is perindopril ((2S,3aS,7aS)-1-[(2S)-2-[[(2S)-1-ethoxy-1-oxopentan-2-yl]amino]propanoyl]-2,3,3a,4,5,6,7,7a-octahydroindole-2-carboxylic acid), a clinically investigated ACE inhibitor. In one particular implementation, the compound, or variations and permutations thereof, is further described in WO2007117560 the contents of which are hereby incorporated by reference for all purposes and the specific purposes identified herein. In some embodiments, such compounds are represented by any one or more of the structures shown in Table 77. Any one of the compounds depicted in Table 77 is suitable for use in the methods of the present disclosure.

TABLE 66

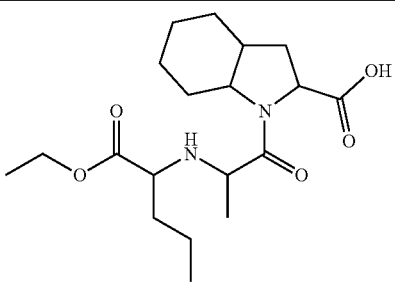

In one or more implementations, the compound is quinapril hydrochloride ((3S)-2-[(2S)-2-[[(2S)-1-ethoxy-1-oxo-4-phenylbutan-2-yl]amino]propanoyl]-3,4-dihydro-1H-isoquinoline-3-carboxylic acid;hydrochloride), a clinically investigated ACE inhibitor. In one particular implementation, the compound, or variations and permutations thereof, is further described in WO2007117560 the contents of which are hereby incorporated by reference for all purposes and the specific purposes identified herein. In some embodiments, such compounds are represented by any one or more of the structures shown in Table 78. Any one of the compounds depicted in Table 78 is suitable for use in the methods of the present disclosure.

TABLE 67

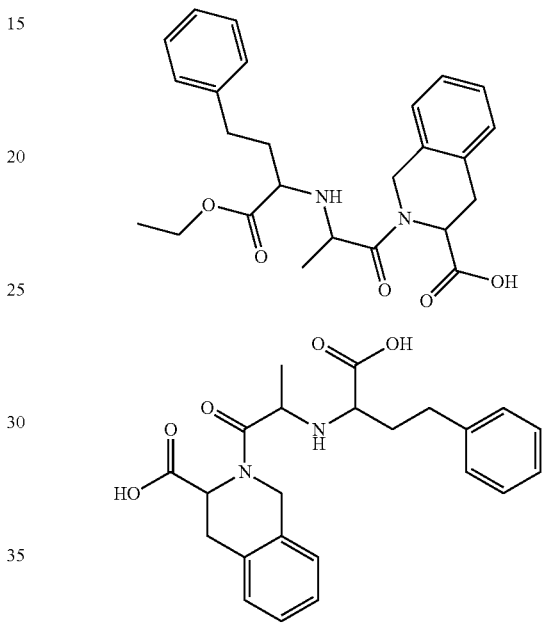

In one or more implementations, the compound is ramipril ((2S,3aS,6aS)-1-[(2S)-2-[[(2S)-1-ethoxy-1-oxo-4-phenylbutan-2-yl]amino]propanoyl]-3,3a,4,5,6,6a-hexahydro-2H-cyclopenta[b]pyrrole-2-carboxylic acid), a clinically investigated ACE inhibitor. In one particular implementation, the compound, or variations and permutations thereof, is further described in WO2007117560 the contents of which are hereby incorporated by reference for all purposes and the specific purposes identified herein. In some embodiments, such compounds are represented by any one or more of the structures shown in Table 79. Any one of the compounds depicted in Table 79 is suitable for use in the methods of the present disclosure.

TABLE 68

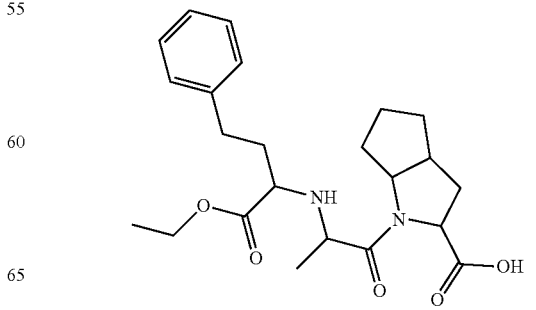

TABLE 68-continued

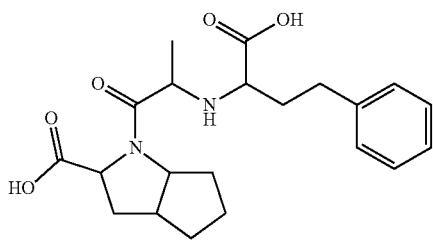 [SMILES: CC(NC(CCc1ccccc1)C(=O)O)C(=O)N1C(C(=O)O)CC2CCCC21]

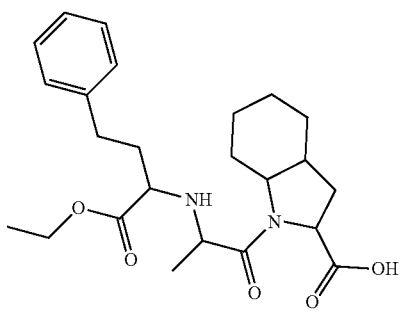 [SMILES: CCOC(=O)C(CCc1ccccc1)NC(C)C(=O)N1C(C(=O)O)CC2CCCCC21]

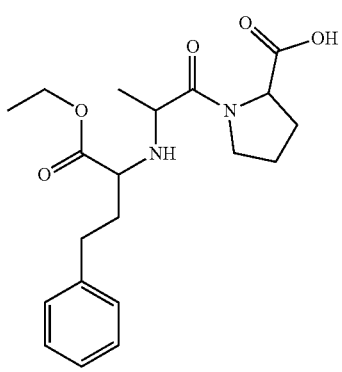 [SMILES: CCOC(=O)C(CCc1ccccc1)NC(C)C(=O)N1CCCC1C(=O)O]

In one implementation, the compound is chlorcyclizine hydrochloride (1-[(4-chlorophenyl)-phenylmethyl]-4-methylpiperazine;hydrochloride), a clinically investigated plasmepsin inhibitor; renin inhibitor; beta secretase inhibitor; aspartic protease inhibitor; HIV protease inhibitor. In one particular implementation, the compound, or variations and permutations thereof, is further described in WO2007117560 the contents of which are hereby incorporated by reference for all purposes and the specific purposes identified herein. In some embodiments, such compounds are represented by any one or more of the structures shown in Table 80. Any one of the compounds depicted in Table 80 is suitable for use in the methods of the present disclosure.

TABLE 69

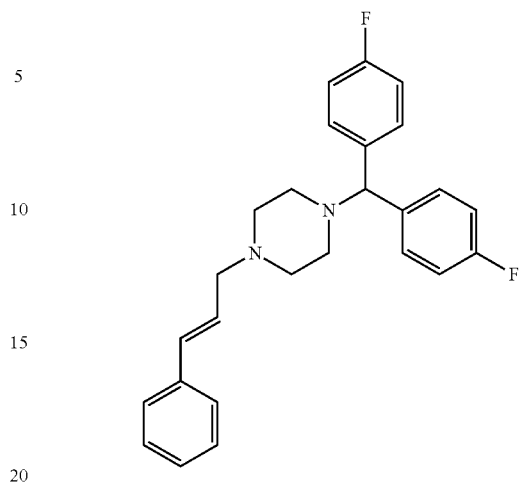

In one implementation, esmolol hydrochloride (methyl 3-[4-[2-hydroxy-3-(propan-2-ylamino)propoxy]phenyl]propanoate;hydrochloride), a clinically investigated beta adrenoceptor antagonist. In one particular implementation, the compound, or variations and permutations thereof, is further described in WO2007117560 the contents of which are hereby incorporated by reference for all purposes and the specific purposes identified herein. In some embodiments, such compounds are represented by any one or more of the structures shown in Table 81. Any one of the compounds depicted in Table 81 is suitable for use in the methods of the present disclosure.

TABLE 70

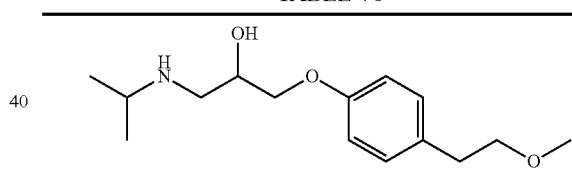

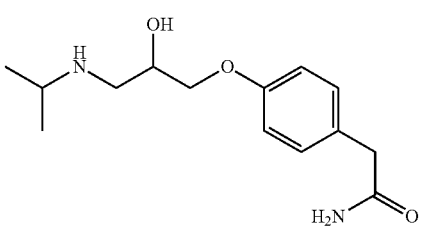 [SMILES: CC(C)NCC(O)COc1ccc(CC(N)=O)cc1]

In one or more implementations, the compound is seraprevir potassium, having the formula:

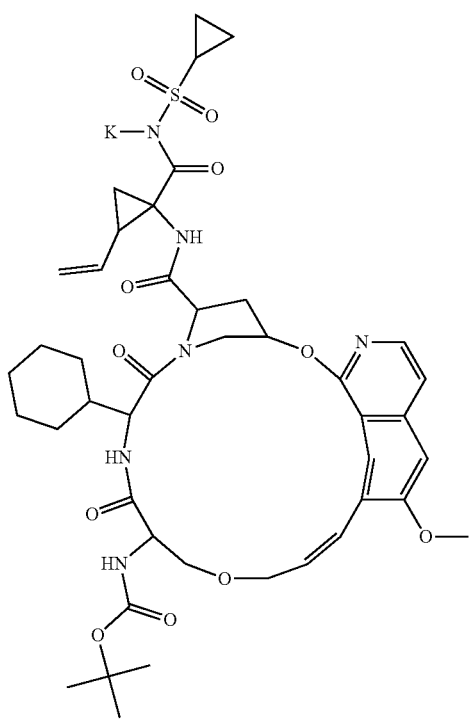

and clinically investigated as a hepatitis C virus NS3 protease inhibitor. In one particular implementation, the compound, or variations and permutations thereof, is further described in WO2007016441 and WO2008057208 the contents of which are hereby incorporated by reference for all purposes and the specific purposes identified herein. In some embodiments, such compounds are represented by any one or more of the structures shown in Table 82. Any one of the compounds depicted in Table 82 is suitable for use in the methods of the present disclosure.

TABLE 71

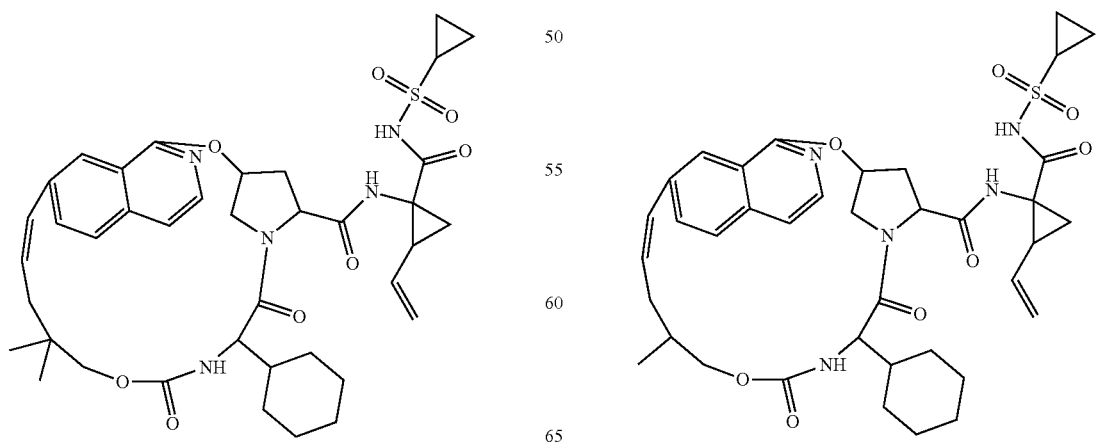

TABLE 71-continued

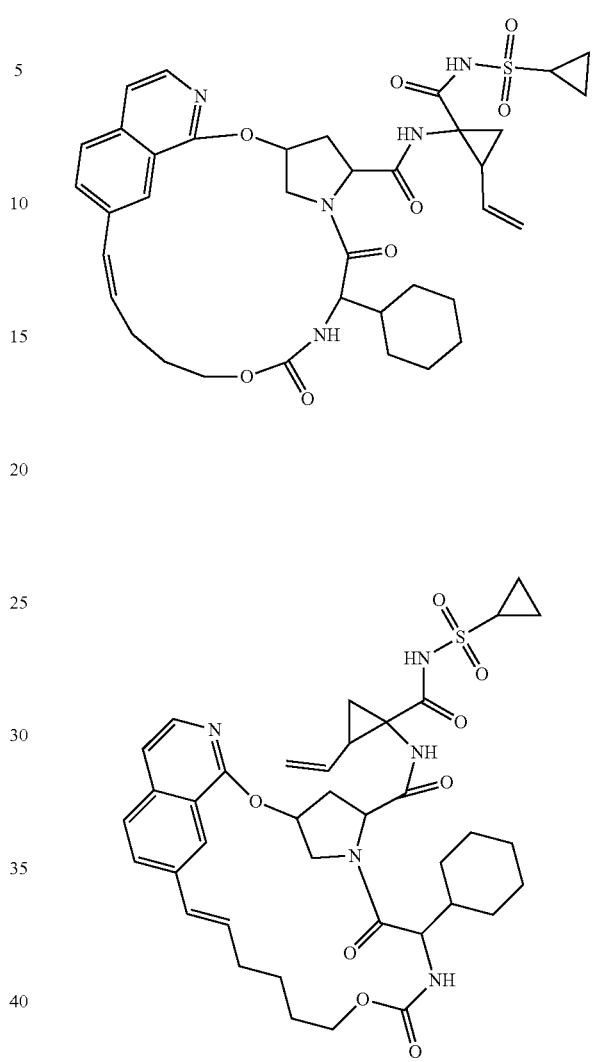

TABLE 71-continued
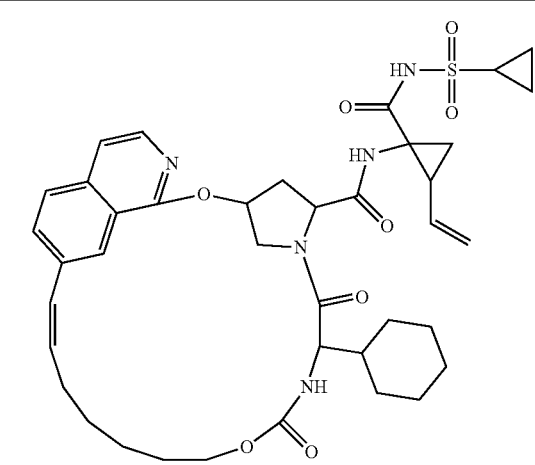
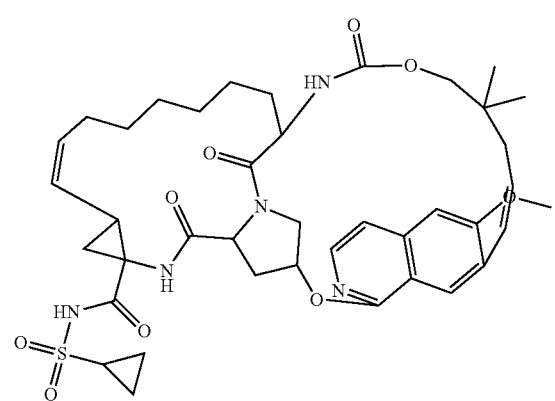 [SMILES: COc1cc2ccnc3c2cc1/C=C\CC(C)(C)COC(=O)NC1CCCCCC/C=C\C2CC2(C(=O)NS(=O)(=O)C2CC2)NC(=O)C2CC(CN2C1=O)O3]
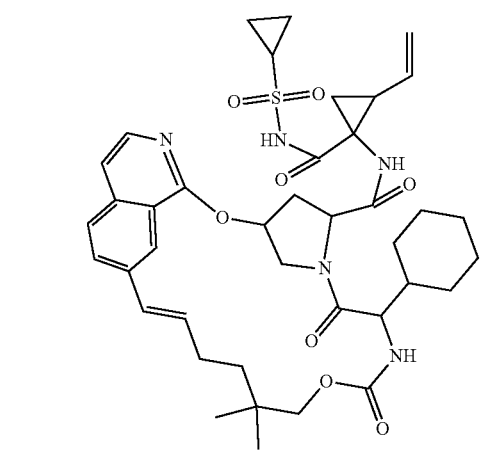 [SMILES: C=CC1CC1(NC(=O)C1CC2CN1C(=O)C(C1CCCCC1)NC(=O)OCC(C)(C)CC/C=C/c1ccc3ccnc(c3c1)O2)C(=O)NS(=O)(=O)C1CC1]
TABLE 71-continued
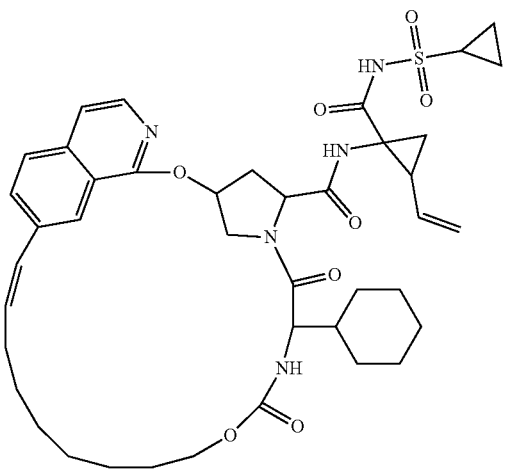 [SMILES: C=CC1CC1(NC(=O)C1CC2CN1C(=O)C(C1CCCCC1)NC(=O)OCCCCCCC/C=C\c1ccc3ccnc(c3c1)O2)C(=O)NS(=O)(=O)C1CC1]
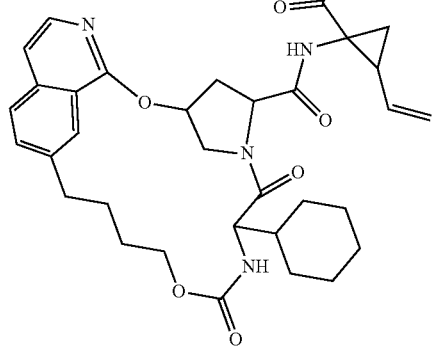
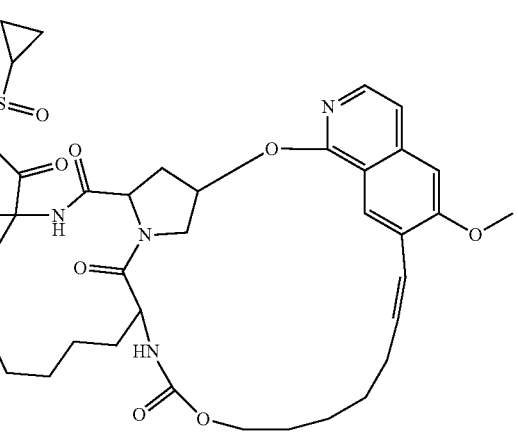

TABLE 71-continued
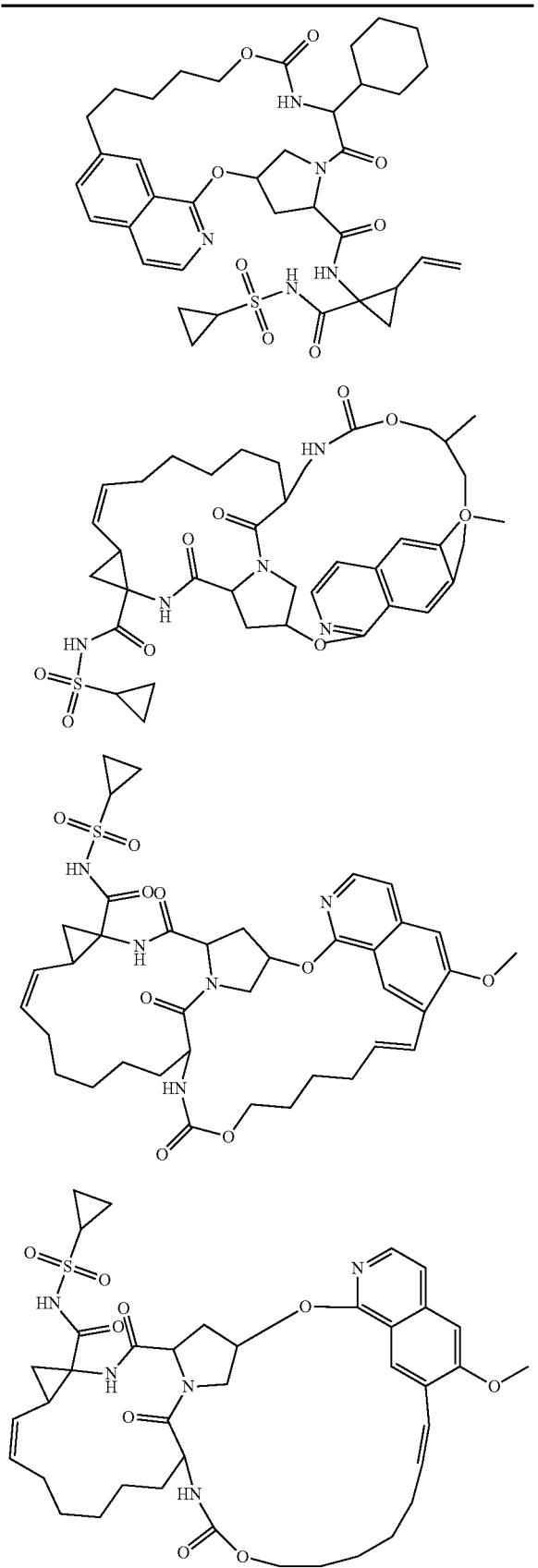
TABLE 71-continued
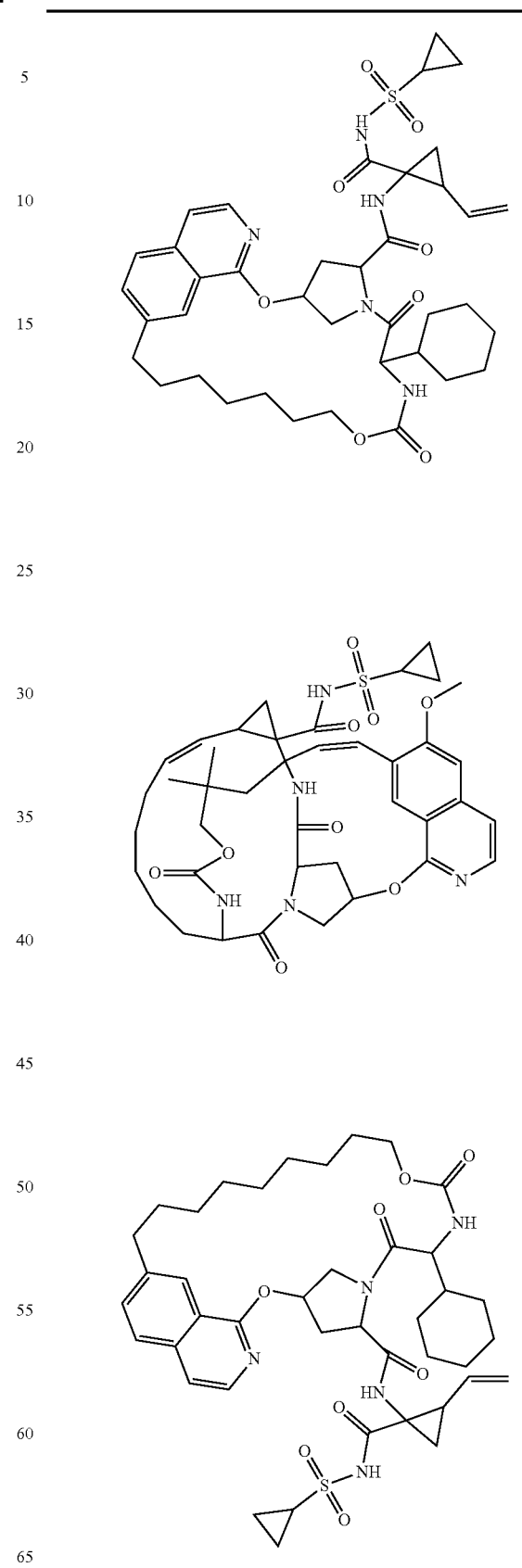

TABLE 71-continued

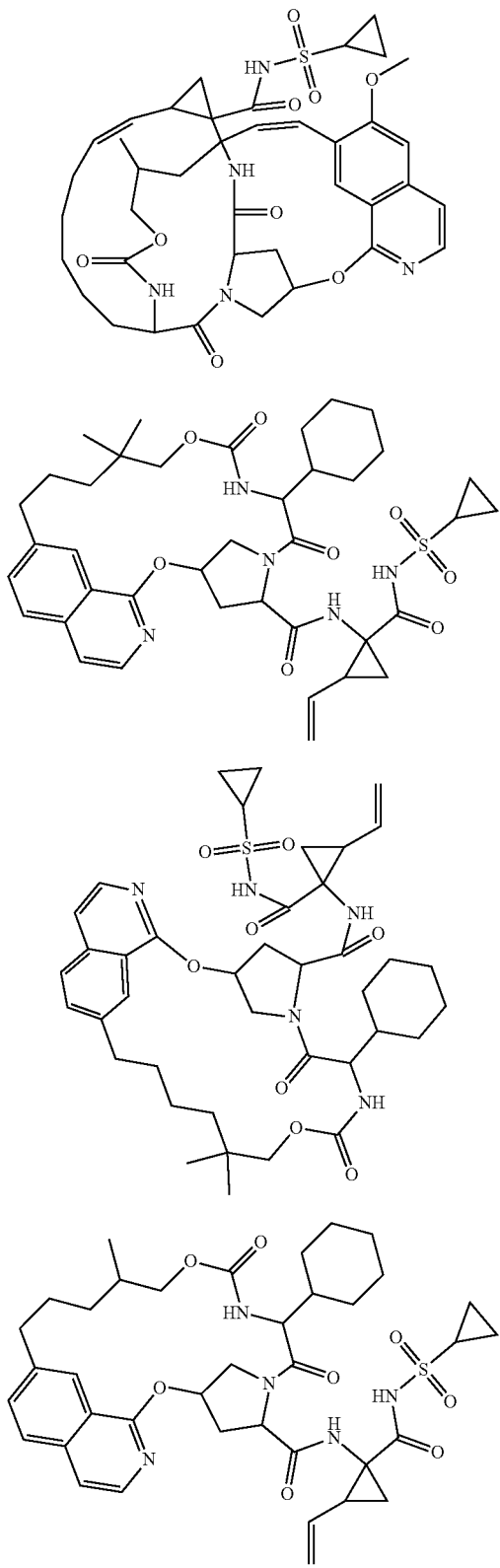

In one implementation, the compound is sobetirome (2-(4-(4-hydroxy-3-isopropylbenzyl)-3,5-dimethylphenoxy) acetic acid), a clinically investigated thyroid hormone receptor beta agonist. In one particular implementation, the compound, or variations and permutations thereof, is further described in WO2005073195 the contents of which are hereby incorporated by reference for all purposes and the specific purposes identified herein. In some embodiments, such compounds are represented by any one or more of the structures shown in Table 83. Any one of the compounds depicted in Table 83 is suitable for use in the methods of the present disclosure.

TABLE 72

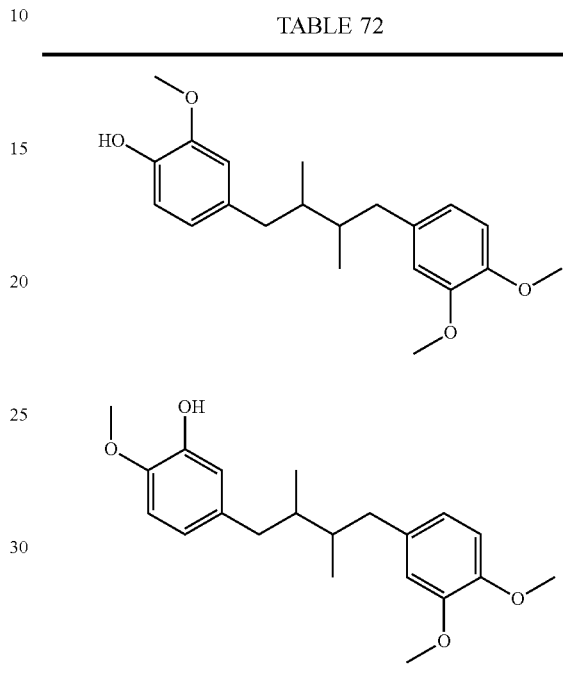

In one implementation, the compound is sodium phenylbutyrate (sodium;4-phenylbutanoate), a clinically investigated histone deacetylase inhibitor and BC ketoacid dehydrogenase kinase inhibitor. In one particular implementation, the compound, or variations and permutations thereof, is further described in WO2000015634 the contents of which are hereby incorporated by reference for all purposes and the specific purposes identified herein. In some embodiments, such compounds are represented by any one or more of the structures shown in Table 84. Any one of the compounds depicted in Table 84 is suitable for use in the methods of the present disclosure.

TABLE 73

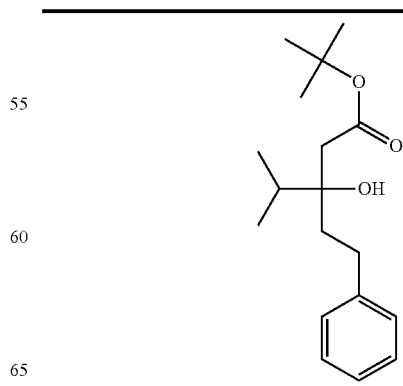

TABLE 73-continued

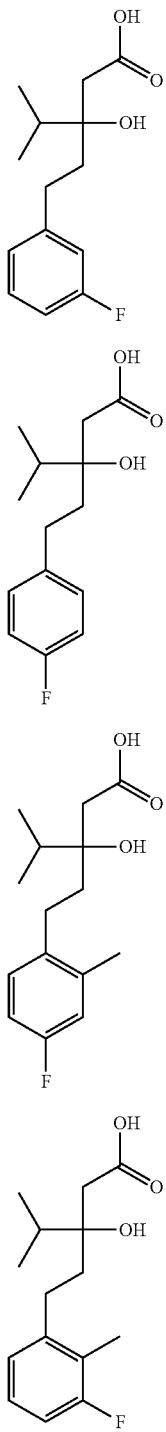

In one or more implementations, the compound is sovaprevir ((2S,4R)—N-[(1R,2S)-1-(cyclopropylsulfonyl-carbamoyl)-2-ethenylcyclopropyl]-1-[(2S)-3,3-dimethyl-2-(2-oxo-2-piperidin-1-ylethyl)butanoyl]-4-(7-methoxy-2-phenylquinolin-4-yl)oxypyrrolidine-2-carboxamide), a clinically investigated hepatitis C virus NS3 protease inhibitor. In one particular implementation, the compound, or variations and permutations thereof, is further described in WO2008008502 the contents of which are hereby incorporated by reference for all purposes and the specific purposes identified herein. In some embodiments, such compounds are represented by any one or more of the structures shown in Table 85. Any one of the compounds depicted in Table 85 is suitable for use in the methods of the present disclosure.

TABLE 74

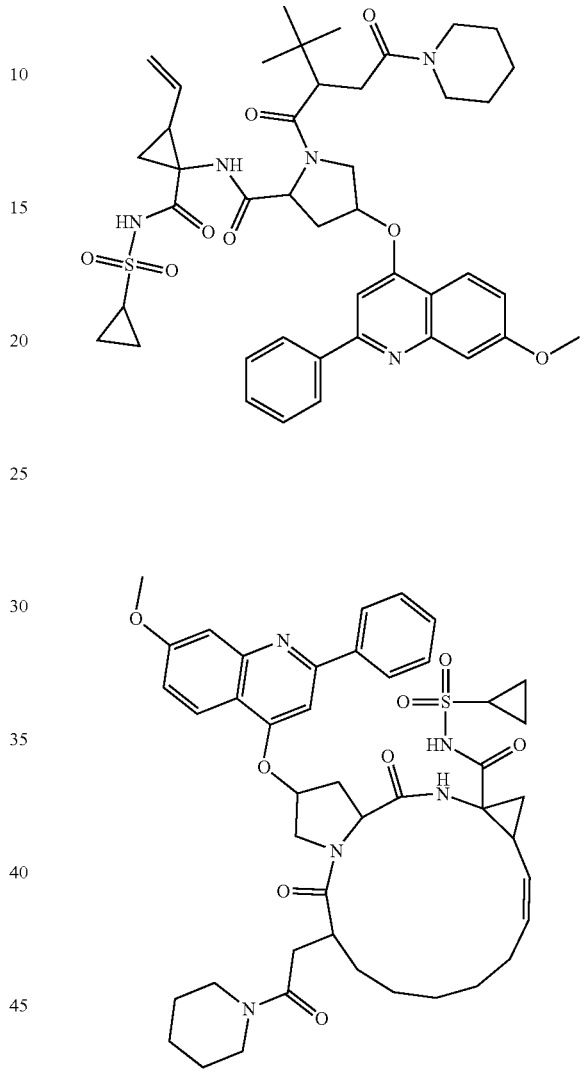

In one or more implementations, the compound is verapamil hydrochloride (2-(3,4-dimethoxyphenyl)-5-[2-(3,4-dimethoxyphenyl)ethyl-methylamino]-2-propan-2-ylpentanenitrile;hydrochloride), verapamil, and verapamil R/S isomers, and dexverapamil, a clinically investigated calcium channel inhibitor, 5-HT 2b receptor modulator; and Melatonin MT1 receptor modulator. In one particular implementation, the compound, or variations and permutations thereof, is further described in WO2007117560 the contents of which are hereby incorporated by reference for all purposes and the specific purposes identified herein. In some embodiments, such compounds are represented by any one or more of the structures shown in Table 86. Any one of the compounds depicted in Table 86 is suitable for use in the methods of the present disclosure.

TABLE 75

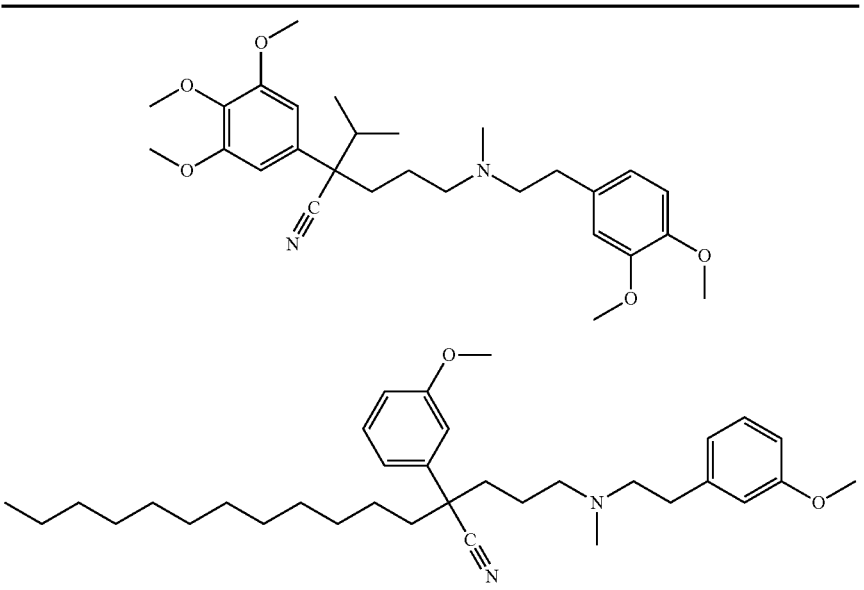

In one or more implementations, the compound is telaprevir ((3S,3aS,6aR)-2-[(2S)-2-[[(2S)-2-cyclohexyl-2-(pyrazine-2-carbonylamino)acetyl]amino]-3,3-dimethylbutanoyl]-N-[(3S)-1-(cyclopropylamino)-1,2-dioxohexan-3-yl]-3,3a,4,5,6,6a-hexahydro-1H-cyclopenta[c]pyrrole-3-carboxamide), a clinically investigated hepatitis C virus NS3 protease inhibitor and P-Glycoprotein inhibitor. In one particular implementation, the compound, or variations and permutations thereof, is further described in CN101448781; U.S. Pat. Nos. 8,188,137; 8,618,152; WO2002018369; WO2004092161; WO2005030796; WO2007121124; WO2007133865 and WO2014187271, the contents of which are hereby incorporated by reference for all purposes and the specific purposes identified herein.

In one or more implementations, the compound is telinavir ((2S)—N—[(2S,3R)-4-[tert-butylcarbamoyl(2-methylpropyl)amino]-3-hydroxy-1-phenylbutan-2-yl]-2-(quinoline-2-carbonylamino)butanediamide), a clinically investigated HIV protease inhibitor.

In one particular implementation, the compound, or variations and permutations thereof, is further described in WO1994004492 the contents of which are hereby incorporated by reference for all purposes and the specific purposes identified herein. In some embodiments, such compounds are represented by any one or more of the structures shown in Table 88. Any one of the compounds depicted in Table 88 is suitable for use in the methods of the present disclosure.

In one or more implementations, the compound is terameprocol (4-[(2S,3R)-4-(3,4-dimethoxyphenyl)-2,3-dimethylbutyl]-1,2-dimethoxybenzene), a clinically investigated survivin protein inhibitor; transcription factor inhibitor. In one particular implementation, the compound, or variations and permutations thereof, is further described in WO2005073195 the contents of which are hereby incorporated by reference for all purposes and the specific purposes identified herein.

In some embodiments, such compounds are represented by any one or more of the structures shown in Table 89. Any one of the compounds depicted in Table 89 is suitable for use in the methods of the present disclosure.

TABLE 77

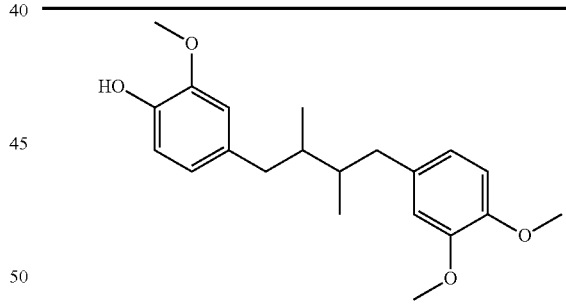

TABLE 76

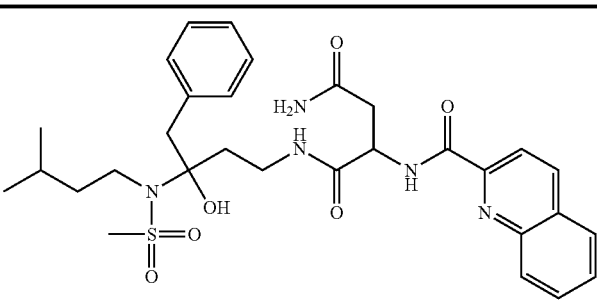

TABLE 77-continued

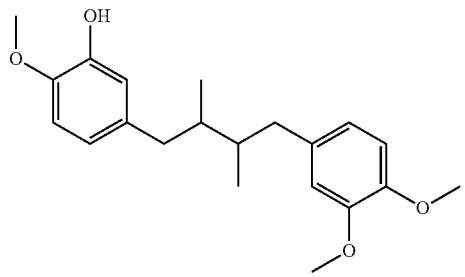 [SMILES: COc1ccc(CC(C)C(C)Cc2ccc(OC)c(OC)c2)cc1O]

In one or more implementations, the compound is thymocartin (2S)-2-[[(2S)-2-[[(2S)-6-amino-2-[(2S)-2-amino-5-(diaminomethylideneamino)pentanoyl]amino]hexanoyl]amino]-3-carboxypropanoyl]amino]-3-methylbutanoic acid), a clinically investigated IL2 gene stimulator. In one particular implementation, the compound, or variations and permutations thereof, is further described in WO2003051910 the contents of which are hereby incorporated by reference for all purposes and the specific purposes identified herein.

In one or more implementations, the compound is thymoctonan ((2S)-2-[[(2S)-2-[[(2S)-6-amino-2-[(2S)-1-[2-[[(2S)-2-[[(2S)-2-[[(2S)-2-amino-4-methylpentanoyl]amino]-4-carboxybutanoyl]amino]-3-carboxypropanoyl]amino]acetyl]pyrrolidine-2-carbonyl]amino]hexanoyl]amino]-3-phenylpropanoyl]amino]-4-methylpentanoic acid), a clinically investigated IL2 gene stimulator. In one particular implementation, the compound, or variations and permutations thereof, is further described in WO2002008256 the contents of which are hereby incorporated by reference for all purposes and the specific purposes identified herein.

In some embodiments, such compounds are represented by any one or more of the structures shown in Table 91. Any one of the compounds depicted in Table 91 is suitable for use in the methods of the present disclosure.

TABLE 78

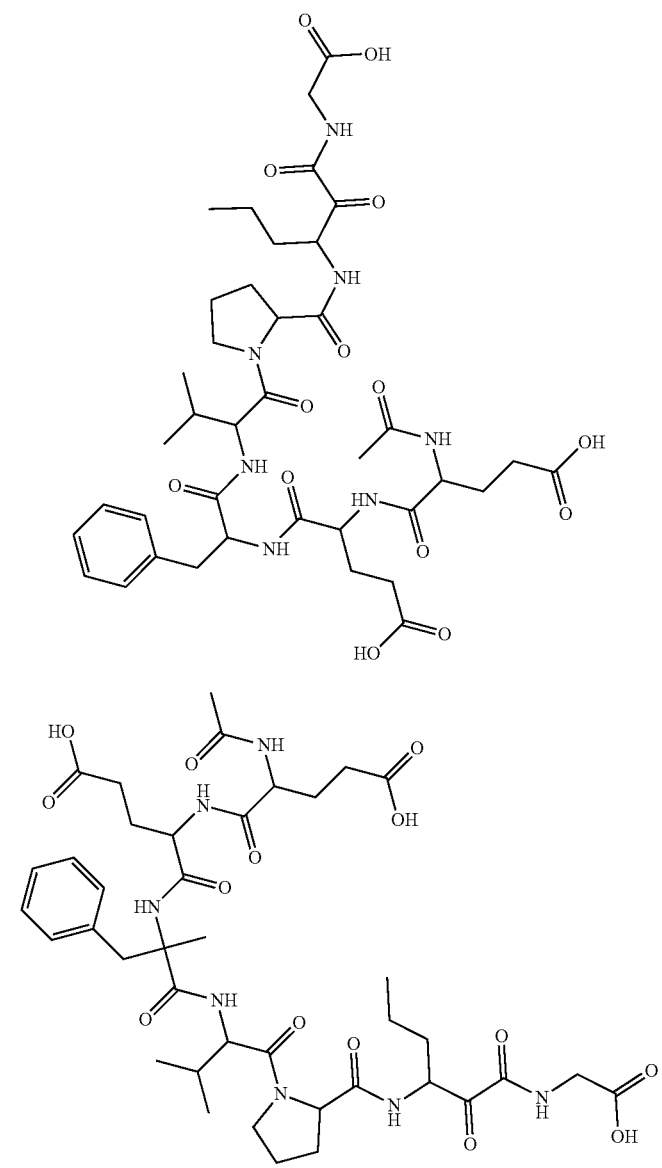

TABLE 78-continued

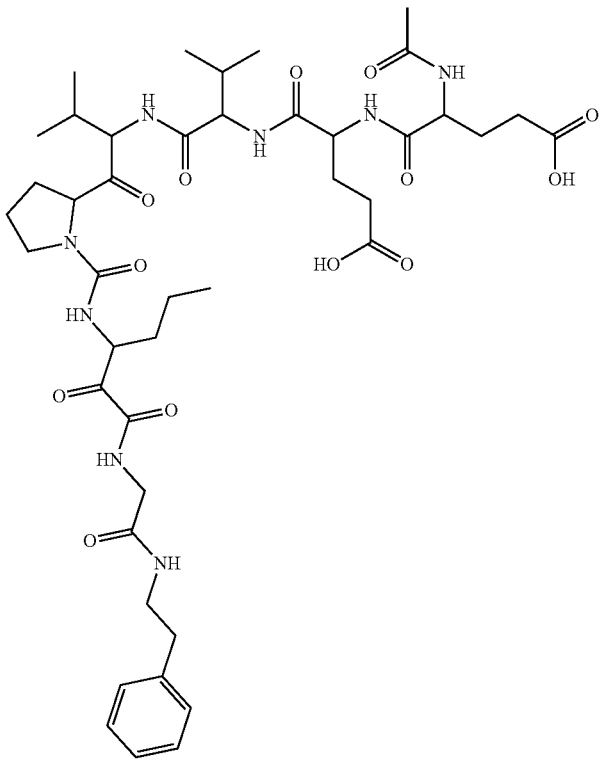 [SMILES: CCCC(NC(=O)N1CCCC1C(=O)C(NC(=O)C(NC(=O)C(CCC(=O)O)NC(=O)C(CCC(=O)O)NC(C)=O)C(C)C)C(C)C)C(=O)C(=O)NCC(=O)NCCc1ccccc1]

In one or more implementations, the compound is trandolapril ((2S,3aR,7aS)-1-[(2S)-2-[[(2S)-1-ethoxy-1-oxo-4-phenylbutan-2-yl]amino]propanoyl]-2,3,3a,4,5,6,7,7a-octahydroindole-2-carboxylic acid), a clinically investigated ACE inhibitor. In one particular implementation, the compound, or variations and permutations thereof, is further described in WO2007117560 the contents of which are hereby incorporated by reference for all purposes and the specific purposes identified herein.

In some embodiments, such compounds are represented by any one or more of the structures shown in Table 92. Any one of the compounds depicted in Table 92 is suitable for use in the methods of the present disclosure.

TABLE 79

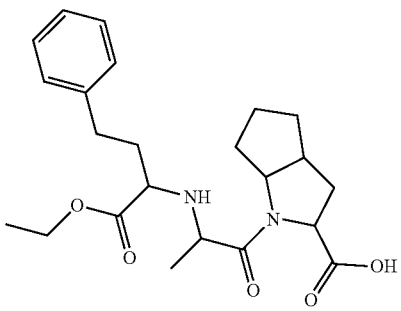 [SMILES: CCOC(=O)C(CCc1ccccc1)NC(C)C(=O)N1C(C(=O)O)CC2CCCC21]

TABLE 79-continued

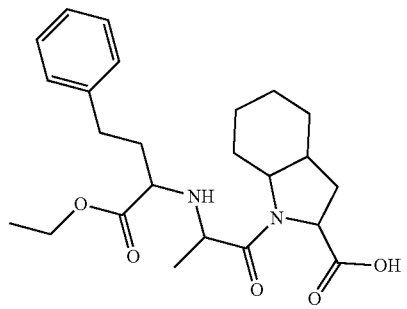 [SMILES: CCOC(=O)C(CCc1ccccc1)NC(C)C(=O)N1C(C(=O)O)CC2CCCCC21]

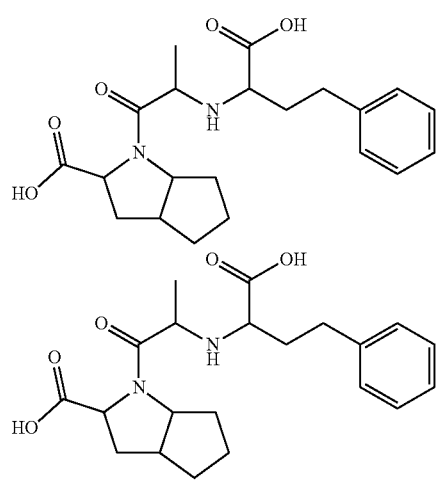

In one or more implementations, the compound is trofinetide ((2S)-2-[[(2S)-1-(2-aminoacetyl)-2-methylpyrrolidine-2-carbonyl]amino]pentanedioic acid), a clinically investigated cytokine receptor antagonist. In one particular implementation, the compound, or variations and permutations thereof, is further described in WO2002008256 the contents of which are hereby incorporated by reference for all purposes and the specific purposes identified herein.

In one or more implementations, the compound is ubenimex ((2S)-2-[[(2S,3R)-3-amino-2-hydroxy-4-phenylbutanoyl]amino]-4-methylpentanoic acid), a clinically evaluated aminopeptidase inhibitor, leukotriene A4 hydrolase inhibitor, and leukotriene BLT receptor antagonist. In one particular implementation, the compound, or variations and permutations thereof, is further described in WO2007002172; WO1999064442; JP2000159746; and WO2002008256 the contents of which are hereby incorporated by reference for all purposes and the specific purposes identified herein. In some embodiments, such compounds are represented by any one or more of the structures shown in Table 94. Any one of the compounds depicted in Table 94 is suitable for use in the methods of the present disclosure.

TABLE 80

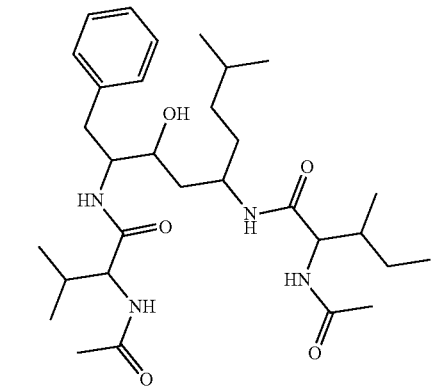 [SMILES: CCC(C)C(NC(C)=O)C(=O)NC(CCC(C)C)CC(O)C(Cc1ccccc1)NC(=O)C(NC(C)=O)C(C)C]

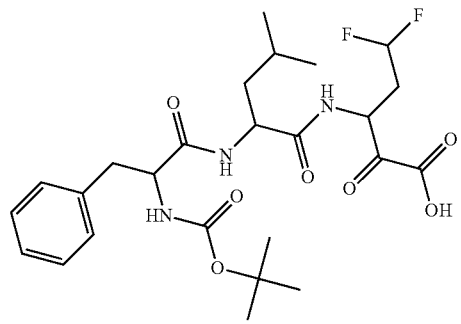 [SMILES: CC(C)CC(NC(=O)C(Cc1ccccc1)NC(=O)OC(C)(C)C)C(=O)NC(CC(F)F)C(=O)C(=O)O]

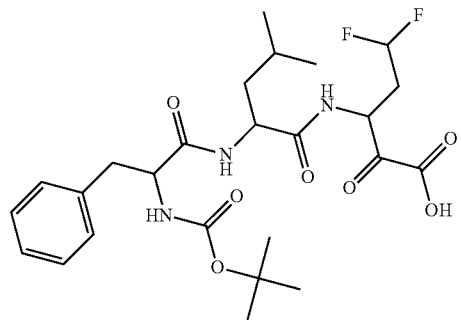 [SMILES: CC(C)CC(NC(=O)C(Cc1ccccc1)NC(=O)OC(C)(C)C)C(=O)NC(CC(F)F)C(=O)C(=O)O]

TABLE 80-continued

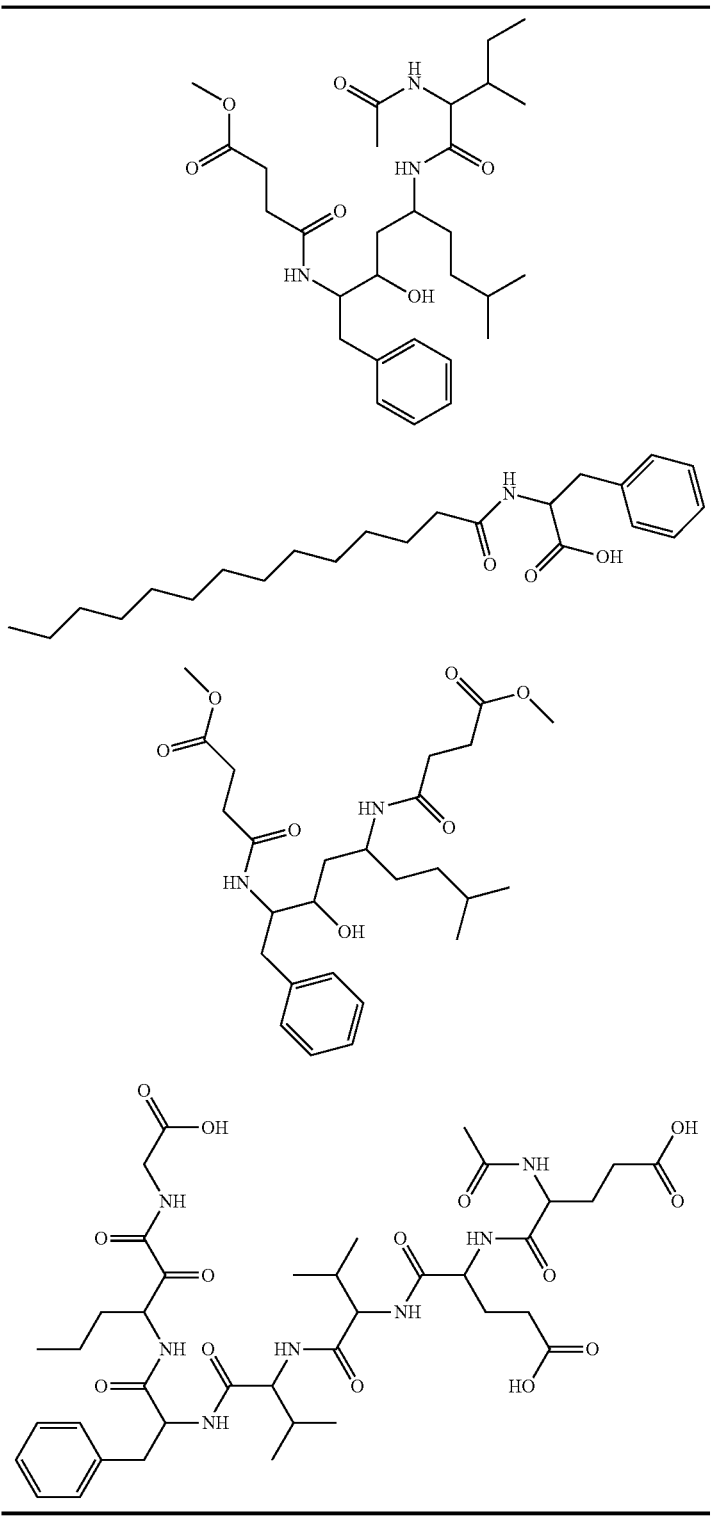

In one or more implementations, the compound is vaniprevir ((1R,21S,24S)-21-tert-butyl-N-[(1R,2R)-1-(cyclopropylsulfonylcarbamoyl)-2-ethylcyclopropyl]-16,16-dimethyl-3,19,22-trioxo-2,18-dioxa-4,20,23-triazatetracyclo[21.2.1.1$^{4,7}$.0$^{6,11}$]heptacosa-6(11),7,9-triene-24-carboxamide), a clinically investigated hepatitis C virus NS3 protease inhibitor.

In one particular implementation, the compound, or variations and permutations thereof, is further described in WO2007015787; WO2008057208; WO2009082697; WO2011002808; WO2012040040 and WO2012040242 the contents of which are hereby incorporated by reference for all purposes and the specific purposes identified herein. In some embodiments, such compounds are represented by any one or more of the structures shown in Table 95. Any one of the compounds depicted in Table 95 is suitable for use in the methods of the present disclosure.
TABLE 81
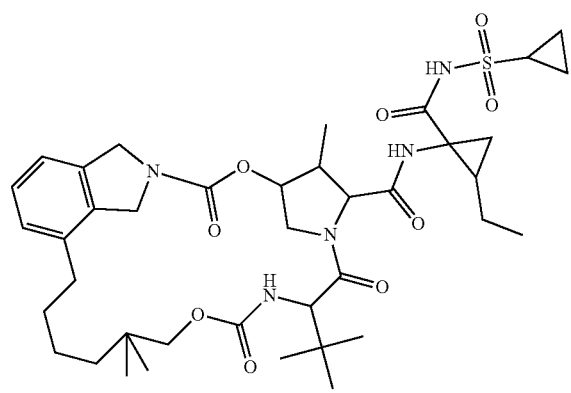 [SMILES: CCC1CC1(NC(=O)C1C(C)C2CN1C(=O)C(C(C)(C)C)NC(=O)OCC(C)(C)CCCCc1cccc3c1CN(C3)C(=O)O2)C(=O)NS(=O)(=O)C1CC1]
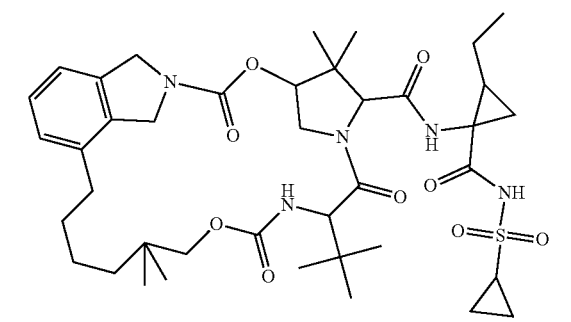 [SMILES: CCC1CC1(NC(=O)C1N2CC(OC(=O)N3Cc4cccc(c4C3)CCCCC(C)(C)COC(=O)NC(C(C)(C)C)C2=O)C1(C)C)C(=O)NS(=O)(=O)C1CC1]
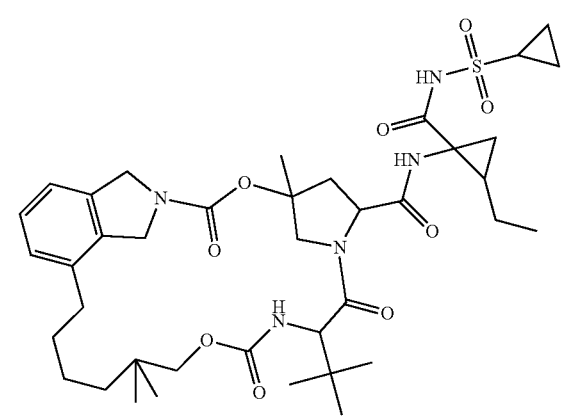 [SMILES: CCC1CC1(NC(=O)C1CC2(C)CN1C(=O)C(C(C)(C)C)NC(=O)OCC(C)(C)CCCCc1cccc3c1CN(C3)C(=O)O2)C(=O)NS(=O)(=O)C1CC1]
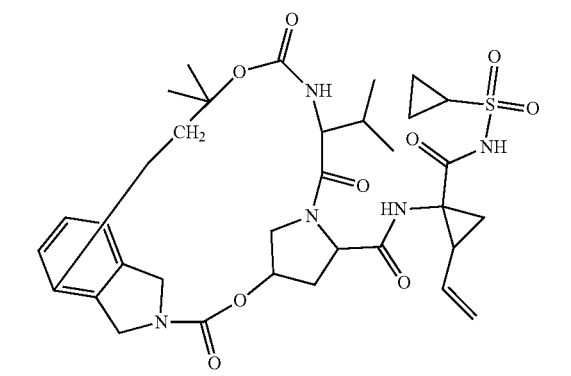 [SMILES: C=CC1CC1(NC(=O)C1CC2CN1C(=O)C(C(C)C)NC(=O)OC(C)(C)CCc1cccc3c1CN(C3)C(=O)O2)C(=O)NS(=O)(=O)C1CC1]
TABLE 81-continued
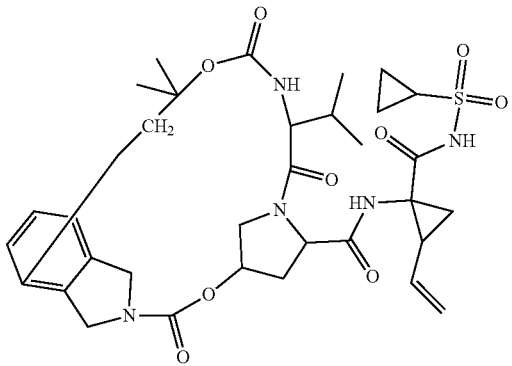 [SMILES: C=CC1CC1(NC(=O)C1CC2CN1C(=O)C(C(C)C)NC(=O)OC(C)(C)CCc1cccc3c1CN(C3)C(=O)O2)C(=O)NS(=O)(=O)C1CC1]
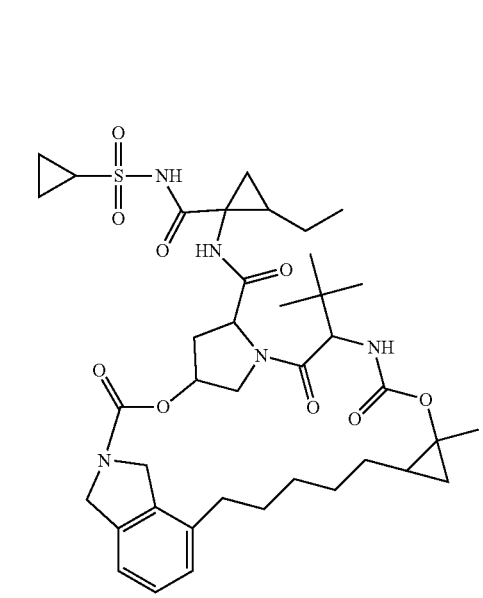 [SMILES: CCC1CC1(NC(=O)C1CC2CN1C(=O)C(C(C)(C)C)NC(=O)OC1(C)CC1CCCCCc1cccc3c1CN(C3)C(=O)O2)C(=O)NS(=O)(=O)C1CC1]
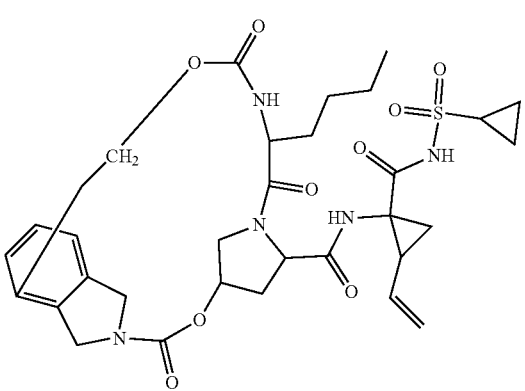 [SMILES: C=CC1CC1(NC(=O)C1CC2CN1C(=O)C(CCCC)NC(=O)OCCc1cccc3c1CN(C3)C(=O)O2)C(=O)NS(=O)(=O)C1CC1]

TABLE 81-continued
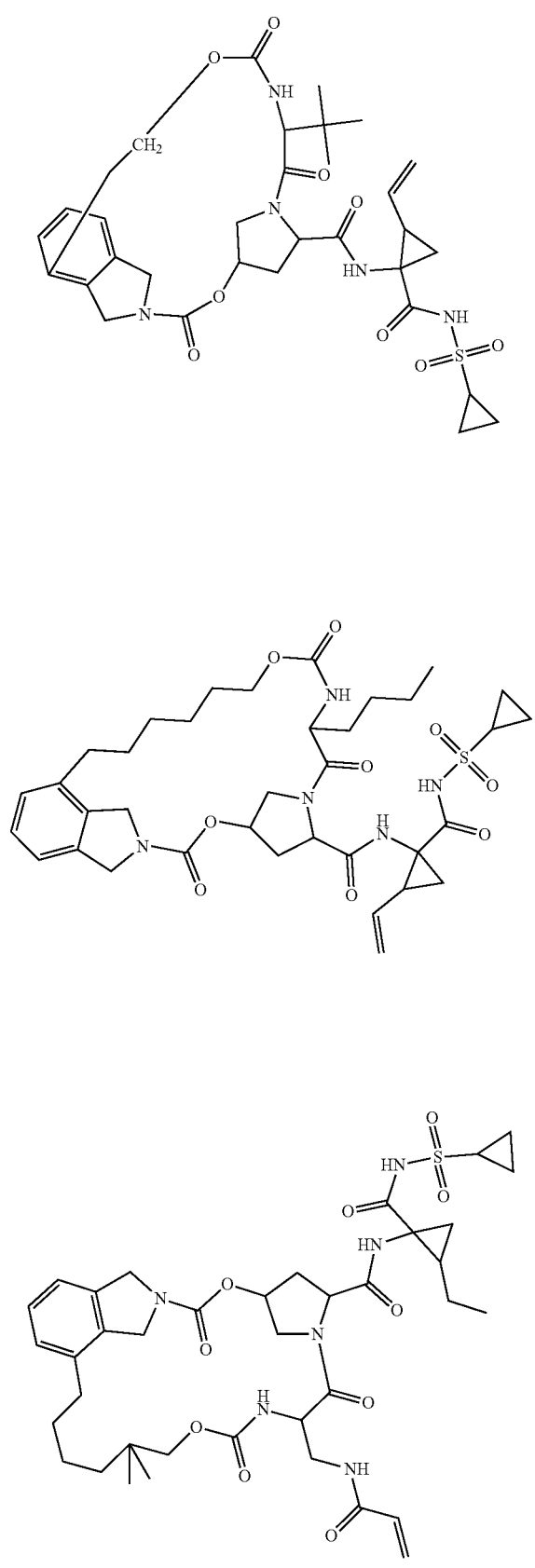
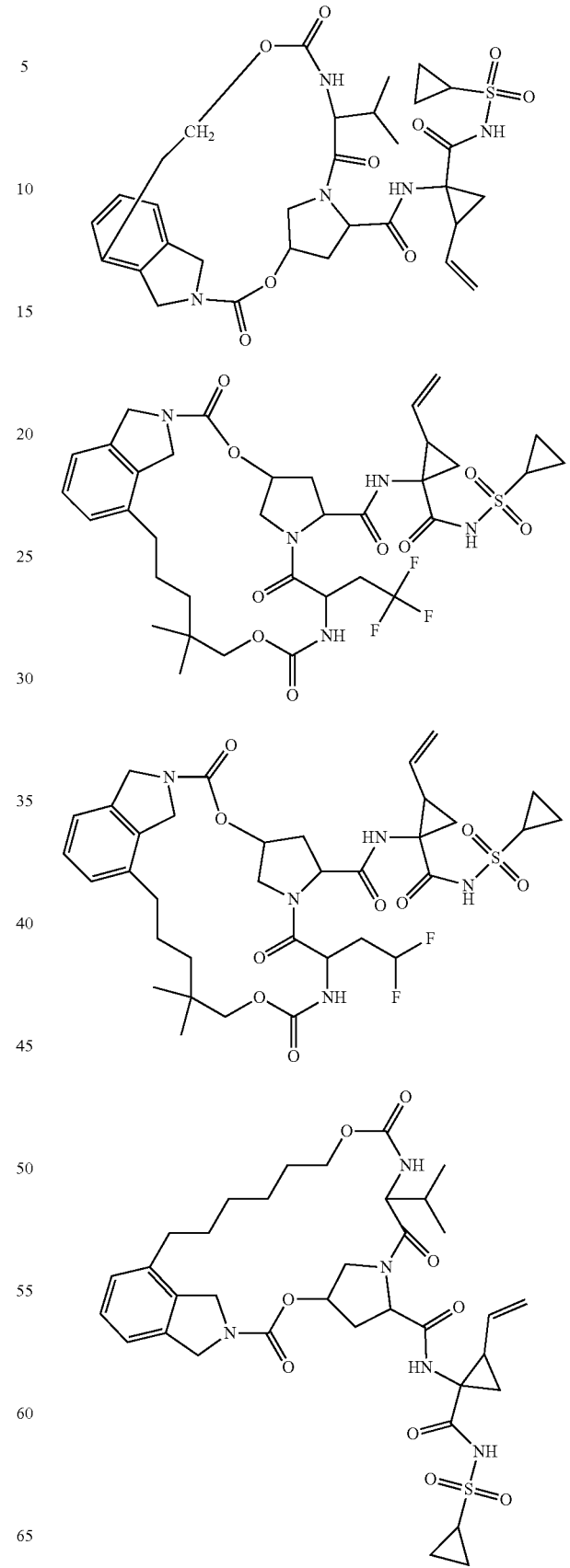

TABLE 81-continued
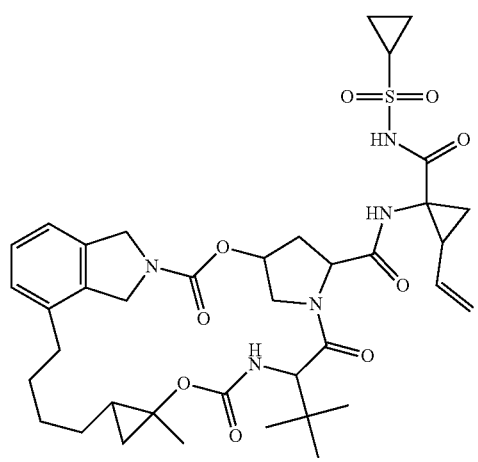 [SMILES: C=CC1CC1(NC(=O)C1CC2CN1C(=O)C(C(C)(C)C)NC(=O)OC1(C)CC1CCCCc1cccc3c1CN(C3)C(=O)O2)C(=O)NS(=O)(=O)C1CC1]
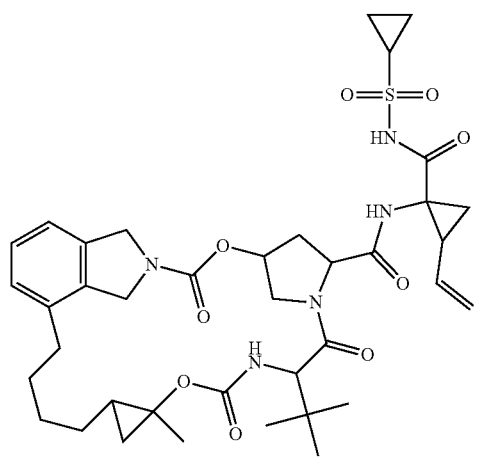 [SMILES: C=CC1CC1(NC(=O)C1CC2CN1C(=O)C(C(C)(C)C)NC(=O)OC1(C)CC1CCCCc1cccc3c1CN(C3)C(=O)O2)C(=O)NS(=O)(=O)C1CC1]
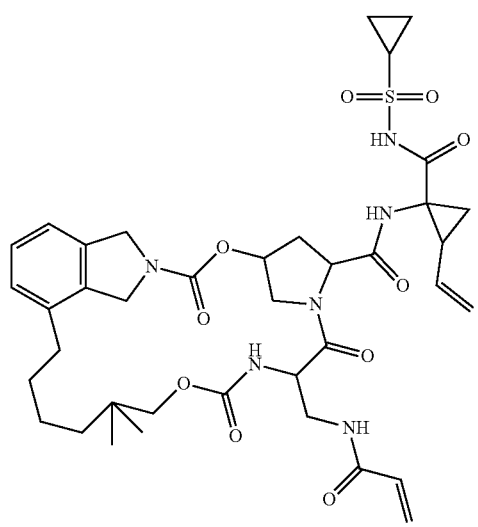 [SMILES: C=CC(=O)NCC1NC(=O)OCC(C)(C)CCCCc2cccc3c2CN(C3)C(=O)OC2CC(C(=O)NC3(C(=O)NS(=O)(=O)C4CC4)CC3C=C)N(C2)C1=O]
TABLE 81-continued
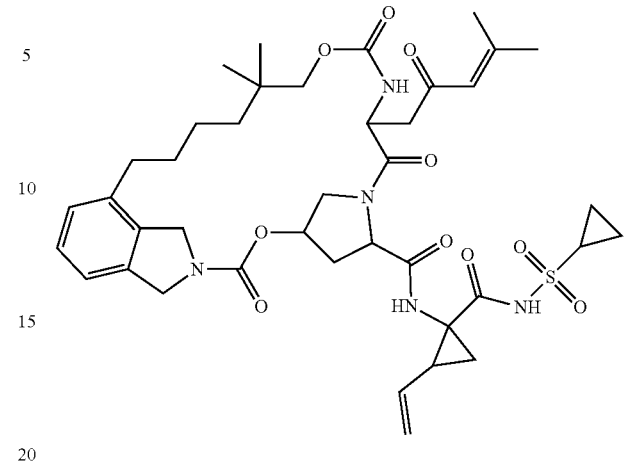
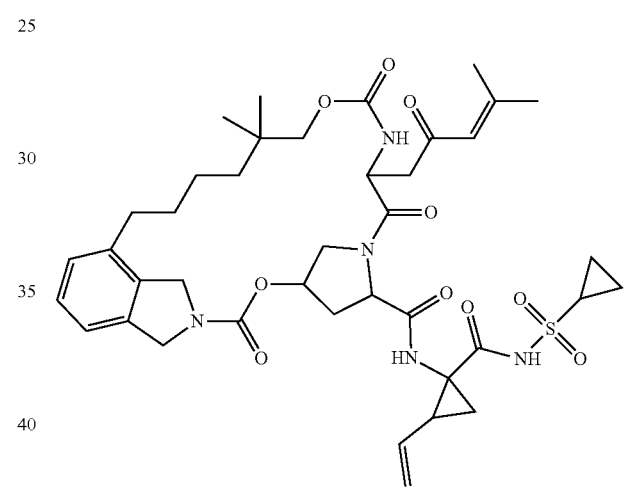
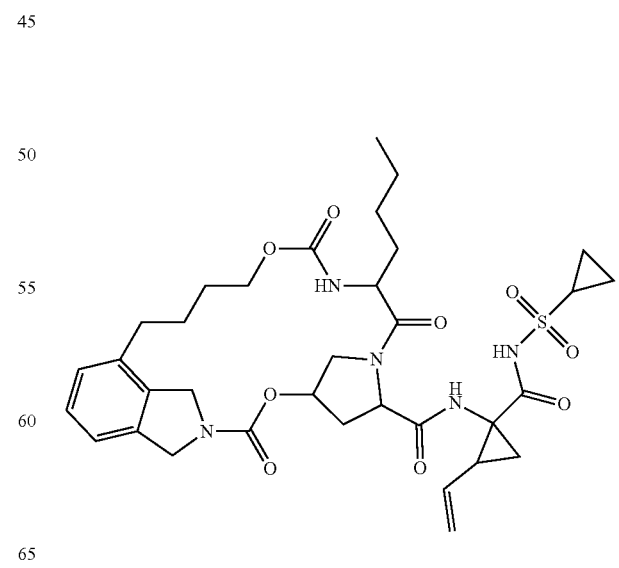

TABLE 81-continued
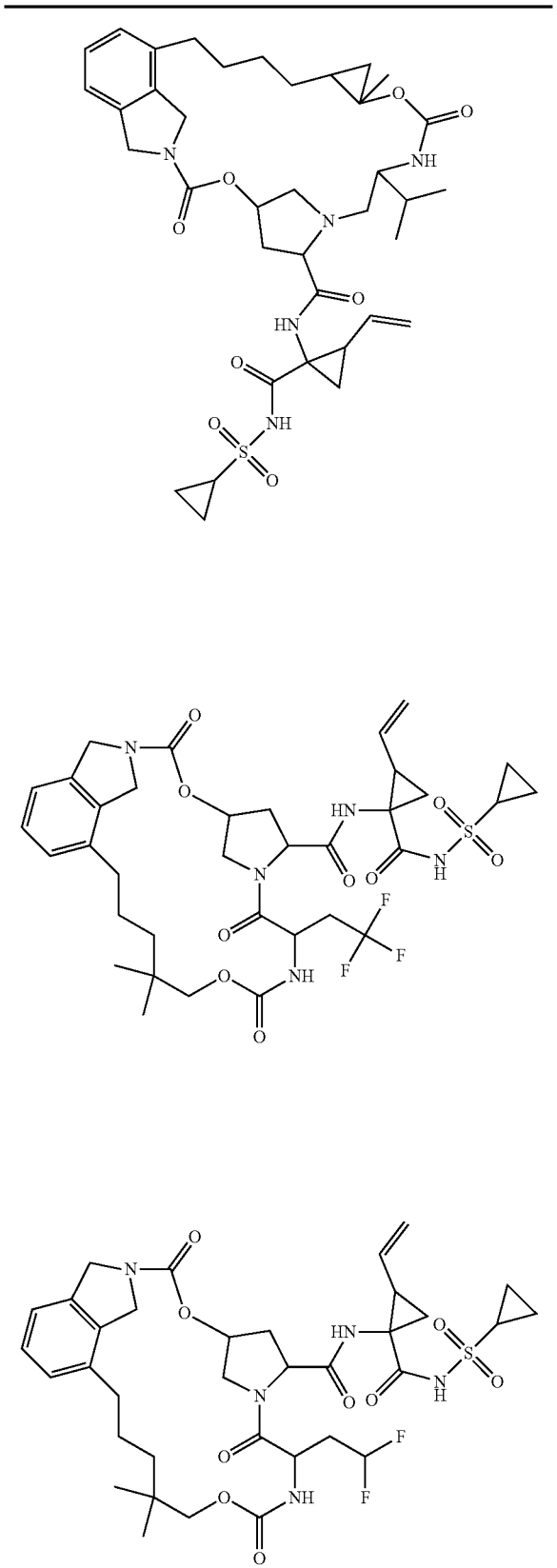
TABLE 81-continued
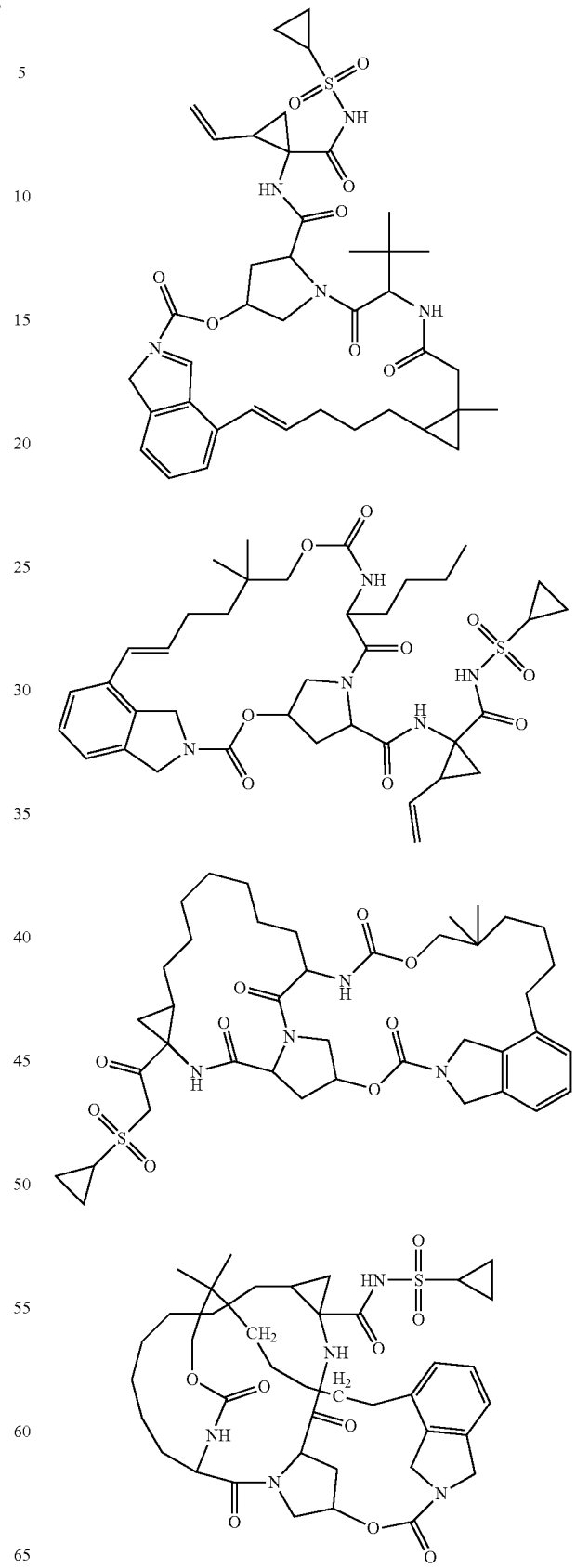

533
TABLE 81-continued
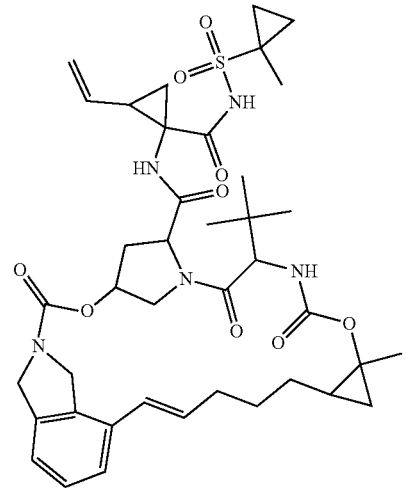 [SMILES: C=CC1CC1(NC(=O)C1CC2CN1C(=O)C(C(C)(C)C)NC(=O)OC1(C)CC1CCC/C=C/c1cccc3c1CN(C3)C(=O)O2)C(=O)NS(=O)(=O)C1(C)CC1]
534
TABLE 81-continued
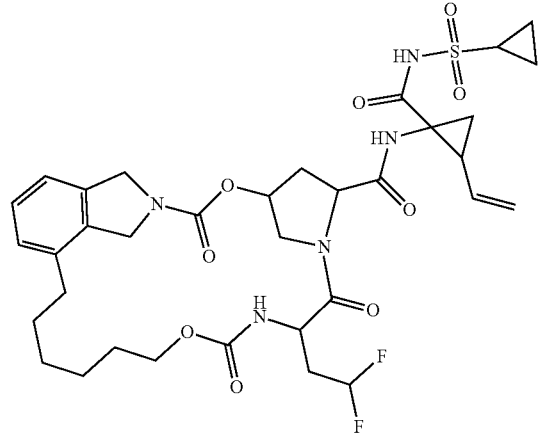 [SMILES: C=CC1CC1(NC(=O)C1CC2CN1C(=O)C(CC(F)F)NC(=O)OCCCCCCc1cccc3c1CN(C3)C(=O)O2)C(=O)NS(=O)(=O)C1CC1]
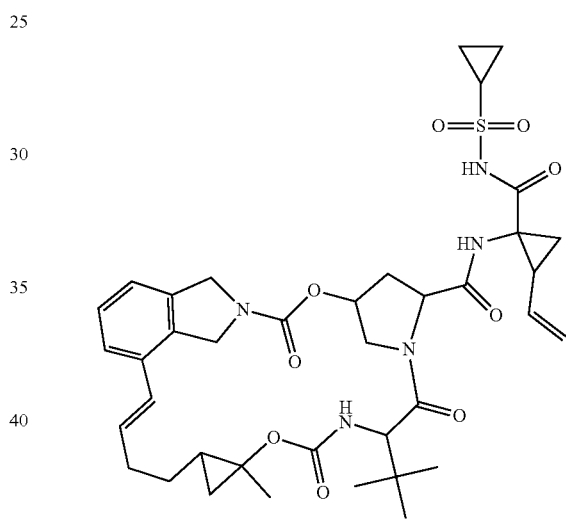
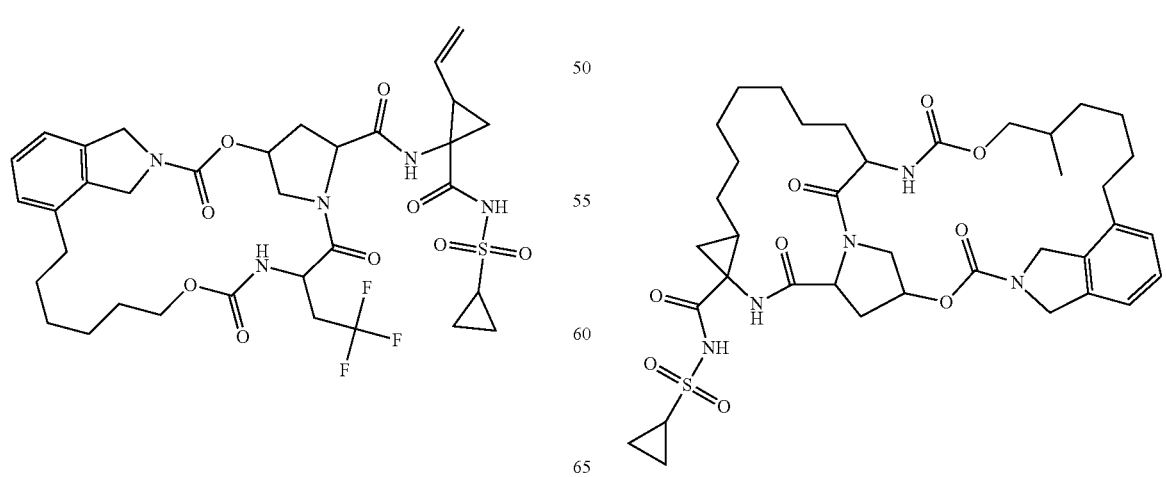

TABLE 81-continued
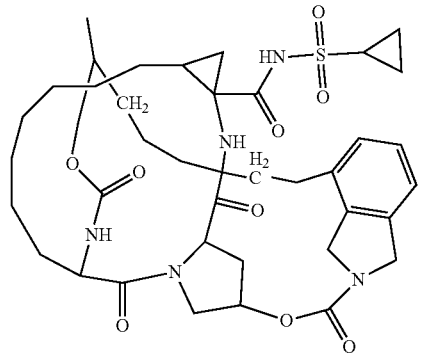 [SMILES: CC1CCCC23CCc4cccc5c4CN(C5)C(=O)OC4CC(C2=O)N(C4)C(=O)C(CCCCCCCC2CC2(C(=O)NS(=O)(=O)C2CC2)N3)NC(=O)OC1]
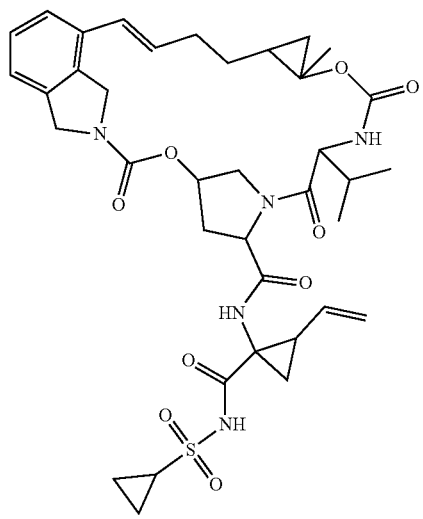 [SMILES: C=CC1CC1(NC(=O)C1CC2CN1C(=O)C(C(C)C)NC(=O)OC1(C)CC1CC/C=C/c1cccc3c1CN(C3)C(=O)O2)C(=O)NS(=O)(=O)C1CC1]
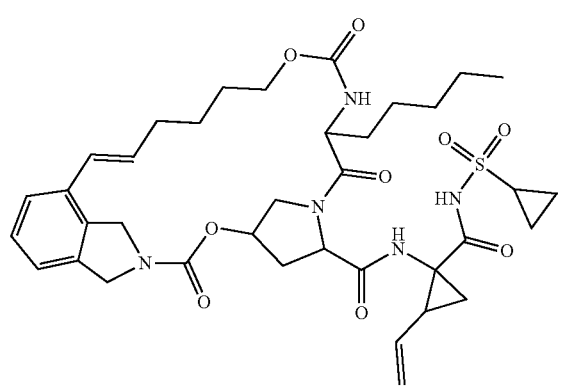 [SMILES: C=CC1CC1(NC(=O)C1CC2CN1C(=O)C(CCCCC)NC(=O)OCCCC/C=C/c1cccc3c1CN(C3)C(=O)O2)C(=O)NS(=O)(=O)C1CC1]
TABLE 81-continued
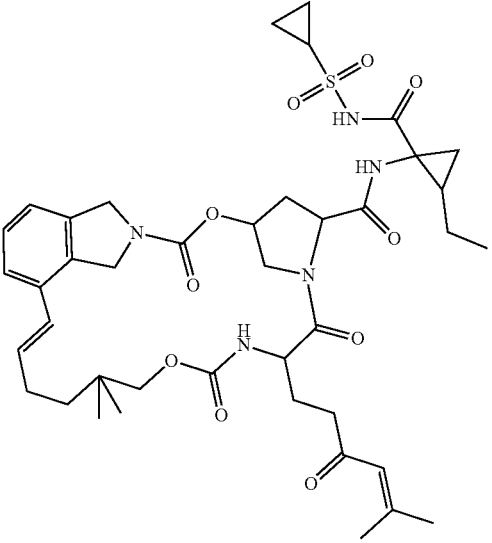 [SMILES: CCC1CC1(NC(=O)C1CC2CN1C(=O)C(CCC(=O)C=C(C)C)NC(=O)OCC(C)(C)CC/C=C/c1cccc3c1CN(C3)C(=O)O2)C(=O)NS(=O)(=O)C1CC1]
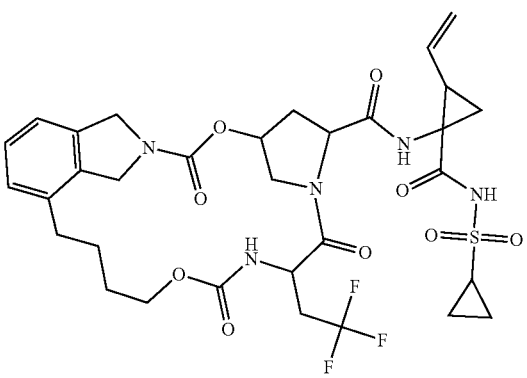 [SMILES: C=CC1CC1(NC(=O)C1CC2CN1C(=O)C(CC(F)(F)F)NC(=O)OCCCCc1cccc3c1CN(C3)C(=O)O2)C(=O)NS(=O)(=O)C1CC1]
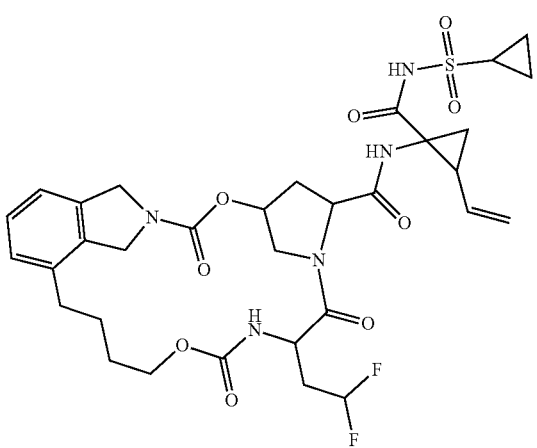 [SMILES: C=CC1CC1(NC(=O)C1CC2CN1C(=O)C(CC(F)F)NC(=O)OCCCCc1cccc3c1CN(C3)C(=O)O2)C(=O)NS(=O)(=O)C1CC1]

TABLE 81-continued
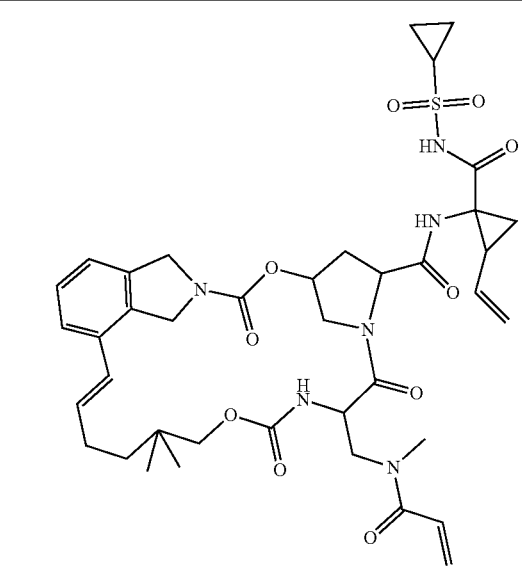
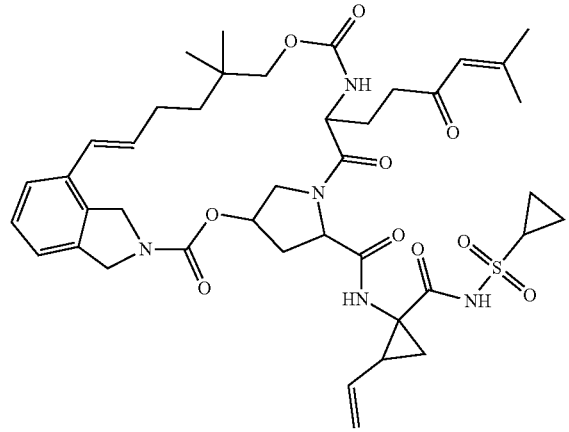 [SMILES: C=CC1CC1(NC(=O)C1CC2CN1C(=O)C(CCC(=O)C=C(C)C)NC(=O)OCC(C)(C)CC/C=C/c1cccc3c1CN(C3)C(=O)O2)C(=O)NS(=O)(=O)C1CC1]
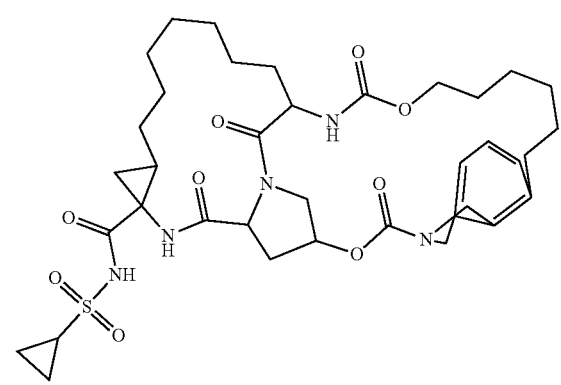
TABLE 81-continued
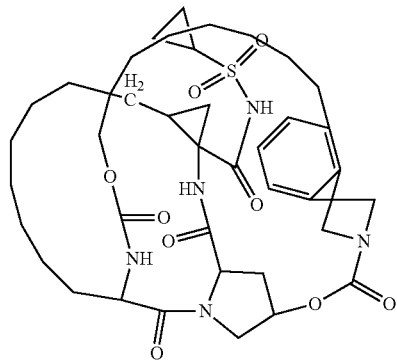 [SMILES: O=C1NC2CCCCCCCC3(CCCCCCc4cccc5c4C54CN(C4)C(=O)OC4CC(C(=O)NC5(C(=O)NS(=O)(=O)C6CC6)CC5C3)N(C4)C2=O)CO1]
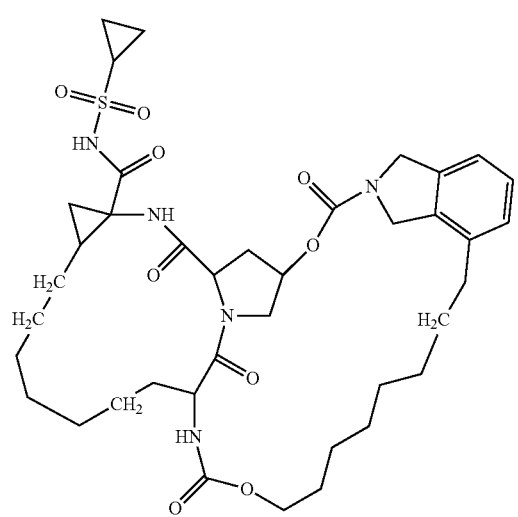 [SMILES: O=C1NC2CCCCCCCC3CC3(C(=O)NS(=O)(=O)C3CC3)NC(=O)C3CC(CN3C2=O)OC(=O)N2Cc3cccc(c3C2)CCCCCCCCO1]
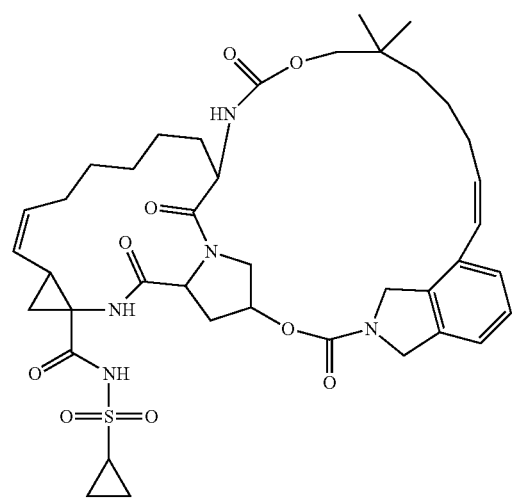 [SMILES: CC1(C)CCC/C=C\c2cccc3c2CN(C3)C(=O)OC2CC3C(=O)NC4(C(=O)NS(=O)(=O)C5CC5)CC4/C=C\CCCCCC(NC(=O)OC1)C(=O)N3C2]

TABLE 81-continued
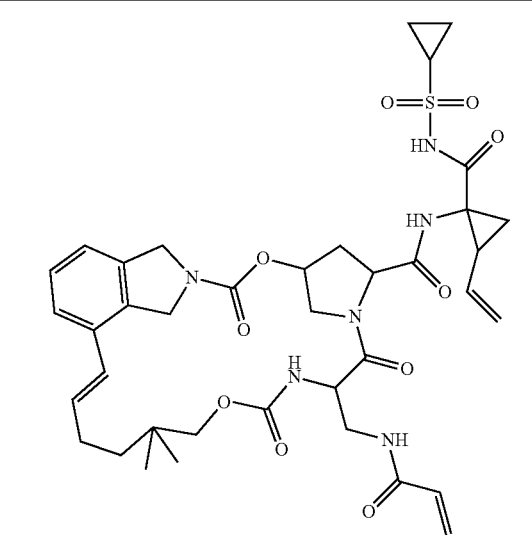
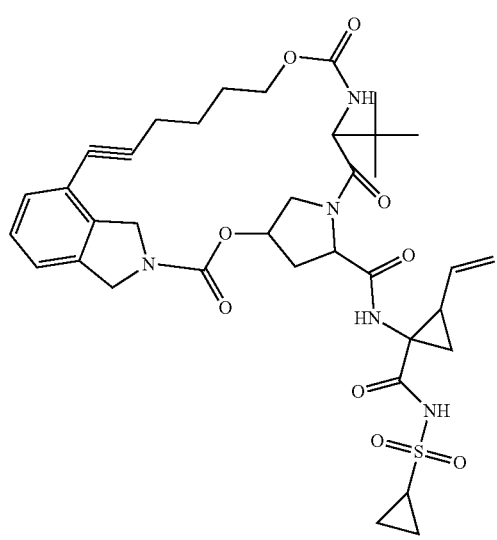 [SMILES: C=CC1CC1(NC(=O)C1CC2CN1C(=O)C(C(C)(C)C)NC(=O)OCCCCC#Cc1cccc3c1CN(C3)C(=O)O2)C(=O)NS(=O)(=O)C1CC1]
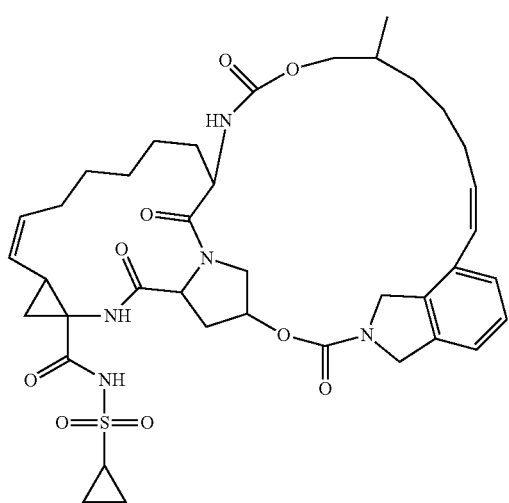 [SMILES: CC1CCC/C=C\c2cccc3c2CN(C3)C(=O)OC2CC3C(=O)NC4(C(=O)NS(=O)(=O)C5CC5)CC4/C=C\CCCCCC(NC(=O)OC1)C(=O)N3C2]
TABLE 81-continued
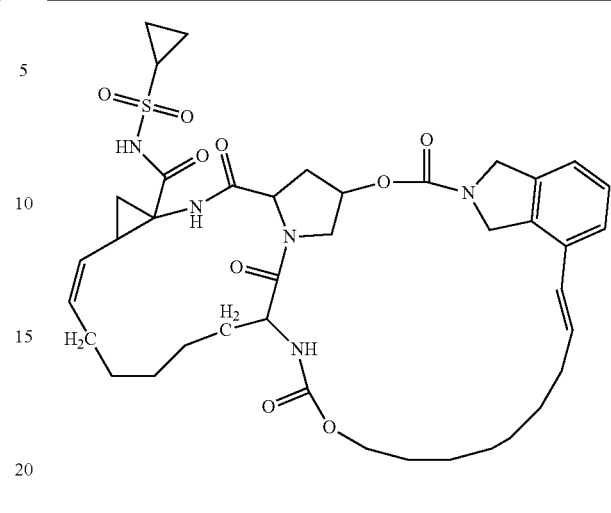
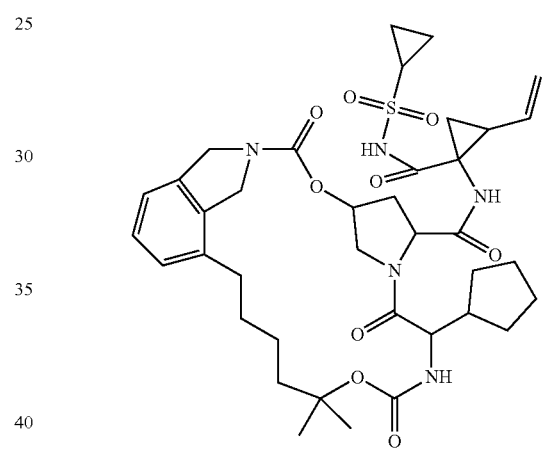
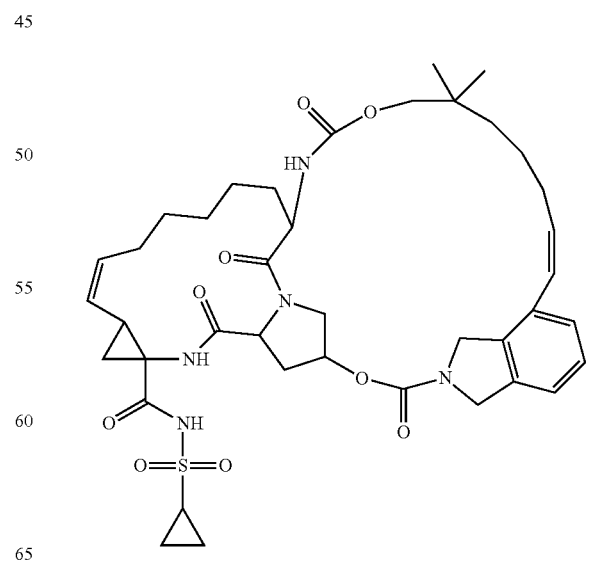

TABLE 81-continued
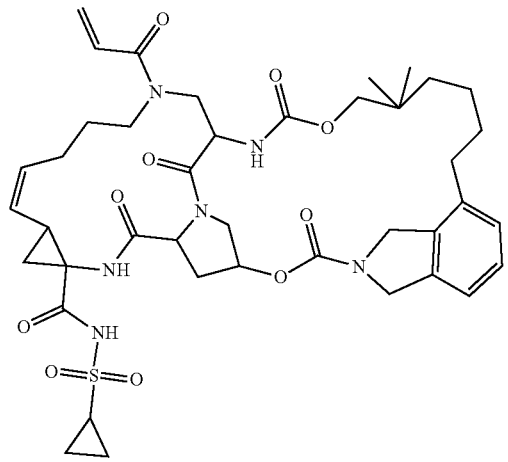 [SMILES: C=CC(=O)N1CCC/C=C\C2CC2(C(=O)NS(=O)(=O)C2CC2)NC(=O)C2CC3CN2C(=O)C(C1)NC(=O)OCC(C)(C)CCCCc1cccc2c1CN(C2)C(=O)O3]
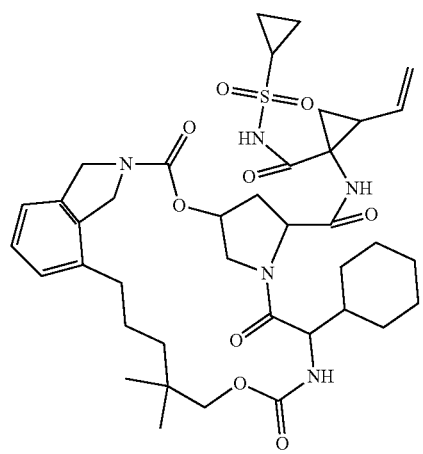 [SMILES: C=CC1CC1(NC(=O)C1CC2CN1C(=O)C(C1CCCCC1)NC(=O)OCC(C)(C)CCCc1cccc3c1CN(C3)C(=O)O2)C(=O)NS(=O)(=O)C1CC1]
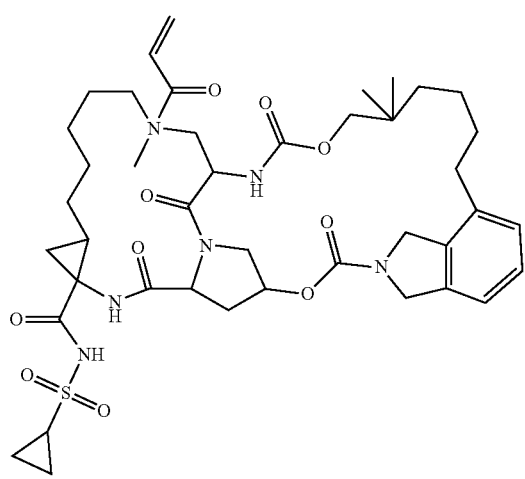
TABLE 81-continued
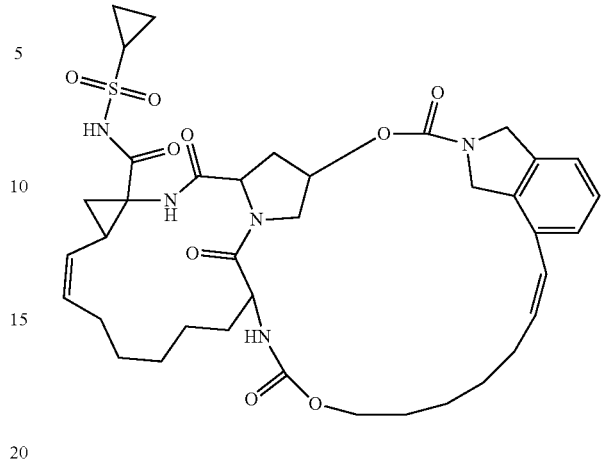
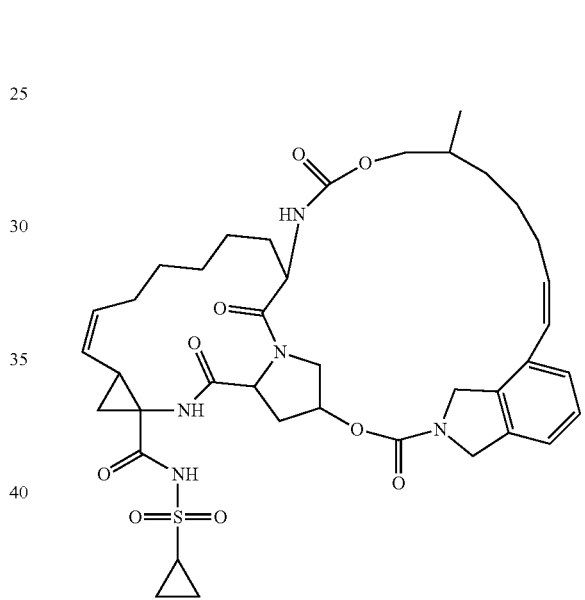
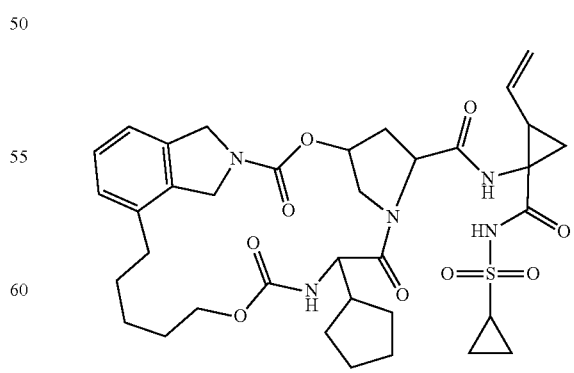

TABLE 81-continued
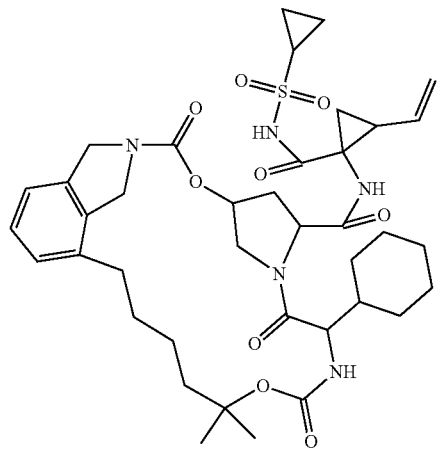 [SMILES: C=CC1CC1(NC(=O)C1CC2CN1C(=O)C(C1CCCCC1)NC(=O)OC(C)(C)CCCCc1cccc3c1CN(C3)C(=O)O2)C(=O)NS(=O)(=O)C1CC1]
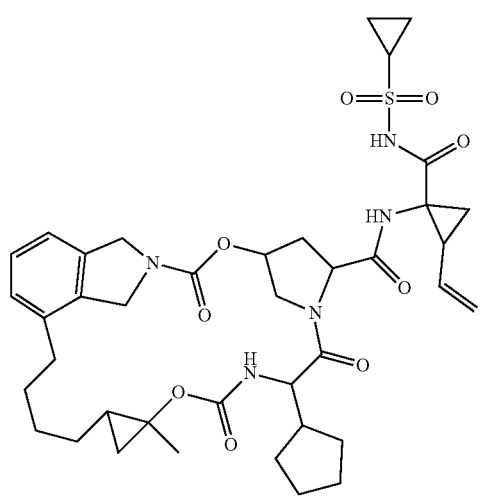 [SMILES: C=CC1CC1(NC(=O)C1CC2CN1C(=O)C(C1CCCC1)NC(=O)OC1(C)CC1CCCCc1cccc3c1CN(C3)C(=O)O2)C(=O)NS(=O)(=O)C1CC1]
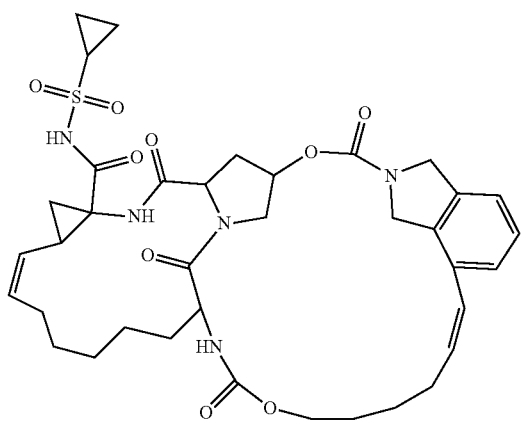 [SMILES: O=C1NC2CCCCC/C=C\C3CC3(C(=O)NS(=O)(=O)C3CC3)NC(=O)C3CC(CN3C2=O)OC(=O)N2Cc3cccc(c3C2)/C=C\CCCCO1]
TABLE 81-continued
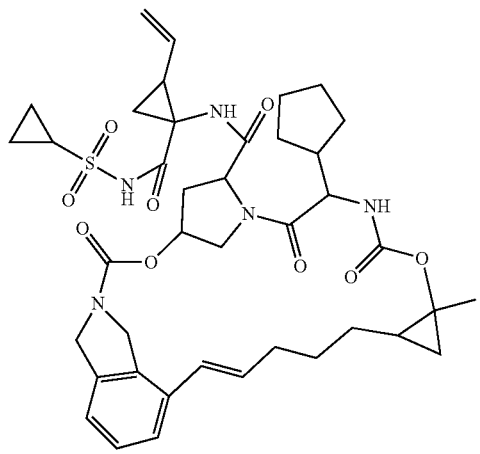 [SMILES: C=CC1CC1(NC(=O)C1CC2CN1C(=O)C(C1CCCC1)NC(=O)OC1(C)CC1CCC/C=C/c1cccc3c1CN(C3)C(=O)O2)C(=O)NS(=O)(=O)C1CC1]
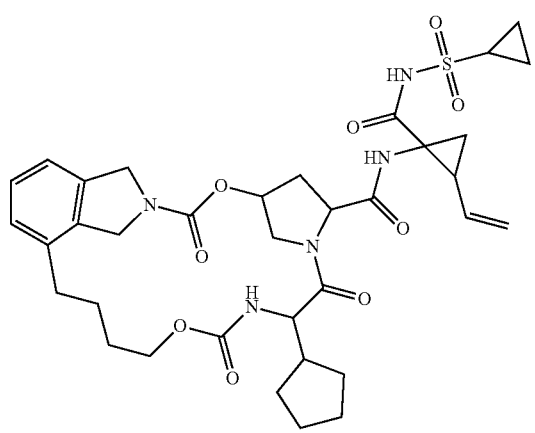 [SMILES: C=CC1CC1(NC(=O)C1CC2CN1C(=O)C(C1CCCC1)NC(=O)OCCCCc1cccc3c1CN(C3)C(=O)O2)C(=O)NS(=O)(=O)C1CC1]
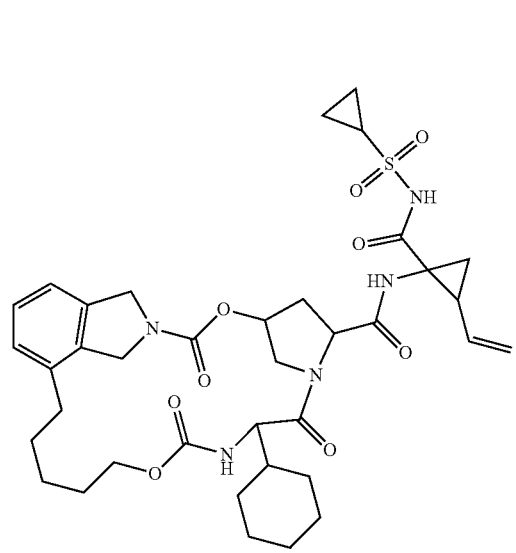 [SMILES: C=CC1CC1(NC(=O)C1CC2CN1C(=O)C(C1CCCCC1)NC(=O)OCCCCCc1cccc3c1CN(C3)C(=O)O2)C(=O)NS(=O)(=O)C1CC1]

TABLE 81-continued

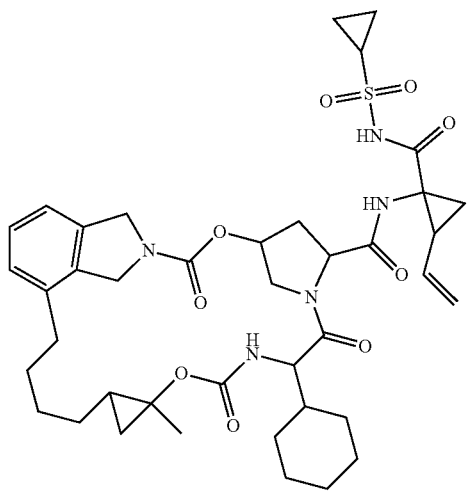 [SMILES: C=CC1CC1(NC(=O)C1CC2CN1C(=O)C(C1CCCCC1)NC(=O)OC1(C)CC1CCCCc1cccc3c1CN(C3)C(=O)O2)C(=O)NS(=O)(=O)C1CC1]

In one or more implementations, the compound is vedroprevir ((1R,2R)-1-[[(2S,4R)-1-[(2S)-2-[[(1R,5S)-3-bicyclo[3.1.0]hexanyl]oxycarbonylamino]-3,3-dimethylbutanoyl]-4-[8-chloro-7-(2-morpholin-4-ylethoxy)-2-[2-(propan-2-ylamino)-1,3-thiazol-4-yl]quinolin-4-yl]oxypyrrolidine-2-carbonyl]amino]-2-ethylcyclopropane-1-carboxylic acid), a clinically investigated hepatitis C virus NS3 protease inhibitor. In one particular implementation, the compound, or variations and permutations thereof, is further described in WO2009005676 the contents of which are hereby incorporated by reference for all purposes and the specific purposes identified herein.

In one or more implementations, the compound is voxilaprevir ((1R,18R,20R,24S,27S,28S)-24-tert-butyl-N-[(1R,2R)-2-(difluoromethyl)-1-[(1-methylcyclopropyl)sulfonylcarbamoyl]cyclopropyl]-28-ethyl-13,13-difluoro-7-methoxy-22,25-dioxo-2,21-dioxa-4,11,23,26-tetrazapentacyclo[24.2.1.0$^{3,12}$.0$^{5,10}$.0$^{18,20}$]nonacosa-3,5(10),6,8,11-pentaene-27-carboxamide), a clinically investigated hepatitis C virus NS3 protease inhibitor. In one particular implementation, the compound, or variations and permutations thereof, is further described in WO2008057209; WO2014145095; WO2014008285; and WO2014145095 the contents of which are hereby incorporated by reference for all purposes and the specific purposes identified herein.

In one or more implementations, the compound is warfarin (4-hydroxy-3-(3-oxo-1-phenylbutyl)chromen-2-one), a clinically investigated Factor IIa antagonist; Factor IX antagonist; Factor VII antagonist; Factor X antagonist; Vitamin K epoxide reductase inhibitor. In one particular implementation, the compound, or variations and permutations thereof, is further described in WO1994011361 the contents of which are hereby incorporated by reference for all purposes and the specific purposes identified herein. In some embodiments, such compounds are represented by any one or more of the structures shown in Table 98. Any one of the compounds depicted in Table 98 is suitable for use in the methods of the present disclosure.

TABLE 82

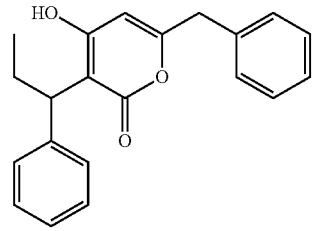 [SMILES: CCC(c1ccccc1)c1c(O)cc(Cc2ccccc2)oc1=O]

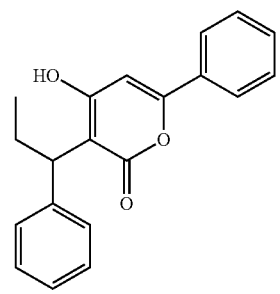 [SMILES: CCC(c1ccccc1)c1c(O)cc(-c2ccccc2)oc1=O]

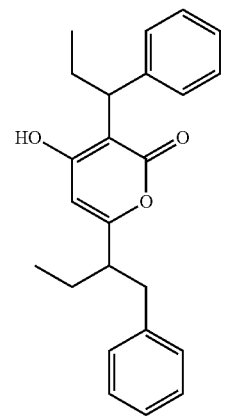 [SMILES: CCC(Cc1ccccc1)c1cc(O)c(C(CC)c2ccccc2)c(=O)o1]

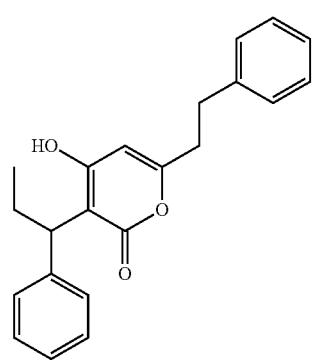 [SMILES: CCC(c1ccccc1)c1c(O)cc(CCc2ccccc2)oc1=O]

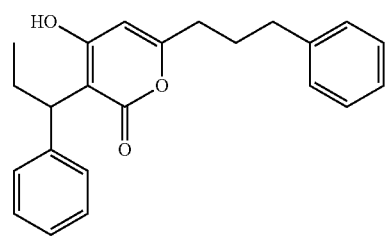 [SMILES: CCC(c1ccccc1)c1c(O)cc(CCCc2ccccc2)oc1=O]

TABLE 82-continued

[Chemical structures shown]

Methods of Treatment

In certain embodiments, the compositions and methods of the present disclosure are useful for the prevention and/or treatment of symptoms of SARS-COV-19 infections. In certain embodiments, the compositions and methods of the present disclosure are useful for the prevention and/or treatment of acute inflammatory responses. In certain embodiments, the compositions and methods of the present disclosure are useful for the prevention and/or treatment of acute inflammatory responses, e.g., cytokine storms that are associates with a coronavirus infection.

The present disclosure is based on the discovery that viral protease inhibitors may have therapeutic utility in the treatment of coronavirus symptoms, in particular in preventing viral replication in critical patients with coronavirus infections, in particular SARS-COV-19. Viral protease inhibitors or reduce viral replication if viruses, thereby decreasing the viral load suffered by an infected patient.

Thus, in some embodiments, viral protease inhibitors may prevent onset of severe SARS-CoV-19 symptoms. For example, viral protease inhibitors may reduce or eliminate the viral load in patients with SARS-COV-19 pneumonia and prevent or ameliorate progress thereof. Successful intervention with viral protease inhibitors may reduce life-threatening complications of SARS-COV-19, including severe respiratory symptoms that often necessitate further medical intervention such as mechanical intervention.

Thus, in some embodiments, the present disclosure relates to a method of treating or alleviating at least one symptom of a coronavirus infection in a subject, by administering to the subject a therapeutically effective amount of viral protease inhibitors. In some embodiments, the subject is a human.

In some embodiments, the symptom is fever. In other embodiments, the symptom is cough. In other embodiments, the symptom is dry cough. In other embodiments, the symptom is tiredness. In other embodiments, the symptom is sore throat. In other embodiments, the symptom is diarrhea. In other embodiments, the symptom is conjunctivitis. In other embodiments, the symptom is headache. In other embodiments, the symptom is loss of taste. In other embodiments, the symptom is loss of smell. In other embodiments, the symptom is a rash. In other embodiments, the symptom is difficulty breathing. In other embodiments, the symptom is shortness of breath. In other embodiments, the symptom is chest pain. In other embodiments, the symptom is chest pressure. In other embodiments, the symptom is Acute Respiratory Distress Syndrome (ARDS). In other embodiments, the symptom is organ failure. In other embodiments, the symptom is multiple organ failure. In other embodiments, the symptom is any combination of the foregoing.

In some embodiments, the present disclosure relates to a method of treating an acute condition in a subject infected with a coronavirus, the method comprising the step of administering to the subject a therapeutically effective amount of viral protease inhibitors. In some embodiments, the condition comprises a high viral load. In some embodiments, the subject is a human.

In some embodiments, the present disclosure relates to a method of reducing or arresting viral load in a subject infected with a coronavirus, the method comprising the step of administering to the subject a therapeutically effective amount of a viral protease inhibitors. In some embodiments, the subject is a human.

Viral load can be measured by any viral diagnostic equipment or technique known in the art. A wide variety of samples can be used for virological testing. Such samples include, but are not limited to, upper respiratory swabs (nasopharyngeal swabs, nasopharyngeal wash/aspirate, oropharyngeal swabs, saliva) and lower respiratory specimens (sputum, bronchoalveolar lavage, lung tissue), as well as stool, rectal swabs, blood, skin, urine, semen, faeces, cerebrospinal fluid, tissue (e.g., biopsies), and the like. Techniques for measuring viral load include, but are not limited to, nucleic acid amplification-based tests (NATs) or non-nucleic acid-based tests. Examples of NATs include, but are not limited to, PCR (polymerase chain reaction), reverse transcription polymerase chain reaction (RT-PCR), and nucleic acid sequence-based amplification (NASBA). Viral load is typically reported as copies the virus in a milliliter (mL) of blood. Changes in viral load are usually reported as a log change (in powers of 10). For example, a three-log increase in viral load (3 log 10) is an increase of 103 or 1,000 times the previously reported level, while a drop from 500,000 to 500 copies would be a three-log-drop.

In one embodiment, the subject is infected with a coronavirus. In some embodiments, the coronavirus is selected from the group consisting of 229E (alpha coronavirus), NL63 (alpha coronavirus), OC43 (beta coronavirus), HKU1 (beta coronavirus), MERS-COV (beta coronavirus that causes Middle East Respiratory Syndrome, or MERS), SARS-COV (the beta coronavirus that causes severe acute respiratory syndrome, or SARS) SARS-COV-2 (the novel coronavirus that causes coronavirus disease 2019, or COVID-19, also referred to herein as SARS-Covid-19). In some embodiments, the coronavirus is a severe acute respiratory syndrome coronavirus (SARS-CoV). In some embodiments, the coronavirus is a novel virus 2019-nCOV (SARS-COV-19). In some embodiments, the coronavirus is a Middle East respiratory syndrome coronavirus (MERS-CoV). In one preferred embodiment, the coronavirus is SARS-COV-19.

Pharmaceutical Compositions

The present disclosure thus provides pharmaceutical compositions comprising viral protease inhibitors and a pharmaceutically acceptable carrier. The compounds of the present disclosure can be formulated as pharmaceutical compositions and administered to a mammalian host, such as a human patient, in a variety of forms adapted to the chosen route of administration.

Routes of administration include, but are not limited to oral, topical, mucosal, nasal, parenteral, gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic, transdermal, rectal, buccal, epidural and sublingual administration.

As used herein, the term "administering" generally refers to any and all means of introducing compounds described herein to the host subject. Compounds described herein may be administered in unit dosage forms and/or compositions containing one or more pharmaceutically-acceptable carriers, adjuvants, diluents, excipients, and/or vehicles, and combinations thereof.

As used herein, the terms "composition" generally refers to any product comprising more than one ingredient, including the compounds described herein. It is to be understood that the compositions described herein may be prepared from compounds described herein or from salts, solutions, hydrates, solvates, and other forms of the compounds described herein. It is appreciated that the compositions may be prepared from various amorphous, non-amorphous, partially crystalline, crystalline, and/or other morphological forms of the compounds described herein, and the compositions may be prepared from various hydrates and/or solvates of the compounds described herein. Accordingly, such pharmaceutical compositions that recite compounds described herein include each of, or any combination of, or individual forms of, the various morphological forms and/or solvate or hydrate forms of the compounds described herein.

In some embodiments, the viral protease inhibitors may be systemically (e.g., orally) administered in combination with a pharmaceutically acceptable vehicle such as an inert diluent or an assimilable edible carrier. For oral therapeutic administration, the active compound may be combined with one or more excipients and used in the form of ingestible tablets, buccal tablets, sublingual tablets, troches, capsules, elixirs, suspensions, syrups, wafers, and the like. The percentage of the compositions and preparations may vary and may be between about 1 to about 99% weight of the active ingredient(s) and excipients such as, but not limited to a binder, a filler, a diluent, a disintegrating agent, a lubricant, a surfactant, a sweetening agent; a flavoring agent, a colorant, a buffering agent, anti-oxidants, a preservative, chelating agents (e.g., ethylenediaminetetraacetic acid), and agents for the adjustment of tonicity such as sodium chloride.

Suitable binders include, but are not limited to, polyvinylpyrrolidone, copovidone, hydroxypropyl methylcellulose, starch, and gelatin.

Suitable fillers include, but are not limited to, sugars such as lactose, sucrose, mannitol or sorbitol and derivatives therefore (e.g. amino sugars), ethylcellulose, microcrystalline cellulose, and silicified microcrystalline cellulose.

Suitable diluents include, but are not limited to, dicalcium phosphate dihydrate, sugars, lactose, calcium phosphate, cellulose, kaolin, mannitol, sodium chloride, and dry starch.

Suitable disintegrants include, but are not limited to, pregelatinized starch, crospovidone, crosslinked sodium carboxymethyl cellulose and combinations thereof.

Suitable lubricants include, but are not limited to, sodium stearyl fumarate, stearic acid, polyethylene glycol or stearates, such as magnesium stearate.

Suitable surfactants or emulsifiers include, but are not limited to, polyvinyl alcohol (PVA), polysorbate, polyethylene glycols, polyoxyethylene-polyoxypropylene block copolymers known as "poloxamer", polyglycerin fatty acid esters such as decaglyceryl monolaurate and decaglyceryl monomyristate, sorbitan fatty acid ester such as sorbitan monostearate, polyoxyethylene sorbitan fatty acid ester such as polyoxyethylene sorbitan monooleate (Tween), polyethylene glycol fatty acid ester such as polyoxyethylene monostearate, polyoxyethylene alkyl ether such as polyoxyethylene lauryl ether, polyoxyethylene castor oil and hardened castor oil such as polyoxyethylene hardened castor oil.

Suitable flavoring agents and sweeteners include, but are not limited to, sweeteners such as sucralose and synthetic flavor oils and flavoring aromatics, natural oils, extracts from plants, leaves, flowers, and fruits, and combinations thereof. Exemplary flavoring agents include cinnamon oils, oil of wintergreen, peppermint oils, clover oil, hay oil, anise oil, *eucalyptus*, vanilla, citrus oil such as lemon oil, orange oil, grape and grapefruit oil, and fruit essences including apple, peach, pear, strawberry, raspberry, cherry, plum, pineapple, and apricot.

Suitable colorants include, but are not limited to, alumina (dried aluminum hydroxide), annatto extract, calcium carbonate, canthaxanthin, caramel, ß-carotene, cochineal extract, carmine, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, mica, dentifrices, talc, titanium dioxide, aluminum powder, bronze powder, copper powder, and zinc oxide.

Suitable buffering or pH adjusting agent include, but are not limited to, acidic buffering agents such as short chain fatty acids, citric acid, acetic acid, hydrochloric acid, sulfuric acid and fumaric acid; and basic buffering agents such as tris, sodium carbonate, sodium bicarbonate, sodium hydroxide, potassium hydroxide and magnesium hydroxide.

Suitable tonicity enhancing agents include, but are not limited to, ionic and non-ionic agents such as, alkali metal or alkaline earth metal halides, urea, glycerol, sorbitol, mannitol, propylene glycol, and dextrose.

Suitable wetting agents include, but are not limited to, glycerin, cetyl alcohol, and glycerol monostearate.

Suitable preservatives include, but are not limited to, benzalkonium chloride, benzoxonium chloride, thiomersal, phenylmercuric nitrate, phenylmercuric acetate, phenylmercuric borate, methylparaben, propylparaben, chlorobutanol, benzyl alcohol, phenyl alcohol, chlorohexidine, and polyhexamethylene biguanide.

Suitable antioxidants include, but are not limited to, sorbic acid, ascorbic acid, ascorbate, glycine, a-tocopherol, butylated hydroxyanisole (BHA), and butylated hydroxytoluene (BHT).

The viral protease inhibitors of the present disclosure may also be administered via infusion or injection (e.g., using needle (including microneedle) injectors and/or needle-free injectors). Solutions of the active composition can be aqueous, optionally mixed with a nontoxic surfactant and/or may contain carriers or excipients such as salts, carbohydrates and buffering agents (preferably at a pH of from 3 to 9), and, for some applications, they may be more suitably formulated as a sterile non-aqueous solution or as a dried form to be used in conjunction with a suitable vehicle such as sterile, pyrogen-free water or phosphate-buffered saline. For example, dispersions can be prepared in glycerol, liquid polyethylene glycols, triacetin, and mixtures thereof and in oils. The preparations may further contain a preservative to prevent the growth of microorganisms.

The pharmaceutical compositions may be formulated for parenteral administration (e.g., subcutaneous, intravenous, intra-arterial, transdermal, intraperitoneal or intramuscular injection) and may include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. Water is a preferred carrier when the pharmaceutical composition is administered intravenously. Saline solutions and aqueous dextrose and glycerol solutions can also be employed as liquid carriers, particularly for injectable solutions. Oils such as petroleum, animal, vegetable, or synthetic oils and soaps such as fatty alkali metal, ammonium, and triethanolamine salts, and suitable detergents may also be used for parenteral administration. Further, the compositions may contain one or more nonionic surfactants. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. Suitable preservatives include e.g. sodium benzoate, benzoic acid, and sorbic acid. Suitable antioxidants include e.g. sulfites, ascorbic acid and □-tocopherol.

The preparation of parenteral compounds/compositions under sterile conditions, for example, by lyophilization, may readily be accomplished using standard pharmaceutical techniques well known to those skilled in the art.

Compositions for inhalation or insulation include solutions and suspensions in pharmaceutically acceptable aqueous or organic solvents, or mixtures thereof, and powders. The liquid or solid compositions may contain suitable pharmaceutically acceptable excipients as described above. In one embodiment, the compositions are administered by the oral or nasal respiratory route for local or systemic effect. Compositions in pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, orally or nasally, from devices that deliver the formulation in an appropriate manner.

In yet another embodiment, the composition is prepared for topical administration, e.g. as an ointment, a gel, a drop, a patch or a cream. For topical administration to body surfaces using, for example, creams, gels, drops, ointments and the like, the compounds of the present disclosure can be prepared and applied in a physiologically acceptable diluent with or without a pharmaceutical carrier. Adjuvants for topical or gel base forms may include, for example, sodium carboxymethylcellulose, polyacrylates, polyoxyethylene-polyoxypropylene-block polymers, polyethylene glycol, wood wax alcohols, isostearic acid, cetyl alcohol, stearyl alcohol, white petrolatum, polysorbate 60, sorbitan monostearate, glycerin, xanthan gum, water, benzyl alcohol, methylparaben, and propylparaben. Additional additives may be selected from the group consisting of waxes, soaps, sorbitan esters, fatty acids, fatty acid esters, fatty acid oils, borates, cresol, chlorocresol, cellulose, methylcellulose, hydroxypropylcellulose, acacia, and the like. Examples of suitable topical dosage forms may be found in e.g., Tarun Garg, Goutam Rath & Amit K. Goyal (2015) Comprehensive review on additives of topical dosage forms for drug delivery, Drug Delivery, 22:8, 969-987, the contents of which are hereby incorporated by reference in their entirety.

Alternative formulations include nasal sprays, liposomal formulations, slow-release formulations, pumps delivering the drugs into the body (including mechanical or osmotic pumps) controlled-release formulations and the like, as are known in the art.

Doses

As used herein, the term "therapeutically effective dose" means (unless specifically stated otherwise) a quantity of a compound which, when administered either one time or over the course of a treatment cycle affects the health, wellbeing or mortality of a subject (e.g., delays the onset of and/or reduces the severity of one or more of the symptoms associated with a coronavirus, e.g., SARS-Covid-19.

A viral protease inhibitors described herein can be present in a composition in an amount of about 0.001 mg, about 0.005 mg, about 0.01 mg, about 0.02 mg, about 0.03 mg, about 0.04 mg, about 0.05 mg, about 0.06 mg, about 0.07 mg, about 0.08 mg, about 0.09 mg about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 1.5 mg, about 2 mg, about 2.5 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 0.5 mg, about 10 mg, about 10.5 mg, about 11 mg, about 12 mg, about 12.5 mg, about 13 mg, about 13.5 mg, about 14 mg, about 14.5 g, about 15 mg, about 15.5 mg, about 16 mg, about 16.5 mg, about 17 mg, about 17.5 mg, about 18 mg, about 18.5 mg, about 19 mg, about 19.5 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg.

Viral protease inhibitors described herein described herein can be present in a composition in a range of from about 0.1 mg to about 100 mg; 0.1 mg to about 75 mg; from about 0.1 mg to about 50 mg; from about 0.1 mg to about 25 mg; from about 0.1 mg to about 10 mg; 0.1 mg to about 7.5 mg, 0.1 mg to about 5 mg; 0.1 mg to about 2.5 mg; from about 0.1 mg to about 1 mg; from about 0.5 mg to about 100 mg; from about 0.5 mg to about 75 mg; from about 0.5 mg to about 50 mg; from about 0.5 mg to about 25 mg; from about 0.5 mg to about 10 mg; from about 0.5 mg to about 5 mg, from about 0.5 mg to about 2.5 mg; from about 0.5 mg to about 1 mg; from about 1 mg to about 100 mg; from about 1 mg to about 75 mg; from about 0.1 mg to about 50 mg; from about 0.1 mg to about 25 mg; from about 0.1 mg to about 10 mg; from about 0.1 mg to about 5 mg; from about 0.1 mg to about 2.5 mg; from about 0.1 mg to about 1 mg.

Dosing Regimens

The compounds described herein can be administered by any dosing schedule or dosing regimen as applicable to the patient and/or the condition being treated. Administration can be once a day (q.d.), twice a day (b.i.d.), thrice a day (t.i.d.), once a week, twice a week, three times a week, once every 2 weeks, once every three weeks, or once a month twice, and the like.

In some embodiments, the viral protease inhibitor is administered for a period of at least one day. In other embodiments, the viral protease inhibitor is administered for a period of at least 2 days. In other embodiments, the viral protease inhibitor antagonist is administered for a period of at least 3 days. In other embodiments, the viral protease inhibitor antagonist is administered for a period of at least 4 days. In other embodiments, the viral protease inhibitor antagonist is administered for a period of at least 5 days. In other embodiments, the viral protease inhibitor is administered for a period of at least 6 days. In other embodiments, the viral protease inhibitor is administered for a period of at least 7 days. In other embodiments, the viral protease inhibitor is administered for a period of at least 10 days. In other embodiments, the viral protease inhibitor is administered for a period of at least 14 days. In other embodiments, the viral protease inhibitor is administered for a period of at least one month. In some embodiments, the viral protease inhibitor is administered chronically for as long as the treatment is needed.

The present subject matter described herein will be illustrated more specifically by the following non-limiting examples, it being understood that changes and variations can be made therein without deviating from the scope and the spirit of the disclosure as hereinafter claimed. It is also understood that various theories as to why the disclosure works are not intended to be limiting.

The foregoing description of the specific embodiments will so fully reveal the general nature of the disclosure that others can, by applying knowledge within the skill of the relevant art(s) (including the contents of the documents cited and incorporated by reference herein for all purposes), readily modify and/or adapt for various applications such specific embodiments, without undue experimentation, without departing from the general concept of the present disclosure. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

While various embodiments of the present disclosure have been described above, it should be understood that they have been presented by way of examples, and not limitation. It would be apparent to one skilled in the relevant art(s) that various changes in form and detail could be made therein without departing from the spirit and scope of the disclosure. Thus, the present disclosure should not be limited by any of the above-described exemplary embodiments but should be defined only in accordance with the following claims and their equivalents.

What is claimed:

1. A method of treating or alleviating at least one symptom of a coronavirus infection in a subject infected with coronavirus, the method comprising the step of administering to the subject a therapeutically effective amount of the viral protease inhibitor.

2. The method according to claim 1, wherein the symptom is selected from the group consisting of fever, cough, tiredness, sore throat, diarrhea, conjunctivitis, headache, loss of taste, loss of smell, rash, difficulty breathing, shortness of breath, chest pain, chest pressure, Acute Respiratory Distress Syndrome (ARDS) and organ failure.

3. The method according to claim 1, wherein the coronavirus is SARS-COV-19.

* * * * *